(12) United States Patent
Klinghoffer et al.

(10) Patent No.: US 7,399,586 B2
(45) Date of Patent: Jul. 15, 2008

(54) MODULATION OF BIOLOGICAL SIGNAL TRANSDUCTION BY RNA INTERFERENCE

(75) Inventors: Richard Klinghoffer, Seattle, WA (US); Stephen Patrick Lewis, Mountlake Terrace, WA (US)

(73) Assignee: Ceptyr, Inc., Redmond, WA (US)

( * ) Notice: Subject to any disclaimer, the term of this patent is extended or adjusted under 35 U.S.C. 154(b) by 557 days.

(21) Appl. No.: 10/444,795

(22) Filed: May 23, 2003

(65) Prior Publication Data

US 2004/0077574 A1    Apr. 22, 2004

Related U.S. Application Data

(60) Provisional application No. 60/462,942, filed on Apr. 14, 2003, provisional application No. 60/383,249, filed on May 23, 2002.

(51) Int. Cl.
*C12Q 1/68*    (2006.01)
*C12P 19/34*    (2006.01)
*C12N 15/03*    (2006.01)
*C12N 15/00*    (2006.01)
*C07N 21/04*    (2006.01)

(52) U.S. Cl. ........................ 435/6; 435/91.1; 435/91.31; 435/320.7; 435/375; 435/455; 536/23.1; 536/24.5

(58) Field of Classification Search .................... 435/6, 435/91.1, 91.31, 455, 458, 320, 375; 536/23.1, 536/24.5; 514/44
See application file for complete search history.

(56) References Cited

U.S. PATENT DOCUMENTS

| 5,912,138 | A | 6/1999 | Tonks et al. ................ 435/21 |
| 5,951,979 | A | 9/1999 | Tonks et al. ................ 424/94.6 |
| 6,135,942 | A | 10/2000 | Leptin ........................ 535/23.5 |
| 6,261,840 | B1 | 7/2001 | Cowsert et al. |
| 6,326,193 | B1 | 12/2001 | Liu et al. ................... 435/320.1 |
| 6,331,614 | B1 | 12/2001 | Wong et al. ................ 536/23.5 |
| 6,342,595 | B1 | 1/2002 | Karin et al. ................ 536/23.5 |
| 6,506,559 | B1 | 1/2003 | Fire et al. ..................... 435/6 |
| 2001/0029617 | A1 | 10/2001 | Ruvkun et al. ............... 800/13 |
| 2002/0007051 | A1 | 1/2002 | Cheo et al. ................. 536/23.1 |
| 2003/0068821 | A1 | 4/2003 | Lois-Caballe et al. ........ 435/456 |
| 2003/0084471 | A1 | 5/2003 | Beach et al. ................ 800/278 |

FOREIGN PATENT DOCUMENTS

| EP | 1 152 056 A1 | 11/2001 |
| WO | WO 97/00315 | 1/1997 |
| WO | WO 98/04712 | 2/1998 |
| WO | WO 99/32619 | 7/1999 |
| WO | WO 99/46268 | 9/1999 |
| WO | WO 00/32779 | 6/2000 |
| WO | WO 00/44895 | 8/2000 |
| WO | WO 00/49035 | 8/2000 |
| WO | WO 00/60092 | 10/2000 |
| WO | WO 00/75339 | 12/2000 |
| WO | WO 01/05983 | 1/2001 |
| WO | WO 01/21812 | 3/2001 |
| WO | WO 01/29058 | 4/2001 |
| WO | WO 01/34815 | 5/2001 |
| WO | WO 01/36646 | 5/2001 |
| WO | WO 01/42443 | 6/2001 |
| WO | WO 01/46394 | 6/2001 |
| WO | WO 01/49844 | 7/2001 |
| WO | WO 01/68836 | 9/2001 |
| WO | WO 01/75164 | 10/2001 |
| WO | WO 01/77350 | 10/2001 |
| WO | WO 01/88121 | 11/2001 |
| WO | WO 01/92513 | 12/2001 |
| WO | WO 02/44321 | 6/2002 |
| WO | WO 02/055692 | 7/2002 |
| WO | WO 02/055693 | 7/2002 |

OTHER PUBLICATIONS

Opalinska, J.B. et al., Nature Rev., vol. 1, pp. 503-514 (2002).*
Chirila, T.V. et al., Biomaterials, vol. 23, pp. 321-342 (2002).*
Branch, A.D., Trends in Biochem. Sci., vol. 23, pp. 45-50 (1998).*
Peracchi, A., Rev. Med. Virolo.; vol. 14, pp. 47-64 (2004).*
Agrawal, S. et al., Molecular Med. Today, vol. 6, pp. 72-81 (2000).*
Crooke, S.T., Antisense Research & Application, Chapter 1, pp. 1-50, S.T. Crooke, ed., Springer-Verlag, Publ. (1998).*
Agami, R. et al., "Distinc Initiation and Maintenance Mechanisms Cooperate to Induce G1 Cell Cycle Arrest in Response to DNA Damage," *Cell* 102(1):55-66, Jul. 2000.
Andersen, J. et al., "Structural and Evolutionary Relationships Among Protein Tyrosine Phosphatase Domains," *Mol. Cell. Biol.* 21(21):7117-7136, Nov. 2001.

(Continued)

*Primary Examiner*—Jane Zara
(74) *Attorney, Agent, or Firm*—Seed IP Law Group PLLC

(57) ABSTRACT

Compositions and methods relating to small interfering RNA (siRNA) polynucleotides are provided as pertains to modulation of biological signal transduction. Shown are siRNA polynucleotides that interfere with expression of members of the protein tyrosine phosphatase (PTP) class of enzymes that mediate signal transduction, and with certain MAP kinase kinases (MKK). In certain preferred embodiments siRNA modulate signal transduction pathways comprising SHP2, cdc14a/b, cdc25A/B/C, KAP, PTP-ε, PRL-3, CD45, dual specificity phosphatase-3 (DSP-3), MKK-4, and/or MKK-7. Modulation of PTP-mediated biological signal transduction has uses in diseases associated with defects in cell proliferation, cell differentiation and/or cell survival, such as metabolic disorders (including diabetes and obesity), cancer, autoimmune disease, infectious and inflammatory disorders and other conditions. The invention also provides siRNA polynucleotides that interfere with expression of chemotherapeutic target polypeptides, such as DHFR, thymidylate synthetase, and topoisomerase I.

22 Claims, 32 Drawing Sheets

OTHER PUBLICATIONS

Bass, B., "The Short Answer," *Nature* 411:428-429, May 2001.
Bass, B., "Double-Stranded RNA as a Template for Gene Silencing," *Cell* 101(3):235-238, Apr. 2000.
Berstein, E. et al., "The Rest is Silence," *RNA* 7:1509-1521, 2001.
Brautigan, D. et al., "Serine Phosphorylation of Protein Tyrosine Phosphatase (PTP1B) in HeLa Cells in Repsonse to Analogues of cAMP or Diacylglycerol Plus Okadaic Acid," *Mol. Cell Biochem.* 127/128:121-129, Nov. 1993.
Brummelkamp, T. et al., "A System for Stable Expression of Short Interfering RNAs in Mammalian Cells," *Science* 296: 550-553, Apr. 2002.
Carthew, R., "Gene Silencing by Double-Stranded RNA," *Curr. Opin. Cell Biol.* 13:244-248, Apr. 2001.
Charbonneau, H. et al., "The Leukocyte Common Antigen (cD45): A Putative Receptor-Linked Protein Tyrosine Phosphatase," *Proc. Natl. Acad. Sci. USA* 85(19):7182-7186, Oct. 1988.
Check, E., "Patent Flurry Casts Cloud Over Gene Silencing," *Nature* 417, p. 779, Jun. 2002.
Cheng, A. et al., "Coordinated Action of Protein Tyrosine Phosphatases in Insulin Signal Transduction," *Eur. J. Biochem* 269:1050-1059, 2002.
Clemens, J. et al., "Use of Double-Stranded RNA Interference in *Drosophila* Cell Lines to Dissect Signal Transduction Pathways," *Proc. Natl. Acad. Sci. USA* 97(12):6499-6503, Jun. 2000.
Dadke, S. et al., "Phosphorylation and Activation of Protein Tyrosine Phosphatase (PTP) 1B by Insulin Receptor," *Mol. Cell. Biochem.* 221(1&2):147-154, May 2001.
Demetrick, D. J. et al., "Chromosomal Mapping of the Genes for the Human Cell Cycle Proteins Cyclin C (CCNC), Cyclin E (CCNE), p. 21(CDKNI), and KAP (CDKN3)," *Cytogenet. and Cell Genet.* 69:190-192, 1995.
Donzelli, M. et al., "Dual Mode of Degradation of Cdc25 A Phosphatase," *The EMBO Journal* 21(18):4875-4884, 2002.
Elbashir, S. et al., "Duplexes of 21-Nucleotide RNAs Mediate RNA Interference in Cultured Mammalian Cells," *Nature* 411:494-498, May 2001.
Elbashir, S. et al., "RNA Interference is Mediated by 21—and 22-Nucleotide RNAs," *Genes & Development* 15:188-200, 2001.
Elchebly, M. et al., "Increased Insulin Sensitivity and Obesity Resistance in Mice Lacking the Protein Tyrosine Phosphatase-1B Gene," *Science* 283:1544-1548, Mar. 1999.
Elson, A., "Protein Tyrosine Phosphatase ε Increases trhe Risk of Mammary Hyperplasia and Mammary Tumors in Transgenic Mice," *Oncogene* 18(52):7535-7542, Dec. 1999.
Fire, A. et al., "Potent and Specific Genetic Interference by Double-Stranded RNA in *Caenorhabditis elegans*," *Nature* 391:806-811, Feb. 1998.
Flint, A. et al., "Multi-Site Phosphorylation of the Protein Tyrosine Phosphatase, PTP1B: Identification of Cell Cycle Regulated and Phorbol Ester Stimulated Sites of Phosphorylation," *EMBO J.* 12(5):1937-1946, May 1993.
Flint, A. et al., "Development of 'Substrate-Trapping' Mutants to Identify Physiological Substrates of Protein Tyrosine Phosphatases," *Proc. Natl. Acad. Sci. USA* 94:1680-1685, Mar. 1997.
Fukada, T. et al., "The Reciprocal Role of Egr-1 and Sp Family Proteins in Regulation of the PTP1B Promoter in Response to the p210 Bcr-Abl Oncoprotein-Tyrosine Kinase," *J. Biol. Chem.* 276(27):25512-25519, Jul. 2001.
Grabarek, J. et al.,"RNA Interference by Production of Short-Hairpin dsRNA in ES Cells, Their Differentiated Derivatives, and in Somatic Cell Lines," *Biotechniques* 34(4):734-744, Apr. 2003.
Hannon, G. et al., "KAP: A Dual Specificity Phosphatase that Interacts with Cyclin-Dependent Kinases," *Proc. Natl. Acad. Sci. USA* 91:1731-1735, Mar. 1994.
Harborth, J. et al., "Identification of Essential Genes in Cultured Mammalian Cells Using Small Interfering RNAs," *J. Cell Sci.* 114(24):4557-4565, 2001.
Hayes, S. et al., "Targeted Suppression of Gene Expression Using siRNA and RiboJuice™ siRNA Transfection Reagent," *inNovations* 14:9-11, 2002.

Hutvágner, G. et al., "RNAi: Nature Abhors a Double-Strand," *Curr. Opin. Genetics & Development* 12:225-232, 2002.
Kisielow, M. et al., "Isoform-Specific Knockdown and Expression of Adaptor Protein SchA Using Small Interfering RNA," *Biochem. J.* 363:1-5, 2002.
Klaman L. et al., "Increase Energy Expenditure, Decreased Adiposity, and Tissue-Specific Insulin Sensitivity in Protein Tyrosine Phosphatase 1B-Deficient Mice," *Mol. Cell. Biol.* 20(15):5479-5489, Aug. 2000.
Lam, M. et al., "Cellular Stress Regulates the Nucleocytoplasmic Distribution of the Protein-Tyrosine Phosphatase TCPTP," *J. Biol. Chem.* 276(40):37700-37707, Oct. 2001.
LaMontagne, K. et al., "Protein Tyrosine Phosphatase 1B Anatagonizes Signalling by Oncoprotein Tyrosine Kinase p210 bcr-abl In Vivo," *Mol. Cel. Biol.* 18(5):2965-2975, May 1998.
LaMontagne, K. et al., "Protein Tyrosine Phosphatase PTP1B Suppresses p210 bcr-abl-Induced Transformation of Rat-1 Fibroblasts and Promotes Differentiation of K562 Cells," *Proc. Natl. Acad. Sci. USA* 95:14094-14099, Nov. 1998.
Lawler, S. et al., "Synergistic Activation of SAPK1/JNK1 by Two MAP Kinase Kinases in Vitro," *Curr. Biology* 8(25):1387-1390, Dec. 1998.
Lee, S. et al., "Overexpression of Kinase-Associated Phosphatase (KAP) in Breast and Prostate Cancer and Inhibition of the Transformed Phenotype by Antisense KAP Expression," *Molecular and Cellular Biology* 20(5):1723-1732, Mar. 2000.
Lee, N., et al., "Expression of Small Interfering RNAs Targeted Against HIV-1 rev Transcripts in Human Cells," *Nat. Biotech.* 20:500-505, May 2002.
Lee, S. et al., "Reversible Inactivation of Protein-Tyrosine Phosphatase 1B in A431 Cells Stimulated with Epidermal Growth Factor," *J. Biol. Chem.* 273(25):15366-15372, Jun. 1998.
Li, L. et al., A Family of Putative Tumor Suppressors is Structurally and Functionally Conserved in Humans and Yeast, *J. Biol. Chem.* 272(47):29403-29406, Nov. 1997.
Mailand, N. et al., "Deregulated Human Cdc14A Phosphatase Disrupts Centrosome Separation and Chromosome Segregation," *Nat. Cell Biol.* 4:317-322, Apr. 2002.
Martinez, J. et al., "Single-Stranded Antisense siRNAs Guide Target RNA Cleavage in RNAi," *Cell* 110(5):563-574, Sep. 2002.
Matzke, M. et al., "RNA: Guiding Gene Silencing," *Science* 293:1080-1083, Aug. 2001.
Meng, T-C. et al., "Reversible Oxidation and Inactivation of Protein Tyrosine Phosphatases In Vivo," *Molecular Cell* 9:387-399, Feb. 2002.
Miyagishi et al., "U6 Promoter-Driven siRNAs with Four Uridine 3' Overhangs Efficiently Suppress Targeted Gene Expression in Mammalian Cells," *Nat. Biotech.* 20:497-500, May 2002.
Myers, M. et al., "P-TEN, The Tumor Suppressor from Human Chromosome 10q23, is a Dual-Specificity Phosphatase," *Proc. Natl. Acad. Sci. USA* 94:9052-9057, Aug. 1997.
Myers, M. et al., "TYK2 and JAK2 are Substrates of Protein-Tyrosine Phosphatase 1B," *J. Biol. Chem.* 276(51):47771-47774, Dec. 2001.
Novina, C. et al., "siRNA-Directed Inhibition of HIV-1 Infection," *Nature Medicine* 8(7):681-686, Jul. 2002.
Paddison, P. et al., "Short Hairpin RNAs (shRNAs) Induce Sequence-Specific Silencing in Mammalian Cells," *Genes & Development* 16:948-958, 2002.
Paul, C. et al., "Effective Expression of Small Interfering RNA in Human Cells," *Nature Biotechnology* 20:505-508, May 2002.
Paul, C. et al., "Localized Expression if Small RNA Inhibitors in Human Cells," *Molecular Therapy* 7(2):237-247, Feb. 2003.
Plasterk, R. et al., "RNA Silencing: The Genome's Immune System," *Science* 296:1263-1265, May 2002.
Regalado, A., "Turning Off Genes Sheds New Light on How They Work," *Wall Street Journal* 240(26), Aug. 2002.
Ruzzene, M. et al., "Specificity of T-Cell Protein Tyrosine Phosphatase Toward Phosphorylated Synthetic Peptides," *Eur. J. Biochem.* 211:289-295, 1993.
Saha, S. et al., "A Phosphatase Associated with Metastasis of Colorectal Cancer," *Science* 294(5545):1343-1346, Nov. 2001.

Salmeen, A. et al., "Molecular Basis for the Dephosphorylation of the Activation Segment of the Insulin Receptor by Protein Tyrosine Phosphatase 1b," *Molecular Cell* 6:1401-1412, Dec. 2000.
Scadden, A. et al., "RNAi is Antagonized by A → I hyper-Editing," *Embo Reports* 2(12):1107-1111, 2001.
Sharp, P., "RNAi and Double Strand RNA," *Genes & Development* 13:139-141, 1999.
Sharp, P., "RNA Interference—2001," *Genes & Development* 15:485-490, 2001.
Shen. Y. et al., "Activation of the Jnk Signaling Pathway by a Dual-Specificity Phosphatase, JSP-1," *Proc. Natl. Acad. Sci. USA* 98(24):13613-13618, Nov. 2001.
Sui, G. et al., "A DNA Vector-Based RNAi Technology to Suppress Gene Expression in Mammalian Cells," *Proc. Natl. Acad. Sci. USA* 99(8):5515-5520, Apr. 2002.
Tiganis, T. et al., "Epidermal Growth Factor Receptor and the Adaptor Protein p52$^{Sch}$ Are Specific Substrates of T-Cell Protein Tyrosine Phosphatase," *Mol. Cell. Biol.* 18(3):1622-1634, Mar. 1998.
Tonks, N. et al. "Combinatorial Control of the Specificity of Protein Tyrosine Phosphatases," *Curr. Opin. Cell Biol.* 13:185-195, Apr. 2001.
Touw, I. et al., "Signaling Mechanisms of Cytokine Receptors and Their Perturbations in Disease," *Molecular and Cellular Endocrinology* 160(1-2):1-9, Feb. 2000.
Tuschl T., "RNA Interference and Small Interfering RNAs," *ChemBiochem* 2:239-445, 2001.
Ui-Tei, K. et al., "Sensitive Assay of RNA Interference in *Drosophila* and Chinese Hamster Cultured Cells Using Firefly Luciferase Gene as Target," *FEBS Letters* 479:79-82, 2000.
Wen, S. et al., "PTEN Controls Tumor-Induced Angiogensis," *Proc. Natl. Acad. Sci. USA* 98(8):4622-4627, Apr. 2001.
Wong, A. et al., "Genomic Structure, Chromosomal Location, and Mutation Analysis of the Human CDC14A Gene," *Genomics* 59(2):248-251, Jul. 1999.
Yang, D. et al., "Targeted Disruption of the MKK4 Gene Causes Embryonic Death, Inhibition of c-Jun NH2-Terminal Kinase Activation, and Defects in AP-1 Transcriptional Activity," *Proc. Natl. Acad. Sci. USA* 94:3004-3009, Apr. 1997.
Yeh, C-T. et al., "Aberrant Transcripts of the Cyclin-Dependent Kinase-Associated Protein Phosphatase in Hepatocellular Carcinoma," *Cancer Research* 60:4697-4700, Sep. 2000.
Yu, J-H. et al., "RNA Interference by Expression of Short-Interfering RNAs and Hairpin RNAs is Mammalian Cells," *Proc. Natl. Acad. Sci. USA* 99(9):6047-6052, Apr. 2002.
Zamore, P. et al., "RNAi: Double-Stranded RNA Directs the ATP-Dependent Cleavage of mRNA at 21 to 23 Nucleotide Intervals," *Cell* 101:25-33, Mar. 2000.
Zamore, P., "Ancient Pathways Programmed by Small RNAs," *Science* 296:1265-1269, May 2002.
Zamore, P., "RNA Interference: Listening to the Sound of Silence," *Nat. Struc. Biol.* 8(9):746-750, Sep. 2001.
Zhang, S-H., et al., "Identification of the Cell Cycle Regulator VCP (p97/CDC48) as a Substrate of the Band 4.1-Related Protein Tyrosine Phosphatase PTPH1," *J. Biol. Chem.* 274(25):17806-17812, Jun. 1999.
Zaho, Z. et al., "Characterization and Genomic Mapping of Genes and Pseudogenes of a New Human Protein Tyrosine Phosphatase," *Genomics* 35(1):172-181, Jul. 1996.
Genbank Database Accession No. AF009225, Aug. 15, 1997.
Genbank Database Accession No. AF012890, Aug. 9, 1997.
Genbank Database Accession No. AF013588, May 14, 1998.
Genbank Database Accession No. AF023158, Dec. 5, 1997.
Genbank Database Accession No. AF026216, Nov. 16, 2000.
Genbank Database Accession No. AF029684, Nov. 15, 1997.
Genbank Database Accession No. AF031416, Oct. 21, 1998.
Genbank Database Accession No. AF064102, Aug. 6, 1999.
Genbank Database Accession No. AF064103, Aug. 6, 1999.
Genbank Database Accession No. AF064104, Aug. 6, 1999.
Genbank Database Accession No. AF064105, Aug. 6, 1999.
Genbank Database Accession No. AF074382, Jun. 15, 2001.
Genbank Database Accession No. AF080157, Jan. 24, 1999.
Genbank Database Accession No. AF080158, Jan. 24, 1999.
Genbank Database Accession No. AF091453, Jun. 10, 1999.
Genbank Database Accession No. AF122013, Aug. 15, 1999.
Genbank Database Accession No. AF527417, Jul. 17, 2002.
Genbank Database Accession No. D13540, Mar. 5, 1999.
Genbank Database Accession No. D84372, Feb. 6, 1999.
Genbank Database Accession No. J03250, Jan. 14, 1995.
Genbank Database Accession No. L03535, Aug. 3, 1993.
Genbank Database Accession No. L07527, Mar. 28, 1994.
Genbank Database Accession No. L08807, Jun. 11, 1993.
Genbank Database Accession No. L27711, May 16, 1995.
Genbank Database Accession No. L36870, Feb. 28, 1995.
Genbank Database Accession No. M25393, May 9, 1995.
Genbank Database Accession No. M31724, Jan. 8, 1995.
Genbank Database Accession No. M33689, Jan. 8, 1995.
Genbank Database Accession No. M33962, Nov. 25, 1998.
Genbank Database Accession No. M80737, Apr. 27, 1993.
Genbank Database Accession No. M81477, Apr. 27, 1993.
Genbank Database Accession No. M81478, Apr. 27, 1993.
Genbank Database Accession No. M81934, Dec. 31, 1994.
Genbank Database Accession No. NM_000791, Dec. 20, 2003.
Genbank Database Accession No. NM_001789, Dec. 20, 2003.
Genbank Database Accession No. NM_001790, Dec. 20, 2003.
Genbank Database Accession No. NM_002827, Dec. 20, 2003.
Genbank Database Accession No. NM_002828, Dec. 20, 2003.
Genbank Database Accession No. NM_002838, Dec. 20, 2003.
Genbank Database Accession No. NM_003479, Dec. 21, 2003.
Genbank Database Accession No. NM_006504, Dec. 20, 2003.
Genbank Database Accession No. NM_007079, Dec. 21, 2003.
Genbank Database Accession No. NM_009157, Dec. 22, 2003.
Genbank Database Accession No. NM_011201, Dec. 20, 2003.
Genbank Database Accession No. NM_021872, Dec. 21, 2003.
Genbank Database Accession No. NM_022809, Dec. 21, 2003.
Genbank Database Accession No. NM_023117, Dec. 21, 2003.
Genbank Database Accession No. NM_032611, Dec. 21, 2003.
Genbank Database Accession No. NM_080391, Dec. 21, 2003.
Genbank Database Accession No. NM_080392, Dec. 21, 2003.
Genbank Database Accession No. NM_08042, Dec. 21, 2003.
Genbank Database Accession No. NM_080921, Dec. 21, 2003.
Genbank Database Accession No. NM_080922, Dec. 21, 2003.
Genbank Database Accession No. NM_080923, Dec. 21, 2003.
Genbank Database Accession No. NM_102637, Sep. 16, 2003.
Genbank Database Accession No. NM_130435, Dec. 21, 2003.
Genbank Database Accession No. NM_133571, Dec. 21, 2003.
Genbank Database Accession No. NM_133572, Dec. 21, 2003.
Genbank Database Accession No. NM_001071, Dec. 23, 2003.
Genbank Database Accession No. S39383, May 25, 1993.
Genbank Database Accession No. S78088, Mar. 7, 2001.
Genbank Database Accession No. U09307, Aug. 6, 1994.
Genbank Database Accession No. X58828, Jul. 30, 1996.
Genbank Database Accession No. X70766, Aug. 30, 1994.
Baker, M., et al., "RNAi of the receptor tyrosine phosphatase HmLAR2 in a single cell of an intact leech embryo leads to growth-cone collapase,". Current Biology, 10(17): 1071-1075, Sep. 1, 2000.
Goldstein, B.J., "Protein-tyrosine phosphatase 1B (PTP1B): a novel therapeutic target for type 2 diabetes mellitus, obesity and related states of insulin resistance," 1(3):265-75, Nov. 2001.

* cited by examiner

HeLa cells, transfected with siRNA duplexes 24 hr before stimulation with FBS.

- Mouse fibroblasts were transfected with 200 nM RNAi oligonucleotides for a total of six days.
- "NT" is non-transfected fibroblasts.

Fig. 12A

Prototypical DSP-18pr encoded by 708 base pairs

GGCCCCCCGTTCCCCGCCAGGCTGCAGGCGTCGGGCCTGGGCCGTCAGGGCAGCTGTGACCGGATCGCTTC
CCGGGCGGCGAGCTGGGGGTGCACCCGGACCGCCGCCCCCGGGATCATGGGCAATGGCATGACCAAGGTAC
TTCCTGGACTCTACCTCGGAAACTTCATTGATGCCAAAGACCTGGATCAGCTGGGCCGAAATAAGATCACA
CACATCATCTCTATCCATGAGTCACCCCAGCCTCTGCTGCAGGATATCACCTACCTTCGCATCCCGGTCGC
TGATACCCCTGAGGTACCCATCAAAAAGCACTTCAAAGAATGTATCAACTTCATCCACTGCTGCCGCCTTA
ATGGGGGGAACTGCCTTGTGCACTGCTTTGCAGGCATCTCTCGCAGCACCACGATTGTGACAGCGTATGTG
ATGACTGTGACGGGGCTAGGCTGGCGGGACGTGCTTGAAGCCATCAAGGCCACCAGGCCCATCGCCAACCC
CAACCCAGGCTTTAGGCAGCAGCTTGAAGAGTTTGGCTGGGCCAGTTCCCAGAAGCTTCGCCGGCAGCTGG
AGGAGCGCTTCGGCGAGAGCCCCTTCCGCGACGAGGAGGAGTTGCGCGCGCTGCTGCCGCTGTGCAAGCGC
TGCCGGCAGGGCTCCGCGACCTCGGCCTCCTCCGCCGGGCCGCACTCAGCAGCCTCCGAGGGAACCGTGCA
GCGCCTGGTGCCGCGCACGCCCCGGGAAGCCCACCGGCCGCTGCCGCTGCTGGCGCGCGTCAAGCAGACTT
TCTCTTGCCTCCCCCGGTGTCTGTCCCGCAAGGGCGGCAAGTGAGGATGCAG

Fig. 12B

Prototypical DSP-18pr polypeptide sequence 235 amino acids

MGNGMTKVLPGLYLGNFIDAKDLDQLGRNKITHIISIHESPQPLLQDITYLRIPVADTPEVPIKKHFKECI
NFIHCCRLNGGNCLVHCFAGISRSTTIVTAYVMTVTGLGWRDVLEAIKATRPIANPNPGFRQQLEEFGWAS
SQKLRRQLEERFGESPFRDEEELRALLPLCKRCRQGSATSASSAGPHSAASEGTVQRLVPRTPREAHRPLP
LLARVKQTFSCLPRCLSRKGGK*

Fig. 13A

DSP-18a cDNA

GGCCCCCCGTTCCCCGCCAGGCTGCAGGCGTCGGGCCTGGGCCGTCAGGGCAGCTGTGACCGGATCGCTTC
CCGGGCGGCGAGCTGGGGGTGCACCCGGACCGCCGCCCCCGGGATCATGGGCAATGGCATGACCAAGGTAC
TTCCTGGACTCTACCTCGGAAACTTCATTGATGCCAAAGACCTGGATCAGCTGGGCCGAAATAAGATCACA
CACATCATCTCTATCCATGAGTCACCCCAGCCTCTGCTGCAGGATATCACCTACCTTCGCATCCCGGTCGC
TGATACCCCTGAGGTACCCATCAAAAAGCACTTCAAAGAATGTATCAACTTCATCCACTGCTGCCGCCTTA
ATGGGGGGAACTGCCTTGTGCACTGCTTTGCAGGCATCTCTCGCAGCACCACGATTGTGACAGCGTATGTG
ATGACTGTGACGGGGCTAGGCTGGCGGGACGTGCTTGAAGCCATCAAGGCCACCAGGCCCATCGCCAACCC
CAACCCAGGCTTTAGGCAGCAGCTTGAAGAGTTTGGCTGGGCCAGTTCCCAGAAGGGTGCCAGACATAGGA
CCTCAAAAACCTCTGGTGCCCAATGCCCTCCGATGACTTCAGCAACCTGGATGGTCACCGGACCCAAAGTA
CCAGATCTGTCTGTGCTTCGGTGAGGAGGACCCGGGCCCCACACAGCACCCCAAGGAGCAGCTCATCATGG
CGGACGTGCAGGTGCAGCTTCGGCCTGGGAGCTCGTCCTGCACTCTAAGTGCCTCAACCGAGCGCCCAGAT
GGGTCCTCAACCCCTGGCAACCCCGATGGCATCACTCACCTTCAATGCAGCTGCCTCCATCCTAAGCGAGC
CGCTTCCTCTTCTTGTACCCGCTGAAGGCAGCCCCCAACAGGGGGGCTCCCTACTCCCACCCAACCCTGCC
CACACTAAGCCCATAGACTTGGGGCCTCCCCCGGCACATCACCCAGGTCTGCCGGACGGCAGAGGTGGATC
GCGGCCTTCCACTCCTCTGTCACGGGGCCCCGGAACTCGAGAGTAGGCCACACCGCCCCCCAGCTGGGCAT
GGGGCTTCGGCAGGAAACTGAACTTGATCTTGAGGCCCCAGAAAGGCAGCAACTGGAGCAGAAGCAAGACT
TCATCTCTTGCTGACAGCCCAATTTGTCAATAGCGCTTTCCTCAGAGCCAGCCTTAACCTGCTGTTGAGTC
CATTAAAACGTTTGCTTAAAGTTTTTACCAATAATTAGATCATCAGGGTTGTTTAGTGTGGGATCAAGCCA
TAACAAAACTGCCTAGCCTCTCAGGGGCCTAGAATTTACAGAACCTTCCTCCTCCCTGCAGCAAGTCTCTC
TTCTTTATTCTGGGGGCTGGGAAGGATCCCAAAACAGGGAACTTGGCCGAACCCTGGGCTTTGGATGCTAA
CCACTGAAGTACCAGCACCTGTAGGATGCTGTCTTTGAAGAAACTGAGGCGGACCTCCAAATGCAGCCCTA
AGGCAGAGGTCAACGTGGAAGACCAGCCCTTCTCCAAGCCCCACTGGTCTTTGCAAGCTGTACGTTGTAGG
CAATCTGAGAACTGGAAAGGGGGACTACAACCAGAAAGTTGGTTACCCTGCCATGGGAATAAAGTAGCTGT
TTTCCACCCCAAAAAAAAAAAAAAAAAAAAAAAA

Fig. 13B

DSP-18a polypeptide (181 amino acids)

MGNGMTKVLPGLYLGNFIDAKDLDQLGRNKITHIISIHESPQPLLQDITYLRIPVADTPEVPIKKHFKECI
NFIHCCRLNGGNCLVHCFAGISRSTTIVTAYVMTVTGLGWRDVLEAIKATRPIANPNPGFRQQLEEFGWAS
SQKGARHRTSKTSGAQCPPMTSATWMVTGPKVPDLSVLR*

Fig. 14A

DSP-18b cDNA

GGCCCCCCGTTCCCCGCCAGGCTGCAGGCGTCGGGCCTGGGCCGTCAGGGCAGCTGTGACCGGATCGCTTC
CCGGGCGGCGAGCTGGGGGTGCACCCGGACCGCCGCCCCGGGATCATGGGCAATGGCATGACCAAGGTAC
TTCCTGGACTCTACCTCGGAAACTTCATTGATGCCAAAGACCTGGATCAGCTGGGCCGAAATAAGATCACA
CACATCATCTCTATCCATGAGTCACCCCAGCCTCTGCTGCAGGATATCACCTACCTTCGCATCCCGGTCGC
TGATACCCCTGAGGTACCCATCAAAAAGCACTTCAAAGAATGTATCAACTTCATCCACTGCTGCCGCCTTA
ATGGGGGGAACTGCCTTGTGCACTGCTTTGCAGGCATCTCTCGCAGCACCACGATTGTGACAGCGTATGTG
ATGACTGTGACGGGGCTAGGCTGGCGGGACGTGCTTGAAGCCATCAAGGCCACCAGGCCCATCGCCAACCC
CAACCCAGGCTTTAGGCAGCAGCTTGAAGAGTTTGGCTGGGCCAGTTCCCAGAAGGGTGCCAGACATAGGA
CCTCAAAAACCTCTGGTGCCCAATGCCCTCCGATGACTTCAGCAACCTGCCTGCTGGCTGCACGTGTGGCT
CTTCTCTCCGCAGCGCTGGTGCGCGAAGCCACCGGGCGCACAGCCCAGCGCTGTCGTCTGAGTCCGCGGGC
GGCCGCCGAGCGCCTGCTGGGGCCGCCACCTCACGTTGCAGCAGGATGGTCACCGGACCCAAAGTACCAGA
TCTGTCTGTGCTTCGGTGAGGAGGACCCGGGCCCCACACAGCACCCCAAGGAGCAGCTCATCATGGCGGAC
GTGCAGGTGCAGCTTCGGCCTGGGAGCTCGTCCTGCACTCTAAGTGCCTCAACCGAGCGCCCAGATGGGTC
CTCAACCCCTGGCAACCCCGATGGCATCACTCACCTTCAATGCAGCTGCCTCCATCCTAAGCGAGCCGCTT
CCTCTTCTTGTACCCGCTGAAGGCAGCCCCCAACAGGGGGGCTCCCTACTCCCACCCAACCCTGCCCACAC
TAAGCCCATAGACTTGGGGCCTCCCCGGCGGCACATCACCCAGGTCTGCCGGACGGCAGAGGTGGATCGCG
GCCTTCCACTCCTCTGTCACGGGGCCCCGGAACTCGAGAGTAGGCCACACCGCCCCCCAGCTGGGCATGGG
GCTTCGGCAGGAAACTGAACTTGATCTTGAGGCCCCAGAAAGGCAGCAACTGGAGCAGAAGCAAGACTTCA
TCTCTTGCTGACAGCCCAATTTGTCAATAGCGCTTTCCTCAGAGCCAGCCTTAACCTGCTGTTGAGTCCAT
TAAAACGTTTGCTTAAAGTTTTTACCAATAATTAGATCATCAGGGTTGTTTAGTGTGGGATCAAGCCATAA
CAAAACTGCCTAGCCTCTCAGGGGCCTAGAATTTACAGAACCTTCCTCCTCCCTGCAGCTAGTCTCTCTTC
TTTATTCTGGGGGCTGGGAAGGATCCCAAAACAGGGAACTTGGCCGAACCCTGGGCTTTGGATGCTAACCA
CTGAAGTACCAGCACCTGTAGGATGCTGTCTTTGAAGAAACTGAGGCGGACCTCCAAATGCAGCCCTAAGG
CAGAGGTCAACGTGGAAGACCAGCCCTTCTCCAAGCCCCACTGGTCTTTGCAAGCTGTACGTTGTAGGCAA
TCTGAGAACTGGAAAGGGGGACTACAACCAGAAAGTTGGTTACCCTGCCATGGGAATAAAGTAGCTGTTTT
CCACCCCAAAAAAAAAAAAAAAAAAAAAAAAAAA

Fig. 14B

DSP-18b polypeptide (298 amino acids)

MGNGMTKVLPGLYLGNFIDAKDLDQLGRNKITHIISIHESPQPLLQDITYLRIPVADTPEVPIKKHFKECI
NFIHCCRLNGGNCLVHCFAGISRSTTIVTAYVMTVTGLGWRDVLEAIKATRPIANPNPGFRQQLEEFGWAS
SQKGARHRTSKTSGAQCPPMTSATCLLAARVALLSAALVREATGRTAQRCRLSPRAAAERLLGPPPHVAAG
WSPDPKYQICLCFGEEDPGPTQHPKEQLIMADVQVQLRPGSSSCTLSASTERPDGSSTPGNPDGITHLQCS
CLHPKRAASSSCTR*

Fig. 15A

DSP-18c cDNA

```
GGCCCCCCGTTCCCCGCCAGGCTGCAGGCGTCGGGCCTGGGCCGTCAGGGCAGCTGTGACCGGAT
CGCTTCCCGGGCGGCGAGCTGGGGGTGCACCCGGACCGCCGCCCCCGGGATCATGGGCAATGGCA
TGACCAAGGTACTTCCTGGACTCTACCTCGGAAACTTCATTGATGCCAAAGACCTGGATCAGCTG
GGCCGAAATAAGATCACACACATCATCTCTATCCATGAGTCACCCCAGCCTCTGCTGCAGGATAT
CACCTACCTTCGCATCCCGGTCGCTGATACCCCTGAGGTACCCATCAAAAAGCACTTCAAAGAAT
GTATCAACTTCATCCACTGCTGCCGCCTTAATGGGGGGAACTGCCTTGTGCACTGCTTTGCAGGC
ATCTCTCGCAGCACCACGATTGTGACAGCGTATGTGATGACTGTGACGGGGCTAGGCTGGCGGGA
CGTGCTTGAAGCCATCAAGGCCACCAGGCCCATCGCCAACCCCAACCCAGGCTTTAGGCAGCAGC
TTGAAGAGTTTGGCTGGGCCAGTTCCCAGAAGGGTGCCAGACATAGGACCTCAAAAACCTCTGGT
GCCCAATGCCCTCCGATGACTTCAGCAACCTGGATGGTCACCGGACCCAAAGTACCAGATCTGTC
TGTGCTTCGGTGAGGAGGACCCGGGCCCCACACAGCACCCCAAGGAGCAGCTCATCATGGCGGAC
GTGCAGGTGCAGCTTCGGCCTGGGAGCTCGTCCTGCACTCTAAGTGCCTCAACCGAGCGCCCAGA
TGGGTCCTCAACCCCTGGCAACCCCGATGGCATCACTCACCTTCAATGCAGCTTGCCTCCATCCT
AAGCGAGCCGCTTCCTCTTCTTGTACCCGCTGAAGGCAAGCCCCCAACAGGGGGGCTCCCTACTC
CCACCCAACCCTGCCCACACTAAGCCCATAGACTTGGGGCCTCCCCCGGCACATCACCCAGGTCT
GCCGGACGGCAGAGGTGGATCGCGGCCTTCCACTCCTCTGTCACGGGGCCCCGGAACTCGAGAGT
AGGCCTCACCGCCCCCAGCTGGGCATGGGGCTTCGGCAGGAAACTGAACTTGATCTTGAGGCCA
GCAGAAAGGCAGCAACTGGAGCAGAAGCAAGACTTCATCTCTTGCTGACAGCCCAATTTGTCAAT
AGCGCTTTCCTCAGAGCCAGCCTTAACCTGCTGTTGAGTCCATTAAAACGTTTGCTTAAAGTTTT
TACCAATAAAAAAAAAAAAAAAAAAAAAAAAAAAA
```

Fig. 15B

DSP-18d cDNA

```
GGCCCCCCGTTCCCCGCCAGGCTGCAGGCGTCGGGCCTGGGCCGTCAGGGCAGCTGTGACCGGATCGCTTC
CCGGGCGGCGAGCTGGGGGTGCACCCGGACCGCCGCCCCCGGGATCATGGGCAATGGCATGACCAAGGTAC
TTCCTGGACTCTACCTCGGAAACTTCATTGATGCCAAAGACCTGGATCAGCTGGGCCGAAATAAGATCACA
CACATCATCTCTATCCATGAGTCACCCCAGCCTCTGCTGCAGGATATCACCTACCTTCGCATCCCGGTCGC
TGATACCCCTGAGGTACCCATCAAAAAGCACTTCAAAGAATGTATCAACTTCATCCACTGCTGCCGCCTTA
ATGGGGGGAACTGCCTTGTGCACTGCTTTGCAGGCATCTCTCGCAGCACCACGATTGTGACAGCGTATGTG
ATGACTGTGACGGGGCTAGGCTGGCGGGACGTGCTTGAAGCCATCAAGGCCACCAGGCCCATCGCCAACCC
CAACCCAGGCTTTAGGCAGCAGCTTGAAGAGTTTGGCTGGGCCAGTTCCCAGAAGGGTGCCAGACATAGGA
CCTCAAAAACCTCTGGTGCCCAATGCCCTCCGATGACTTCAGCAACCTGGATGGTCACCGGACCCAAAGTA
CCAGATCTGTCTGTGCTTCGGTGAGGAGGACCCGGGCCCCACACAGCACCCCAAGGAGCAGCTCATCATGG
CGGACCTAGTCTCTCTTCTTTATTCTGGGGGCTGGGAAGGATCCCAAAACAGGGAACTTGGCCGAACCCTG
GGCTTTGGATGCTAACCACTGAAGTACCAGCACCTGTAGGATGCTGTCTTTGAAGAAACTGAGGCGGACCT
CCAAATGCAGCCCTAAGGCAGAGGTCAACGTGGAAGACCAGCCCTTCTCCAAGCCCCACTGGTCTTTGCAA
GCTGTACGTTGTAGGCAATCTGAGAACTGGAAAGGGGGACTACAACCAGAAAGTTGGTTACCCTGCCATGG
GAATAAAGTAGCTGTTTTCCACCCCATAAAAAAAAAAAAAAAAAAAAAAAA
```

Fig. 16A

DSP-18e cDNA

```
GGCCCCCCGTTCCCCGCCAGGCTGCAGGCGTCGGGCCTGGGCCGTCAGGGCAGCTGTGACCGGATCGCTTC
CCGGGCGGCGAGCTGGGGGTGCACCCGGACCGCCGCCCCCGGGATCATGGGCAATGGCATGACCAAGGTAC
TTCCTGGACTCTACCTCGGAAACTTCATTGATGCCAAAGACCTGGATCAGCTGGGCCGAAATAAGATCACA
CACATCATCTCTATCCATGAGTCACCCCAGCCTCTGCTGCAGGATATCACCTACCTTCGCATCCCGGTCGC
TGATACCCCTGAGGTACCCATCAAAAAGCACTTCAAAGAATGTATCAACTTCATCCACTGCTGCCGCCTTA
ATGGGGGGAACTGCCTTGTGCACTGCTTTGCAGGCATCTCTCGCAGCACCACGATTGTGACAGCGTATGTG
ATGACTGTGACGGGGCTAGGCTGGCGGGACGTGCTTGAAGCCATCAAGGCCACCAGGCCCATCGCCAACCC
CAACCCAGGCTTTAGGCAGCAGCTTAAGAGTTTGGCTGGGCCAGTTCCCAGAAGGATGGTCACCGGACCCA
AAGTACCAGATCTGTCTGTGCTTCGGTGAGGAGGACCCGGGCCCCACACAGCACCCCAAGGAGCAGCTCAT
CATGGCGGACCTAGTCTCTCTTCTTTATTCTGGGGGCTGGGAAGGATCCCAAAACAGGGAACTTGGCCGAA
CCCTGGGCTTTGGATGCTAACCACTGAAGTACCAGCACCTGTAGGATGCTGTCTTTGAAGAAACTGAGGCG
GACCTCCAAATGCAGCCCTAAGGCAGAGGTCAACGTGGAAGACCAGCCCTTCTCCAAGCCCCACTGGTCTT
TGCAAGCTGTACGTTGTAGGCAATCTGAGAACTGGAAAGGGGGACTACAACCAGAAAGTTGGTTACCCTGC
CATGGGAATAAAGTAGCTGTTTTCCACCCCCCAAAAAAAAAAAAAAAAAAAAAAAAAAAAA
```

Fig. 16B

DSP-18e polypeptide (159 amino acids)

```
MGNGMTKVLPGLYLGNFIDAKDLDQLGRNKITHIISIHESPQPLLQDITYLRIPVADTPEVPIKKHFKECI
NFIHCCRLNGGNCLVHCFAGISRSTTIVTAYVMTVTGLGWRDVLEAIKATRPIANPNPGFRQQLKSLAGPV
PRRMVTGPKVPDLSVLR*
```

Fig. 17A

DSP-18f cDNA

GGCCCCCCGTTCCCCGCCAGGCTGCAGGCGTCGGGCCTGGGCCGTCAGGGCAGCTGTGACCGGATCGCTTC
CCGGGCGGCGAGCTGGGGGTGCACCCGGACGCCGCCCCCGGGATCATGGGCAATGGCATGACCAAGGTAC
TTCCTGGACTCTACCTCGGAAACTTCATTGATGCCAAAGACCTGGATCAGCTGGGCCGAAATAAGATCACA
CACATCATCTCTATCCATGAGTCACCCCAGCCTCTGCTGCAGGATATCACCTACCTTCGCATCCCGGTCGC
TGATACCCCTGAGGTACCCATCAAAAAGCACTTCAAAGAATGTATCAACTTCATCCACTGCTGCCGCCTTA
ATGGGGGGAACTGCCTTGTGCACTGCTTTGCAGGCATCTCTCGCAGCACCACGATTGTGACAGCGTATGTG
ATGACTGTGACGGGGCTAGGCTGGCGGGACGTGCTTGAAGCCATCAAGGCCACCAGGCCCATCGCCAACCC
CAACCCAGGCTTTAGGCAGCAGCTTGAAGAGTTTGGCTGGGCCAGTTCCCAGAAGGGCTTTTACCAACCTC
ATAAGCTGTTGTGAGAACCAATTGAGACACTGCAGGAAAGTGTTTAGCCAGGCCCAGCACTGATGAGCAGT
CGGATGGTCACCGGACCCAAAGTACCAGATCTGTCTGTGCTTCGGTGAGGAGGACCCGGGCCCCACACAGC
ACCCCAAGGAGCAGCTCATCATGGCGGACCTAGTCTCTCTTCTTTATTCTGGGGGCTGGGAAGGATCCCAA
AACAGGGAACTTGGCCGAACCCTGGGCTTTGGATGCTAACCACTGAAGTACCAGCACCTGTAGGATGCTGT
CTTTGAAGAAACTGAGGCGGACCTCCAAATGCAGCCCTAAGGCAGAGGTCAACGTGGAAGACCAGCCCTTC
TCCAAGCCCCACTGGTCTTTGCAAGCTGTACGTTGTAGGCAATCTGAGAACTGGAAAGGGGGACTACAACC
AGAAAGTTGGTTACCCTGCCATGGGAATAAAGTAGCTGTTTTCCAAAAAAAAAAAAAAAAAAAAAAAAAAA

Fig. 17B

DSP-18f polypeptide (154 amino acids)

MGNGMTKVLPGLYLGNFIDAKDLDQLGRNKITHIISIHESPQPLLQDITYLRIPVADTPEVPIKKHFKECI
NFIHCCRLNGGNCLVHCFAGISRSTTIVTAYVMTVTGLGWRDVLEAIKATRPIANPNPGFRQQLEEFGWAS
SQKGFYQPHKLL*

DSP-13 Encoding Polynucleotide

```
cctgggaaga agttatctat ctctcgagtg acattcaaga tataccgtac ccctcggttc    60
tgtaagtcct ctaagttgga ggcattccat tctgagccgg ccccatgacc ctgagcacgt   120
tggcccgcaa gaggaaggcg cccctcgctt gcacctgcag cctcggtggc cccgacatga   180
ttccttactt ctccgccaac gcggtcatct cgcagaacgc catcaaccag ctcatcagcg   240
agagctttct aactgtcaaa ggtgctgccc tttttctacc acggggaaat ggctcatcca   300
caccaagaat cagccacaga cggaacaagc atgcaggcga tctccaacag catctccaag   360
caatgttcat tttactccgc ccagaagaca acatcaggct ggctgtaaga ctggaaagta   420
cttaccagaa tcgaacacgc tatatggtag tggtttcaac taatggtaga caagacactg   480
aagaaagcat cgtcctagga atggatttct cctctaatga cagtagcact tgtaccatgg   540
gcttagtttt gcctctctgg agcgacacgc taattcattt ggatggtgat ggtgggttca   600
gtgtatcgac ggataacaga gttcacatat tcaaacctgt atctgtgcag gcaatgtggt   660
ctgcactaca gagcttacac aaggcttgtg aagtcgccag agcgcataac tactacccag   720
gcagcctatt tctcacttgg gtgagttatt atgagagcca tatcaactca gatcaatcct   780
cagtcaatga atggaatgca atgcaagatg tacagtccca ccggcccgac tctccagctc   840
tcttcaccga catacctact gaacgtgaac gaacagaaag gctaattaaa accaaattaa   900
gggagatcat gatgcagaag gatttggaga atattacatc caaagagata agaacagagt   960
tggaaatgca aatggtgtgc aacttgcggg aattcaagga atttatagac aatgaaatga  1020
tagtgatcct tggtcaaatg gatagcccta cacagatatt tgagcatgtg ttcctgggct  1080
cagaatggaa tgcctccaac ttagaggact acagaaccg aggggtacgg tatatcttga  1140
atgtcactcg agagatagat aacttcttcc caggagtctt tgagtatcat aacattcggg  1200
tatatgatga agaggcaacg gatctcctgg cgtactggaa tgacacttac aaattcatct  1260
ctaaagcaaa gaaacatgga tctaaatgcc ttgtgcactg caaaatgggg gtgagtcgct  1320
cagcctccac cgtgattgcc tatgcaatga aggaatatgg ctggaatctg gaccgagcct  1380
atgactatgt gaaagaaaga cgaacggtaa ccaagcccaa cccaagcttc atgagacaac  1440
tggaagagta tcaggggatc ttgctggcaa gcttcctagg cttgattcat ggagggaggg  1500
acaagccctg gggagagaaa agcacagaat ttgagtcagt agatctggtt tccattcctg  1560
gttcaccctc ttgctgcaac cctgagaagt tacttcacat ttctcatcct tacctgaccc  1620
catctataaa atgaaaatca agagatccat ctcacagggt tattgtgaat aaaaatgtgt  1680
ttgaatgttt ataaaaaaaa aaaaaaaaa a                                   1711
```

Fig. 29A

DSP-13 Polypeptide Sequence, 509 Amino Acids

Met Thr Leu Ser Thr Leu Ala Arg Lys Arg Lys Ala Pro Leu Ala Cys
Thr Cys Ser Leu Gly Gly Pro Asp Met Ile Pro Tyr Phe Ser Ala Asn
Ala Val Ile Ser Gln Asn Ala Ile Asn Gln Leu Ile Ser Glu Ser Phe
Leu Thr Val Lys Gly Ala Ala Leu Phe Leu Pro Arg Gly Asn Gly Ser
Ser Thr Pro Arg Ile Ser His Arg Arg Asn Lys His Ala Gly Asp Leu
Gln Gln His Leu Gln Ala Met Phe Ile Leu Leu Arg Pro Glu Asp Asn
Ile Arg Leu Ala Val Arg Leu Glu Ser Thr Tyr Gln Asn Arg Thr Arg
Tyr Met Val Val Val Ser Thr Asn Gly Arg Gln Asp Thr Glu Glu Ser
Ile Val Leu Gly Met Asp Phe Ser Ser Asn Asp Ser Ser Thr Cys Thr
Met Gly Leu Val Leu Pro Leu Trp Ser Asp Thr Leu Ile His Leu Asp
Gly Asp Gly Gly Phe Ser Val Ser Thr Asp Asn Arg Val His Ile Phe
Lys Pro Val Ser Val Gln Ala Met Trp Ser Ala Leu Gln Ser Leu His
Lys Ala Cys Glu Val Ala Arg Ala His Asn Tyr Tyr Pro Gly Ser Leu
Phe Leu Thr Trp Val Ser Tyr Tyr Glu Ser His Ile Asn Ser Asp Gln
Ser Ser Val Asn Glu Trp Asn Ala Met Gln Asp Val Gln Ser His Arg
Pro Asp Ser Pro Ala Leu Phe Thr Asp Ile Pro Thr Glu Arg Glu Arg
Thr Glu Arg Leu Ile Lys Thr Lys Leu Arg Glu Ile Met Met Gln Lys
Asp Leu Glu Asn Ile Thr Ser Lys Glu Ile Arg Thr Glu Leu Glu Met
Gln Met Val Cys Asn Leu Arg Glu Phe Lys Glu Phe Ile Asp Asn Glu
Met Ile Val Ile Leu Gly Gln Met Asp Ser Pro Thr Gln Ile Phe Glu
His Val Phe Leu Gly Ser Glu Trp Asn Ala Ser Asn Leu Glu Asp Leu
Gln Asn Arg Gly Val Arg Tyr Ile Leu Asn Val Thr Arg Glu Ile Asp
Asn Phe Phe Pro Gly Val Phe Glu Tyr His Asn Ile Arg Val Tyr Asp
Glu Glu Ala Thr Asp Leu Leu Ala Tyr Trp Asn Asp Thr Tyr Lys Phe
Ile Ser Lys Ala Lys Lys His Gly Ser Lys Cys Leu Val His Cys Lys
Met Gly Val Ser Arg Ser Ala Ser Thr Val Ile Ala Tyr Ala Met Lys
Glu Tyr Gly Trp Asn Leu Asp Arg Ala Tyr Asp Tyr Val Lys Glu Arg
Arg Thr Val Thr Lys Pro Asn Pro Ser Phe Met Arg Gln Leu Glu Glu
Tyr Gln Gly Ile Leu Leu Ala Ser Phe Leu Gly Leu Ile His Gly Gly
Arg Asp Lys Pro Trp Gly Glu Lys Ser Thr Glu Phe Glu Ser Val Asp
Leu Val Ser Ile Pro Gly Ser Pro Ser Cys Cys Asn Pro Glu Lys Leu
Leu His Ile Ser His Pro Tyr Leu Thr Pro Ser Ile Lys

*Fig. 29B*

DSP-14 Encoding Polynucleotide

```
ggccagtggg ggtggctggg cgtgcggctg ctacatgccc cacggaccag aacctcccga    60
cgcggccagg ccccggcaca cccagctgca gaaaggagag aaaatccctt ggctctaaaa   120
tgacatctgg agaagtgaag acaagcctca agaatgccta ctcatctgcc aagaggctgt   180
cgccgaagat ggaggaggaa ggggaggagg aggactactg caccccctgga gcctttgagc  240
tggagcggct cttctggaag ggcagtcccc agtacaccca cgtcaacgag gtctggccca   300
agctctacat tggcgatgag gcgacggcgc tggaccgcta taggctgcag aaggcggggt   360
tcacgcacgt gctgaacgcg gcccacggcc gctggaacgt ggacactggg cccgactact   420
accgcgacat ggacatccag taccacggcg tggaggccga cgacctgccc accttcgacc   480
tcagtgtctt cttctacccg gcggcagcct tcatcgacag agcgctaagc gacgaccaca   540
gtaagatcct ggttcactgc gtcatgggcc gcagccggtc agccaccctg gtcctggcct   600
acctgatgat ccacaaggac atgaccctgg tggacgccat ccagcaagtg gccaagaacc   660
gctgcgtcct cccgaaccgg ggcttttga agcagctccg ggagctggac aagcagctgg   720
tgcagcagag gcgacggtcc cagcgccagg acggtgagga ggaggatggc agggagctgt   780
aggcccgact cacagggcca gcagaggcac ttgggggacag aggggagagg cagaacatag   840
ccctggccta ggactccaga gaagggatgg tgaaaccgaa gctcgactct tccaaaccat   900
cttgttcaac ttccccatgt gtgctgggga cagggaggac ccagagctgc ccccgggcag   960
agctgagcgc tcagcctctc agcaaaatgg gagggacggg ctccccggct ctgggtcaca  1020
gaggagcatg ccacgctgca ccaagtctcc tgctttggtt ttgttttttt ggtgagaagg  1080
aagagggaaa aagattttta aaatgtgtag gcagtatgtt gtgattaaac gtttggcttt  1140
gtccaaaaaa aaaaaaaaaa aaaaa                                        1165
```

*Fig. 30A*

DSP-14 Polypeptide Sequence

Met Thr Ser Gly Glu Val Lys Thr Ser Leu Lys Asn Ala Tyr Ser Ser
Ala Lys Arg Leu Ser Pro Lys Met Glu Glu Glu Gly Glu Glu Glu Asp
Tyr Cys Thr Pro Gly Ala Phe Glu Leu Glu Arg Leu Phe Trp Lys Gly
Ser Pro Gln Tyr Thr His Val Asn Glu Val Trp Pro Lys Leu Tyr Ile
Gly Asp Glu Ala Thr Ala Leu Asp Arg Tyr Arg Leu Gln Lys Ala Gly
Phe Thr His Val Leu Asn Ala Ala His Gly Arg Trp Asn Val Asp Thr
Gly Pro Asp Tyr Tyr Arg Asp Met Asp Ile Gln Tyr His Gly Val Glu
Ala Asp Asp Leu Pro Thr Phe Asp Leu Ser Val Phe Phe Tyr Pro Ala
Ala Ala Phe Ile Asp Arg Ala Leu Ser Asp Asp His Ser Lys Ile Leu
Val His Cys Val Met Gly Arg Ser Arg Ser Ala Thr Leu Val Leu Ala
Tyr Leu Met Ile His Lys Asp Met Thr Leu Val Asp Ala Ile Gln Gln
Val Ala Lys Asn Arg Cys Val Leu Pro Asn Arg Gly Phe Leu Lys Gln
Leu Arg Glu Leu Asp Lys Gln Leu Val Gln Gln Arg Arg Arg Ser Gln
Arg Gln Asp Gly Glu Glu Glu Asp Gly Arg Glu Leu

*Fig. 30B*

MODULATION OF BIOLOGICAL SIGNAL TRANSDUCTION BY RNA INTERFERENCE

CROSS-REFERENCE TO RELATED APPLICATION

This application claims the benefit of U.S. Provisional Patent Application No. 60/383,249 filed May 23, 2002, and U.S. Provisional Patent Application No. 60/462,942 filed Apr. 14, 2003, which are incorporated herein by reference in their entirety.

BACKGROUND OF THE INVENTION

1. Technical Field

The present invention relates generally to compositions and methods useful for treating conditions associated with defects in cell proliferation, cell differentiation, and cell survival. The invention is more particularly related to double-stranded RNA polynucleotides that interfere with expression of protein tyrosine phosphatases, and polypeptide variants thereof. The invention is also particularly related to double-stranded RNA polynucleotides that interfere with expression of MAP kinases and MAP kinase kinases and chemotherapeutic target polypeptides, and polypeptide variants thereof. The present invention is also related to the use of such RNA polynucleotides to alter activation of signal transduction pathway components or to alter cellular metabolic processes that lead to proliferative responses, cell differentiation and development, and cell survival.

2. Description of the Related Art

Reversible protein tyrosine phosphorylation, coordinated by the action of protein tyrosine kinases (PTKs) that phosphorylate certain tyrosine residues in polypeptides, and protein tyrosine phosphatases (PTPs) that dephosphorylate certain phosphotyrosine residues, is a key mechanism in regulating many cellular activities. It is becoming apparent that the diversity and complexity of the PTPs and PTKs are comparable, and that PTPs are equally important in delivering both positive and negative signals for proper function of cellular machinery. Regulated tyrosine phosphorylation contributes to specific pathways for biological signal transduction, including those associated with cell division, cell survival, apoptosis, proliferation and differentiation. Defects and/or malfunctions in these pathways may underlie certain disease conditions for which effective means for intervention remain elusive, including for example, malignancy, autoimmune disorders, diabetes, obesity and infection.

The protein tyrosine phosphatase (PTP) family of enzymes consists of more than 100 structurally diverse proteins in vertebrates, including almost 40 human PTPs that have in common the conserved 250 amino acid PTP catalytic domain, but which display considerable variation in their non-catalytic segments (Charbonneau and Tonks, 1992 *Annu. Rev. Cell Biol.* 8:463-493; Tonks, 1993 *Semin. Cell Biol.* 4:373-453; Andersen et al., *Mol. Cell Biol.* 21:7117-36 (2001)). This structural diversity presumably reflects the diversity of physiological roles of individual PTP family members, which in certain cases have been demonstrated to have specific functions in growth, development and differentiation (Desai et al., 1996 *Cell* 84:599-609; Kishihara et al., 1993 *Cell* 74:143-156; Perkins et al., 1992 *Cell* 70:225-236; Pingel and Thomas, 1989 *Cell* 58:1055-1065; Schultz et al., 1993 *Cell* 73:1445-1454). The PTP family includes receptor-like and non-transmembrane enzymes that exhibit exquisite substrate specificity in vivo and that are involved in regulating a wide variety of cellular signaling pathways (Andersen et al., *Mol. Cell. Biol.* 21:7117 (2001); Tonks and Neel, *Curr. Opin. Cell Biol.* 13:182 (2001)). PTPs thus participate in a variety of physiologic functions, providing a number of opportunities for therapeutic intervention in physiologic processes through alteration (i.e., a statistically significant increase or decrease) or modulation (e.g., up-regulation or down-regulation) of PTP activity.

Although recent studies have also generated considerable information regarding the structure, expression and regulation of PTPs, the nature of many tyrosine phosphorylated substrates through which the PTPs exert their effects remains to be determined. Studies with a limited number of synthetic phosphopeptide substrates have demonstrated some differences in the substrate selectivities of different PTPs (Cho et al., 1993 *Protein Sci.* 2: 977-984; Dechert et al., 1995 *Eur. J. Biochem.* 231:673-681). Analyses of PTP-mediated dephosphorylation of PTP substrates suggest that catalytic activity may be favored by the presence of certain amino acid residues at specific positions in the substrate polypeptide relative to the phosphorylated tyrosine residue (Salmeen et al., 2000 *Molecular Cell* 6:1401; Myers et al., 2001 *J. Biol. Chem.* 276:47771; Myers et al., 1997 *Proc. Natl. Acad. Sci. USA* 94:9052; Ruzzene et al., 1993 *Eur. J. Biochem.* 211:289295; Zhang et al., 1994 *Biochemistry* 33:2285-2290). Thus, although the physiological relevance of the substrates used in these studies is unclear, PTPs display a certain level of substrate selectivity in vitro.

The PTP family of enzymes contains a common evolutionarily conserved segment of approximately 250 amino acids known as the PTP catalytic domain. Within this conserved domain is a unique signature sequence motif, $CX_5R$ (SEQ ID NO:1), that is invariant among all PTPs. In a majority of PTPs, an 11 amino acid conserved sequence ([IIV]HCX-AGXXR[S/T]G (SEQ ID NO: 2)) containing the signature sequence motif is found. The cysteine residue in this motif is invariant in members of the family and is essential for catalysis of the phosphotyrosine dephosphorylation reaction. It functions as a nucleophile to attack the phosphate moiety present on a phosphotyrosine residue of the incoming substrate. If the cysteine residue is altered by site-directed mutagenesis to serine (e.g., in cysteine-to-serine or "CS" mutants) or alanine (e.g., cysteine-to-alanine or "CA" mutants), the resulting PTP is catalytically deficient but retains the ability to complex with, or bind, its substrate, at least in vitro.

The CS mutant of one PTP, PTP1B (PTP-1B), is an example of such a PTP. Catalytically deficient mutants of such enzymes that are capable of forming stable complexes with phosphotyrosyl polypeptide substrates may be derived by mutating a wildtype protein tyrosine phosphatase catalytic domain invariant aspartate residue and replacing it with an amino acid that does not cause significant alteration of the Km of the enzyme but that results in a reduction in Kcat, as disclosed, for example, in U.S. Pat. Nos. 5,912,138 and 5,951,979, in U.S. application Ser. No. 09/323,426 and in PCT/US97/13016 and PCT/JUS00/14211. For instance, mutation of Asp 181 in PTP1B to alanine to create the aspartate-to-alanine (D to A or DA) mutant PTP1B-D181A results in a PTP1B "substrate trapping" mutant enzyme that forms a stable complex with its phosphotyrosyl polypeptide substrate (e.g., Flint et al., 1997 *Proc. Natl. Acad. Sci.* 94:1680). Substrates of other PTPs can be identified using a similar substrate trapping approach, for example substrates of the PTP family members PTP-PEST (Garton et al., 1996 *J. Mol. Cell. Biol.* 16:6408), TCPTP (Tiganis et al., 1998 *Mol. Cell Biol.*

18:1622), PTP-HSCF (Spencer et al., 1997 *J. Cell Biol.* 138: 845), and PTP-H1 (Zhang et al., 1999 *J. Biol. Chem.* 274: 17806).

Mitogen-activated protein kinases (MAP-kinases) are components of conserved cellular signal transduction pathways that have a variety of conserved members and that that are integral to the cell's response to stimuli such as growth factors, hormones, cytokines, and environmental stresses. MAP-kinases are activated by phosphorylation by MAP-kinase kinases at a dual phosphorylation motif that has the sequence Thr-X-Tyr, in which phosphorylation at the tyrosine and threonine residues is required for activity. Activated MAP-kinases phosphorylate several transduction targets, including effector protein kinases and transcription factors. Inactivation of MAP-kinases is mediated by dephosphorylation at the Thr-X-Tyr site by dual-specificity phosphatases referred to as MAP-kinase phosphatases. In higher eukaryotes, the physiological role of MAP-kinase signaling has been correlated with cellular events such as proliferation, oncogenesis, development, and differentiation. Accordingly, the ability to regulate signal transduction via these pathways could lead to the development of treatments and preventive therapies for human diseases associated with MAP-kinase signaling, such as cancer.

Dual-specificity protein tyrosine phosphatases (dual-specificity phosphatases) dephosphorylate both phosphotyrosine and phosphothreonine/serine residues (Walton et al., *Ann. Rev. Biochem.* 62:101-120, 1993). More than 50 dual-specificity phosphatases that dephosphorylate and inactivate a MAP-kinase have been identified (Shen et al., *Proc. Natl. Acad. Sci. USA* 98:13613-18 (2001)), including MKP-1 (WO 97/00315; Keyse and Emslie, *Nature* 59:644-647 (1992)); MKP-2 (WO97/00315); MKP-4, MKP-5, MKP-7, Hb5 (WO 97/06245); PAC1 (Ward et al., *Nature* 367:651-654 (1994)); HVH2 (Guan and Butch, *J. Biol. Chem.* 270:7197-7203 (1995)); and PYST1 (Groom et al., *EMBO J.* 15:3621-3632 (1996)). These dual-specificity phosphatases differ in expression, tissue and subcellular distribution, and specificity for MAP-kinase family members. Expression of certain dual-specificity phosphatases is induced by stress or mitogens, but others appear to be expressed constitutively in specific cell types. The regulation of dual-specificity phosphatase expression and activity is critical for control of MAP-kinase mediated cellular functions, including cell proliferation, cell differentiation and cell survival. For example, dual-specificity phosphatases may function as negative regulators of cell proliferation. It is likely that there are many such dual-specificity phosphatases, with varying specificity with regard to cell type or activation.

In contrast to the role of most dual-specificity phosphatases to inactivate MAP-kinases, one enzyme, herein referred to as dual-specificity phosphatase 3 (DSP-3), has been reported to have the capability to function as a selective activator of the JNK MAP-kinase signaling pathway (Shen et al., supra; WO 01/21812). DSP-3 appears also to affect the activity of other kinases involved in the JNK pathway (Shen et al., supra; WO 01/21812). For example, overexpression of DSP-3 leads to activation of MKK4, a MAP-kinase kinase that functions upstream of JNK (Shen et al., supra; Lawler et al., *Curr. Biol.* 8:1387-90 (1998); Yang et al., *Proc. Natl. Acad. Sci. USA* 94: 3004-3009 (1997)).

Activation of JNK is believed to be involved in several physiological processes, including embryonic morphogenesis, cell survival, and apoptosis. A number of JNK signaling pathway substrates have been identified, including c-Jun, ATF2, ELK-1 and others. JNK signaling has also been associated with various disease conditions, such as tumor development, ischemia and reperfusion injury, diabetes, hyperglycemia-induced apoptosis, cardiac hypertrophy, inflammation, and neurodegenerative disorders.

One non-transmembrane PTP, PTP1B, recognizes several tyrosine-phosphorylated proteins as substrates, many of which are involved in human disease. For example, therapeutic inhibition of PTP1B in the insulin signaling pathway may serve to augment insulin action, thereby ameliorating the state of insulin resistance common in Type II diabetes patients. PTP1B acts as a negative regulator of signaling that is initiated by several growth factor/hormone receptor PTKs, including p210 Bcr-Abl (LaMontagne et al., *Mol. Cell Biol.* 18:2965-75 (1998); LaMontagne et al., *Proc. Natl. Acad. Sci. USA* 95:14094-99 (1998)), receptor tyrosine kinases, such as EGF receptor, PDGF receptor, and insulin receptor (IR) (Tonks et al., *Curr. Opin. Cell Biol.* 13:182-95 (2001)), and JAK family members such as Jak2 and others (Myers et al., *J. Biol. Chem.* 276:47771-74 (2001)), as well as signaling events induced by cytokines (Tonks and Neel, 2001). Activity of PTP1B is regulated by modifications of several amino acid residues, such as phosphorylation of Ser residues (Brautigan and Pinault, 1993; Dadke et al., 2001; Flint et al., 1993), and oxidation of the active Cys residue in its catalytic motif (Lee et al., 1998; Meng et al., 2002) which is evolutionary conserved among protein tyrosine phosphatases and dual phosphatase family members (Andersen et al., 2001).

Disruption of the murine PTP1B gene homolog in a knock-out mouse model results in PTP1B$^{-/-}$ mice exhibiting enhanced insulin sensitivity, decreased levels of circulating insulin and glucose, and resistance to weight gain even on a high-fat diet, relative to control animals having at least one functional PTP1B gene (Elchebly et al., *Science* 283:1544 (1999)). Insulin receptor hyperphosphorylation has also been detected in certain tissues of PTP1B deficient mice, consistent with a PTP1B contribution to the physiologic regulation of insulin and glucose metabolism (Id.). PTP-1B-deficient mice exhibit decreased adiposity (reduced fat cell mass but not fat cell number), increased basal metabolic rate and energy expenditure, and enhanced insulin-stimulated glucose utilization (Klaman et al., 2000 *Mol. Cell. Biol.* 20:5479). Additionally, altered PTP activity has been correlated with impaired glucose metabolism in other biological systems (e.g., McGuire et al., *Diabetes* 40:939 (1991); Myerovitch et al., *J. Clin. Invest.* 84:976 (1989); Sredy et al., *Metabolism* 44:1074 (1995)), including PTP involvement in biological signal transduction via the insulin receptor (see, e.g., WO 99/46268 and references cited therein).

An integration of crystallographic, kinetic, and PTP1B-peptide binding assays illustrated the interaction of PTP1B and insulin receptor (IR) (Salmeen et al., *Mol. Cell* 6:1401-12 (2000)). The insulin receptor (IR) comprises two extracellular α subunits and two transmembrane β subunits. Activation of the receptor results in autophosphorylation of tyrosine residues in both β subunits, each of which contains a protein kinase domain. Extensive interactions that form between PTP1B and insulin receptor kinase (IRK) encompass tandem pTyr residues at 1162 and 1163 of IRK, such that pTyr-1162 is located in the active site of PTP1B (id.). The Asp/Glu-pTyr-pTyr-Arg/Lys motif has been implicated for optimal recognition by PTP1B for IRK. This motif is also present in other receptor PTKs, including Trk, FGFR, and Axl. In addition, this motif is found in the JAK family of PTKs, members of which transmit signals from cytokine receptors, including a classic cytokine receptor that is recognized by the satiety hormone leptin (Touw et al., *Mol. Cell. Endocrinol.* 160:1-9 (2000)).

Changes in the expression levels of PTP1B have been observed in several human diseases, particularly in diseases associated with disruption of the normal patterns of tyrosine phosphorylation. For example, the expression of PTP1B is induced specifically by the p210 Bcr-Abl oncoprotein, a PTK that is directly responsible for the initial manifestations of chronic myelogenous leukemia (CML) (LaMontagne et al., *Mol. Cell. Biol.* 18:2965-75 (1998); LaMontagne et al., *Proc. Natl. Acad. Sci. USA* 95:14094-99 (1998)). Expression of PTPB1 in response to this oncoprotein is regulated, in part, by transcription factors Sp1, Sp3, and Egr-1 (Fukada et al., *J. Biol. Chem.* 276:25512-19 (2001)). These transcription factors have been shown to bind to a p210 Bcr-Abl responsive sequence (PRS) in the human PTP1B promoter, located between 49 to –37 base pairs from the transcription start site, but do not appear to mediate certain additional, independent PTP1B transcriptional events, for which neither transcription factor(s) nor transcription factor recognition element(s) have been defined (id.).

Diabetes mellitus is a common, degenerative disease affecting 5-10% of the human population in developed countries, and in many countries, it may be one of the five leading causes of death. Approximately 2% of the world's population has diabetes, the overwhelming majority of cases (>97%) being type 2 diabetes and the remainder being type 1. In type 1 diabetes, which is frequently diagnosed in children or young adults, insulin production by pancreatic islet beta cells is destroyed. Type 2 diabetes, or "late onset" or "adult onset" diabetes, is a complex metabolic disorder in which cells and tissues cannot effectively use available insulin; in some cases insulin production is also inadequate. At the cellular level, the degenerative phenotype that may be characteristic of late onset diabetes mellitus includes, for example, impaired insulin secretion and decreased insulin sensitivity, i.e., an impaired response to insulin.

Studies have shown that diabetes mellitus may be preceded by or is associated with certain related disorders. For example, an estimated forty million individuals in the U.S. suffer from late onset impaired glucose tolerance (IGT). IGT patients fail to respond to glucose with increased insulin secretion. Each year a small percentage (5-10%) of IGT individuals progress to insulin deficient non-insulin dependent diabetes (NIDDM). Some of these individuals further progress to insulin dependent diabetes mellitus (IDDM). NIDDM and IDDM are associated with decreased release of insulin by pancreatic beta cells and/or a decreased response to insulin by cells and tissues that normally exhibit insulin sensitivity. Other symptoms of diabetes mellitus and conditions that precede or are associated with diabetes mellitus include obesity, vascular pathologies, and various neuropathies, including blindness and deafness.

Type 1 diabetes is treated with lifelong insulin therapy, which is often associated with undesirable side effects such as weight gain and an increased risk of hypoglycemia. Current therapies for type 2 diabetes (NIDDM) include altered diet, exercise therapy, and pharmacological intervention with injected insulin or oral agents that are designed to lower blood glucose levels. Examples of such presently available oral agents include sulfonylureas, biguanides, thiazolidinediones, repaglinide, and acarbose, each of which alters insulin and/or glucose levels. None of the current pharmacological therapies, however, controls the disease over its full course, nor do any of the current therapies correct all of the physiological abnormalities in type 2 NIDDM, such as impaired insulin secretion, insulin resistance, and excessive hepatic glucose output. In addition, treatment failures are common with these agents, such that multi-drug therapy is frequently necessary.

In certain metabolic diseases or disorders, one or more biochemical processes, which may be either anabolic or catabolic (e.g., build-up or breakdown of substances, respectively), are altered (e.g., increased or decreased in a statistically significant manner) or modulated (e.g., up- or down-regulated to a statistically significant degree) relative to the levels at which they occur in a disease-free or normal subject such as an appropriate control individual. The alteration may result from an increase or decrease in a substrate, enzyme, cofactor, or any other component in any biochemical reaction involved in a particular process. Altered (i.e., increased or decreased in a statistically significant manner relative to a normal state) PTP activity can underlie certain disorders and suggests a PTP role in certain metabolic diseases.

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., *Nature* 391:806-11 (1998); Sharp, *Genes Dev.* 13:139-41 (1999); Elbashir et al. *Nature* 411:494-98 (2001); Harborth et al., *J. Cell Sci.* 114:4557-65 (2001)). RNAi is mediated by double-stranded polynucleotides as also described hereinbelow, for example, double-stranded RNA (dsRNA), having sequences that correspond to exonic sequences encoding portions of the polypeptides for which expression is compromised. RNAi reportedly is not effected by double-stranded RNA polynucleotides that share sequence identity with intronic or promoter sequences (Elbashir et al., 2001). RNAi pathways have been best characterized in *Drosophila* and *Caenorhabditis elegans*, but "small interfering RNA" (siRNA) polynucleotides that interfere with expression of specific polypeptides in higher eukaryotes such as mammals (including humans) have also been considered (e.g., Tuschl, 2001 *Chembiochem.* 2:239-245; Sharp, 2001 *Genes Dev.* 15:485; Bernstein et al., 2001 *RNA* 7:1509; Zamore, 2002 *Science* 296:1265; Plasterk, 2002 *Science* 296:1263; Zamore 2001 *Nat. Struct. Biol.* 8:746; Matzke et al., 2001 *Science* 293:1080; Scadden et al., 2001 *EMBO Rep.* 2:1107).

According to a current non-limiting model, the RNAi pathway is initiated by ATP-dependent, processive cleavage of long dsRNA into double-stranded fragments of about 18-27 (e.g., 19, 20, 21, 22, 23, 24, 25, 26, etc.) nucleotide base pairs in length, called small interfering RNAs (siRNAs) (see review by Hutvagner et al., *Curr. Opin. Gen. Dev.* 12:225-32 (2002); Elbashir et al., 2001; Nykänen et al., *Cell* 107:309-21 (2001); Zamore et al., *Cell* 101:25-33 (2000); Bass, *Cell* 101:235-38 (2000)). In Drosophila, an enzyme known as "Dicer" cleaves the longer double-stranded RNA into siRNAs; Dicer belongs to the RNase III family of dsRNA-specific endonucleases (WO 01/68836; Bernstein et al., *Nature* 409:363-66 (2001)). Further according to this non-limiting model, the siRNA duplexes are incorporated into a protein complex, followed by ATP-dependent unwinding of the siRNA, which then generates an active RNA-induced silencing complex (RISC) (WO 01/68836). The complex recognizes and cleaves a target RNA that is complementary to the guide strand of the siRNA, thus interfering with expression of a specific protein (Hutvagner et al., supra).

In *C. elegans* and *Drosophila*, RNAi may be mediated by long double-stranded RNA polynucleotides (WO 99/32619; WO 01/75164; Fire et al., 1998; Clemens et al., *Proc. Natl. Acad. Sci. USA* 97:6499-6503 (2000); Kisielow et al., *Biochem. J.* 363:1-5 (2002); see also WO 01/92513 (RNAi-mediated silencing in yeast)). In mammalian cells, however, transfection with long dsRNA polynucleotides (i.e., greater than 30 base pairs) leads to activation of a non-specific sequence response that globally blocks the initiation of protein synthesis and causes mRNA degradation (Bass, *Nature* 411:428-29 (2001)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., *Genes Dev.* 15:188-200 (2001)); Harborth et al., *J. Cell Sci.* 114:4557-65 (2001); Carthew et al., *Curr. Opin. Cell Biol.* 13:244-48 (2001); Mailand et al., *Nature Cell Biol.* Advance Online Publication (Mar. 18, 2002); Mailand et al. 2002 *Nature Cell Biol.* 4:317).

siRNA polynucleotides may offer certain advantages over other polynucleotides known to the art for use in sequence-specific alteration or modulation of gene expression to yield altered levels of an encoded polypeptide product. These advantages include lower effective siRNA polynucleotide concentrations, enhanced siRNA polynucleotide stability, and shorter siRNA polynucleotide oligonucleotide lengths relative to such other polynucleotides (e.g., antisense, ribozyme or triplex polynucleotides). By way of a brief background, "antisense" polynucleotides bind in a sequence-specific manner to target nucleic acids, such as mRNA or DNA, to prevent transcription of DNA or translation of the mRNA (see, e.g., U.S. Pat. No. 5,168,053; U.S. Pat. No. 5,190,931; U.S. Pat. No. 5,135,917; U.S. Pat. No. 5,087,617; see also, e.g., Clusel et al., 1993 *Nuc. Acids Res.* 21:3405-11, describing "dumbbell" antisense oligonucleotides). "Ribozyme" polynucleotides can be targeted to any RNA transcript and are capable of catalytically cleaving such transcripts, thus impairing translation of mRNA (see, e.g., U.S. Pat. No. 5,272, 262; U.S. Pat. No. 5,144,019; and U.S. Pat. Nos. 5,168,053, 5,180,818, 5,116,742 and 5,093,246; U.S. 2002/193579). "Triplex" DNA molecules refers to single DNA strands that bind duplex DNA to form a colinear triplex molecule, thereby preventing transcription (see, e.g., U.S. Pat. No. 5,176,996, describing methods for making synthetic oligonucleotides that bind to target sites on duplex DNA). Such triple-stranded structures are unstable and form only transiently under physiological conditions. Because single-stranded polynucleotides do not readily diffuse into cells and are therefore susceptible to nuclease digestion, development of single-stranded DNA for antisense or triplex technologies often requires chemically modified nucleotides to improve stability and absorption by cells. siRNAs, by contrast, are readily taken up by intact cells, are effective at interfering with the expression of specific polypeptides at concentrations that are several orders of magnitude lower than those required for either antisense or ribozyme polynucleotides, and do not require the use of chemically modified nucleotides.

Importantly, despite a number of attempts to devise selection criteria for identifying oligonucleotide sequences that will be effective in siRNA based on features of the desired target mRNA sequence (e.g., percent GC content, position from the translation start codon, or sequence similarities based on an in silico sequence database search for homologues of the proposed siRNA) it is presently not possible to predict with any degree of confidence which of myriad possible candidate siRNA sequences that can be generated as nucleotide sequences that correspond to a desired target mRNA (e.g., dsRNA of about 18-27 nucleotide base pairs) will in fact exhibit siRNA activity (i.e., interference with expression of the polypeptide encoded by the mRNA). Instead, individual specific candidate siRNA polynucleotide or oligonucleotide sequences must be generated and tested to determine whether interference with expression of a desired polypeptide target can be effected. Accordingly, no routine method exists in the art for designing a siRNA polynucleotide that is, with certainty, capable of specifically altering the expression of a given PTP polypeptide, and thus for the overwhelming majority of PTPs no effective siRNA polynucleotide sequences are presently known.

Currently, therefore, desirable goals for therapeutic regulation of biological signal transduction include modulation of PTP (e.g., PTP-1B, DSP-3, SHP-2, KAP, PRL-3, cdc14 or cdc25 or other PTP)-mediated cellular events include, inter alia, inhibition or potentiation of interactions among PTP-binding molecules, substrates and binding partners, or of other agents that regulate PTP activities. Accordingly, a need exists in the art for an improved ability to intervene in the regulation of phosphotyrosine signaling, including regulating PTPs by altering PTP catalytic activity, PTP binding to PTP substrate molecules, and/or PTP-encoding gene expression. An increased ability to so regulate PTPs may facilitate the development of methods for modulating the activity of proteins involved in phosphotyrosine signaling pathways and for treating conditions associated with such pathways. The present invention fulfills these needs and further provides other related advantages.

SUMMARY OF THE INVENTION

Briefly stated, the present invention provides siRNA compositions and methods for modulating biological signal transduction. In one aspect the present invention provides isolated small interfering RNA (siRNA) polynucleotide, comprising at least one nucleotide sequence selected from the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, and the complementary polynucleotide thereto. The small interfering RNA polynucleotide is capable of interfering with expression of a polypeptide, which polypeptide comprises an amino acid sequence as set forth in a sequence SEQ ID NO: 779, SEQ ID NO 789, SEQ ID NO 791, SEQ ID NO 797, SEQ ID NO 799, SEQ ID NO 801, SEQ ID NO 803, SEQ ID NO 805, SEQ ID NO 807, SEQ ID NO 809, SEQ ID NO 811, or SEQ ID NO 813.

In certain embodiments, the nucleotide sequence of the siRNA polynucleotide differs by one, two, three or four nucleotides at any of positions 1-19 of a sequence selected from the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493. In other embodiments, the nucleotide sequence of the siRNA polynucleotide differs by at least two, three or four nucleotides at any of positions 1-19 of a sequence selected from the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493. In particular embodiments the invention provides an isolated siRNA polynucleotide comprising a nucleotide sequence selected from SEQ ID NOS: 4, or the complement thereof; from SEQ ID NOS: 100, 105, or the complement thereof; from SEQ ID NOS: 120, 125, or 130; or the complement thereof, from SEQ ID NOS: 140, 145, or 150, or the complement thereof; from SEQ ID NOS: 440 or 445, or the complement thereof; from SEQ ID NOS: 455 or 460; from SEQ ID NO: 465, or the complement thereof; from SEQ ID NOS: 470 or 475, or the complement thereof; from SEQ ID NOS: 480, 485, or 490, or the complement thereof.

In certain embodiments the invention provides the above siRNA polynucleotides that comprise at least one synthetic nucleotide analogue of a naturally occurring nucleotide. In certain other embodiments, the siRNA polynucleotide is linked to a detectable label, wherein the detectable label is a reporter molecule. In particular embodiments, the reporter molecule is a dye, a radionuclide, a luminescent group, a fluorescent group, or biotin. In other particular embodiments, the fluorescent group is fluorescein isothiocyanate and in other particular embodiments, the detectable label is a magnetic particle.

The invention also provides a pharmaceutical composition comprising an siRNA polynucleotide selectted from the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, and a physiologically acceptable carrier. In particular embodiments, the the carrier comprises a liposome.

The invention also provides a recombinant nucleic acid construct comprising a polynucleotide that is capable of directing transcription of a small interfering RNA (siRNA), the polynucleotide comprising: (i) a first promoter; (ii) a second promoter; and (iii) at least one DNA polynucleotide segment comprising at least one nucleotide sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, or a complement thereto, wherein each DNA polynucleotide segment and its complement are operably linked to at least one of the first and second promoters, and wherein the promoters are oriented to direct transcription of the DNA polynucleotide segment and its reverse complement. In certain embodiments, the recombinant nucleic acid construct comprises at least one enhancer that is selected from a first enhancer operably linked to the first promoter and a second enhancer operably linked to the second promoter. In certain other embodiments, the recombinant nucleic acid construct comprises at least one transcriptional terminator that is selected from (i) a first transcriptional terminator that is positioned in the construct to terminate transcription directed by the first promoter and (ii) a second transcriptional terminator that is positioned in the construct to terminate transcription directed by the second promoter. The invention also provides that the siRNA transcribed from the recombinant nucleic acid construct is capable of interfering with expression of a polypeptide, wherein the polypeptide comprises an amino acid sequence as set forth in a sequence selected from SEQ ID NO: 779, SEQ ID NO 789, SEQ ID NO 791, SEQ ID NO 797, SEQ ID NO 799, SEQ ID NO 801, SEQ ID NO 803, SEQ ID NO 805, SEQ ID NO 807, SEQ ID NO 809, SEQ ID NO 811, or SEQ ID NO 813.

The present invention also provides a recombinant nucleic acid construct comprising a polynucleotide that is capable of directing transcription of a small interfering RNA (siRNA), the polynucleotide comprising at least one promoter and a DNA polynucleotide segment, wherein the DNA polynucleotide segment is operably linked to the promoter, and wherein the DNA polynucleotide segment comprises (i) at least one DNA polynucleotide that comprises at least one nucleotide sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, or a complement thereto; (ii) a spacer sequence comprising at least 4 nucleotides operably linked to the DNA polynucleotide of (i); and (iii) the reverse complement of the DNA polynucleotide of (i) operably linked to the spacer sequence. In certain embodiments, the siRNA polynucleotide transcribed from the recombinant nucleic acid construct comprises an overhang of at least one and no more than four nucleotides, the overhang being located immediately 3' to (iii). In certain particular embodiments, the spacer sequence comprises at least 9 nucleotides. In certain other specific embodiments the spacer sequence comprises two uridine nucleotides that are contiguous with (iii). In one embodiment, the recombinant nucleic acid construct comprises at least one transcriptional terminator that is operably linked to the DNA polynucleotide segment. The invention also provides a host cell that is transformed or transfected with such a recombinant nucleic acid construct as disclosed herein.

In one embodiment, the invention provides a pharmaceutical composition comprising an siRNA polynucleotide and a physiologically acceptable carrier, wherein the siRNA polynucleotide is selected from (i) an RNA polynucleotide that comprises at least one nucleotide sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493; (ii) an RNA polynucleotide that comprises at least one nucleotide sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, and the complementary polynucleotide thereto; (iii) an RNA polynucleotide according to (i) or (ii) wherein the nucleotide sequence of the siRNA polynucleotide differs by one, two or three nucleotides at any of positions 1-19 of a sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, or (iv) an RNA polynucleotide according to (i) or (ii) wherein the nucleotide sequence of the siRNA polynucleotide differs by two, three or four nucleotides at any of positions 1-19 of a sequence selected from the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493. In certain particular embodiments, the physiologically acceptable carrier comprises a liposome.

The present invention also provides a method for interfering with expression of a polypeptide, or variant thereof, comprising contacting a subject that comprises at least one cell which is capable of expressing the polypeptide with a siRNA polynucleotide for a time and under conditions sufficient to interfere with expression of the polypeptide, wherein: (a) the polypeptide comprises an amino acid sequence as set forth in a sequence selected from SEQ ID NO: 779, SEQ ID NO 789, SEQ ID NO 791, SEQ ID NO 797, SEQ ID NO 799, SEQ ID NO 801, SEQ ID NO 803, SEQ ID NO 805, SEQ ID NO 807, SEQ ID NO 809, SEQ ID NO 811, or SEQ ID NO 813, (b) the siRNA polynucleotide is selected from (i) an RNA polynucleotide which comprises at least one nucleotide sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, (ii) an RNA polynucleotide that comprises at least one nucleotide sequence selected from the group consisting of SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, and the complementary polynucleotide thereto, (iii) an RNA polynucleotide according to (i) or (ii) wherein the nucleotide sequence of the siRNA polynucleotide differs by one, two or three nucleotides at any of positions 1-19 of a sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, or (iv) an RNA polynucleotide according to (i) or (ii) wherein the nucleotide sequence of the siRNA polynucleotide differs by two, three or four nucleotides at any of positions 1-19 of a sequence selected from the group consisting of the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493.

In another embodiment, the invention provides a method for interfering with expression of a polypeptide that comprises an amino acid sequence as set forth in a sequence selected from SEQ ID NO: 779, SEQ ID NO 789, SEQ ID NO 791, SEQ ID NO 797, SEQ ID NO 799, SEQ ID NO 801, SEQ ID NO 803, SEQ ID NO 805, SEQ ID NO 807, SEQ ID NO 809, SEQ ID NO 811, or SEQ ID NO 813, or a variant of said polypeptide, said method comprising contacting, under conditions and for a time sufficient to interfere with expression of the polypeptide, (i) a subject that comprises at least one cell that is capable of expressing the polypeptide, and (ii) a recombinant nucleic acid construct according to the present invention as described herein.

In another embodiment, the invention provides a method for identifying a component of a signal transduction pathway comprising: (A) contacting a siRNA polynucleotide and a first biological sample comprising at least one cell that is capable of expressing a target polypeptide, or a variant of said polypeptide, under conditions and for a time sufficient for target polypeptide expression when the siRNA polynucleotide is not present, wherein (i) the target polypeptide comprises an amino acid sequence as set forth in a sequence selected from SEQ ID NO: 779, SEQ ID NO 789, SEQ ID NO 791, SEQ ID NO 797, SEQ ID NO 799, SEQ ID NO 801, SEQ ID NO 803, SEQ ID NO 805, SEQ ID NO 807, SEQ ID NO 809, SEQ ID NO 811, SEQ ID NO 813, SEQ ID NO 823, SEQ ID NO 825, or SEQ ID NO:827; (2) the siRNA polynucleotide is selected from (i) an RNA polynucleotide which comprises at least one nucleotide sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, (ii) an RNA polynucleotide that comprises at least one nucleotide sequence selected from SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, and the complementary polynucleotide thereto; (iii) an RNA polynucleotide according to (i) or (ii) wherein the nucleotide sequence of the siRNA polynucleotide differs by one, two or three nucleotides at any of positions 1-19 of a sequence selected from the group consisting of the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493, (iv) an RNA polynucleotide according to (i) or (ii) wherein the nucleotide sequence of the siRNA polynucleotide differs by two, three or four nucleotides at any of positions 1-19 of a sequence selected from the group consisting of the sequences set forth in SEQ ID NOS: 4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493; and (B) comparing a level of phosphorylation of at least one protein that is capable of being phosphorylated in the cell with a level of phosphorylation of the protein in a control sample that has not been contacted with the siRNA polynucleotide, wherein an altered level of phosphorylation of the protein in the presence of the siRNA polynucleotide relative to the level of phosphorylation of the protein in an absence of the siRNA polynucleotide indicates that the protein is a component of a signal transduction pathway. The invention also provides a small interfering RNA (siRNA) polynucleotide, comprising an RNA polynucleotide which comprises at least one nucleotide sequence selected from SEQ ID NOS:4-7, 100-103, 105-108, 120-123, 125-128, 130-133, 140-143, 145-148, 150-153, 440-443, 445-448, 455-458, 460-463, 465-468, 470-473, 475-478, 480-483, 485-488, or 490-493. Certain further embodiments relate to isolated siRNA polynucleotides that comprise nucleotide sequences having the above recited SEQ ID NOS, including compositions and methods for producing and therapeutically using such siRNA.

These and other embodiments of the present invention will become apparent upon reference to the following detailed description and attached drawings. All references disclosed herein are hereby incorporated by reference in their entireties as if each was incorporated individually. Also incorporated by reference are co-pending application Ser. No. 10/444,925 and Ser. No. 10/444,926, which have been filed concurrently.

BRIEF DESCRIPTION OF THE DRAWINGS

FIG. 12 presents an extended consensus cDNA sequence encoding prototypical DSP-18 (DSP-18pr) (FIG. 12A) (SEQ ID NO: 782) and the deduced DSP-18pr amino acid sequence (FIG. 12B) (SEQ ID NO: 783). In FIG. 12A, initiating methionine (ATG) and stop (TGA) codons and intron/exon splice junctions are depicted in bold type with the splice donor sequences in bold without underscore, and the splice acceptor sequences in bold with underscore. In FIG. 12B, initiating methionine and the phosphatase active site are depicted in bold type.

FIG. 13 presents nucleotide and amino acid sequences for a DSP-18 isoform, DSP-18a. FIG. 13A presents a cDNA sequence for DSP-18a (SEQ ID NO: 830), with the start (ATG) and stop (TGA) codons and intron/exon splice junctions indicated in bold; intron/exon splice junctions are depicted in bold type with the splice donor sequences in bold without underscore and the splice acceptor sequences in bold with underscore. FIG. 13B presents the amino acid sequence of the DSP-18a polypeptide (SEQ ID NO: 831) encoded by (SEQ ID NO: 830), with the phosphatase active site depicted in bold type.

FIG. 14 presents nucleotide and amino acid sequences for a DSP-18 isoform, DSP-18b. FIG. 14A presents a cDNA sequence for DSP-18b (SEQ ID NO: 832), with the start (ATG) and stop (TGA) codons and intron/exon splice junctions indicated in bold; intron/exon splice junctions are depicted in bold type with the splice donor sequences in bold without underscore and the splice acceptor sequences in bold with underscore. FIG. 14B presents the amino acid sequence of the DSP-18b polypeptide (SEQ ID NO: 833) encoded by (SEQ ID NO: 832), with the phosphatase active site depicted in bold type.

FIG. 15 presents nucleotide sequences for DSP-18 isoforms, DSP-18c and DSP-18d. FIG. 15A presents a cDNA sequence for DSP-18c (SEQ ID NO: 834) with the start (ATG) and stop (TGA) codons and intron/exon splice junctions indicated in bold. FIG. 15B presents a cDNA sequence for DSP-18d (SEQ ID NO: 836), with the start (ATG) and stop (TGA) codons and intron/exon splice junctions indicated in bold. DSP-18c (835) encoded by (SEQ ID NO: 834), and DSP-18d (SEQ ID NO: 837) encoded by (SEQ ID NO: 836), both share the 181 amino acid sequence encoded by the open reading frame of DSP-18a (see FIG. 15).

FIG. 16 presents nucleotide and amino acid sequences for DSP-18 isoforms, DSP-18e and DSP-18f. FIG. 16A presents a cDNA sequence for DSP-18e (SEQ ID NO: 838), with the start (ATG) and stop (TGA) codons and intron/exon splice junctions indicated in bold. FIG. 16B presents the amino acid sequence of DSP-18e polypeptide (SEQ ID NO: 839) encoded by (SEQ ID NO: 838), with the phosphatase active site sequence in boldface type.

FIG. 17A presents nucleotide and amino acid sequences for DSP-18f. FIG. 17A presents a cDNA sequence for DSP-18f (SEQ ID NO: 840), with the start (ATG) and stop (TGA) codons and intron/exon splice junctions indicated in bold. FIG. 17B presents the amino acid sequence of DSP-18f polypeptide (SEQ ID NO: 841) encoded by (SEQ ID NO: 840), with the phosphatase active site sequence in boldface type.

FIG. 20 illustrates insulin-induced activation of PKB/Akt in HepG2 cells following ablation of TC45 by RNA interference.

FIG. 29 presents nucleotide and amino acid sequences for DSP-13. FIG. 29A presents a cDNA sequence for DSP-13 (SEQ ID NO: 784), with the start (ATG) and stop (TGA) codons indicated in bold and underlined. FIG. 29B presents the amino acid sequence of the DSP-13 polypeptide (SEQ ID NO: 785) encoded by (SEQ ID NO: 784).

FIG. 30 presents nucleotide and amino acid sequences for DSP-14. FIG. 30A presents a cDNA sequence for DSP-14 (SEQ ID NO: 786), with the start (ATG) and stop (TGA) codons indicated in bold and underlined. FIG. 30B presents the amino acid sequence of the DSP-14 polypeptide (SEQ ID NO: 787) encoded by (SEQ ID NO: 786).

DETAILED DESCRIPTION OF THE INVENTION

Figure 1:
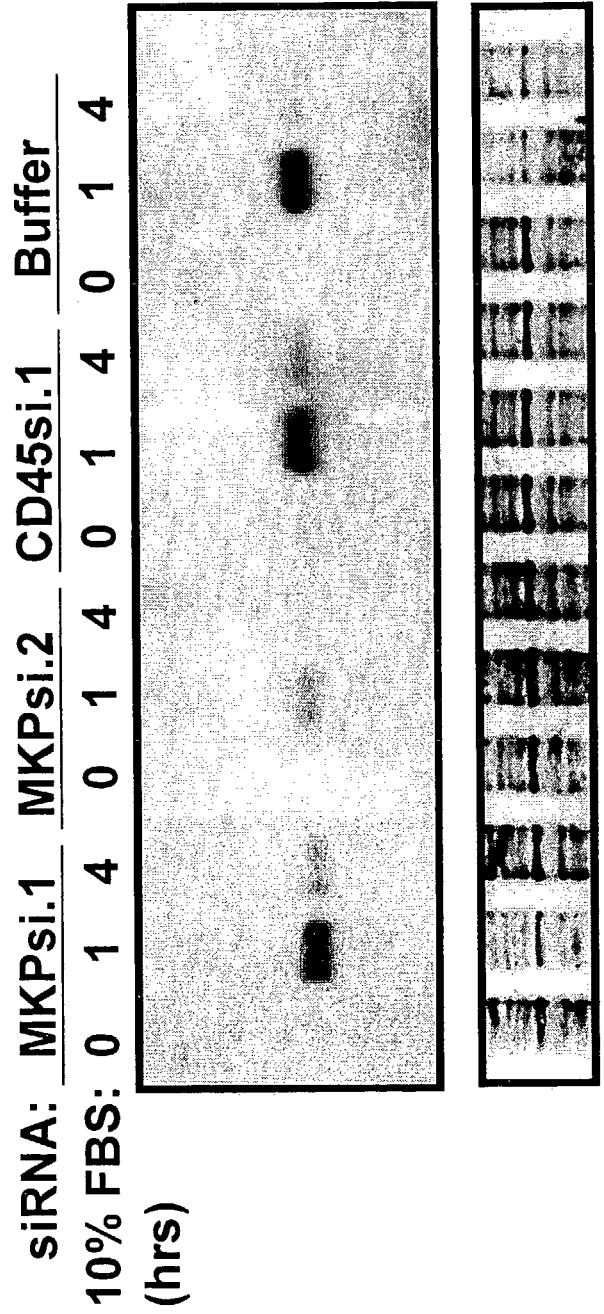
FIG. 1 presents an immunoblot analysis of the expression of MKP-1 polypeptide in HeLa cells co-transfected with sequence-specific siRNA polynucleotides (MKPsi.1 (MKP.1, SEQ ID NO: 18), lanes 1-3; MKPsi.2 (MKP.2, SEQ ID NO: 23), lanes 4-6) and a non-specific sequence siRNA (CD45si.1, lanes 7-9). The immunoblot of HeLa cell extracts was probed with an anti-MKP-1 antibody (upper). A second SDS-PAGE gel in which the HeLa cell extracts were separated was stained with Coomassie Blue (lower).

The present invention is directed in part to the unexpected discovery of short RNA polynucleotide sequences that are capable of specifically modulating expression of a desired polypeptide, such as a DSP-3, SHP-2, KAP, PRL-3, cdc14 or cdc25 polypeptide, or a variant of any such polypeptide. Without wishing to be bound by theory, the RNA polynucleotides of the present invention specifically reduce expression of a desired target polypeptide through recruitment of small interfering RNA (siRNA) mechanisms. In particular, and as described in greater detail herein, according to the present invention there are provided compositions and methods that relate to the surprising identification of certain specific RNAi oligonucleotide sequences of 19, 20, 21, 22, 23, 24, 25, 26 or 27 nucleotides that can be derived from corresponding polynucleotide sequences encoding the desired DSP-3, SHP-2, KAP, PRL-3, cdc14, cdc25, or other specified target polypeptide. These sequences cannot be predicted through any algorithm, sequence alignment routine, or other systematic paradigm, but must instead be obtained through generation and functional testing for RNAi activity of actual candidate oligonucleotides, such as those disclosed for the first time herein.

In preferred embodiments of the invention, the siRNA polynucleotide interferes with expression of a DSP-3, SHP-2, KAP, PRL-3, cdc14, cdc25, or other herein specified target polypeptide or a variant thereof, and comprises a RNA oligonucleotide or RNA polynucleotide uniquely corresponding in its nucleotide base sequence to the sequence of a portion of a target polynucleotide encoding the target polypeptide, for instance, a target mRNA sequence or an exonic sequence encoding such mRNA. Hence, according to non-limiting theory, the siRNA polynucleotides of the present invention direct sequence-specific degradation of mRNA encoding a desired DSP-3, SHP-2, KAP, PRL-3, cdc14 or cdc25 target polypeptide, the expression of which is consequently compromised. As also described herein, certain embodiments of the invention relate to siRNA polynucleotides that specifically interfere with expression of PTPs that are dual specificity phosphatases, including DSP-3, DSP-11, DSP-13, DSP-14, and DSP-18; certain other embodiments relate to RNAi interference with expression of the MAP kinase kinase (MKK) target polypeptide MKK4; certain other embodiments relate to RNAi interference with expression of target polypeptides that interact with chemotherapeutic agents, for example, the target polypeptides dihydrofolate reductase (DHFR), thymidylate synthetase, and topoisomerase I. The invention relates in preferred embodiments to siRNA polynucleotides that interfere with expression of specific polypeptides in mammals, which in certain particularly preferred embodiments are humans and in certain other particularly preferred embodiments are non-human mammals.

Exemplary sequences for the target polypeptides described herein include, for instance, DSP-3 (WO 00/60092; (SEQ ID NO: 779) encoded by (SEQ ID NO: 778)); cdc14A (e.g., GenBank Accession Nos. AF122013, (SEQ ID NO: 803) encoded by (SEQ ID NO: 802), AF064102, AF064103; Li et al., 1997 *J. Biol. Chem.* 272:29403; U.S. Pat. No. 6,331,614; e.g., or cdc14B (e.g., GenBank Accession Nos. AF064104, AF064105, AF023158 (SEQ ID NO: 805) encoded by (SEQ ID NO: 804); Li et al., 1997 *J. Biol. Chem.* 272:29403; e.g.,); cdc25A ((e.g., GenBank Accession Nos. NM_001789, AF527417 (SEQ ID NO: 809) encoded by (SEQ ID NO: 808), NM_133571 (SEQ ID NO: 807) encoded by (SEQ ID NO: 806)); cdc25B (e.g., GenBank Accession Nos. NM_133572, NM_023117, NM_021872; NM_021872; M81934 (SEQ ID NO: 811) encoded by (SEQ ID NO: 810)); and cdc25C (e.g., GenBank Accession Nos. NM_001790 (SEQ ID NO: 813) encoded by (SEQ ID NO: 812), NM_022809); PTPε (e.g., Genbank Accession Nos. NM_006504 (SEQ ID NO: 793) encoded by (SEQ ID NO: 792) and NM_130435(SEQ ID NO: 795) encoded by (SEQ ID NO: 794)); KAP (e.g., Genbank Accession No. L27711 (SEQ ID NO: 797) encoded by (SEQ ID NO: 796); Hannon et al., *Proc. Natl. Acad. Sci. USA* 91:1731-35 (1994); Demetrick et al., *Cytogenet. Cell Genet.* 69:190-92 (1995)); PRL-3 (e.g., Zhao et al., *Genomics* 35:172-81 (1996); Genbank Accession Nos. (NM_003479, NM_080392 (SEQ ID NO:801) encoded by (SEQ ID NO: 800), NM_080391, NM_032611 (SEQ ID NO: 799) encoded by 9SEQ ID NO: 798), and NM_007079); SHP-2 (GenBank Accession Nos. D13540); L03535) (SEQ ID NO: 789) encoded by (SEQ ID NO: 788); L07527 (SEQ ID NO: 791) encoded by (SEQ ID NO: 790); X70766); S78088; S39383); D84372); U09307); CD45 (e.g., (Charbonneau et al., *Proc. Natl. Acad. Sci. USA* 85:7182-86 91988); Genbank Accession Nos. NM_080922), NM_080921), NM_002838), and NM_080923); DSP-11 (WO 01/05983, (SEQ ID NO: 781) encoded by (SEQ ID NO: 780)); DSP-18pr (U.S. application Ser. No. 10/151,320, (SEQ ID NO: 783) encoded by (SEQ ID NO: 782)); DSP-13 (U.S. application Ser. No. 09/775,925; SEQ ID NO: 785 encoded by SEQ ID NO: 784); DSP-14 (U.S. application Ser. No. 09/847,519; SEQ ID NO: 787 encoded by SEQ ID NO: 786); WO 01/46394); MKP-1 (WO 97/00315; Keyse et al., 1992 *Nature* 59:644. According to the contemplated invention, the siRNA polynucleotide expressly does not consist of a CDC14a.5 polynucleotide having a sequence set forth in SEQ ID NO:10 (Mailand et al., 2002 *Nature Cell Biol.* 4:317).

In certain embodiments of the invention, an siRNA polynucleotide interferes with expression of a component of a signaling transduction pathway, for example, components of the JNK signaling transduction pathway such as MKK4 (e.g., GenBank Accession Nos. L36870), NM_009157, and NM_009157;) and MKK7 (e.g., GenBank Accession Nos. AF013588) and AF026216, and to related compositions and methods. (See also Shen et al., *Proc. Natl. Acad. Sci. USA* 98:13613-18 (2001)). In certain other embodiments of the invention, the siRNA polynucleotide interferes with expression of a cellular polypeptide or enzyme that is associated with a cellular malfunction or defect (e.g., in a cancer or malignancy, an enzyme that is overexpressed or constitutively expressed and is associated with cell survival, proliferation, apoptosis, cell division, and differentiation). For example, the siRNA polynucleotide may comprise a sequence specific for dihydrofolate reductase (DHFR) (e.g., GenBank Accession No: NM_000791;); thymidylate synthetase e.g., GenBank Accession No: NM_001071); topoisomerase I (e.g., GenBank Accession No: J03250;); IkappaB kinase (IKK) alpha (e.g., GenBank Accession No. AF080157;); GenBank Accession No. AF009225; GenBank Accession No. AF012890); IKKbeta e.g., GenBank Accession No. AF080158;); GenBank Accession No. AF031416; GenBank Accession No. AF029684); or IKKgamma e.g., GenBank Accession No. AF074382;); GenBank Accession No. AF091453).

In another preferred embodiment, the siRNA polynucleotides provided interfere with expression of DSP-3, SHP-2, CD45, PTPε, KAP, cdc14a, cdc14b, cdc25A, cdc25B, cdc25C, and PRL-3. According to non-limiting theory, the siRNA polynucleotides of the present invention direct sequence-specific degradation of mRNA encoding a PTP such as SHP2, PTPε, or a dual specificity phosphatase (e.g., DSP-3, KAP, cdc14a, cdc14b, cdc25A, cdc25B, cdc25C, CD45, or PRL-3) by a mechanism known as RNA interference (RNAi). The invention is not intended, however, to be so limited, and certain embodiments relate to RNA interference of other PTPs and dual specificity phosphatases (e.g., DSP-11, DSP-13, DSP-14, and DSP-18), and to interference with expression of other polypeptides and components of signal transduction pathways including mitogen activated protein (MAP) kinases, which include a MAP kinase kinase (e.g., MAPKKK or MEKK) that activates a MAP/ERK kinase (e.g., MAPKK or MEK), which then stimulates a phosphorylation-dependent increase in the activity of the MAP kinase. Upon activation, a MAP kinase can phosphorylate a variety of intracellular targets including transcription factors, transcriptional adaptor proteins, membrane and cytoplasmic substrates, and other protein kinases. In certain preferred embodiments, a siRNA polynucleotide interferes with expression of a MAP kinase kinase that is a component of the JNK signal transduction pathway, for example, MKK4 or MKK7. In other preferred embodiments, a siRNA polynucleotide interferes with expression of a cellular polypeptide or enzyme that is associated with a cellular malfunction or defect in cancer or malignancy, and which may be overexpressed or constitutively expressed in the tumor cell.

In addition, other preferred polypeptides include polypeptides that are targets of chemotherapeutic agents or drugs. Examples of chemotherapeutic target polypeptides include enzymes in the folate metabolic pathway, for example, thymidylate synthetase, which is a target of fluoropyrmidines. Another enzyme in this pathway is dihydrofolate reductase (DHFR), which is targeted by antifolate agents, such as methotrexate. DNA processing enzymes, including topoisomerase I and topoisomerase II, are also targets of chemotherapeutic agents. Other examples of chemotherapeutic target polypeptides include microtubule polypeptides, which are chemotherapeutic targets of taxanes and vinca alkaloids. According to non-limiting theory, these chemotherapeutic target polypeptides may become resistant to a drug or agent, that is, resistance may be manifested by overexpression or constitutive expression of the chemotherapeutic target polypeptide in a target cell. The overexpression of such a target polypeptide may be reduced by introducing a specific siRNA polynucleotide into the cell. In certain embodiments of the invention, a siRNA polynucleotide interferes with expression of such chemotherapeutic target polypeptides. For example, siRNA polynucleotides of the present invention that interfere with expression of a chemotherapeutic target polypeptide comprise sequences specific for dihydrofolate reductase (DHFR), thymidylate synthetase, topoisomerase I, and IKKgamma.

SiRNA Polynucleotides

As used herein, the term "siRNA" means either: (i) a double stranded RNA oligonucleotide, or polynucleotide, that is 18 base pairs, 19 base pairs, 20 base pairs, 21 base pairs, 22 base pairs, 23 base pairs, 24 base pairs, 25 base pairs, 26 base pairs, 27 base pairs, 28 base pairs, 29 base pairs or 30 base pairs in length and that is capable of interfering with expression and activity of a PTP-1B polypeptide, or a variant of the PTP-1B polypeptide, wherein a single strand of the siRNA comprises a portion of a RNA polynucleotide sequence that encodes the PTP-1B polypeptide, its variant, or a complementary sequence thereto; (ii) a single stranded oligonucleotide, or polynucleotide of 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides or 30 nucleotides in length and that is either capable of interfering with expression and/or activity of a target polypeptide such as DSP-3, SHP-2, KAP, PRL-3, cdc14 or cdc25, or a variant of the target polypeptide, or that anneals to a complementary sequence to result in a dsRNA that is capable of interfering with target polypeptide expression, wherein such single stranded oligonucleotide comprises a portion of a RNA polynucleotide sequence that encodes the target polypeptide, its variant, or a complementary sequence thereto; or (iii) an oligonucleotide, or polynucleotide, of either (i) or (ii) above wherein such oligonucleotide, or polynucleotide, has one, two, three or four nucleic acid alterations or substitutions therein.

A siRNA polynucleotide is a RNA nucleic acid molecule that mediates the effect of RNA interference, a post-transcriptional gene silencing mechanism. A siRNA polynucleotide preferably comprises a double-stranded RNA (dsRNA) but is not intended to be so limited and may comprise a single-stranded RNA (see, e.g., Martinez et al. *Cell* 110:563-74 (2002)). A siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the subject invention siRNA polynucleotides are also intended to describe the corresponding RNA sequences and their complements, given the well established principles of complementary nucleotide base-pairing. A siRNA may be transcribed using as a template a DNA (genomic, cDNA, or synthetic) that contains a RNA polymerase promoter, for example, a U6 promoter or the H1 RNA polymerase III promoter, or the siRNA may be a synthetically derived RNA molecule. In certain embodiments the subject invention siRNA polynucleotide may have blunt ends, that is, each nucleotide in one strand of the duplex is perfectly complementary (e.g., by Watson-Crick base-pairing) with a nucleotide of the opposite strand. In certain other embodiments, at least one strand of the subject invention siRNA polynucleotide has at least one, and preferably two nucleotides that "overhang" (i.e., that do not base pair with a complementary base in the opposing strand) at the 3' end of either strand, or preferably both strands, of the siRNA polynucleotide. In a preferred embodiment of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

Preferred siRNA polynucleotides comprise double-stranded oligomeric nucleotides of about 18-30 nucleotide base pairs, preferably about 18, 19, 20, 21, 22, 23, 24, 25, 26, or 27 base pairs, and in other preferred embodiments about 19, 20, 21, 22 or 23 base pairs, or about 27 base pairs, whereby the use of "about" indicates, as described above, that in certain embodiments and under certain conditions the processive cleavage steps that may give rise to functional siRNA polynucleotides that are capable of interfering with expression of a selected polypeptide may not be absolutely efficient. Hence, siRNA polynucleotides, for instance, of "about" 18, 19, 20, 21, 22, 23, 24, or 25 base pairs may include one or more siRNA polynucleotide molecules that may differ (e.g., by nucleotide insertion or deletion) in length by one, two, three or four base pairs, by way of non-limiting theory as a consequence of variability in processing, in biosynthesis, or in artificial synthesis. The contemplated siRNA polynucleotides of the present invention may also comprise a polynucleotide sequence that exhibits variability by differing (e.g., by nucleotide substitution, including transition or transversion) at one, two, three or four nucleotides from a particular sequence, the differences occurring at any of positions 1, 2, 3, 4, 5, 6, 7, 8, 9, 10, 11, 12, 13, 14, 15, 16, 17, 18, or 19 of a particular siRNA polynucleotide sequence, or at positions 20, 21, 22, 23, 24, 25, 26, or 27 of siRNA polynucleotides depending on the length of the molecule, whether situated in a sense or in an antisense strand of the double-stranded polynucleotide. The nucleotide substitution may be found only in one strand, by way of example in the antisense strand, of a double-stranded polynucleotide, and the complementary nucleotide with which the substitute nucleotide would typically form hydrogen bond base pairing may not necessarily be correspondingly substituted in the sense strand. In preferred embodiments, the siRNA polynucleotides are homogeneous with respect to a specific nucleotide sequence. As described herein, preferred siRNA polynucleotides interfere with expression of a DSP-3, SHP-2, KAP, PRL-3, cdc14 or cdc25 polypeptide. These polynucleotides may also find uses as probes or primers.

Polynucleotides that are siRNA polynucleotides of the present invention may in certain embodiments be derived from a single-stranded polynucleotide that comprises a single-stranded oligonucleotide fragment (e.g., of about 18-30 nucleotides, which should be understood to include any whole integer of nucleotides including and between 18 and 30) and its reverse complement, typically separated by a spacer sequence. According to certain such embodiments, cleavage of the spacer provides the single-stranded oligonucleotide fragment and its reverse complement, such that they may anneal to form (optionally with additional processing steps that may result in addition or removal of one, two, three or more nucleotides from the 3' end and/or the 5' end of either or both strands) the double-stranded siRNA polynucleotide of the present invention. In certain embodiments the spacer is of a length that permits the fragment and its reverse complement to anneal and form a double-stranded structure (e.g., like a hairpin polynucleotide) prior to cleavage of the spacer (and, optionally, subsequent processing steps that may result in addition or removal of one, two, three, four, or more nucleotides from the 3' end and/or the 5' end of either or both strands). A spacer sequence may therefore be any polynucleotide sequence as provided herein that is situated between two complementary polynucleotide sequence regions which, when annealed into a double-stranded nucleic acid, comprise a siRNA polynucleotide. Preferably a spacer sequence comprises at least 4 nucleotides, although in certain embodiments the spacer may comprise 5, 6, 7, 8, 9, 10, 11, 12, 13, 14, 15, 16, 17, 18, 19, 20, 21-25, 26-30, 31-40, 41-50, 51-70, 71-90, 91-110, 111-150, 151-200 or more nucleotides. Examples of siRNA polynucleotides derived from a single nucleotide strand comprising two complementary nucleotide sequences separated by a spacer have been described (e.g., Brummelkamp et al., 2002 *Science* 296:550; Paddison et al., 2002 *Genes Develop.* 16:948; Paul et al. *Nat. Biotechnol.* 20:505-508 (2002); Grabarek et al., *BioTechniques* 34:734-44 (2003)).

Polynucleotide variants may contain one or more substitutions, additions, deletions, and/or insertions such that the activity of the siRNA polynucleotide is not substantially diminished, as described above. The effect on the activity of the siRNA polynucleotide may generally be assessed as described herein, or using conventional methods. Variants preferably exhibit at least about 75%, 78%, 80%, 85%, 87%, 88% or 89% identity and more preferably at least about 90%, 92%, 95%, 96%, or 97% identity to a portion of a polynucleotide sequence that encodes a native DSP-3, SHP-2, KAP, PRL-3, cdc14 or cdc25. The percent identity may be readily determined by comparing sequences of the polynucleotides to the corresponding portion of the target polynucleotide, using any method including using computer algorithms well known to those having ordinary skill in the art, such as Align or the BLAST algorithm (Altschul, *J. Mol. Biol.* 219:555-565, 1991; Henikoff and Henikoff, *Proc. Natl. Acad. Sci. USA* 89:10915-10919, 1992), which is available at the NCBI website (see [online] Internet:<URL:http://www/ncbi.nlm.nih.gov/cgi-bin/BLAST). Default parameters may be used.

Certain siRNA polynucleotide variants are substantially homologous to a portion of a native gene that encodes a desired target polypeptide. Single-stranded nucleic acids derived (e.g., by thermal denaturation) from such polynucleotide variants are capable of hybridizing under moderately stringent conditions to a naturally occurring DNA or RNA sequence encoding a native target polypeptide. In a preferred embodiment of the invention, a siRNA polynucleotide that detectably hybridizes under moderately stringent conditions to a target polypeptide-encoding polynucleotide comprises a nucleotide sequence other than SEQ ID NO:449, which is disclosed in Mailand et al. (2002 *Nature Cell Biol.* 4:317). A siRNA polynucleotide that detectably hybridizes under moderately stringent conditions may have a nucleotide sequence that includes at least 10 consecutive nucleotides, more preferably 11, 12, 13, 14, 15, 16, 17, 18, 19, 20, 21, 22, 23, 24, 25, 26, 27, 28, 29 or 30 consecutive nucleotides that are complementary to a particular target polynucleotide. In certain preferred embodiments such a siRNA sequence (or its complement) will be unique to a single particular target polypeptide for which interference with expression is desired, and in certain other embodiments the sequence (or its complement) may be shared by two or more related target polypeptides for which interference with polypeptide expression is desired.

Suitable moderately stringent conditions include, for example, pre-washing in a solution of 5×SSC, 0.5% SDS, 1.0 mM EDTA (pH 8.0); hybridizing at 50° C.-70° C., 5×SSC for 1-16 hours (e.g., overnight); followed by washing once or twice at 22-65° C. for 20-40 minutes with one or more each of 2×, 0.5× and 0.2×SSC containing 0.05-0.1% SDS. For additional stringency, conditions may include a wash in 0.1×SSC and 0.1% SDS at 50-60° C. for 15-40 minutes. As known to those having ordinary skill in the art, variations in stringency of hybridization conditions may be achieved by altering the time, temperature, and/or concentration of the solutions used for pre-hybridization, hybridization, and wash steps. Suitable conditions may also depend in part on the particular nucleotide sequences of the probe used, and of the blotted, proband nucleic acid sample. Accordingly, it will be appreciated that suitably stringent conditions can be readily selected without undue experimentation when a desired selectivity of the probe is identified, based on its ability to hybridize to one or more certain proband sequences while not hybridizing to certain other proband sequences.

Sequence specific siRNA polynucleotides of the present invention may be designed using one or more of several criteria. For example, to design a siRNA polynucleotide that has 19 consecutive nucleotides identical to a sequence encoding a polypeptide of interest (e.g., PTP1B and other polypeptides described herein), the open reading frame of the polynucleotide sequence may be scanned for 21-base sequences that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 16 consecutive nucleotides not identified as being present in any other known polynucleotide sequence (such an evaluation can be readily determined using computer programs available to a skilled artisan such as BLAST to search publicly available databases). Alternatively, a siRNA polynculeotide sequence may be designed and chosen using a computer software available commercially from various vendors (e.g., OligoEngine™ (Seattle, Wash.); Dharmacon, Inc. (Lafayette, Colo.); Ambion Inc. (Austin, Tex.); and QIAGEN, Inc. (Valencia, Calif.)). (See also Elbashir et al., *Genes & Development* 15:188-200 (2000); Elbashir et al., *Nature* 411:494-98 (2001); and [online] Internet:URL<http://www.mpibpc.gwdg.de/abteilungen/100/105/Tusch1_MIV2(3) 2002.pdf.) The siRNA polynucleotides may then be tested for their ability to interfere with the expression of the target polypeptide according to methods known in the art and described herein. The determination of the effectiveness of an siRNA polynucleotide includes not only consideration of its ability to interfere with polypeptide expression but also includes consideration of whether the siRNA polynucleotide manifests undesirably toxic effects, for example, apoptosis of a cell for which cell death is not a desired effect of RNA interference (e.g., interference of PTP1B expression in a cell).

It should be appreciated that not all siRNAs designed using the above methods will be effective at silencing or interfering with expression of a desired target polypeptide. And further, that the siRNAs will effect silencing to different degrees. Such siRNAs must be tested for their effectiveness, and selections made therefrom based on the ability of a given siRNA to interfere with or modulate (e.g., decrease in a statistically significant manner) the expression of the target. Accordingly, identification of specific siRNA polynucleotide sequences that are capable of interfering with expression of a desired target polypeptide requires production and testing of each siRNA, as demonstrated in greater detail below (see Examples).

Furthermore, not all siRNAs that interfere with protein expression will have a physiologically important effect. The inventors here have designed, and describe herein, physiologically relevant assays for measuring the influence of modulated target polypeptide expression, for instance, cellular proliferation, induction of apoptosis, and/or altered levels of protein tyrosine phosphorylation (e.g., insulin receptor phosphorylation), to determine if the levels of interference with target protein expression that were observed using the siRNAs of the invention have clinically relevant significance. Additionally, and according to non-limiting theory, the invention contemplates altered (e.g., decreased or increased in a statistically significant manner) expression levels of one or more polypeptides of interest, and/or altered (i.e., increased or decreased) phosphorylation levels of one or more phosphoproteins of interest, which altered levels may result from impairment of target protein expression and/or cellular compensatory mechanisms that are induced in response to RNAi-mediated inhibition of a specific target polypeptide expression.

Persons having ordinary skill in the art will also readily appreciate that as a result of the degeneracy of the genetic code, many nucleotide sequences may encode a polypeptide as described herein. That is, an amino acid may be encoded by one of several different codons and a person skilled in the art can readily determine that while one particular nucleotide sequence may differ from another (which may be determined by alignment methods disclosed herein and known in the art), the sequences may encode polypeptides with identical amino acid sequences. By way of example, the amino acid leucine in a polypeptide may be encoded by one of six different codons (TTA, TTG, CTT, CTC, CTA, and CTG) as can serine (TCT, TCC, TCA, TCG, AGT, and AGC). Other amino acids, such as proline, alanine, and valine, for example, may be encoded by any one of four different codons (CCT, CCC, CCA, CCG for proline; GCT, GCC, GCA, GCG for alanine; and GTT, GTC, GTA, GTG for valine). Some of these polynucleotides bear minimal homology to the nucleotide sequence of any native gene. Nonetheless, polynucleotides that vary due to differences in codon usage are specifically contemplated by the present invention.

Polynucleotides, including target polynucleotides, may be prepared using any of a variety of techniques, which will be useful for the preparation of specifically desired siRNA polynucleotides and for the identification and selection of desirable sequences to be used in siRNA polynucleotides. For example, a polynucleotide may be amplified from cDNA prepared from a suitable cell or tissue type. Such polynucleotides may be amplified via polymerase chain reaction (PCR). For this approach, sequence-specific primers may be designed based on the sequences provided herein and may be purchased or synthesized. An amplified portion may be used to isolate a full-length gene, or a desired portion thereof, from a suitable library (e.g., human skeletal muscle cDNA) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences. Suitable sequences for a siRNA polynucleotide contemplated by the present invention may also be selected from a library of siRNA polynucleotide sequences.

For hybridization techniques, a partial sequence may be labeled (e.g., by nick-translation or end-labeling with $^{32}P$) using well known techniques. A bacterial or bacteriophage library may then be screened by hybridizing filters containing denatured bacterial colonies (or lawns containing phage plaques) with the labeled probe (see, e.g., Sambrook et al., *Molecular Cloning: A Laboratory Manual*, Cold Spring Harbor Laboratories, Cold Spring Harbor, N.Y., 2001). Hybridizing colonies or plaques are selected and expanded, and the DNA is isolated for further analysis. Clones may be analyzed to determine the amount of additional sequence by, for example, PCR using a primer from the partial sequence and a primer from the vector. Restriction maps and partial sequences may be generated to identify one or more overlapping clones. A full-length cDNA molecule can be generated by ligating suitable fragments, using well known techniques.

Alternatively, numerous amplification techniques are known in the art for obtaining a full-length coding sequence from a partial cDNA sequence. Within such techniques, amplification is generally performed via PCR. One such technique is known as "rapid amplification of cDNA ends" or RACE. This technique involves the use of an internal primer and an external primer, which hybridizes to a polyA region or vector sequence, to identify sequences that are 5' and 3' of a known sequence. Any of a variety of commercially available kits may be used to perform the amplification step. Primers may be designed using, for example, software well known in the art. Primers (or oligonucleotides for other uses contemplated herein, including, for example, probes and antisense oligonucleotides) are preferably 15, 16, 17, 18, 19, 20, 21, 22, 23, 24, 25, 26, 27, 28, 29, 30, 31 or 32 nucleotides in length, have a GC content of at least 40% and anneal to the target sequence at temperatures of about 54° C. to 72° C. The amplified region may be sequenced as described above, and overlapping sequences assembled into a contiguous sequence. Certain oligonucleotides contemplated by the present invention may, for some preferred embodiments, have lengths of 18, 19, 20, 21, 22, 23, 24, 25, 26, 27, 28, 29, 30, 31, 32, 33-35, 35-40, 41-45, 46-50, 56-60, 61-70, 71-80, 81-90 or more nucleotides.

A number of specific siRNA polynucleotide sequences useful for interfering with target polypeptide expression, and are presented in the Examples, the Drawings, and the Sequence Listing. SiRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated to improve theur serum stability and/or delivery properties. Included as an aspect of the invention are the siRNAs described herein wherein the ribose has been removed therefrom. Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as T7, U6, H1, or SP6). In addition, a siRNA polynucleotide may be administered to a patient, as may be a DNA sequence (e.g., a recombinant nucleic acid construct as provided herein) that supports transcription (and optionally appropriate processing steps) such that a desired siRNA is generated in vivo.

Accordingly, a siRNA polynucleotide that is complementary to at least a portion of a target polypeptide-encoding sequence may be used to modulate gene expression, or as a probe or primer. Identification of siRNA polynucleotide sequences and DNA encoding genes for their targeted delivery involves techniques described herein. Identification of such siRNA polynucleotide sequences and DNA encoding genes for their targeted delivery involves techniques that are also described herein. As discussed above, siRNA polynucleotides exhibit desirable stability characteristics and may, but need not, be further designed to resist degradation by endogenous nucleolytic enzymes by using such linkages as phosphorothioate, methylphosphonate, sulfone, sulfate, ketyl, phosphorodithioate, phosphoramidate, phosphate esters, and other such linkages (see, e.g., Agrwal et al., *Tetrahedron Lett.* 28:3539-3542 (1987); Miller et al., *J. Am. Chem. Soc.* 93:6657-6665 (1971); Stec et al., *Tetrahedron Lett.* 26:2191-2194 (1985); Moody et al., *Nucleic Acids Res.* 12:4769-4782 (1989); Uznanski et al., *Nucleic Acids Res.* (1989); Letsinger et al., *Tetrahedron* 40:137-143 (1984); Eckstein, *Annu. Rev. Biochem.* 54:367402 (1985); Eckstein, *Trends Biol. Sci.* 14:97-100 (1989); Stein, In: *Oligodeoxynucleotides. Antisense Inhibitors of Gene Expression*, Cohen, ed., Macmillan Press, London, pp. 97-117 (1989); Jager et al., *Biochemistry* 27:7237-7246 (1988)).

Any polynucleotide of the invention may be further modified to increase stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives, and cosmids. Vectors of particular interest include expression vectors, replication vectors, probe generation vectors, and sequencing vectors. In general, a suitable vector contains an origin of replication functional in at least one organism, convenient restriction endonuclease sites, and one or more selectable markers. (See, e.g., WO 01/96584; WO 01/29058; U.S. Pat. No. 6,326,193; U.S. 2002/0007051). Other elements will depend upon the desired use, and will be apparent to those having ordinary skill in the art. For example, the invention contemplates the use of siRNA polynucleotide sequences in the preparation of recombinant nucleic acid constructs including vectors for interfering with the expression of a desired target polypeptide such as a PTP polypeptide, a MAP kinase kinase polypeptide, or a chemotherapeutic target polypeptide in vivo; the invention also contemplates the generation of siRNA transgenic or "knock-out" animals and cells (e.g., cells, cell clones, lines or lineages, or organisms in which expression of one or more desired polypeptides (e.g., a target polypeptide) is fully or partially compromised). An siRNA polynucleotide that is capable of interfering with expression of a desired polypeptide (e.g., a target polypeptide) as provided herein thus includes any siRNA polynucleotide that, when contacted with a subject or biological source as provided herein under conditions and for a time sufficient for target polypeptide expression to take place in the absence of the siRNA polynucleotide, results in a statistically significant decrease (alternatively referred to as "knockdown" of expression) in the level of target polypeptide expression that can be detected. Preferably the decrease is greater than 10%, more preferably greater than 20%, more preferably greater than 30%, more preferably greater than 40%, 50%, 60%, 70%, 75%, 80%, 85%, 90%, 95% or 98% relative to the expression level of the polypeptide detected in the absence of the siRNA, using conventional methods for determining polypeptide expression as known to the art and provided herein. Preferably, the presence of the siRNA polynucleotide in a cell does not result in or cause any undesired toxic effects, for example, apoptosis or death of a cell in which apoptosis is not a desired effect of RNA interference.

Within certain embodiments, siRNA polynucleotides may be formulated so as to permit entry into a cell of a mammal, and expression therein. Such formulations are particularly useful for therapeutic purposes, as described below. Those having ordinary skill in the art will appreciate that there are many ways to achieve expression of a polynucleotide in a target cell, and any suitable method may be employed. For example, a polynucleotide may be incorporated into a viral vector using well known techniques (see also, e.g., U.S. 2003/ 0068821). A viral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those having ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Within other embodiments, one or more promoters may be identified, isolated and/or incorporated into recombinant nucleic acid constructs of the present invention, using standard techniques. The present invention provides nucleic acid molecules comprising such a promoter sequence or one or more cis- or trans-acting regulatory elements thereof. Such regulatory elements may enhance or suppress expression of a siRNA. A 5' flanking region may be generated using standard techniques, based on the genomic sequence provided herein. If necessary, additional 5' sequences may be generated using PCR-based or other standard methods. The 5' region may be subcloned and sequenced using standard methods. Primer extension and/or RNase protection analyses may be used to verify the transcriptional start site deduced from the cDNA.

To define the boundary of the promoter region, putative promoter inserts of varying sizes may be subcloned into a heterologous expression system containing a suitable reporter gene without a promoter or enhancer. Suitable reporter genes may include genes encoding luciferase, beta-galactosidase, chloramphenicol acetyl transferase, secreted alkaline phosphatase, or the Green Fluorescent Protein gene (see, e.g., Ui-Tei et al., *FEBS Lett.* 479:79-82 (2000). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Once a functional promoter is identified, cis- and trans-acting elements may be located. Cis-acting sequences may generally be identified based on homology to previously characterized transcriptional motifs. Point mutations may then be generated within the identified sequences to evaluate the regulatory role of such sequences. Such mutations may be generated using site-specific mutagenesis techniques or a PCR-based strategy. The altered promoter is then cloned into a reporter gene expression vector, as described above, and the effect of the mutation on reporter gene expression is evaluated.

In general, polypeptides and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment. A "gene" includes the segment of DNA involved in producing a polypeptide chain; it further includes regions preceding and following the coding region "leader and trailer," for example promoter and/or enhancer and/or other regulatory sequences and the like, as well as intervening sequences (introns) between individual coding segments (exons).

As noted above, according to certain embodiments of the invention compositions and methods are provided that relate to altering or altered expression of a PTP as described herein (including DSPs) or of other target polypeptides as disclosed herein, and/or to a PTP associated disorder. A PTP associated disorder includes any disease, disorder, condition, syndrome, pathologic or physiologic state, or the like, wherein at least one undesirable deviation or departure from a physiological norm causes, correlates with, is accompanied by or results from an inappropriate alteration (i.e., a statistically significant change) to the structure, activity, function, expression level, physicochemical or hydrodynamic property, or stability of a PTP or of a molecular component of a biological signal transduction pathway that comprises a PTP, for instance, a MAP kinase such as JNK (e.g., Shen et al., 2001 *Proc. Nat. Acad. Sci. USA* 98:13613; see also U.S. Pat. No. 6,342,595), TYK2 or Jak2 (e.g., Myers et al., 2001.*J. Biol. Chem.* 276: 47771), or a MAP kinase kinase MKK4 or MKK7 (e.g., Shen et al., *Proc. Natl. Acad. Sci. USA* 98:13613-18 (2001) and references cited therein), a receptor such as IR (Salmeen et al., 2000), or leptin receptor (e.g., Kalman et al. 2000 and references cited therein) or other such pathways comprising PTPs as known to the art. In preferred embodiments the molecular component may be a protein, peptide or polypeptide, and in certain other preferred embodiments the alteration may be an altered level of PTP expression. In certain other preferred embodiments the alteration may be manifest as an a typical or unusual phosphorylation state of a protein under particular conditions, for example, hypophosphorylation or hyperphosphorylation of a phosphoprotein, wherein those familiar with the art will appreciate that phosphorylated proteins typically comprise one or more phosphotyrosine, phosphoserine, or phosphothreonine residues.

PTP associated disorders therefore include, for example, diabetes mellitus, obesity, impaired glucose tolerance and other metabolic disorders wherein alteration of a biological signaling pathway component is associated with the disorder The effect of siRNA interference with expression of a component in the signal transduction pathway induced by insulin, for example, may be evaluated by determining the level of tyrosine phosphorylation of insulin receptor beta (IR-β) and/or of the downstream signaling molecule PKB/Akt and/or of any other downstream polypeptide that may be a component of a particular signal transduction pathway as provided herein. The invention is not intended, however, to be so limited and contemplates other disorders, such as JNK-associated disorders (e.g., cancer, cardiac hypertrophy, ischemia, diabetes, hyperglycemia-induced apoptosis, inflammation, neurodegenerative disorders), and other disorders associated with different signal transduction pathways, for instance, cancer, autoimmunity, cellular proliferative disorders, neurodegenerative disorders, and infectious diseases (see, e.g., Fukada et al., 2001 *J. Biol. Chem.* 276:25512; Tonks et al., 2001 *Curr. Opin. Cell Biol.* 13:182; Salmeen et al., 2000 *Mol. Cell* 6:1401; Hu et al., *J. Neurochem.* 85:432-42 (2003); and references cited therein).

Cancer is also associated with other dual specificity phosphatases, such as DSP-3, PRL-3 (see, e.g., Saha et al., *Science* 294:1343-46 (2001), PTPε (Elson, *Oncogene* 18:7535-42 (1999)), and the cell cycle dual specificity phosphatases cdc25 (see, e.g., Donzelli et al., *EMBO* 21:4875-84 (2002), cdc14 (Wong et al., *Genomics* 59:248-51 (1999)), and KAP (see, e.g., Lee et al., *Mol. Cell Biol.* 20:1723-32 (2000); Yeh et al., *Cancer Res.* 60:4697-700 (2000); see also, e.g., Donato et al., *J. Clin. Invest.* 109:51-58 (2002)). Another dual specificity phosphatase believed to be involved in the cell cycle, cdc14, is reported to interact with the tumor suppressor protein p53 (Li et al., *J. Biol. Chem.* 275:2410014 (2000); see also Agami et al., *Cell* 102:55-66 (2000)). In normal cells, cdc14 is reported to be a part of the mitotic exit network, which involves intricate regulatory pathways that coordinate chromosome segregation and mitotic exit with physical separation of two nascent cells, and in cytokineses (see, e.g., Gruneberg et al., *J. Cell Biol.* 158:901-14 (2002); Trautman et al., *Curr. Biol.* 12:R733-R735 (2002); Visintin et al., *Mol. Cell* 2:709-18 (1998); see also Mailand et al., supra). Persons skilled in the art will be familiar with an array of criteria according to which it may be recognized what are, for instance, biological, physiological, pathological and/or clinical signs and/or symptoms of PTP associated and other disorders as provided herein (see, e.g., Irie-Sasaki et al., *Curr. Top. Med. Chem.* 3:783-96 (2003) (discussing role of CD45 in signal transduction pathways); Oh et al., *Mol. Cell Biol.* 19:3205-15 (1999) (describing regulation of early events in integrin signaling by SHP-2); Musante et al., *Eur. J. Hum. Genet.* 11:201-206 (2003), Tartaglia et al., *Nat. Genet.* 29:465-68 (2001), and Ion et al., *Hum. Genet.* 111:421-27 (2002) (discussing correlation between mutations in the PTPN11 gene that encodes SHP-2 and Noonan Syndrome)); Tanuma et al., *Blood* 98:3030-34 (2001) (reporting that PTPε inhibits IL-6 and IL-10 induced JAK-STAT signaling)).

Also contemplated by the invention are disorders associated with the NF-kappaB signaling pathway, for example, in cancer cells in which NF-kappaB is overexpressed or constitutively activated (see, e.g., Bayon et al., *Mol. Cell Biol.* 23:1061-74 (2003); Arsura et al., *Oncogene* 22:412-25 (2003)). Other disorders associated with the NF-kappaB signaling pathway include those associated with other components of the pathway, for example, inflammation associated with IkappaB kinase gamma (IKKgamma), which is an upstream regulator of NF-kappaB that is required for NF-kappaB activation by various stimuli (see, e.g., Makris et al., *Mol. Cell Biol.* 22:6573-81 (2002); Li et al., *J. Biol. Chem.* 277:45129-40 (2002); Sadikot et al., *J. Immunol.* 170:1091-98 (2003)).

As noted above, regulated tyrosine phosphorylation contributes to specific pathways for biological signal transduction, including those associated with cell division, cell survival, apoptosis, proliferation and differentiation, and "biological signal transduction pathways," or "inducible signaling pathways" in the context of the present invention include transient or stable associations or interactions among molecular components involved in the control of these and similar processes in cells. Depending on the particular pathway of interest, an appropriate parameter for determining induction of such pathway may be selected. For example, for signaling pathways associated with cell proliferation, a variety of well known methodologies are available for quantifying proliferation, including, for example, incorporation of tritiated thymidine into cellular DNA, monitoring of detectable (e.g., fluorimetric or calorimetric) indicators of cellular respiratory activity (for example, conversion of the tetrazolium salts (yellow) 3-(4,5-dimethylthiazol-2-yl)-2,5-diphenyltetrazolium bromide (MTT) or 3-(4,5-dimethylthiazol-2-yl)-5-(3-carboxymethoxyphenyl)-2-(4-sulphophenyl)-2H-tetrazolium (MTS) to formazan dyes (purple) in metabolically active cells), or cell counting, or the like. Similarly, in the cell biology arts, multiple techniques are known for assessing cell survival (e.g., vital dyes, metabolic indicators, etc.) and for determining apoptosis (for example, annexin V binding, DNA fragmentation assays, caspase activation, marker analysis, e.g., poly(ADP-ribose) polymerase (PARP), etc.). Other signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, etc.), altered cell cycle profiles, or altered cellular morphology, and the like, such that cellular responsiveness to a particular stimulus as provided herein can be readily identified to determine whether a particular cell comprises an inducible signaling pathway.

In addition, according to certain embodiments of the invention compositions and methods are provided that relate to altering or altered expression of chemotherapeutic target polypeptides. Sequence specific siRNA polynucleotides may be used as a conjunctive therapy with chemotherapeutic drugs or may provide an alternative therapy in circumstances when a cancer becomes refractory to chemotherapeutic treatment regimens. Resistance to chemotherapeutic drugs may develop when a chemotherapeutic target polypeptide is overexpressed or when its expression becomes constitutive. Overexpression or amplified expression of such a target polypeptide could be reduced by introducing a specific siRNA polynucleotide into the cell. In particular, chemotherapeutic target polypeptides that may become resistant to drug therapies include, for example, components of the thymidylate biosynthesis pathway, thymidylate synthetase and DHFR, which become refractory to anti-neoplastic drugs such as 5-FU and methotrexate, respectively, and contribute to a drug resistance phenotype. Also contemplated by the invention are sequence specific siRNA polynucleotides that interfere with expression of DNA-processing enzymes such as topoisomerase I and that would have anti-cancer or anti-bacterial effects. The effect of siRNA interference on expression of such chemotherapeutic target polypeptides may alter cell division, cell survival, apoptosis, proliferation, and differentiation, which may be assessed by any of the techniques and methods described herein.

PTPs

As used herein, a phosphatase is a member of the PTP family if it contains the signature motif $CX_5R$ (SEQ ID NO: 1). Dual specificity PTPs, i.e., PTPs that dephosphorylate both phosphorylated tyrosine and phosphorylated serine or threonine, are also suitable for use in the invention. PTPs for use in the present invention include PTP1B (e.g., GenBank Accession Nos. M31724); NM_002827 (SEQ ID NOS:816-817); NM_011201 (SEQ ID NOS: 818-819); M31724); M33689); M33962). In certain preferred embodiments, TC-PTP (e.g., GenBank Accession Nos. M25393); M81478 (SEQ ID NOS: 828-829); M80737; M81477); X58828); NM_002828) and TC45 (e.g., NM_080422 (SEQ ID NOS: 826 and 827)) may be used. In certain other embodiments PTPs and DSPs for use in the present invention include DSP-3 (WO00/60092); SHP2, (e.g., GenBank Accession Nos. D13540); L03535 (SEQ ID NOS: 788-789); L07527 (SEQ ID NOS: 790-791); X70766); L08807); S78088); S39383); D84372); U09307); cdc14 (which includes cdc14a (e.g., GenBank Accession Nos. AF122013 (SEQ ID NOS: 802-803); AF064102); AF064103); Li et al., 1997 *J. Biol. Chem.* 272:29403; U.S. Pat. No. 6,331,614) and cdc14b (e.g., Gen-Bank Accession Nos. AF064104); AF064105); CDC25A ((e.g., GenBank Accession Nos. NM_001789), AF527417), (SEQ ID NO: 808-809), NM_133571); CDC25B (e.g., Gen-Bank Accession Nos. NM_133572), NM_023117), NM_021872); M81934) (SEQ ID NOS: 810-811); and CDC25C (e.g., GenBank Accession Nos. NM_001790) (seq id nos: 812-813), NM_022809); CD45 (Charbonneau et al., *Proc. Natl. Acad. Sci. USA* 85:7182-86 (1988); Genbank Accession Nos. NM_080922), NM_080921), NM_002838), and NM_080923); GenBank Acc. No. XM_16748; KAP (Genbank Accession No. L27711); Hannon et al., *Proc. Natl. Acad. Sci. USA* 91:1731-35 (1994)); PTPϵ (e.g., Genbank Accession Nos. NM_006504) (SEQ ID NOS: 800-801), NM_080392), NM_080391), NM_032611 (SEQ ID NOS: 798-799), and NM_007079). In certain preferred embodiments PTPs and DSPs include, but are not limited to, U.S. application Ser. No. 10/151,320 (DSP18); WO 01/05983 (DSP-11); U.S. application Ser. No. 09/775,925 (DSP-12 and DSP-13); U.S. application Ser. No. 09/847,519 and WO 01/46394 (DSP-14); The invention also contemplates using mutated forms of the PTPs and DSPs, which may include PTPs and DSPs that contain single nucleotide polymorphisms (SNPs), or may include allelic forms.

Specific substitutions of individual amino acids through introduction of site-directed mutations are well-known and may be made according to methodologies with which those having ordinary skill in the art will be familiar. The effects on catalytic activity of the resulting mutant PTP may be determined empirically by testing the resulting modified protein for the preservation of the Km and reduction of Kcat to less than 1 per minute as provided herein and as previously disclosed (e.g., WO98/04712; Flint et al., 1997 *Proc. Nat. Acad. Sci. USA* 94:1680). In addition, the effect on phosphorylatation of one or more tyrosine residues of the resulting mutant PTP molecule can also be determined empirically merely by testing such a mutant for the presence of phosphotyrosine, as also provided herein, for example, following exposure of the mutant to conditions in vitro or in vivo where it may act as a phosphate acceptor for a protein tyrosine kinase.

In particular, portions of two PTP polypeptide sequences are regarded as "corresponding" amino acid sequences, regions, fragments or the like, based on a convention of numbering one PTP sequence according to amino acid position number, and then aligning the sequence to be compared in a manner that maximizes the number of amino acids that match or that are conserved residues, for example, that remain polar (e.g., D, E, K, R, H, S, T, N, Q), hydrophobic (e.g., A, P, V, L, I, M, F, W, Y) or neutral (e.g., C, G) residues at each position. Similarly, a DNA sequence encoding a candidate PTP that is to be mutated as provided herein, or a portion, region, fragment or the like, may correspond to a known wildtype PTP-encoding DNA sequence according to a convention for numbering nucleic acid sequence positions in the known wildtype PTP DNA sequence, whereby the candidate PTP DNA sequence is aligned with the known PTP DNA such that at least 70%, preferably at least 80% and more preferably at least 90% of the nucleotides in a given sequence of at least 20 consecutive nucleotides of a sequence are identical. In certain preferred embodiments, a candidate PTP DNA sequence is greater than 95% identical to a corresponding known PTP DNA sequence. In certain particularly preferred embodiments, a portion, region or fragment of a candidate PTP DNA sequence is identical to a corresponding known PTP DNA sequence. As is well known in the art, an individual whose DNA contains no irregularities (e.g., a common or prevalent form) in a particular gene responsible for a given trait may be said to possess a wildtype genetic complement (genotype) for that gene, while the presence of irregularities known as mutations in the DNA for the gene, for example, substitutions, insertions or deletions of one or more nucleotides, indicates a mutated or mutant genotype. The invention need not be so limited, however, and contemplates other embodiments wherein two or more non-PTP polypeptides of interest (e.g., as siRNA targets), such as MAP kinase kinases or chemotherapeutic target polypeptides, are structurally related and have portions of polypeptide sequences that may be regarded as "corresponding" amino acid sequences, regions, fragments or the like, according to the alignment and identity criteria discussed above.

Modification of DNA may be performed by a variety of methods, including site-specific or site-directed mutagenesis of DNA encoding the polypeptide of interest (e.g., a siRNA target polypeptide) and the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (e.g., a member of the PTP family, a MAP kinase kinase, or a chemotherapeutic target polypeptide). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. Additional disclosure relating to site-directed mutagenesis may be found, for example, in Kunkel et al. (*Methods in Enzymol.* 154:367, 1987) and in U.S. Pat. Nos. 4,518,584 and 4,737,462. The heteroduplex is introduced into appropriate bacterial cells, and clones that include the desired mutation are selected. The resulting altered DNA molecules may be expressed recombinantly in appropriate host cells to produce the modified protein.

SiRNAs of the invention may be fused to other nucleotide molecules, or to polypeptides, in order to direct their delivery or to accomplish other functions. Thus, for example, fusion proteins comprising a siRNA oligonucleotide that is capable of specifically interfering with expression of a target polypeptide may comprise affinity tag polypeptide sequences, which refers to polypeptides or peptides that facilitate detection and isolation of the such polypeptide via a specific affinity interaction with a ligand. The ligand may be any molecule, receptor, counterreceptor, antibody or the like with which the affinity tag may interact through a specific binding interaction as provided herein. Such peptides include, for example, poly-His or "FLAG®" or the like, e.g., the antigenic identification peptides described in U.S. Pat. No. 5,011,912 and in Hopp et al., (1988 *Bio/Technology* 6:1204), or the XPRESS™ epitope tag (Invitrogen, Carlsbad, Calif.). The affinity sequence may be a hexa-histidine tag as supplied, for example, by a pBAD/His (Invitrogen) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

The present invention also relates to vectors and to constructs that include or encode siRNA polynucleotides of the present invention, and in particular to "recombinant nucleic acid constructs" that include any nucleic acids that may be transcribed to yield target polynucleotide-specific siRNA polynucleotides (i.e., siRNA specific for a polynucleotide that encodes a target polypeptide, such as a mRNA) according to the invention as provided above; to host cells which are genetically engineered with vectors and/or constructs of the invention and to the production of siRNA polynucleotides, polypeptides, and/or fusion proteins of the invention, or fragments or variants thereof, by recombinant techniques. SiRNA sequences disclosed herein as RNA polynucleotides may be engineered to produce corresponding DNA sequences using well established methodologies such as those described herein. Thus, for example, a DNA polynucleotide may be generated from any siRNA sequence described herein (including in the Sequence Listing), such that the present siRNA sequences will be recognized as also providing corresponding DNA polynucleotides (and their complements). These DNA polynucleotides are therefore encompassed within the contemplated invention, for example, to be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al, *Nat. Biotechnol.* 20:497-500 (2002); Lee et al., *Nat. Biotechnol.* 20:500-505 (2002); Paul et al., *Nat. Biotechnol.* 20:505-508 (2002); Grabarek et al., *BioTechniques* 34:73544 (2003); see also Sui et al., *Proc. Natl. Acad. Sci. USA* 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for a PTP1B sequence may be transcribed under the control of a single promoter such that the siRNA polynucleotide forms a hairpin molecule (Paul et al., supra). In such an instance, the complementary strands of the siRNA specific sequences are separated by a spacer that comprises at least four nucleotides, but may comprise at least 5, 6, 7, 8, 9, 10, 11, 12, 14, 16, 94 18 nucleotides or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. SiRNA polynucleotides with such overhangs effectively interfere with expression of the target polypeptide (see id.). A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., Science 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

PTP polypeptides and other target polypeptides of interest can be expressed in mammalian cells, yeast, bacteria, or other cells under the control of appropriate promoters, providing ready systems for evaluation of siRNA polynucleotides that are capable of interfering with polypeptide expression as provided herein. Appropriate cloning and expression vectors for use with prokaryotic and eukaryotic hosts are described, for example, by Sambrook, et al., *Molecular Cloning: A Laboratory Manual*, Third Edition, Cold Spring Harbor, N.Y., (2001).

Generally, recombinant expression vectors for use in the preparation of recombinant nucleic acid constructs or vectors of the invention will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence (e.g., a siRNA polynucleotide sequence). Such promoters can be derived from operons encoding glycolytic enzymes such as 3-phosphoglycerate kinase (PGK), α-factor, acid phosphatase, or heat shock proteins, among others. For PTP polypeptide expression (including PTP fusion proteins and substrate trapping mutant PTPs), and for other expression of other polypeptides of interest, the heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression constructs for bacterial use are constructed by inserting into an expression vector a structural DNA sequence encoding a desired siRNA polynucleotide, together with suitable transcription initiation and termination signals in operable linkage, for example, with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice. Any other plasmid or vector may be used as long as they are replicable and viable in the host.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter, if it is a regulated promoter as provided herein, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Thus, for example, the nucleic acids of the invention as described herein (e.g., DNA sequences from which siRNA may be transcribed) herein may be included in any one of a variety of expression vector constructs as a recombinant nucleic acid construct for expressing a target polynucleotide-specific siRNA polynucleotide. Such vectors and constructs include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA, such as vaccinia, adenovirus, fowl pox virus, and pseudorabies. However, any other vector may be used for preparation of a recombinant nucleic acid construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (2001 *Molecular Cloning*, Third Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda PL promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a polypeptide (e.g., PTP, MAP kinase kinase, or chemotherapeutic target polypeptide) is described herein.

As noted above, in certain embodiments the vector may be a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, 1:5-14 (1990), which is incorporated herein by reference in its entirety. The vector may transduce the packaging cells through any means known in the art. Such means include, but are not limited to, electroporation, the use of liposomes, and calcium phosphate precipitation. In one alternative, the retroviral plasmid vector may be encapsulated into a liposome, or coupled to a lipid, and then administered to a host.

The producer cell line generates infectious retroviral vector particles that include the nucleic acid sequence(s) encoding the PTP polypeptides or other polypeptide of interest and fusion proteins thereof. Such retroviral vector particles then may be employed, to transduce eukaryotic cells, either in vitro or in vivo. The transduced eukaryotic cells will express the nucleic acid sequence(s) encoding the siRNA polynucleotide that is capable of specifically interfering with expression of a polypeptide or fusion protein. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, bronchial epithelial cells and various other culture-adapted cell lines.

In another aspect, the present invention relates to host cells containing the above described recombinant PTP expression constructs and to host cells containing the above described recombinant expression constructs comprising a (non-PTP) polypeptide of interest as described herein. Host cells are genetically engineered (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as E. coli, Streptomyces, Salmonella typhimurium; fungal cells, such as yeast; insect cells, such as Drosophila S2 and Spodoptera Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to produce siRNA polynucleotides from recombinant nucleic acid constructs of the present invention. The invention is therefore directed in part to a method of producing a siRNA polynucleotide, by culturing a host cell comprising a recombinant nucleic acid construct that comprises at least one promoter operably linked to a nucleic acid sequence encoding a siRNA polynucleotide specific for a desired target polypeptide. In certain embodiments, the promoter may be a regulated promoter as provided herein, for example a tetracylcine-repressible promoter. In certain embodiments the recombinant expression construct is a recombinant viral expression construct as provided herein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant siRNA polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAF-Dextran mediated transfection, or electroporation (Davis et al., 1986 Basic Methods in Molecular Biology), or other suitable technique.

The expressed recombinant siRNA polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed recombinant siRNA polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

Samples

According to the present invention, a method is provided for interfering with expression of a desired target polypeptide as provided herein, comprising contacting a siRNA polynucleotide with a cell that is capable of expressing the target polypeptide, typically in a biological sample or in a subject or biological source. A "sample" as used herein refers to a biological sample containing at least one protein tyrosine phosphatase or a MAP kinase kinase or a chemotherapeutic target polypeptide, and may be provided by obtaining a blood sample, biopsy specimen, tissue explant, organ culture or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication or any other means for processing a sample derived from a subject or biological source. In certain preferred embodiments, the sample is a cell that comprises at least one PTP and/or at least one MAP kinase, and/or at least one MAP kinase kinase, and in certain particularly preferred embodiments the cell comprises an inducible biological signaling pathway, at least one component of which is a specific target polypeptidee. In particularly preferred embodiments the cell is a mammalian cell, for example, Rat-1 fibroblasts, COS cells, CHO cells, HEK-293 cells, HepG2, HII4E-C3, L6, and 3T3-L1, or other well known model cell lines, which are available from the American Type Culture Collection (ATCC, Manassas, Va.). In other preferred embodiments, the cell line is derived from PTP-1B knockout animals and which may be transfected with human insulin receptor (HIR), for example, 1BKO mouse embryo fibroblasts.

In certain other preferred embodiments the sample is a cell that comprises a chemotherapeutic target polypeptide, which includes, for example, a cell line that is derived from a tumor cell. The cell line may be a primary tumor cell line, that is, a cell line prepared directly from a tumor sample removed from a human or a non-human animal. Alternatively, the cell line may be one of several established tumor cell lines known in the art, including but not limited to MCF7, T47D, SW620, HS578T, MDA-MB-435, MDA MB 231, HCT-116, HT-29, HeLa, Raji, Ramos, and the like (see ATCC collection).

The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. Optionally, in certain situations it may be desirable to treat cells in a biological sample with hydrogen peroxide and/or with another agent that directly or indirectly promotes reactive oxygen species (ROS) generation, including biological stimuli as described herein; in certain other situations it may be desirable to treat cells in a biological sample with a ROS scavenger, such as N-acetyl cysteine (NAC) or superoxide dismutase (SOD) or other ROS scavengers known in the art; in other situations cellular glutathione (GSH) may be depleted by treating cells with L-buthionine-SR-sulfoximine (Bso); and in other circumstances cells may be treated with pervanadate to enrich the sample in tyrosine phosphorylated proteins. Other means may also be employed to effect an increase in the population of tyrosine phosphorylated proteins present in the sample, including the use of a subject or biological source that is a cell line that has been transfected with at least one gene encoding a protein tyrosine kinase.

Additionally or alternatively, a biological signaling pathway may be induced in subject or biological source cells by contacting such cells with an appropriate stimulus, which may vary depending upon the signaling pathway under investigation, whether known or unknown. For example, a signaling pathway that, when induced, results in protein tyrosine phosphorylation and/or protein tyrosine dephosphorylation may be stimulated in subject or biological source cells using any one or more of a variety of well known methods and compositions known in the art to stimulate protein tyrosine kinase (PTK) and/or PTP activity. These stimuli may include, without limitation, exposure of cells to cytokines, growth factors, hormones, peptides, small molecule mediators, cell stressors (e.g., ultraviolet light; temperature shifts; osmotic shock; ROS or a source thereof, such as hydrogen peroxide, superoxide, ozone, etc. or any agent that induces or promotes ROS production (see, e.g., Halliwell and Gutteridge, *Free Radicals in Biology and Medicine* ($3^{rd}$ Ed.) 1999 Oxford University Press, Oxford, UK); heavy metals; alcohol) or other agents that induce PTK-mediated protein tyrosine phosphorylation and/or PTP-mediated phosphoprotein tyrosine dephosphorylation. Such agents may include, for example, interleukins (e.g., IL-1, IL-3), interferons (e.g., IFN-γ), human growth hormone, insulin, epidermal growth factor (EGF), platelet derived growth factor (PDGF), granulocyte colony stimulating factor (G-CSF), granulocyte-megakaryocyte colony stimulating factor (GM-CSF), transforming growth factor (e.g., TGF-β1), tumor necrosis factor (e.g., TNF-α) and fibroblast growth factor (FGF; e.g., basic FGF (bFGF)), any agent or combination of agents capable of triggering T lymphocyte activation via the T cell receptor for antigen (TCR; TCR-inducing agents may include superantigens, specifically recognized antigens and/or MHC-derived peptides, MHC peptide tetramers (e.g., Altman et al., 1996 *Science* 274:94-96); TCR-specific antibodies or fragments or derivatives thereof), lectins (e.g., PHA, PWM, ConA, etc.), mitogens, G-protein coupled receptor agonists such as angiotensin-2, thrombin, thyrotropin, parathyroid hormone, lysophosphatidic acid (LPA), sphingosine-1-phosphate, serotonin, endothelin, acetylcholine, platelet activating factor (PAF) or bradykinin, as well as other agents with which those having ordinary skill in the art will be familiar (see, e.g., Rhee et al., [online] Oct. 10, 2000 *Science's stke*, Internet: URL<www.stke.org/cgl/content/full/OC_sigtrans;2000/53/pel>), and references cited therein).

As noted above, regulated tyrosine phosphorylation contributes to specific pathways for biological signal transduction, including those associated with cell division, cell survival, apoptosis, proliferation and differentiation, and "inducible signaling pathways" in the context of the present invention include transient or stable associations or interactions among molecular components involved in the control of these and similar processes in cells. Depending on the particular pathway of interest, an appropriate parameter for determining induction of such pathway may be selected. For example, for signaling pathways associated with cell proliferation, a variety of well known methodologies are available for quantifying proliferation, including, for example, incorporation of tritiated thymidine into cellular DNA, monitoring of detectable (e.g., fluorimetric or colorimetric) indicators of cellular respiratory activity, (e.g., MTT assay) or cell counting, or the like. Similarly, in the cell biology arts there are known multiple techniques for assessing cell survival (e.g., vital dyes, metabolic indicators, etc.) and for determining apoptosis (e.g., annexin V binding, DNA fragmentation assays, caspase activation, PARP cleavage, etc.). Other signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, etc.), altered cell cycle profiles, or altered cellular morphology, and the like, such that cellular responsiveness to a particular stimulus as provided herein can be readily identified to determine whether a particular cell comprises an inducible signaling pathway.

In preferred embodiments where a siRNA of the invention is being used to interfere with expression of a target polypeptide that is a PTP or that is a component of a biological signaling pathway that comprises a PTP, a PTP substrate may be any naturally or non-naturally occurring phosphorylated peptide, polypeptide or protein that can specifically bind to and/or be dephosphorylated by a PTP (including dual specificity phosphatases) as provided herein, or any other phosphorylated molecule that can be a substrate of a PTP family member as provided herein. Non-limiting examples of known PTP substrates include the proteins VCP (see, e.g., Zhang et al., 1999 *J. Biol. Chem.* 274:17806, and references cited therein), $p130^{cas}$, EGF receptor, p210 bcr:abl, MAP kinase, Shc (Tiganis et al., 1998 *Mol Cell. Biol.* 18:1622-1634), insulin receptor, lck (lymphocyte specific protein tyrosine kinase, Marth et al., 1985 *Cell* 43:393), T cell receptor zeta chain, and phosphatidylinositol 3,4,5-triphosphate (Maehama et al., 1998 *J. Biol. Chem.* 273:13375).

Identification and selection of PTP substrates as provided herein, for use in the present invention, may be performed according to procedures with which those having ordinary skill in the art will be familiar, or may, for example, be conducted according to the disclosures of WO 00/75339, U.S. application Ser. No. 09/334,575, or U.S. application Ser. No. 10/366,547, and references cited therein. The phosphorylated protein/PTP complex may be isolated, for example, by conventional isolation techniques as described in U.S. Pat. No. 5,352,660, including salting out, chromatography, electrophoresis, gel filtration, fractionation, absorption, polyacrylamide gel electrophoresis, agglutination, combinations thereof or other strategies. PTP substrates that are known may also be prepared according to well known procedures that employ principles of molecular biology and/or peptide synthesis (e.g., Ausubel et al., *Current Protocols in Molecular Biology*, Greene Publ. Assoc. Inc. & John Wiley & Sons, Inc., Boston, Mass. (1993); Sambrook et al., *Molecular Cloning*, Third Ed., Cold Spring Harbor Laboratory, Plainview, N.Y. (2001); Fox, *Molec. Biotechnol.* 3:249 (1995); Maeji et al., *Pept. Res.* 8:33 (1995)).

The PTP substrate peptides of the present invention may therefore be derived from PTP substrate proteins, polypeptides and peptides as provided herein having amino acid sequences that are identical or similar to tyrosine phosphorylated PTP substrate sequences known in the art. For example by way of illustration and not limitation, peptide sequences derived from the known PTP substrate proteins referred to above are contemplated for use according to the instant invention, as are peptides having at least 70% similarity (preferably 70% identity), more preferably 80% similarity (more preferably 80% identity), more preferably 90% similarity (more preferably 90% identity) and still more preferably 95% similarity (still more preferably 95% identity) to the polypeptides described in references cited herein and in the Examples and to portions of such polypeptides as disclosed herein. As known in the art "similarity" between two polypeptides is determined by comparing the amino acid sequence and conserved amino acid substitutes thereto of the polypeptide to the sequence of a second polypeptide (e.g., using GENE-WORKS, Align or the BLAST algorithm, or another algorithm, as described above).

In certain preferred embodiments of the present invention, the siRNA polynucleotide and/or the PTP substrate is detectably labeled, and in particularly preferred embodiments the siRNA polynucleotide and/or PTP substrate is capable of generating a radioactive or a fluorescent signal. The siRNA polynucleotide and/or PTP substrate can be detectably labeled by covalently or non-covalently attaching a suitable reporter molecule or moiety, for example a radionuclide such as $^{32}P$ (e.g., Pestka et al., 1999 *Protein Expr. Purif.* 17:203-14), a radiohalogen such as iodine [$^{125}I$ or $^{131}I$] (e.g., Wilbur, 1992 *Bioconjug. Chem.* 3:433-70), or tritium [$^{3}H$]; an enzyme; or any of various luminescent (e.g., chemiluminescent) or fluorescent materials (e.g., a fluorophore) selected according to the particular fluorescence detection technique to be employed, as known in the art and based upon the present disclosure. Fluorescent reporter moieties and methods for labeling siRNA polynucleotides and/or PTP substrates as provided herein can be found, for example in Haugland (1996 *Handbook of Fluorescent Probes and Research Chemicals—Sixth Ed.*, Molecular Probes, Eugene, Oreg.; 1999 *Handbook of Fluorescent Probes and Research Chemicals—Seventh Ed.*, Molecular Probes, Eugene, Oreg., Internet: http://www.probes.com/lit/) and in references cited therein. Particularly preferred for use as such a fluorophore in the subject invention methods are fluorescein, rhodamine, Texas Red, AlexaFluor-594, AlexaFluor-488, Oregon Green, BODIPY-FL, umbelliferone, dichlorotriazinylamine fluorescein, dansyl chloride, phycoerythrin or Cy-5. Examples of suitable enzymes include, but are not limited to, horseradish peroxidase, biotin, alkaline phosphatase, β-galactosidase and acetylcholinesterase. Appropriate luminescent materials include luminol, and suitable radioactive materials include radioactive phosphorus [$^{32}P$]. In certain other preferred embodiments of the present invention, a detectably labeled siRNA polynucleotide comprises a magnetic particle, for example a paramagnetic or a diamagnetic particle or other magnetic particle or the like (preferably a microparticle) known to the art and suitable for the intended use. Without wishing to be limited by theory, according to certain such embodiments there is provided a method for selecting a cell that has bound, adsorbed, absorbed, internalized or otherwise become associated with a siRNA polynucleotide that comprises a magnetic particle. For example, selective isolation of a population or subpopulation of cells containing one or more PTP-specific siRNA polynucleotide-magnetic particle conjugates may offer certain advantages in the further characterization or regulation of PTP signaling pathways.

In certain embodiments of the present invention, particular PTP-specific siRNA polynucleotides of interest may be identified by contacting a candidate siRNA polynucleotide with a sample comprising a cell that comprises a target polypeptide-encoding gene and that is capable of target polypeptide gene transcription or expression (e.g., translation), under conditions and for a time sufficient to detect such gene transcription or expression, and comparing target transcription levels, polypeptide expression and/or functional expression (e.g., PTP catalytic activity) in the absence and presence of the candidate siRNA polynucleotide. Preferably target transcription or expression is decreased in the presence of the siRNA polynucleotide, which in the case of targets that are PTPs provides an alternative to PTP active site directed approaches to modulating PTP activity. (The invention need not be so limited, however, and contemplates other embodiments wherein transcription and/or expression levels of a signal transduction component other than that which is specifically targeted by the siRNA may be increased in the presence of a certain target-specific siRNA polynucleotide. By way of non-limiting theory, such an increase may result from a cellular compensatory mechanism that is induced as a result of the siRNA.)

Activity of a siRNA target polypeptide of interest may also be measured in whole cells transfected with a reporter gene whose expression is dependent upon the activation of an appropriate substrate. For example, appropriate cells (i.e., cells that express the target polypeptide and that have also been transfected with a target-specific siRNA polynucleotide that is either known or suspected of being capable of interfering with target polypeptide expression) may be transfected with a substrate-dependent promoter linked to a reporter gene. In such a system, expression of the reporter gene (which may be readily detected using methods well known to those of ordinary skill in the art) depends upon activation of the substrate via its interaction with the target polypeptide. For example, dephosphorylation of substrate may be detected based on a decrease in reporter activity in situations where the target polypeptide regulates substrate phosphorylation.

Within other aspects, the present invention provides animal models in which an animal, by virtue of introduction of an appropriate target polypeptide-specific siRNA polynucleotide, for example, as a transgene, does not express (or expresses a significantly reduced amount of) a functional PTP. Such animals may be generated, for example, using standard homologous recombination strategies, or alternatively, for instance, by oocyte microinjection with a plasmid comprising the siRNA-encoding sequence that is regulated by a suitable promoter (e.g., ubiquitous or tissue-specific) followed by implantation in a surrogate mother. Animal models generated in this manner may be used to study activities of PTP signaling pathway components and modulating agents in vivo.

Therapeutic Methods

One or more siRNA polynucleotides capable of interfering with target polypeptide expression and identified according to the above-described methods may also be used to modulate (e.g., inhibit or potentiate) target polypeptide activity in a patient. As used herein, a "patient" may be any mammal, including a human, and may be afflicted with a condition associated with undesired target polypeptide activity or may be free of detectable disease. Accordingly, the treatment may be of an existing disease or may be prophylactic. Conditions associated with signal transduction and/or with inappropriate activity of specific siRNA target polypeptides described herein include obesity, impaired glucose tolerance and diabetes and cancer, disorders associated with cell proliferation, including cancer, graft-versus-host disease (GVHD), autoimmune diseases, allergy or other conditions in which immunosuppression may be involved, metabolic diseases, abnormal cell growth or proliferation and cell cycle abnormalities.

For administration to a patient, one or more specific siRNA polynucleotides, either alone, with or without chemical modification or removal of ribose, or comprised in an appropriate vector as described herein (e.g., including a vector which comprises a DNA sequence from which a specific siRNA can be transcribed) are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Such compositions may be in the form of a solid, liquid or gas (aerosol). Alternatively, compositions of the present invention may be formulated as a lyophilizate or compounds may be encapsulated within liposomes using well known technology. Pharmaceutical compositions within the scope of the present invention may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable carrier known to those of ordinary skill in the art may be employed in the pharmaceutical compositions of the present invention. Carriers for therapeutic use are well known, and are described, for example, in *Remingtons Pharmaceutical Sciences*, Mack Publishing Co. (A. R. Gennaro ed. 1985). In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Within a pharmaceutical composition, a therapeutic agent comprising a polypeptide-directed siRNA polynucleotide as described herein (or, e.g., a recombinant nucleic acid construct encoding a siRNA polynucleotide) may be linked to any of a variety of compounds. For example, such an agent may be linked to a targeting moiety (e.g., a monoclonal or polyclonal antibody, a protein or a liposome) that facilitates the delivery of the agent to the target site. As used herein, a "targeting moiety" may be any substance (such as a compound or cell) that, when linked to an agent enhances the transport of the agent to a target cell or tissue, thereby increasing the local concentration of the agent. Targeting moieties include antibodies or fragments thereof, receptors, ligands and other molecules that bind to cells of, or in the vicinity of, the target tissue. An antibody targeting agent may be an intact (whole) molecule, a fragment thereof, or a functional equivalent thereof. Examples of antibody fragments are $F(ab')_2$, Fab', Fab and F[v] fragments, which may be produced by conventional methods or by genetic or protein engineering. Linkage is generally covalent and may be achieved by, for example, direct condensation or other reactions, or by way of bi- or multi-functional linkers. Targeting moieties may be selected based on the cell(s) or tissue(s) toward which the agent is expected to exert a therapeutic benefit.

Pharmaceutical compositions may be administered in a manner appropriate to the disease to be treated (or prevented). An appropriate dosage and a suitable duration and frequency of administration will be determined by such factors as the condition of the patient, the type and severity of the patient's disease, the particular form of the active ingredient and the method of administration. In general, an appropriate dosage and treatment regimen provides the agent(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of or diminish the severity of a disease associated with cell proliferation.

Optimal dosages may generally be determined using experimental models and/or clinical trials. In general, the amount of siRNA polynucleotide present in a dose, or produced in situ by DNA present in a dose (e.g., from a recombinant nucleic acid construct comprising a siRNA polynucleotide), ranges from about 0.01 µg to about 1001 g per kg of host, typically from about 0.1 µg to about 10 µg. The use of the minimum dosage that is sufficient to provide effective therapy is usually preferred. Patients may generally be monitored for therapeutic or prophylactic effectiveness using assays suitable for the condition being treated or prevented, which will be familiar to those having ordinary skill in the art. Suitable dose sizes will vary with the size of the patient, but will typically range from about 10 mL to about 500 mL for 10-60 kg animal.

The following Examples are offered by way of illustration and not by way of limitation.

EXAMPLE 1

Interference of Dual Specificity Phosphatase Expression by Small Interfering RNA This example describes the effect on dual specificity phosphatase (DSP) expression in cells transfected with sequence-specific small interfering RNA (siRNA) polynucleotides. Interference with expression of MKP-1 and DSP-3 was examined by transfecting sequence-specific siRNAs into mammalian cells expressing the DSP polypeptide and then detecting expression by immunoblot.

The siRNA nucleotide sequences specific for each DSP were chosen by first scanning the open reading frame of the target cDNA for 21-base sequences that were flanked on the 5' end by two adenine bases (AA) and that had A+T/G+C ratios that were nearly 1:1. Twenty-one-base sequences with an A+T/G+C ratio greater than 2:1 or 1:2 were excluded. If no 21-base sequences were identified that met this criteria, the polynucleotide sequence encoding the DSP was searched for a 21-base sequence having the bases CA at the 5' end. The polynucleotide sequences examined were the sequences encoding DSP-3 polypeptide (SEQ ID NO: 779) and MKP-1). For the selection of sequences for some of the siRNA polynucleotides, the sense and antisense sequences of each 21-mer that met the above criteria were then analyzed to determine if the sequence had the potential to form an internal hairpin loop or homodimer. Such an analysis can be performed using computer software programs known to those in the art. Any 21-mer that had an internal hairpin loop melting temperature of greater than 55° C. and a homodimer melting temperature of greater than 37° C. was excluded. The specificity of each 21-mer was determined by performing a BLAST search of public databases. Sequences that contained at least 16 of 21 consecutive nucleotides with 100% identity with a polynucleotide sequence other than the target sequence were not used in the experiments. In each of the Examples provided herein, each siRNA sequence represents the sense strand of the siRNA polynucleotide and its corresponding sequence identifier. "Related sequence identifiers" referred to in the Examples identify sequences in the sequence listing that contain the same nucleotides at positions 1-19 of the siRNA sequence with and without two additional nucleotides (NN) at the 3' end (which would correspond to a two-nucleotide overhang in a double stranded polynucleotide), and the reverse complement of each. Unless otherwise stated, it is to be understood that the siRNA transfected into a cell is composed of the sense strand and its complementary antisense strand, which form a duplex siRNA polynucleotide. The sequences chosen for these experiments were as follows.

DSP-3 specific:

```
DSP3.1:
5'-cgauagugccaggccuaugtt-3'     [SEQ ID NO: 3]
(see also related sequences
(SEQ ID NOS: 4-7)

DSP3.2:
5'-gcaugagguccaucaguautt-3'     [SEQ ID NO: 8]
(see also related sequences
(SEQ ID NOS: 9-12)

DSP3.3:
5'-cgauacugccaggcccaugtt-3'     [SEQ ID NO: 13]
(see also related sequences
(SEQ ID NOS: 14-17)
```

MKP-1 specific:

```
MKP.1: 5'-auccugcccuuucuguacctt-3'   [SEQ ID NO: 18]
       (see also related sequences
       (SEQ ID NOS: 19-22)

MKP.2: 5'-gcagaggcaaagcaucauctt-3'   [SEQ ID NO: 23]
       (see also related sequences
       (SEQ ID NOS: 24-27)
```

Sense and antisense oligonucleotides for MKP.1, MKP.2, DSP3.1, DSP3.2, and DSP3.3 were synthesized according to the standard protocol of the vendor (Dharmacon Research, Inc., Lafayette, Colo.). For some experiments described in this and other examples, the vendor gel-purified the double-stranded siRNA polynucleotide, which was then used. In the instances when the vendor did not prepare double-stranded siRNA, just before transfection, double-stranded siRNAs were prepared by annealing the sense and anti-sense oligonucleotides in annealing buffer (100 mM potassium acetate, 30 mM HEPES-KOH, pH 7.4, 2 mM magnesium acetate) for 1 minute at 90° C., followed by a 60 minute incubation at 37° C.

Recombinant nucleic acid expression vectors containing encoding sequences for the MKP-1 polypeptide and DSP-3 polypeptide were prepared according to standard molecular biology techniques. Polynucleotides comprising the MKP-1 coding sequence (see WO 97/00315) and comprising the DSP-3 coding sequence of (SEQ ID NO: 778) were cloned into recombinant expression vectors according to methods known to those skilled in the molecular biology art.

HeLa cells (ATCC, Manassas, Va.) were maintained in Dulbecco's modified Eagle's medium (DMEM, Life Technologies, Inc., Gaithersburg, Md.) plus 10% fetal bovine serum (FBS), 100 units/ml penicillin, and 100 μg/ml streptomycin. Cells were plated in 6-well tissue culture plates at a density of approximately $5 \times 10^4$ cells per well at the time of transfection.

HeLa cells were transfected with 60 pmoles of MKP.1, MKP.2, or CD45.1 siRNA. For each cell culture well, the siRNA polynucleotides were diluted into 250 μl of $O_{PTI}$-MEM® Reduced Serum Medium (Gibco™, Life Technologies), and 15 μl Oligofectamine™ (Invitrogen Life Technologies, Carlsbad, Calif.) was diluted into 250 μl of $O_{PTI}$MEM®. A control solution without siRNA was also prepared. Each solution was incubated at room temperature for 5 minutes. The two solutions were mixed and then incubated for 20 minutes at room temperature to allow the liposome-nucleic acid complexes to form. FBS-containing media was removed from the HeLa cell cultures and replaced with $O_{PTI}$MEM®. The liposome-nucleic acid mixture then was added to the HeLa cell culture, and the transfected cells incubated at 37° C. for 22-24 hours. Media were removed from the cell cultures and replaced with DMEM containing 10% FBS. Cells were incubated at 37° C. in the media plus FBS solution for 0, 1, or 4 hours.

Expression of MKP-1 was analyzed by immunoblotting HeLa cell extracts. The cells were rinsed twice in phosphate buffered saline (PBS) (4° C.) and then lysed in 250 μl of ice-cold RIPA buffer RIPA buffer (150 mM NaCl, 10 mM $NaPO_4$, 2 mM EDTA, 1% deoxycholate, 1% Nonidet® P40, 0.1% SDS, 5 mM NaF, 14.3 mM beta-mercaptoethanol, and Complete Protease Inhibitor (Roche Applied Bioscience, Indianapolis, Ind.). The lysates were centrifuged and aliquots of supernatant (10 μl) from each transfected cell culture sample were combined with 10 μl of 2×SDS-PAGE reducing sample buffer. The samples were heated at 95° C. for five minutes, and then applied to a 14% Tris-glycine SDS-PAGE gel (NOVEX® from Invitrogen Life Technologies, Carlsbad, Calif.). After electrophoresis, the separated proteins were electrophoretically transferred from the gel onto an Immobilon-P polyvinylidene fluoride (PVDF) membrane (Millipore, Bedford, Mass.). The PVDF membrane was blocked in 5% milk in TBST (20 mM Tris pH 7.5, 150 mM NaCl, 0.05% Tween-20), incubated with an anti-MKP-1 antibody (Santa Cruz Biotechnology, Inc., Santa Cruz, Calif.) for 2-16 hours at room temperature, washed 3×10 minutes with TBST, and then incubated with an appropriate horseradish peroxidase (HRP) conjugate IgG (1:10,000) (Amersham Biosciences, Piscataway, N.J.) for 30 minutes at room temperature. Binding was detected with the ECL chemiluminescent reagent used according to the manufacturer's instructions (Amersham Biosciences, Piscataway, N.J.) as shown in FIG. 1 (upper). A second SDS-PAGE gel in which the HeLa cell extracts were separated was stained with Coomassie Blue (FIG. 1, lower).

Interference with DSP-3 polypeptide expression was analyzed in HeLa cells transfected with siRNA polynucleotides. To determine the transfection efficiency of a siRNA polynucleotide, HeLa cells cultured as described above were plated at different cell densities and then transfected with a sequence-specific siRNA. DSP3.1 siRNA (SEQ ID NO: 3) was synthesized and conjugated to fluorescein isothiocyanate (FITC) according to the vendor's standard methods (Synthetic Genetics, San Diego, Calif.). HeLa cells plated at varying cell densities to achieve approximately $1 \times 10^4$ cells/well, $3 \times 10^4$ cells/well, $5 \times 10^4$ cells/well, $1 \times 10^5$ cells/well, $2 \times 10^5$ cells/well, and $4 \times 10^5$ cells/well were transfected with FITC-DSP3.1 as described above. Controls included HeLa cells exposed to Lipofectamine™ 2000 alone and to media alone. The transfected cells were harvested after 24-48 hours and analyzed by a fluorescence-activated cell sorter (FACS). Transfection was more efficient at cell densities of $5 \times 10^4$ cells/well or less.

Interference of DSP-3 expression by two different DSP-3 sequence specific siRNA polynucleotides, DSP3.1 (SEQ ID NO: 3) and DSP3.2 (SEQ ID NO: 8). Transfection of HeLa cells was performed as described for MKP-1. As controls, HeLa cells were transfected with non-specific MKP.1 (SEQ ID NO: 18) and with transfection solution not containing the expression vector or siRNA.

Twenty-four hours after transfection, cell extracts were prepared either using RIPA buffer (see above) or 1% Triton X-100®. The extracts were analyzed by immunoblot (see above) using an anti-DSP-3 monoclonal antibody, clone 17, diluted 1:10,000 in TBST and binding was detected with HRP-conjugated anti-mouse IgG. DSP3.1 effectively decreased expression of DSP-3, whereas the level of expression in cells transfected with siRNA DSP3.2 was comparable to expression in the cells transfected with the non-specific MKP.1 siRNA. The cell extracts were also immunoblotted against an anti-PTP1B antibody, which demonstrated that protein expression of another protein expressed in the cells was not affected by the presence of siRNA polynucleotides. The data suggest that the decrease in the level of DSP-3 expression varies depending upon the particular sequence of the siRNA.

To evaluate the sensitivity of interference by specific siRNA polynucleotides, DSP3.1 siRNA (SEQ ID NO: 3) was titrated in HeLa cells. HeLa cells were transfected as described above with DSP3.1 siRNA (SEQ ID NO:3) at a concentration of 1, 2, 5, 10, 20, and 100 nM. HeLa cells were also transfected at the same concentrations with non-specific siRNAs, cdc14a.1 (5'-caucgugcgaagguuccugtt-3' (SEQ ID NO:28)) and CD45.2 (5'-gccgagaacaaaguggaugtt-3' (SEQ ID NO: 33)). An immunoblot of cell extracts prepared using RIPA buffer was probed with anti-DSP-3 monoclonal antibody clone 17. A second immunoblot was probed with an anti-JNK2 antibody. DSP-3 expression decreased to approximately the same level in cells transfected with 5, 10, 20, and 100 nM of the specific siRNA DSP3.1. The level of expression of DSP-3 also decreased in the presence of the lowest concentrations of siRNA DSP3.1 compared with DSP-3 expression in cells transfected with non-specific siRNAs. Expression of JNK2 was not affected.

The specificity of siRNA interference was demonstrated by co-transfecting HeLa cells with the DSP-3 expression vector and an siRNA, DSP3.3 (SEQ ID NO: 13) that had two base differences from siDSP3.1. Transfection and immunoblotting were performed as described above for the titration experiment. The expression levels of DSP-3 polypeptide was effectively decreased in the presence of 1, 5, 10, 20, or 100 nM of DSP3.1 but not in cells transfected with DSP3.3. The level of expression of JNK2 was not affected.

EXAMPLE 2

Interference with Expression of Protein Tyrosine Phosphatases by Sequence-Specific Small Interfering RNA This example describes RNA interference of transient and endogenous expression of various protein tyrosine phosphatases (PTPs).

Co-Transfection Assays to Determine Interference of PTP Expression by siRNA

DSP-11 and DSP-18

Interference of expression of FLAG®-tagged DSP-11 polypeptide and FLAG®-tagged DSP-18pr polypeptide (DSP-18) by sequence specific siRNA polynucleotides was determined. (FLAG® sequence: Asp-Tyr-Lys-Asp-Asp-Asp-Asp-Lys (SEQ ID NO: 13)) (Sigma Aldrich, St. Louis, Mo.). Two siRNA sequences that were specific for DSP-11 polynucleotide (SEQ ID NO: 780) encoding a DSP-11 polypeptide (SEQ ID NO: 781) and two siRNA sequences specific for DSP-18pr polynucleotide (DSP-18, SEQ ID NO: 782) encoding a DSP-18 polypeptide (SEQ ID NO: 783) were designed using the criteria described in Example 1. The following sequences were used in the experiments.

DSP-11 specific:

```
DSP11.2:
5'-cuggcaccaugcuggccugtt-3'      [SEQ ID NO: 39]
(see also related sequences
(SEQ ID NOS: 40-43)

DSP11.4:
5'-agcagucuuccaguucuactt-3'      [SEQ ID NO: 44]
(see also related sequences
(SEQ ID NOS: 45-48)
```

DSP-18 specific:

```
DSP18.2:
5'-cugccuugugcacugcuuutt-3'      [SEQ ID NO: 49]
(see also related sequences
(SEQ ID NOS: 50-53)

DSP18.4:
5'-gaguuuggcugggccaguutt-3'      [SEQ ID NO: 54]
(see also related sequences
(SEQ ID NOS: 55-58)
```

Vectors for expression of DSP-18 and DSP-11 were prepared as follows. Vector pCMVTag2B (Stratagene, La Jolla, Calif.) was digested with restriction endonuclease BamHI (New England Biolabs, Beverly, Mass.) for 3 hours at 37° C.

The digested vector was then incubated with Klenow polymerase (New England Biolabs) for 15 minutes at 25° C. to fill in the recessed 3' termini, followed by an incubation of 30 minutes at 37° C. with calf intestinal phosphatase (New England Biolabs). The GATEWAY™ Reading Frame Cassette B (Invitrogen, Carlsbad, Calif.) was inserted into the pCMVTag2B vector by ligation with T4 DNA ligase (Invitrogen) overnight at 16° C. according to the supplier's instructions. DB3.1™ competent *E. coli* cells were transformed with the ligated vector (GWpCMVTag2), and DNA was isolated by standard molecular biology methods. DSP-11 and DSP-18 constructs were prepared by ligating a polynucleotide encoding DSP-11 (SEQ ID NO:781) and a polynucleotide encoding DSP-18 (SEQ ID NO:783) into a modified bacterial pGEX-6PKG expression vector (Amersham Biosciences), referred to as pGEX-6P1, according to standard methods known in the molecular biology art. DSP-11 and DSP18 constructs and the pENTR™ 1A entry vector (Invitrogen) were digested with EcoRI (New England Biolabs) for 3 hours at 37° C. The pENTR™ 1A clone was treated with calf intestinal phosphatase for 30 minutes at 37° C., and then DSP-11 and DSP-18 constructs were inserted into separate pENTR™ vectors by ligation overnight at 16° C. with T4 DNA ligase. Vector DNA was prepared from LIBRARY EFFICIENCY® DH5α™ cells (Invitrogen) that were transformed with each construct according to the supplier's recommendation.

FLAG® epitope-tagged DSP-11 and DSP-18 polypeptides were prepared by cloning the pENTR™ 1A-DSP-18 and substrate trapping mutant constructs into the GWpCMVTag2 vector. The pENTR™ 1A constructs containing the DSP-11 and the DSP-18 polynucleotides were linearized by digesting the constructs with Vsp I (Promega Corp., Madison, Wis.) for 2 hours at 37° C. The DNA was purified using a QIAGEN PCR Purification kit (QIAGEN, Inc., Valencia, Calif.), and 30 μl (100 ng/μl) was combined in a GATEWAY™ LR reaction with 6 μl linearized pENTR™ 1A-DSP-11, pENTR™ 1A-DSP-18, 3 μl TE buffer, 4 μl Clonase™ Enzyme, and 4 μl LR reaction buffer (Invitrogen) for 1 hour at room temperature. After addition of Proteinase K (Invitrogen) to each reaction for 10 minutes, LIBRARY EFFICIENCY® DH5α™ cells were transformed with each expression vector. For controls, FLAG®-DSP-3 and FLAG®-cdc14b were also prepared according to the above method.

Figure 2:
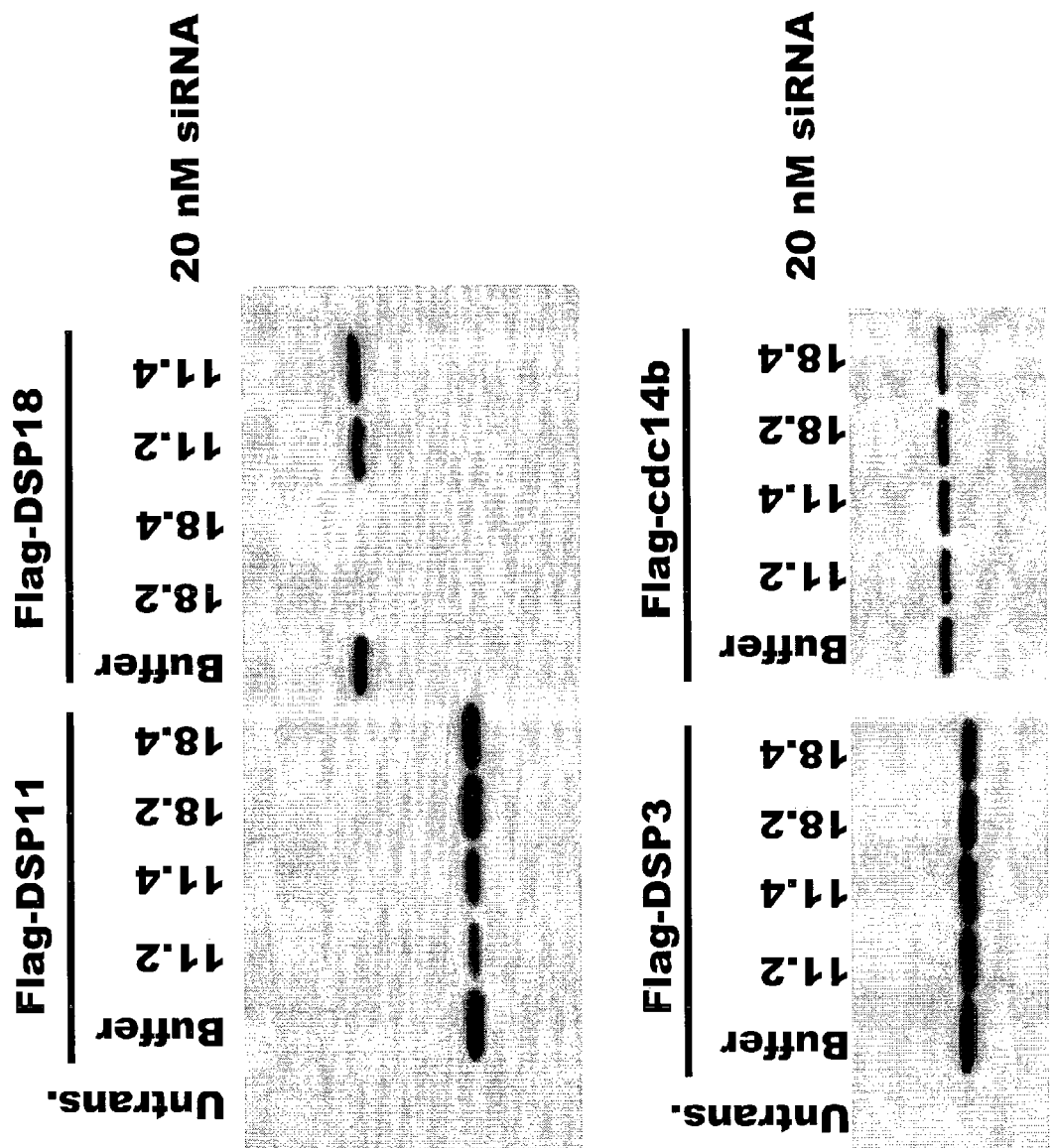
FIG. 2 shows an immunoblot analysis of 292-HEK cell lysates from cells co-transfected with FLAG®-DSP-11, FLAG®-DSP-18, FLAG®-DSP-3, and FLAG®-cdc14b expression vectors and siRNAs specific for DSP-11 or DSP-18. The presence of each polypeptide was detected using an anti-FLAG® antibody (Sigma-Aldrich, St. Louis, Mo.). The upper immunoblot shows the level of expression of FLAG®-DSP-11 in untransfected 293-HEK cells (lane 1); 293-HEK cells transfected with FLAG®-DSP-11 vector DNA only (buffer) (lane 2), siRNA DSP11.2 (lane 3), siRNA DSP11.4 (lane 4), siRNA DSP18.2 (lane 5), and siRNA DSP18.2 (lane 6); and the level of expression of 293-HEK cells transfected with FLAG®-DSP-18 vector DNA only (buffer) (lane 7); 293-HEK cells co-transfected with siRNA DSP11.2 (lane 8), siRNA DSP11.4 (lane 9), siRNA DSP18.2 (lane 10), and siRNA DSP18.2 (lane 11). The lower immunoblot shows the level of FLAG®-DSP-3 in untransfected 293-HEK cells (lane 1); 293-HEK cells transfected with FLAG®-DSP-3 vector DNA only (buffer) (lane 2); 293-HEK cells co-transfected with siRNA DSP11.2 (lane 3), siRNA DSP11.4 (lane 4), siRNA DSP18.2 (lane 5), and siRNA DSP18.2 (lane 6); and the level of expression of FLAG®-cdc14b in 293-HEK cells transfected with FLAG®-cdc14b vector DNA only (buffer) (lane 7); 293-HEK cells co-transfected with siRNA DSP11.2 (lane 8), siRNA DSP11.4 (lane 9), siRNA DSP18.2 (lane 10), and siRNA DSP18.2 (lane 11).

293-HEK cells, maintained in DMEM, 10% FBS at 37° C. and 5% $CO_2$, were co-transfected with the FLAG®-DSP-11, FLAG®-DSP-18, FLAG®-DSP-3, and FLAG®-cdc14b expression vectors and DSP11.2, DSP11.4, DSP18.2, and DSP18.4 siRNAs (20 nM) (double-stranded RNA was prepared as described in Example 1) using the Lipofectamine™ 2000 reagent (Invitrogen). After incubating the transfected cells for 22-24 hours at 37° C., cells were rinsed twice in phosphate buffered saline (PBS) (4° C.) and then lysed in 250 μl of ice-cold RIPA buffer (see Example 1). The cell debris was pelleted and aliquots of each supernatant were separated by SDS-PAGE and immunoblotted as described in Example 1. DSP-11 and DSP-18 polypeptides were detected by probing the immunoblots with an anti-FLAG® antibody (Sigma-Aldrich, St. Louis, Mo.) followed by probing with an HRP-conjugated goat anti-mouse reagent (see Example 1). Binding of the anti-FLAG® antibody was detected by chemiluminescence development (see Example 1). FIG. 2 shows that expression of FLAG®-DSP-11 and FLAG®-DSP-18 was inhibited in the presence of sequence-specific siRNA.

DSP-13 and DSP-14

Expression constructs of DSP-13) and DSP-14) and FLAG® epitope-tagged DSP-13 and DSP-14 polypeptides (see SEQ ID NO: 785 and SEQ ID NO: 787, respectively) were prepared essentially as described above. Four siRNA sequences specific for a DSP-13 polynucleotide (see SEQ ID NO: 784) and four siRNA sequences specific for a DSP-14 (SEQ ID NO: 786) were designed according to the criteria described in Example 1 except that melting temperatures were not necessarily calculated. After performing the BLAST search to analyze the specificity of a sequence, sequences that contained at least 16 consecutive nucleotides with 100% identity with a polynucleotide sequence other than the target sequence were not used in the experiments. The siRNA polynucleotides were manufactured by Dharmacon Research Inc. The sequences of the siRNA polynucleotides are as follows.

DSP-13 Specific:

```
DSP13.1:
5'-cuugcgggaauucaaggaatt-3'    (SEQ ID NO: 59)
(see also related sequences
(SEQ ID NOS: 60-63)

DSP13.2:
5'-ccgagggguacgguauauctt-3'    (SEQ ID NO: 64)
(see also related sequences
(SEQ ID NOS: 65-68)

DSP13.3:
5'-caucaggcuggcuguaagatt-3'    (SEQ ID NO: 69)
(see also related sequences
(SEQ ID NOS: 70-73)

DSP13.4:
5'-cauggaucuaaaugccuugtt-3'    (SEQ ID NO: 74)
(see also related sequences
(SEQ ID NOS: 75-78)
```

DSP-14 Specific:

```
DSP-14.1:
5'-gugaagacaagccucaagatt-3'    (SEQ ID NO: 79)
(see also related sequences
(SEQ ID NOS: 80-83)

DSP-14.2:
5'-gcucuacauuggcgaugagtt-3'    (SEQ ID NO: 84)
(see also related sequences
(SEQ ID NOS: 85-88)

DSP-14.3:
5'-gcgacgaccacaguaagautt-3'    (SEQ ID NO: 89)
(see also related sequences
(SEQ ID NOS: 90-93)

DSP-14.4:
5'-ggacaugacccuggugactt-3'     (SEQ ID NO: 94)
(see also related sequences
(SEQ ID NOS: 95-98)
```

293-HEK cells were co-transfected with 1-2 μg of the FLAG®-DSP-13 or FLAG®-DSP-14 expression vector and 20 nM of siRNA and expression detected by immunoblot as described above. As controls, cells co-transfected with a DSP expression vector and a non-specific siRNA and untransfected 293-HEK cells were included in the analysis.

The amount of of FLAG®-DSP-13 polypeptide expressed in 293-HEK cells co-transfected with the FLAG®-DSP-13 construct and either DSP13.3 or DSP13.4 siRNA decreased more than 95% compared with cells transfected with the DSP-13 expression constructs only. Expression of the DSP-13 polypeptide in cells co-transfected with DSP13.2 siRNA was comparable to expression in cells co-transfected with a non-specific siRNA (DSP14.1). Expression of FLAG®-DSP-14 polypeptide decreased 70% in 293-HEK cells when the cells were co-transfected with DSP14.1 siRNA and decreased 90% when the cells were co-transfected with DSP-14.3 siRNA. Expression of DSP-14 in the presence of siRNA 14.4 was only slightly lower than observed with a non-specific siRNA (DSP13.1).

DSP-3

Transient co-transfection experiments in 293-HEK cells were also performed with DSP3.1 siRNA (SEQ ID NO:3) and a DSP-3 polypeptide recombinant expression vector (prepared according to standard molecular biology techniques). Expression of DSP-3 was determined by immunoblot probed with anti-DSP-3 monoclonal antibody clone 17. The results showed that the amount of DSP-3 polypeptide expressed in the 293-HEK cells decreased 80% in the presence of sequence specific siRNA.

SHP-2

Inhibition of expression of the protein tyrosine phosphatase (PTP) SHP-2 (src homology protein-2) was also examined in the 293-HEK co-transfection assay. Four different siRNAs specific for the polynucleotide sequence (see SEQ ID NOS: 788 and 790) encoding SHP-2 (see SEQ ID NOS: 789 and 791) were co-transfected with a FLAG®-SHP-2 expression construct prepared according to the molecular biology methods described above. SHP-2 specific siRNAs had the following sequences.

```
SHP2.1:
5'-gauucagaacacuggugautt-3'    (SEQ ID NO: 99)
(see also related sequences
(SEQ ID NOS: 100-103)

SHP2.2:
5'-gaauauggcgucaugcgugtt-3'    (SEQ ID NO: 104)
(see also related sequences
(SEQ ID NOS: 105-108)

SHP2.3:
```

```
                  -continued
5'-cggucuggcaauaccacuutt-3'    (SEQ ID NO: 109)
(see also related sequences
(SEQ ID NOS: 110-113)

SHP2.4:
5'-ugacggcaagucuaaagugtt-3'    (SEQ ID NO: 114)
(see also related sequences
(SEQ ID NOS: 115-118)
```

The siRNA SHP2.1 effectively impaired expression of SHP-2 in transfected 293-HEK cells, decreasing the amount of FLAG®-SHP-2 polypeptide detected by more than 95%. In the presence of siRNA SHP2.2, FLAG®-SHP-2 polypeptide expression decreased by 85%. SHP2-4 had no specific effect on SHP-2 expression.

PRL-3 and KAP

Inhibition of expression of the human protein tyrosine phosphatases (PTP) PRL-3 and KAP were also examined in the 293-HEK co-transfection assay. Four different siRNAs specific for the polynucleotide sequence (see SEQ ID NOS: 798 and 800) encoding PRL-3 (see SEQ ID NOS: 799 and 801) were co-transfected with a FLAG®-PRL-3 expression construct prepared according to the molecular biology methods described above. Similarly, four different siRNAs specific for the polynucleotide sequence (SEQ ID NO: 796) encoding KAP (SEQ ID NO: 797) were co-transfected with a FLAG®-KAP expression construct. The siRNA sequences and the percent decrease in the level of expression of the PTP in cells transfected with the each siRNA is presented in Table 1 below, and it is noted that each 21-mer sequence below contains a dinucleotide "overhang" at the 3' end, and that the invention herein should be considered to include the 19-mer polynucleotide sequences beginning at the 5' end therein as well as the 21-mer polynucleotide shown in the Table.

TABLE 1 siRNA INTERFERENCE WITH PRL-3 AND KAP IN CO-TRANSFECTION ASSAYS

| Target | siRNA Sequence (SEQ ID NO) | siRNA Name | Related SEQ ID NO: | Decrease in Expression |
|---|---|---|---|---|
| KAP | 5'-GAGCCUAUUGAAGAUGAACTT-3' (SEQ ID NO: 119) | KAP.1 | (SEQ ID NOS: 120-123) | >90% |
| KAP | 5'-GAGCUGUGGUAUACAAGACTT-3' (SEQ ID NO: 124) | KAP.2 | (SEQ ID NOS: 125-128) | >90% |
| KAP | 5'-GAGCUUACAACCUGCCUUATT-3' (SEQ ID NO: 129) | KAP.3 | (SEQ ID NOS: 130-133) | >90% |
| KAP | 5'-UACACUGCUAUGGAGGACUTT-3' (SEQ ID NO: 134) | KAP.4 | (SEQ ID NOS: 135-138) | <10% |
| PRL-3 | 5'-GUGACCUAUGACAAAACGCTT-3' (SEQ ID NO: 139) | Prl3.1 | (SEQ ID NOS: 140-143) | 50% |
| PRL-3 | 5'-GGCCAAGUUCUGUGAGGCCTT-3' (SEQ ID NO: 144) | Prl3.2 | (SEQ ID NOS: 145-143) | 50% |
| PRL-3 | 5'-GUACGAGGACGCCAUCCAGTT-3' (SEQ ID NO: 149) | Prl3.3 | (SEQ ID NO: 150-153) | 50% |
| PRL-3 | 5'-UACCGGCCCAAACAGAGGCTT (SEQ ID NO: 154) | Prl3.4 | (SEQ ID 155-158) | <10% |

PTPε

Inhibition of expression of human PTPε is examined in the 293-HEK co-transfection assay. Four different siRNAs specific for the polynucleotide sequence (see SEQ ID NOS: 792 and 794) encoding PTPε (see SEQ ID NOS: 793 and 795) are co-transfected with a FLAG®-PTPε expression construct prepared according to the molecular biology methods described above. The siRNA sequences that are analyzed have AA leader sequences (not included in the siRNA polynucleotide transfected into HEK cells) and the following sequences.

```
RPTPE.1: 5'GCAGAGGAAAGCUGUGGUCTT3'   (SEQ ID NO: 159)
         (see also related
         sequences
         (SEQ ID NOS: 160-163)

RPTPE.2: 5'GUCUGCGACCAUCGUCAUGTT3'   (SEQ ID NO: 164)
         (see also related
         sequences
         (SEQ ID NOS: 165-168)

RPTPE.3: 5'GCCUUACUCGAGUACUACCTT3'   (SEQ ID NO: 169)
         (see also related
         sequences
         (SEQ ID NOS: 170-173)

RPTPE.4: 5'GGACUAUUUCAUCGCCACCTT3'   (SEQ ID NO: 174)
         (see also related
         sequences
         (SEQ ID NOS: 175-178)
```

Interference by siRNA Polynucleotides of Endogenous PTP Expression

The effect of sequence specific siRNA polynucleotides on expression of protein tyrosine phosphatases endogenously expressed in cells was also determined. Inhibition of expression of SHP-2 in HeLa cells by specific siRNAs was examined. HeLa cells were transfected with 10 nM of SHP2.1 (SEQ ID NO: 99); SHP2.2 (SEQ ID NO: 104); DSP13.3 (SEQ ID NO: 69); DSP14.1 (SEQ ID NO: 79); and DSP14.3 (SEQ ID NO: 89). Each siRNA was diluted in 50 µl Opti-MEM® to provide a final concentration of 10 nM per well of cells in six well tissue culture plate. In a separate tube, 3 µl of Lipofectamine™ was combined with 10 µl OptiMEM®. Each solution was incubated for 7 minutes. The two solutions were then mixed and incubated at room temperature for 22 minutes. The final volume of the mixed solution was adjusted to 500 µl and then was added to the HeLa cells. Cells were transfected with the siRNAs or with annealing buffer alone. The transfected cells were incubated with siRNAs for 60 hours.

Cell lysates were prepared by extracting the cells in RIPA buffer as described in Example 1. The lysates were separated by SDS-PAGE gel and analyzed by immunoblot according to the procedures described in Examples 1 and above in Example 2 using an anti-SHP-2 murine monoclonal antibody (Santa Cruz Biotechnology, Inc., Santa Cruz, Calif.). The levels of expression of endogenous SHP-2 decreased by 75% in the presence of SHP2.2 and by 90% in the presence of SHP2.1. The expression of SHP-2 in the siRNAs presence of DSP13.3, DSP14.1, or DSP14.3 was comparable to the level of expression observed in cells treated with buffer only.

A similar experiment was performed to determine the level of endogenous expression of DSP-3 in HeLa cells and in MDA-MB-435 cells (ATCC) in the presence of sequence specific siRNA. DSP3.1 siRNA (SEQ ID NO:3) was transfected into each cell line as described above, and the level of expression of DSP-3 polypeptide was analyzed by immunoblot (see Example 1 for immunoblot procedure to detect DSP-3). Expression of DSP-3 polypeptide decreased 70-100% in HeLa cells and decreased 100% in MDA-MB-435 cells in the presence of the specific mRNA.

Particular siRNA polynucleotide sequences that are specific for CD45, SHP2, cdc14a, cdc14b, cdc25A, cdc25B, cdc25C, PRL-3, KAP, DSP-3, and PTPε are provided below. The level of expression of each PTP and DSP in cells that are capable of expressing the PTP or DSP and that are transfected with any one of the following specific siRNA polynucleotides is determined according to methods and procedures described above. The siRNA sequences that are incorporated into a vector from which a hairpin vector is transcribed and/or that are transfected via liposomes according to methods described in Examples 1 and 2 are presented in the following tables. The human TCPTP target sequences were derived from a human TCPTP nucleotide sequence (see GenBank Accession No. M25393, NM 002828, NM_080422); the CD45 target sequences were derived from a human CD45 nucleotide sequence, (see Charbonneau et al.); the SHP-2 target sequences were derived from a human SHP-2 nucleotide sequence (see GenBank Accession No. L03535 (SEQ ID NOS: 788-789) and L07527 (SEQ ID NOS: 790-791)); the cdc14a target sequences were derived from a human cdc14a nucleotide sequence (see GenBank Accession No. AF122013) (SEQ ID NO: 802)); the cdc14b target sequences were derived from a human cdc14b nucleotide sequence (GenBank Accession No. AF023158 (SEQ ID NO: 804)); the cdc25A target sequences were derived from a human cdc25A nucleotide sequence (see GenBank Accession No. NM_133571 and AF527417 (SEQ ID NO: 808); the cdc25B target sequences were derived from a human cdc25B nucleotide sequence (see GenBank Accession No. M81934 (SEQ ID NO: 810)); the cdc25C target sequences were derived from a human cdc25C nucleotide sequence (see GenBank Accession No. NM_001790 (SEQ ID NO: 812); the PRL-3 target sequences are derived from the human PRL-3 nucleotide sequence (see GenBank Accession No. NM_032611 and NM_003479 (SEQ ID NO: 800); the KAP target sequences are derived from the human KAP nucleotide sequence (see GenBank Accession No. L2711 (SEQ ID NO: 796)); the DSP-3 target sequences were derived from the human DSP-3 nucleotide sequence set forth in (SEQ ID NO:778); and the PTPε target sequences were derived from the human PTPε nucleotide sequence (see GenBank Accession No. NM_006504 (SEQ ID NO: 792) and NM_130435) (SEQ ID NO: 794)).

siRNA polynucleotide sequences were selected using the Dharmacon siDESIGN system (Dharmacon Research). These sequences were generated using the following parameters: (1) leader sequences included dinucleotides AA, CA, TA, and GA; (2) the coding region (CR) was scanned; (4) the G+C content varied from approximately 31-63%; (5) overlaps of sequences within different 19 nucleotide sequences were permitted. These sequences were then compared to known human genome sequences using the BLAST program. Potential target sequences were eliminated if 16 or more consecutive nucleotides within the 19-nucleotide target sequence were identified in another human polynucleotide sequence. The remaining 19-nucleotide siRNA sequences are presented in the tables below. Each siRNA sequence represented in Tables 2-12 lists the sequence of the sense strand of the siRNA and its corresponding sequence identifier. For PRL-3, only one sequence (AGACCCGGUGCUGCG-UUAU, SEQ ID NO: 842) was identified by this method. An siRNA polynucleotide as described herein is understood to be composed of the 19 nucleotide sense strand and its complementary (or antisense) strand. In addition, a siRNA polynucleotide of the present invention typically has a dinucleotide overhang at the 3' end of each strand, which may be any two nucleotides. Accordingly, it is noted that each 21-mer sequence below contains a dinucleotide "overhang" at the 3' end, and that the invention herein should be considered to include the 19-mer polynucleotide sequences beginning at the 5' end therein as well as the 21-mer polynucleotide shown in the Tables.

TABLE 2

HUMAN CD45 siRNA POLYNCULEOTIDE SEQUENCES (POST-BLAST)

| 19-Nucleotide Target Sequence | Region | SEQ ID NO. |
|---|---|---|
| CCACCAUCACAGCGAACAC | CR | 179 |
| AGCGCUGUCAUUUCAACCA | CR | 180 |
| ACCACAACAAUAGCUACUA | CR | 181 |
| GCUACUACUCCAUCUAAGC | CR | 182 |
| AAUGCGUCUGUUUCCAUAU | CR | 183 |
| AUGCGUCUGUUUCCAUAUC | CR | 184 |
| UGCGUCUGUUUCCAUAUCU | CR | 185 |
| ACCUUUACUUGUGAUACAC | CR | 186 |
| CAGAUUUCAGUGUGGUAAU | CR | 187 |
| ACCCGAACAUGAGUAUAAG | CR | 188 |
| CCCGAACAUGAGUAUAAGU | CR | 189 |
| CAAGUUUACUAACGCAAGU | CR | 190 |
| GGAGUAAUUACCUGGAAUC | CR | 191 |
| CAUGCCUACAUCAUUGCAA | CR | 192 |
| AUAGUAUGCAUGUCAAGUG | CR | 193 |
| UGAACGUUACCAUUUGGAA | CR | 194 |
| AUGAGUCGCAUAAGAAUUG | CR | 195 |
| UGAGUCGCAUAAGAAUUGC | CR | 196 |
| GAAUUGCGAUUUCCGUGUA | CR | 197 |
| AUUGCGAUUUCCGUGUAAA | CR | 198 |
| GCCAAUCCAUGCAGAUAUU | CR | 199 |
| UUAUAACCGUGUUGAACUC | CR | 200 |
| UAACCGUGUUGAACUCUCU | CR | 201 |
| ACGGAGAUGCAGGGUCAAA | CR | 202 |
| GAUGCAGGGUCAAACUACA | CR | 203 |
| ACCCAGGAAAUACAUUGCU | CR | 204 |
| UGUCCAGAUUACAUCAUUC | CR | 205 |
| AUGCCUUCAGCAAUUUCUU | CR | 206 |
| CAGGAACCUAUAUCGGAAU | CR | 207 |
| GGAACCUAUAUCGGAAUUG | CR | 208 |
| ACCUAUAUCGGAAUUGAUG | CR | 209 |
| GUGGAUGUUUAUGGUUAUG | CR | 210 |
| GGCGACAGAGAUGCCUGAU | CR | 211 |
| GAGGCCCAGUACAUCUUGA | CR | 212 |
| GGCCCAGUACAUCUUGAUC | CR | 213 |
| GCUACUGGAAACCUGAAGU | CR | 214 |
| ACCUGAAGUGAUGAUUGCU | CR | 215 |
| AGUUGACCUGAAAGACACA | CR | 216 |
| ACUAUACCCUUCUGUCU | CR | 217 |
| CUUUAUACCCUUCUGUGUCUU | CR | 218 |
| GGAAAGACUCUCGAACUGU | CR | 219 |
| ACCCAAGGAAUUAAUCUCU | CR | 220 |
| CCCAAGGAAUUAAUCUCUA | CR | 221 |
| UGAUUCAGGUCGUCAAACA | CR | 222 |
| GGGAUGGAUCUCAGCAAAC | CR | 223 |
| UCUCAGCAAACGGGAAUAU | CR | 224 |
| UUCGAGCAAUAUCAAUUCC | CR | 225 |
| CCUACCCUGCUCAGAAUGG | CR | 226 |

TABLE 3

HUMAN SHP-2 siRNA POLYNCULEOTIDE SEQUENCES (POST-BLAST)

| 19-Nucleotide Target Sequence | Region | SEQ ID NO. |
|---|---|---|
| AUGGAGCUGUCACCCACAU | CR | 227 |
| UGGAACAUCACGGGCAAUU | CR | 228 |
| GCAAUGACGGCAAGUCUAA | CR | 229 |
| AUGACGGCAAGUCUAAAGU | CR | 230 |
| UGACGGCAAGUCUAAAGUG | CR | 231 |
| GUCUAAAGUGACCCAUGUU | CR | 232 |

TABLE 3-continued

HUMAN SHP-2 siRNA POLYNCULEOTIDE SEQUENCES (POST-BLAST)

| 19-Nucleotide Target Sequence | Region | SEQ ID NO. |
|---|---|---|
| UGAUUCGCUGUCAGGAACU | CR | 233 |
| CGACGUUGGUGGAGGAGAA | CR | 234 |
| ACGGUUUGAUUCUUUGACA | CR | 235 |
| UUCUUUGACAGAUCUUGUG | CR | 236 |
| GAAUCCUAUGGUGGAAACA | CR | 237 |
| AUCCUAUGGUGGAAACAUU | CR | 238 |
| UCCUAUGGUGGAAACAUUG | CR | 239 |
| CAGUACUACAACUCAAGCA | CR | 240 |
| UUUGAGACACUACAACAAC | CR | 241 |
| AACUUCUCUACAGCCGAAA | CR | 242 |
| ACAUCCUGCCCUUUGAUCA | CR | 243 |
| UCAUACCAGGGUUGUCCUA | CR | 244 |
| UACCAGGGUUGUCCUACAC | CR | 245 |
| UUUGAAACCAAGUGCAACA | CR | 246 |
| AGAGUUACAUUGCCACACA | CR | 247 |
| GAGUUACAUUGCCACACAA | CR | 248 |
| AAACACGGUGAAUGACUUU | CR | 249 |
| CUGGCCUGAUGAGUAUGCU | CR | 250 |
| UGGCGUCAUGCGUGUUAGG | CR | 251 |
| UGCGUGUUAGGAACGUCAA | CR | 252 |
| UGACUAUACGCUAAGAGAA | CR | 253 |
| CUAUACGCUAAGAGAACUU | CR | 254 |
| GGUUGGACAAGGGAAUACG | CR | 255 |
| GAACGGUCUGGCAAUACCA | CR | 256 |
| CGGUCUGGCAAUACCACUU | CR | 257 |
| AAGGUGUUGACUGCGAUAU | CR | 258 |
| AGGUGUUGACUGCGAUAUU | CR | 259 |
| GGUGUUGACUGCGAUAUUG | CR | 260 |
| UAUGGCGGUCCAGCAUUAU | CR | 261 |
| UGGCGGUCCAGCAUUAUAU | CR | 262 |
| AACACUACAGCGCAGGAUU | CR | 263 |
| ACACUACAGCGCAGGAUUG | CR | 264 |
| GCGCAGGAUUGAAGAAGAG | CR | 265 |
| GAGGAAAGGGCACGAAUAU | CR | 266 |
| GGAAAGGGCACGAAUAUAC | CR | 267 |
| GGGCACGAAUAUACAAAUA | CR | 268 |
| AAACGUGGGCCUGAUGCAA | CR | 269 |
| ACGUGGGCCUGAUGCAACA | CR | 270 |

TABLE 4

HUMAN CDC14A siRNA POLYNCULEOTIDE SEQUENCES (POST-BLAST)

| 19-Nucleotide Target Sequence | Region | SEQ ID NO. |
|---|---|---|
| GCACAGUAAAUACCCACUA | CR | 271 |
| CUAUUUCUCCAUCGAUGAG | CR | 272 |
| ACUUGGCAAUGGUGUACAG | CR | 273 |
| GGUGCCUAUGCAGUAAUCU | CR | 274 |
| UCUCACCAUUCUCGACUGU | CR | 275 |
| AAGGGAUUACAACAUGGAU | CR | 276 |
| AGGGAUUACAACAUGGAUU | CR | 277 |
| GGGAUUACAACAUGGAUUU | CR | 278 |
| GAAUGGUUAUCCUCUUCAC | CR | 279 |
| GCAUAAUGUGACUGCAGUU | CR | 280 |
| CGCUGGCUUCGAGCACUAU | CR | 281 |
| GCACACCCAGUGACAACAU | CR | 282 |
| ACAUCGUGCGAAGGUUCCU | CR | 283 |
| AGAACAGGGACAUUGAUAG | CR | 284 |
| GAACAGGGACAUUGAUAGC | CR | 285 |
| GGGACAUUGAUAGCCUGUU | CR | 286 |
| CAUUGAUAGCCUGUUAUGU | CR | 287 |
| CUACAGGUUUACACAUGCU | CR | 288 |
| AAAUCGACCAUCCAGUGAA | CR | 289 |
| AAUCGACCAUCCAGUGAAG | CR | 290 |
| UCGACCAUCCAGUGAAGGA | CR | 291 |
| AAAUUCUUUCUGGCCUAGA | CR | 292 |
| UGUCUAUUGGUGGAAAUCU | CR | 293 |
| ACGAUUUGGAGAGGUAAGU | CR | 294 |
| CGAUUUGGAGAGGUAAGUU | CR | 295 |

TABLE 5

HUMAN CDC14B siRNA POLYNCULEOTIDE SEQUENCES (POST-BLAST)

| 19-Nucteotide Target Sequence | Region | SEQ ID NO. |
|---|---|---|
| GAGACAUCCUAUAUUCCUU | CR | 296 |
| AUACCAGACCGAUUUAUUG | CR | 297 |
| UACCAGACCGAUUUAUUGC | CR | 298 |
| GACCGAUUUAUUGCCUUCU | CR | 299 |
| AAGGAUGUAUGAUGCCAAA | CR | 300 |
| AGGAUGUAUGAUGCCAAAC | CR | 301 |
| GGAUGUAUGAUGCCAAACU | CR | 302 |
| CGGAUGCUGGCUUCGAUCA | CR | 303 |
| UGCCAUUGUCAAAGAAUUC | CR | 304 |
| GGGUGCCAUUGCAGUACAU | CR | 305 |
| GACCUGGCUCGGUGAUUGG | CR | 306 |
| CCCGAACCGUACAGUGAUG | CR | 307 |
| ACCGUACAGUGAUGAUGAC | CR | 308 |
| UAGACUUCGGGCCUUGAAA | CR | 309 |
| ACAAACGCUAUUCCUCUCA | CR | 310 |

TABLE 6

HUMAN CDC25A siRNA POLYNCULEOTIDE SEQUENCES (POST-BLAST)

| 19-Nucleotide Target Sequence | Region | SEQ ID NO. |
|---|---|---|
| GGGUCUGGGCAGUGAUUAU | CR | 311 |
| GCAACCACUGGAGGUGAAG | CR | 312 |
| AUCCUAUGAGAAGAAUACA | CR | 313 |
| UCCUAUGAGAAGAAUACAU | CR | 314 |
| AAAGCUGUUGGGAUGUAGU | CR | 315 |
| UUCUGAUUCUCUUGACCAU | CR | 316 |
| GAAGCCAGUAAGACCUGUA | CR | 317 |
| CAGCCACUUUGUCUGAUGA | CR | 318 |
| AACCUUGACAACCGAUGCA | CR | 319 |
| CAACCGAUGCAAGCUGUUU | CR | 320 |
| ACCGAUGCAAGCUGUUUGA | CR | 321 |
| CUCGGUCAGUGUUGAAGAG | CR | 322 |
| ACGUUCUCAAGAGGAGUCU | CR | 323 |
| GUCAACUAAUCCAGAGAAG | CR | 324 |
| AGGCCCAUGAGACUCUUCA | CR | 325 |
| AGGGACCUUAUAGGAGACU | CR | 326 |
| GGGACCUUAUAGGAGACUU | CR | 327 |
| GACUUCUCCAAGGGUUAUC | CR | 328 |
| GUUUGUUAUCAUCGACUGU | CR | 329 |
| CUGUCGAUACCCAUAUGAA | CR | 330 |
| GAAGCCCAUUGUACCUACU | CR | 331 |
| AGCCCAUUGUACCUACUGA | CR | 332 |
| GCCCAUUGUACCUACUGAU | CR | 333 |
| UGGCAAGCGUGUCAUUGUU | CR | 334 |
| AGCGUGUCAUUGUUGUGUU | CR | 335 |
| UGUGCCGGUAUGUGAGAGA | CR | 336 |
| GAGAGAUCGCCUGGGUAAU | CR | 337 |
| GAGAUCGCCUGGGUAAUGA | CR | 338 |
| GAUCGCCUGGGUAAUGAAU | CR | 339 |

TABLE 7

HUMAN CDC25B siRNA POLYNCULEOTIDE SEQUENCES (POST-BLAST)

| 19-Nucleotide Target Sequence | Region | SEQ ID NO. |
|---|---|---|
| AUCCUCCCUGUCGUCUGAA | CR | 340 |
| UCCUCCCUGUCGUCUGAAU | CR | 341 |
| UGGCGGAGCAGACGUUUGA | CR | 342 |
| CGUUUGAACAGGCCAUCCA | CR | 343 |
| GCCGGAUCAUUCGAAACGA | CR | 344 |
| UCAUUCGAAACGAGCAGUU | CR | 345 |
| GUCUAUGCCGGAUGGAUUU | CR | 346 |
| UGCGGAUGGAUUUGUCUU | CR | 347 |
| AAAGGACCUCGUCAUGUAC | CR | 348 |

TABLE 7-continued

HUMAN CDC25B siRNA POLYNCULEOTIDE SEQUENCES (POST-BLAST)

| 19-Nucleotide Target Sequence | Region | SEQ ID NO. |
|---|---|---|
| AAUCACUGUGUCACGAUGA | CR | 349 |
| AUCACUGUGUCACGAUGAG | CR | 350 |
| GAGCUGAUUGGAGAUUACU | CR | 351 |
| GCUGAUUGGAGAUUACUCU | CR | 352 |
| CUCUAAGGCCUUCCUCCUA | CR | 353 |
| CAGACAGUAGACGGAAAGC | CR | 354 |
| AGCACCAAGACCUCAAGUA | CR | 355 |
| GAAACGAUGGUGGCCCUAU | CR | 356 |
| AACGAUGGUGGCCCUAUUG | CR | 357 |
| CGCCGAGAGCUUCCUACUG | CR | 358 |

TABLE 8

HUMAN CDC25C siRNA POLYNCULEOTIDE SEQUENCES (POST-BLAST)

| 19-Nucleotide Target Sequence | Region | SEQ ID NO. |
|---|---|---|
| GAACUCCAGUGGGCAAAUU | CR | 359 |
| UUUAGCUGGGAUGCAAAUG | CR | 360 |
| UUCAAGGACAACACAAUAC | CR | 361 |
| ACACAAUACCAGAUAAAGU | CR | 362 |
| CACAAUACCAGAUAAAGUU | CR | 363 |
| GGAAGGGCUUAUGUUUAAA | CR | 364 |
| CACCAAGAUCUGAAGUAUG | CR | 365 |
| AGUAUGUCAACCCAGAAAC | CR | 366 |
| GUAUGUCAACCCAGAAACA | CR | 367 |
| UGUCAUUGAUUGUCGCUAU | CR | 368 |
| UUGAUUGUCGCUAUCCAUA | CR | 369 |
| UUGUCGCUAUCCAUAUGAC | CR | 370 |
| UCCAGGGAGCCUUAAACUU | CR | 371 |
| GGGGAGCCUUAAACUAUAU | CR | 372 |
| GUCAGGAAGAACUGUUUAA | CR | 373 |
| AGAAGCCAUCGUCCCUUU | CR | 374 |
| GAAGCCCAUCGUCCCUUUG | CR | 375 |
| AGCCCAUCGUCCCUUUGGA | CR | 376 |
| CACCCAGAAGAGAAUAAUC | CR | 377 |
| UUGUACUACCCAGAGCUAU | CR | 378 |
| CUACCCAGAGCUAUAUAUC | CR | 379 |
| CCCAGAGCUAUAUAUCCUU | CR | 380 |
| UAUAUGGAACUGUGUGAAC | CR | 381 |
| UAUGGAACUGUGUGAACCA | CR | 382 |
| CAGAGCUACUGCCCUAUGC | CR | 383 |
| GAGCUACUGCCCUAUGCAU | CR | 384 |
| GCUACUGCCCUAUGCAUCA | CR | 385 |

TABLE 9

HUMAN KAP siRNA POLYNCULEOTIDE SEQUENCES (POST-BLAST)

| 19-Nucleotide Target Sequence | Region | SEQ ID NO. |
|---|---|---|
| GAUGAAGAGCCUAUUGAAG | CR | 386 |
| AGAUGAACAGACUCCAAUU | CR | 387 |
| GAUGAACAGACUCCAAUUC | CR | 388 |
| UCACCCAUCAUCAUCCAAU | CR | 389 |
| GAGCUUACAACCUGCCUUA | CR | 390 |
| CACUGCUAUGGAGGACUUG | CR | 391 |
| UCACCAGAGCAAGCCAUAG | CR | 392 |
| CCAGAGCAAGCCAUAGACA | CR | 393 |
| CAGCCUGCCAGACCUAAGA | CR | 394 |
| GUUUCGGGACAAAUUAGCU | CR | 395 |
| AAUUAGCUGCACAUCUAUC | CR | 396 |
| AUUAGCUGCACAUCUAUCA | CR | 397 |
| UUAGCUGCACAUCUAUCAU | CR | 398 |

TABLE 10

HUMAN DSP-3 siRNA POLYNUCLEOTIDE SEQUENCES (POST-BLAST)

| 19-Nucleotide Target Sequence | Region | SEQ ID NO. |
|---|---|---|
| GAGACGCGGAACAAUUGAG | CR | 399 |
| AGAACAAGGUGACACAUAU | CR | 400 |
| GAACAAGGUGACACAUAUU | CR | 401 |
| GCAGCGGAUUCACCAUCUC | CR | 402 |
| GCGGAUUCACCAUCUCAAA | CR | 403 |
| CACUGGUGAUCGCAUACAU | CR | 404 |
| GUAUCGGCAGUGGCUGAAG | CR | 405 |

TABLE 11

HUMAN PTP EPSILON siRNA POLYNUCLEOTIDE SEQUENCES (POST-BLAST)

| 19-Nucleotide Target Sequence | Region | SEQ ID NO. |
|---|---|---|
| GAUCCGCCGACGACUGCAA | CR | 406 |
| GUUUCGGGAGGAGUUCAAC | CR | 407 |
| AUGACCAUUCUAGGGUGAU | CR | 408 |
| CCAUUCUAGGGUGAUUCUG | CR | 409 |
| CAUAGAUGGUUACAAAGAG | CR | 410 |
| AACAGGAAACGGUUAACGA | CR | 411 |
| GGAAACGGUUAACGACUUC | CR | 412 |
| CCAUCGUCAUGUUAACAAA | CR | 413 |
| CUACACCAUCCGGAAGUUC | CR | 414 |
| UCCGGAAGUUCUGCAUACA | CR | 415 |
| GAAAGUAAAGACGCUCAAC | CR | 416 |
| GCGCCCUCAGAUGGUUCAA | CR | 417 |
| CGGAUAUGCAGUACACGUU | CR | 418 |
| CCACCCACUUCGACAAGAU | CR | 419 |
| CAAAUGUCCGGAUCAUGAA | CR | 420 |
| CAUGAGGACGGCAACUUG | CR | 421 |
| UGACUUCAACCGAGUGAUC | CR | 422 |
| ACCGAGUGAUCCUUUCCAU | CR | 423 |
| AGAAUACACAGACUACAUC | CR | 424 |
| GACUACAUCAACGCAUCCU | CR | 425 |
| UCAACGCAUCCUUCAUAGA | CR | 426 |
| CACACGGUUGAGGACUUCU | CR | 427 |
| AAUCCCACACUAUCGUGAU | CR | 428 |
| AUCCCACACUAUCGUGAUG | CR | 429 |
| ACCGAGGGCUCAGUUACUC | CR | 430 |
| CCGAGGGCUCAGUUACUCA | CR | 431 |
| CUCAUGGAGAAAUAACGAU | CR | 432 |
| UGGAGAAAUAACGAUUGAG | CR | 433 |
| GCCAUCAGUAUACGAGACU | CR | 434 |
| UCAGUAUACGAGACUUUCU | CR | 435 |
| GGGCAAAGGCAUGAUUGAC | CR | 436 |
| GCUGGGCGAACAGGUACAU | CR | 437 |
| CUUCAGAGACCACAUAUGG | CR | 438 |

EXAMPLE 3

Decreased Activation of JNK in the Presence of siRNA Specific for DSP-3

This Example describes the effect on JNK activation by sequence-specific siRNA interference of DSP-3 polypeptide expression.

HeLa cells were transfected with 60 pmoles of DSP3.1 siRNA (SEQ ID NO:3) or 60 pmoles CD45.2 (SEQ ID NO:33) as described in Example 1. After the incubation following transfection, cells were stimulated with 10 ng/ml TNF-α or 10 ng/ml EGF for 10 minutes or with 500 mM sorbitol for 30 minutes, which are known stimulators of the JNK signal transduction pathway (WO 01/21812; Shen et al. *Proc. Natl. Acad. Sci.* 98:13613-18 (2001)). After the stimulators were decanted, the 6-well plate of cells was frozen. The cells were treated with 0.5 ml Extraction Buffer (20 mM Tris, pH 8, 136 mM NaCl, 50 mM NaF; 1 mM V04; 0.2 mM EDTA, 0.2 mM EGTA, 20 nM Calyculin, 10% glycerol, 0.5% nonidet P40, 1 µg/ml of aprotinin, pepstatin, and leupeptin; and 1 mM Benzamidine) (4° C.). When the cells had partially thawed, the wells of the plates were scraped and the cells were collected. The wells were washed 3× with Extraction Buffer and the washes were combined with the cells. After centrifugation of the extracted cells, the supernatants were decanted. The protein concentration of each extract was determined by the Bradford protein assay. Volumes of the different extracts were adjusted with Extraction Buffer to the concentration of the extract having the lowest protein concentration.

Figure 3:
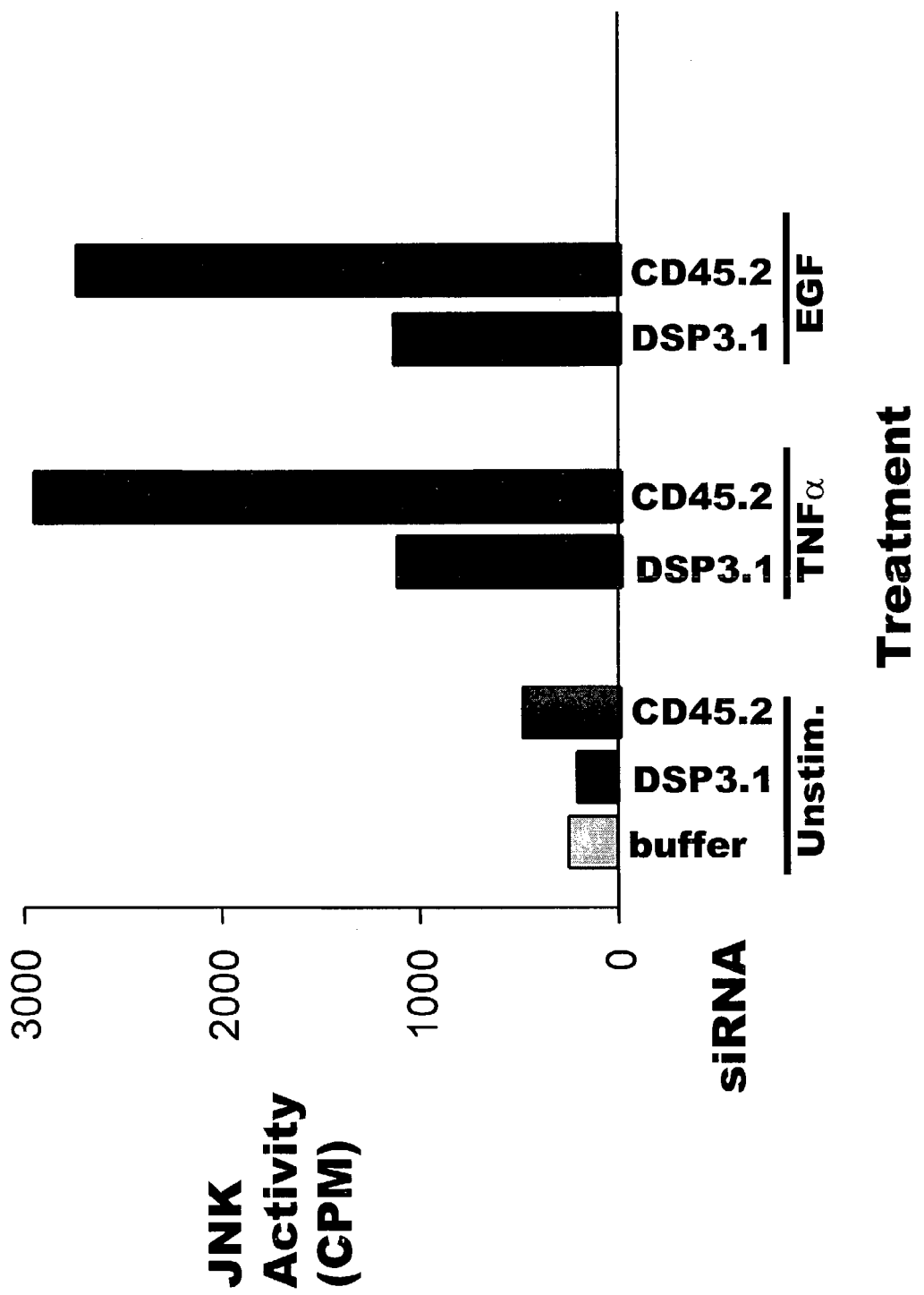
FIG. 3 shows the effect on JNK activation by sequence-specific siRNA interference of DSP-3 polypeptide expression. HeLa cells were co-transfected with a DSP-3 recombinant expression vector and DSP3.1 siRNA (SEQ ID NO:3) or 60 pmoles (100 nM final) CD45.2 (SEQ ID NO: 33). After transfection, cells were stimulated with either tumor necrosis factor-alpha (TNF-α) or epidermal growth factor (EGF) or were unstimulated (Unstim.).
Figure 4:
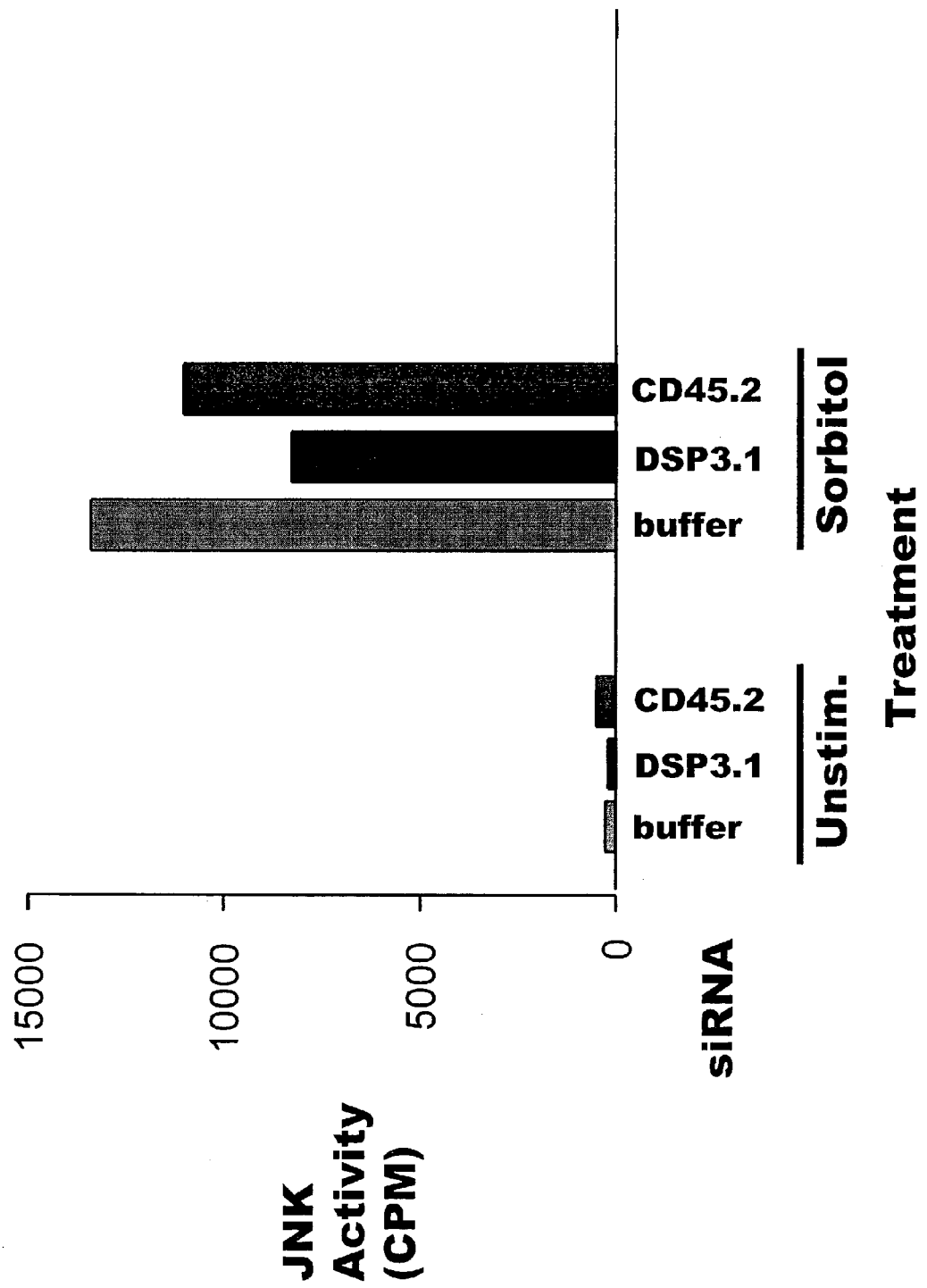
FIG. 4 shows the effect on JNK activation by sequence-specific siRNA interference of DSP-3 polypeptide expression. HeLa cells were co-transfected with a DSP-3 recombinant expression vector and DSP3.1 siRNA (SEQ ID NO: 3) or 60 pmoles (100 nM final) CD45.2 (SEQ ID NO: 33). After transfection, cells were stimulated with sorbitol.

JUN, a substrate of JNK, conjugated to glutathione (GSH) (GST-cJUN) (Shen et al., supra) in 20 mM Tris, pH 7.2, 1 nM EDTA, and 150 mM NaCl was combined with 200-250 µl of Glutathione-Sepharose (Amersham Biosciences, Piscataway, N.J.). After mixing for 45 minutes at 4° C., the conjugated sepharose beads were washed twice in Extraction Buffer and then resuspended in 1 ml of Extraction Buffer.

cJUN-Sepharose (20 µl) was added to each cell extract sample. The mixtures were gently mixed for 2 hours at 4° C., followed by one wash in 1 ml Extraction Buffer and once in 1 ml kinase buffer (20 mM Pipes, pH 7.2, 10 mM $MgCl_2$, 1 mM DTT, 0.1% Triton X-100, and 1 MM sodium vanadate). The mixtures were centrifuged and the pellets were kept on ice. ATP mix (300° C./ml of [$\gamma$-$^{32}$P]ATP (3000 Ci/mmole) in kinase buffer) was incubated in a heat block to bring the solution to 30° C. ATP mix (15 µl) was added to each cold cJUN-Sepharose pellet at time intervals of 20 seconds. After the ATP mix was added, each sample was vortexed gently for 5 seconds and then placed in the 30° C. heat block. Each sample was gently mixed again for 5 seconds at 20-second intervals. After 20 minutes, the reactions were stopped at 20-second intervals with 15 µl 2×SDS-PAGE sample buffer. The samples were immediately heated at 100° C. for 5 minutes, then mixed and frozen at −20° C. The extracts were thawed and applied to 8-16% NOVEX® gels. After electrophoresis, the gels were dried and the cJUN band was cut from the gel and the radioactivity was counted (Cerenkov measurement). As shown in FIGS. 3 and 4, JNK activation as measured by the presence of phosphorylated JUN was mediated less by cells transfected with siRNA specific for DSP-3 than in cells transfected with a non-specific siRNA.

Figure 5:
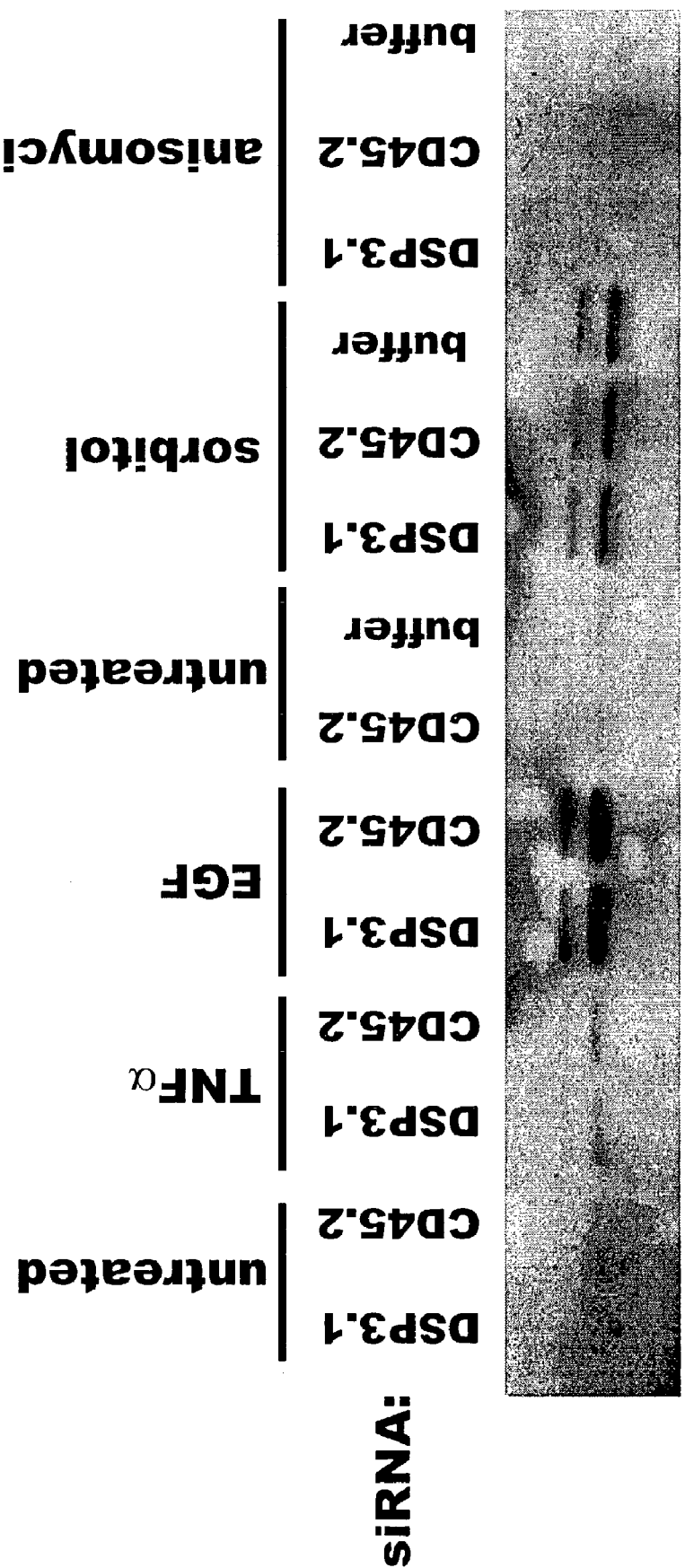
FIG. 5 presents an immunoblot analysis of ERK phosphorylation in HeLa cells co-transfected with a DSP-3 recombinant expression vector and DSP-3 specific siRNA DSP3.1, non-specific CD45.2 siRNA, or siRNA annealing buffer and then stimulated with TNF-α, EGF, sorbitol, and anisomycin. Lane 1: unstimulated cells transfected with DSP3.1 siRNA; lane 2: unstimulated cells transfected with CD45.2 siRNA; lane 3: cells transfected with DSP3.1 siRNA and stimulated with TNF-α; lane 4: cells transfected with CD45.2 siRNA and stimulated with TNF-α; lane 5: cells transfected with DSP3.1 siRNA and stimulated with EGF; lane 6: cells transfected with CD45.2 siRNA and stimulated with EGF; lane 7: unstimulated cells transfected with CD45.2 siRNA; lane 8: unstimulated cells transfected with siRNA annealing buffer; lane 9: cells transfected with DSP3.1 siRNA and stimulated with sorbitol; lane 10: cells transfected with CD45.2 siRNA and stimulated with sorbitol; lane 11: cells transfected with siRNA annealing buffer and stimulated with sorbitol; lane 12: cells transfected with DSP3.1 siRNA and stimulated with anisomycin; lane 13: cells transfected with CD45.2 siRNA and stimulated with anisomycin; lane 14: cells transfected with siRNA annealing buffer and stimulated with anisomycin.

Because EGF induces a signaling pathway involving the ERK MAP kinase family, the effect on ERK phosphorylation in HeLa cells transfected with DSP-3 specific siRNA was determined. Transfection of HeLa cells and stimulation of the JNK signaling pathway was performed as in the previous experiment. Additional transfected cell cultures were stimulated with anisomycin. Phosphorylation of ERK was determined in a similar manner as described above for cJUN except that after electrophoresis of the cell extract samples, the proteins separated in the gel were transferred to a PVDF membrane. The immunoblot was probed with an anti-phospho-ERK antibody (1:1000) followed by incubation with the appropriate HRP-conjugated reagent and detection by chemiluminescence. As shown in FIG. 5, phosphorylation of ERK induced by stimulation of the cells with EGF and sorbitol was not affected by interference of DSP-3 polypeptide expression by specific siRNA DSP3.1.

EXAMPLE 4

Interference of Expression and Function of Cell Division Cycle Proteins by Specific siRNA This example describes interference of expression of cell division cycle (cdc) proteins, cdc14a, cdc14b, and cdc25A, cdc25B, and cdc25C polypeptides by sequence specific siRNA polynucleotides. The effect on the function of these polypeptides in the presence of siRNA was also determined.

Interference with Cell Division Cycle Protein Expression by Specific siRNA

Two siRNA sequences that were specific for cdc14a polynucleotide (SEQ ID NO:802) encoding a cdc14a polypeptide (SEQ ID NO: 803) and two siRNA sequences specific for cdc14b polynucleotide (SEQ ID NO:805) encoding a cdc14b polypeptide (SEQ ID NO:36) were designed using the criteria described in Example 1. Recombinant expression vectors containing polynucleotide sequences encoding FLAG®-tagged cdc14a polypeptide and FLAG®-tagged cdc14b polypeptide were prepared essentially according to methods described in Example 2 with the following exceptions. 293-HEK cells were cultured in 35 mm culture dishes and were transfected with FLAG vectors at a concentration of 1 µg per well.

Figure 6:
FIG. 6 shows an immunoblot analysis of FLAG®-tagged cdc14a expression in 293-HEK cells co-transfected with cdc14a.2 (SEQ ID NO: 439)(lane 3); cdc14a.3 (SEQ ID NO: 444)(lane 4); cdc14a.4 (land 5); cdc14a.5 (SEQ ID NO: 449) (lane 6); DSP3.1 (SEQ ID NO: 3) (lane 7); DSP3.2 (SEQ ID NO: 8)(lane 8); cdc14b.3 (SEQ ID NO: 454)(lane 9); cdc14b.4 (SEQ ID NO: 459)(lane 10); MKP.2 (SEQ ID NO: 23)(lane 11); CD45.3 (lane 12); no siRNA (lane 2). Untransfected cells were prepared as a control (lane 1). Expression was detected using an anti-FLAG® antibody (Sigma-Aldrich).

293-HEK cells were co-transfected with FLAG®-tagged cdc14a expression vector and the following siRNAs at 20 nM per well: cdc14a.2 (5'-caucugugagaacaccgaatt-3', SEQ ID NO: 439) (see also related SEQ ID NOS: 440-443)); cdc14a.3 (5'-cuuggcaauggguguacagatt-3', SEQ ID NO: 444) (see also related (SEQ ID NOS: 445-448)); cdc14a.4,), cdc14a.5 (5'-gcacaguaaauacccacuatt-3', SEQ ID NO: 449) (see also related (SEQ ID NOS: 450-453)); DSP3.1 (SEQ ID NO: 3) (see also related (SEQ ID NOS: 4-8); DSP3.2 (SEQ ID NO: 9) (see also related (SEQ ID NOS: 10-13); cdc14b.3 (5'-caagcaaaugcugccuucctt-3', SEQ ID NO: 454 (see also related SEQE ID NOS: 455-458)); cdc14b.4 (5'-gagccagacu-ugaaagggtt-3', SEQ ID NO: 459 (see also related SEQ ID NOS: 460-463)); MKP.2 (SEQ ID NO: 23) see also related (SEQ ID NOS: 24-27); and CD45.3 (negative control). Controls included 293-HEK cells that were not transfected with any vector or siRNA and 293-HEK cells transfected with FLAG®-tagged cdc14a in the presence of siRNA annealing buffer. The level of expression in each sample was analyzed by immunoblot as described in Example 2 using an anti-FLAG® antibody. As shown in FIG. 6, specific siRNAs, cdc14a.2, cdc14a.3, and cdc14a.5 interfered with expression of cdc14a polypeptide most effectively.

Figure 7:
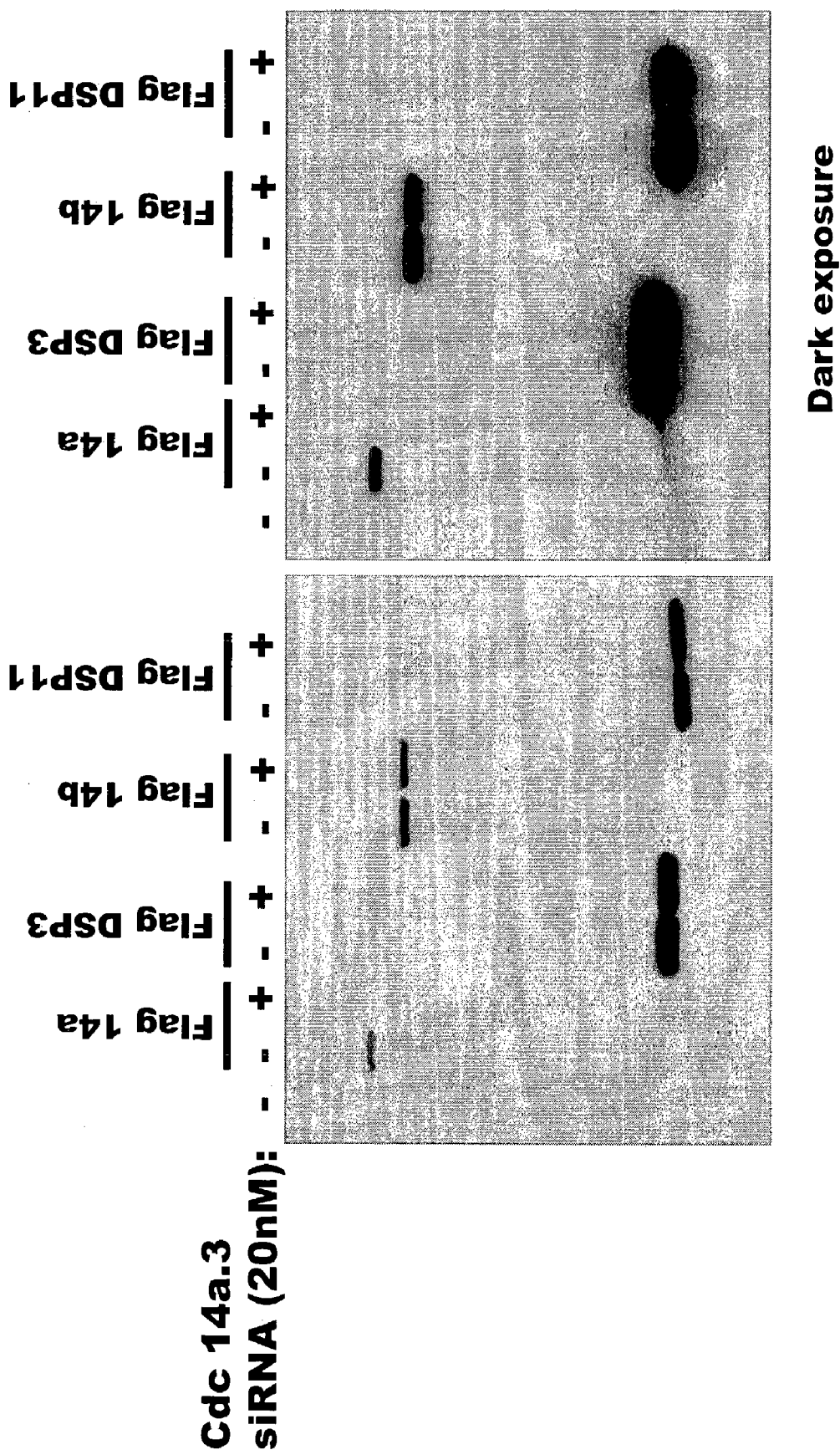
FIG. 7 presents an immunoblot of expression of FLAG®-tagged dual specificity phosphatases in 293-HEK cells that were co-transfected with cdc14a.3 siRNA (denoted by +). Lanes 2 and 3: expression of FLAG®-tagged cdc14a; lanes 4 and 5: expression of FLAG®-tagged DSP-3; lanes 6 and 7: expression of FLAG®-tagged cdc14b; lanes 8 and 9: FLAG®-tagged DSP-11. The immunoblot to the right is an over-exposure of the immunoblot on the left to detect low concentrations of expressed polypeptides.

Specificity of cdc14a.3 siRNA for interfering with expression of cdc14a and not other dual specificity phosphatases was shown by co-transfecting cdc14a.3 siRNA with FLAG®-tagged cdc14a (1 µg per 35 mm well of cells), FLAG®-tagged DSP-3, FLAG®tagged cdc14b, and FLAG®-tagged DSP-11. A FLAG® recombinant expression construct containing a polynucleotide sequence (SEQ ID NO: 778) encoding a DSP-3 polypeptide (SEQ ID NO: 779) was prepared as described for constructing other FLAG vectors. 293-HEK cell transfections and analysis of polypeptide expression levels were performed as described in Example 2. FIG. 7 shows that siRNA cdc14a.3 interfered with expression of only the cdc14a dual specificity phosphatase.

Figure 8:
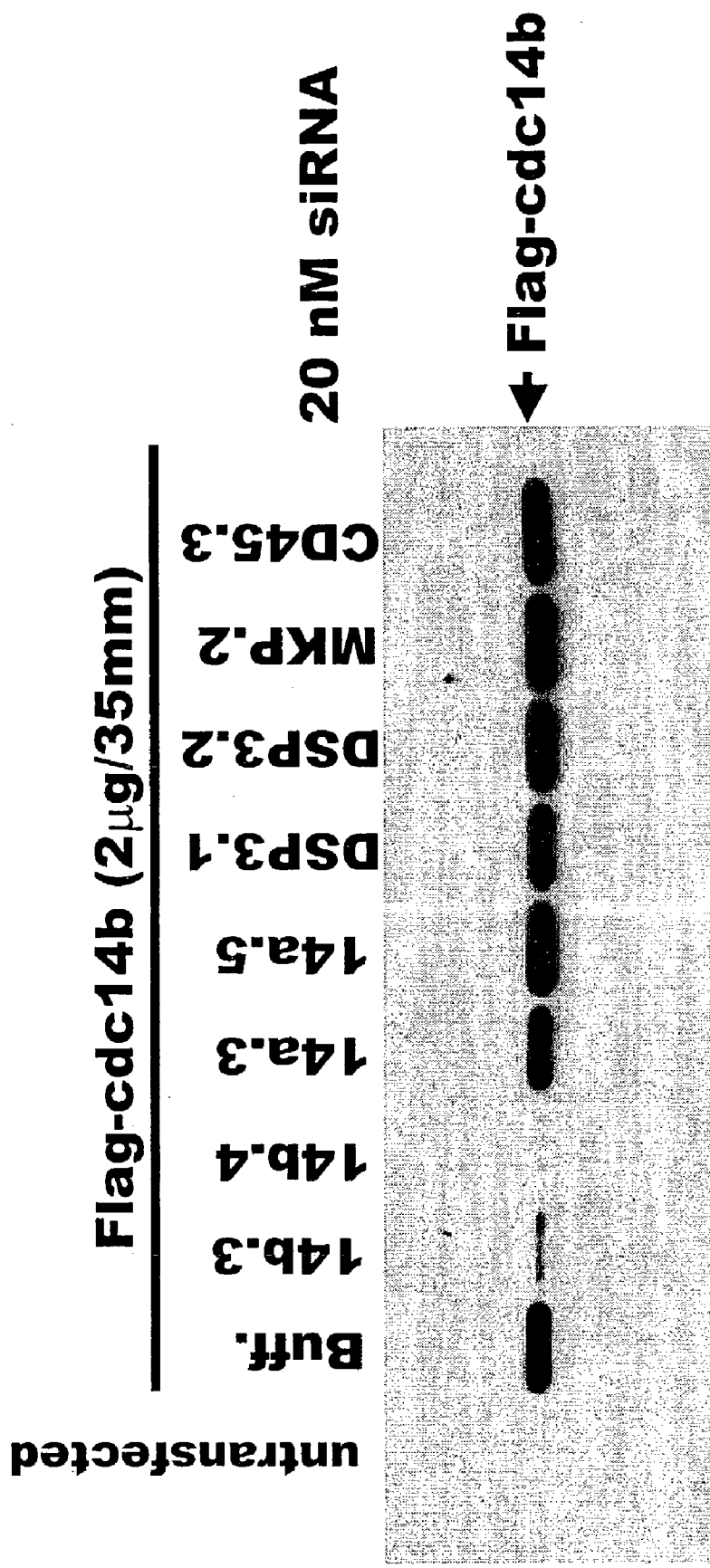
FIG. 8 shows an immunoblot analysis of FLAG®-tagged cdc14b expression in 293-HEK cells co-transfected with cdc14b.3 (SEQ ID NO: 454)(lane 3); cdc14b.4 (SEQ ID NO: 459)(lane 4); cdc14a.3 (SEQ ID NO: 444)(land 5); cdc14a.5 (SEQ ID NO: 449)(lane 6); DSP3.1 (SEQ ID NO: 3)(lane 7); DSP3.2 (SEQ ID NO: 8)(lane 8); MKP.2 (SEQ ID NO: 23) (lane 9); CD45.3 (lane 10); no siRNA (lane 2). Untransfected cells were prepared as a control (lane 1). Expression was detected using an anti-FLAG® antibody (Sigma-Aldrich).

293-HEK cells were co-transfected with FLAG®-tagged cdc14b expression vector (2 µg/35 mm well) and the following siRNAs at 20 nM per well: cdc14b.3 (SEQ ID NO: 454); cdc14b.4 (SEQ ID NO: 449); cdc14a.3 (SEQ ID NO: 444)); cdc14a.5 (SEQ ID NO: 449)); DSP3.1 (SEQ ID NO: 3); DSP3.2 (SEQ ID NO: 8); MKP.2 (SEQ ID NO: 23); and CD45.3. Controls included 293-HEK cells that were not transfected with any vector or siRNA and 293-HEK cells transfected with FLAG®-tagged cdc14b in the presence of siRNA annealing buffer. The level of expression in each sample was analyzed by immunoblot as described in Example 2 using an anti-FLAG® antibody. As shown in FIG. 8, only specific siRNAs, cdc14b.3 and cdc14b.4 interfered with expression of cdc14b polypeptide.

Figure 9:
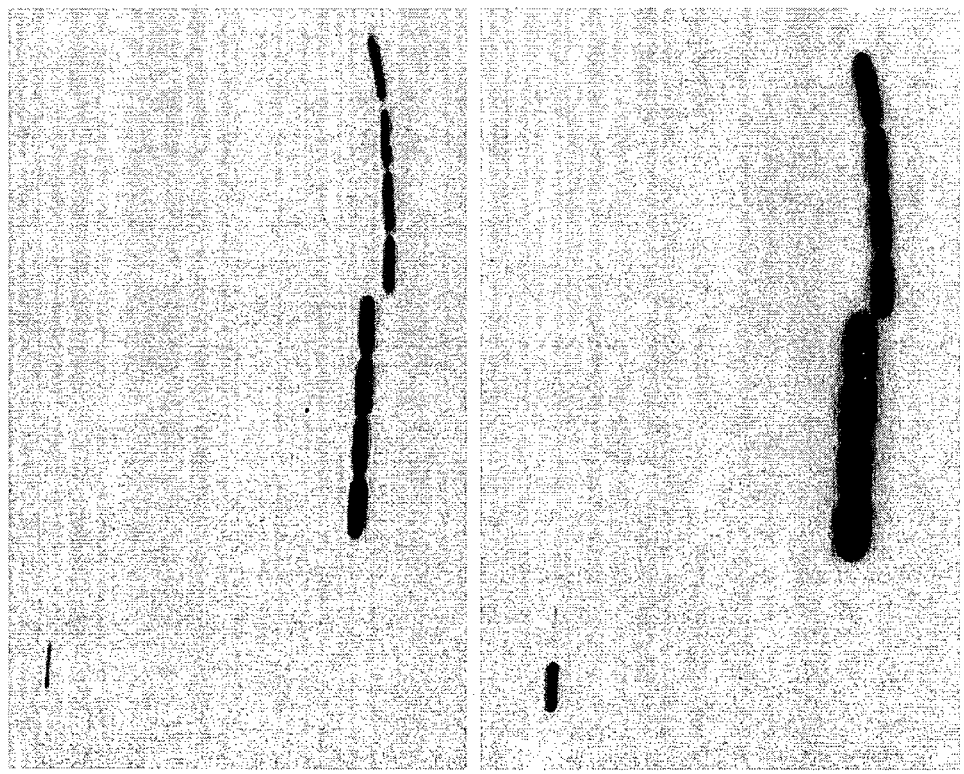
FIG. 9 presents an immunoblot of expression of FLAG®-tagged dual specificity phosphatases in 293-HEK cells co-transfected with either cdc14a or cdc14b specific siRNAs. Expression of the phosphatases was detected with an anti-FLAG® antibody. 293-HEK cells were transfected as follows: no expression vector or siRNA (lane 1); FLAG®-tagged cdc14b only (lane 2); FLAG®-tagged cdc14b and cdc14b.3 siRNA (lane 3); FLAG®-tagged cdc14b and cdc14b.4 (SEQ ID NO: 459)(lane 5); FLAG®-tagged DSP-3 only (lane 5); FLAG®-tagged DSP-3 and cdc14b.3 siRNA (lane 6); FLAG®-tagged DSP3 and cdc14b.4 siRNA (lane 7); FLAG®-tagged DSP-3 and cdc14a.5 (SEQ ID NO: 449) siRNA (lane 8); FLAG®-tagged DSP-11 only (lane 9); FLAG®-tagged DSP-11 and cdc14b.3 siRNA (land 10); FLAG®-tagged DSP-11 and cdc14b.4 siRNA (lane 11); and FLAG®-tagged DSP-11 and cdc14a.5 siRNA.

Specificity of cdc14b.3 and cdc14b.4 siRNAs for interfering with expression of cdc14b and not other dual specificity phosphatases was shown by co-transfecting the siRNAs with FLAG®-tagged cdc14b (2 µg per 35 mm well), FLAG®-tagged DSP-3, and FLAG®-tagged DSP-11. Cells transfected with FLAG®-tagged DSP-3 and FLAG®-tagged DSP-11 were also co-transfected with cdc14a.5 siRNA. 293-HEK cell transfections and analysis of polypeptide expression levels were performed as described in Example 2. FIG. 9 shows that cdc14b.3 and cdc14b.4 siRNAs interfered with expression of only the cdc14b dual specificity phosphatase.

Figure 10:
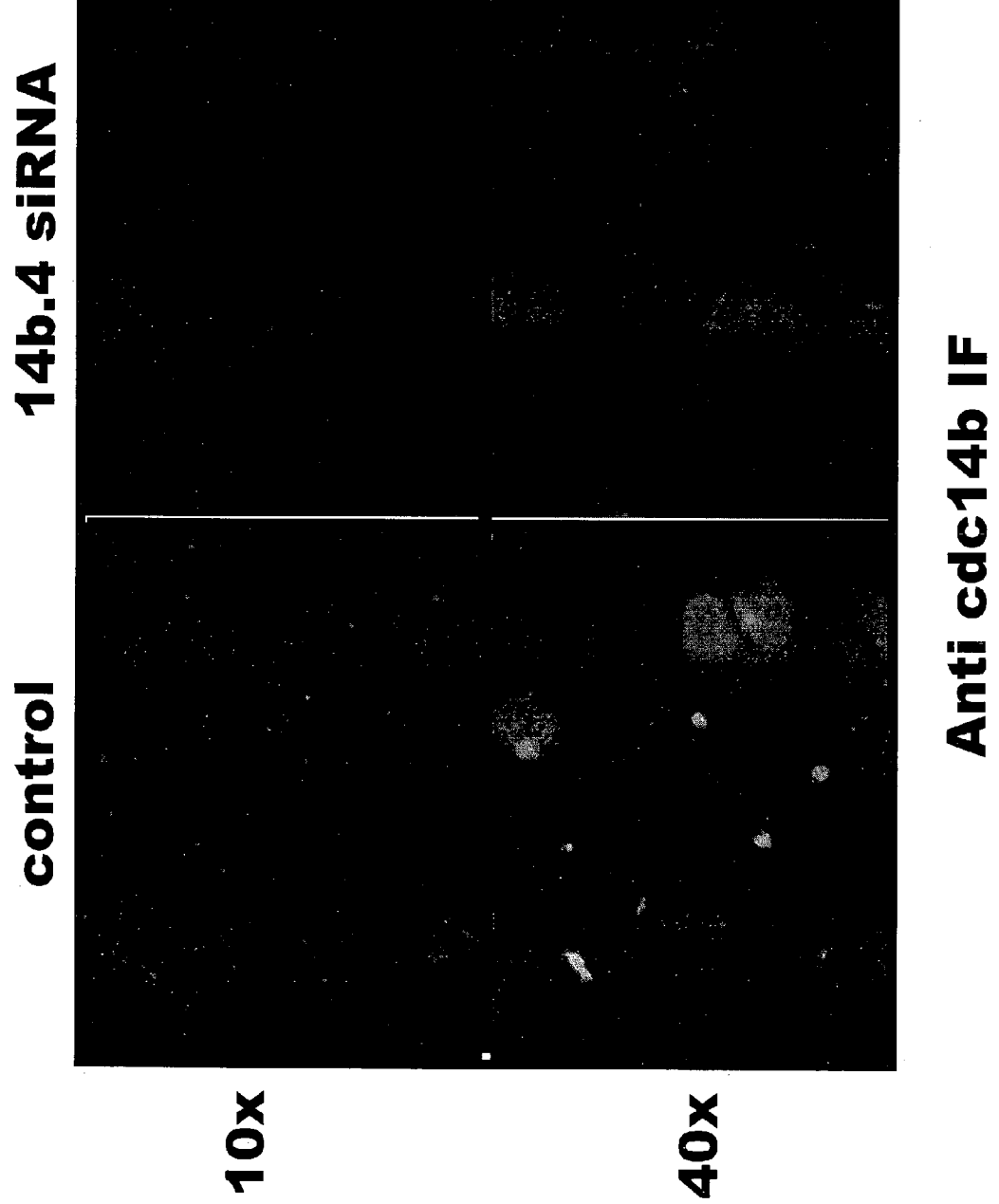
FIG. 10 depicts the expression of cdc14b polypeptide in HeLa cells co-transfected with cdc14b.4 siRNA detected by immunocytochemistry (top right, 10× magnification; bottom right, 40× magnification) and in the absence of a specific siRNA (top left, 10× magnification; bottom right, 40× magnification).

Expression of cdc14b polypeptide co-transfected with cdc14b.4 siRNA in HeLa cells was analyzed by immunocytochemistry. HeLa cells were co-transfected with a cdc14b recombinant expression vector and siRNA. Expression of cdc14b was detected by standard immunocytochemistry methods. As shown in FIG. 10, cdc14b.4 siRNA interfered with expression of cdc 14b polypeptide (top and bottom right panels).

The efficacy of RNAi against FLAG®-tagged Cdc25A expression in 293-HEK cells was also determined. Cells were co-transfected with a FLAG®-Cdc25A expression construct (prepared as described in Example 2) and specific siRNAs 25A.1, 25A.2, 25A.3, and 25A.4 (20 nM) and non-specific siRNAs (25B.1-0.4 and 25C.1-0.4). The level of expression of Cdc25A was determined by immunoblotting with an anti-FLAG® antibody. Only siRNA 25A.2 (5'-gaggagccauucuga-uucutt-3' (SEQ ID NO: 464) (see also related SEQ ID NOS: 465-468)) effectively inhibited expression of Cdc25A.

The effect of RNAi on endogenous expression of Cdc25B and Cdc25C was examined in HeLa cells. The experiments were performed essentially as described in Example 2, except that HeLa cells were exposed to 10 nM siRNA polynucleotides for 48 hours. Four siRNAs specific for Cdc25A: 25A.1, 25A.2, 25A.3, and 25A.4 (20 nM); four siRNAs specific for Cdc25B: 25B.1, 25B.2, 25B.3, and 25B.4 (20 nM); and four siRNAs specific for Cdc25C: 25C.1, 25C.2, 25C.3, and 25C.4 (20 nM) were transfected into HeLa cells and expression was analyzed by immunoblotting cell lysates separated by SDS-PAGE using a Cdc25B antibody (Santa Cruz Biotechnololgy, Cat. No. c-20) and a Cdc25C antibody (Santa Cruz Biotechnololgy, Cat. No. h-85). The level of expression of Cdc25B was decreased 40-50% in HeLa cells transfected with siRNA cdc25B.2 (5'-aggcggcuacaaggaguuctt-3' (SEQ ID NO: 469) see also related SEQ ID NOS: 470-473), and 50-60% in cells transfected with cdc25B.4 siRNA 5'-gaugccauggaagccca-catt-3' (SEQ ID NO: 474)(see also related SEQ ID NOS: 475-478)). In HeLa cells transfected with siRNAs specific for Cdc25C, the level of expression of Cdc25C decreased 90% in HeLa cells transfected with cdc25C.1 (5'-cugccacucagcuuac-cactt-3' (SEQ ID NO:479)(see also related SEQ ID NOS: 480-483)); decreased 70-80% in cells transfected with cdc25C.3 (5'-cccagaaacaguggcugcctt-3' (SEQ ID NO: 484) (see also related SEQ ID NOS: 485-488)); and decreased 70-80% in cells transfected with Cdc25C.4 (5'-aggcggcuaca-gagacuuctt-3' (SEQ ID NO: 489) (see also related SEQ ID NOS: 490-493)).

The ability of cancer cell lines to mediate RNA interference was examined by co-transfecting several cancer cell lines with a FLAG® cdc14b expression construct and specific siRNAs. The cell lines included SW620 (colon cancer); MCF7 (breast cancer); HS578T (breast cancer); MDA MB 231 (breast cancer); and T47D (breast cancer) (ATCC, NCI 60 panel). The FLAG® cdc14b expression construct (1–2 µg) was co-transfected with 20 nM of 14b.3 siRNA (SEQ ID NO: 454); 14b.4 siRNA (SEQ ID NO: 459); or MKP.2 siRNA (SEQ ID NO: 23) (non-specific control) into each cell line as described in Example 2. The level of expression was analyzed by immunoblotting with an anti-FLAG® antibody according to the method described in Example 2. Expression of cdc14b was decreased in each of the five cell lines that were co-transfected with a cdc14b specific siRNA polynucleotide.

Effect of CDC-Specific siRNA on Cell Proliferation

Proliferation of cancer cells in the presence of siRNA polynucleotides specific for cdc14a, cdc14b, and Cdc25A, Cdc25B, and Cdc25C was determined. Cell proliferation was assessed according to a quantitative metabolic assay that measures the enzymatic conversion by cellular dehydrogenase in viable cells of a yellow tetrazolium salt (methylthiazoletetrazolium (MTT)) to purple formazan crystals. MDA-MB-231, SW620, and HeLa cell lines were transfected according to the procedures described in Examples 1 and 2 with the following siRNA polynucleotides (5 nM): cdc14a.3 (5'-cuuggcaaugguguacagatt-3' (SEQ ID NO: 444)); cdc14a.5 (5'-gcacaguaaauacccacuatt-3' (SEQ ID NO: 449)); cdc14b.3 (5'-caagcaaaugcugccuucctt-3' SEQ ID NO: 454); cdc14b.4 (5'-gagccagacuugaaaguggtt-3' SEQ ID NO: 459); cdc25A.2 (SEQ ID NO: 464); cdc25B.4 (SEQ ID NO: 474); cdc25C.1 (SEQ ID NO: 479). The transfected cells were seeded at in a tissue culture plate and maintained for 5 days. A MTT assay was performed according to manufacturer's instructions (ATCC MTT Cell Proliferation Assay Kit, Cat. NO. 30-1010K, ATCC). The MTT-containing media was removed from the wells and was added to solubilize the formazan. The amount of formazan formed was determined by measuring absorbance at 570 m. Compared to the buffer only control, a significant decrease in proliferation was observed in MDA-MB-231 cells transfected with cdc14a.3, cdc14a.5, cdc14b.3, cdc14b.4, and cdc25B.4, and in HeLa cells transfected with cdc14a.3, cdc14a.5, cdc14b.4, and cdc25B.4. A significant decrease in cell proliferation of SW620 cells transfected with cdc14a.3 or cdc14a.5 was also observed.

Effect of CDC-Specific siRNA on Proapoptotic Signaling

Poly(ADP-ribose) polymerase (PARP) is a nuclear DNA binding protein that participates in genome repair, DNA replication, and the regulation of transcription. Cleavage of PARP (approximately 115 kDa) by members of the caspase family into polypeptide fragments of approximately 85 kDa and 25 kDa prevents PARP from performing its normal repair functions and appears to be an early event in apoptotic cell death. The cleaved PARP fragments can be detected by a variety of immunodetection methods.

HeLa cells were transfected with cdc14a.5 (SEQ ID NO: 449); cdc14b.4 (SEQ ID NO: 459); cdc25A.2 (SEQ ID NO: 464); cdc25B.4 (SEQ ID NO: 474); and cdc25C.1 (SEQ ID NO: 479) at a concentration of 10 nM. After incubating the transfected cells for at 37° C., cell lysates were prepared and an immunoblot performed an antibody that specifically binds to cleaved PARP and an antibody that binds to PARP (Cell Signaling Technology, Beverly, Mass.). The results are presented in FIG. 24. The data indicated that inhibiting expression of cdc14a by specific siRNA induces proapoptotic signaling to a greater extent than inhibition of expression of the other cell division cycle proteins.

EXAMPLE 5

Interference of PTP-1B and TC-PTP Expression by Specific siRNA

This Example describes interference with expression of two protein tyrosine phosphatases, PTP-1B and TC-PTP, using sequence specific siRNA polynucleotides.

Interference of Endogenous Expression of Murine PTP-1B in Mouse Fibroblasts by Sequence Specific siRNA Polynucleotides Three siRNA sequences that were specific for murine PTP-1B polynucleotide (GenBank Acc. No. NM_011201, SEQ ID NO: 818) encoding a murine PTP-1B polypeptide (GenBank Acc. No. NM_011201, SEQ ID NO: 819) and one siRNA sequences specific for human PTP-1B polynucleotide (GenBank Ace. No. NM_02827, SEQ ID NO: 816) encoding a human PTP-1B polypeptide (GenBank Ace. No. NM_02827, SEQ ID NO: 817) were designed using the criteria described in Examples 1 and 2. Mouse C57B16 #3 cells, clones 3 and 10, were maintained in cell culture according to standard cell culture methods. Each C57B16 #3 clone was transfected with 200 nM of the following siRNAs: mPTP1B.1 (SEQ ID NO: 496), mPTP1B.2 (SEQ ID NO: 501), mPTP1B.3 (SEQ ID NO: 506), and hPTP1B.1 (SEQ ID NO: 556). Each siRNA was diluted in 50 µl $O_{PTI}$MEM® to provide a final concentration of 200 nM per well. In a separate tube, 3 µl of Lipofectamine™ was combined with 10 µl $O_{PTI}$MEM®. Each solution was incubated for 7 minutes. The two solutions were then mixed and incubated at room temperature for 22 minutes. The final volume of the mixed solution was adjusted to 100 µl and then the C57B16 #3 cells were added. Cells were transfected with the specific siRNAs, the human PTP1B siRNA, or annealing buffer alone. The transfected cells were incubated with siRNAs for six days.

Figure 11:
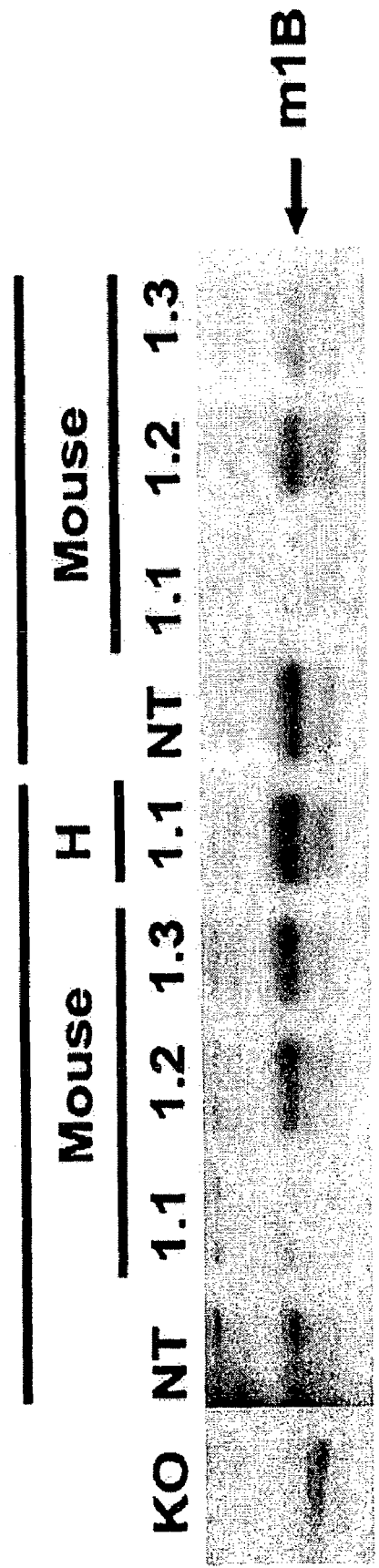
FIG. 11 depicts an immunoblot of the effect on endogenous expression of murine PTP1B by siRNAs specific for the murine PTP1B or the human PTP1B polynucleotide sequences. Expression was detected using a murine anti-PTP1B monoclonal antibody. Data are presented for two different clones of C57B16 #3 murine cells. Both clones were transfected with mPTP1B1.1 siRNA (lanes 3 and 8); MPTP1B1.2 (lanes 4 and 9); mPTP1B1.3 (lanes 5 and 10). One clone, C57B16 #3 clone 3, was transfected with hPTP1B1.1 (lane 6). Lane 2: untransfected C57B16 #3, clone 3; lane 7: untransfected C57B16 #3, clone 10.
Figure 18:
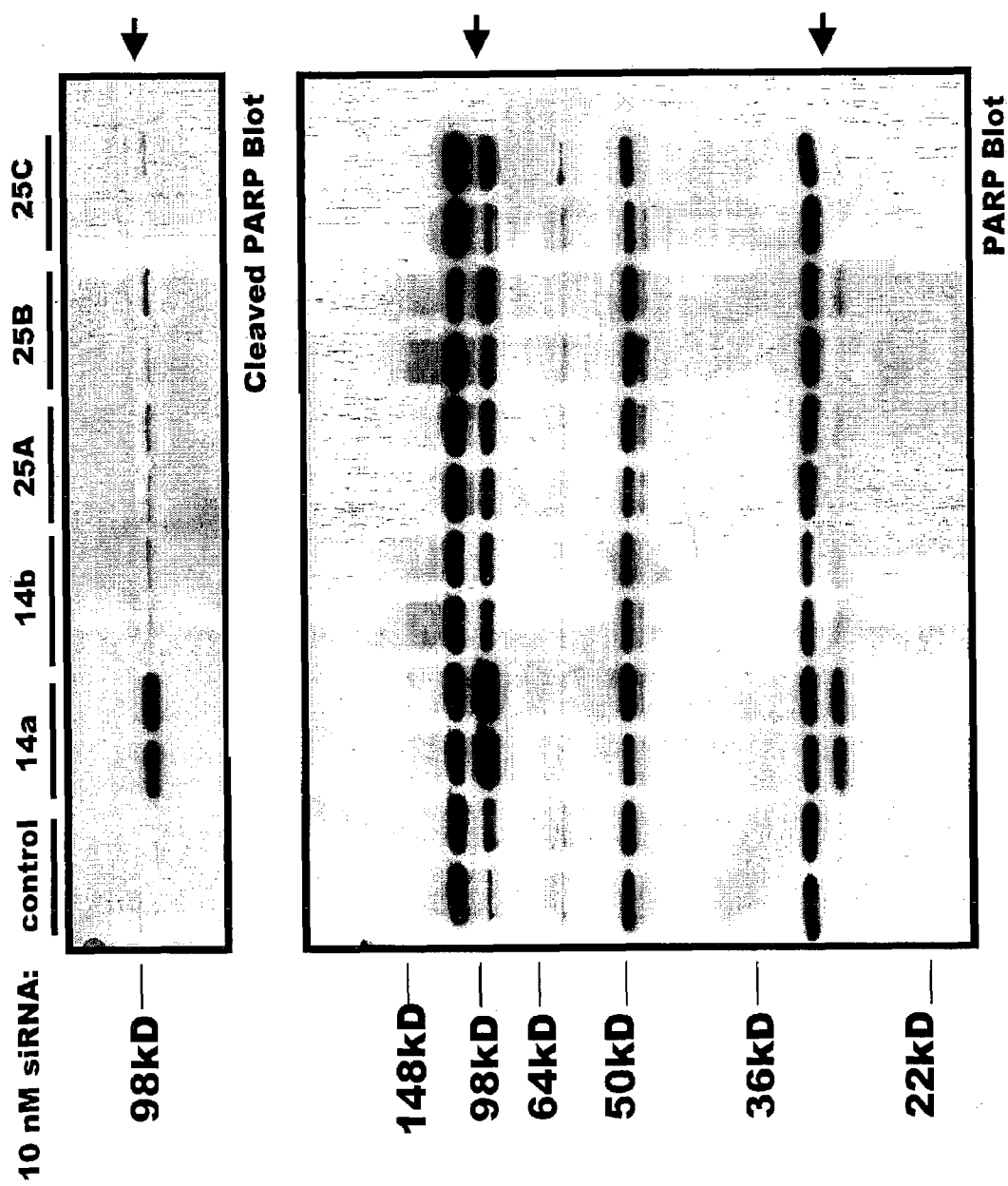
FIG. 18 represents an immunoblot of cleavage of poly (ADP-ribose) polymerase (PARP) in HeLa cells transfected with cell division cycle protein sequence specific siRNA polynucleotides (10 nM). The upper immunoblot was probed with an antibody that specifically binds to cleaved PARP, and the lower immunoblot was probed with an anti-PARP antibody. The siRNA polynucleotides transfected into the HeLa cells were as follows: lanes 1 and 2, no siRNA; lanes 3 and 4, cdc14a.5; lanes 5 and 6, cdc14b.4; lanes 7 and 8 Cdc25A.2; lanes 9 and 10, Cdc25B.4; and lanes 11 and 12, Cdc25C.1.

Cell lysates were prepared by extracting the cells in ELISA extraction buffer (50 mM Tris-HCl, pH 7.5 (room temperature); 2 mM EDTA, pH 7-8; 1 mM phosphate (polyphosphate); 1 mM NaVO4 (monomeric), pH 10; 0.1% Triton X-100; Protease Inhibitor Cocktail set III, (Calbiochem, San Diego, Calif., catalog #539134)). The lysates were separated by SDS-PAGE gel and analyzed by immunoblot according to the procedures described in Examples 1 and 2 using an anti-PTP1B murine monoclonal antibody (Dr. Ben Neel, Harvard University, Cambridge, Mass.). As shown in FIG. 11, the levels of expression of endogenous PTP1B were decreased only in C57B16 cells transfected with the murine PTP1B sequence specific siRNAs.

The effect of RNAi on endogenous expression of murine PTP1B in a second murine cell line was examined. Mouse PTP1B:3T31R fibroblasts were transfected with 20 nM mPTP1B1.1 (SEQ ID NO: 496); mPTP1B1.6 (SEQ ID NO: 521); and mPTP1B1.8 (SEQ ID NO: 531) according to the method described above. The level of murine PTP1B expression in the cells transfected with mPTPB11.1 decreased approximately 80% compared with cells transfected with a non-specific siRNA (hPTP1B1.3 (SEQ ID NO: 566)); cells transfected with mPTP1B1.6 decreased approximately 40%; and cells transfected with mPTP1B1.8 decreased approximately 60%.

Interference with Murine PTP1B Expression by siRNA in Co-Transfection Assays

A recombinant expression construct was prepared that encodes wild-type murine PTP1B (mPTP1B) (GenBank Accession No. NM_011201, SEQ ID NOS: 818-819). The following oligonucleotide primers were used for the wild-type construct. The sequences of the BamHI and EcoRI restriction sites are underlined.

```
mPTP1B-sense (mPTP1B 5'BamHI)
                             (SEQ ID NO: 494)
5'-GGGGGGGATCCATGGAGATGGAGAAGGAGTTCGAGG-3' mPTP1B anti sense (mPTP1B 3'EcoRI)
                             (SEQ ID NO: 495)
5'-GGGGGAATTCTCAGTGAAAACACACCCGGTAGCAC-3'
```

Vector pCMVTag2B (Stratagene, La Jolla, Calif.) was digested with restriction endonuclease BamHI (New England Biolabs, Beverly, Mass.) for 3 hours at 37° C. The digested vector was then incubated with Klenow polymerase (New England Biolabs) for 15 minutes at 25° C. to fill in the recessed 3' termini, followed by an incubation of 30 minutes at 37° C. with calf intestinal phosphatase (New England Biolabs). The GATEWAY™ Reading Frame Cassette B (Invitrogen Life Technologies, Carlsbad, Calif.) was inserted into the pCMVTag2B vector by ligation with T4 DNA ligase (Invitrogen Life Technologies) overnight at 16° C. according to the supplier's instructions. DB3.1™ competent *E. Coli* cells were transformed with the ligated vector (GWpCMVTag2) and DNA was isolated by standard molecular biology methods.

Vectors for expression of mPTP1 B wild type were prepared as follows. The mPTP1B construct was subcloned into a GATEWAY™ entry vector pENTR3 C™ (Invitrogen Life Technologies) by digesting 20 μl of the mPTP1B cDNA or 20 μl of the pENTR3C™ vector with 1 μl of BamHI (New England Biolabs); 1 μl of EcoRI (New England Biolabs); 5 μl 10×EcoRI buffer (New England Biolabs); 5 μl 10×BSA (New England Biolabs); and 18 μl distilled water for 3 hours at 37° C. Digested DNA was run on a 1% agarose gel, digested bands were excised, and the DNA was gel-purified using a QIAGEN Gel Extraction kit (QIAGEN, Inc., Valencia, Calif.). Four microliters of the mPTP1B cDNA was ligated into 2 μl of the pENTR3C™ vector overnight at 16° C. with 1 μl 10× Ligation Buffer (Invitrogen Life Technologies), 1 μl T4 DNA Ligase (4U/μl) (Invitrogen, Carlsbad, Calif.), and 2 μl distilled water. The construct was transformed into LIBRARY EFFICIENCY® DH5α™ cells. The FLAG® epitope-tagged mPTP1B construct was prepared by cloning the pENTR3 C™ mPTP1B WT construct into the GWpCMVTag2 vector. The pENTR3C™ construct containing the mPTP1B polynucleotide was linearized by digesting the construct with Vsp I (Promega Corp., Madison, Wis.) at 37° C. for 2 hours. The DNA was purified using a QIAGEN PCR Purification kit (QIAGEN, Inc.). Three microliters (100 ng/μl) of the GWpCMVTag2 vector were combined in a GATEWAY™ LR reaction with 6 μl linearized pENTR3C™ mPTP1B WT, 3 μl TE buffer, 4 μl Clonase™ Enzyme, and 4 μl LR reaction buffer (Invitrogen Life Technologies) for 1 hour at room temperature. After addition of Proteinase K (Invitrogen Life Technologies) to the reaction for 10 minutes, LIBRARY EFFICIENCY® DH5α™ cells were transformed with the expression construct.

The murine PTP1B expression vector (0.5 μg) was co-transfected with 20 nM murine PTP1B sequence-specific siRNA polynucleotides into PTP1B knockout mouse fibroblasts (PTP1B KO mouse embryonic fibroblasts were prepared from 13-day embryos from PTP1B knock out mice to establish the cell line, which was then transfected with human insulin receptor (1BKO+HIR) (HIR, Julie Moyers, Eli Lilly and Company, Indianapolis, Ind.)). Transfections were performed as described in Example 1. After incubating the transfected cells for 18 hours at 37° C., cell lysates were prepared, separated by 4-12% SDS-PAGE, and immunoblotted using the anti-PTP1B murine monoclonal antibody (see above). The results are summarized in Table 13.

TABLE 12 siRNA INTERFERENCE WITH MURINE PTP-1B EXPRESSION IN CO-TRANSFECTION ASSAYS

| Target | siRNA Sequence (SEQ ID NO) | siRNA Name | Related SEQ ID NO: | Decrease in Expression |
|---|---|---|---|---|
| Murine PTP1B | 5'-gaagcccagaggagcuauatt-3' (SEQ ID NO: 496) | mPTP1B1.1 | (SEQ ID NOS: 497-500 | 95% |
| | 5'-cuacaccacauggccugactt-3' (SEQ ID NO: 501) | mPTP1B1.2 | (SEQ ID NOS: 502-505 | Not analyzed |
| | 5'-gacugccgaccagcugcgctt-3' (SEQ ID NO: 506) | mPTP1B1.3 | (SEQ ID NOS: 507-510 | Not analyzed |
| | 5'-gguaccgagaugucagcccttt-3' (SEQ ID NO: 511) | mPTP1B1.4 | (SEQ ID NOS: 512-515) | 25% |
| | 5'-ugacuauaucaaugccagctt-3' (SEQ ID NO: 516) | mPTP1B1.5 | (SEQ ID NOS: 517-520) | Not analyzed |
| | 5'-agaagaaaaggagauggucttt-3' (SEQ ID NO: 521) | mPTP1B1.6 | (SEQ ID NOS: 522-525) | 80% |

TABLE 12-continued siRNA INTERFERENCE WITH MURINE PTP-1B EXPRESSION
IN CO-TRANSFECTION ASSAYS

| Target | siRNA Sequence (SEQ ID NO) | siRNA Name | Related SEQ ID NO: | Decrease in Expression |
|---|---|---|---|---|
| | 5'-cgggaagugcaaggagcuctt-3' (SEQ ID NO: 526) | mPTP1B1.7 | (SEQ ID NOS: 527-530) | Not analyzed |
| | 5'-ggaucaguggaaggagcuctc-3' (SEQ ID NO: 531) | mPTP1B1.8 | (SEQ ID NOS: 532-535) | 80% |

Interference with Rat PTP1B Expression by siRNA in Co-Transfection Assays

A co-transfection assay was performed as described above in which 1BKO+HIR mouse fibroblasts were co-transfected with an expression vector containing the sequence encoding the peptide FLAG® in frame with a nucleotide sequence that encoded a rat PTP1B polypeptide (SEQ ID NO: 821) (GenBank Accession No. NM_012637) and a sequence specific siRNA, rPTP1B1.1 (5'-agaagaaaaagagaugguctt-3' (SEQ ID NO: 536)(see also related SEQ ID NOS: 537-540)) (20 nM). Additional rat PTP1B specific siRNA polynucleotides examined in the co-transfection assay included rPTP1B1.2 (5'-cggauggugggugaggucutt-3' (SEQ ID NO: 541)(see also related SEQ ID NOS: 542-545)); rPTP1B1.3 (5'-uggcaagugcaaggagcuctt-3' (SEQ ID NO: 546)(see also related SEQ ID NOS: 547-550)); and rPTP1B1.4 (5'-cuacaccaccuggccugactt-3' (SEQ ID NO: 551) (see also related SEQ ID NOS: 552-555)). The level of expression of the rat PTP1B polypeptide was determined by immunoblotting cell lysates with an anti-human PTP1B antibody that also specifically binds to rat PTP1B ((PHO2, Oncogene Research Products™, Inc. San Diego, Calif.). Expression of rat PTP1B decreased approximately 50% in cells transfected with rPTP1B1.1.

Interference with Human PTP-1B Expression by siRNA in Co-Transfection Assays

Human PTP1B encoding sequence was cloned into a Pmt vector according to standard molecular biology procedures (see Flint et al., *EMBO J.* 12:1937-46 (1993)). 1BKO+HIR cells were co-transfected with the human PTP-1B expression vector and siRNA polynucleotides (20 nM) specific for human PTP-1B sequences overnight using Lipofectamine 2000. Cells were lysed as described above, and the lysates were separated by 4-12% SDS-PAGE and transferred onto a PDVF membrane. The level of expression of human PTP-1B was determined by immunoblotting with an anti-human PTP-1B antibody (PHO2, Oncogene Research Products™, Inc. San Diego, Calif.). Interference with expression of human PTP-1B was observed with four siRNA polynucleotides as indicated in Table 14.

TABLE 13 siRNA INTERFERENCE WITH HUMAN PTP-1B EXPRESSION
IN CO-TRANSFECTION ASSAYS

| Target | siRNA Sequence (SEQ ID NO) | siRNA Name | Related SEQ ID NO: | Decrease in Expression |
|---|---|---|---|---|
| Human PTP1B | 5'-cuuaccacauggccugactt-3' (SEQ ID NO: 556) | hPTP1B1.1 | (SEQ ID NOS: 557-560) | Not analyzed |
| | 5'-gcccaaaggaguuacauuctt-3' (SEQ ID NO: 561) | hPTP1B1.2 | (SEQ ID NOS: 562-565) | >95% |
| | 5'-ggaagaaaaaggaagcccctt-3' (SEQ ID NO: 566) | hPTP1B1.3 | (SEQ ID NOS: 567-570) | >95% |
| | 5'-caaugggaaaugcagggagtt-3' (SEQ ID NO: 571) | hPTP1B1.4 | (SEQ ID NOS: 572-575) | >95% |
| | 5'-ggaucaguggaaggagcuutc-3' (SEQ ID NO: 576) | hPTP1B1.5 | (SEQ ID NOS: 577-580) | >95% |

Interference of Endogenous Expression of Human PTP-1B by siRNA

The effect of sequence specific siRNA on endogenous expression of human PTP-1B was examined in two different cell lines. HeLa cells were transfected as described above with HPTP1B1.1, hPTP1B1.2, hPTP1B1.3, hPTP1B1.4, and hPTP1B1.5 at 20 nM using Lipofectamine 2000, and after three days, the level of expression of PTP1B was analyzed by immunoblot. No significant decrease in expression of human PTP-1B was observed in HeLa cells transfected with the siRNA hPTP1B1.1. In HeLa cells transfected with hPTP1B1.2 and hPTP1B1.4, the level of expression of human PTP-1B decreased 80%, and in cells transfected with hPTP1B1.3, the level of expression decreased 90%. Endogenous expression of human PTP-1B in the second cell line, 293-HEK-HIR, (gift from Julie Moyers, Eli Lilly and Company) transfected with sequence specific siRNAs hPTP1B1.2, hPTP1B1.3, hPTP1B1.4, hPTP1B1.5 (20 nM) was reduced by 90%.

Interference with Expression of Murine TCPTP by siRNA in Co-Transfection Assays

A co-transfection assay was performed in which 1BKO+HIR murine fibroblasts were co-transfected as described above with an expression vector comprising a polynucleotide sequence encoding murine TCPTP (SEQ ID NO: 829) and siRNA mTCPTP1.1 (5'-guugucaugcuaaaccgaact-3' (SEQ ID NO: 581)(see also related SEQ ID NOS: 582-585)) (1 nM) or mTCPTP1.2 (5'-cagaacagagugauggguugag-3' (SEQ ID NO: 586) (see also related SEQ ID NOS: 587-590)) (20 nM). The level of TCPTP expression was determined by immunoblotting with an anti-human TCPTP antibody (Curt Diltz, CEP-TYR, Inc.). The siRNA mTCPTP1.2 did not interfere with expression of murine TCPTP. Expression of murine TCPTP decreased more than 95% in cells transfected with siRNA, mTCPTP1.1.

Interference with Expression of Human TCPTP by siRNA in Co-Transfection Assays

Co-transfection assays were performed essentially as described above for PTP1B expression analysis to determine siRNA inhibition of human TCPTP expression. A recombinant expression construct was prepared that encodes wild-type human TC45. The following oligonucleotide primers were used for the wild-type construct. The sequences of the BamHI and EcoRi restriction sites are underlined.

Vector pCMVTag2B (Stratagene, La Jolla, Calif.) was digested with restriction endonuclease BamHI (New England Biolabs, Beverly, Mass.) for 3 hours at 37° C. The digested vector was then incubated with Klenow polymerase (New England Biolabs) for 15 minutes at 25° C. to fill in the recessed 3' termini, followed by an incubation of 30 minutes at 37° C. with calf intestinal phosphatase (New England Biolabs). The GATEWAY™ Reading Frame Cassette B (Invitrogen Life Technologies) was inserted into the pCMVTag2B vector by ligation with T4 DNA ligase (Invitrogen Life Technologies) overnight at 16° C. according to the supplier's instructions. DB3.1™ competent E. coli cells were transformed with the ligated vector (GWpCMVTag2) and DNA was isolated by standard molecular biology methods.

Vectors for expression of TC45 wild type were prepared as follows: The TC45 construct was subcloned into a GATEWAY™ entry vector pENTR3C™ (Invitrogen Life Technologies) by digesting 10 µl of the TC45 cDNA with 1 µl of BamHI (New England Biolabs), 1 µl of EcoRI (New England Biolabs), 3 µl 10×EcoRI buffer (New England Biolabs), 3 µl 10×BSA (New England Biolabs), and 12 µl distilled water for 3 hours at 37° C. Two microliters of the pENTR3C™ vector was digested with 0.5 µl of BamHI (New England Biolabs), 0.5 µl of EcoRI (New England Biolabs), 2 µl 10×EcoRI buffer (New England Biolabs), 2 µl 10×BSA (New England Biolabs), and 13 µl distilled water for 3 hours at 37° C., followed by an incubation of 30 minutes at 37° C. with calf intestinal phosphatase (New England Biolabs). Digested DNA was run on a 1% agarose gel, digested bands were excised and gel purified using a QIAGEN Gel Extraction kit (QIAGEN, Inc.). Four microliters of the TC45 cDNA was ligated into 2 µl of the pENTR3C™ vector overnight at 16° C. with 11 µl 10× Ligation Buffer (Invitrogen Life Technologies), 1 µl T4 DNA Ligase (4U/µl) (Invitrogen Life Technologies), and 2 µl distilled water. The construct was transformed into LIBRARY EFFICIENCY® DH5α™ cells. The FLAG® epitope-tagged TC45 construct was prepared by cloning the pENTR3C™ TC45 WT construct into the GWpCMVTag2 vector. The pENTR3C™ construct containing the TC45 polynucleotide was linearized by digesting the construct with Pvu I (New England Biolabs)) at 37° C. for 2 hours. The DNA was purified using a QIAGEN PCR Purification kit (QIAGEN, Inc.). Two microliters (150 ng/µl) of the GWpCMVTag2 vector were combined in a GATEWAY™ LR reaction with 3 µl linearized pENTR3C™ TC45 WT, 5 µl TE buffer, 4 µl Clonase™ Enzyme, and 4 µl LR reaction buffer (Invitrogen Life Technologies) overnight at room temperature. After addition of Proteinase K (Invitrogen Life Technologies) to the reaction for 10 minutes, LIBRARY EFFICIENCY® DH5α™ cells were transformed with the expression construct.

Cells (1BKO+HIR murine embryo fibroblasts) were co-transfected with an expression vector containing a nucleotide sequence encoding human TCPTP (SEQ ID NO: 823) and siRNAs, hTCPTP1.4 (5'-guugucaugcugaaccgcatt-3' (SEQ ID NO: 593)(see also related SEQ ID NOS: 594-597)) (20 nM); hTCPTP1.5 (5'-gcccauaugaucacagucgtg-3' (SEQ ID NO: 598) (see also related SEQ ID NOS: 599-602))(10 nM); hTCPTP1.6 (5'-ucgguuaaaugugcacaguac-3' (SEQ ID NO: 603)(see also related SEQ ID NOS: 604-607)) (10 nM); or

```
Human TC45 sense (TC45 5'BamHI)
5'-GGGGGGATCCATGCCCACCACCATCGAGCGGGAGTT-3'                          (SEQ ID NO: 591)

Human TC45 antisense (TC45 3'EcoRI)
5'-GGGGAATTCTTAGGTGTCTGTCAATCTTGGCCTTTTTCTTTTTCGTTCA-3'             (SEQ ID NO: 592)
``` hTCPTP1.7 (5'-ugacuauccucauagaguggg-3' (SEQ ID NO: 608)(see also related SEQ ID NOS: 609-612)) (20 nM). Additional human TCPTP specific siRNA polynucleotides were prepared; the sequences of each are as follows: hTCPTP1.1 (5'-agugagagaaucuggcucctt-3' (SEQ ID NO: 613) (see also related SEQ ID NOS: 614-617)); hTCPTP1.2 (5'-ggaagacuuaucuccugcctt-3' (SEQ ID NO: 618) (see also related SEQ ID NOS: 619-622)); and hTCPTP1.3 (5'-ggugaccgauguacagactt-3' (SEQ ID NO: 623) (see also related SEQ ID NOS: 624-627)). The level of TCPTP expression was determined by immunoblotting with an anti-human TCPTP antibody. The level of expression of human TCPTP was not affected by siRNA hTCPTP1.7. Expression levels decreased more than 95% in the cells co-transfected with hTCPTP1.4; 80% in cells co-transfected with hTCPTP1.5; and greater than 90% in cells transfected with hTCPTP1.6.

Interference of Endogenous Expression of Human TCPTP by siRNA

293-HEK HIR cells were transfected with either hTCPTP1.4 (SEQ ID NO: 593) or rPTP1B1.2, a rat PTP1B sequence specific siRNA (5'-cggauggugggguggagguctt-3' (SEQ ID NO: 541), which was included as a nonspecific siRNA control, at concentrations of 2, 5, 10, 20 and 50 nM. Endogenous expression of human TCPTP in the cells transfected with sequence specific hTCPTP1.4 decreased 90%.

Transient Transfection of Human PTP1B and Sequence Specific Hairpin Vectors

Effectiveness of a human PTP1B sequence-specific siRNA in the form of a hairpin insert was examined in a transient co-transfection assay. Cells (1BKO+HIR mouse fibroblasts) were transfected with a human PTP1B expression vector (see above) and co-transfected with hPTP1B hairpin vectors (1, 0.5, and 0.25 µg) according to the transfection method described above. The human PTP1B specific sequences were inserted in frame with a human U6 small nuclear RNA promoter into a vector, which was a gift from David Engelke (University of Michigan, Ann Arbor, Mich.) (see also Paul et al., *Nat. Biotechnol.* 20:446-48 (2002)). The sequences of each strand inserted into the hairpin vectors are as follows.

EXAMPLE 6

Regulatory Role of TCPTP in Insulin Signaling

The protein tyrosine phosphatase TC-PTP exists in two alternatively spliced forms, TC45 (see SEQ ID NOS: 826 and 827) and TC48, that share the same catalytic domain but differ at their extreme carboxy-termini (Mosinger et al., *Proc. Natl. Acad. Sci. USA* 89:499-503 (1992)). Insulin-induced oxidation and inactivation of TC45 suggested that it functions as a negative regulator of insulin signaling (see U.S. Ser. No. 10/366,547). This Example examines the regulatory role of TC45 in insulin signaling by inhibiting expression of the PTP by RNAi.

The specific siRNA duplexes were designed by first scanning through the open reading frame of TC45 mRNA and selecting sequences of 5'AA($N_{19}$)3' (N=any nucleotide) for further characterization. The following 2 oligonucleotides were chosen: 5'-AACAGAUACAGAGAUGUAAGC-3' (TCPTP1) (SEQ ID NO: 644)(see also related SEQ ID NOS: 770-773)) and 5'-AAGCCCA UAUGAUC ACAGUCG-3' (TCPTP2) (SEQ ID NO: 645)(see also related SEQ ID NOS: 774-777)). These sequences were submitted to a BLAST search against human, rat, and mouse genome databases to ensure specificity for TC-PTP. The 21-nt siRNA duplexes were obtained in a deprotected and desalted form (Dharma-

```
hPTP1B H1.2-HP4
5'-tttGCCCAAAGGAGTTACATTCGTAAGAATGTAACTCCTTTGGGCttttt-3'         (SEQ ID NO: 628)

3' GGGTTTCCTCAATGTAAGCATTCTTACATTGAGGAAACCCGaaaaagatc-5'         (SEQ ID NO: 629)
(See also SEQ ID NOS: 630-631, respectively (RNA sequence).)

hPTP1B H1.2-HP9
5'-tttGCCCAAAGGAGTTACATTCCCTGGGTAAGAATGTAACTCCTTTGGGCttttt-3'   (SEQ ID NO: 632)

3' GGGTTTCCTCAATGTAAGGGACCCATTCTTACATTGAGGAAACCCGaaaaagatc-5'   (SEQ ID NO: 633)
(See also SEQ ID NOS: 634-635, respectively (RNA sequence).)
```

Figure 19:
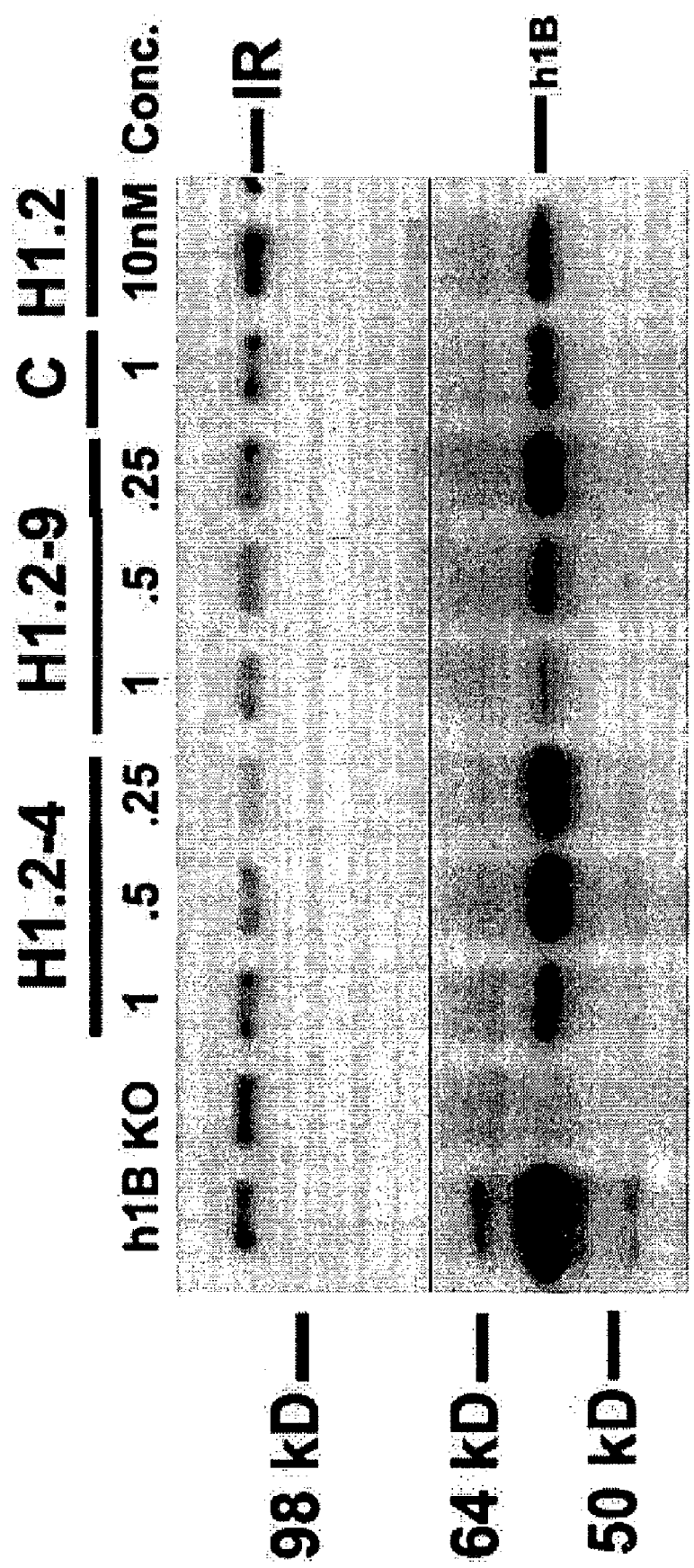
FIG. 19 depicts an immunoblot analysis of the expression of human PTP-1B co-transfected into 1BKO+HIR murine fibroblasts with human PTP-1B siRNA hairpin vectors. Expression was detected with an anti-human PTP1B antibody (h1B) (lower portion of immunoblot). As a protein expression control, cell lysates were probed with an anti-human insulin receptor (IR) antibody (upper portion of immunoblot).

Twenty-four hours after the cells were transfected, cell lysates were prepared and expression of human PTP1B was determined by immunoblotting with an antihuman PTP1B antibody (see above). Cell lysates were also immunoblotted with an antibody specific for human insulin receptor beta chain (IRβ) (Cat. No. C-19, Santa Cruz Biotechnology). The results are presented in FIG. 19.

Hairpin vectors are also prepared that contain sequences specific for murine PTP1B. The following sequences of each strand are inserted into a hairpin vector.

con Research). Rat-1 fibroblasts (Fischer rat fibroblast 3T3 like cell line) and HepG2 (human hepatocellular carcinoma) cells (American Type Culture Collection (ATCC), Manasass, Va.) were transfected with each siRNA at 100 nM. Both siRNA oligonucleotides suppressed expression of endogenous TC45 in the transfected HepG2 cells and Rat-1 fibroblasts, with TCPTP1 being more efficient.

Rat-1 (fibroblasts) and HepG2 (human hepatocellular carcinoma) cells were routinely maintained in DMEM supplemented with 10% FBS, 1% glutamine, 100 U/ml penicillin

```
mPTP1BM1.1-HP4
5'-tttGAAGCCCAGAGGAGCTATAAGAATATAGCTCCTCTGGGCTTCttttt-3'        (SEQ ID NO: 636)

3' TTCGGGTCTCCTCGATATTCTTATATCGAGGAGACCCGAAGaaaaagatc-5'        (SEQ ID NO: 637)
(See also SEQ ID NOS: 638-639, respectively (RNA sequence).)

mPTP1BM1.1-HP9
5'-tttGAAGCCCAGAGGAGCTATAGGGTGAGAATATAGCTCCTCTGGGCTTCttttt-3'   (SEQ ID NO: 640)

3' TTCGGGTCTCCTCGATATCCCACTCTTATATCGAGGAGACCCGAAGaaaaagatc-5'   (SEQ ID NO: 641)
(See also SEQ ID NOS: 642-643, respectively (RNA sequence).)
``` and 100 μg/ml streptomycin. For stimulation with insulin, cells were plated in media containing 10% FBS for 48 hours, then serum-starved for 16 hours before treatment. For transient transfection, cells were plated in DMEM supplemented with 10% FBS for 16 hours, then in OptiMEM (Invitrogen) without serum, after which the plasmid (5 μg/dish for Rat-1, 30 μg/dish for HepG2) was introduced by LipofectAMINE and PLUS reagents (Invitrogen), according to the manufacture's recommendations. The transfection efficiency was routinely 40%. For RNAi experiments, cells were plated as above and the TCPTP siRNA duplexes were introduced by Oligofectamine (Invitrogen) according to the guidelines provided by Dharmacon Research Inc.

Figure 20A:
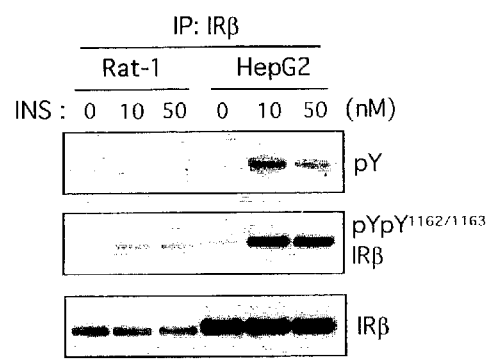
FIG. 20A represents an immunoblot of serum-deprived Rat-1 and HEPG2 cells that were exposed to varying concentrations of insulin (INS) as shown. The insulin receptor (IR) was immunoprecipitated from cell lysates with an anti-IR-$\beta$ antibody followed by immunoblotting with an anti-phosphotyrosine antibody (pY) (top panel); an anti-pYpY$^{1162/1163}$-IR-$\beta$ antibody (middle panel); and an anti-IR $\beta$ antibody.

The potential regulatory role of TC45 in insulin signaling was investigated by examining the phosphorylation status of PKB/Akt, which is a critical effector in the P13 kinase pathway that mediates various intracellular responses to insulin, following ablation of the PTP by RNAi. The human hepatoma cell line HepG2 has been used extensively as a model to study insulin signaling (see Huang et al., *J. Biol. Chem.* 277:18151-60 (2002); Haj et al., *Science* 295 1708-11 (2002)). Serum-deprived Rat-I and HepG2 cells were exposed to 10 or 50 nM insulin for 5 min and lysed. The insulin receptor (IR) was immunoprecipitated from 500 μg of cell lysate with anti-IR-β antibody 29B4 (Santa Cruz Biotechnology), then immunoblotted with anti-phosphotyrosine, anti-pYpY$^{1162/1162}$-IR-β (Biosource International, Camarillo, Calif.) and anti-IR-β (C-19) (Santa Cruz Biotechnology) antibodies. HepG2 cells expressed higher levels of IR-β than Rat-1 cells as shown in FIG. 20A and displayed a robust response to insulin stimulation, as shown by the overall tyrosine phosphorylation level of IR-β and autophosphorylation of the activation loop tyrosines 1162 and 1163 (see FIG. 20A).

Figure 20B:
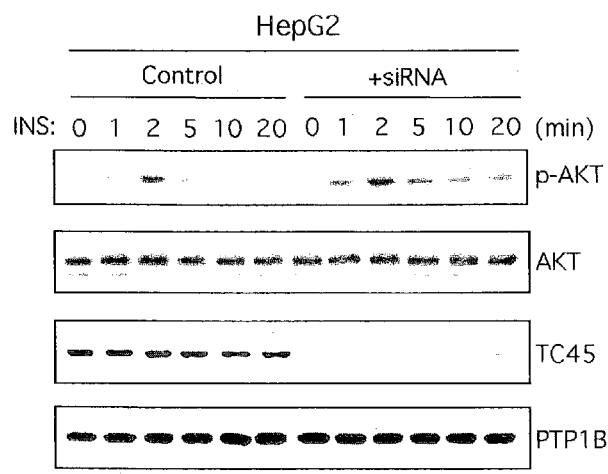
FIG. 20B represents an immunoblot of HepG2 cell lysates prepared from cells that were untransfected (control) or transfected with TCPTP1 siRNA (SEQ ID NO: 644)(+siRNA). The lysates were immunoblotted with an anti-phospho-PKB/Akt antibody (p-AKT) (first immunoblot); anti-PKB/Akt antibody (AKT) (second immunoblot); anti-TC45 (TC45) antibody (third immunoblot); and an anti-PTP1B antibody (PTP1B).
Figure 20C:
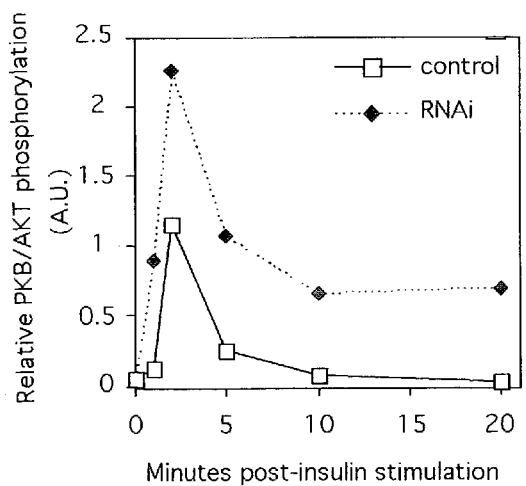
FIG. 20C represents a densitometric analysis of the gel image to illustrate the ratio of phosphorylated PKB/Akt to total PKB/Akt.

For the RNAi experiment, HepG2 cells were untransfected (control) or transfected (+siRNA) with 100 nM siRNA TCPTP1 oligonucleotide. Two days after transfection, cells were serum-starved for 16 hours and then stimulated with 10 nM insulin for 0, 1, 2, 5, 10, and 20 minutes. Total lysates (30 μg) were immunoblotted with anti-phospho-PKB/Akt (Cell Signaling Technology, Beverly, Mass.); anti-PKB/Akt (Cell Signaling Technology); anti-TC45 (1910H (Lorenzen et al., *J. Cell. Biol.* 131:631-43 (1995))); and anti-PTP1B (FG6 (LaMontagne et al., *Mol. Cell. Biol.* 18:2965-75 (1998))) antibodies. The results presented in FIG. 20B indicate that depletion of TC45 enhanced both the intensity and duration of the signaling response. FIG. 20C illustrates a densitometric analysis of the gel image to show the ratio of phosphorylated PKB/Akt relative to total PKB/Akt. Similar results were observed in three independent experiments.

Figure 21A:
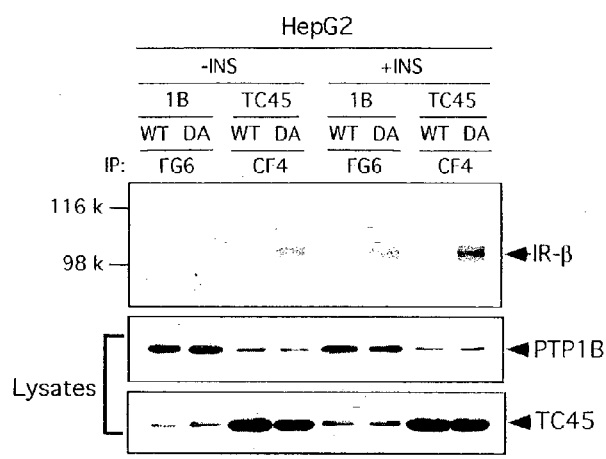
FIG. 21 provides an immunoblot indicating that tyrosine phosphorylated IR-$\beta$ is a substrate of TC45. HepG2 cells overexpressing wild-type (WT) or substrate trapping mutant (DA) forms of PTP1B (1B) and TC45 were either not treated with insulin (−INS) or stimulated with insulin for 5 minutes (+INS), lysed, separated by SDS-PAGE, and immunoprecipitated with anti-PTP1B antibody (FG6) or anti-TC45 antibody (CF4). The immunoprecipitates were immunoblotted with an anti-IR-$\beta$ antibody (top panel, FIG. 21A); anti-PTP1B antibody FG6 (middle panel, FIG. 21A); and anti-TCPTP antibody CF4 (bottom panel, FIG. 21A).
FIG. 21B depicts immunoblots of HepG2 cells that were serum-starved and untransfected (control) or transfected with TC45 siRNA (100 nM) and then stimulated with 10 nM insulin (INS) for the indicated times. The insulin receptor was immunoprecipitated from cell lysates with an anti-IR-$\beta$ antibody, which was then immunoblotted with the following antibodies: anti-phosphotyrosine (p-Tyr) (first immunoblot); anti-pY$^{972}$-IR-$\beta$ (second immunoblot); anti-pYpY$^{1162/1163}$-IR-$\beta$ (third immunoblot); and anti-IR-$\beta$ (fourth immunoblot).
FIG. 21C presents densitometric analyses of the gel image to show the ratio of phosphorylated IR-$\beta$ to total IR-$\beta$ for total phosphotyrosine (top panel); phosphorylation of Tyr 972 (middle panel); and phosphorylation of the activation loop tyrosines 1162 and 1163 (lower panel).

The role of TC45 in insulin signaling was further investigated by preparing a TC45 substrate trapping mutant. Substitution of an alanine residue for the invariant aspartate, which functions as a general acid in catalysis, into the vector expressing TC45 and into a vector expressing PTP1B was performed by standard site-directed mutagenesis protocols. HepG2 cells overexpressing wild type (WT) or trapping mutant (DA) forms of PTP1B and TC45 were either left untreated (−INS) or stimulated with 10 nM insulin for 5 min (+INS), then lysed in trapping buffer (20 mM Tris (pH 7.4), 1% NP-40, 150 mM NaCl, 10% glycerol, 10 mM IAA and 25 μg/ml each of aprotinin and leupeptin). Aliquots (1 mg) of cell lysate were incubated with anti-PTP1B antibody (FG6) or anti-TC45 antibody (CF4). The immunocomplexes were washed with lysis buffer, subjected to SDS-PAGE then immunoblotted with anti-IR-β (C-19) antibody. An aliquot of lysate (30 μg) was immunoblotted with anti-PTP1B antibody (FG6) or anti-TC-PTP antibody (CF4) to verify PTP expression. The data are shown in FIG. 21A and are representative of three independent experiments. These data suggest that TC45 recognizes IR-β as a substrate.

Figure 21B:
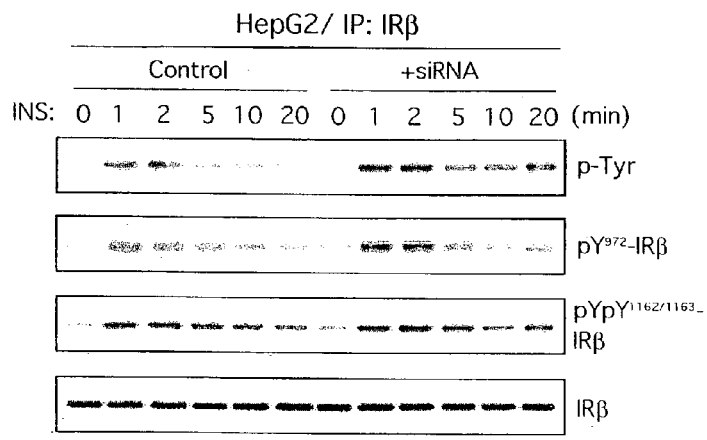
Figure 21C:
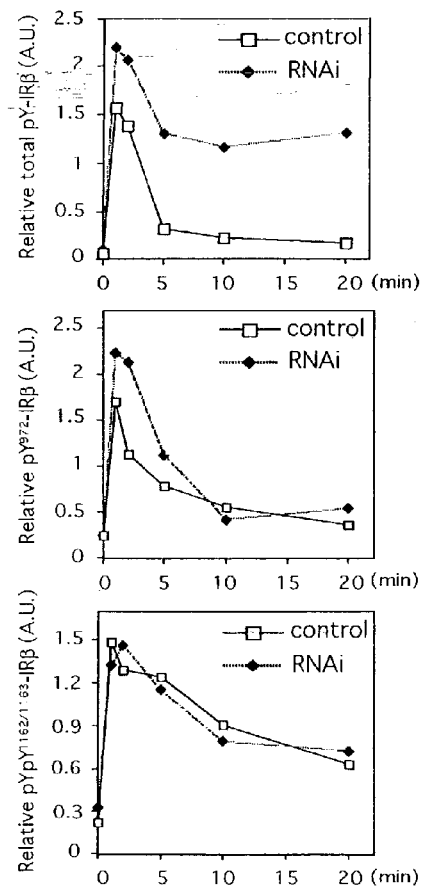

Serum starved, untransfected (control) or TC45 siRNA (100 nM) transfected (+siRNA) HepG2 cells were stimulated with 10 nM insulin for 0, 1, 2, 5, 10, and 20 minutes. The insulin receptor was immunoprecipitated from 750 μg of cell lysate with anti-IR-β antibody 29B4 and immunoblotted with anti-phosphotyrosine (G104), anti-pY$^{972}$-β (Biosource), anti-pYpY$^{1162/1163}$-IR-β, and anti-IR-β (C-19) antibodies as shown in FIG. 21B. FIG. 21C illustrates densitometric analyses of the gel image to show the ratio of phosphorylated IR-β relative to total IR-β for total phosphotyrosine (upper panel), phosphorylation of Tyr 972 (middle panel), and phosphorylation of the activation loop tyrosines 1162 and 1163 (lower panel). Similar results were observed in two independent experiments.

EXAMPLE 7

Effect of siRNAs Specific for PTP1B and TCPTP on Insulin Receptor Tyrosine Phosphorylation This example illustrates the effect of RNAi on the function of components in a cell signaling pathway. The role of PTP1B in the down regulation of insulin signaling has been illustrated by data derived from a variety of approaches (Cheng et al., *Eur. J. Biochem.* 269:1050-59 (2002)), including the phenotype of the PTP1B knockout mouse (Elchebly et al., *Science* 283:1544-48 (1999); Klaman et al., *Mol. Cell Biol* 20:5479-89 (2000); see also U.S. patent application Ser. No. 10/366,547).

Figure 22A:
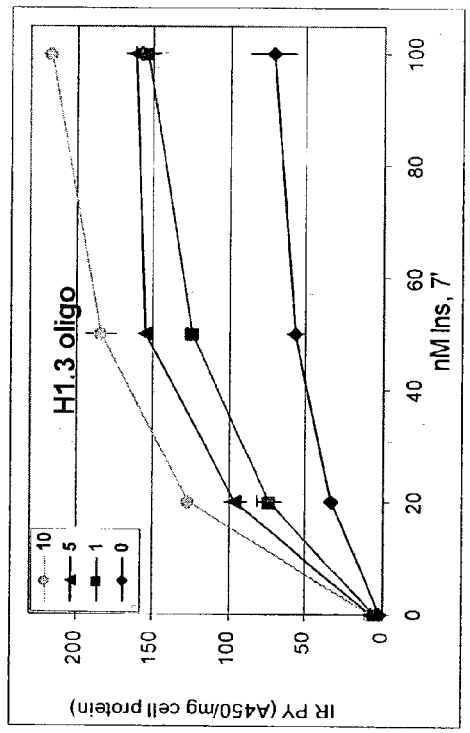
FIG. 22 presents the results of an ELISA in which the level of insulin receptor (IR) phosphorylated tyrosine was measured in 293-HEK HIR cells transfected with 0, 0.5, 3, or 10 nM hPTP1B1.3 (H1.3, SEQ ID NO: 566)(FIG. 22A) or mPTP1B1.1 (M1.1, SEQ ID NO: 496) (FIG. 22B) siRNAs. The level of expression of human PTP1B in the cells was compared by immunoblot (see tables to right of each figure).
Figure 22B:
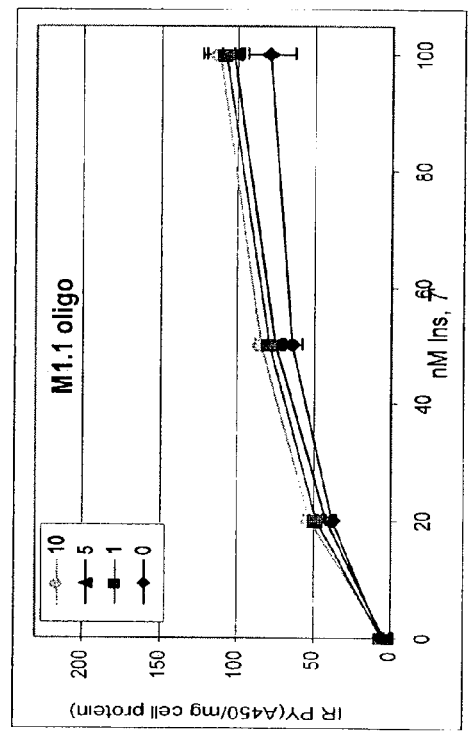
Figure 23B:
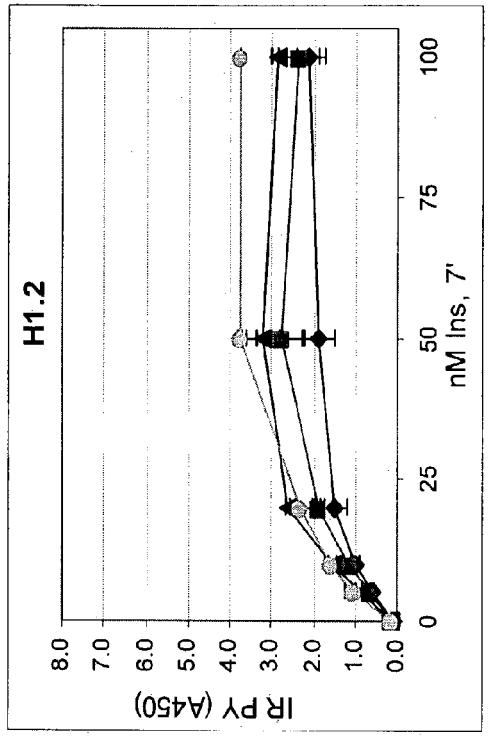
FIG. 23 depicts the results of an ELISA in which the level of insulin receptor (IR) phosphorylated tyrosine was measured in 293-HEK HIR cells transfected with 0, 0.5, 3, or 10 nM siRNAs. The siRNA polynucleotides transfected into the cells included hPTP1B1.2 (H1.2, SEQ ID NO: 561); hPTP1B1.3 (H1.3, SEQ ID NO: 566); mPTP1B1.1 (M1.1, SEQ ID NO: 496); and rPTP1B1.2 (R1.2, SEQ ID NO: 541). Seventy-two hours after transfection, cells were exposed to insulin for 7 minutes at the designated concentrations. Cell lysates were prepared and coated onto 96-well plates and probed with an anti-pY-IR-$\beta$ antibody.
Figure 23D:
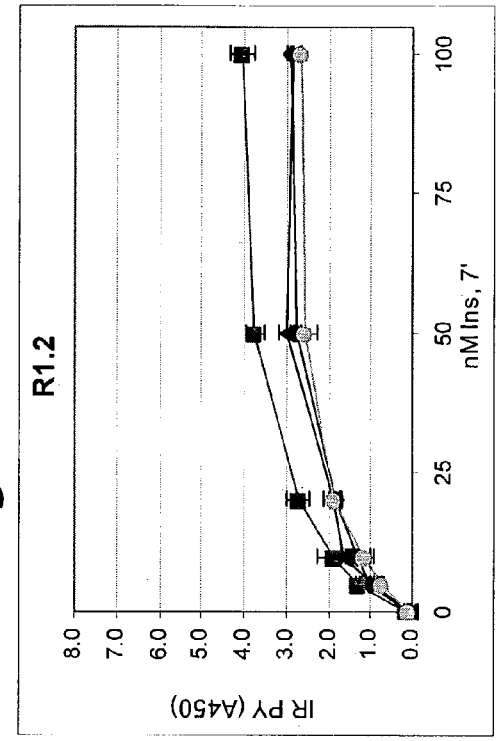
Figure 23A:
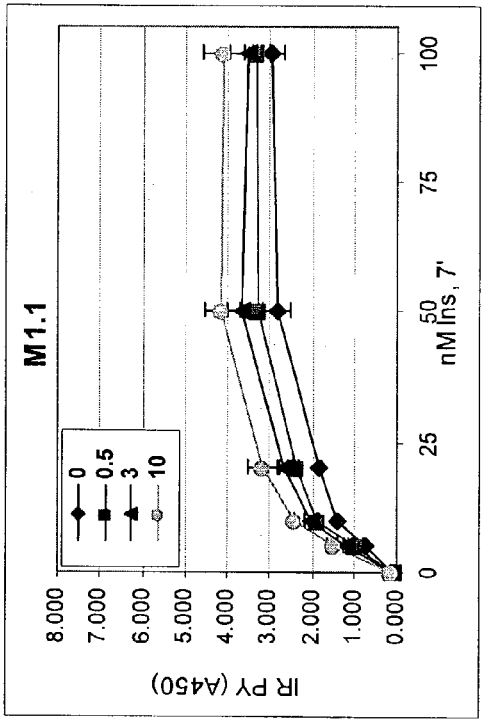
Figure 23C:
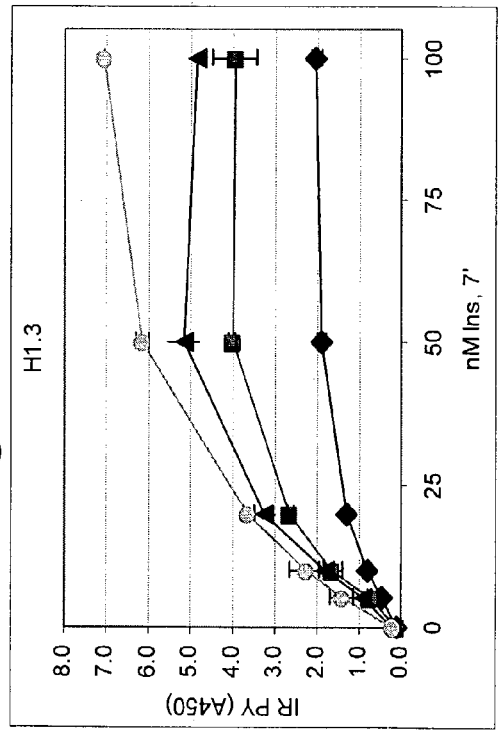

The effect of human PTP1B siRNA and of human TCPTP siRNA on the level of phosphorylation of IR-β was evaluated by ELISA. 292-HEK HIR cells were transfected with 0, 0.5, 3, or 10 nM siRNAs. The siRNA polynucleotides transfected into the cells included hPTP1B1.2 (SEQ ID NO: 561), hPTP1B1.3 (SEQ ID NO: 566), mPTP1B1.1 (SEQ ID NO: 496), rPTP1B1.2 (SEQ ID NO: 541), hTCPTP1.4 (SEQ ID NO: 593), and the combination of hPTP1B1.3 and hTCPTP1.4. Seventy-two hours after transfection, cells were exposed to insulin for 7 minutes at concentrations of 0, 25, 50, 75, and 100 nM. Cell lysates were prepared as described in Example 1, and total cell protein was quantified by the Bio-Rad Protein Assay performed according to the manufacturer's instructions (BioRad, Hercules, Calif.). An ELISA was performed as follows. Dynex Immulon HB4X plates were coated with anti-insulin receptor antibody Ab-1 (1 mg/ml; NeoMarkers, Inc., Fremont, Calif.) that was diluted 1:1000 in CMF (calcium magnesium free)-PBS containing 5 μg/ml fatty acid free BSA (faf-BSA). The plates were incubated at 4° C. for at least four hours. The antibody solution was removed by aspiration, followed by the addition of 300 μl of 3% faf-BSA+CMF-PBS. The plates were incubated for 1 hr with agitation on a vortex platform shaker (setting #5) at room temperature. After aspirating the 3% faf-BSA+CMF-PBS solution, approximately 10-20 μg of lysate were added to the wells and incubated at room temperature for one hour. Plates were washed three times with TBST (20 mM Tris-HCl, pH 7.5 150 mM NaCl; 0.05% Tween 20). An anti-insulin receptor phosphotyrosine specific antibody (pTyr 1162/63, Biosource International, Camarillo, Calif., Catalog #44-804) was diluted 1:2000 in TBST and added to the plates for one hour at room temperature. The plates were washed three times with TBST. HRP-conjugated anti-rabbit antibody (Amersham Biosciences, catalog #NA934V) (1:2000 in TBST) was then added to the wells and incubated at room temperature for one hour. The plates were washed three times with TBST and once with deionized, sterile water. TMB solution (Sigma Aldrich) (100 μl per well) was added and developed until a modest color change (10-30 minutes depending on cell type and insulin response). The reaction was stopped with 100 μl of 1.8 N H₂SO₄ and then mixed. The optical density of each well was measured at 450 nM in a Spectramax plate reader (Molecular Devices Corp., Sunnyvale, Calif.). The data are presented in FIG. 22. The level of expression of PTP1B in each cell lysates was determined by immunoblot as described above. PTP1B polypeptide was detected using an anti-human PTP-1B antibody (PHO2, Oncogene Research Products™, Inc.). The amount of PTP1B expressed in cells transfected with varying concentrations of either siRNA was quantified by densitometric analysis of the immunoblot. The level of expression of human PTP1B is presented as a percent of the level of expression in cells that were not transfected with hPTP1B1.3 siRNA (i.e., the level of expression in untransfected cells equals 100%) (see tables in FIG. 22).

Figure 24B:
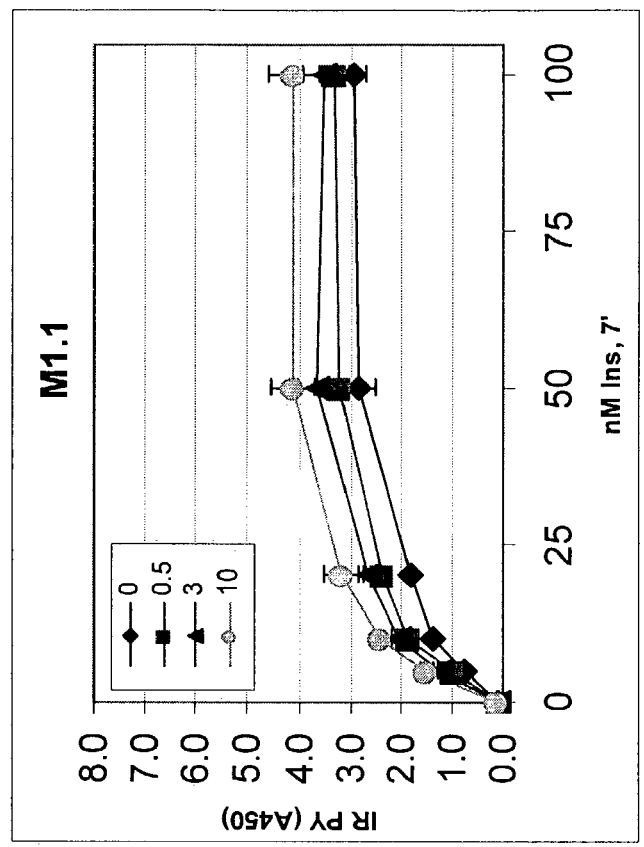
FIG. 24 depicts the results of an ELISA in which the level of insulin receptor (IR) phosphorylated tyrosine was measured in 293-HEK HIR cells transfected with 0, 0.5, 3, or 10 nM hTCPTP1.4 siRNA (TC1.4, SEQ ID NO: 593) (FIG. 24A) and mPTP1B1.1 siRNA (M1.1, SEQ ID NO: 496) (FIG. 24B). Seventy-two hours after transfection, cells were exposed to insulin for 7 minutes at the designated concentrations. Cell lysates were prepared and coated onto 96-well plates and probed with an anti-pY-IR-$\beta$ antibody.
Figure 24A:
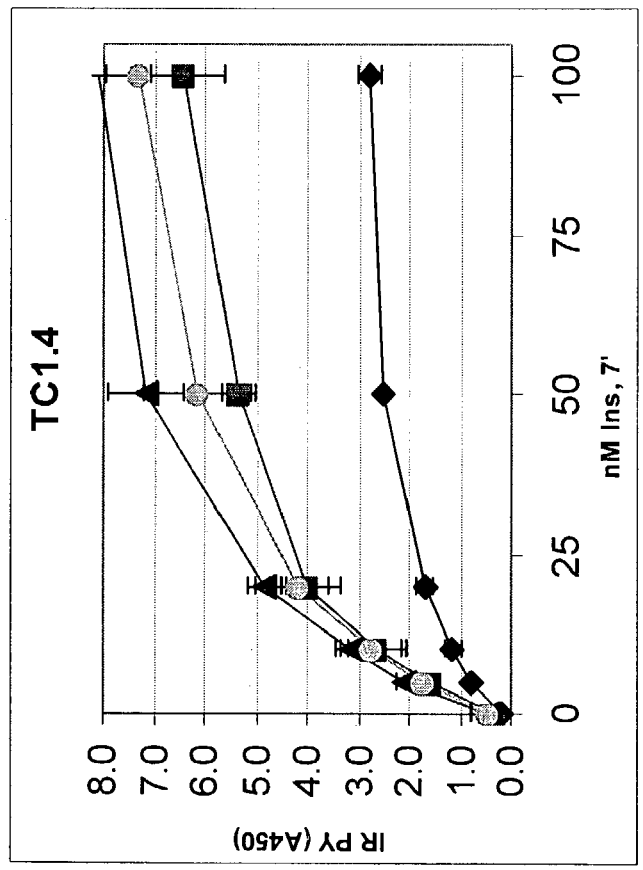

In a second experiment, 292-HEK HIR cells were transfected with 0, 0.5, 3, or 10 nM siRNAs. The siRNA polynucleotides transfected into the cells included hPTP1B1.2 (SEQ ID NO: 561), hPTP1B1.3 (SEQ ID NO: 566), mPTP1B1.1 (SEQ ID NO: 496), hTCPTP1.4 (SEQ ID NO: 593), and rPTP1B1.2 (SEQ ID NO: 541). Seventy-two hours after transfection, cells were exposed to insulin for 7 minutes at concentrations of 0, 5, 10, 20, 50, and 100 nM. Cell lysates were prepared and total cell protein was quantified as described above. An ELISA was performed as described above. Cell lysates were coated onto 96-well plates, blocked, and probed with an anti-pYpY$^{1162/1163}$-IR-β antibody. Binding was detected using an enzyme conjugated secondary reagent. As shown in FIGS. 23 and 24, respectively, increased phosphorylation of the insulin receptor was observed in cells transfected with hPTP1B1.3 and with hTCPTP1.4.

Figure 25:
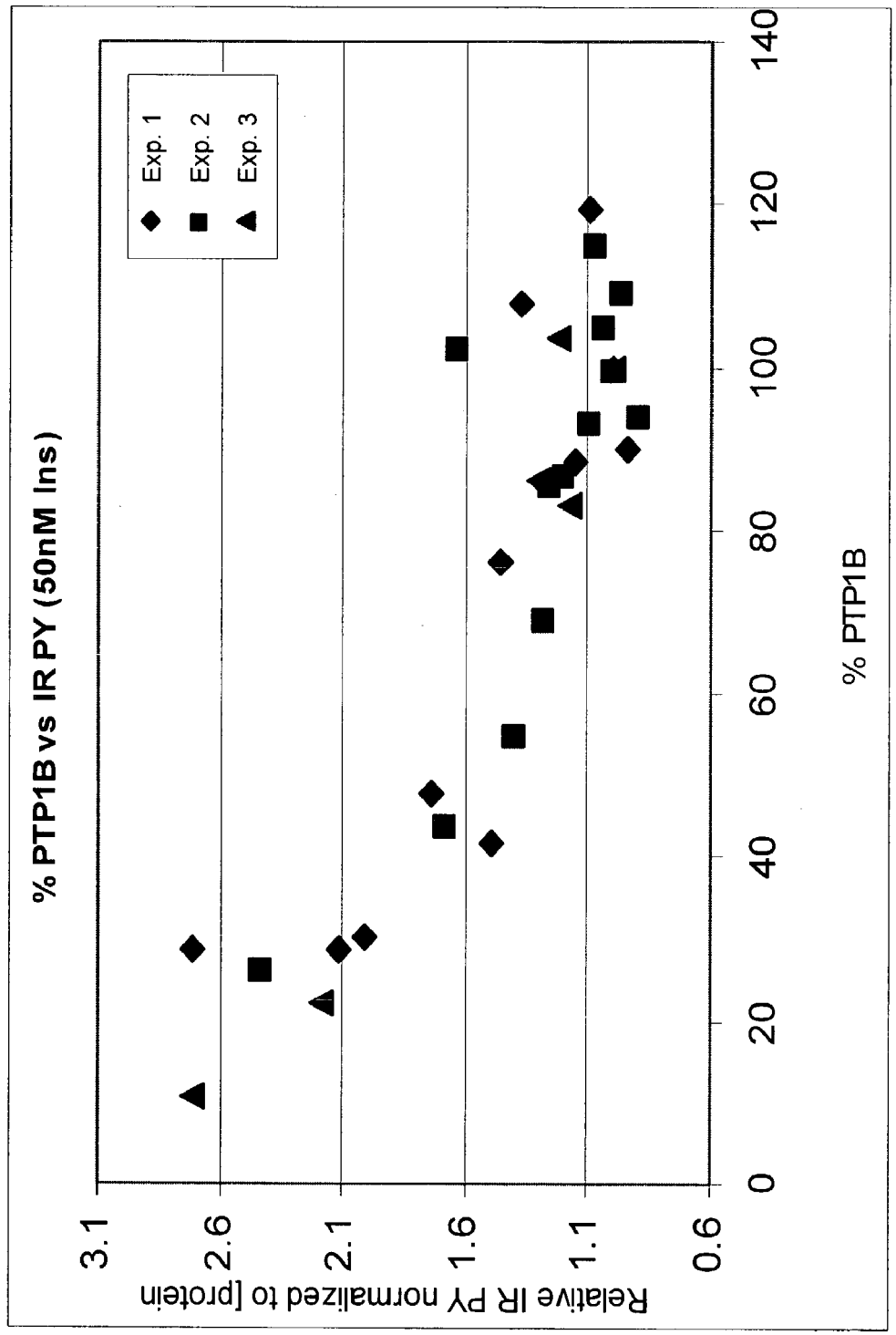
FIG. 25 represents ELISA data from three separate experiments that represent the level of insulin receptor phosphorylation in cells transfected with hPTP1B1.3 and stimulated with 50 nM insulin (Ins). Each data point represents the average optical density measured in duplicate wells.

The percent decrease in the level of PTP1B expression was compared with the level of phosphorylation of the insulin receptor. In three separate experiments, 292-HEK HIR cells were transfected with 0, 0.5, 3, or 10 nM hPTP1B1.3 siRNA and then exposed to insulin for 7 minutes at concentrations of 0, 5, 10, 20, 50, and 100 nM. An ELISA and immunoblot of cell lysates were performed as described above. The effect of hPTP1B1.3 siRNA on the phosphorylation state of the insulin receptor is summarized in FIG. 25. Each data point represents the average optical density measured in duplicate wells.

EXAMPLE 8

Identification of Oncology Targets and Decreased Expression of the Targets by Specific siRNAs This Example describes validation of DSP-3 as a target for oncology therapeutics. The Example also describes identification of siRNA polynucleotides that effectively interfere with expression of known chemotherapeutic target polypeptides.

Expression of DSP-3 polypeptide was evaluated in several cancer cell lines transfected with sequence specific DSP-3 siRNA polynucleotides and nonspecific siRNA polynucleotides. Cell lines included HeLa, HS578T; MDA-MB-231; MDA-MB-435 (breast cancer cell line that is ER⁻, Her2⁺, EGFR⁺, p53$^{mut}$, and invasive); MCF7 (breast cancer cell line that is ER⁺, Her2$^{low}$, EGFR$^{low}$, p53$^{WT}$, and non-invasive); T47D (breast cancer cell line that is ER⁺, Her2⁻, EGFR⁻, p53$^{mut}$, and non-invasive); HCT-116 (p53$^{WT}$); and HT-29 (p53$^{mut}$). Cells were transfected with 10 nM DSP3.1 (SEQ ID NO: 3), DSP3.4 (5'-ggugacacauauucugucutt-3', (SEQ ID NO: 646)(see also related SEQ ID NOS: 647-650)), or Scr.2 (scrambled, a non-specific siRNA sequence not found in a human genome database), and then cell lysates were prepared and evaluated for expression of DSP-3 and inhibition of expression by specific siRNAs, as described in Example 1. Transfection efficiency of some cell lines with siRNA, for example, MC7 and T47D, was improved by using Lipofectamine™ 2000 according to manufacturer's recommendations (Invitrogen Life Technologies) rather than Oligofectamine™ (Invitrogen Life Technologies) for the transfection procedure. The level of expression of DSP-3 polypeptide in the presence of specific siRNA 4compared with the non-specific siRNA control was significantly decreased in MCF7, T47D, MD-MB-435, HCT-116, and HT-29 cells.

Interference with expression of known chemotherapeutic targets by RNAi was examined, and siRNA polynucleotides that effectively interfere with expression of the targets were identified. Targets included dihydrofolate reductase (DHFR) (GenBank Accession No. NM_000791); thymidylate synthetase (GenBank Accession No. NM_001071); and topoisomerase I (GenBank Accession No. J03250). The siRNA polynucleotides were designed according to methods described in Examples 1 and 2 and were manufactured by Dharmacon. Each siRNA was transfected into HeLa cells, and the effect of each on the endogenous expression of DHFR, thymidylate synthetase, and topoisomerase I was evaluated by immunoblotting of cell lysates as described in Example 1. The level of expression of the targets was determined by immunoblotting with an anti-DHFR monoclonal antibody (BD monoclonal antibody (diluted 1:250)); an anti-topoisomerase I antibody (Santa Cruz Biotechnology, Cat. No. sc-10783, diluted 1:200); and an anti-thymidylate synthetase antibody (Rockland sheep polyclonal antibody diluted 1:2000). The results are presented in Table 3.

TABLE 14 siRNA INTERFERENCE WITH ENDOGENOUS EXPRESSION
OF DHFR, THYMIDYLATE SYNTHETASE, AND TOPOISOMERASE I

| Target | siRNA Sequence (SEQ ID NO) | Related siRNA Name | SEQ ID NO: | Decrease in Expression |
|---|---|---|---|---|
| DHFR | 5'-gaccugguucuccauuccutt-3' (SEQ ID NO: 651) | DHFR.1 | (SEQ ID NOS: 652-655) | >90% |
|  | 5'-gcaguguauuugcuagguctt-3' (SEQ ID NO: 656) | DHFR.3 | (SEQ ID NOS: 657-660) | >80% |

TABLE 14-continued siRNA INTERFERENCE WITH ENDOGENOUS EXPRESSION
OF DHFR, THYMIDYLATE SYNTHETASE, AND TOPOISOMERASE I

| Target | siRNA Sequence (SEQ ID NO) | siRNA Name | Related SEQ ID NO: | Decrease in Expression |
|---|---|---|---|---|
| | 5'-gucagcgagcagguucucatt-3' (SEQ ID NO: 661) | DHFR.4 | (SEQ ID NOS: 662-665) | >90% |
| Thymidylate Synthetase | 5'-ccaaacguguguucuggaatt-3' (SEQ ID NO: 666) | TYMS.1 | (SEQ ID NOS: 667-670) | >95% |
| | 5'-ccaacccugacgacagaagtt-3' (SEQ ID NO: 671) | TYMS.2 | (SEQ ID NOS: 672-675 | >90% |
| | 5'-gccaggugacuuuauacactt-3' (SEQ ID NO: 676) | TYMS.3 | (SEQ ID NOS: 677-680) | >95% |
| | 5'-cccagaccuuucccaaagctt-3' (SEQ ID NO: 681) | TYMS.4 | (SEQ ID NOS: 682-685) | >90% |
| Topoisomerase I | 5'-gauagagccuccuggacuutt-3' (SEQ ID NO: 686) | TOP1.1 | (SEQ ID NOS: 687-690) | >90% |
| | 5'-guccggcaugauaacaaggtt-3' (SEQ ID NO: 691) | TOP1.2 | (SEQ ID NOS: 692-695) | >90% |
| | 5'-ggagaaacagcggacacugtt-3' (SEQ ID NO: 696) | TOP1.3 | (SEQ ID NOS: 697-700) | >80% |
| | 5'-gcagcccgaggaugaucuutt-3' (SEQ ID NO: 701) | TOP1.4 | (SEQ ID NOS: 702-705) | >80% |

Interference of expression of another chemotherapeutic polypeptide target IKKgamma is performed according to the same procedures described above. The siRNA polynucleotides that are tested are IKK.1 (5'-gagucuccucugggggaagctt-3' (SEQ ID NO: (706); see also related SEQ ID NOS: 701-710); IKK.2 (5'-ggaguuccucaugugcaagtt-3' (SEQ ID NO: 711); see also related SEQ ID NOS: 712-715); IKK.3 (5'-ggccucugugaaagcccagtt-3' (SEQ ID NO: 716); see also related SEQ ID NOS: 717-720); and IKK.4 (5'-cacgcugcucuugauguggtt-3' (SEQ ID NO: 721); see also related SEQ ID NOS: 722-725).

Figure 26:
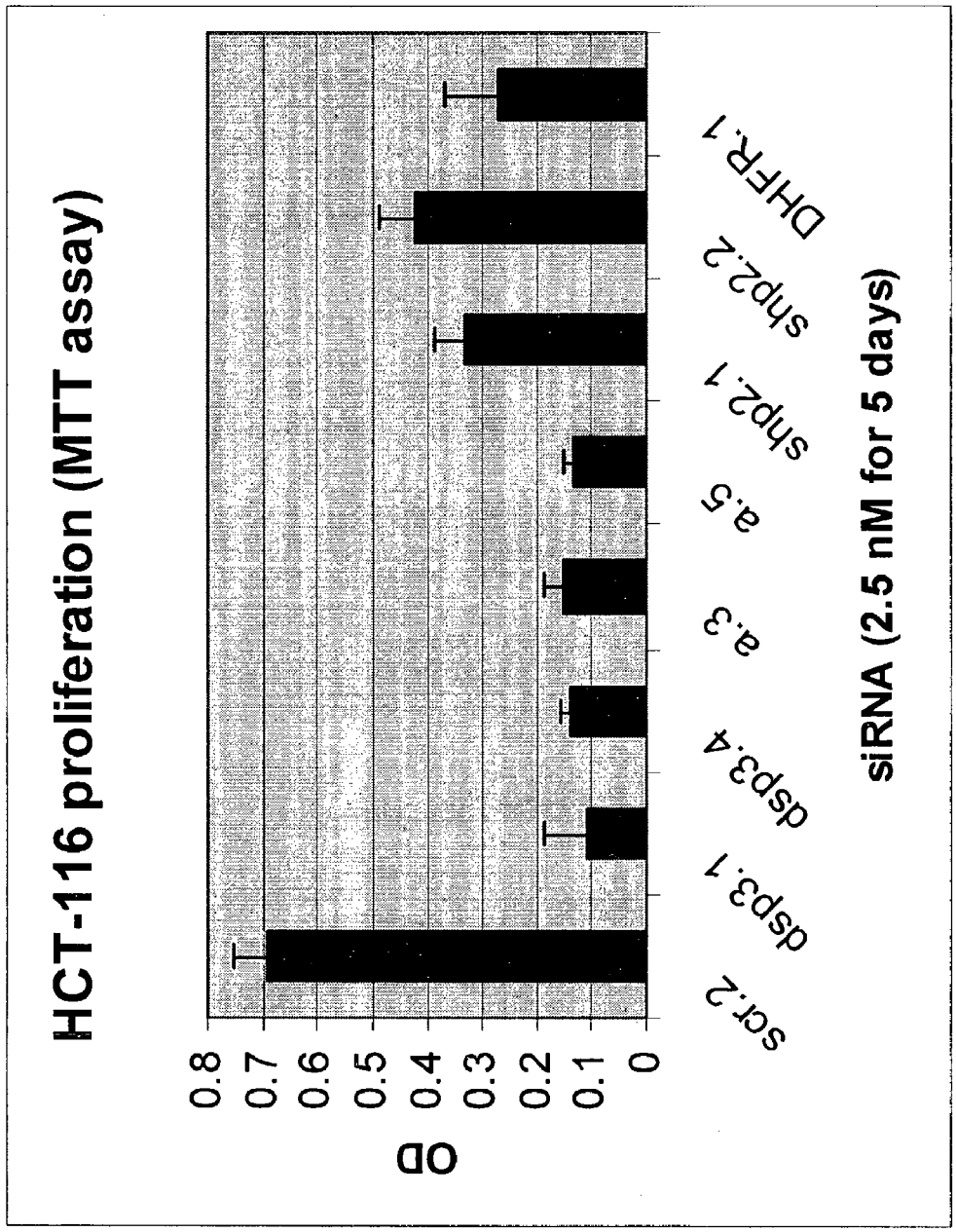
FIG. 26 illustrates an MTT assay comparing proliferation of HCT-116 cells transfected with siRNAs specific for DSP-3 (dsp3.1 (SEQ ID NO: 3) and dsp3.4 (SEQ ID NO: 646)); cdc14a (a.3 (SEQ ID NO: 444) and a.5 (SEQ ID NO: 449)); SHP-2 (shp2.1 (SEQ ID NO: 99) and shp2.2 (SEQ ID NO: 104); and DHFR (DHFR.1 (SEQ ID NO: 651). As a control, HCT-116 cells were transfected with nonspecific siRNA (scr.2). Each bar represents the average optical density for six wells.

The effect of RNAi silencing on expression of DHFR was compared with silencing of DSP-3, Cdc14a, and SHP-2 polypeptide expression in a HCT-116 cell proliferation assay. HCT-116 cells were transfected with 2.5 nM of the following siRNA oligonucleotides: scr.2); DSP3.1 (SEQ ID NO: 3); DSP3.4 (SEQ ID NO: 646); cdc14a.3 (SEQ ID NO: 444); cdc14a.5 (SEQ ID NO: 449); SHP2.1 (SEQ ID NO: 99); SHP2.2 (SEQ ID NO: 104); and DHFR.1 (SEQ ID NO: 651). After 5 days, cell proliferation was evaluated by performing an MTT assay essentially as described in Example 4. The results are presented in FIG. 26. The optical density (OD) measured for each siRNA represents an average of six wells.

Figure 27:
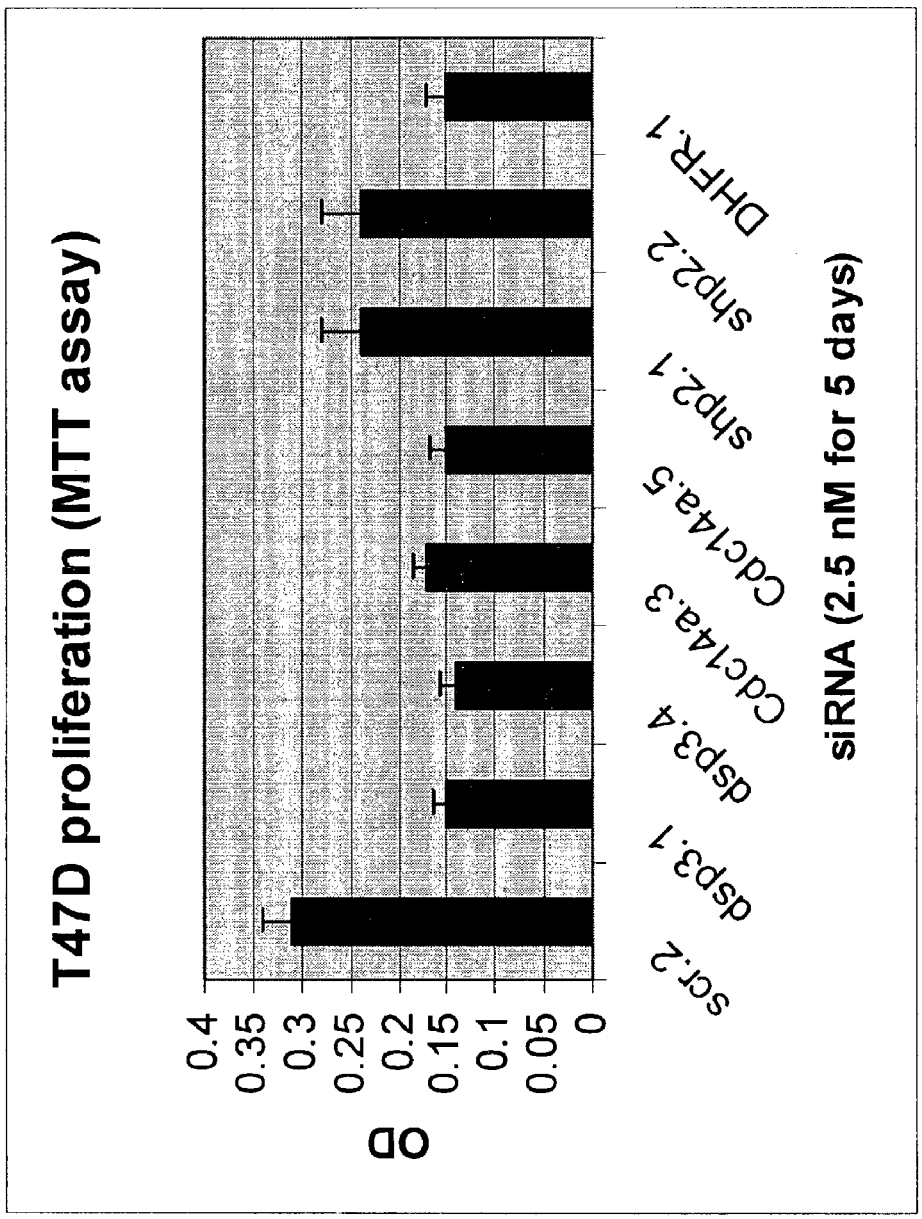
FIG. 27 illustrates an MTT assay comparing proliferation of T47D cells transfected with siRNAs specific for DSP-3 (dsp3.1 (SEQ ID NO: 3) and dsp3.4 (SEQ ID NO: 646)); cdc14a (Cdc14a.3 (SEQ ID NO: 444) and Cdc14a.5 (SEQ ID NO: 449)); SHP-2 (shp2.1 (SEQ ID NO: 99) and shp2.2 (SEQ ID NO: 104); and DHFR (DHFR.1 (SEQ ID NO: 651). As a control, T47D cells were transfected with nonspecific siRNA (scr.2).

A cell proliferation assay was also performed using a different cell line, T47D, and the same siRNAs. The data are presented in FIG. 27. The effect of silencing on proliferation was confirmed by cell counting. The number of T47D cells transfected with the nonspecific control siRNA scr.2 was approximately 200×10⁴. In T47D cells transfected with either DSP3.1 or DSP3.4 siRNA, the number of cells was approximately 75% of the negative control, and in the presence of DHFR.1, the number of cells was approximately 50% compared with cells transfected with the nonspecific control. Significantly decreased expression of DSP-3 and DHFR in cells transfected with the respective siRNAs was confirmed by immunoblot.

Figures 28A, 28B:
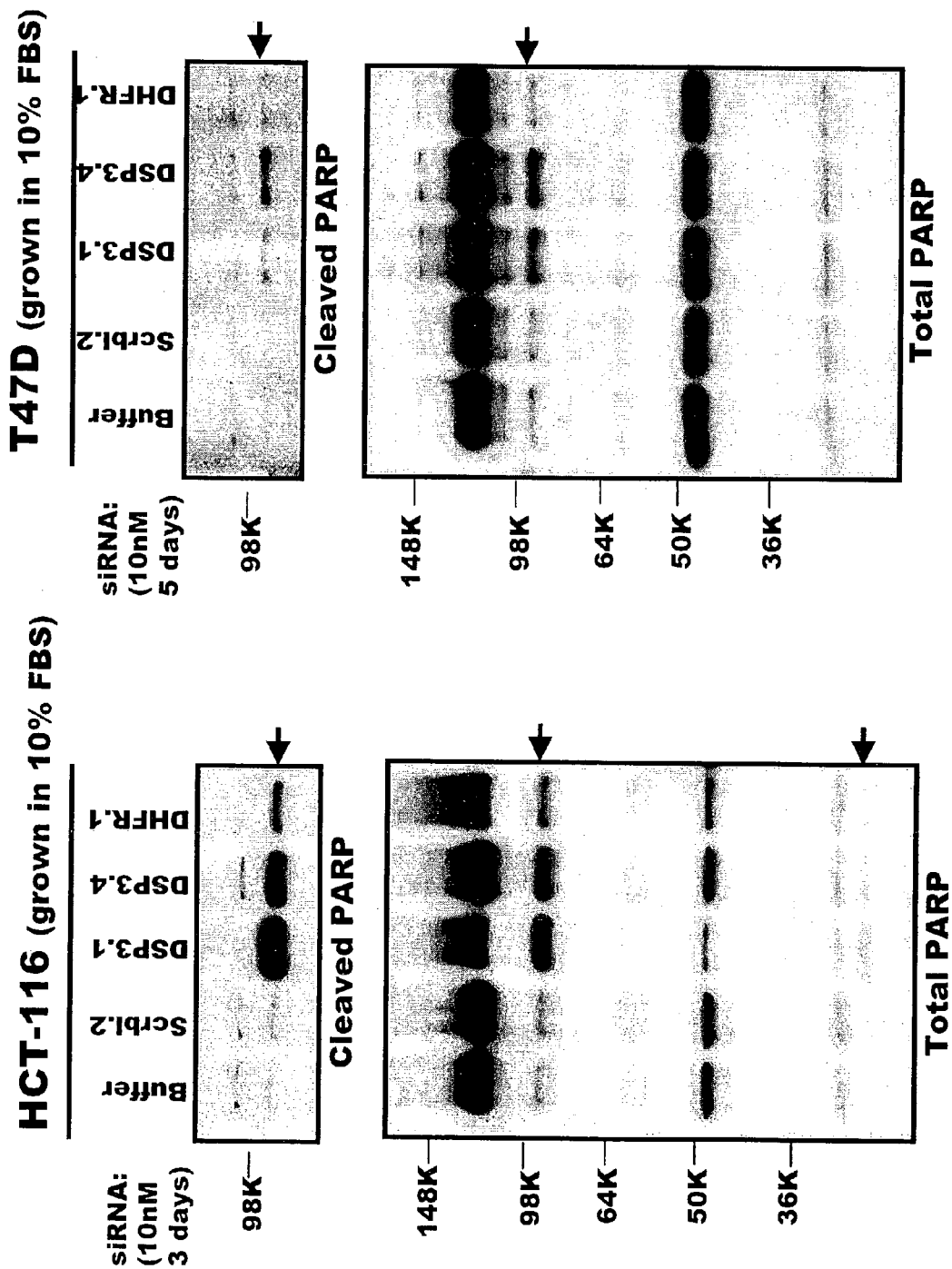
FIG. 28 represents an immunoblot of cleavage of PARP in HCT-116 cells (FIG. 28A) and T47D (FIG. 28B) transfected with buffer only (lane 1); (scrb1.2) (lane 2); DSP3.1 (SEQ ID NO: 3)(lane 3); DSP3.4 (SEQ ID NO: 646) (lane 4); and DHFR.1 (SEQ ID NO: 651)(lane 5).

Silencing of DSP-3 in HCT-116 and T47D cells also induced proapoptotic signaling. HCT-116 cells and T47D cells were transfected with 10 nM of non-specific si RNA control scrb1.2) (identical sequence to scr.2 described above), DSP3.1, DSP3.4, or DHFR.1. Three days after transfection of HCT-116 cells and five days after transfection of T47D cells, PARP assays were performed as described in Example 4. The results are presented in FIG. 28.

EXAMPLE 9

Inhibition of MAP Kinase Kinase Expression by RNAi

This Example describes interference of expression of MAP kinase kinases that are involved in the JNK signal transduction pathway in cells transfected with sequence specific siRNA polynucleotides.

Transient co-transfection experiments were performed as described in Example 2. 293-HEK cells were co-transfected with an expression vector that contained a polynucleotide sequence (GenBank Accession No. L36870) that encoded FLAG®-tagged human MKK4 polypeptide (GenBank Accession No. L36870) or with an expression vector that contained a polynucleotide sequence (GenBank Accession No. AF013588) that encoded FLAG®-tagged human MKK7 polypeptide (GenBank Accession No. AF013588). The siRNA oligonucleotides were designed and prepared as described in Examples 1 and 2. The cells were transfected and the level of expression of each kinase was determined by immunoblotting with an anti-FLAG® monoclonal antibody as described in Example 2. The results are presented in Table 4.

TABLE 15 siRNA INTERFERENCE WITH MKK4 AND MKK7 EXPRESSION IN CO-TRANSFECTION ASSAYS

| Target | siRNA Sequence (SEQ ID NO) | siRNA Name | Related SEQ ID NOs | Decrease in Expression |
|---|---|---|---|---|
| MKK4 | 5'-gugggcaaauaauggcagutt-3' (SEQ ID NO: 726) | MKK4.1 | (SEQ ID NOS: 727-730) | 80% |
|  | 5'-cugugaaagcacuaaaccatt-3' (SEQ ID NO: 731) | MKK4.2 | (SEQ ID NOS: 732-735) | 90% |
|  | 5'-ggagauccuccgcagcugatt-3' (SEQ ID NO: 736) | MKK4.3 | (SEQ ID NOS: 737-740) | 90% |
|  | 5'-gcucuuuauacuuuggccutt-3' (SEQ ID NO: 741) | MKK4.4 | (SEQ ID NOS: 742-745) | 80% |
| MKK7 | 5'-gcagacgggcuaccugacctt-3' (SEQ ID NO: 746) | MKK7.1 | (SEQ ID NOS: 747-750) | 10% |
|  | 5'-cacggacgucuucaucgcctt-3' (SEQ ID NO: 751) | MKK7.2 | (SEQ ID NOS: 752-755) | 10% |
|  | 5'-gaagcggaugcagggcccctt-3' (SEQ ID NO: 756) | MKK7.3 | (SEQ ID NOS: 757-760) | 10% |
|  | 5'-cugcaagacggacuuugagtt-3' (SEQ ID NO: 761) | MKK7.4 | (SEQ ID NOS: 762-765) | 10% |

EXAMPLE 10

Inhibition of Human P53 Expression by RNAi

An hairpin vector is prepared that contains a polynucleotide insert comprising a sequence that is a portion of a polynucleotide that encodes human p53 as described in Example 5. This sequence may be incorporated into a hairpin vector and transfected into a cell line known to express p53 (see Example 5). The level of expression of p53 is then determined by methods well known in the art, such as immunoblotting using an anti-p53 antibody (see Example 5). The p53 sequence incorporated into a hairpin vector is as follows.

HP53-HP9

5'-tttGACTCCAGTGGTMTCTACTTCM-GAGAGTAGATTACCACTGGAGTCttttt-3' (SEQ ID NO: 766)

3' tgaggtcaccattagatgaagttctct-catctaatggtgacctcagAAAAAGATC-5' (SEQ ID NO: 767) (See also SEQ ID NOS: 768-769, respectively (RNA sequence).)

ADDITIONAL REFERENCES

Agami et al., *Cell* 102:55-66 (2000)
Bass, Brenda L., *Cell* 101:235:238 (2000)
Brummelkamp et al., *Science* 296:550-53 (2002)
Carthew, Richard W., *Current Opinion in Cell Biology* 13:244-248 (2001)
Clemens et al., *Proc. Natl. Acad. Sci. USA* 97:6499-6503 (2000)
Elbashir et al., *Genes & Development* 15:188-200 (2001)
Elbashir, et al., *Nature* 411:494-498 (2001)
Fire et al., *Nature* 391:806-11 (1993)
Flint et al., *Proc. Natl. Acad. Sci. USA* 94:1680-1685 (1997)
Fukada et al., *J. Biol. Chem.* 276:25512-25519 (2001)
Harborth et al., *J. Cell Sci.* 114:4557-4565 (2001)
Hutvagner et al., *Curr. Opin. Gen. & Dev.* 12:225-232 (2002)
Kisielow et al., *Biochem. J.* 363:1-5 (2002)
Paddison et al., *Genes & Development* 16:948-958 (2002)
Salmeen et al., *Moleular Cell* 6:1401-1412 (2000)
Scadden et al., *EMBO Reports* 2:1107-1111 (2001)
Sharp, Phillip A., *Genes & Development* 13:139-141 (1999)
Sharp, Phillip A., *Genes & Development* 15:485-490 (2001)
Shen et al., *Proc. Natl. Acad. Sci. USA* 24:13613-13618 (2001)
Sui et al., *Proc. Natl. Acad. Sci. USA* 99:5515-5520 (2002)
Tonks et al, *Curr. Opin. Cell Biol.* 13:182-195 (2001)
Tuschl, Thomas, *Chembiochem.* 2:239-245 (2001)
Ui-Tei et al., *FEBS Letters* 479:79-82 (2000)
Wen et al., *Proc. Natl. Acad. Sci.* 98:4622-4627 (2001)
Zamore et al., *Cell* 101:25-33 (2000)
EP1 152 056
U.S. Pat. No. 2001/0029617
U.S. Pat. No. 2002/0007051
U.S. Pat. No. 6,326,193
U.S. Pat. No. 6,342,595

U.S. Pat. No. 6,506,559
WO 01/29058
WO 01/34815
WO 01/42443
WO 01/68836
WO 01/75164
WO 01/92513
WO 01/96584
WO 99/32619

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

What is claimed is:

1. An isolated small interfering RNA (siRNA) polynucleotide, comprising at least one polynucleotide that is selected from the group consisting of (i) a polynucleotide comprising the nucleotide sequence set forth in SEQ ID NO:445, (ii) a polynucleotide comprising the nucleotide sequence set forth in SEQ ID NO:446, (iii) a polynucleotide comprising the nucleotide sequence set forth in SEQ ID NO:447 and (iv) a polynucleotide comprising the nucleotide sequence set forth in SEQ ID NO:448.

2. The small interfering RNA polynucleotide of claim 1 that is selected from the group consisting of (i) the polynucleotide comprising the nucleotide sequence set forth in SEQ ID NO:445 and a complementary polynucleotide thereto of at least 18 nucleotides, (ii) the polynucleotide comprising the nucleotide sequence set forth in SEQ ID NO:446 and a complementary polynucleotide thereto of at least 18 nucleotides, (iii) the polynucleotide comprising the nucleotide sequence set forth in SEQ ID NO:447 and a complementary polynucleotide thereto of at least 18 nucleotides, and (iv) the polynucleotide comprising the nucleotide sequence set forth in SEQ ID NO:448 and a complementary polynucleotide thereto of at least 18 nucleotides.

3. A small interfering RNA polynucleotide of either claim 1 or claim 2 that is capable of interfering with expression of a polypeptide, which polypeptide comprises the amino acid sequence as set forth in SEQ ID NO:803.

4. An isolated siRNA polynucleotide comprising the nucleotide sequence set forth in SEQ ID NO:444, or a complementary polynucleotide thereto of at least 18 nucleotides.

5. An isolated siRNA polynucleotide comprising the nucleotide sequence set forth in SEQ ID NO:445, or a complementary polynucleotide thereto of at least 18 nucleotides.

6. The siRNA polynucleotide of claim 1, claim 2 or claim 4 wherein the polynucleotide comprises at least one synthetic nucleotide analogue of a naturally occurring nucleotide.

7. The siRNA polynucleotide of claim 1, claim 2 or claim 4 wherein the polynucleotide is linked to a detectable label.

8. The siRNA polynucleotide of claim 7 wherein the detectable label is a reporter molecule.

9. The siRNA of claim 8 wherein the reporter molecule is selected from the group consisting of a dye, a radionuclide, a luminescent group, a fluorescent group, and biotin.

10. The siRNA polynucleotide of claim 9 wherein the fluorescent group is fluorescein isothiocyanate.

11. The siRNA polynucleotide of claim 7 wherein the detectable label is a magnetic particle.

12. A recombinant nucleic acid construct comprising a nucleic acid that is capable of directing transcription of a small interfering RNA (siRNA), the nucleic acid comprising:
(a) a first promoter; (b) a second promoter; and (c) at least one DNA polynucleotide segment comprising at least one polynucleotide that is selected from the group consisting of (i) a polynucleotide comprising the nucleotide sequence set forth in SEQ ID NO:444, (ii) a polynucleotide comprising the nucleotide sequence set forth in SEQ ID NO:445, (iii) a polynucleotide comprising the nucleotide sequence set forth in SEQ ID NO:446, (iv) a polynucleotide comprising the nucleotide sequence set forth in SEQ ID NO:447, (v) a polynucleotide comprising the nucleotide sequence set forth in SEQ ID NO:448, and (vi) a polynucleotide of at least 18 nucleotides that is complementary to one of (i)-(v), wherein the DNA polynucleotide segment is operably linked to at least one of the first and second promoters, and wherein the promoters are oriented to direct transcription of the DNA polynucleotide segment and of the complement thereto.

13. The recombinant nucleic acid construct of claim 12, comprising at least one enhancer that is selected from a first enhancer operably linked to the first promoter and a second enhancer operably linked to the second promoter.

14. The recombinant nucleic acid construct of claim 12, comprising at least one transcriptional terminator that is selected from (i) a first transcriptional terminator that is positioned in the construct to terminate transcription directed by the first promoter and (ii) a second transcriptional terminator that is positioned in the construct to terminate transcription directed by the second promoter.

15. The recombinant nucleic acid construct of claim 13 wherein the siRNA is capable of interfering with expression of a polypeptide, wherein the polypeptide comprises the amino acid sequence as set forth in SEQ ID NO:803.

16. A recombinant nucleic acid construct comprising a nucleic acid that is capable of directing transcription of a small interfering RNA (siRNA), the nucleic acid comprising (a) at least one promoter; (b) a DNA polynucleotide segment that is operably linked to the promoter, said DNA polynucleotide segment comprising a first polynucleotide that is selected from the group consisting of (i) a polynucleotide comprising the nucleotide sequence set forth in SEQ ID NO:444, (ii) a polynucleotide comprising the nucleotide sequence set forth in SEQ ID NO:445, (iii) a polynucleotide comprising the nucleotide sequence set forth in SEQ ID NO:446, (iv) a polynucleotide comprising the nucleotide sequence set forth in SEQ ID NO:447, (v) a polynucleotide comprising the nucleotide sequence set forth in SEQ ID NO:448, and (vi) a polynucleotide of at least 18 nucleotides that is complementary to one of (i)-(v); (c) a spacer sequence comprising at least 4 nucleotides operably linked to the DNA polynucleotide segment of (b); and (d) operably linked to the spacer sequence a second polynucleotide of at least 18 nucleotides that is complementary to at least one of (b)(i)-(vi).

17. The recombinant nucleic acid construct of claim 16 wherein the siRNA comprises an overhang of at least one and no more than four nucleotides, the overhang being located immediately 3' to (d).

18. The recombinant nucleic acid construct of claim 16 wherein the spacer sequence comprises at least 9 nucleotides.

19. The recombinant nucleic acid construct of claim 16 wherein the spacer sequence comprises two uridine nucleotides that are contiguous with (d).

20. The recombinant nucleic acid construct of claim 16 comprising at least one transcriptional terminator that is operably linked to the DNA polynucleotide segment.

21. An isolated host cell transformed or transfected with the recombinant nucleic acid construct of any one of claims 12-20.

22. A method for identifying a component of a signal transduction pathway comprising:
A. contacting a siRNA polynucleotide and a first biological sample comprising at least one cell that is capable of expressing a target polypeptide, or a variant of said polypeptide, under conditions and for a time sufficient for target polypeptide expression when the siRNA polynucleotide is not present, wherein
(1) the target polypeptide comprises the amino acid sequence as set forth in SEQ ID NO: 803,
(2) the siRNA polynucleotide is selected from the group consisting of
(a) the siRNA polynucleotide of claim 1,
(b) the siRNA polynucleotide of claim 2, and
(c) the siRNA polynucleotide of claim 4; and
B. comparing a level of phosphorylation of at least one protein that is capable of being phosphorylated in the cell with a level of phosphorylation of the protein in a control sample that has not been contacted with the siRNA polynucleotide,
wherein an altered level of phosphorylation of the protein in the presence of the siRNA polynucleotide relative to the level of phosphorylation of the protein in an absence of the siRNA polynucleotide indicates that the protein is a component of a signal transduction pathway.

* * * * *

SEQUENCE LISTING

<160> NUMBER OF SEQ ID NOS: 842

<210> SEQ ID NO 1
<211> LENGTH: 7
<212> TYPE: PRT
<213> ORGANISM: Unknown
<220> FEATURE:
<223> OTHER INFORMATION: Unique signature sequence motif contained
      within the conserved domain of  the PTP family of enzymes
<220> FEATURE:
<221> NAME/KEY: VARIANT
<222> LOCATION: 2, 3, 4, 5, 6
<223> OTHER INFORMATION: Xaa = Any Amino Acid

<400> SEQUENCE: 1

Cys Xaa Xaa Xaa Xaa Xaa Arg
1               5

<210> SEQ ID NO 2
<211> LENGTH: 11
<212> TYPE: PRT
<213> ORGANISM: UNKNOWN
<220> FEATURE:
<223> OTHER INFORMATION: 11 amino acid conserved sequence conatining the
      signature sequence motif for the majority of PTPs.
<220> FEATURE:
<221> NAME/KEY: VARIANT
<222> LOCATION: 1
<223> OTHER INFORMATION: Xaa = Ile or Val
<220> FEATURE:
<221> NAME/KEY: VARIANT
<222> LOCATION: 4,7,8
<223> OTHER INFORMATION: Xaa = any amino acid
<220> FEATURE:
<221> NAME/KEY: VARIANT
<222> LOCATION: 10
<223> OTHER INFORMATION: Xaa = Ser or Thr

<400> SEQUENCE: 2

Xaa His Cys Xaa Ala Gly Xaa Xaa Arg Xaa Gly
1               5                   10

<210> SEQ ID NO 3
<211> LENGTH: 21
<212> TYPE: DNA
<213> ORGANISM: Artificial Sequence
<220> FEATURE:
<223> OTHER INFORMATION: Small interfering RNA - DSP3.1

<400> SEQUENCE: 3
cgauagugcc aggccuaugt t                                         21

<210> SEQ ID NO 4
<211> LENGTH: 19
<212> TYPE: RNA
<213> ORGANISM: Artificial Sequence
<220> FEATURE:
<223> OTHER INFORMATION: Small interfering RNA - DSP3.1

```
<400> SEQUENCE: 4
cgauagugcc aggccuaug                                                 19

<210> SEQ ID NO 5
<211> LENGTH: 19
<212> TYPE: RNA
<213> ORGANISM: Artificial Sequence
<220> FEATURE:
<223> OTHER INFORMATION: Small interfering RNA - DSP3.1

<400> SEQUENCE: 5
cauaggccug gcacuaucg                                                 19

<210> SEQ ID NO 6
<211> LENGTH: 21
<212> TYPE: DNA
<213> ORGANISM: Artificial Sequence
<220> FEATURE:
<223> OTHER INFORMATION: Small interfering RNA - DSP3.1
<220> FEATURE:
<221> NAME/KEY: misc_feature
<222> LOCATION: 20, 21
<223> OTHER INFORMATION: n = A,T,C,G or U

<400> SEQUENCE: 6
cgauagugcc aggccuaugn n                                              21

<210> SEQ ID NO 7
<211> LENGTH: 21
<212> TYPE: DNA
<213> ORGANISM: Artificial Sequence
<220> FEATURE:
<223> OTHER INFORMATION: Small interfering RNA - DSP3.1
<220> FEATURE:
<221> NAME/KEY: misc_feature
<222> LOCATION: 1, 2
<223> OTHER INFORMATION: n = A,T,C,G or U

<400> SEQUENCE: 7
nncauaggcc uggcacuauc g                                              21

<210> SEQ ID NO 8
<211> LENGTH: 21
<212> TYPE: DNA
<213> ORGANISM: Artificial Sequence
<220> FEATURE:
<223> OTHER INFORMATION: Small interfering RNA - DSP3.2

<400> SEQUENCE: 8
gcaugagguc caucaguaut t                                              21

<210> SEQ ID NO 9
<211> LENGTH: 19
<212> TYPE: RNA
<213> ORGANISM: Artificial Sequence
<220> FEATURE:
<223> OTHER INFORMATION: Small interfering RNA - DSP3.2

<400> SEQUENCE: 9
gcaugagguc caucaguau                                                 19

<210> SEQ ID NO 10
<211> LENGTH: 19
<212> TYPE: RNA
<213> ORGANISM: Artificial Sequence
<220> FEATURE:
<223> OTHER INFORMATION: Small interfering RNA - DSP3.2
```

```
<400> SEQUENCE: 10
auacugaugg accucaugc                                              19

<210> SEQ ID NO 11
<211> LENGTH: 21
<212> TYPE: DNA
<213> ORGANISM: Artificial Sequence
<220> FEATURE:
<223> OTHER INFORMATION: Small interfering RNA - DSP3.2
<220> FEATURE:
<221> NAME/KEY: misc_feature
<222> LOCATION: 20, 21
<223> OTHER INFORMATION: n = A,T,C,G or U

<400> SEQUENCE: 11
gcaugagguc caucaguaun n                                           21

<210> SEQ ID NO 12
<211> LENGTH: 21
<212> TYPE: DNA
<213> ORGANISM: Artificial Sequence
<220> FEATURE:
<223> OTHER INFORMATION: Small interfering RNA - DSP3.2
<220> FEATURE:
<221> NAME/KEY: misc_feature
<222> LOCATION: 1, 2
<223> OTHER INFORMATION: n = A,T,C,G or U

<400> SEQUENCE: 12
nnauacugau ggaccucaug c                                           21

<210> SEQ ID NO 13
<211> LENGTH: 21
<212> TYPE: DNA
<213> ORGANISM: Artificial Sequence
<220> FEATURE:
<223> OTHER INFORMATION: Small interfering RNA - DSP3.3

<400> SEQUENCE: 13
cgauacugcc aggcccaugt t                                           21

<210> SEQ ID NO 14
<211> LENGTH: 19
<212> TYPE: RNA
<213> ORGANISM: Artificial Sequence
<220> FEATURE:
<223> OTHER INFORMATION: Small interfering RNA - DSP3.3

<400> SEQUENCE: 14
cgauacugcc aggcccaug                                              19

<210> SEQ ID NO 15
<211> LENGTH: 19
<212> TYPE: RNA
<213> ORGANISM: Artificial Sequence
<220> FEATURE:
<223> OTHER INFORMATION: Small interfering RNA - DSP3.3

<400> SEQUENCE: 15
caugggccug gcaguaucg                                              19

<210> SEQ ID NO 16
<211> LENGTH: 21
<212> TYPE: DNA
<213> ORGANISM: Artificial Sequence
<220> FEATURE:
```

```
<223> OTHER INFORMATION: Small interfering RNA - DSP3.3
<220> FEATURE:
<221> NAME/KEY: misc_feature
<222> LOCATION: 20, 21
<223> OTHER INFORMATION: n = A,T,C,G or U

<400> SEQUENCE: 16
cgauacugcc aggcccaugn n                                              21

<210> SEQ ID NO 17
<211> LENGTH: 21
<212> TYPE: DNA
<213> ORGANISM: Artificial Sequence
<220> FEATURE:
<223> OTHER INFORMATION: Small interfering RNA - DSP3.3
<220> FEATURE:
<221> NAME/KEY: misc_feature
<222> LOCATION: 1, 2
<223> OTHER INFORMATION: n = A,T,C,G or U

<400> SEQUENCE: 17
nncaugggcc uggcaguauc g                                              21

<210> SEQ ID NO 18
<211> LENGTH: 21
<212> TYPE: DNA
<213> ORGANISM: Artificial Sequence
<220> FEATURE:
<223> OTHER INFORMATION: Small interfering RNA - MKP.1

<400> SEQUENCE: 18
auccugcccu uucuguacct t                                              21

<210> SEQ ID NO 19
<211> LENGTH: 19
<212> TYPE: RNA
<213> ORGANISM: Artificial Sequence
<220> FEATURE:
<223> OTHER INFORMATION: Small interfering RNA - MKP.1

<400> SEQUENCE: 19
auccugcccu uucuguacc                                                 19

<210> SEQ ID NO 20
<211> LENGTH: 19
<212> TYPE: RNA
<213> ORGANISM: Artificial Sequence
<220> FEATURE:
<223> OTHER INFORMATION: Small interfering RNA - MKP.1

<400> SEQUENCE: 20
gguacagaaa gggcaggau                                                 19

<210> SEQ ID NO 21
<211> LENGTH: 21
<212> TYPE: DNA
<213> ORGANISM: Artificial Sequence
<220> FEATURE:
<223> OTHER INFORMATION: Small interfering RNA - MKP.1
<220> FEATURE:
<221> NAME/KEY: misc_feature
<222> LOCATION: 20, 21
<223> OTHER INFORMATION: n = A,T,C,G or U

<400> SEQUENCE: 21
auccugcccu uucuguaccn n                                              21
```

```
<210> SEQ ID NO 22
<211> LENGTH: 21
<212> TYPE: DNA
<213> ORGANISM: Artificial Sequence
<220> FEATURE:
<223> OTHER INFORMATION: Small interfering RNA - MKP.1
<220> FEATURE:
<221> NAME/KEY: misc_feature
<222> LOCATION: 1, 2
<223> OTHER INFORMATION: n = A,T,C,G or U

<400> SEQUENCE: 22
nngguacaga aagggcagga u                                              21

<210> SEQ ID NO 23
<211> LENGTH: 21
<212> TYPE: DNA
<213> ORGANISM: Artificial Sequence
<220> FEATURE:
<223> OTHER INFORMATION: Small interfering RNA - MKP.2

<400> SEQUENCE: 23
gcagaggcaa agcaucauct t                                              21

<210> SEQ ID NO 24
<211> LENGTH: 19
<212> TYPE: RNA
<213> ORGANISM: Artificial Sequence
<220> FEATURE:
<223> OTHER INFORMATION: Small interfering RNA - MKP.2

<400> SEQUENCE: 24
gcagaggcaa agcaucauc                                                 19

<210> SEQ ID NO 25
<211> LENGTH: 19
<212> TYPE: RNA
<213> ORGANISM: Artificial Sequence
<220> FEATURE:
<223> OTHER INFORMATION: Small interfering RNA - MKP.2

<400> SEQUENCE: 25
gaugaugcuu ugccucugc                                                 19

<210> SEQ ID NO 26
<211> LENGTH: 21
<212> TYPE: DNA
<213> ORGANISM: Artificial Sequence
<220> FEATURE:
<223> OTHER INFORMATION: Small interfering RNA - MKP.2
<220> FEATURE:
<221> NAME/KEY: misc_feature
<222> LOCATION: 20, 21
<223> OTHER INFORMATION: n = A,T,C,G or U

<400> SEQUENCE: 26
gcagaggcaa agcaucaucn n                                              21

<210> SEQ ID NO 27
<211> LENGTH: 21
<212> TYPE: DNA
<213> ORGANISM: Artificial Sequence
<220> FEATURE:
<223> OTHER INFORMATION: Small interfering RNA - MKP.2
<220> FEATURE:
<221> NAME/KEY: misc_feature
<222> LOCATION: 1, 2
<223> OTHER INFORMATION: n = A,T,C,G or U
```

-continued

```
<400> SEQUENCE: 27
nngaugaugc uuugccucug c                                              21

<210> SEQ ID NO 28
<211> LENGTH: 21
<212> TYPE: DNA
<213> ORGANISM: Artificial Sequence
<220> FEATURE:
<223> OTHER INFORMATION: Small interfering RNA - cdc14a.1

<400> SEQUENCE: 28
caucgugcga agguuccugt t                                              21

<210> SEQ ID NO 29
<211> LENGTH: 19
<212> TYPE: RNA
<213> ORGANISM: Artificial Sequence
<220> FEATURE:
<223> OTHER INFORMATION: Small interfering RNA - cdc14a.1

<400> SEQUENCE: 29
caucgugcga agguuccug                                                 19

<210> SEQ ID NO 30
<211> LENGTH: 19
<212> TYPE: RNA
<213> ORGANISM: Artificial Sequence
<220> FEATURE:
<223> OTHER INFORMATION: Small interfering RNA - cdc14a.1

<400> SEQUENCE: 30
caggaaccuu cgcacgaug                                                 19

<210> SEQ ID NO 31
<211> LENGTH: 21
<212> TYPE: DNA
<213> ORGANISM: Artificial Sequence
<220> FEATURE:
<223> OTHER INFORMATION: Small interfering RNA - cdc14a.1
<220> FEATURE:
<221> NAME/KEY: misc_feature
<222> LOCATION: 20, 21
<223> OTHER INFORMATION: n = A,T,C,G or U

<400> SEQUENCE: 31
caucgugcga agguuccugn n                                              21

<210> SEQ ID NO 32
<211> LENGTH: 21
<212> TYPE: DNA
<213> ORGANISM: Artificial Sequence
<220> FEATURE:
<223> OTHER INFORMATION: Small interfering RNA - cdc14a.1
<220> FEATURE:
<221> NAME/KEY: misc_feature
<222> LOCATION: 1, 2
<223> OTHER INFORMATION: n = A,T,C,G or U

<400> SEQUENCE: 32
nncaggaacc uucgcacgau g                                              21

<210> SEQ ID NO 33
<211> LENGTH: 21
<212> TYPE: DNA
<213> ORGANISM: Artificial Sequence
<220> FEATURE:
<223> OTHER INFORMATION: Small interfering RNA - CD45.2
```

-continued

<400> SEQUENCE: 33
gccgagaaca aaguggaugt t                                              21

<210> SEQ ID NO 34
<211> LENGTH: 19
<212> TYPE: RNA
<213> ORGANISM: Artificial Sequence
<220> FEATURE:
<223> OTHER INFORMATION: Small interfering RNA - CD45.2

<400> SEQUENCE: 34
gccgagaaca aaguggaug                                                 19

<210> SEQ ID NO 35
<211> LENGTH: 19
<212> TYPE: RNA
<213> ORGANISM: Artificial Sequence
<220> FEATURE:
<223> OTHER INFORMATION: Small interfering RNA - CD45.2

<400> SEQUENCE: 35
cauccacuuu guucucggc                                                 19

<210> SEQ ID NO 36
<211> LENGTH: 21
<212> TYPE: DNA
<213> ORGANISM: Artificial Sequence
<220> FEATURE:
<223> OTHER INFORMATION: Small interfering RNA - CD45.2
<220> FEATURE:
<221> NAME/KEY: misc_feature
<222> LOCATION: 20, 21
<223> OTHER INFORMATION: n = A,T,C,G or U

<400> SEQUENCE: 36
gccgagaaca aaguggaugn n                                              21

<210> SEQ ID NO 37
<211> LENGTH: 21
<212> TYPE: DNA
<213> ORGANISM: Artificial Sequence
<220> FEATURE:
<223> OTHER INFORMATION: Small interfering RNA - CD45.2
<220> FEATURE:
<221> NAME/KEY: misc_feature
<222> LOCATION: 1, 2
<223> OTHER INFORMATION: n = A,T,C,G or U

<400> SEQUENCE: 37
nncauccacu uguucucgg c                                               21

<210> SEQ ID NO 38
<211> LENGTH: 8
<212> TYPE: PRT
<213> ORGANISM: Artificial Sequence
<220> FEATURE:
<223> OTHER INFORMATION: FLAG sequence

<400> SEQUENCE: 38

Asp Tyr Lys Asp Asp Asp Asp Lys
1               5

<210> SEQ ID NO 39
<211> LENGTH: 21
<212> TYPE: DNA
<213> ORGANISM: Artificial Sequence

```
<220> FEATURE:
<223> OTHER INFORMATION: Small interfering RNA - DSP11.2

<400> SEQUENCE: 39
cuggcaccau gcuggccugt t                                              21

<210> SEQ ID NO 40
<211> LENGTH: 19
<212> TYPE: RNA
<213> ORGANISM: Artificial Sequence
<220> FEATURE:
<223> OTHER INFORMATION: Small interfering RNA - DSP11.2

<400> SEQUENCE: 40
cuggcaccau gcuggccug                                                 19

<210> SEQ ID NO 41
<211> LENGTH: 19
<212> TYPE: RNA
<213> ORGANISM: Artificial Sequence
<220> FEATURE:
<223> OTHER INFORMATION: Small interfering RNA - DSP11.2

<400> SEQUENCE: 41
caggccagca uggugccag                                                 19

<210> SEQ ID NO 42
<211> LENGTH: 21
<212> TYPE: DNA
<213> ORGANISM: Artificial Sequence
<220> FEATURE:
<223> OTHER INFORMATION: Small interfering RNA - DSP11.2
<220> FEATURE:
<221> NAME/KEY: misc_feature
<222> LOCATION: 20, 21
<223> OTHER INFORMATION: n = A,T,C,G or U

<400> SEQUENCE: 42
cuggcaccau gcuggccugn n                                              21

<210> SEQ ID NO 43
<211> LENGTH: 21
<212> TYPE: DNA
<213> ORGANISM: Artificial Sequence
<220> FEATURE:
<223> OTHER INFORMATION: Small interfering RNA - DSP11.2
<220> FEATURE:
<221> NAME/KEY: misc_feature
<222> LOCATION: 1, 2
<223> OTHER INFORMATION: n = A,T,C,G or U

<400> SEQUENCE: 43
nncaggccag cauggugcca g                                              21

<210> SEQ ID NO 44
<211> LENGTH: 21
<212> TYPE: DNA
<213> ORGANISM: Artificial Sequence
<220> FEATURE:
<223> OTHER INFORMATION: Small interfering RNA - DSP11.4

<400> SEQUENCE: 44
agcagucuuc caguucuact t                                              21

<210> SEQ ID NO 45
<211> LENGTH: 19
<212> TYPE: RNA
```

```
<213> ORGANISM: Artificial Sequence
<220> FEATURE:
<223> OTHER INFORMATION: Small interfering RNA - DSP11.4

<400> SEQUENCE: 45
agcagucuuc caguucuac                                            19

<210> SEQ ID NO 46
<211> LENGTH: 19
<212> TYPE: RNA
<213> ORGANISM: Artificial Sequence
<220> FEATURE:
<223> OTHER INFORMATION: Small interfering RNA - DSP11.4

<400> SEQUENCE: 46
guagaacugg aagacugcu                                            19

<210> SEQ ID NO 47
<211> LENGTH: 21
<212> TYPE: DNA
<213> ORGANISM: Artificial Sequence
<220> FEATURE:
<223> OTHER INFORMATION: Small interfering RNA - DSP11.4
<220> FEATURE:
<221> NAME/KEY: misc_feature
<222> LOCATION: 20, 21
<223> OTHER INFORMATION: n = A,T,C,G or U

<400> SEQUENCE: 47
agcagucuuc caguucuacn n                                         21

<210> SEQ ID NO 48
<211> LENGTH: 21
<212> TYPE: DNA
<213> ORGANISM: Artificial Sequence
<220> FEATURE:
<223> OTHER INFORMATION: Small interfering RNA - DSP11.4
<220> FEATURE:
<221> NAME/KEY: misc_feature
<222> LOCATION: 1, 2
<223> OTHER INFORMATION: n = A,T,C,G or U

<400> SEQUENCE: 48
nnguagaacu ggaagacugc u                                         21

<210> SEQ ID NO 49
<211> LENGTH: 21
<212> TYPE: DNA
<213> ORGANISM: Artificial Sequence
<220> FEATURE:
<223> OTHER INFORMATION: Small interfering RNA - DSP18.2

<400> SEQUENCE: 49
cugccuugug cacugcuuut t                                         21

<210> SEQ ID NO 50
<211> LENGTH: 19
<212> TYPE: RNA
<213> ORGANISM: Artificial Sequence
<220> FEATURE:
<223> OTHER INFORMATION: Small interfering RNA - DSP18.2

<400> SEQUENCE: 50
cugccuugug cacugcuuu                                            19

<210> SEQ ID NO 51
<211> LENGTH: 19
```

```
<212> TYPE: RNA
<213> ORGANISM: Artificial Sequence
<220> FEATURE:
<223> OTHER INFORMATION: Small interfering RNA - DSP18.2

<400> SEQUENCE: 51
aaagcagugc acaaggcag                                              19

<210> SEQ ID NO 52
<211> LENGTH: 21
<212> TYPE: DNA
<213> ORGANISM: Artificial Sequence
<220> FEATURE:
<223> OTHER INFORMATION: Small interfering RNA - DSP18.2
<220> FEATURE:
<221> NAME/KEY: misc_feature
<222> LOCATION: 20, 21
<223> OTHER INFORMATION: n = A,T,C,G or U

<400> SEQUENCE: 52
cugccuugug cacugcuuun n                                           21

<210> SEQ ID NO 53
<211> LENGTH: 21
<212> TYPE: DNA
<213> ORGANISM: Artificial Sequence
<220> FEATURE:
<223> OTHER INFORMATION: Small interfering RNA - DSP18.2
<220> FEATURE:
<221> NAME/KEY: misc_feature
<222> LOCATION: 1, 2
<223> OTHER INFORMATION: n = A,T,C,G or U

<400> SEQUENCE: 53
nnaaagcagu gcacaaggca g                                           21

<210> SEQ ID NO 54
<211> LENGTH: 21
<212> TYPE: DNA
<213> ORGANISM: Artificial Sequence
<220> FEATURE:
<223> OTHER INFORMATION: Small interfering RNA - DSP18.4

<400> SEQUENCE: 54
gaguuuggcu gggccaguut t                                           21

<210> SEQ ID NO 55
<211> LENGTH: 19
<212> TYPE: RNA
<213> ORGANISM: Artificial Sequence
<220> FEATURE:
<223> OTHER INFORMATION: Small interfering RNA - DSP18.4

<400> SEQUENCE: 55
gaguuuggcu gggccaguu                                              19

<210> SEQ ID NO 56
<211> LENGTH: 19
<212> TYPE: RNA
<213> ORGANISM: Artificial Sequence
<220> FEATURE:
<223> OTHER INFORMATION: Small interfering RNA - DSP18.4

<400> SEQUENCE: 56
aacuggccca gccaaacuc                                              19

<210> SEQ ID NO 57
```

```
<211> LENGTH: 21
<212> TYPE: DNA
<213> ORGANISM: Artificial Sequence
<220> FEATURE:
<223> OTHER INFORMATION: Small interfering RNA - DSP18.4
<220> FEATURE:
<221> NAME/KEY: misc_feature
<222> LOCATION: 20, 21
<223> OTHER INFORMATION: n = A,T,C,G or U

<400> SEQUENCE: 57
gaguuuggcu gggccaguun n                                              21

<210> SEQ ID NO 58
<211> LENGTH: 21
<212> TYPE: DNA
<213> ORGANISM: Artificial Sequence
<220> FEATURE:
<223> OTHER INFORMATION: Small interfering RNA - DSP18.4
<220> FEATURE:
<221> NAME/KEY: misc_feature
<222> LOCATION: 1, 2
<223> OTHER INFORMATION: n = A,T,C,G or U

<400> SEQUENCE: 58
nnaacuggcc cagccaaacu c                                              21

<210> SEQ ID NO 59
<211> LENGTH: 21
<212> TYPE: DNA
<213> ORGANISM: Artificial Sequence
<220> FEATURE:
<223> OTHER INFORMATION: Small interfering RNA - DSP13.1

<400> SEQUENCE: 59
cuugcgggaa uucaaggaat t                                              21

<210> SEQ ID NO 60
<211> LENGTH: 19
<212> TYPE: RNA
<213> ORGANISM: Artificial Sequence
<220> FEATURE:
<223> OTHER INFORMATION: Small interfering RNA - DSP13.1

<400> SEQUENCE: 60
cuugcgggaa uucaaggaa                                                 19

<210> SEQ ID NO 61
<211> LENGTH: 19
<212> TYPE: RNA
<213> ORGANISM: Artificial Sequence
<220> FEATURE:
<223> OTHER INFORMATION: Small interfering RNA - DSP13.1

<400> SEQUENCE: 61
uuccuugaau ucccgcaag                                                 19

<210> SEQ ID NO 62
<211> LENGTH: 21
<212> TYPE: DNA
<213> ORGANISM: Artificial Sequence
<220> FEATURE:
<223> OTHER INFORMATION: Small interfering RNA - DSP13.1
<220> FEATURE:
<221> NAME/KEY: misc_feature
<222> LOCATION: 20, 21
<223> OTHER INFORMATION: n = A,T,C,G or U

<400> SEQUENCE: 62
```
cuugcgggaa uucaaggaan n                                          21

<210> SEQ ID NO 63
<211> LENGTH: 21
<212> TYPE: DNA
<213> ORGANISM: Artificial Sequence
<220> FEATURE:
<223> OTHER INFORMATION: Small interfering RNA - DSP13.1
<220> FEATURE:
<221> NAME/KEY: misc_feature
<222> LOCATION: 1, 2
<223> OTHER INFORMATION: n = A,T,C,G or U

<400> SEQUENCE: 63
nnuuccuuga auccccgcaa g                                          21

<210> SEQ ID NO 64
<211> LENGTH: 21
<212> TYPE: DNA
<213> ORGANISM: Artificial Sequence
<220> FEATURE:
<223> OTHER INFORMATION: Small interfering RNA - DSP13.2

<400> SEQUENCE: 64
ccgaggggua cgguauauct t                                          21

<210> SEQ ID NO 65
<211> LENGTH: 19
<212> TYPE: RNA
<213> ORGANISM: Artificial Sequence
<220> FEATURE:
<223> OTHER INFORMATION: Small interfering RNA - DSP13.2

<400> SEQUENCE: 65
ccgaggggua cgguauauc                                             19

<210> SEQ ID NO 66
<211> LENGTH: 19
<212> TYPE: RNA
<213> ORGANISM: Artificial Sequence
<220> FEATURE:
<223> OTHER INFORMATION: Small interfering RNA - DSP13.2

<400> SEQUENCE: 66
gauauaccgu accccucgg                                             19

<210> SEQ ID NO 67
<211> LENGTH: 21
<212> TYPE: DNA
<213> ORGANISM: Artificial Sequence
<220> FEATURE:
<223> OTHER INFORMATION: Small interfering RNA - DSP13.2
<220> FEATURE:
<221> NAME/KEY: misc_feature
<222> LOCATION: 20, 21
<223> OTHER INFORMATION: n = A,T,C,G or U

<400> SEQUENCE: 67
ccgaggggua cgguauaucn n                                          21

<210> SEQ ID NO 68
<211> LENGTH: 21
<212> TYPE: DNA
<213> ORGANISM: Artificial Sequence
<220> FEATURE:
<223> OTHER INFORMATION: Small interfering RNA - DSP13.2
<220> FEATURE:

```
<221> NAME/KEY: misc_feature
<222> LOCATION: 1, 2
<223> OTHER INFORMATION: n = A,T,C,G or U

<400> SEQUENCE: 68
nngauauacc guaccccucg g                                              21

<210> SEQ ID NO 69
<211> LENGTH: 21
<212> TYPE: DNA
<213> ORGANISM: Artificial Sequence
<220> FEATURE:
<223> OTHER INFORMATION: Small interfering RNA - DSP13.3

<400> SEQUENCE: 69
caucaggcug gcuguaagat t                                              21

<210> SEQ ID NO 70
<211> LENGTH: 19
<212> TYPE: RNA
<213> ORGANISM: Artificial Sequence
<220> FEATURE:
<223> OTHER INFORMATION: Small interfering RNA - DSP13.3

<400> SEQUENCE: 70
caucaggcug gcuguaaga                                                 19

<210> SEQ ID NO 71
<211> LENGTH: 19
<212> TYPE: RNA
<213> ORGANISM: Artificial Sequence
<220> FEATURE:
<223> OTHER INFORMATION: Small interfering RNA - DSP13.3

<400> SEQUENCE: 71
ucuuacagcc agccugaug                                                 19

<210> SEQ ID NO 72
<211> LENGTH: 21
<212> TYPE: DNA
<213> ORGANISM: Artificial Sequence
<220> FEATURE:
<223> OTHER INFORMATION: Small interfering RNA - DSP13.3
<220> FEATURE:
<221> NAME/KEY: misc_feature
<222> LOCATION: 20, 21
<223> OTHER INFORMATION: n = A,T,C,G or U

<400> SEQUENCE: 72
caucaggcug gcuguaagan n                                              21

<210> SEQ ID NO 73
<211> LENGTH: 21
<212> TYPE: DNA
<213> ORGANISM: Artificial Sequence
<220> FEATURE:
<223> OTHER INFORMATION: Small interfering RNA - DSP13.3
<220> FEATURE:
<221> NAME/KEY: misc_feature
<222> LOCATION: 1, 2
<223> OTHER INFORMATION: n = A,T,C,G or U

<400> SEQUENCE: 73
nnucuuacag ccagccugau g                                              21

<210> SEQ ID NO 74
<211> LENGTH: 21
```

```
<212> TYPE: DNA
<213> ORGANISM: Artificial Sequence
<220> FEATURE:
<223> OTHER INFORMATION: Small interfering RNA - DSP13.4

<400> SEQUENCE: 74
cauggaucua aaugccuugt t                                               21

<210> SEQ ID NO 75
<211> LENGTH: 19
<212> TYPE: RNA
<213> ORGANISM: Artificial Sequence
<220> FEATURE:
<223> OTHER INFORMATION: Small interfering RNA - DSP13.4

<400> SEQUENCE: 75
cauggaucua aaugccuug                                                  19

<210> SEQ ID NO 76
<211> LENGTH: 19
<212> TYPE: RNA
<213> ORGANISM: Artificial Sequence
<220> FEATURE:
<223> OTHER INFORMATION: Small interfering RNA - DSP13.4

<400> SEQUENCE: 76
caaggcauuu agauccaug                                                  19

<210> SEQ ID NO 77
<211> LENGTH: 21
<212> TYPE: DNA
<213> ORGANISM: Artificial Sequence
<220> FEATURE:
<223> OTHER INFORMATION: Small interfering RNA - DSP13.4
<220> FEATURE:
<221> NAME/KEY: misc_feature
<222> LOCATION: 20, 21
<223> OTHER INFORMATION: n = A,T,C,G or U

<400> SEQUENCE: 77
cauggaucua aaugccuugn n                                               21

<210> SEQ ID NO 78
<211> LENGTH: 21
<212> TYPE: DNA
<213> ORGANISM: Artificial Sequence
<220> FEATURE:
<223> OTHER INFORMATION: Small interfering RNA - DSP13.4
<220> FEATURE:
<221> NAME/KEY: misc_feature
<222> LOCATION: 1, 2
<223> OTHER INFORMATION: n = A,T,C,G or U

<400> SEQUENCE: 78
nncaaggcau uuagauccau g                                               21

<210> SEQ ID NO 79
<211> LENGTH: 21
<212> TYPE: DNA
<213> ORGANISM: Artificial Sequence
<220> FEATURE:
<223> OTHER INFORMATION: Small interfering RNA - DSP14.1

<400> SEQUENCE: 79
gugaagacaa gccucaagat t                                               21

<210> SEQ ID NO 80
```

```
<211> LENGTH: 19
<212> TYPE: RNA
<213> ORGANISM: Artificial Sequence
<220> FEATURE:
<223> OTHER INFORMATION: Small interfering RNA - DSP14.1

<400> SEQUENCE: 80
gugaagacaa gccucaaga                                                  19

<210> SEQ ID NO 81
<211> LENGTH: 19
<212> TYPE: RNA
<213> ORGANISM: Artificial Sequence
<220> FEATURE:
<223> OTHER INFORMATION: Small interfering RNA - DSP14.1

<400> SEQUENCE: 81
ucuugaggcu ugucuucac                                                  19

<210> SEQ ID NO 82
<211> LENGTH: 21
<212> TYPE: DNA
<213> ORGANISM: Artificial Sequence
<220> FEATURE:
<223> OTHER INFORMATION: Small interfering RNA - DSP14.1
<220> FEATURE:
<221> NAME/KEY: misc_feature
<222> LOCATION: 20, 21
<223> OTHER INFORMATION: n = A,T,C,G or U

<400> SEQUENCE: 82
gugaagacaa gccucaagan n                                               21

<210> SEQ ID NO 83
<211> LENGTH: 21
<212> TYPE: DNA
<213> ORGANISM: Artificial Sequence
<220> FEATURE:
<223> OTHER INFORMATION: Small interfering RNA - DSP14.1
<220> FEATURE:
<221> NAME/KEY: misc_feature
<222> LOCATION: 1, 2
<223> OTHER INFORMATION: n = A,T,C,G or U

<400> SEQUENCE: 83
nnucuugagg cuugucuuca c                                               21

<210> SEQ ID NO 84
<211> LENGTH: 21
<212> TYPE: DNA
<213> ORGANISM: Artificial Sequence
<220> FEATURE:
<223> OTHER INFORMATION: Small interfering RNA - DSP14.2

<400> SEQUENCE: 84
gcucuacauu ggcgaugagt t                                               21

<210> SEQ ID NO 85
<211> LENGTH: 19
<212> TYPE: RNA
<213> ORGANISM: Artificial Sequence
<220> FEATURE:
<223> OTHER INFORMATION: Small interfering RNA - DSP14.2

<400> SEQUENCE: 85
gcucuacauu ggcgaugag                                                  19
```

```
<210> SEQ ID NO 86
<211> LENGTH: 19
<212> TYPE: RNA
<213> ORGANISM: Artificial Sequence
<220> FEATURE:
<223> OTHER INFORMATION: Small interfering RNA - DSP14.2

<400> SEQUENCE: 86
cucaucgcca auguagagc                                                19

<210> SEQ ID NO 87
<211> LENGTH: 21
<212> TYPE: DNA
<213> ORGANISM: Artificial Sequence
<220> FEATURE:
<223> OTHER INFORMATION: Small interfering RNA - DSP14.2
<220> FEATURE:
<221> NAME/KEY: misc_feature
<222> LOCATION: 20, 21
<223> OTHER INFORMATION: n = A,T,C,G or U

<400> SEQUENCE: 87
gcucuacauu ggcgaugagn n                                             21

<210> SEQ ID NO 88
<211> LENGTH: 21
<212> TYPE: DNA
<213> ORGANISM: Artificial Sequence
<220> FEATURE:
<223> OTHER INFORMATION: Small interfering RNA - DSP14.2
<220> FEATURE:
<221> NAME/KEY: misc_feature
<222> LOCATION: 1, 2
<223> OTHER INFORMATION: n = A,T,C,G or U

<400> SEQUENCE: 88
nncucaucgc caauguagag c                                             21

<210> SEQ ID NO 89
<211> LENGTH: 21
<212> TYPE: DNA
<213> ORGANISM: Artificial Sequence
<220> FEATURE:
<223> OTHER INFORMATION: Small interfering RNA - DSP14.3

<400> SEQUENCE: 89
gcgacgacca caguaagaut t                                             21

<210> SEQ ID NO 90
<211> LENGTH: 19
<212> TYPE: RNA
<213> ORGANISM: Artificial Sequence
<220> FEATURE:
<223> OTHER INFORMATION: Small interfering RNA - DSP14.3

<400> SEQUENCE: 90
gcgacgacca caguaagau                                                19

<210> SEQ ID NO 91
<211> LENGTH: 19
<212> TYPE: RNA
<213> ORGANISM: Artificial Sequence
<220> FEATURE:
<223> OTHER INFORMATION: Small interfering RNA - DSP14.3

<400> SEQUENCE: 91
aucuuacugu ggucgucgc                                                19
```

```
<210> SEQ ID NO 92
<211> LENGTH: 21
<212> TYPE: DNA
<213> ORGANISM: Artificial Sequence
<220> FEATURE:
<223> OTHER INFORMATION: Small interfering RNA - DSP14.3
<220> FEATURE:
<221> NAME/KEY: misc_feature
<222> LOCATION: 20, 21
<223> OTHER INFORMATION: n = A,T,C,G or U

<400> SEQUENCE: 92
gcgacgacca caguaagaun n                                              21

<210> SEQ ID NO 93
<211> LENGTH: 21
<212> TYPE: DNA
<213> ORGANISM: Artificial Sequence
<220> FEATURE:
<223> OTHER INFORMATION: Small interfering RNA - DSP14.3
<220> FEATURE:
<221> NAME/KEY: misc_feature
<222> LOCATION: 1, 2
<223> OTHER INFORMATION: n = A,T,C,G or U

<400> SEQUENCE: 93
nnaucuuacu guggucgucg c                                              21

<210> SEQ ID NO 94
<211> LENGTH: 21
<212> TYPE: DNA
<213> ORGANISM: Artificial Sequence
<220> FEATURE:
<223> OTHER INFORMATION: Small interfering RNA - DSP14.4

<400> SEQUENCE: 94
ggacaugacc cugguggact t                                              21

<210> SEQ ID NO 95
<211> LENGTH: 19
<212> TYPE: RNA
<213> ORGANISM: Artificial Sequence
<220> FEATURE:
<223> OTHER INFORMATION: Small interfering RNA - DSP14.4

<400> SEQUENCE: 95
ggacaugacc cugguggac                                                 19

<210> SEQ ID NO 96
<211> LENGTH: 19
<212> TYPE: RNA
<213> ORGANISM: Artificial Sequence
<220> FEATURE:
<223> OTHER INFORMATION: Small interfering RNA - DSP14.4

<400> SEQUENCE: 96
guccaccagg gucaugucc                                                 19

<210> SEQ ID NO 97
<211> LENGTH: 21
<212> TYPE: DNA
<213> ORGANISM: Artificial Sequence
<220> FEATURE:
<223> OTHER INFORMATION: Small interfering RNA - DSP14.4
<220> FEATURE:
<221> NAME/KEY: misc_feature
<222> LOCATION: 20, 21
<223> OTHER INFORMATION: n = A,T,C,G or U
```

```
<400> SEQUENCE: 97
ggacaugacc cugguggacn n                                              21

<210> SEQ ID NO 98
<211> LENGTH: 21
<212> TYPE: DNA
<213> ORGANISM: Artificial Sequence
<220> FEATURE:
<223> OTHER INFORMATION: Small interfering RNA - DSP14.4
<220> FEATURE:
<221> NAME/KEY: misc_feature
<222> LOCATION: 1, 2
<223> OTHER INFORMATION: n = A,T,C,G or U

<400> SEQUENCE: 98
nnguccacca gggucauguc c                                              21

<210> SEQ ID NO 99
<211> LENGTH: 21
<212> TYPE: DNA
<213> ORGANISM: Artificial Sequence
<220> FEATURE:
<223> OTHER INFORMATION: Small interfering RNA - SHP2.1

<400> SEQUENCE: 99
gauucagaac acuggugaut t                                              21

<210> SEQ ID NO 100
<211> LENGTH: 19
<212> TYPE: RNA
<213> ORGANISM: Artificial Sequence
<220> FEATURE:
<223> OTHER INFORMATION: Small interfering RNA - SHP2.1

<400> SEQUENCE: 100
gauucagaac acuggugau                                                 19

<210> SEQ ID NO 101
<211> LENGTH: 19
<212> TYPE: RNA
<213> ORGANISM: Artificial Sequence
<220> FEATURE:
<223> OTHER INFORMATION: Small interfering RNA - SHP2.1

<400> SEQUENCE: 101
aucaccagug uucugaauc                                                 19

<210> SEQ ID NO 102
<211> LENGTH: 21
<212> TYPE: DNA
<213> ORGANISM: Artificial Sequence
<220> FEATURE:
<223> OTHER INFORMATION: Small interfering RNA - SHP2.1
<220> FEATURE:
<221> NAME/KEY: misc_feature
<222> LOCATION: 20, 21
<223> OTHER INFORMATION: n = A,T,C,G or U

<400> SEQUENCE: 102
gauucagaac acuggugaun n                                              21

<210> SEQ ID NO 103
<211> LENGTH: 21
<212> TYPE: DNA
<213> ORGANISM: Artificial Sequence
<220> FEATURE:
```

```
<223> OTHER INFORMATION: Small interfering RNA - SHP2.1
<220> FEATURE:
<221> NAME/KEY: misc_feature
<222> LOCATION: 1, 2
<223> OTHER INFORMATION: n = A,T,C,G or U

<400> SEQUENCE: 103
nnaucaccag uguucugaau c                                              21

<210> SEQ ID NO 104
<211> LENGTH: 21
<212> TYPE: DNA
<213> ORGANISM: Artificial Sequence
<220> FEATURE:
<223> OTHER INFORMATION: Small interfering RNA - SHP2.2

<400> SEQUENCE: 104
gaauauggcg ucaugcgugt t                                              21

<210> SEQ ID NO 105
<211> LENGTH: 19
<212> TYPE: RNA
<213> ORGANISM: Artificial Sequence
<220> FEATURE:
<223> OTHER INFORMATION: Small interfering RNA - SHP2.2

<400> SEQUENCE: 105
gaauauggcg ucaugcgug                                                 19

<210> SEQ ID NO 106
<211> LENGTH: 19
<212> TYPE: RNA
<213> ORGANISM: Artificial Sequence
<220> FEATURE:
<223> OTHER INFORMATION: Small interfering RNA - SHP2.2

<400> SEQUENCE: 106
cacgcaugac gccauauuc                                                 19

<210> SEQ ID NO 107
<211> LENGTH: 21
<212> TYPE: DNA
<213> ORGANISM: Artificial Sequence
<220> FEATURE:
<223> OTHER INFORMATION: Small interfering RNA - SHP2.2
<220> FEATURE:
<221> NAME/KEY: misc_feature
<222> LOCATION: 20, 21
<223> OTHER INFORMATION: n = A,T,C,G or U

<400> SEQUENCE: 107
gaauauggcg ucaugcgugn n                                              21

<210> SEQ ID NO 108
<211> LENGTH: 21
<212> TYPE: RNA
<213> ORGANISM: Artificial Sequence
<220> FEATURE:
<223> OTHER INFORMATION: Small interfering RNA - SHP2.2
<220> FEATURE:
<221> NAME/KEY: misc_feature
<222> LOCATION: 1, 2
<223> OTHER INFORMATION: n = A,T,C,G or U

<400> SEQUENCE: 108
nncacgcaug acgccauauu c                                              21
```

```
<210> SEQ ID NO 109
<211> LENGTH: 21
<212> TYPE: DNA
<213> ORGANISM: Artificial Sequence
<220> FEATURE:
<223> OTHER INFORMATION: Small interfering RNA - SHP2.3

<400> SEQUENCE: 109
cggucuggca auaccacuut t                                              21

<210> SEQ ID NO 110
<211> LENGTH: 19
<212> TYPE: RNA
<213> ORGANISM: Artificial Sequence
<220> FEATURE:
<223> OTHER INFORMATION: Small interfering RNA - SHP2.3

<400> SEQUENCE: 110
cggucuggca auaccacuu                                                 19

<210> SEQ ID NO 111
<211> LENGTH: 19
<212> TYPE: RNA
<213> ORGANISM: Artificial Sequence
<220> FEATURE:
<223> OTHER INFORMATION: Small interfering RNA - SHP2.3

<400> SEQUENCE: 111
aagugguauu gccagaccg                                                 19

<210> SEQ ID NO 112
<211> LENGTH: 21
<212> TYPE: DNA
<213> ORGANISM: Artificial Sequence
<220> FEATURE:
<223> OTHER INFORMATION: Small interfering RNA - SHP2.3
<220> FEATURE:
<221> NAME/KEY: misc_feature
<222> LOCATION: 20, 21
<223> OTHER INFORMATION: n = A,T,C,G or U

<400> SEQUENCE: 112
cggucuggca auaccacuun n                                              21

<210> SEQ ID NO 113
<211> LENGTH: 21
<212> TYPE: DNA
<213> ORGANISM: Artificial Sequence
<220> FEATURE:
<223> OTHER INFORMATION: Small interfering RNA - SHP2.3
<220> FEATURE:
<221> NAME/KEY: misc_feature
<222> LOCATION: 1, 2
<223> OTHER INFORMATION: n = A,T,C,G or U

<400> SEQUENCE: 113
nnaaguggua uugccagacc g                                              21

<210> SEQ ID NO 114
<211> LENGTH: 21
<212> TYPE: DNA
<213> ORGANISM: Artificial Sequence
<220> FEATURE:
<223> OTHER INFORMATION: Small interfering RNA - SHP2.4

<400> SEQUENCE: 114
ugacggcaag ucuaaagugt t                                              21
```

<210> SEQ ID NO 115
<211> LENGTH: 19
<212> TYPE: RNA
<213> ORGANISM: Artificial Sequence
<220> FEATURE:
<223> OTHER INFORMATION: Small interfering RNA - SHP2.4

<400> SEQUENCE: 115
ugacggcaag ucuaaagug                                                    19

<210> SEQ ID NO 116
<211> LENGTH: 19
<212> TYPE: RNA
<213> ORGANISM: Artificial Sequence
<220> FEATURE:
<223> OTHER INFORMATION: Small interfering RNA - SHP2.4

<400> SEQUENCE: 116
cacuuuagac uugccguca                                                    19

<210> SEQ ID NO 117
<211> LENGTH: 21
<212> TYPE: DNA
<213> ORGANISM: Artificial Sequence
<220> FEATURE:
<223> OTHER INFORMATION: Small interfering RNA - SHP2.4
<220> FEATURE:
<221> NAME/KEY: misc_feature
<222> LOCATION: 20, 21
<223> OTHER INFORMATION: n = A,T,C,G or U

<400> SEQUENCE: 117
ugacggcaag ucuaaagugn n                                                 21

<210> SEQ ID NO 118
<211> LENGTH: 21
<212> TYPE: DNA
<213> ORGANISM: Artificial Sequence
<220> FEATURE:
<223> OTHER INFORMATION: Small interfering RNA - SHP2.4
<220> FEATURE:
<221> NAME/KEY: misc_feature
<222> LOCATION: 1, 2
<223> OTHER INFORMATION: n = A,T,C,G or U

<400> SEQUENCE: 118
nncacuuuag acuugccguc a                                                 21

<210> SEQ ID NO 119
<211> LENGTH: 21
<212> TYPE: DNA
<213> ORGANISM: Artificial Sequence
<220> FEATURE:
<223> OTHER INFORMATION: Small interfering RNA - KAP.1

<400> SEQUENCE: 119
gagccuauug aagaugaact t                                                 21

<210> SEQ ID NO 120
<211> LENGTH: 19
<212> TYPE: RNA
<213> ORGANISM: Artificial Sequence
<220> FEATURE:
<223> OTHER INFORMATION: Small interfering RNA - KAP.1

<400> SEQUENCE: 120
gagccuauug aagaugaac                                                    19

```
<210> SEQ ID NO 121
<211> LENGTH: 19
<212> TYPE: RNA
<213> ORGANISM: Artificial Sequence
<220> FEATURE:
<223> OTHER INFORMATION: Small interfering RNA - KAP.1

<400> SEQUENCE: 121
guucaucuuc aauaggcuc                                                    19

<210> SEQ ID NO 122
<211> LENGTH: 21
<212> TYPE: DNA
<213> ORGANISM: Artificial Sequence
<220> FEATURE:
<223> OTHER INFORMATION: Small interfering RNA - KAP.1
<220> FEATURE:
<221> NAME/KEY: misc_feature
<222> LOCATION: 20, 21
<223> OTHER INFORMATION: n = A,T,C,G or U

<400> SEQUENCE: 122
gagccuauug aagaugaacn n                                                 21

<210> SEQ ID NO 123
<211> LENGTH: 21
<212> TYPE: DNA
<213> ORGANISM: Artificial Sequence
<220> FEATURE:
<223> OTHER INFORMATION: Small interfering RNA - KAP.1
<220> FEATURE:
<221> NAME/KEY: misc_feature
<222> LOCATION: 1, 2
<223> OTHER INFORMATION: n = A,T,C,G or U

<400> SEQUENCE: 123
nnguucaucu ucaauaggcu c                                                 21

<210> SEQ ID NO 124
<211> LENGTH: 21
<212> TYPE: DNA
<213> ORGANISM: Artificial Sequence
<220> FEATURE:
<223> OTHER INFORMATION: Small interfering RNA - KAP.2

<400> SEQUENCE: 124
gagcuguggu auacaagact t                                                 21

<210> SEQ ID NO 125
<211> LENGTH: 19
<212> TYPE: RNA
<213> ORGANISM: Artificial Sequence
<220> FEATURE:
<223> OTHER INFORMATION: Small interfering RNA - KAP.2

<400> SEQUENCE: 125
gagcuguggu auacaagac                                                    19

<210> SEQ ID NO 126
<211> LENGTH: 19
<212> TYPE: RNA
<213> ORGANISM: Artificial Sequence
<220> FEATURE:
<223> OTHER INFORMATION: Small interfering RNA - KAP.2

<400> SEQUENCE: 126
```
gucuuguaua ccacagcuc    19

<210> SEQ ID NO 127
<211> LENGTH: 21
<212> TYPE: DNA
<213> ORGANISM: Artificial Sequence
<220> FEATURE:
<223> OTHER INFORMATION: Small interfering RNA - KAP.2
<220> FEATURE:
<221> NAME/KEY: misc_feature
<222> LOCATION: 20, 21
<223> OTHER INFORMATION: n = A,T,C,G or U

<400> SEQUENCE: 127
gagcuguggu auacaagacn n    21

<210> SEQ ID NO 128
<211> LENGTH: 21
<212> TYPE: DNA
<213> ORGANISM: Artificial Sequence
<220> FEATURE:
<223> OTHER INFORMATION: Small interfering RNA - KAP.2
<220> FEATURE:
<221> NAME/KEY: misc_feature
<222> LOCATION: 1, 2
<223> OTHER INFORMATION: n = A,T,C,G or U

<400> SEQUENCE: 128
nngucuugua uaccacagcu c    21

<210> SEQ ID NO 129
<211> LENGTH: 21
<212> TYPE: DNA
<213> ORGANISM: Artificial Sequence
<220> FEATURE:
<223> OTHER INFORMATION: Small interfering RNA - KAP.3

<400> SEQUENCE: 129
gagcuuacaa ccugccuuat t    21

<210> SEQ ID NO 130
<211> LENGTH: 19
<212> TYPE: RNA
<213> ORGANISM: Artificial Sequence
<220> FEATURE:
<223> OTHER INFORMATION: Small interfering RNA - KAP.3

<400> SEQUENCE: 130
gagcuuacaa ccugccuua    19

<210> SEQ ID NO 131
<211> LENGTH: 19
<212> TYPE: RNA
<213> ORGANISM: Artificial Sequence
<220> FEATURE:
<223> OTHER INFORMATION: Small interfering RNA - KAP.3

<400> SEQUENCE: 131
uaaggcaggu uguaagcuc    19

<210> SEQ ID NO 132
<211> LENGTH: 21
<212> TYPE: DNA
<213> ORGANISM: Artificial Sequence
<220> FEATURE:
<223> OTHER INFORMATION: Small interfering RNA - KAP.3
<220> FEATURE:
<221> NAME/KEY: misc_feature

```
<222> LOCATION: 20, 21
<223> OTHER INFORMATION: n = A,T,C,G or U

<400> SEQUENCE: 132
gagcuuacaa ccugccuuan n                                              21

<210> SEQ ID NO 133
<211> LENGTH: 21
<212> TYPE: DNA
<213> ORGANISM: Artificial Sequence
<220> FEATURE:
<223> OTHER INFORMATION: Small interfering RNA - KAP.3
<220> FEATURE:
<221> NAME/KEY: misc_feature
<222> LOCATION: 1, 2
<223> OTHER INFORMATION: n = A,T,C,G or U

<400> SEQUENCE: 133
nnuaaggcag guuguaagcu c                                              21

<210> SEQ ID NO 134
<211> LENGTH: 21
<212> TYPE: DNA
<213> ORGANISM: Artificial Sequence
<220> FEATURE:
<223> OTHER INFORMATION: Small interfering RNA - KAP.4

<400> SEQUENCE: 134
uacacugcua uggaggacut t                                              21

<210> SEQ ID NO 135
<211> LENGTH: 19
<212> TYPE: RNA
<213> ORGANISM: Artificial Sequence
<220> FEATURE:
<223> OTHER INFORMATION: Small interfering RNA - KAP.4

<400> SEQUENCE: 135
uacacugcua uggaggacu                                                 19

<210> SEQ ID NO 136
<211> LENGTH: 19
<212> TYPE: RNA
<213> ORGANISM: Artificial Sequence
<220> FEATURE:
<223> OTHER INFORMATION: Small interfering RNA - KAP.4

<400> SEQUENCE: 136
aguccuccau agcagugua                                                 19

<210> SEQ ID NO 137
<211> LENGTH: 21
<212> TYPE: DNA
<213> ORGANISM: Artificial Sequence
<220> FEATURE:
<223> OTHER INFORMATION: Small interfering RNA - KAP.4
<220> FEATURE:
<221> NAME/KEY: misc_feature
<222> LOCATION: 20, 21
<223> OTHER INFORMATION: n = A,T,C,G or U

<400> SEQUENCE: 137
uacacugcua uggaggacun n                                              21

<210> SEQ ID NO 138
<211> LENGTH: 21
<212> TYPE: DNA
```

```
<213> ORGANISM: Artificial Sequence
<220> FEATURE:
<223> OTHER INFORMATION: Small interfering RNA - KAP.4
<220> FEATURE:
<221> NAME/KEY: misc_feature
<222> LOCATION: 1, 2
<223> OTHER INFORMATION: n = A,T,C,G or U

<400> SEQUENCE: 138
nnaguccucc auagcagugu a                                              21

<210> SEQ ID NO 139
<211> LENGTH: 21
<212> TYPE: DNA
<213> ORGANISM: Artificial Sequence
<220> FEATURE:
<223> OTHER INFORMATION: Small interfering RNA - Prl3.1

<400> SEQUENCE: 139
gugaccuaug acaaaacgct t                                              21

<210> SEQ ID NO 140
<211> LENGTH: 19
<212> TYPE: RNA
<213> ORGANISM: Artificial Sequence
<220> FEATURE:
<223> OTHER INFORMATION: Small interfering RNA - Prl3.1

<400> SEQUENCE: 140
gugaccuaug acaaaacgc                                                 19

<210> SEQ ID NO 141
<211> LENGTH: 19
<212> TYPE: RNA
<213> ORGANISM: Artificial Sequence
<220> FEATURE:
<223> OTHER INFORMATION: Small interfering RNA - Prl3.1

<400> SEQUENCE: 141
gcguuuuguc auaggucac                                                 19

<210> SEQ ID NO 142
<211> LENGTH: 21
<212> TYPE: DNA
<213> ORGANISM: Artificial Sequence
<220> FEATURE:
<223> OTHER INFORMATION: Small interfering RNA - Prl3.1
<220> FEATURE:
<221> NAME/KEY: misc_feature
<222> LOCATION: 20, 21
<223> OTHER INFORMATION: n = A,T,C,G or U

<400> SEQUENCE: 142
gugaccuaug acaaaacgcn n                                              21

<210> SEQ ID NO 143
<211> LENGTH: 21
<212> TYPE: DNA
<213> ORGANISM: Artificial Sequence
<220> FEATURE:
<223> OTHER INFORMATION: Small interfering RNA - Prl3.1
<220> FEATURE:
<221> NAME/KEY: misc_feature
<222> LOCATION: 1, 2
<223> OTHER INFORMATION: n = A,T,C,G or U

<400> SEQUENCE: 143
nngcguuuug ucauagguca c                                              21
```

<210> SEQ ID NO 144
<211> LENGTH: 21
<212> TYPE: DNA
<213> ORGANISM: Artificial Sequence
<220> FEATURE:
<223> OTHER INFORMATION: Small interfering RNA - Prl3.2

<400> SEQUENCE: 144
ggccaaguuc ugugaggcct t                                                 21

<210> SEQ ID NO 145
<211> LENGTH: 19
<212> TYPE: RNA
<213> ORGANISM: Artificial Sequence
<220> FEATURE:
<223> OTHER INFORMATION: Small interfering RNA - Prl3.2

<400> SEQUENCE: 145
ggccaaguuc ugugaggcc                                                    19

<210> SEQ ID NO 146
<211> LENGTH: 19
<212> TYPE: RNA
<213> ORGANISM: Artificial Sequence
<220> FEATURE:
<223> OTHER INFORMATION: Small interfering RNA - Prl3.2

<400> SEQUENCE: 146
ggccucacag aacuuggcc                                                    19

<210> SEQ ID NO 147
<211> LENGTH: 21
<212> TYPE: DNA
<213> ORGANISM: Artificial Sequence
<220> FEATURE:
<223> OTHER INFORMATION: Small interfering RNA - Prl3.2
<220> FEATURE:
<221> NAME/KEY: misc_feature
<222> LOCATION: 20, 21
<223> OTHER INFORMATION: n = A,T,C,G or U

<400> SEQUENCE: 147
ggccaaguuc ugugaggccn n                                                 21

<210> SEQ ID NO 148
<211> LENGTH: 21
<212> TYPE: DNA
<213> ORGANISM: Artificial Sequence
<220> FEATURE:
<223> OTHER INFORMATION: Small interfering RNA - Prl3.2
<220> FEATURE:
<221> NAME/KEY: misc_feature
<222> LOCATION: 1, 2
<223> OTHER INFORMATION: n = A,T,C,G or U

<400> SEQUENCE: 148
nnggccucac agaacuuggc c                                                 21

<210> SEQ ID NO 149
<211> LENGTH: 21
<212> TYPE: DNA
<213> ORGANISM: Artificial Sequence
<220> FEATURE:
<223> OTHER INFORMATION: Small interfering RNA - Prl3.3

<400> SEQUENCE: 149

```
guacgaggac gccauccagt t                                              21

<210> SEQ ID NO 150
<211> LENGTH: 19
<212> TYPE: RNA
<213> ORGANISM: Artificial Sequence
<220> FEATURE:
<223> OTHER INFORMATION: Small interfering RNA - Prl3.3

<400> SEQUENCE: 150
guacgaggac gccauccag                                                 19

<210> SEQ ID NO 151
<211> LENGTH: 19
<212> TYPE: RNA
<213> ORGANISM: Artificial Sequence
<220> FEATURE:
<223> OTHER INFORMATION: Small interfering RNA - Prl3.3

<400> SEQUENCE: 151
cuggauggcg uccucguac                                                 19

<210> SEQ ID NO 152
<211> LENGTH: 21
<212> TYPE: DNA
<213> ORGANISM: Artificial Sequence
<220> FEATURE:
<223> OTHER INFORMATION: Small interfering RNA - Prl3.3
<220> FEATURE:
<221> NAME/KEY: misc_feature
<222> LOCATION: 20, 21
<223> OTHER INFORMATION: n = A,T,C,G or U

<400> SEQUENCE: 152
guacgaggac gccauccagn n                                              21

<210> SEQ ID NO 153
<211> LENGTH: 21
<212> TYPE: DNA
<213> ORGANISM: Artificial Sequence
<220> FEATURE:
<223> OTHER INFORMATION: Small interfering RNA - Prl3.3
<220> FEATURE:
<221> NAME/KEY: misc_feature
<222> LOCATION: 1, 2
<223> OTHER INFORMATION: n = A,T,C,G or U

<400> SEQUENCE: 153
nncuggaugg cguccucgua c                                              21

<210> SEQ ID NO 154
<211> LENGTH: 21
<212> TYPE: DNA
<213> ORGANISM: Artificial Sequence
<220> FEATURE:
<223> OTHER INFORMATION: Small interfering RNA - Prl3.4

<400> SEQUENCE: 154
uaccggccca aacagaggct t                                              21

<210> SEQ ID NO 155
<211> LENGTH: 19
<212> TYPE: RNA
<213> ORGANISM: Artificial Sequence
<220> FEATURE:
<223> OTHER INFORMATION: Small interfering RNA - Prl3.4

<400> SEQUENCE: 155
```

```
uaccggccca aacagaggc                                             19

<210> SEQ ID NO 156
<211> LENGTH: 19
<212> TYPE: RNA
<213> ORGANISM: Artificial Sequence
<220> FEATURE:
<223> OTHER INFORMATION: Small interfering RNA - Prl3.4

<400> SEQUENCE: 156
gccucuguuu gggccggua                                             19

<210> SEQ ID NO 157
<211> LENGTH: 21
<212> TYPE: DNA
<213> ORGANISM: Artificial Sequence
<220> FEATURE:
<223> OTHER INFORMATION: Small interfering RNA - Prl3.4
<220> FEATURE:
<221> NAME/KEY: misc_feature
<222> LOCATION: 20, 21
<223> OTHER INFORMATION: n = A,T,C,G or U

<400> SEQUENCE: 157
uaccggccca aacagaggcn n                                          21

<210> SEQ ID NO 158
<211> LENGTH: 21
<212> TYPE: DNA
<213> ORGANISM: Artificial Sequence
<220> FEATURE:
<223> OTHER INFORMATION: Small interfering RNA - Prl3.4
<220> FEATURE:
<221> NAME/KEY: misc_feature
<222> LOCATION: 1, 2
<223> OTHER INFORMATION: n = A,T,C,G or U

<400> SEQUENCE: 158
nngccucugu uugggccggu a                                          21

<210> SEQ ID NO 159
<211> LENGTH: 21
<212> TYPE: DNA
<213> ORGANISM: Artificial Sequence
<220> FEATURE:
<223> OTHER INFORMATION: Small interfering RNA - RPTPE.1

<400> SEQUENCE: 159
gcagaggaaa gcugugguct t                                          21

<210> SEQ ID NO 160
<211> LENGTH: 19
<212> TYPE: RNA
<213> ORGANISM: Artificial Sequence
<220> FEATURE:
<223> OTHER INFORMATION: Small interfering RNA - RPTPE.1

<400> SEQUENCE: 160
gcagaggaaa gcugugguc                                             19

<210> SEQ ID NO 161
<211> LENGTH: 19
<212> TYPE: RNA
<213> ORGANISM: Artificial Sequence
<220> FEATURE:
<223> OTHER INFORMATION: Small interfering RNA - RPTPE.1
```

```
<400> SEQUENCE: 161
gaccacagcu uuccucugc                                                    19

<210> SEQ ID NO 162
<211> LENGTH: 21
<212> TYPE: DNA
<213> ORGANISM: Artificial Sequence
<220> FEATURE:
<223> OTHER INFORMATION: Small interfering RNA - RPTPE.1
<220> FEATURE:
<221> NAME/KEY: misc_feature
<222> LOCATION: 20, 21
<223> OTHER INFORMATION: n = A,T,C,G or U

<400> SEQUENCE: 162
gcagaggaaa gcuguggucn n                                                 21

<210> SEQ ID NO 163
<211> LENGTH: 21
<212> TYPE: DNA
<213> ORGANISM: Artificial Sequence
<220> FEATURE:
<223> OTHER INFORMATION: Small interfering RNA - RPTPE.1
<220> FEATURE:
<221> NAME/KEY: misc_feature
<222> LOCATION: 1, 2
<223> OTHER INFORMATION: n = A,T,C,G or U

<400> SEQUENCE: 163
nngaccacag cuuuccucug c                                                 21

<210> SEQ ID NO 164
<211> LENGTH: 21
<212> TYPE: DNA
<213> ORGANISM: Artificial Sequence
<220> FEATURE:
<223> OTHER INFORMATION: Small interfering RNA - RPTPE.2

<400> SEQUENCE: 164
gucugcgacc aucgucaugt t                                                 21

<210> SEQ ID NO 165
<211> LENGTH: 19
<212> TYPE: RNA
<213> ORGANISM: Artificial Sequence
<220> FEATURE:
<223> OTHER INFORMATION: Small interfering RNA - RPTPE.2

<400> SEQUENCE: 165
gucugcgacc aucgucaug                                                    19

<210> SEQ ID NO 166
<211> LENGTH: 19
<212> TYPE: RNA
<213> ORGANISM: Artificial Sequence
<220> FEATURE:
<223> OTHER INFORMATION: Small interfering RNA - RPTPE.2

<400> SEQUENCE: 166
caugacgaug gucgcagac                                                    19

<210> SEQ ID NO 167
<211> LENGTH: 21
<212> TYPE: DNA
<213> ORGANISM: Artificial Sequence
<220> FEATURE:
<223> OTHER INFORMATION: Small interfering RNA - RPTPE.2
```

```
<220> FEATURE:
<221> NAME/KEY: misc_feature
<222> LOCATION: 20, 21
<223> OTHER INFORMATION: n = A,T,C,G or U

<400> SEQUENCE: 167
gucugcgacc aucgucaugn n                                              21

<210> SEQ ID NO 168
<211> LENGTH: 21
<212> TYPE: DNA
<213> ORGANISM: Artificial Sequence
<220> FEATURE:
<223> OTHER INFORMATION: Small interfering RNA - RPTPE.2
<220> FEATURE:
<221> NAME/KEY: misc_feature
<222> LOCATION: 1, 2
<223> OTHER INFORMATION: n = A,T,C,G or U

<400> SEQUENCE: 168
nncaugacga uggucgcaga c                                              21

<210> SEQ ID NO 169
<211> LENGTH: 21
<212> TYPE: DNA
<213> ORGANISM: Artificial Sequence
<220> FEATURE:
<223> OTHER INFORMATION: Small interfering RNA - RPTPE.3

<400> SEQUENCE: 169
gccuuacucg aguacuacct t                                              21

<210> SEQ ID NO 170
<211> LENGTH: 19
<212> TYPE: RNA
<213> ORGANISM: Artificial Sequence
<220> FEATURE:
<223> OTHER INFORMATION: Small interfering RNA - RPTPE.3

<400> SEQUENCE: 170
gccuuacucg aguacuacc                                                 19

<210> SEQ ID NO 171
<211> LENGTH: 19
<212> TYPE: RNA
<213> ORGANISM: Artificial Sequence
<220> FEATURE:
<223> OTHER INFORMATION: Small interfering RNA - RPTPE.3

<400> SEQUENCE: 171
gguaguacuc gaguaaggc                                                 19

<210> SEQ ID NO 172
<211> LENGTH: 21
<212> TYPE: DNA
<213> ORGANISM: Artificial Sequence
<220> FEATURE:
<223> OTHER INFORMATION: Small interfering RNA - RPTPE.3
<220> FEATURE:
<221> NAME/KEY: misc_feature
<222> LOCATION: 20, 21
<223> OTHER INFORMATION: n = A,T,C,G or U

<400> SEQUENCE: 172
gccuuacucg aguacuaccn n                                              21

<210> SEQ ID NO 173
```

```
<211> LENGTH: 21
<212> TYPE: DNA
<213> ORGANISM: Artificial Sequence
<220> FEATURE:
<223> OTHER INFORMATION: Small interfering RNA - RPTPE.3
<220> FEATURE:
<221> NAME/KEY: misc_feature
<222> LOCATION: 1, 2
<223> OTHER INFORMATION: n = A,T,C,G or U

<400> SEQUENCE: 173
nngguaguac ucgaguaagg c                                              21

<210> SEQ ID NO 174
<211> LENGTH: 21
<212> TYPE: DNA
<213> ORGANISM: Artificial Sequence
<220> FEATURE:
<223> OTHER INFORMATION: Small interfering RNA - RPTPE.4

<400> SEQUENCE: 174
ggacuauuuc aucgccacct t                                              21

<210> SEQ ID NO 175
<211> LENGTH: 19
<212> TYPE: RNA
<213> ORGANISM: Artificial Sequence
<220> FEATURE:
<223> OTHER INFORMATION: Small interfering RNA - RPTPE.4

<400> SEQUENCE: 175
ggacuauuuc aucgccacc                                                 19

<210> SEQ ID NO 176
<211> LENGTH: 19
<212> TYPE: RNA
<213> ORGANISM: Artificial Sequence
<220> FEATURE:
<223> OTHER INFORMATION: Small interfering RNA - RPTPE.4

<400> SEQUENCE: 176
gguggcgaug aaauagucc                                                 19

<210> SEQ ID NO 177
<211> LENGTH: 21
<212> TYPE: DNA
<213> ORGANISM: Artificial Sequence
<220> FEATURE:
<223> OTHER INFORMATION: Small interfering RNA - RPTPE.4
<220> FEATURE:
<221> NAME/KEY: misc_feature
<222> LOCATION: 20, 21
<223> OTHER INFORMATION: n = A,T,C,G or U

<400> SEQUENCE: 177
ggacuauuuc aucgccaccn n                                              21

<210> SEQ ID NO 178
<211> LENGTH: 21
<212> TYPE: DNA
<213> ORGANISM: Artificial Sequence
<220> FEATURE:
<223> OTHER INFORMATION: Small interfering RNA - RPTPE.4
<220> FEATURE:
<221> NAME/KEY: misc_feature
<222> LOCATION: 1, 2
<223> OTHER INFORMATION: n = A,T,C,G or U

<400> SEQUENCE: 178
```
nngguggcga ugaaauaguc c                                              21

<210> SEQ ID NO 179
<211> LENGTH: 19
<212> TYPE: RNA
<213> ORGANISM: Artificial Sequence
<220> FEATURE:
<223> OTHER INFORMATION: Small interfering RNA

<400> SEQUENCE: 179
ccaccaucac agcgaacac                                                 19

<210> SEQ ID NO 180
<211> LENGTH: 19
<212> TYPE: RNA
<213> ORGANISM: Artificial Sequence
<220> FEATURE:
<223> OTHER INFORMATION: Small interfering RNA

<400> SEQUENCE: 180
agcgcuguca uuucaacca                                                 19

<210> SEQ ID NO 181
<211> LENGTH: 19
<212> TYPE: RNA
<213> ORGANISM: Artificial Sequence
<220> FEATURE:
<223> OTHER INFORMATION: Small interfering RNA

<400> SEQUENCE: 181
accacaacaa uagcuacua                                                 19

<210> SEQ ID NO 182
<211> LENGTH: 19
<212> TYPE: RNA
<213> ORGANISM: Artificial Sequence
<220> FEATURE:
<223> OTHER INFORMATION: Small interfering RNA

<400> SEQUENCE: 182
gcuacuacuc caucuaagc                                                 19

<210> SEQ ID NO 183
<211> LENGTH: 19
<212> TYPE: RNA
<213> ORGANISM: Artificial Sequence
<220> FEATURE:
<223> OTHER INFORMATION: Small interfering RNA

<400> SEQUENCE: 183
aaugcgucug uuuccauau                                                 19

<210> SEQ ID NO 184
<211> LENGTH: 19
<212> TYPE: RNA
<213> ORGANISM: Artificial Sequence
<220> FEATURE:
<223> OTHER INFORMATION: Small interfering RNA

<400> SEQUENCE: 184
augcgucugu uuccauauc                                                 19

<210> SEQ ID NO 185
<211> LENGTH: 19
<212> TYPE: RNA

```
<213> ORGANISM: Artificial Sequence
<220> FEATURE:
<223> OTHER INFORMATION: Small interfering RNA

<400> SEQUENCE: 185
ugcgucuguu uccauaucu                                                19

<210> SEQ ID NO 186
<211> LENGTH: 19
<212> TYPE: RNA
<213> ORGANISM: Artificial Sequence
<220> FEATURE:
<223> OTHER INFORMATION: Small interfering RNA

<400> SEQUENCE: 186
accuuuacuu gugauacac                                                19

<210> SEQ ID NO 187
<211> LENGTH: 19
<212> TYPE: RNA
<213> ORGANISM: Artificial Sequence
<220> FEATURE:
<223> OTHER INFORMATION: Small interfering RNA

<400> SEQUENCE: 187
cagauuucag ugugguaau                                                19

<210> SEQ ID NO 188
<211> LENGTH: 19
<212> TYPE: RNA
<213> ORGANISM: Artificial Sequence
<220> FEATURE:
<223> OTHER INFORMATION: Small interfering RNA

<400> SEQUENCE: 188
acccgaacau gaguauaag                                                19

<210> SEQ ID NO 189
<211> LENGTH: 19
<212> TYPE: RNA
<213> ORGANISM: Artificial Sequence
<220> FEATURE:
<223> OTHER INFORMATION: Small interfering RNA

<400> SEQUENCE: 189
cccgaacaug aguauaagu                                                19

<210> SEQ ID NO 190
<211> LENGTH: 19
<212> TYPE: RNA
<213> ORGANISM: Artificial Sequence
<220> FEATURE:
<223> OTHER INFORMATION: Small interfering RNA

<400> SEQUENCE: 190
caaguuuacu aacgcaagu                                                19

<210> SEQ ID NO 191
<211> LENGTH: 19
<212> TYPE: RNA
<213> ORGANISM: Artificial Sequence
<220> FEATURE:
<223> OTHER INFORMATION: Small interfering RNA

<400> SEQUENCE: 191
ggaguaauua ccuggaauc                                                19
```

<210> SEQ ID NO 192
<211> LENGTH: 19
<212> TYPE: RNA
<213> ORGANISM: Artificial Sequence
<220> FEATURE:
<223> OTHER INFORMATION: Small interfering RNA

<400> SEQUENCE: 192
caugccuaca ucauugcaa                                                        19

<210> SEQ ID NO 193
<211> LENGTH: 19
<212> TYPE: RNA
<213> ORGANISM: Artificial Sequence
<220> FEATURE:
<223> OTHER INFORMATION: Small interfering RNA

<400> SEQUENCE: 193
auaguaugca ugucaagug                                                        19

<210> SEQ ID NO 194
<211> LENGTH: 19
<212> TYPE: RNA
<213> ORGANISM: Artificial Sequence
<220> FEATURE:
<223> OTHER INFORMATION: Small interfering RNA

<400> SEQUENCE: 194
ugaacguuac cauuuggaa                                                        19

<210> SEQ ID NO 195
<211> LENGTH: 19
<212> TYPE: RNA
<213> ORGANISM: Artificial Sequence
<220> FEATURE:
<223> OTHER INFORMATION: Small interfering RNA

<400> SEQUENCE: 195
augagucgca uaagaauug                                                        19

<210> SEQ ID NO 196
<211> LENGTH: 19
<212> TYPE: RNA
<213> ORGANISM: Artificial Sequence
<220> FEATURE:
<223> OTHER INFORMATION: Small interfering RNA

<400> SEQUENCE: 196
ugagucgcau aagaauugc                                                        19

<210> SEQ ID NO 197
<211> LENGTH: 19
<212> TYPE: RNA
<213> ORGANISM: Artificial Sequence
<220> FEATURE:
<223> OTHER INFORMATION: Small interfering RNA

<400> SEQUENCE: 197
gaauugcgau uuccgugua                                                        19

<210> SEQ ID NO 198
<211> LENGTH: 19
<212> TYPE: RNA
<213> ORGANISM: Artificial Sequence
<220> FEATURE:

<223> OTHER INFORMATION: Small interfering RNA

<400> SEQUENCE: 198
auugcgauuu ccguguaaa                                                19

<210> SEQ ID NO 199
<211> LENGTH: 19
<212> TYPE: RNA
<213> ORGANISM: Artificial Sequence
<220> FEATURE:
<223> OTHER INFORMATION: Small interfering RNA

<400> SEQUENCE: 199
gccaauccau gcagauauu                                                19

<210> SEQ ID NO 200
<211> LENGTH: 19
<212> TYPE: RNA
<213> ORGANISM: Artificial Sequence
<220> FEATURE:
<223> OTHER INFORMATION: Small interfering RNA

<400> SEQUENCE: 200
uuauaaccgu guugaacuc                                                19

<210> SEQ ID NO 201
<211> LENGTH: 19
<212> TYPE: RNA
<213> ORGANISM: Artificial Sequence
<220> FEATURE:
<223> OTHER INFORMATION: Small interfering RNA

<400> SEQUENCE: 201
uaaccguguu gaacucucu                                                19

<210> SEQ ID NO 202
<211> LENGTH: 19
<212> TYPE: RNA
<213> ORGANISM: Artificial Sequence
<220> FEATURE:
<223> OTHER INFORMATION: Small interfering RNA

<400> SEQUENCE: 202
acggagaugc agggucaaa                                                19

<210> SEQ ID NO 203
<211> LENGTH: 19
<212> TYPE: RNA
<213> ORGANISM: Artificial Sequence
<220> FEATURE:
<223> OTHER INFORMATION: Small interfering RNA

<400> SEQUENCE: 203
gaugcagggu caaacuaca                                                19

<210> SEQ ID NO 204
<211> LENGTH: 19
<212> TYPE: RNA
<213> ORGANISM: Artificial Sequence
<220> FEATURE:
<223> OTHER INFORMATION: Small interfering RNA

<400> SEQUENCE: 204
acccaggaaa uacauugcu                                                19

<210> SEQ ID NO 205
<211> LENGTH: 19
<212> TYPE: RNA
<213> ORGANISM: Artificial Sequence
<220> FEATURE:
<223> OTHER INFORMATION: Small interfering RNA

<400> SEQUENCE: 205
uguccagauu acaucauuc                                                    19

<210> SEQ ID NO 206
<211> LENGTH: 19
<212> TYPE: RNA
<213> ORGANISM: Artificial Sequence
<220> FEATURE:
<223> OTHER INFORMATION: Small interfering RNA

<400> SEQUENCE: 206
augccuucag caauuucuu                                                    19

<210> SEQ ID NO 207
<211> LENGTH: 19
<212> TYPE: RNA
<213> ORGANISM: Artificial Sequence
<220> FEATURE:
<223> OTHER INFORMATION: Small interfering RNA

<400> SEQUENCE: 207
caggaaccua uaucggaau                                                    19

<210> SEQ ID NO 208
<211> LENGTH: 19
<212> TYPE: RNA
<213> ORGANISM: Artificial Sequence
<220> FEATURE:
<223> OTHER INFORMATION: Small interfering RNA

<400> SEQUENCE: 208
ggaaccuaua ucggaauug                                                    19

<210> SEQ ID NO 209
<211> LENGTH: 19
<212> TYPE: RNA
<213> ORGANISM: Artificial Sequence
<220> FEATURE:
<223> OTHER INFORMATION: Small interfering RNA

<400> SEQUENCE: 209
accuauaucg gaauugaug                                                    19

<210> SEQ ID NO 210
<211> LENGTH: 19
<212> TYPE: RNA
<213> ORGANISM: Artificial Sequence
<220> FEATURE:
<223> OTHER INFORMATION: Small interfering RNA

<400> SEQUENCE: 210
guggauguuu augguuaug                                                    19

<210> SEQ ID NO 211
<211> LENGTH: 19
<212> TYPE: RNA
<213> ORGANISM: Artificial Sequence
<220> FEATURE:
<223> OTHER INFORMATION: Small interfering RNA

<400> SEQUENCE: 211
ggcgacagag augccugau                                            19

<210> SEQ ID NO 212
<211> LENGTH: 19
<212> TYPE: RNA
<213> ORGANISM: Artificial Sequence
<220> FEATURE:
<223> OTHER INFORMATION: Small interfering RNA

<400> SEQUENCE: 212
gaggcccagu acaucuuga                                            19

<210> SEQ ID NO 213
<211> LENGTH: 19
<212> TYPE: RNA
<213> ORGANISM: Artificial Sequence
<220> FEATURE:
<223> OTHER INFORMATION: Small interfering RNA

<400> SEQUENCE: 213
ggcccaguac aucuugauc                                            19

<210> SEQ ID NO 214
<211> LENGTH: 19
<212> TYPE: RNA
<213> ORGANISM: Artificial Sequence
<220> FEATURE:
<223> OTHER INFORMATION: Small interfering RNA

<400> SEQUENCE: 214
gcuacuggaa accugaagu                                            19

<210> SEQ ID NO 215
<211> LENGTH: 19
<212> TYPE: RNA
<213> ORGANISM: Artificial Sequence
<220> FEATURE:
<223> OTHER INFORMATION: Small interfering RNA

<400> SEQUENCE: 215
accugaagug augauugcu                                            19

<210> SEQ ID NO 216
<211> LENGTH: 19
<212> TYPE: RNA
<213> ORGANISM: Artificial Sequence
<220> FEATURE:
<223> OTHER INFORMATION: Small interfering RNA

<400> SEQUENCE: 216
aguugaccug aaagacaca                                            19

<210> SEQ ID NO 217
<211> LENGTH: 19
<212> TYPE: RNA
<213> ORGANISM: Artificial Sequence
<220> FEATURE:
<223> OTHER INFORMATION: Small interfering RNA

<400> SEQUENCE: 217
acuuauaccc uucgugucu                                            19

<210> SEQ ID NO 218
<211> LENGTH: 19

```
<212> TYPE: RNA
<213> ORGANISM: Artificial Sequence
<220> FEATURE:
<223> OTHER INFORMATION: Small interfering RNA

<400> SEQUENCE: 218
cuuauacccu ucgugucuu                                                    19

<210> SEQ ID NO 219
<211> LENGTH: 19
<212> TYPE: RNA
<213> ORGANISM: Artificial Sequence
<220> FEATURE:
<223> OTHER INFORMATION: Small interfering RNA

<400> SEQUENCE: 219
ggaaagacuc ucgaacugu                                                    19

<210> SEQ ID NO 220
<211> LENGTH: 19
<212> TYPE: RNA
<213> ORGANISM: Artificial Sequence
<220> FEATURE:
<223> OTHER INFORMATION: Small interfering RNA

<400> SEQUENCE: 220
acccaaggaa uuaaucucu                                                    19

<210> SEQ ID NO 221
<211> LENGTH: 19
<212> TYPE: RNA
<213> ORGANISM: Artificial Sequence
<220> FEATURE:
<223> OTHER INFORMATION: Small interfering RNA

<400> SEQUENCE: 221
cccaaggaau uaaucucua                                                    19

<210> SEQ ID NO 222
<211> LENGTH: 19
<212> TYPE: RNA
<213> ORGANISM: Artificial Sequence
<220> FEATURE:
<223> OTHER INFORMATION: Small interfering RNA

<400> SEQUENCE: 222
ugauucaggu cgucaaaca                                                    19

<210> SEQ ID NO 223
<211> LENGTH: 19
<212> TYPE: RNA
<213> ORGANISM: Artificial Sequence
<220> FEATURE:
<223> OTHER INFORMATION: Small interfering RNA

<400> SEQUENCE: 223
gggauggauc ucagcaaac                                                    19

<210> SEQ ID NO 224
<211> LENGTH: 19
<212> TYPE: RNA
<213> ORGANISM: Artificial Sequence
<220> FEATURE:
<223> OTHER INFORMATION: Small interfering RNA

<400> SEQUENCE: 224
```

-continued ucucagcaaa cgggaauau          19

<210> SEQ ID NO 225
<211> LENGTH: 19
<212> TYPE: RNA
<213> ORGANISM: Artificial Sequence
<220> FEATURE:
<223> OTHER INFORMATION: Small interfering RNA

<400> SEQUENCE: 225
uucgagcaau aucaauucc          19

<210> SEQ ID NO 226
<211> LENGTH: 19
<212> TYPE: RNA
<213> ORGANISM: Artificial Sequence
<220> FEATURE:
<223> OTHER INFORMATION: Small interfering RNA

<400> SEQUENCE: 226
ccuacccugc ucagaaugg          19

<210> SEQ ID NO 227
<211> LENGTH: 19
<212> TYPE: RNA
<213> ORGANISM: Artificial Sequence
<220> FEATURE:
<223> OTHER INFORMATION: Small interfering RNA

<400> SEQUENCE: 227
auggagcugu cacccacau          19

<210> SEQ ID NO 228
<211> LENGTH: 19
<212> TYPE: RNA
<213> ORGANISM: Artificial Sequence
<220> FEATURE:
<223> OTHER INFORMATION: Small interfering RNA

<400> SEQUENCE: 228
uggaacauca cgggcaauu          19

<210> SEQ ID NO 229
<211> LENGTH: 19
<212> TYPE: RNA
<213> ORGANISM: Artificial Sequence
<220> FEATURE:
<223> OTHER INFORMATION: Small interfering RNA

<400> SEQUENCE: 229
gcaaugacgg caagucuaa          19

SEQ ID NO 2   30
<211> LENGTH: 19
<212> TYPE: RNA
ORGANISM: Artificial Sequen    ce
<220> FEATURE:
<223> OTHER INFORMATION: Small interfering RNA

<400> SEQUENCE: 230
augacggcaa gucuaaagu          19

<210> SEQ ID NO 231
<211> LENGTH: 19
<212> TYPE: RNA
<213> ORGANISM: Artificial Sequence

```
<220> FEATURE:
<223> OTHER INFORMATION: Small interfering RNA

<400> SEQUENCE: 231
ugacggcaag ucuaaagug                                                    19

<210> SEQ ID NO 232
<211> LENGTH: 19
<212> TYPE: RNA
<213> ORGANISM: Artificial Sequence
<220> FEATURE:
<223> OTHER INFORMATION: Small interfering RNA

<400> SEQUENCE: 232
gucuaaagug acccauguu                                                    19

<210> SEQ ID NO 233
<211> LENGTH: 19
<212> TYPE: RNA
<213> ORGANISM: Artificial Sequence
<220> FEATURE:
<223> OTHER INFORMATION: Small interfering RNA

<400> SEQUENCE: 233
ugauucgcug ucaggaacu                                                    19

<210> SEQ ID NO 234
<211> LENGTH: 19
<212> TYPE: RNA
<213> ORGANISM: Artificial Sequence
<220> FEATURE:
<223> OTHER INFORMATION: Small interfering RNA

<400> SEQUENCE: 234
cgacguuggu ggaggagaa                                                    19

<210> SEQ ID NO 235
<211> LENGTH: 19
<212> TYPE: RNA
<213> ORGANISM: Artificial Sequence
<220> FEATURE:
<223> OTHER INFORMATION: Small interfering RNA

<400> SEQUENCE: 235
acgguuugau ucuuugaca                                                    19

<210> SEQ ID NO 236
<211> LENGTH: 19
<212> TYPE: RNA
<213> ORGANISM: Artificial Sequence
<220> FEATURE:
<223> OTHER INFORMATION: Small interfering RNA

<400> SEQUENCE: 236
uucuuugaca gaucuugug                                                    19

<210> SEQ ID NO 237
<211> LENGTH: 19
<212> TYPE: RNA
<213> ORGANISM: Artificial Sequence
<220> FEATURE:
<223> OTHER INFORMATION: Small interfering RNA

<400> SEQUENCE: 237
gaauccuaug guggaaaca                                                    19
```

```
<210> SEQ ID NO 238
<211> LENGTH: 19
<212> TYPE: RNA
<213> ORGANISM: Artificial Sequence
<220> FEATURE:
<223> OTHER INFORMATION: Small interfering RNA

<400> SEQUENCE: 238
auccuauggu ggaaacauu                                                      19

<210> SEQ ID NO 239
<211> LENGTH: 19
<212> TYPE: RNA
<213> ORGANISM: Artificial Sequence
<220> FEATURE:
<223> OTHER INFORMATION: Small interfering RNA

<400> SEQUENCE: 239
uccuauggug gaaacauug                                                      19

<210> SEQ ID NO 240
<211> LENGTH: 19
<212> TYPE: RNA
<213> ORGANISM: Artificial Sequence
<220> FEATURE:
<223> OTHER INFORMATION: Small interfering RNA

<400> SEQUENCE: 240
caguacuaca acucaagca                                                      19

<210> SEQ ID NO 241
<211> LENGTH: 19
<212> TYPE: RNA
<213> ORGANISM: Artificial Sequence
<220> FEATURE:
<223> OTHER INFORMATION: Small interfering RNA

<400> SEQUENCE: 241
uuugagacac uacaacaac                                                      19

<210> SEQ ID NO 242
<211> LENGTH: 19
<212> TYPE: RNA
<213> ORGANISM: Artificial Sequence
<220> FEATURE:
<223> OTHER INFORMATION: Small interfering RNA

<400> SEQUENCE: 242
aacuucucua cagccgaaa                                                      19

<210> SEQ ID NO 243
<211> LENGTH: 19
<212> TYPE: RNA
<213> ORGANISM: Artificial Sequence
<220> FEATURE:
<223> OTHER INFORMATION: Small interfering RNA

<400> SEQUENCE: 243
acauccugcc cuuugauca                                                      19

<210> SEQ ID NO 244
<211> LENGTH: 19
<212> TYPE: RNA
<213> ORGANISM: Artificial Sequence
<220> FEATURE:
<223> OTHER INFORMATION: Small interfering RNA
```

-continued

<400> SEQUENCE: 244
ucauaccagg guguccua                                                    19

<210> SEQ ID NO 245
<211> LENGTH: 19
<212> TYPE: RNA
<213> ORGANISM: Artificial Sequence
<220> FEATURE:
<223> OTHER INFORMATION: Small interfering RNA

<400> SEQUENCE: 245
uaccaggguu guccuacac                                                   19

<210> SEQ ID NO 246
<211> LENGTH: 19
<212> TYPE: RNA
<213> ORGANISM: Artificial Sequence
<220> FEATURE:
<223> OTHER INFORMATION: Small interfering RNA

<400> SEQUENCE: 246
uuugaaacca agugcaaca                                                   19

<210> SEQ ID NO 247
<211> LENGTH: 19
<212> TYPE: RNA
<213> ORGANISM: Artificial Sequence
<220> FEATURE:
<223> OTHER INFORMATION: Small interfering RNA

<400> SEQUENCE: 247
agaguuacau ugccacaca                                                   19

<210> SEQ ID NO 248
<211> LENGTH: 19
<212> TYPE: RNA
<213> ORGANISM: Artificial Sequence
<220> FEATURE:
<223> OTHER INFORMATION: Small interfering RNA

<400> SEQUENCE: 248
gaguuacauu gccacacaa                                                   19

<210> SEQ ID NO 249
<211> LENGTH: 19
<212> TYPE: RNA
<213> ORGANISM: Artificial Sequence
<220> FEATURE:
<223> OTHER INFORMATION: Small interfering RNA

<400> SEQUENCE: 249
aaacacggug aaugacuuu                                                   19

<210> SEQ ID NO 250
<211> LENGTH: 19
<212> TYPE: RNA
<213> ORGANISM: Artificial Sequence
<220> FEATURE:
<223> OTHER INFORMATION: Small interfering RNA

<400> SEQUENCE: 250
cuggccugau gaguaugcu                                                   19

<210> SEQ ID NO 251

```
<211> LENGTH: 19
<212> TYPE: RNA
<213> ORGANISM: Artificial Sequence
<220> FEATURE:
<223> OTHER INFORMATION: Small interfering RNA

<400> SEQUENCE: 251
uggcgucaug cguguuagg                                                    19

<210> SEQ ID NO 252
<211> LENGTH: 19
<212> TYPE: RNA
<213> ORGANISM: Artificial Sequence
<220> FEATURE:
<223> OTHER INFORMATION: Small interfering RNA

<400> SEQUENCE: 252
ugcguguuag gaacgucaa                                                    19

<210> SEQ ID NO 253
<211> LENGTH: 19
<212> TYPE: RNA
<213> ORGANISM: Artificial Sequence
<220> FEATURE:
<223> OTHER INFORMATION: Small interfering RNA

<400> SEQUENCE: 253
ugacuauacg cuaagagaa                                                    19

<210> SEQ ID NO 254
<211> LENGTH: 19
<212> TYPE: RNA
<213> ORGANISM: Artificial Sequence
<220> FEATURE:
<223> OTHER INFORMATION: Small interfering RNA

<400> SEQUENCE: 254
cuauacgcua agagaacuu                                                    19

<210> SEQ ID NO 255
<211> LENGTH: 19
<212> TYPE: RNA
<213> ORGANISM: Artificial Sequence
<220> FEATURE:
<223> OTHER INFORMATION: Small interfering RNA

<400> SEQUENCE: 255
gguuggacaa gggaauacg                                                    19

<210> SEQ ID NO 256
<211> LENGTH: 19
<212> TYPE: RNA
<213> ORGANISM: Artificial Sequence
<220> FEATURE:
<223> OTHER INFORMATION: Small interfering RNA

<400> SEQUENCE: 256
gaacggucug gcaauacca                                                    19

<210> SEQ ID NO 257
<211> LENGTH: 19
<212> TYPE: RNA
<213> ORGANISM: Artificial Sequence
<220> FEATURE:
<223> OTHER INFORMATION: Small interfering RNA

<400> SEQUENCE: 257
```

-continued cggucuggca auaccacuu                                                    19

<210> SEQ ID NO 258
<211> LENGTH: 19
<212> TYPE: RNA
<213> ORGANISM: Artificial Sequence
<220> FEATURE:
<223> OTHER INFORMATION: Small interfering RNA

<400> SEQUENCE: 258
aagguguuga cugcgauau                                                    19

<210> SEQ ID NO 259
<211> LENGTH: 19
<212> TYPE: RNA
<213> ORGANISM: Artificial Sequence
<220> FEATURE:
<223> OTHER INFORMATION: Small interfering RNA

<400> SEQUENCE: 259
agguguugac ugcgauauu                                                    19

<210> SEQ ID NO 260
<211> LENGTH: 19
<212> TYPE: RNA
<213> ORGANISM: Artificial Sequence
<220> FEATURE:
<223> OTHER INFORMATION: Small interfering RNA

<400> SEQUENCE: 260
gguguugacu gcgauauug                                                    19

<210> SEQ ID NO 261
<211> LENGTH: 19
<212> TYPE: RNA
<213> ORGANISM: Artificial Sequence
<220> FEATURE:
<223> OTHER INFORMATION: Small interfering RNA

<400> SEQUENCE: 261
uauggcgguc cagcauuau                                                    19

<210> SEQ ID NO 262
<211> LENGTH: 19
<212> TYPE: RNA
<213> ORGANISM: Artificial Sequence
<220> FEATURE:
<223> OTHER INFORMATION: Small interfering RNA

<400> SEQUENCE: 262
uggcggucca gcauuauau                                                    19

<210> SEQ ID NO 263
<211> LENGTH: 19
<212> TYPE: RNA
<213> ORGANISM: Artificial Sequence
<220> FEATURE:
<223> OTHER INFORMATION: Small interfering RNA

<400> SEQUENCE: 263
aacacuacag cgcaggauu                                                    19

<210> SEQ ID NO 264
<211> LENGTH: 19
<212> TYPE: RNA

```
<213> ORGANISM: Artificial Sequence
<220> FEATURE:
<223> OTHER INFORMATION: Small interfering RNA

<400> SEQUENCE: 264
acacuacagc gcaggauug                                              19

<210> SEQ ID NO 265
<211> LENGTH: 19
<212> TYPE: RNA
<213> ORGANISM: Artificial Sequence
<220> FEATURE:
<223> OTHER INFORMATION: Small interfering RNA

<400> SEQUENCE: 265
gcgcaggauu gaagaagag                                              19

<210> SEQ ID NO 266
<211> LENGTH: 19
<212> TYPE: RNA
<213> ORGANISM: Artificial Sequence
<220> FEATURE:
<223> OTHER INFORMATION: Small interfering RNA

<400> SEQUENCE: 266
gaggaaaggg cacgaauau                                              19

<210> SEQ ID NO 267
<211> LENGTH: 19
<212> TYPE: RNA
<213> ORGANISM: Artificial Sequence
<220> FEATURE:
<223> OTHER INFORMATION: Small interfering RNA

<400> SEQUENCE: 267
ggaaagggca cgaauauac                                              19

<210> SEQ ID NO 268
<211> LENGTH: 19
<212> TYPE: RNA
<213> ORGANISM: Artificial Sequence
<220> FEATURE:
<223> OTHER INFORMATION: Small interfering RNA

<400> SEQUENCE: 268
gggcacgaau auacaaaua                                              19

<210> SEQ ID NO 269
<211> LENGTH: 19
<212> TYPE: RNA
<213> ORGANISM: Artificial Sequence
<220> FEATURE:
<223> OTHER INFORMATION: Small interfering RNA

<400> SEQUENCE: 269
aaacgugggc cugaugcaa                                              19

<210> SEQ ID NO 270
<211> LENGTH: 19
<212> TYPE: RNA
<213> ORGANISM: Artificial Sequence
<220> FEATURE:
<223> OTHER INFORMATION: Small interfering RNA

<400> SEQUENCE: 270
acgugggccu gaugcaaca                                              19
```

```
<210> SEQ ID NO 271
<211> LENGTH: 19
<212> TYPE: RNA
<213> ORGANISM: Artificial Sequence
<220> FEATURE:
<223> OTHER INFORMATION: Small interfering RNA

<400> SEQUENCE: 271
gcacaguaaa uacccacua                                                  19

<210> SEQ ID NO 272
<211> LENGTH: 19
<212> TYPE: RNA
<213> ORGANISM: Artificial Sequence
<220> FEATURE:
<223> OTHER INFORMATION: Small interfering RNA

<400> SEQUENCE: 272 cuauucucc aucgaugag                                                   19

<210> SEQ ID NO 273
<211> LENGTH: 19
<212> TYPE: RNA
<213> ORGANISM: Artificial Sequence
<220> FEATURE:
<223> OTHER INFORMATION: Small interfering RNA

<400> SEQUENCE: 273
acuuggcaau gguguacag                                                  19

<210> SEQ ID NO 274
<211> LENGTH: 19
<212> TYPE: RNA
<213> ORGANISM: Artificial Sequence
<220> FEATURE:
<223> OTHER INFORMATION: Small interfering RNA

<400> SEQUENCE: 274
ggugccuaug caguaaucu                                                  19

<210> SEQ ID NO 275
<211> LENGTH: 19
<212> TYPE: RNA
<213> ORGANISM: Artificial Sequence
<220> FEATURE:
<223> OTHER INFORMATION: Small interfering RNA

<400> SEQUENCE: 275
ucucaccauu cucgacugu                                                  19

<210> SEQ ID NO 276
<211> LENGTH: 19
<212> TYPE: RNA
<213> ORGANISM: Artificial Sequence
<220> FEATURE:
<223> OTHER INFORMATION: Small interfering RNA

<400> SEQUENCE: 276
aagggauuac aacauggau                                                  19

<210> SEQ ID NO 277
<211> LENGTH: 19
<212> TYPE: RNA
<213> ORGANISM: Artificial Sequence
<220> FEATURE:
```

<223> OTHER INFORMATION: Small interfering RNA

<400> SEQUENCE: 277
agggauuaca acauggauu                                                    19

<210> SEQ ID NO 278
<211> LENGTH: 19
<212> TYPE: RNA
<213> ORGANISM: Artificial Sequence
<220> FEATURE:
<223> OTHER INFORMATION: Small interfering RNA

<400> SEQUENCE: 278
gggauuacaa cauggauuu                                                    19

<210> SEQ ID NO 279
<211> LENGTH: 19
<212> TYPE: RNA
<213> ORGANISM: Artificial Sequence
<220> FEATURE:
<223> OTHER INFORMATION: Small interfering RNA

<400> SEQUENCE: 279
gaaugguuau ccucuucac                                                    19

<210> SEQ ID NO 280
<211> LENGTH: 19
<212> TYPE: RNA
<213> ORGANISM: Artificial Sequence
<220> FEATURE:
<223> OTHER INFORMATION: Small interfering RNA

<400> SEQUENCE: 280
gcauaaugug acugcaguu                                                    19

<210> SEQ ID NO 281
<211> LENGTH: 19
<212> TYPE: RNA
<213> ORGANISM: Artificial Sequence
<220> FEATURE:
<223> OTHER INFORMATION: Small interfering RNA

<400> SEQUENCE: 281
cgcuggcuuc gagcacuau                                                    19

<210> SEQ ID NO 282
<211> LENGTH: 19
<212> TYPE: RNA
<213> ORGANISM: Artificial Sequence
<220> FEATURE:
<223> OTHER INFORMATION: Small interfering RNA

<400> SEQUENCE: 282
gcacacccag ugacaacau                                                    19

<210> SEQ ID NO 283
<211> LENGTH: 19
<212> TYPE: RNA
<213> ORGANISM: Artificial Sequence
<220> FEATURE:
<223> OTHER INFORMATION: Small interfering RNA

<400> SEQUENCE: 283
acaucgugcg aagguuccu                                                    19

```
<210> SEQ ID NO 284
<211> LENGTH: 19
<212> TYPE: RNA
<213> ORGANISM: Artificial Sequence
<220> FEATURE:
<223> OTHER INFORMATION: Small interfering RNA

<400> SEQUENCE: 284
agaacaggga cauugauag                                                    19

<210> SEQ ID NO 285
<211> LENGTH: 19
<212> TYPE: RNA
<213> ORGANISM: Artificial Sequence
<220> FEATURE:
<223> OTHER INFORMATION: Small interfering RNA

<400> SEQUENCE: 285
gaacagggac auugauagc                                                    19

<210> SEQ ID NO 286
<211> LENGTH: 19
<212> TYPE: RNA
<213> ORGANISM: Artificial Sequence
<220> FEATURE:
<223> OTHER INFORMATION: Small interfering RNA

<400> SEQUENCE: 286
gggacauuga uagccuguu                                                    19

<210> SEQ ID NO 287
<211> LENGTH: 19
<212> TYPE: RNA
<213> ORGANISM: Artificial Sequence
<220> FEATURE:
<223> OTHER INFORMATION: Small interfering RNA

<400> SEQUENCE: 287
cauugauagc cuguuaugu                                                    19

<210> SEQ ID NO 288
<211> LENGTH: 19
<212> TYPE: RNA
<213> ORGANISM: Artificial Sequence
<220> FEATURE:
<223> OTHER INFORMATION: Small interfering RNA

<400> SEQUENCE: 288
cuacagguuu acacaugcu                                                    19

<210> SEQ ID NO 289
<211> LENGTH: 19
<212> TYPE: RNA
<213> ORGANISM: Artificial Sequence
<220> FEATURE:
<223> OTHER INFORMATION: Small interfering RNA

<400> SEQUENCE: 289
aaaucgacca uccagugaa                                                    19

<210> SEQ ID NO 290
<211> LENGTH: 19
<212> TYPE: RNA
<213> ORGANISM: Artificial Sequence
<220> FEATURE:
<223> OTHER INFORMATION: Small interfering RNA
```

```
<400> SEQUENCE: 290
aaucgaccau ccagugaag                                           19

<210> SEQ ID NO 291
<211> LENGTH: 19
<212> TYPE: RNA
<213> ORGANISM: Artificial Sequence
<220> FEATURE:
<223> OTHER INFORMATION: Small interfering RNA

<400> SEQUENCE: 291
ucgaccaucc agugaagga                                           19

<210> SEQ ID NO 292
<211> LENGTH: 19
<212> TYPE: RNA
<213> ORGANISM: Artificial Sequence
<220> FEATURE:
<223> OTHER INFORMATION: Small interfering RNA

<400> SEQUENCE: 292
aaauucuuuc uggccuaga                                           19

<210> SEQ ID NO 293
<211> LENGTH: 19
<212> TYPE: RNA
<213> ORGANISM: Artificial Sequence
<220> FEATURE:
<223> OTHER INFORMATION: Small interfering RNA

<400> SEQUENCE: 293
ugucuauugg uggaaaucu                                           19

<210> SEQ ID NO 294
<211> LENGTH: 19
<212> TYPE: RNA
<213> ORGANISM: Artificial Sequence
<220> FEATURE:
<223> OTHER INFORMATION: Small interfering RNA

<400> SEQUENCE: 294
acgauuugga gagguaagu                                           19

<210> SEQ ID NO 295
<211> LENGTH: 19
<212> TYPE: RNA
<213> ORGANISM: Artificial Sequence
<220> FEATURE:
<223> OTHER INFORMATION: Small interfering RNA

<400> SEQUENCE: 295
cgauuuggag agguaaguu                                           19

<210> SEQ ID NO 296
<211> LENGTH: 19
<212> TYPE: RNA
<213> ORGANISM: Artificial Sequence
<220> FEATURE:
<223> OTHER INFORMATION: Small interfering RNA

<400> SEQUENCE: 296
gagacauccu auauuccuu                                           19

<210> SEQ ID NO 297
<211> LENGTH: 19
```

```
<212> TYPE: RNA
<213> ORGANISM: Artificial Sequence
<220> FEATURE:
<223> OTHER INFORMATION: Small interfering RNA

<400> SEQUENCE: 297
auaccagacc gauuuauug                                                    19

<210> SEQ ID NO 298
<211> LENGTH: 19
<212> TYPE: RNA
<213> ORGANISM: Artificial Sequence
<220> FEATURE:
<223> OTHER INFORMATION: Small interfering RNA

<400> SEQUENCE: 298
uaccagaccg auuuauugc                                                    19

<210> SEQ ID NO 299
<211> LENGTH: 19
<212> TYPE: RNA
<213> ORGANISM: Artificial Sequence
<220> FEATURE:
<223> OTHER INFORMATION: Small interfering RNA

<400> SEQUENCE: 299
gaccgauuua uugccuucu                                                    19

<210> SEQ ID NO 300
<211> LENGTH: 19
<212> TYPE: RNA
<213> ORGANISM: Artificial Sequence
<220> FEATURE:
<223> OTHER INFORMATION: Small interfering RNA

<400> SEQUENCE: 300
aaggauguau gaugccaaa                                                    19

<210> SEQ ID NO 301
<211> LENGTH: 19
<212> TYPE: RNA
<213> ORGANISM: Artificial Sequence
<220> FEATURE:
<223> OTHER INFORMATION: Small interfering RNA

<400> SEQUENCE: 301
aggauguaug augccaaac                                                    19

<210> SEQ ID NO 302
<211> LENGTH: 19
<212> TYPE: RNA
<213> ORGANISM: Artificial Sequence
<220> FEATURE:
<223> OTHER INFORMATION: Small interfering RNA

<400> SEQUENCE: 302
ggauguauga ugccaaacg                                                    19

<210> SEQ ID NO 303
<211> LENGTH: 19
<212> TYPE: RNA
<213> ORGANISM: Artificial Sequence
<220> FEATURE:
<223> OTHER INFORMATION: Small interfering RNA

<400> SEQUENCE: 303
```
cggaugcugg cuucgauca     19

<210> SEQ ID NO 304
<211> LENGTH: 19
<212> TYPE: RNA
<213> ORGANISM: Artificial Sequence
<220> FEATURE:
<223> OTHER INFORMATION: Small interfering RNA

<400> SEQUENCE: 304
ugccauuguc aaagaauuc     19

<210> SEQ ID NO 305
<211> LENGTH: 19
<212> TYPE: RNA
<213> ORGANISM: Artificial Sequence
<220> FEATURE:
<223> OTHER INFORMATION: Small interfering RNA

<400> SEQUENCE: 305
gggugccauu gcaguacau     19

<210> SEQ ID NO 306
<211> LENGTH: 19
<212> TYPE: RNA
<213> ORGANISM: Artificial Sequence
<220> FEATURE:
<223> OTHER INFORMATION: Small interfering RNA

<400> SEQUENCE: 306
gaccuggcuc ggugauugg     19

<210> SEQ ID NO 307
<211> LENGTH: 19
<212> TYPE: RNA
<213> ORGANISM: Artificial Sequence
<220> FEATURE:
<223> OTHER INFORMATION: Small interfering RNA

<400> SEQUENCE: 307
cccgaaccgu acagugaug     19

<210> SEQ ID NO 308
<211> LENGTH: 19
<212> TYPE: RNA
<213> ORGANISM: Artificial Sequence
<220> FEATURE:
<223> OTHER INFORMATION: Small interfering RNA

<400> SEQUENCE: 308
accguacagu gaugaugac     19

<210> SEQ ID NO 309
<211> LENGTH: 19
<212> TYPE: RNA
<213> ORGANISM: Artificial Sequence
<220> FEATURE:
<223> OTHER INFORMATION: Small interfering RNA

<400> SEQUENCE: 309
uagacuucgg gccuugaaa     19

<210> SEQ ID NO 310
<211> LENGTH: 19
<212> TYPE: RNA
<213> ORGANISM: Artificial Sequence

```
<220> FEATURE:
<223> OTHER INFORMATION: Small interfering RNA

<400> SEQUENCE: 310
acaaacgcua uuccucuca                                                    19

<210> SEQ ID NO 311
<211> LENGTH: 19
<212> TYPE: RNA
<213> ORGANISM: Artificial Sequence
<220> FEATURE:
<223> OTHER INFORMATION: Small interfering RNA

<400> SEQUENCE: 311
gggucugggc agugauuau                                                    19

<210> SEQ ID NO 312
<211> LENGTH: 19
<212> TYPE: RNA
<213> ORGANISM: Artificial Sequence
<220> FEATURE:
<223> OTHER INFORMATION: Small interfering RNA

<400> SEQUENCE: 312
gcaaccacug gaggugaag                                                    19

<210> SEQ ID NO 313
<211> LENGTH: 19
<212> TYPE: RNA
<213> ORGANISM: Artificial Sequence
<220> FEATURE:
<223> OTHER INFORMATION: Small interfering RNA

<400> SEQUENCE: 313 auccaugag aagaauaca                                                     19

<210> SEQ ID NO 314
<211> LENGTH: 19
<212> TYPE: RNA
<213> ORGANISM: Artificial Sequence
<220> FEATURE:
<223> OTHER INFORMATION: Small interfering RNA

<400> SEQUENCE: 314
uccuaugaga agaauacau                                                    19

<210> SEQ ID NO 315
<211> LENGTH: 19
<212> TYPE: RNA
<213> ORGANISM: Artificial Sequence
<220> FEATURE:
<223> OTHER INFORMATION: Small interfering RNA

<400> SEQUENCE: 315
aaagcuguug ggauguagu                                                    19

<210> SEQ ID NO 316
<211> LENGTH: 19
<212> TYPE: RNA
<213> ORGANISM: Artificial Sequence
<220> FEATURE:
<223> OTHER INFORMATION: Small interfering RNA

<400> SEQUENCE: 316
uucugauucu cuugaccau                                                    19
```

```
<210> SEQ ID NO 317
<211> LENGTH: 19
<212> TYPE: RNA
<213> ORGANISM: Artificial Sequence
<220> FEATURE:
<223> OTHER INFORMATION: Small interfering RNA

<400> SEQUENCE: 317
gaagccagua agaccugua                                                     19

<210> SEQ ID NO 318
<211> LENGTH: 19
<212> TYPE: RNA
<213> ORGANISM: Artificial Sequence
<220> FEATURE:
<223> OTHER INFORMATION: Small interfering RNA

<400> SEQUENCE: 318
cagccacuuu gucugauga                                                     19

<210> SEQ ID NO 319
<211> LENGTH: 19
<212> TYPE: RNA
<213> ORGANISM: Artificial Sequence
<220> FEATURE:
<223> OTHER INFORMATION: Small interfering RNA

<400> SEQUENCE: 319
aaccuugaca accgaugca                                                     19

<210> SEQ ID NO 320
<211> LENGTH: 19
<212> TYPE: RNA
<213> ORGANISM: Artificial Sequence
<220> FEATURE:
<223> OTHER INFORMATION: Small interfering RNA

<400> SEQUENCE: 320
caaccgaugc aagcuguuu                                                     19

<210> SEQ ID NO 321
<211> LENGTH: 19
<212> TYPE: RNA
<213> ORGANISM: Artificial Sequence
<220> FEATURE:
<223> OTHER INFORMATION: Small interfering RNA

<400> SEQUENCE: 321
accgaugcaa gcuguuuga                                                     19

<210> SEQ ID NO 322
<211> LENGTH: 19
<212> TYPE: RNA
<213> ORGANISM: Artificial Sequence
<220> FEATURE:
<223> OTHER INFORMATION: Small interfering RNA

<400> SEQUENCE: 322
cucggucagu guugaagag                                                     19

<210> SEQ ID NO 323
<211> LENGTH: 19
<212> TYPE: RNA
<213> ORGANISM: Artificial Sequence
<220> FEATURE:
<223> OTHER INFORMATION: Small interfering RNA
```

<400> SEQUENCE: 323
acguucucaa gaggagucu                                                19

<210> SEQ ID NO 324
<211> LENGTH: 19
<212> TYPE: RNA
<213> ORGANISM: Artificial Sequence
<220> FEATURE:
<223> OTHER INFORMATION: Small interfering RNA

<400> SEQUENCE: 324
gucaacuaau ccagagaag                                                19

<210> SEQ ID NO 325
<211> LENGTH: 19
<212> TYPE: RNA
<213> ORGANISM: Artificial Sequence
<220> FEATURE:
<223> OTHER INFORMATION: Small interfering RNA

<400> SEQUENCE: 325
aggcccauga gacucuuca                                                19

<210> SEQ ID NO 326
<211> LENGTH: 19
<212> TYPE: RNA
<213> ORGANISM: Artificial Sequence
<220> FEATURE:
<223> OTHER INFORMATION: Small interfering RNA

<400> SEQUENCE: 326
agggaccuua uaggagacu                                                19

<210> SEQ ID NO 327
<211> LENGTH: 19
<212> TYPE: RNA
<213> ORGANISM: Artificial Sequence
<220> FEATURE:
<223> OTHER INFORMATION: Small interfering RNA

<400> SEQUENCE: 327
gggaccuuau aggagacuu                                                19

<210> SEQ ID NO 328
<211> LENGTH: 19
<212> TYPE: RNA
<213> ORGANISM: Artificial Sequence
<220> FEATURE:
<223> OTHER INFORMATION: Small interfering RNA

<400> SEQUENCE: 328
gacuucucca aggguuauc                                                19

<210> SEQ ID NO 329
<211> LENGTH: 19
<212> TYPE: RNA
<213> ORGANISM: Artificial Sequence
<220> FEATURE:
<223> OTHER INFORMATION: Small interfering RNA

<400> SEQUENCE: 329
guuuguuauc aucgacugu                                                19

<210> SEQ ID NO 330

```
<211> LENGTH: 19
<212> TYPE: RNA
<213> ORGANISM: Artificial Sequence
<220> FEATURE:
<223> OTHER INFORMATION: Small interfering RNA

<400> SEQUENCE: 330
cugucgauac ccauaugaa                                                19

<210> SEQ ID NO 331
<211> LENGTH: 19
<212> TYPE: RNA
<213> ORGANISM: Artificial Sequence
<220> FEATURE:
<223> OTHER INFORMATION: Small interfering RNA

<400> SEQUENCE: 331
gaagcccauu guaccuacu                                                19

<210> SEQ ID NO 332
<211> LENGTH: 19
<212> TYPE: RNA
<213> ORGANISM: Artificial Sequence
<220> FEATURE:
<223> OTHER INFORMATION: Small interfering RNA

<400> SEQUENCE: 332
agcccauugu accuacuga                                                19

<210> SEQ ID NO 333
<211> LENGTH: 19
<212> TYPE: RNA
<213> ORGANISM: Artificial Sequence
<220> FEATURE:
<223> OTHER INFORMATION: Small interfering RNA

<400> SEQUENCE: 333
gcccauugua ccuacugau                                                19

<210> SEQ ID NO 334
<211> LENGTH: 19
<212> TYPE: RNA
<213> ORGANISM: Artificial Sequence
<220> FEATURE:
<223> OTHER INFORMATION: Small interfering RNA

<400> SEQUENCE: 334
uggcaagcgu gucauuguu                                                19

<210> SEQ ID NO 335
<211> LENGTH: 19
<212> TYPE: RNA
<213> ORGANISM: Artificial Sequence
<220> FEATURE:
<223> OTHER INFORMATION: Small interfering RNA

<400> SEQUENCE: 335 agcgucau uguugguu                                                   19

<210> SEQ ID NO 336
<211> LENGTH: 19
<212> TYPE: RNA
<213> ORGANISM: Artificial Sequence
<220> FEATURE:
<223> OTHER INFORMATION: Small interfering RNA

<400> SEQUENCE: 336
```
ugugccggua ugugagaga                                            19

<210> SEQ ID NO 337
<211> LENGTH: 19
<212> TYPE: RNA
<213> ORGANISM: Artificial Sequence
<220> FEATURE:
<223> OTHER INFORMATION: Small interfering RNA

<400> SEQUENCE: 337
gagagaucgc cuggguaau                                            19

<210> SEQ ID NO 338
<211> LENGTH: 19
<212> TYPE: RNA
<213> ORGANISM: Artificial Sequence
<220> FEATURE:
<223> OTHER INFORMATION: Small interfering RNA

<400> SEQUENCE: 338
gagaucgccu ggguaauga                                            19

<210> SEQ ID NO 339
<211> LENGTH: 19
<212> TYPE: RNA
<213> ORGANISM: Artificial Sequence
<220> FEATURE:
<223> OTHER INFORMATION: Small interfering RNA

<400> SEQUENCE: 339
gaucgccugg guaaugaau                                            19

<210> SEQ ID NO 340
<211> LENGTH: 19
<212> TYPE: RNA
<213> ORGANISM: Artificial Sequence
<220> FEATURE:
<223> OTHER INFORMATION: Small interfering RNA

<400> SEQUENCE: 340
auccucccug ucgucugaa                                            19

<210> SEQ ID NO 341
<211> LENGTH: 19
<212> TYPE: RNA
<213> ORGANISM: Artificial Sequence
<220> FEATURE:
<223> OTHER INFORMATION: Small interfering RNA

<400> SEQUENCE: 341
uccucccugu cgucugaau                                            19

<210> SEQ ID NO 342
<211> LENGTH: 19
<212> TYPE: RNA
<213> ORGANISM: Artificial Sequence
<220> FEATURE:
<223> OTHER INFORMATION: Small interfering RNA

<400> SEQUENCE: 342
uggcggagca gacguuuga                                            19

<210> SEQ ID NO 343
<211> LENGTH: 19
<212> TYPE: RNA

```
<213> ORGANISM: Artificial Sequence
<220> FEATURE:
<223> OTHER INFORMATION: Small interfering RNA

<400> SEQUENCE: 343
cguuugaaca ggccaucca                                                    19

<210> SEQ ID NO 344
<211> LENGTH: 19
<212> TYPE: RNA
<213> ORGANISM: Artificial Sequence
<220> FEATURE:
<223> OTHER INFORMATION: Small interfering RNA

<400> SEQUENCE: 344
gccggaucau ucgaaacga                                                    19

<210> SEQ ID NO 345
<211> LENGTH: 19
<212> TYPE: RNA
<213> ORGANISM: Artificial Sequence
<220> FEATURE:
<223> OTHER INFORMATION: Small interfering RNA

<400> SEQUENCE: 345
ucauucgaaa cgagcaguu                                                    19

<210> SEQ ID NO 346
<211> LENGTH: 19
<212> TYPE: RNA
<213> ORGANISM: Artificial Sequence
<220> FEATURE:
<223> OTHER INFORMATION: Small interfering RNA

<400> SEQUENCE: 346
gucuaugccg gauggauuu                                                    19

<210> SEQ ID NO 347
<211> LENGTH: 19
<212> TYPE: RNA
<213> ORGANISM: Artificial Sequence
<220> FEATURE:
<223> OTHER INFORMATION: Small interfering RNA

<400> SEQUENCE: 347
ugccggaugg auuugucuu                                                    19

<210> SEQ ID NO 348
<211> LENGTH: 19
<212> TYPE: RNA
<213> ORGANISM: Artificial Sequence
<220> FEATURE:
<223> OTHER INFORMATION: Small interfering RNA

<400> SEQUENCE: 348
aaaggaccuc gucauguac                                                    19

<210> SEQ ID NO 349
<211> LENGTH: 19
<212> TYPE: RNA
<213> ORGANISM: Artificial Sequence
<220> FEATURE:
<223> OTHER INFORMATION: Small interfering RNA

<400> SEQUENCE: 349
aaucacugug ucacgauga                                                    19
```

<210> SEQ ID NO 350
<211> LENGTH: 19
<212> TYPE: RNA
<213> ORGANISM: Artificial Sequence
<220> FEATURE:
<223> OTHER INFORMATION: Small interfering RNA

<400> SEQUENCE: 350
aucacugugu cacgaugag                                               19

<210> SEQ ID NO 351
<211> LENGTH: 19
<212> TYPE: RNA
<213> ORGANISM: Artificial Sequence
<220> FEATURE:
<223> OTHER INFORMATION: Small interfering RNA

<400> SEQUENCE: 351
gagcugauug gagauuacu                                               19

<210> SEQ ID NO 352
<211> LENGTH: 19
<212> TYPE: RNA
<213> ORGANISM: Artificial Sequence
<220> FEATURE:
<223> OTHER INFORMATION: Small interfering RNA

<400> SEQUENCE: 352
gcugauugga gauuacucu                                               19

<210> SEQ ID NO 353
<211> LENGTH: 19
<212> TYPE: RNA
<213> ORGANISM: Artificial Sequence
<220> FEATURE:
<223> OTHER INFORMATION: Small interfering RNA

<400> SEQUENCE: 353
cucuaaggcc uuccuccua                                               19

<210> SEQ ID NO 354
<211> LENGTH: 19
<212> TYPE: RNA
<213> ORGANISM: Artificial Sequence
<220> FEATURE:
<223> OTHER INFORMATION: Small interfering RNA

<400> SEQUENCE: 354
cagacaguag acggaaagc                                               19

<210> SEQ ID NO 355
<211> LENGTH: 19
<212> TYPE: RNA
<213> ORGANISM: Artificial Sequence
<220> FEATURE:
<223> OTHER INFORMATION: Small interfering RNA

<400> SEQUENCE: 355
agcaccaaga ccucaagua                                               19

<210> SEQ ID NO 356
<211> LENGTH: 19
<212> TYPE: RNA
<213> ORGANISM: Artificial Sequence
<220> FEATURE:

```
<223> OTHER INFORMATION: Small interfering RNA

<400> SEQUENCE: 356
gaaacgaugg uggcccuau                                                19

<210> SEQ ID NO 357
<211> LENGTH: 19
<212> TYPE: RNA
<213> ORGANISM: Artificial Sequence
<220> FEATURE:
<223> OTHER INFORMATION: Small interfering RNA

<400> SEQUENCE: 357
aacgauggug gcccuauug                                                19

<210> SEQ ID NO 358
<211> LENGTH: 19
<212> TYPE: RNA
<213> ORGANISM: Artificial Sequence
<220> FEATURE:
<223> OTHER INFORMATION: Small interfering RNA

<400> SEQUENCE: 358
cgccgagagc uuccuacug                                                19

<210> SEQ ID NO 359
<211> LENGTH: 19
<212> TYPE: RNA
<213> ORGANISM: Artificial Sequence
<220> FEATURE:
<223> OTHER INFORMATION: Small interfering RNA

<400> SEQUENCE: 359
gaacuccagu gggcaaauu                                                19

<210> SEQ ID NO 360
<211> LENGTH: 19
<212> TYPE: RNA
<213> ORGANISM: Artificial Sequence
<220> FEATURE:
<223> OTHER INFORMATION: Small interfering RNA

<400> SEQUENCE: 360
uuuagcuggg augacaaug                                                19

<210> SEQ ID NO 361
<211> LENGTH: 19
<212> TYPE: RNA
<213> ORGANISM: Artificial Sequence
<220> FEATURE:
<223> OTHER INFORMATION: Small interfering RNA

<400> SEQUENCE: 361
uucaaggaca acacaauac                                                19

<210> SEQ ID NO 362
<211> LENGTH: 19
<212> TYPE: RNA
<213> ORGANISM: Artificial Sequence
<220> FEATURE:
<223> OTHER INFORMATION: Small interfering RNA

<400> SEQUENCE: 362
acacaauacc agauaaagu                                                19
```

```
<210> SEQ ID NO 363
<211> LENGTH: 19
<212> TYPE: RNA
<213> ORGANISM: Artificial Sequence
<220> FEATURE:
<223> OTHER INFORMATION: Small interfering RNA

<400> SEQUENCE: 363
cacaauacca gauaaaguu                                                     19

<210> SEQ ID NO 364
<211> LENGTH: 19
<212> TYPE: RNA
<213> ORGANISM: Artificial Sequence
<220> FEATURE:
<223> OTHER INFORMATION: Small interfering RNA

<400> SEQUENCE: 364
ggaagggcuu auguuuaaa                                                     19

<210> SEQ ID NO 365
<211> LENGTH: 19
<212> TYPE: RNA
<213> ORGANISM: Artificial Sequence
<220> FEATURE:
<223> OTHER INFORMATION: Small interfering RNA

<400> SEQUENCE: 365
caccaagauc ugaaguaug                                                     19

<210> SEQ ID NO 366
<211> LENGTH: 19
<212> TYPE: RNA
<213> ORGANISM: Artificial Sequence
<220> FEATURE:
<223> OTHER INFORMATION: Small interfering RNA

<400> SEQUENCE: 366
aguaugucaa cccagaaac                                                     19

<210> SEQ ID NO 367
<211> LENGTH: 19
<212> TYPE: RNA
<213> ORGANISM: Artificial Sequence
<220> FEATURE:
<223> OTHER INFORMATION: Small interfering RNA

<400> SEQUENCE: 367
guaugucaac ccagaaaca                                                     19

<210> SEQ ID NO 368
<211> LENGTH: 19
<212> TYPE: RNA
<213> ORGANISM: Artificial Sequence
<220> FEATURE:
<223> OTHER INFORMATION: Small interfering RNA

<400> SEQUENCE: 368
ugucauugau ugucgcuau                                                     19

<210> SEQ ID NO 369
<211> LENGTH: 19
<212> TYPE: RNA
<213> ORGANISM: Artificial Sequence
<220> FEATURE:
<223> OTHER INFORMATION: Small interfering RNA
```

```
<400> SEQUENCE: 369
uugauugucg cuauccaua                                          19

<210> SEQ ID NO 370
<211> LENGTH: 19
<212> TYPE: RNA
<213> ORGANISM: Artificial Sequence
<220> FEATURE:
<223> OTHER INFORMATION: Small interfering RNA

<400> SEQUENCE: 370
uugucgcuau ccauaugag                                          19

<210> SEQ ID NO 371
<211> LENGTH: 19
<212> TYPE: RNA
<213> ORGANISM: Artificial Sequence
<220> FEATURE:
<223> OTHER INFORMATION: Small interfering RNA

<400> SEQUENCE: 371
uccagggagc cuuaaacuu                                          19

<210> SEQ ID NO 372
<211> LENGTH: 19
<212> TYPE: RNA
<213> ORGANISM: Artificial Sequence
<220> FEATURE:
<223> OTHER INFORMATION: Small interfering RNA

<400> SEQUENCE: 372
gggagccuua aacuuauau                                          19

<210> SEQ ID NO 373
<211> LENGTH: 19
<212> TYPE: RNA
<213> ORGANISM: Artificial Sequence
<220> FEATURE:
<223> OTHER INFORMATION: Small interfering RNA

<400> SEQUENCE: 373
gucaggaaga acuguuuaa                                          19

<210> SEQ ID NO 374
<211> LENGTH: 19
<212> TYPE: RNA
<213> ORGANISM: Artificial Sequence
<220> FEATURE:
<223> OTHER INFORMATION: Small interfering RNA

<400> SEQUENCE: 374
agaagcccau cgucccuuu                                          19

<210> SEQ ID NO 375
<211> LENGTH: 19
<212> TYPE: RNA
<213> ORGANISM: Artificial Sequence
<220> FEATURE:
<223> OTHER INFORMATION: Small interfering RNA

<400> SEQUENCE: 375
gaagcccauc gucccuug                                           19

<210> SEQ ID NO 376
<211> LENGTH: 19
```

```
<212> TYPE: RNA
<213> ORGANISM: Artificial Sequence
<220> FEATURE:
<223> OTHER INFORMATION: Small interfering RNA

<400> SEQUENCE: 376
agcccaucgu cccuuugga                                                19

<210> SEQ ID NO 377
<211> LENGTH: 19
<212> TYPE: RNA
<213> ORGANISM: Artificial Sequence
<220> FEATURE:
<223> OTHER INFORMATION: Small interfering RNA

<400> SEQUENCE: 377
cacccagaag agaauaauc                                                19

<210> SEQ ID NO 378
<211> LENGTH: 19
<212> TYPE: RNA
<213> ORGANISM: Artificial Sequence
<220> FEATURE:
<223> OTHER INFORMATION: Small interfering RNA

<400> SEQUENCE: 378
uuguacuacc cagagcuau                                                19

<210> SEQ ID NO 379
<211> LENGTH: 19
<212> TYPE: RNA
<213> ORGANISM: Artificial Sequence
<220> FEATURE:
<223> OTHER INFORMATION: Small interfering RNA

<400> SEQUENCE: 379
cuacccagag cuauauauc                                                19

<210> SEQ ID NO 380
<211> LENGTH: 19
<212> TYPE: RNA
<213> ORGANISM: Artificial Sequence
<220> FEATURE:
<223> OTHER INFORMATION: Small interfering RNA

<400> SEQUENCE: 380
cccagagcua uauauccuu                                                19

<210> SEQ ID NO 381
<211> LENGTH: 19
<212> TYPE: RNA
<213> ORGANISM: Artificial Sequence
<220> FEATURE:
<223> OTHER INFORMATION: Small interfering RNA

<400> SEQUENCE: 381
uauauggaac ugugugaac                                                19

<210> SEQ ID NO 382
<211> LENGTH: 19
<212> TYPE: RNA
<213> ORGANISM: Artificial Sequence
<220> FEATURE:
<223> OTHER INFORMATION: Small interfering RNA

<400> SEQUENCE: 382
```
uauggaacug ugugaacca 19

<210> SEQ ID NO 383
<211> LENGTH: 19
<212> TYPE: RNA
<213> ORGANISM: Artificial Sequence
<220> FEATURE:
<223> OTHER INFORMATION: Small interfering RNA

<400> SEQUENCE: 383
cagagcuacu gcccuaugc 19

<210> SEQ ID NO 384
<211> LENGTH: 19
<212> TYPE: RNA
<213> ORGANISM: Artificial Sequence
<220> FEATURE:
<223> OTHER INFORMATION: Small interfering RNA

<400> SEQUENCE: 384
gagcuacugc ccuaugcau 19

<210> SEQ ID NO 385
<211> LENGTH: 19
<212> TYPE: RNA
<213> ORGANISM: Artificial Sequence
<220> FEATURE:
<223> OTHER INFORMATION: Small interfering RNA

<400> SEQUENCE: 385
gcuacugccc uaugcauca 19

<210> SEQ ID NO 386
<211> LENGTH: 19
<212> TYPE: RNA
<213> ORGANISM: Artificial Sequence
<220> FEATURE:
<223> OTHER INFORMATION: Small interfering RNA

<400> SEQUENCE: 386
gaugaagagc cuauugaag 19

<210> SEQ ID NO 387
<211> LENGTH: 19
<212> TYPE: RNA
<213> ORGANISM: Artificial Sequence
<220> FEATURE:
<223> OTHER INFORMATION: Small interfering RNA

<400> SEQUENCE: 387
agaugaacag acuccaauu 19

<210> SEQ ID NO 388
<211> LENGTH: 19
<212> TYPE: RNA
<213> ORGANISM: Artificial Sequence
<220> FEATURE:
<223> OTHER INFORMATION: Small interfering RNA

<400> SEQUENCE: 388
gaugaacaga cuccaauuc 19

<210> SEQ ID NO 389
<211> LENGTH: 19
<212> TYPE: RNA
<213> ORGANISM: Artificial Sequence

```
<220> FEATURE:
<223> OTHER INFORMATION: Small interfering RNA

<400> SEQUENCE: 389
ucacccauca ucauccaau                                                    19

<210> SEQ ID NO 390
<211> LENGTH: 19
<212> TYPE: RNA
<213> ORGANISM: Artificial Sequence
<220> FEATURE:
<223> OTHER INFORMATION: Small interfering RNA

<400> SEQUENCE: 390
gagcuuacaa ccugccuua                                                    19

<210> SEQ ID NO 391
<211> LENGTH: 19
<212> TYPE: RNA
<213> ORGANISM: Artificial Sequence
<220> FEATURE:
<223> OTHER INFORMATION: Small interfering RNA

<400> SEQUENCE: 391
cacugcuaug gaggacuug                                                    19

<210> SEQ ID NO 392
<211> LENGTH: 19
<212> TYPE: RNA
<213> ORGANISM: Artificial Sequence
<220> FEATURE:
<223> OTHER INFORMATION: Small interfering RNA

<400> SEQUENCE: 392
ucaccagagc aagccauag                                                    19

<210> SEQ ID NO 393
<211> LENGTH: 19
<212> TYPE: RNA
<213> ORGANISM: Artificial Sequence
<220> FEATURE:
<223> OTHER INFORMATION: Small interfering RNA

<400> SEQUENCE: 393
ccagagcaag ccauagaca                                                    19

<210> SEQ ID NO 394
<211> LENGTH: 19
<212> TYPE: RNA
<213> ORGANISM: Artificial Sequence
<220> FEATURE:
<223> OTHER INFORMATION: Small interfering RNA

<400> SEQUENCE: 394
cagccugcga gaccuaaga                                                    19

<210> SEQ ID NO 395
<211> LENGTH: 19
<212> TYPE: RNA
<213> ORGANISM: Artificial Sequence
<220> FEATURE:
<223> OTHER INFORMATION: Small interfering RNA

<400> SEQUENCE: 395
guuucgggac aaauuagcu                                                    19
```

```
<210> SEQ ID NO 396
<211> LENGTH: 19
<212> TYPE: RNA
<213> ORGANISM: Artificial Sequence
<220> FEATURE:
<223> OTHER INFORMATION: Small interfering RNA

<400> SEQUENCE: 396
aauuagcugc acaucuauc                                              19

<210> SEQ ID NO 397
<211> LENGTH: 19
<212> TYPE: RNA
<213> ORGANISM: Artificial Sequence
<220> FEATURE:
<223> OTHER INFORMATION: Small interfering RNA

<400> SEQUENCE: 397
auuagcugca caucuauca                                              19

<210> SEQ ID NO 398
<211> LENGTH: 19
<212> TYPE: RNA
<213> ORGANISM: Artificial Sequence
<220> FEATURE:
<223> OTHER INFORMATION: Small interfering RNA

<400> SEQUENCE: 398
uuagcugcac aucuaucau                                              19

<210> SEQ ID NO 399
<211> LENGTH: 19
<212> TYPE: RNA
<213> ORGANISM: Artificial Sequence
<220> FEATURE:
<223> OTHER INFORMATION: Small interfering RNA

<400> SEQUENCE: 399
gagacgcgga acaauugag                                              19

<210> SEQ ID NO 400
<211> LENGTH: 19
<212> TYPE: RNA
<213> ORGANISM: Artificial Sequence
<220> FEATURE:
<223> OTHER INFORMATION: Small interfering RNA

<400> SEQUENCE: 400
agaacaaggu gacacauau                                              19

<210> SEQ ID NO 401
<211> LENGTH: 19
<212> TYPE: RNA
<213> ORGANISM: Artificial Sequence
<220> FEATURE:
<223> OTHER INFORMATION: Small interfering RNA

<400> SEQUENCE: 401
gaacaaggug acacauauu                                              19

<210> SEQ ID NO 402
<211> LENGTH: 19
<212> TYPE: RNA
<213> ORGANISM: Artificial Sequence
<220> FEATURE:
<223> OTHER INFORMATION: Small interfering RNA
```

-continued

<400> SEQUENCE: 402
gcagcggauu caccaucuc                                          19

<210> SEQ ID NO 403
<211> LENGTH: 19
<212> TYPE: RNA
<213> ORGANISM: Artificial Sequence
<220> FEATURE:
<223> OTHER INFORMATION: Small interfering RNA

<400> SEQUENCE: 403
gcggauucac caucucaaa                                          19

<210> SEQ ID NO 404
<211> LENGTH: 19
<212> TYPE: RNA
<213> ORGANISM: Artificial Sequence
<220> FEATURE:
<223> OTHER INFORMATION: Small interfering RNA

<400> SEQUENCE: 404
cacuggugau cgcauacau                                          19

<210> SEQ ID NO 405
<211> LENGTH: 19
<212> TYPE: RNA
<213> ORGANISM: Artificial Sequence
<220> FEATURE:
<223> OTHER INFORMATION: Small interfering RNA

<400> SEQUENCE: 405
guaucggcag uggcugaag                                          19

<210> SEQ ID NO 406
<211> LENGTH: 19
<212> TYPE: RNA
<213> ORGANISM: Artificial Sequence
<220> FEATURE:
<223> OTHER INFORMATION: Small interfering RNA

<400> SEQUENCE: 406
gauccgccga cgacugcaa                                          19

<210> SEQ ID NO 407
<211> LENGTH: 19
<212> TYPE: RNA
<213> ORGANISM: Artificial Sequence
<220> FEATURE:
<223> OTHER INFORMATION: Small interfering RNA

<400> SEQUENCE: 407
guuucgggag gaguucaac                                          19

<210> SEQ ID NO 408
<211> LENGTH: 19
<212> TYPE: RNA
<213> ORGANISM: Artificial Sequence
<220> FEATURE:
<223> OTHER INFORMATION: Small interfering RNA

<400> SEQUENCE: 408
augaccauuc uagggugau                                          19

<210> SEQ ID NO 409

```
<211> LENGTH: 19
<212> TYPE: RNA
<213> ORGANISM: Artificial Sequence
<220> FEATURE:
<223> OTHER INFORMATION: Small interfering RNA

<400> SEQUENCE: 409 ccaucuagg gugauucug                                                    19

<210> SEQ ID NO 410
<211> LENGTH: 19
<212> TYPE: RNA
<213> ORGANISM: Artificial Sequence
<220> FEATURE:
<223> OTHER INFORMATION: Small interfering RNA

<400> SEQUENCE: 410
cauagauggu uacaaagag                                                   19

<210> SEQ ID NO 411
<211> LENGTH: 19
<212> TYPE: RNA
<213> ORGANISM: Artificial Sequence
<220> FEATURE:
<223> OTHER INFORMATION: Small interfering RNA

<400> SEQUENCE: 411
aacaggaaac gguuaacga                                                   19

<210> SEQ ID NO 412
<211> LENGTH: 19
<212> TYPE: RNA
<213> ORGANISM: Artificial Sequence
<220> FEATURE:
<223> OTHER INFORMATION: Small interfering RNA

<400> SEQUENCE: 412
ggaaacgguu aacgacuuc                                                   19

<210> SEQ ID NO 413
<211> LENGTH: 19
<212> TYPE: RNA
<213> ORGANISM: Artificial Sequence
<220> FEATURE:
<223> OTHER INFORMATION: Small interfering RNA

<400> SEQUENCE: 413
ccaucgucau guuaacaaa                                                   19

<210> SEQ ID NO 414
<211> LENGTH: 19
<212> TYPE: RNA
<213> ORGANISM: Artificial Sequence
<220> FEATURE:
<223> OTHER INFORMATION: Small interfering RNA

<400> SEQUENCE: 414
cuacaccauc cggaaguuc                                                   19

<210> SEQ ID NO 415
<211> LENGTH: 19
<212> TYPE: RNA
<213> ORGANISM: Artificial Sequence
<220> FEATURE:
<223> OTHER INFORMATION: Small interfering RNA

<400> SEQUENCE: 415
```

-continued uccggaaguu cugcauaca 19

<210> SEQ ID NO 416
<211> LENGTH: 19
<212> TYPE: RNA
<213> ORGANISM: Artificial Sequence
<220> FEATURE:
<223> OTHER INFORMATION: Small interfering RNA

<400> SEQUENCE: 416
gaaaguaaag acgcucaac 19

<210> SEQ ID NO 417
<211> LENGTH: 19
<212> TYPE: RNA
<213> ORGANISM: Artificial Sequence
<220> FEATURE:
<223> OTHER INFORMATION: Small interfering RNA

<400> SEQUENCE: 417
gcgcccucag augguucaa 19

<210> SEQ ID NO 418
<211> LENGTH: 19
<212> TYPE: RNA
<213> ORGANISM: Artificial Sequence
<220> FEATURE:
<223> OTHER INFORMATION: Small interfering RNA

<400> SEQUENCE: 418
cggauaugca guacacguu 19

<210> SEQ ID NO 419
<211> LENGTH: 19
<212> TYPE: RNA
<213> ORGANISM: Artificial Sequence
<220> FEATURE:
<223> OTHER INFORMATION: Small interfering RNA

<400> SEQUENCE: 419
ccacccacuu cgacaagau 19

<210> SEQ ID NO 420
<211> LENGTH: 19
<212> TYPE: RNA
<213> ORGANISM: Artificial Sequence
<220> FEATURE:
<223> OTHER INFORMATION: Small interfering RNA

<400> SEQUENCE: 420
caaauguccg gaucaugaa 19

<210> SEQ ID NO 421
<211> LENGTH: 19
<212> TYPE: RNA
<213> ORGANISM: Artificial Sequence
<220> FEATURE:
<223> OTHER INFORMATION: Small interfering RNA

<400> SEQUENCE: 421
caugaggacg ggcaacuug 19

<210> SEQ ID NO 422
<211> LENGTH: 19
<212> TYPE: RNA

```
<213> ORGANISM: Artificial Sequence
<220> FEATURE:
<223> OTHER INFORMATION: Small interfering RNA

<400> SEQUENCE: 422
ugacuucaac cgagugauc                                                      19

<210> SEQ ID NO 423
<211> LENGTH: 19
<212> TYPE: RNA
<213> ORGANISM: Artificial Sequence
<220> FEATURE:
<223> OTHER INFORMATION: Small interfering RNA

<400> SEQUENCE: 423
accgagugau ccuuuccau                                                      19

<210> SEQ ID NO 424
<211> LENGTH: 19
<212> TYPE: RNA
<213> ORGANISM: Artificial Sequence
<220> FEATURE:
<223> OTHER INFORMATION: Small interfering RNA

<400> SEQUENCE: 424
agaauacaca gacuacauc                                                      19

<210> SEQ ID NO 425
<211> LENGTH: 19
<212> TYPE: RNA
<213> ORGANISM: Artificial Sequence
<220> FEATURE:
<223> OTHER INFORMATION: Small interfering RNA

<400> SEQUENCE: 425
gacuacauca acgcauccu                                                      19

<210> SEQ ID NO 426
<211> LENGTH: 19
<212> TYPE: RNA
<213> ORGANISM: Artificial Sequence
<220> FEATURE:
<223> OTHER INFORMATION: Small interfering RNA

<400> SEQUENCE: 426
ucaacgcauc cuucauaga                                                      19

<210> SEQ ID NO 427
<211> LENGTH: 19
<212> TYPE: RNA
<213> ORGANISM: Artificial Sequence
<220> FEATURE:
<223> OTHER INFORMATION: Small interfering RNA

<400> SEQUENCE: 427
cacacgguug aggacuucu                                                      19

<210> SEQ ID NO 428
<211> LENGTH: 19
<212> TYPE: RNA
<213> ORGANISM: Artificial Sequence
<220> FEATURE:
<223> OTHER INFORMATION: Small interfering RNA

<400> SEQUENCE: 428
aaucccacac uaucgugau                                                      19
```

```
<210> SEQ ID NO 429
<211> LENGTH: 19
<212> TYPE: RNA
<213> ORGANISM: Artificial Sequence
<220> FEATURE:
<223> OTHER INFORMATION: Small interfering RNA

<400> SEQUENCE: 429
aucccacacu aucgugaug                                                   19

<210> SEQ ID NO 430
<211> LENGTH: 19
<212> TYPE: RNA
<213> ORGANISM: Artificial Sequence
<220> FEATURE:
<223> OTHER INFORMATION: Small interfering RNA

<400> SEQUENCE: 430
accgagggcu caguuacuc                                                   19

<210> SEQ ID NO 431
<211> LENGTH: 19
<212> TYPE: RNA
<213> ORGANISM: Artificial Sequence
<220> FEATURE:
<223> OTHER INFORMATION: Small interfering RNA

<400> SEQUENCE: 431
ccgagggcuc aguuacuca                                                   19

<210> SEQ ID NO 432
<211> LENGTH: 19
<212> TYPE: RNA
<213> ORGANISM: Artificial Sequence
<220> FEATURE:
<223> OTHER INFORMATION: Small interfering RNA

<400> SEQUENCE: 432
cucauggaga aauaacgau                                                   19

<210> SEQ ID NO 433
<211> LENGTH: 19
<212> TYPE: RNA
<213> ORGANISM: Artificial Sequence
<220> FEATURE:
<223> OTHER INFORMATION: Small interfering RNA

<400> SEQUENCE: 433
uggagaaaua acgauugag                                                   19

<210> SEQ ID NO 434
<211> LENGTH: 19
<212> TYPE: RNA
<213> ORGANISM: Artificial Sequence
<220> FEATURE:
<223> OTHER INFORMATION: Small interfering RNA

<400> SEQUENCE: 434
gccaucagua uacgagacu                                                   19

<210> SEQ ID NO 435
<211> LENGTH: 19
<212> TYPE: RNA
<213> ORGANISM: Artificial Sequence
<220> FEATURE:
```

```
<223> OTHER INFORMATION: Small interfering RNA

<400> SEQUENCE: 435
ucaguauacg agacuuucu                                                    19

<210> SEQ ID NO 436
<211> LENGTH: 19
<212> TYPE: RNA
<213> ORGANISM: Artificial Sequence
<220> FEATURE:
<223> OTHER INFORMATION: Small interfering RNA

<400> SEQUENCE: 436
gggcaaaggc augauugac                                                    19

<210> SEQ ID NO 437
<211> LENGTH: 19
<212> TYPE: RNA
<213> ORGANISM: Artificial Sequence
<220> FEATURE:
<223> OTHER INFORMATION: Small interfering RNA

<400> SEQUENCE: 437
gcugggcgaa cagguacau                                                    19

<210> SEQ ID NO 438
<211> LENGTH: 19
<212> TYPE: RNA
<213> ORGANISM: Artificial Sequence
<220> FEATURE:
<223> OTHER INFORMATION: Small interfering RNA

<400> SEQUENCE: 438
cuucagagac cacauaugg                                                    19

<210> SEQ ID NO 439
<211> LENGTH: 21
<212> TYPE: DNA
<213> ORGANISM: Artificial Sequence
<220> FEATURE:
<223> OTHER INFORMATION: Small interfering RNA - cdc14a.2

<400> SEQUENCE: 439
caucugugag aacaccgaat t                                                 21

<210> SEQ ID NO 440
<211> LENGTH: 19
<212> TYPE: RNA
<213> ORGANISM: Artificial Sequence
<220> FEATURE:
<223> OTHER INFORMATION: Small interfering RNA - cdc14a.2

<400> SEQUENCE: 440
caucugugag aacaccgaa                                                    19

<210> SEQ ID NO 441
<211> LENGTH: 19
<212> TYPE: RNA
<213> ORGANISM: Artificial Sequence
<220> FEATURE:
<223> OTHER INFORMATION: Small interfering RNA - cdc14a.2

<400> SEQUENCE: 441 uucggguguuc ucacagaug                                                   19
```

```
<210> SEQ ID NO 442
<211> LENGTH: 21
<212> TYPE: DNA
<213> ORGANISM: Artificial Sequence
<220> FEATURE:
<223> OTHER INFORMATION: Small interfering RNA - cdc14a.2
<220> FEATURE:
<221> NAME/KEY: misc_feature
<222> LOCATION: 20, 21
<223> OTHER INFORMATION: n = A,T,C,G or U

<400> SEQUENCE: 442
caucugugag aacaccgaan n                                      21

<210> SEQ ID NO 443
<211> LENGTH: 21
<212> TYPE: DNA
<213> ORGANISM: Artificial Sequence
<220> FEATURE:
<223> OTHER INFORMATION: Small interfering RNA - cdc14a.2
<220> FEATURE:
<221> NAME/KEY: misc_feature
<222> LOCATION: 1, 2
<223> OTHER INFORMATION: n = A,T,C,G or U

<400> SEQUENCE: 443
nnuucggugu ucucacagau g                                      21

<210> SEQ ID NO 444
<211> LENGTH: 21
<212> TYPE: DNA
<213> ORGANISM: Artificial Sequence
<220> FEATURE:
<223> OTHER INFORMATION: Small interfering RNA - cdc14a.3

<400> SEQUENCE: 444
cuuggcaaug guguacagat t                                      21

<210> SEQ ID NO 445
<211> LENGTH: 19
<212> TYPE: RNA
<213> ORGANISM: Artificial Sequence
<220> FEATURE:
<223> OTHER INFORMATION: Small interfering RNA - cdc14a.3

<400> SEQUENCE: 445
cuuggcaaug guguacaga                                         19

<210> SEQ ID NO 446
<211> LENGTH: 19
<212> TYPE: RNA
<213> ORGANISM: Artificial Sequence
<220> FEATURE:
<223> OTHER INFORMATION: Small interfering RNA - cdc14a.3

<400> SEQUENCE: 446
ucuguacacc auugccaag                                         19

<210> SEQ ID NO 447
<211> LENGTH: 21
<212> TYPE: DNA
<213> ORGANISM: Artificial Sequence
<220> FEATURE:
<223> OTHER INFORMATION: Small interfering RNA - cdc14a.3
<220> FEATURE:
<221> NAME/KEY: misc_feature
<222> LOCATION: 20, 21
<223> OTHER INFORMATION: n = A,T,C,G or U
```

-continued

```
<400> SEQUENCE: 447
cuuggcaaug guguacagan n                                                 21

<210> SEQ ID NO 448
<211> LENGTH: 21
<212> TYPE: DNA
<213> ORGANISM: Artificial Sequence
<220> FEATURE:
<223> OTHER INFORMATION: Small interfering RNA - cdc14a.3
<220> FEATURE:
<221> NAME/KEY: misc_feature
<222> LOCATION: 1, 2
<223> OTHER INFORMATION: n = A,T,C,G or U

<400> SEQUENCE: 448
nnucuguaca ccauugccaa g                                                 21

<210> SEQ ID NO 449
<211> LENGTH: 21
<212> TYPE: DNA
<213> ORGANISM: Artificial Sequence
<220> FEATURE:
<223> OTHER INFORMATION: Small interfering RNA - cdc14a.5

<400> SEQUENCE: 449
gcacaguaaa uacccacuat t                                                 21

<210> SEQ ID NO 450
<211> LENGTH: 19
<212> TYPE: RNA
<213> ORGANISM: Artificial Sequence
<220> FEATURE:
<223> OTHER INFORMATION: Small interfering RNA - cdc14a.5

<400> SEQUENCE: 450
gcacaguaaa uacccacua                                                    19

<210> SEQ ID NO 451
<211> LENGTH: 19
<212> TYPE: RNA
<213> ORGANISM: Artificial Sequence
<220> FEATURE:
<223> OTHER INFORMATION: Small interfering RNA - cdc14a.5

<400> SEQUENCE: 451
uaguggguau uuacugugc                                                    19

<210> SEQ ID NO 452
<211> LENGTH: 21
<212> TYPE: DNA
<213> ORGANISM: Artificial Sequence
<220> FEATURE:
<223> OTHER INFORMATION: Small interfering RNA - cdc14a.5
<220> FEATURE:
<221> NAME/KEY: misc_feature
<222> LOCATION: 20, 21
<223> OTHER INFORMATION: n = A,T,C,G or U

<400> SEQUENCE: 452
gcacaguaaa uacccacuan n                                                 21

<210> SEQ ID NO 453
<211> LENGTH: 21
<212> TYPE: DNA
<213> ORGANISM: Artificial Sequence
<220> FEATURE:
<223> OTHER INFORMATION: Small interfering RNA - cdc14a.5
```

```
<220> FEATURE:
<221> NAME/KEY: misc_feature
<222> LOCATION: 1, 2
<223> OTHER INFORMATION: n = A,T,C,G or U

<400> SEQUENCE: 453
nnuagugggu auuuacugug c                                          21

<210> SEQ ID NO 454
<211> LENGTH: 21
<212> TYPE: DNA
<213> ORGANISM: Artificial Sequence
<220> FEATURE:
<223> OTHER INFORMATION: Small interfering RNA - cdc14b.3

<400> SEQUENCE: 454
caagcaaaug cugccuucct t                                          21

<210> SEQ ID NO 455
<211> LENGTH: 19
<212> TYPE: RNA
<213> ORGANISM: Artificial Sequence
<220> FEATURE:
<223> OTHER INFORMATION: Small interfering RNA - cdc14b.3

<400> SEQUENCE: 455
caagcaaaug cugccuucc                                             19

<210> SEQ ID NO 456
<211> LENGTH: 19
<212> TYPE: RNA
<213> ORGANISM: Artificial Sequence
<220> FEATURE:
<223> OTHER INFORMATION: Small interfering RNA - cdc14b.3

<400> SEQUENCE: 456
ggaaggcagc auuugcuug                                             19

<210> SEQ ID NO 457
<211> LENGTH: 21
<212> TYPE: DNA
<213> ORGANISM: Artificial Sequence
<220> FEATURE:
<223> OTHER INFORMATION: Small interfering RNA - cdc14b.3
<220> FEATURE:
<221> NAME/KEY: misc_feature
<222> LOCATION: 20, 21
<223> OTHER INFORMATION: n = A,T,C,G or U

<400> SEQUENCE: 457
caagcaaaug cugccuuccn n                                          21

<210> SEQ ID NO 458
<211> LENGTH: 21
<212> TYPE: DNA
<213> ORGANISM: Artificial Sequence
<220> FEATURE:
<223> OTHER INFORMATION: Small interfering RNA - cdc14b.3
<220> FEATURE:
<221> NAME/KEY: misc_feature
<222> LOCATION: 1, 2
<223> OTHER INFORMATION: n = A,T,C,G or U

<400> SEQUENCE: 458
nnggaaggca gcauuugcuu g                                          21

<210> SEQ ID NO 459
```

```
<211> LENGTH: 21
<212> TYPE: DNA
<213> ORGANISM: Artificial Sequence
<220> FEATURE:
<223> OTHER INFORMATION: Small interfering RNA - cdc14b.4

<400> SEQUENCE: 459
gagccagacu ugaaaguggt t                                               21

<210> SEQ ID NO 460
<211> LENGTH: 19
<212> TYPE: RNA
<213> ORGANISM: Artificial Sequence
<220> FEATURE:
<223> OTHER INFORMATION: Small interfering RNA - cdc14b.4

<400> SEQUENCE: 460
gagccagacu ugaaagugg                                                  19

<210> SEQ ID NO 461
<211> LENGTH: 19
<212> TYPE: RNA
<213> ORGANISM: Artificial Sequence
<220> FEATURE:
<223> OTHER INFORMATION: Small interfering RNA - cdc14b.4

<400> SEQUENCE: 461
ccacuuucaa gucuggcuc                                                  19

<210> SEQ ID NO 462
<211> LENGTH: 21
<212> TYPE: DNA
<213> ORGANISM: Artificial Sequence
<220> FEATURE:
<223> OTHER INFORMATION: Small interfering RNA - cdc14b.4
<220> FEATURE:
<221> NAME/KEY: misc_feature
<222> LOCATION: 20, 21
<223> OTHER INFORMATION: n = A,T,C,G or U

<400> SEQUENCE: 462
gagccagacu ugaaaguggn n                                               21

<210> SEQ ID NO 463
<211> LENGTH: 21
<212> TYPE: DNA
<213> ORGANISM: Artificial Sequence
<220> FEATURE:
<223> OTHER INFORMATION: Small interfering RNA - cdc14b.4
<220> FEATURE:
<221> NAME/KEY: misc_feature
<222> LOCATION: 1, 2
<223> OTHER INFORMATION: n = A,T,C,G or U

<400> SEQUENCE: 463
nnccacuuuc aagucuggcu c                                               21

<210> SEQ ID NO 464
<211> LENGTH: 21
<212> TYPE: DNA
<213> ORGANISM: Artificial Sequence
<220> FEATURE:
<223> OTHER INFORMATION: Small interfering RNA - 25 A.2

<400> SEQUENCE: 464
gaggagccau ucugauucut t                                               21
```

<210> SEQ ID NO 465
<211> LENGTH: 19
<212> TYPE: RNA
<213> ORGANISM: Artificial Sequence
<220> FEATURE:
<223> OTHER INFORMATION: Small interfering RNA - 25 A.2

<400> SEQUENCE: 465
gaggagccau ucugauucu                                                  19

<210> SEQ ID NO 466
<211> LENGTH: 19
<212> TYPE: RNA
<213> ORGANISM: Artificial Sequence
<220> FEATURE:
<223> OTHER INFORMATION: Small interfering RNA - 25 A.2

<400> SEQUENCE: 466
agaaucagaa uggcuccuc                                                  19

<210> SEQ ID NO 467
<211> LENGTH: 21
<212> TYPE: DNA
<213> ORGANISM: Artificial Sequence
<220> FEATURE:
<223> OTHER INFORMATION: Small interfering RNA - 25 A.2
<220> FEATURE:
<221> NAME/KEY: misc_feature
<222> LOCATION: 20, 21
<223> OTHER INFORMATION: n = A,T,C,G or U

<400> SEQUENCE: 467
gaggagccau ucugauucun n                                               21

<210> SEQ ID NO 468
<211> LENGTH: 21
<212> TYPE: DNA
<213> ORGANISM: Artificial Sequence
<220> FEATURE:
<223> OTHER INFORMATION: Small interfering RNA - 25 A.2
<220> FEATURE:
<221> NAME/KEY: misc_feature
<222> LOCATION: 1, 2
<223> OTHER INFORMATION: n = A,T,C,G or U

<400> SEQUENCE: 468
nnagaaucag aauggcuccu c                                               21

<210> SEQ ID NO 469
<211> LENGTH: 21
<212> TYPE: DNA
<213> ORGANISM: Artificial Sequence
<220> FEATURE:
<223> OTHER INFORMATION: Small interfering RNA - cdc25B.2

<400> SEQUENCE: 469
aggcggcuac aaggaguuct t                                               21

<210> SEQ ID NO 470
<211> LENGTH: 19
<212> TYPE: RNA
<213> ORGANISM: Artificial Sequence
<220> FEATURE:
<223> OTHER INFORMATION: Small interfering RNA - cdc25B.2

<400> SEQUENCE: 470
aggcggcuac aaggaguuc                                                  19

<210> SEQ ID NO 471
<211> LENGTH: 19
<212> TYPE: RNA
<213> ORGANISM: Artificial Sequence
<220> FEATURE:
<223> OTHER INFORMATION: Small interfering RNA - cdc25B.2

<400> SEQUENCE: 471
gaacuccuug uagccgccu                                                    19

<210> SEQ ID NO 472
<211> LENGTH: 21
<212> TYPE: DNA
<213> ORGANISM: Artificial Sequence
<220> FEATURE:
<223> OTHER INFORMATION: Small interfering RNA - cdc25B.2
<220> FEATURE:
<221> NAME/KEY: misc_feature
<222> LOCATION: 20, 21
<223> OTHER INFORMATION: n = A,T,C,G or U

<400> SEQUENCE: 472
aggcggcuac aaggaguucn n                                                 21

<210> SEQ ID NO 473
<211> LENGTH: 21
<212> TYPE: DNA
<213> ORGANISM: Artificial Sequence
<220> FEATURE:
<223> OTHER INFORMATION: Small interfering RNA - cdc25B.2
<220> FEATURE:
<221> NAME/KEY: misc_feature
<222> LOCATION: 1, 2
<223> OTHER INFORMATION: n = A,T,C,G or U

<400> SEQUENCE: 473
nngaacuccu uguagccgcc u                                                 21

<210> SEQ ID NO 474
<211> LENGTH: 21
<212> TYPE: DNA
<213> ORGANISM: Artificial Sequence
<220> FEATURE:
<223> OTHER INFORMATION: Small interfering RNA - cdc25B.4

<400> SEQUENCE: 474
gaugccaugg aagcccacat t                                                 21

<210> SEQ ID NO 475
<211> LENGTH: 19
<212> TYPE: RNA
<213> ORGANISM: Artificial Sequence
<220> FEATURE:
<223> OTHER INFORMATION: Small interfering RNA - cdc25B.4

<400> SEQUENCE: 475
gaugccaugg aagcccaca                                                    19

<210> SEQ ID NO 476
<211> LENGTH: 19
<212> TYPE: RNA
<213> ORGANISM: Artificial Sequence
<220> FEATURE:
<223> OTHER INFORMATION: Small interfering RNA - cdc25B.4

<400> SEQUENCE: 476 uguggguuc cauggcauc                                                     19

<210> SEQ ID NO 477
<211> LENGTH: 21
<212> TYPE: DNA
<213> ORGANISM: Artificial Sequence
<220> FEATURE:
<223> OTHER INFORMATION: Small interfering RNA - cdc25B.4
<220> FEATURE:
<221> NAME/KEY: misc_feature
<222> LOCATION: 20, 21
<223> OTHER INFORMATION: n = A,T,C,G or U

<400> SEQUENCE: 477
gaugccaugg aagcccacan n                                              21

<210> SEQ ID NO 478
<211> LENGTH: 21
<212> TYPE: DNA
<213> ORGANISM: Artificial Sequence
<220> FEATURE:
<223> OTHER INFORMATION: Small interfering RNA - cdc25B.4
<220> FEATURE:
<221> NAME/KEY: misc_feature
<222> LOCATION: 1, 2
<223> OTHER INFORMATION: n = A,T,C,G or U

<400> SEQUENCE: 478
nnugugggcu uccauggcau c                                              21

<210> SEQ ID NO 479
<211> LENGTH: 21
<212> TYPE: DNA
<213> ORGANISM: Artificial Sequence
<220> FEATURE:
<223> OTHER INFORMATION: Small interfering RNA - cdc25C.1

<400> SEQUENCE: 479
cugccacuca gcuuaccact t                                              21

<210> SEQ ID NO 480
<211> LENGTH: 19
<212> TYPE: RNA
<213> ORGANISM: Artificial Sequence
<220> FEATURE:
<223> OTHER INFORMATION: Small interfering RNA - cdc25C.1

<400> SEQUENCE: 480
cugccacuca gcuuaccac                                                 19

<210> SEQ ID NO 481
<211> LENGTH: 19
<212> TYPE: RNA
<213> ORGANISM: Artificial Sequence
<220> FEATURE:
<223> OTHER INFORMATION: Small interfering RNA - cdc25C.1

<400> SEQUENCE: 481
gugguaagcu gaguggcag                                                 19

<210> SEQ ID NO 482
<211> LENGTH: 21
<212> TYPE: DNA
<213> ORGANISM: Artificial Sequence
<220> FEATURE:
<223> OTHER INFORMATION: Small interfering RNA - cdc25C.1
<220> FEATURE:
<221> NAME/KEY: misc_feature
<222> LOCATION: 20, 21

```
<223> OTHER INFORMATION: n = A,T,C,G or U

<400> SEQUENCE: 482
cugccacuca gcuuaccacn n                                              21

<210> SEQ ID NO 483
<211> LENGTH: 21
<212> TYPE: DNA
<213> ORGANISM: Artificial Sequence
<220> FEATURE:
<223> OTHER INFORMATION: Small interfering RNA - cdc25C.1
<220> FEATURE:
<221> NAME/KEY: misc_feature
<222> LOCATION: 1, 2
<223> OTHER INFORMATION: n = A,T,C,G or U

<400> SEQUENCE: 483 nnguggua ag cugaguggca g                                             21

<210> SEQ ID NO 484
<211> LENGTH: 21
<212> TYPE: DNA
<213> ORGANISM: Artificial Sequence
<220> FEATURE:
<223> OTHER INFORMATION: Small interfering RNA - cdc25C.3

<400> SEQUENCE: 484
cccagaaaca guggcugcct t                                              21

<210> SEQ ID NO 485
<211> LENGTH: 19
<212> TYPE: RNA
<213> ORGANISM: Artificial Sequence
<220> FEATURE:
<223> OTHER INFORMATION: Small interfering RNA - cdc25C.3

<400> SEQUENCE: 485
cccagaaaca guggcugcc                                                 19

<210> SEQ ID NO 486
<211> LENGTH: 19
<212> TYPE: RNA
<213> ORGANISM: Artificial Sequence
<220> FEATURE:
<223> OTHER INFORMATION: Small interfering RNA - cdc25C.3

<400> SEQUENCE: 486
ggcagccacu guuucuggg                                                 19

<210> SEQ ID NO 487
<211> LENGTH: 21
<212> TYPE: DNA
<213> ORGANISM: Artificial Sequence
<220> FEATURE:
<223> OTHER INFORMATION: Small interfering RNA - cdc25C.3
<220> FEATURE:
<221> NAME/KEY: misc_feature
<222> LOCATION: 20, 21
<223> OTHER INFORMATION: n = A,T,C,G or U

<400> SEQUENCE: 487
cccagaaaca guggcugccn n                                              21

<210> SEQ ID NO 488
<211> LENGTH: 21
<212> TYPE: DNA
<213> ORGANISM: Artificial Sequence
```

```
<220> FEATURE:
<223> OTHER INFORMATION: Small interfering RNA - cdc25C.3
<220> FEATURE:
<221> NAME/KEY: misc_feature
<222> LOCATION: 1, 2
<223> OTHER INFORMATION: n = A,T,C,G or U

<400> SEQUENCE: 488
nnggcagcca cguuucugg g                                              21

<210> SEQ ID NO 489
<211> LENGTH: 21
<212> TYPE: DNA
<213> ORGANISM: Artificial Sequence
<220> FEATURE:
<223> OTHER INFORMATION: Small interfering RNA - cdc25C.4

<400> SEQUENCE: 489
aggcggcuac agagacuuct t                                             21

<210> SEQ ID NO 490
<211> LENGTH: 19
<212> TYPE: RNA
<213> ORGANISM: Artificial Sequence
<220> FEATURE:
<223> OTHER INFORMATION: Small interfering RNA - cdc25C.4

<400> SEQUENCE: 490
aggcggcuac agagacuuc                                                19

<210> SEQ ID NO 491
<211> LENGTH: 19
<212> TYPE: RNA
<213> ORGANISM: Artificial Sequence
<220> FEATURE:
<223> OTHER INFORMATION: Small interfering RNA - cdc25C.4

<400> SEQUENCE: 491
gaagucucug uagccgccu                                                19

<210> SEQ ID NO 492
<211> LENGTH: 21
<212> TYPE: DNA
<213> ORGANISM: Artificial Sequence
<220> FEATURE:
<223> OTHER INFORMATION: Small interfering RNA - cdc25C.4
<220> FEATURE:
<221> NAME/KEY: misc_feature
<222> LOCATION: 20, 21
<223> OTHER INFORMATION: n = A,T,C,G or U

<400> SEQUENCE: 492
aggcggcuac agagacuucn n                                             21

<210> SEQ ID NO 493
<211> LENGTH: 21
<212> TYPE: DNA
<213> ORGANISM: Artificial Sequence
<220> FEATURE:
<223> OTHER INFORMATION: Small interfering RNA - cdc25C.4
<220> FEATURE:
<221> NAME/KEY: misc_feature
<222> LOCATION: 1, 2
<223> OTHER INFORMATION: n = A,T,C,G or U

<400> SEQUENCE: 493
nngaagucuc uguagccgcc u                                             21
```

-continued

<210> SEQ ID NO 494
<211> LENGTH: 36
<212> TYPE: DNA
<213> ORGANISM: Artificial Sequence
<220> FEATURE:
<223> OTHER INFORMATION: Oligonucleotide primer mPTP1B-sense

<400> SEQUENCE: 494 ggggggatc catggagatg gagaaggagt tcgagg                36

<210> SEQ ID NO 495
<211> LENGTH: 35
<212> TYPE: DNA
<213> ORGANISM: Artificial Sequence
<220> FEATURE:
<223> OTHER INFORMATION: Oligonucleotide primer mPTP1B anti-sense

<400> SEQUENCE: 495
gggggaattc tcagtgaaaa cacaccggt agcac                35

<210> SEQ ID NO 496
<211> LENGTH: 21
<212> TYPE: DNA
<213> ORGANISM: Artificial Sequence
<220> FEATURE:
<223> OTHER INFORMATION: Small interfering RNA - mPTP1B1.1

<400> SEQUENCE: 496
gaagcccaga ggagcuauat t                              21

<210> SEQ ID NO 497
<211> LENGTH: 19
<212> TYPE: RNA
<213> ORGANISM: Artificial Sequence
<220> FEATURE:
<223> OTHER INFORMATION: Small interfering RNA - mPTP1B1.1

<400> SEQUENCE: 497
gaagcccaga ggagcuaua                                 19

<210> SEQ ID NO 498
<211> LENGTH: 19
<212> TYPE: RNA
<213> ORGANISM: Artificial Sequence
<220> FEATURE:
<223> OTHER INFORMATION: Small interfering RNA - mPTP1B1.1

<400> SEQUENCE: 498
uauagcuccu cugggcuuc                                 19

<210> SEQ ID NO 499
<211> LENGTH: 21
<212> TYPE: DNA
<213> ORGANISM: Artificial Sequence
<220> FEATURE:
<223> OTHER INFORMATION: Small interfering RNA - mPTP1B1.1
<220> FEATURE:
<221> NAME/KEY: misc_feature
<222> LOCATION: 20, 21
<223> OTHER INFORMATION: n = A,T,C,G or U

<400> SEQUENCE: 499
gaagcccaga ggagcuauan n                              21

<210> SEQ ID NO 500
<211> LENGTH: 21

```
<212> TYPE: DNA
<213> ORGANISM: Artificial Sequence
<220> FEATURE:
<223> OTHER INFORMATION: Small interfering RNA - mPTP1B1.1
<220> FEATURE:
<221> NAME/KEY: misc_feature
<222> LOCATION: 1, 2
<223> OTHER INFORMATION: n = A,T,C,G or U

<400> SEQUENCE: 500
nnuauagcuc cucgggcuu c                                              21

<210> SEQ ID NO 501
<211> LENGTH: 21
<212> TYPE: DNA
<213> ORGANISM: Artificial Sequence
<220> FEATURE:
<223> OTHER INFORMATION: Small interfering RNA - mPTP1B1.2

<400> SEQUENCE: 501
cuacaccaca uggccugact t                                             21

<210> SEQ ID NO 502
<211> LENGTH: 19
<212> TYPE: RNA
<213> ORGANISM: Artificial Sequence
<220> FEATURE:
<223> OTHER INFORMATION: Small interfering RNA - mPTP1B1.2

<400> SEQUENCE: 502
cuacaccaca uggccugac                                                19

<210> SEQ ID NO 503
<211> LENGTH: 19
<212> TYPE: RNA
<213> ORGANISM: Artificial Sequence
<220> FEATURE:
<223> OTHER INFORMATION: Small interfering RNA - mPTP1B1.2

<400> SEQUENCE: 503
gucaggccau gugguguag                                                19

<210> SEQ ID NO 504
<211> LENGTH: 21
<212> TYPE: DNA
<213> ORGANISM: Artificial Sequence
<220> FEATURE:
<223> OTHER INFORMATION: Small interfering RNA - mPTP1B1.2
<220> FEATURE:
<221> NAME/KEY: misc_feature
<222> LOCATION: 20, 21
<223> OTHER INFORMATION: n = A,T,C,G or U

<400> SEQUENCE: 504
cuacaccaca uggccugacn n                                             21

<210> SEQ ID NO 505
<211> LENGTH: 21
<212> TYPE: DNA
<213> ORGANISM: Artificial Sequence
<220> FEATURE:
<223> OTHER INFORMATION: Small interfering RNA - mPTP1B1.2
<220> FEATURE:
<221> NAME/KEY: misc_feature
<222> LOCATION: 1, 2
<223> OTHER INFORMATION: n = A,T,C,G or U

<400> SEQUENCE: 505
```
nngucaggcc auguggugua g    21

<210> SEQ ID NO 506
<211> LENGTH: 21
<212> TYPE: DNA
<213> ORGANISM: Artificial Sequence
<220> FEATURE:
<223> OTHER INFORMATION: Small interfering RNA - mPTP1B1.3

<400> SEQUENCE: 506
gacugccgac cagcugcgct t    21

<210> SEQ ID NO 507
<211> LENGTH: 19
<212> TYPE: RNA
<213> ORGANISM: Artificial Sequence
<220> FEATURE:
<223> OTHER INFORMATION: Small interfering RNA - mPTP1B1.3

<400> SEQUENCE: 507
gacugccgac cagcugcgc    19

<210> SEQ ID NO 508
<211> LENGTH: 19
<212> TYPE: RNA
<213> ORGANISM: Artificial Sequence
<220> FEATURE:
<223> OTHER INFORMATION: Small interfering RNA - mPTP1B1.3

<400> SEQUENCE: 508
gcgcagcugg ucggcaguc    19

<210> SEQ ID NO 509
<211> LENGTH: 21
<212> TYPE: DNA
<213> ORGANISM: Artificial Sequence
<220> FEATURE:
<223> OTHER INFORMATION: Small interfering RNA - mPTP1B1.3
<220> FEATURE:
<221> NAME/KEY: misc_feature
<222> LOCATION: 20, 21
<223> OTHER INFORMATION: n = A,T,C,G or U

<400> SEQUENCE: 509
gacugccgac cagcugcgcn n    21

<210> SEQ ID NO 510
<211> LENGTH: 21
<212> TYPE: DNA
<213> ORGANISM: Artificial Sequence
<220> FEATURE:
<223> OTHER INFORMATION: Small interfering RNA - mPTP1B1.3
<220> FEATURE:
<221> NAME/KEY: misc_feature
<222> LOCATION: 1, 2
<223> OTHER INFORMATION: n = A,T,C,G or U

<400> SEQUENCE: 510
nngcgcagcu ggucggcagu c    21

<210> SEQ ID NO 511
<211> LENGTH: 21
<212> TYPE: DNA
<213> ORGANISM: Artificial Sequence
<220> FEATURE:
<223> OTHER INFORMATION: Small interfering RNA - mPTP1B1.4

<400> SEQUENCE: 511
gguaccgaga ugucagccct t                            21

<210> SEQ ID NO 512
<211> LENGTH: 19
<212> TYPE: RNA
<213> ORGANISM: Artificial Sequence
<220> FEATURE:
<223> OTHER INFORMATION: Small interfering RNA - mPTP1B1.4

<400> SEQUENCE: 512
gguaccgaga ugucagccc                               19

<210> SEQ ID NO 513
<211> LENGTH: 19
<212> TYPE: RNA
<213> ORGANISM: Artificial Sequence
<220> FEATURE:
<223> OTHER INFORMATION: Small interfering RNA - mPTP1B1.4

<400> SEQUENCE: 513
gggcugacau cucgguacc                               19

<210> SEQ ID NO 514
<211> LENGTH: 21
<212> TYPE: DNA
<213> ORGANISM: Artificial Sequence
<220> FEATURE:
<223> OTHER INFORMATION: Small interfering RNA - mPTP1B1.4
<220> FEATURE:
<221> NAME/KEY: misc_feature
<222> LOCATION: 20, 21
<223> OTHER INFORMATION: n = A,T,C,G or U

<400> SEQUENCE: 514
gguaccgaga ugucagcccn n                            21

<210> SEQ ID NO 515
<211> LENGTH: 21
<212> TYPE: DNA
<213> ORGANISM: Artificial Sequence
<220> FEATURE:
<223> OTHER INFORMATION: Small interfering RNA - mPTP1B1.4
<220> FEATURE:
<221> NAME/KEY: misc_feature
<222> LOCATION: 1, 2
<223> OTHER INFORMATION: n = A,T,C,G or U

<400> SEQUENCE: 515
nngggcugac aucucgguac c                            21

<210> SEQ ID NO 516
<211> LENGTH: 21
<212> TYPE: DNA
<213> ORGANISM: Artificial Sequence
<220> FEATURE:
<223> OTHER INFORMATION: Small interfering RNA - mPTP1B1.5

<400> SEQUENCE: 516
ugacuauauc aaugccagct t                            21

<210> SEQ ID NO 517
<211> LENGTH: 19
<212> TYPE: RNA
<213> ORGANISM: Artificial Sequence
<220> FEATURE:
<223> OTHER INFORMATION: Small interfering RNA - mPTP1B1.5

-continued

```
<400> SEQUENCE: 517
ugacuauauc aaugccagc                                                    19

<210> SEQ ID NO 518
<211> LENGTH: 19
<212> TYPE: RNA
<213> ORGANISM: Artificial Sequence
<220> FEATURE:
<223> OTHER INFORMATION: Small interfering RNA - mPTP1B1.5

<400> SEQUENCE: 518
gcuggcauug auauaguca                                                    19

<210> SEQ ID NO 519
<211> LENGTH: 21
<212> TYPE: DNA
<213> ORGANISM: Artificial Sequence
<220> FEATURE:
<223> OTHER INFORMATION: Small interfering RNA - mPTP1B1.5
<220> FEATURE:
<221> NAME/KEY: misc_feature
<222> LOCATION: 20, 21
<223> OTHER INFORMATION: n = A,T,C,G or U

<400> SEQUENCE: 519
ugacuauauc aaugccagcn n                                                 21

<210> SEQ ID NO 520
<211> LENGTH: 21
<212> TYPE: DNA
<213> ORGANISM: Artificial Sequence
<220> FEATURE:
<223> OTHER INFORMATION: Small interfering RNA - mPTP1B1.5
<220> FEATURE:
<221> NAME/KEY: misc_feature
<222> LOCATION: 1, 2
<223> OTHER INFORMATION: n = A,T,C,G or U

<400> SEQUENCE: 520
nngcuggcau ugauauaguc a                                                 21

<210> SEQ ID NO 521
<211> LENGTH: 21
<212> TYPE: DNA
<213> ORGANISM: Artificial Sequence
<220> FEATURE:
<223> OTHER INFORMATION: Small interfering RNA - mPTP1B1.6

<400> SEQUENCE: 521
agaagaaaag gagaugguct t                                                 21

<210> SEQ ID NO 522
<211> LENGTH: 19
<212> TYPE: RNA
<213> ORGANISM: Artificial Sequence
<220> FEATURE:
<223> OTHER INFORMATION: Small interfering RNA - mPTP1B1.6

<400> SEQUENCE: 522
agaagaaaag gagaugguc                                                    19

<210> SEQ ID NO 523
<211> LENGTH: 19
<212> TYPE: RNA
<213> ORGANISM: Artificial Sequence
<220> FEATURE:
<223> OTHER INFORMATION: Small interfering RNA - mPTP1B1.6
```

<400> SEQUENCE: 523
gaccaucucc uuucuucu                                                    19

<210> SEQ ID NO 524
<211> LENGTH: 21
<212> TYPE: DNA
<213> ORGANISM: Artificial Sequence
<220> FEATURE:
<223> OTHER INFORMATION: Small interfering RNA - mPTP1B1.6
<220> FEATURE:
<221> NAME/KEY: misc_feature
<222> LOCATION: 20, 21
<223> OTHER INFORMATION: n = A,T,C,G or U

<400> SEQUENCE: 524
agaagaaaag gagauggucn n                                                21

<210> SEQ ID NO 525
<211> LENGTH: 21
<212> TYPE: DNA
<213> ORGANISM: Artificial Sequence
<220> FEATURE:
<223> OTHER INFORMATION: Small interfering RNA - mPTP1B1.6
<220> FEATURE:
<221> NAME/KEY: misc_feature
<222> LOCATION: 1, 2
<223> OTHER INFORMATION: n = A,T,C,G or U

<400> SEQUENCE: 525
nngaccaucu ccuuuucuuc u                                                21

<210> SEQ ID NO 526
<211> LENGTH: 21
<212> TYPE: DNA
<213> ORGANISM: Artificial Sequence
<220> FEATURE:
<223> OTHER INFORMATION: Small interfering RNA - mPTP1B1.7

<400> SEQUENCE: 526
cgggaagugc aaggagcuct t                                                21

<210> SEQ ID NO 527
<211> LENGTH: 19
<212> TYPE: RNA
<213> ORGANISM: Artificial Sequence
<220> FEATURE:
<223> OTHER INFORMATION: Small interfering RNA - mPTP1B1.7

<400> SEQUENCE: 527
cgggaagugc aaggagcuc                                                   19

<210> SEQ ID NO 528
<211> LENGTH: 19
<212> TYPE: RNA
<213> ORGANISM: Artificial Sequence
<220> FEATURE:
<223> OTHER INFORMATION: Small interfering RNA - mPTP1B1.7

<400> SEQUENCE: 528
gagcuccuug cacuucccg                                                   19

<210> SEQ ID NO 529
<211> LENGTH: 21
<212> TYPE: DNA
<213> ORGANISM: Artificial Sequence
<220> FEATURE:

-continued

<223> OTHER INFORMATION: Small interfering RNA - mPTP1B1.7
<220> FEATURE:
<221> NAME/KEY: misc_feature
<222> LOCATION: 20, 21
<223> OTHER INFORMATION: n = A,T,C,G or U

<400> SEQUENCE: 529
cgggaagugc aaggagcucn n                                              21

<210> SEQ ID NO 530
<211> LENGTH: 21
<212> TYPE: DNA
<213> ORGANISM: Artificial Sequence
<220> FEATURE:
<223> OTHER INFORMATION: Small interfering RNA - mPTP1B1.7
<220> FEATURE:
<221> NAME/KEY: misc_feature
<222> LOCATION: 1, 2
<223> OTHER INFORMATION: n = A,T,C,G or U

<400> SEQUENCE: 530
nngagcuccu ugcacuuccc g                                              21

<210> SEQ ID NO 531
<211> LENGTH: 21
<212> TYPE: DNA
<213> ORGANISM: Artificial Sequence
<220> FEATURE:
<223> OTHER INFORMATION: Small interfering RNA - mPTP1B1.8

<400> SEQUENCE: 531
ggaucagugg aaggagcuct c                                              21

<210> SEQ ID NO 532
<211> LENGTH: 19
<212> TYPE: RNA
<213> ORGANISM: Artificial Sequence
<220> FEATURE:
<223> OTHER INFORMATION: Small interfering RNA - mPTP1B1.8

<400> SEQUENCE: 532
ggaucagugg aaggagcuc                                                 19

<210> SEQ ID NO 533
<211> LENGTH: 19
<212> TYPE: RNA
<213> ORGANISM: Artificial Sequence
<220> FEATURE:
<223> OTHER INFORMATION: Small interfering RNA - mPTP1B1.8

<400> SEQUENCE: 533
gagcuccuuc cacugaucc                                                 19

<210> SEQ ID NO 534
<211> LENGTH: 21
<212> TYPE: DNA
<213> ORGANISM: Artificial Sequence
<220> FEATURE:
<223> OTHER INFORMATION: Small interfering RNA - mPTP1B1.8
<220> FEATURE:
<221> NAME/KEY: misc_feature
<222> LOCATION: 20, 21
<223> OTHER INFORMATION: n = A,T,C,G or U

<400> SEQUENCE: 534
ggaucagugg aaggagcucn n                                              21

```
<210> SEQ ID NO 535
<211> LENGTH: 21
<212> TYPE: DNA
<213> ORGANISM: Artificial Sequence
<220> FEATURE:
<223> OTHER INFORMATION: Small interfering RNA - mPTP1B1.8
<220> FEATURE:
<221> NAME/KEY: misc_feature
<222> LOCATION: 1, 2
<223> OTHER INFORMATION: n = A,T,C,G or U

<400> SEQUENCE: 535
nngagcuccu uccacugauc c                                        21

<210> SEQ ID NO 536
<211> LENGTH: 21
<212> TYPE: DNA
<213> ORGANISM: Artificial Sequence
<220> FEATURE:
<223> OTHER INFORMATION: Small interfering RNA - rPTP1B1.1

<400> SEQUENCE: 536
agaagaaaaa gagaugguct t                                        21

<210> SEQ ID NO 537
<211> LENGTH: 19
<212> TYPE: RNA
<213> ORGANISM: Artificial Sequence
<220> FEATURE:
<223> OTHER INFORMATION: Small interfering RNA - rPTP1B1.1

<400> SEQUENCE: 537
agaagaaaaa gagaugguc                                           19

<210> SEQ ID NO 538
<211> LENGTH: 19
<212> TYPE: RNA
<213> ORGANISM: Artificial Sequence
<220> FEATURE:
<223> OTHER INFORMATION: Small interfering RNA - rPTP1B1.1

<400> SEQUENCE: 538
gaccaucucu uuucuucu                                            19

<210> SEQ ID NO 539
<211> LENGTH: 21
<212> TYPE: DNA
<213> ORGANISM: Artificial Sequence
<220> FEATURE:
<223> OTHER INFORMATION: Small interfering RNA - rPTP1B1.1
<220> FEATURE:
<221> NAME/KEY: misc_feature
<222> LOCATION: 20, 21
<223> OTHER INFORMATION: n = A,T,C,G or U

<400> SEQUENCE: 539
agaagaaaaa gagauggucn n                                        21

<210> SEQ ID NO 540
<211> LENGTH: 21
<212> TYPE: DNA
<213> ORGANISM: Artificial Sequence
<220> FEATURE:
<223> OTHER INFORMATION: Small interfering RNA - rPTP1B1.1
<220> FEATURE:
<221> NAME/KEY: misc_feature
<222> LOCATION: 1, 2
<223> OTHER INFORMATION: n = A,T,C,G or U
```

-continued

<400> SEQUENCE: 540
nngaccaucu cuuuuucuuc u                                              21

<210> SEQ ID NO 541
<211> LENGTH: 21
<212> TYPE: DNA
<213> ORGANISM: Artificial Sequence
<220> FEATURE:
<223> OTHER INFORMATION: Small interfering RNA - rPTP1B1.2

<400> SEQUENCE: 541
cggauggugg guggagguct t                                              21

<210> SEQ ID NO 542
<211> LENGTH: 19
<212> TYPE: RNA
<213> ORGANISM: Artificial Sequence
<220> FEATURE:
<223> OTHER INFORMATION: Small interfering RNA - rPTP1B1.2

<400> SEQUENCE: 542
cggauggugg guggagguc                                                 19

<210> SEQ ID NO 543
<211> LENGTH: 19
<212> TYPE: RNA
<213> ORGANISM: Artificial Sequence
<220> FEATURE:
<223> OTHER INFORMATION: Small interfering RNA - rPTP1B1.2

<400> SEQUENCE: 543
gaccuccacc caccauccg                                                 19

<210> SEQ ID NO 544
<211> LENGTH: 21
<212> TYPE: DNA
<213> ORGANISM: Artificial Sequence
<220> FEATURE:
<223> OTHER INFORMATION: Small interfering RNA - rPTP1B1.2
<220> FEATURE:
<221> NAME/KEY: misc_feature
<222> LOCATION: 20, 21
<223> OTHER INFORMATION: n = A,T,C,G or U

<400> SEQUENCE: 544
cggauggugg guggaggucn n                                              21

<210> SEQ ID NO 545
<211> LENGTH: 21
<212> TYPE: DNA
<213> ORGANISM: Artificial Sequence
<220> FEATURE:
<223> OTHER INFORMATION: Small interfering RNA - rPTP1B1.2
<220> FEATURE:
<221> NAME/KEY: misc_feature
<222> LOCATION: 1, 2
<223> OTHER INFORMATION: n = A,T,C,G or U

<400> SEQUENCE: 545
nngaccucca cccaccaucc g                                              21

<210> SEQ ID NO 546
<211> LENGTH: 21
<212> TYPE: DNA
<213> ORGANISM: Artificial Sequence
<220> FEATURE:
<223> OTHER INFORMATION: Small interfering RNA - rPTP1B1.3

-continued

```
<400> SEQUENCE: 546
uggcaagugc aaggagcuct t                                                   21

<210> SEQ ID NO 547
<211> LENGTH: 19
<212> TYPE: RNA
<213> ORGANISM: Artificial Sequence
<220> FEATURE:
<223> OTHER INFORMATION: Small interfering RNA - rPTP1B1.3

<400> SEQUENCE: 547
uggcaagugc aaggagcuc                                                      19

<210> SEQ ID NO 548
<211> LENGTH: 19
<212> TYPE: RNA
<213> ORGANISM: Artificial Sequence
<220> FEATURE:
<223> OTHER INFORMATION: Small interfering RNA - rPTP1B1.3

<400> SEQUENCE: 548
gagcuccuug cacuugcca                                                      19

<210> SEQ ID NO 549
<211> LENGTH: 21
<212> TYPE: DNA
<213> ORGANISM: Artificial Sequence
<220> FEATURE:
<223> OTHER INFORMATION: Small interfering RNA - rPTP1B1.3
<220> FEATURE:
<221> NAME/KEY: misc_feature
<222> LOCATION: 20, 21
<223> OTHER INFORMATION: n = A,T,C,G or U

<400> SEQUENCE: 549
uggcaagugc aaggagcucn n                                                   21

<210> SEQ ID NO 550
<211> LENGTH: 21
<212> TYPE: DNA
<213> ORGANISM: Artificial Sequence
<220> FEATURE:
<223> OTHER INFORMATION: Small interfering RNA - rPTP1B1.3
<220> FEATURE:
<221> NAME/KEY: misc_feature
<222> LOCATION: 1, 2
<223> OTHER INFORMATION: n = A,T,C,G or U

<400> SEQUENCE: 550
nngagcuccu ugcacuugcc a                                                   21

<210> SEQ ID NO 551
<211> LENGTH: 21
<212> TYPE: DNA
<213> ORGANISM: Artificial Sequence
<220> FEATURE:
<223> OTHER INFORMATION: Small interfering RNA - rPTP1B1.4

<400> SEQUENCE: 551
cuacaccacc uggccugact t                                                   21

<210> SEQ ID NO 552
<211> LENGTH: 19
<212> TYPE: RNA
<213> ORGANISM: Artificial Sequence
<220> FEATURE:
```

<223> OTHER INFORMATION: Small interfering RNA - rPTP1B1.4

<400> SEQUENCE: 552
cuacaccacc uggccugac                                                    19

<210> SEQ ID NO 553
<211> LENGTH: 19
<212> TYPE: RNA
<213> ORGANISM: Artificial Sequence
<220> FEATURE:
<223> OTHER INFORMATION: Small interfering RNA - rPTP1B1.4

<400> SEQUENCE: 553
gucaggccag gugguguag                                                    19

<210> SEQ ID NO 554
<211> LENGTH: 21
<212> TYPE: DNA
<213> ORGANISM: Artificial Sequence
<220> FEATURE:
<223> OTHER INFORMATION: Small interfering RNA - rPTP1B1.4
<220> FEATURE:
<221> NAME/KEY: misc_feature
<222> LOCATION: 20, 21
<223> OTHER INFORMATION: n = A,T,C,G or U

<400> SEQUENCE: 554
cuacaccacc uggccugacn n                                                 21

<210> SEQ ID NO 555
<211> LENGTH: 21
<212> TYPE: DNA
<213> ORGANISM: Artificial Sequence
<220> FEATURE:
<223> OTHER INFORMATION: Small interfering RNA - rPTP1B1.4
<220> FEATURE:
<221> NAME/KEY: misc_feature
<222> LOCATION: 1, 2
<223> OTHER INFORMATION: n = A,T,C,G or U

<400> SEQUENCE: 555
nngucaggcc agguggugua g                                                 21

<210> SEQ ID NO 556
<211> LENGTH: 21
<212> TYPE: DNA
<213> ORGANISM: Artificial Sequence
<220> FEATURE:
<223> OTHER INFORMATION: Small interfering RNA - hPTP1B1.1

<400> SEQUENCE: 556
cuauaccaca uggccugact t                                                 21

<210> SEQ ID NO 557
<211> LENGTH: 19
<212> TYPE: RNA
<213> ORGANISM: Artificial Sequence
<220> FEATURE:
<223> OTHER INFORMATION: Small interfering RNA - hPTP1B1.1

<400> SEQUENCE: 557
cuauaccaca uggccugac                                                    19

<210> SEQ ID NO 558
<211> LENGTH: 19
<212> TYPE: RNA
<213> ORGANISM: Artificial Sequence

```
<220> FEATURE:
<223> OTHER INFORMATION: Small interfering RNA - hPTP1B1.1

<400> SEQUENCE: 558
gucaggccau gugguauag                                                    19

<210> SEQ ID NO 559
<211> LENGTH: 21
<212> TYPE: DNA
<213> ORGANISM: Artificial Sequence
<220> FEATURE:
<223> OTHER INFORMATION: Small interfering RNA - hPTP1B1.1
<220> FEATURE:
<221> NAME/KEY: misc_feature
<222> LOCATION: 20, 21
<223> OTHER INFORMATION: n = A,T,C,G or U

<400> SEQUENCE: 559
cuauaccaca uggccugacn n                                                 21

<210> SEQ ID NO 560
<211> LENGTH: 21
<212> TYPE: DNA
<213> ORGANISM: Artificial Sequence
<220> FEATURE:
<223> OTHER INFORMATION: Small interfering RNA - hPTP1B1.1
<220> FEATURE:
<221> NAME/KEY: misc_feature
<222> LOCATION: 1, 2
<223> OTHER INFORMATION: n = A,T,C,G or U

<400> SEQUENCE: 560
nngucaggcc augugguaua g                                                 21

<210> SEQ ID NO 561
<211> LENGTH: 21
<212> TYPE: DNA
<213> ORGANISM: Artificial Sequence
<220> FEATURE:
<223> OTHER INFORMATION: Small interfering RNA - hPTP1B1.2

<400> SEQUENCE: 561
gcccaaagga guuacauuct t                                                 21

<210> SEQ ID NO 562
<211> LENGTH: 19
<212> TYPE: RNA
<213> ORGANISM: Artificial Sequence
<220> FEATURE:
<223> OTHER INFORMATION: Small interfering RNA - hPTP1B1.2

<400> SEQUENCE: 562
gcccaaagga guuacauuc                                                    19

<210> SEQ ID NO 563
<211> LENGTH: 19
<212> TYPE: RNA
<213> ORGANISM: Artificial Sequence
<220> FEATURE:
<223> OTHER INFORMATION: Small interfering RNA - hPTP1B1.2

<400> SEQUENCE: 563
gaauguaacu ccuuugggc                                                    19

<210> SEQ ID NO 564
<211> LENGTH: 21
<212> TYPE: DNA
```

```
<213> ORGANISM: Artificial Sequence
<220> FEATURE:
<223> OTHER INFORMATION: Small interfering RNA - hPTP1B1.2
<220> FEATURE:
<221> NAME/KEY: misc_feature
<222> LOCATION: 20, 21
<223> OTHER INFORMATION: n = A,T,C,G or U

<400> SEQUENCE: 564
gcccaaagga guuacauucn n                                              21

<210> SEQ ID NO 565
<211> LENGTH: 21
<212> TYPE: DNA
<213> ORGANISM: Artificial Sequence
<220> FEATURE:
<223> OTHER INFORMATION: Small interfering RNA - hPTP1B1.2
<220> FEATURE:
<221> NAME/KEY: misc_feature
<222> LOCATION: 1, 2
<223> OTHER INFORMATION: n = A,T,C,G or U

<400> SEQUENCE: 565
nngaauguaa cuccuuuggg c                                              21

<210> SEQ ID NO 566
<211> LENGTH: 21
<212> TYPE: DNA
<213> ORGANISM: Artificial Sequence
<220> FEATURE:
<223> OTHER INFORMATION: Small interfering RNA - hPTP1B1.3

<400> SEQUENCE: 566
ggaagaaaaa ggaagcccct t                                              21

<210> SEQ ID NO 567
<211> LENGTH: 19
<212> TYPE: RNA
<213> ORGANISM: Artificial Sequence
<220> FEATURE:
<223> OTHER INFORMATION: Small interfering RNA - hPTP1B1.3

<400> SEQUENCE: 567
ggaagaaaaa ggaagcccc                                                 19

<210> SEQ ID NO 568
<211> LENGTH: 19
<212> TYPE: RNA
<213> ORGANISM: Artificial Sequence
<220> FEATURE:
<223> OTHER INFORMATION: Small interfering RNA - hPTP1B1.3

<400> SEQUENCE: 568
ggggcuuccu uuucuucc                                                  19

<210> SEQ ID NO 569
<211> LENGTH: 21
<212> TYPE: DNA
<213> ORGANISM: Artificial Sequence
<220> FEATURE:
<223> OTHER INFORMATION: Small interfering RNA - hPTP1B1.3
<220> FEATURE:
<221> NAME/KEY: misc_feature
<222> LOCATION: 20, 21
<223> OTHER INFORMATION: n = A,T,C,G or U

<400> SEQUENCE: 569
ggaagaaaaa ggaagccccn n                                              21
```

<210> SEQ ID NO 570
<211> LENGTH: 21
<212> TYPE: DNA
<213> ORGANISM: Artificial Sequence
<220> FEATURE:
<223> OTHER INFORMATION: Small interfering RNA - hPTP1B1.3
<220> FEATURE:
<221> NAME/KEY: misc_feature
<222> LOCATION: 1, 2
<223> OTHER INFORMATION: n = A,T,C,G or U

<400> SEQUENCE: 570 nngggcuuc cuuuucuuc c                                         21

<210> SEQ ID NO 571
<211> LENGTH: 21
<212> TYPE: DNA
<213> ORGANISM: Artificial Sequence
<220> FEATURE:
<223> OTHER INFORMATION: Small interfering RNA - hPTP1B1.4

<400> SEQUENCE: 571
caaugggaaa ugcagggagt t                                       21

<210> SEQ ID NO 572
<211> LENGTH: 19
<212> TYPE: RNA
<213> ORGANISM: Artificial Sequence
<220> FEATURE:
<223> OTHER INFORMATION: Small interfering RNA - hPTP1B1.4

<400> SEQUENCE: 572
caaugggaaa ugcagggag                                          19

<210> SEQ ID NO 573
<211> LENGTH: 19
<212> TYPE: RNA
<213> ORGANISM: Artificial Sequence
<220> FEATURE:
<223> OTHER INFORMATION: Small interfering RNA - hPTP1B1.4

<400> SEQUENCE: 573
cucccugcau ucccauug                                           19

<210> SEQ ID NO 574
<211> LENGTH: 21
<212> TYPE: DNA
<213> ORGANISM: Artificial Sequence
<220> FEATURE:
<223> OTHER INFORMATION: Small interfering RNA - hPTP1B1.4
<220> FEATURE:
<221> NAME/KEY: misc_feature
<222> LOCATION: 20, 21
<223> OTHER INFORMATION: n = A,T,C,G or U

<400> SEQUENCE: 574
caaugggaaa ugcagggagn n                                       21

<210> SEQ ID NO 575
<211> LENGTH: 21
<212> TYPE: DNA
<213> ORGANISM: Artificial Sequence
<220> FEATURE:
<223> OTHER INFORMATION: Small interfering RNA - hPTP1B1.4
<220> FEATURE:
<221> NAME/KEY: misc_feature
<222> LOCATION: 1, 2

<223> OTHER INFORMATION: n = A,T,C,G or U

<400> SEQUENCE: 575
nncucccugc auuucccauu g        21

<210> SEQ ID NO 576
<211> LENGTH: 21
<212> TYPE: DNA
<213> ORGANISM: Artificial Sequence
<220> FEATURE:
<223> OTHER INFORMATION: Small interfering RNA - hPTP1B1.5

<400> SEQUENCE: 576
ggaucagugg aaggagcuut c        21

<210> SEQ ID NO 577
<211> LENGTH: 19
<212> TYPE: RNA
<213> ORGANISM: Artificial Sequence
<220> FEATURE:
<223> OTHER INFORMATION: Small interfering RNA - hPTP1B1.5

<400> SEQUENCE: 577
ggaucagugg aaggagcuu        19

<210> SEQ ID NO 578
<211> LENGTH: 19
<212> TYPE: RNA
<213> ORGANISM: Artificial Sequence
<220> FEATURE:
<223> OTHER INFORMATION: Small interfering RNA - hPTP1B1.5

<400> SEQUENCE: 578
aagcuccuuc cacugaucc        19

<210> SEQ ID NO 579
<211> LENGTH: 21
<212> TYPE: DNA
<213> ORGANISM: Artificial Sequence
<220> FEATURE:
<223> OTHER INFORMATION: Small interfering RNA - hPTP1B1.5
<220> FEATURE:
<221> NAME/KEY: misc_feature
<222> LOCATION: 20, 21
<223> OTHER INFORMATION: n = A,T,C,G or U

<400> SEQUENCE: 579
ggaucagugg aaggagcuun n        21

<210> SEQ ID NO 580
<211> LENGTH: 21
<212> TYPE: DNA
<213> ORGANISM: Artificial Sequence
<220> FEATURE:
<223> OTHER INFORMATION: Small interfering RNA - hPTP1B1.5
<220> FEATURE:
<221> NAME/KEY: misc_feature
<222> LOCATION: 1, 2
<223> OTHER INFORMATION: n = A,T,C,G or U

<400> SEQUENCE: 580
nnaagcuccu uccacugauc c        21

<210> SEQ ID NO 581
<211> LENGTH: 21
<212> TYPE: DNA
<213> ORGANISM: Artificial Sequence

```
<220> FEATURE:
<223> OTHER INFORMATION: Small interfering RNA - mTCPTP1.1

<400> SEQUENCE: 581
guugucaugc uaaaccgaac t                                              21

<210> SEQ ID NO 582
<211> LENGTH: 19
<212> TYPE: RNA
<213> ORGANISM: Artificial Sequence
<220> FEATURE:
<223> OTHER INFORMATION: Small interfering RNA - mTCPTP1.1

<400> SEQUENCE: 582
guugucaugc uaaaccgaa                                                 19

<210> SEQ ID NO 583
<211> LENGTH: 19
<212> TYPE: RNA
<213> ORGANISM: Artificial Sequence
<220> FEATURE:
<223> OTHER INFORMATION: Small interfering RNA - mTCPTP1.1

<400> SEQUENCE: 583
uucgguuuag caugacaac                                                 19

<210> SEQ ID NO 584
<211> LENGTH: 21
<212> TYPE: RNA
<213> ORGANISM: Artificial Sequence
<220> FEATURE:
<223> OTHER INFORMATION: Small interfering RNA - mTCPTP1.1
<220> FEATURE:
<221> NAME/KEY: misc_feature
<222> LOCATION: 20, 21
<223> OTHER INFORMATION: n = A,T,C,G or U

<400> SEQUENCE: 584
guugucaugc uaaaccgaan n                                              21

<210> SEQ ID NO 585
<211> LENGTH: 21
<212> TYPE: DNA
<213> ORGANISM: Artificial Sequence
<220> FEATURE:
<223> OTHER INFORMATION: Small interfering RNA - mTCPTP1.1
<220> FEATURE:
<221> NAME/KEY: misc_feature
<222> LOCATION: 1, 2
<223> OTHER INFORMATION: n = A,T,C,G or U

<400> SEQUENCE: 585
nnuucgguuu agcaugacaa c                                              21

<210> SEQ ID NO 586
<211> LENGTH: 21
<212> TYPE: RNA
<213> ORGANISM: Artificial Sequence
<220> FEATURE:
<223> OTHER INFORMATION: Small interfering RNA - mTCPTP1.2

<400> SEQUENCE: 586
cagaacagag ugaugguuga g                                              21

<210> SEQ ID NO 587
<211> LENGTH: 19
<212> TYPE: RNA
```

<213> ORGANISM: Artificial Sequence
<220> FEATURE:
<223> OTHER INFORMATION: Small interfering RNA - mTCPTP1.2

<400> SEQUENCE: 587
cagaacagag ugaugguug                                                    19

<210> SEQ ID NO 588
<211> LENGTH: 19
<212> TYPE: RNA
<213> ORGANISM: Artificial Sequence
<220> FEATURE:
<223> OTHER INFORMATION: Small interfering RNA - mTCPTP1.2

<400> SEQUENCE: 588
caaccaucac ucuguucug                                                    19

<210> SEQ ID NO 589
<211> LENGTH: 21
<212> TYPE: DNA
<213> ORGANISM: Artificial Sequence
<220> FEATURE:
<223> OTHER INFORMATION: Small interfering RNA - mTCPTP1.2
<220> FEATURE:
<221> NAME/KEY: misc_feature
<222> LOCATION: 20, 21
<223> OTHER INFORMATION: n = A,T,C,G or U

<400> SEQUENCE: 589
cagaacagag ugaugguugn n                                                 21

<210> SEQ ID NO 590
<211> LENGTH: 21
<212> TYPE: DNA
<213> ORGANISM: Artificial Sequence
<220> FEATURE:
<223> OTHER INFORMATION: Small interfering RNA - mTCPTP1.2
<220> FEATURE:
<221> NAME/KEY: misc_feature
<222> LOCATION: 1, 2
<223> OTHER INFORMATION: n = A,T,C,G or U

<400> SEQUENCE: 590
nncaaccauc acucuguucu g                                                 21

<210> SEQ ID NO 591
<211> LENGTH: 36
<212> TYPE: DNA
<213> ORGANISM: Artificial Sequence
<220> FEATURE:
<223> OTHER INFORMATION: Oligonucleotide primer (TC45 5' BamHI)

<400> SEQUENCE: 591 gggggatcc atgcccacca ccatcgagcg ggagtt                                  36

<210> SEQ ID NO 592
<211> LENGTH: 49
<212> TYPE: DNA
<213> ORGANISM: Artificial Sequence
<220> FEATURE:
<223> OTHER INFORMATION: Oligonucleotide primer (TC45 3' EcoRI)

<400> SEQUENCE: 592
ggggaattct taggtgtctg tcaatcttgg ccttttttctt tttcgttca                  49

<210> SEQ ID NO 593
<211> LENGTH: 21

```
<212> TYPE: DNA
<213> ORGANISM: Artificial Sequence
<220> FEATURE:
<223> OTHER INFORMATION: Small interfering RNA - hTCPTP1.4

<400> SEQUENCE: 593
guugucaugc ugaaccgcat t                                              21

<210> SEQ ID NO 594
<211> LENGTH: 19
<212> TYPE: RNA
<213> ORGANISM: Artificial Sequence
<220> FEATURE:
<223> OTHER INFORMATION: Small interfering RNA - hTCPTP1.4

<400> SEQUENCE: 594
guugucaugc ugaaccgca                                                 19

<210> SEQ ID NO 595
<211> LENGTH: 19
<212> TYPE: RNA
<213> ORGANISM: Artificial Sequence
<220> FEATURE:
<223> OTHER INFORMATION: Small interfering RNA - hTCPTP1.4

<400> SEQUENCE: 595
ugcgguucag caugacaac                                                 19

<210> SEQ ID NO 596
<211> LENGTH: 21
<212> TYPE: DNA
<213> ORGANISM: Artificial Sequence
<220> FEATURE:
<223> OTHER INFORMATION: Small interfering RNA - hTCPTP1.4
<220> FEATURE:
<221> NAME/KEY: misc_feature
<222> LOCATION: 20, 21
<223> OTHER INFORMATION: n = A,T,C,G or U

<400> SEQUENCE: 596
guugucaugc ugaaccgcan n                                              21

<210> SEQ ID NO 597
<211> LENGTH: 21
<212> TYPE: DNA
<213> ORGANISM: Artificial Sequence
<220> FEATURE:
<223> OTHER INFORMATION: Small interfering RNA - hTCPTP1.4
<220> FEATURE:
<221> NAME/KEY: misc_feature
<222> LOCATION: 1, 2
<223> OTHER INFORMATION: n = A,T,C,G or U

<400> SEQUENCE: 597
nnugcgguuc agcaugacaa c                                              21

<210> SEQ ID NO 598
<211> LENGTH: 21
<212> TYPE: DNA
<213> ORGANISM: Artificial Sequence
<220> FEATURE:
<223> OTHER INFORMATION: Small interfering RNA - hTCPTP1.5

<400> SEQUENCE: 598
gcccauauga ucacagucgt g                                              21

<210> SEQ ID NO 599
```

-continued

```
<211> LENGTH: 19
<212> TYPE: RNA
<213> ORGANISM: Artificial Sequence
<220> FEATURE:
<223> OTHER INFORMATION: Small interfering RNA - hTCPTP1.5

<400> SEQUENCE: 599
gcccauauga ucacagucg                                              19

<210> SEQ ID NO 600
<211> LENGTH: 19
<212> TYPE: RNA
<213> ORGANISM: Artificial Sequence
<220> FEATURE:
<223> OTHER INFORMATION: Small interfering RNA - hTCPTP1.5

<400> SEQUENCE: 600
cgacugugau cauaugggc                                              19

<210> SEQ ID NO 601
<211> LENGTH: 21
<212> TYPE: DNA
<213> ORGANISM: Artificial Sequence
<220> FEATURE:
<223> OTHER INFORMATION: Small interfering RNA - hTCPTP1.5
<220> FEATURE:
<221> NAME/KEY: misc_feature
<222> LOCATION: 20, 21
<223> OTHER INFORMATION: n = A,T,C,G or U

<400> SEQUENCE: 601
gcccauauga ucacagucgn n                                           21

<210> SEQ ID NO 602
<211> LENGTH: 21
<212> TYPE: DNA
<213> ORGANISM: Artificial Sequence
<220> FEATURE:
<223> OTHER INFORMATION: Small interfering RNA - hTCPTP1.5
<220> FEATURE:
<221> NAME/KEY: misc_feature
<222> LOCATION: 1, 2
<223> OTHER INFORMATION: n = A,T,C,G or U

<400> SEQUENCE: 602
nncgacugug aucauauggg c                                           21

<210> SEQ ID NO 603
<211> LENGTH: 21
<212> TYPE: RNA
<213> ORGANISM: Artificial Sequence
<220> FEATURE:
<223> OTHER INFORMATION: Small interfering RNA - hTCPTP1.6

<400> SEQUENCE: 603
ucgguuaaau gugcacagua c                                           21

<210> SEQ ID NO 604
<211> LENGTH: 19
<212> TYPE: RNA
<213> ORGANISM: Artificial Sequence
<220> FEATURE:
<223> OTHER INFORMATION: Small interfering RNA - hTCPTP1.6

<400> SEQUENCE: 604
ucgguuaaau gugcacagu                                              19
```

```
<210> SEQ ID NO 605
<211> LENGTH: 19
<212> TYPE: RNA
<213> ORGANISM: Artificial Sequence
<220> FEATURE:
<223> OTHER INFORMATION: Small interfering RNA - hTCPTP1.6

<400> SEQUENCE: 605
acugugcaca uuuaaccga                                                    19

<210> SEQ ID NO 606
<211> LENGTH: 21
<212> TYPE: DNA
<213> ORGANISM: Artificial Sequence
<220> FEATURE:
<223> OTHER INFORMATION: Small interfering RNA - hTCPTP1.6
<220> FEATURE:
<221> NAME/KEY: misc_feature
<222> LOCATION: 20, 21
<223> OTHER INFORMATION: n = A,T,C,G or U

<400> SEQUENCE: 606
ucgguuaaau gugcacagun n                                                 21

<210> SEQ ID NO 607
<211> LENGTH: 21
<212> TYPE: DNA
<213> ORGANISM: Artificial Sequence
<220> FEATURE:
<223> OTHER INFORMATION: Small interfering RNA - hTCPTP1.6
<220> FEATURE:
<221> NAME/KEY: misc_feature
<222> LOCATION: 1, 2
<223> OTHER INFORMATION: n = A,T,C,G or U

<400> SEQUENCE: 607
nnacugugca cauuuaaccg a                                                 21

<210> SEQ ID NO 608
<211> LENGTH: 21
<212> TYPE: RNA
<213> ORGANISM: Artificial Sequence
<220> FEATURE:
<223> OTHER INFORMATION: Small interfering RNA - hTCPTP1.7

<400> SEQUENCE: 608
ugacuauccu cauagagugg g                                                 21

<210> SEQ ID NO 609
<211> LENGTH: 19
<212> TYPE: RNA
<213> ORGANISM: Artificial Sequence
<220> FEATURE:
<223> OTHER INFORMATION: Small interfering RNA - hTCPTP1.7

<400> SEQUENCE: 609
ugacuauccu cauagagug                                                    19

<210> SEQ ID NO 610
<211> LENGTH: 19
<212> TYPE: RNA
<213> ORGANISM: Artificial Sequence
<220> FEATURE:
<223> OTHER INFORMATION: Small interfering RNA - hTCPTP1.7

<400> SEQUENCE: 610
cacucuauga ggauaguca                                                    19
```

```
<210> SEQ ID NO 611
<211> LENGTH: 21
<212> TYPE: DNA
<213> ORGANISM: Artificial Sequence
<220> FEATURE:
<223> OTHER INFORMATION: Small interfering RNA - hTCPTP1.7
<220> FEATURE:
<221> NAME/KEY: misc_feature
<222> LOCATION: 20, 21
<223> OTHER INFORMATION: n = A,T,C,G or U

<400> SEQUENCE: 611
ugacuauccu cauagagugn n                                              21

<210> SEQ ID NO 612
<211> LENGTH: 21
<212> TYPE: DNA
<213> ORGANISM: Artificial Sequence
<220> FEATURE:
<223> OTHER INFORMATION: Small interfering RNA - hTCPTP1.7
<220> FEATURE:
<221> NAME/KEY: misc_feature
<222> LOCATION: 1, 2
<223> OTHER INFORMATION: n = A,T,C,G or U

<400> SEQUENCE: 612
nncacucuau gaggauaguc a                                              21

<210> SEQ ID NO 613
<211> LENGTH: 21
<212> TYPE: DNA
<213> ORGANISM: Artificial Sequence
<220> FEATURE:
<223> OTHER INFORMATION: Small interfering RNA - hTCPTP1.1

<400> SEQUENCE: 613
agugagagaa ucuggcucct t                                              21

<210> SEQ ID NO 614
<211> LENGTH: 19
<212> TYPE: RNA
<213> ORGANISM: Artificial Sequence
<220> FEATURE:
<223> OTHER INFORMATION: Small interfering RNA - hTCPTP1.1

<400> SEQUENCE: 614
agugagagaa ucuggcucc                                                 19

<210> SEQ ID NO 615
<211> LENGTH: 19
<212> TYPE: RNA
<213> ORGANISM: Artificial Sequence
<220> FEATURE:
<223> OTHER INFORMATION: Small interfering RNA - hTCPTP1.1

<400> SEQUENCE: 615
ggagccagau ucucucacu                                                 19

<210> SEQ ID NO 616
<211> LENGTH: 21
<212> TYPE: DNA
<213> ORGANISM: Artificial Sequence
<220> FEATURE:
<223> OTHER INFORMATION: Small interfering RNA - hTCPTP1.1
<220> FEATURE:
<221> NAME/KEY: misc_feature
<222> LOCATION: 20, 21
<223> OTHER INFORMATION: n = A,T,C,G or U
```

```
<400> SEQUENCE: 616
agugagagaa ucuggcuccn n                                              21

<210> SEQ ID NO 617
<211> LENGTH: 21
<212> TYPE: DNA
<213> ORGANISM: Artificial Sequence
<220> FEATURE:
<223> OTHER INFORMATION: Small interfering RNA - hTCPTP1.1
<220> FEATURE:
<221> NAME/KEY: misc_feature
<222> LOCATION: 1, 2
<223> OTHER INFORMATION: n = A,T,C,G or U

<400> SEQUENCE: 617
nnggagccag auucucucac u                                              21

<210> SEQ ID NO 618
<211> LENGTH: 21
<212> TYPE: DNA
<213> ORGANISM: Artificial Sequence
<220> FEATURE:
<223> OTHER INFORMATION: Small interfering RNA - hTCPTP1.2

<400> SEQUENCE: 618
ggaagacuua ucuccugcct t                                              21

<210> SEQ ID NO 619
<211> LENGTH: 19
<212> TYPE: RNA
<213> ORGANISM: Artificial Sequence
<220> FEATURE:
<223> OTHER INFORMATION: Small interfering RNA - hTCPTP1.2

<400> SEQUENCE: 619
ggaagacuua ucuccugcc                                                 19

<210> SEQ ID NO 620
<211> LENGTH: 19
<212> TYPE: RNA
<213> ORGANISM: Artificial Sequence
<220> FEATURE:
<223> OTHER INFORMATION: Small interfering RNA - hTCPTP1.2

<400> SEQUENCE: 620
ggcaggagau aagucuucc                                                 19

<210> SEQ ID NO 621
<211> LENGTH: 21
<212> TYPE: DNA
<213> ORGANISM: Artificial Sequence
<220> FEATURE:
<223> OTHER INFORMATION: Small interfering RNA - hTCPTP1.2
<220> FEATURE:
<221> NAME/KEY: misc_feature
<222> LOCATION: 20, 21
<223> OTHER INFORMATION: n = A,T,C,G or U

<400> SEQUENCE: 621
ggaagacuua ucuccugccn n                                              21

<210> SEQ ID NO 622
<211> LENGTH: 21
<212> TYPE: DNA
<213> ORGANISM: Artificial Sequence
<220> FEATURE:
```

```
<223> OTHER INFORMATION: Small interfering RNA - hTCPTP1.2
<220> FEATURE:
<221> NAME/KEY: misc_feature
<222> LOCATION: 1, 2
<223> OTHER INFORMATION: n = A,T,C,G or U

<400> SEQUENCE: 622
nnggcaggag auaagucuuc c                                              21

<210> SEQ ID NO 623
<211> LENGTH: 21
<212> TYPE: DNA
<213> ORGANISM: Artificial Sequence
<220> FEATURE:
<223> OTHER INFORMATION: Small interfering RNA - hTCPTP1.3

<400> SEQUENCE: 623
ggugaccgau guacaggact t                                              21

<210> SEQ ID NO 624
<211> LENGTH: 19
<212> TYPE: RNA
<213> ORGANISM: Artificial Sequence
<220> FEATURE:
<223> OTHER INFORMATION: Small interfering RNA - hTCPTP1.3

<400> SEQUENCE: 624
ggugaccgau guacaggac                                                 19

<210> SEQ ID NO 625
<211> LENGTH: 19
<212> TYPE: RNA
<213> ORGANISM: Artificial Sequence
<220> FEATURE:
<223> OTHER INFORMATION: Small interfering RNA - hTCPTP1.3

<400> SEQUENCE: 625
guccuguaca ucggucacc                                                 19

<210> SEQ ID NO 626
<211> LENGTH: 21
<212> TYPE: DNA
<213> ORGANISM: Artificial Sequence
<220> FEATURE:
<223> OTHER INFORMATION: Small interfering RNA - hTCPTP1.3
<220> FEATURE:
<221> NAME/KEY: misc_feature
<222> LOCATION: 20, 21
<223> OTHER INFORMATION: n = A,T,C,G or U

<400> SEQUENCE: 626
ggugaccgau guacaggacn n                                              21

<210> SEQ ID NO 627
<211> LENGTH: 21
<212> TYPE: DNA
<213> ORGANISM: Artificial Sequence
<220> FEATURE:
<223> OTHER INFORMATION: Small interfering RNA - hTCPTP1.3
<220> FEATURE:
<221> NAME/KEY: misc_feature
<222> LOCATION: 1, 2
<223> OTHER INFORMATION: n = A,T,C,G or U

<400> SEQUENCE: 627
nnguccugua caucggucac c                                              21
```

<210> SEQ ID NO 628
<211> LENGTH: 50
<212> TYPE: DNA
<213> ORGANISM: Artificial Sequence
<220> FEATURE:
<223> OTHER INFORMATION: Hairpin vector - hPTP1B H1.2-HP4

<400> SEQUENCE: 628
tttgcccaaa ggagttacat tcgtaagaat gtaactcctt tgggcttttt         50

<210> SEQ ID NO 629
<211> LENGTH: 50
<212> TYPE: DNA
<213> ORGANISM: Artificial Sequence
<220> FEATURE:
<223> OTHER INFORMATION: Hairpin vector - hPTP1B H1.2-HP4

<400> SEQUENCE: 629
ctagaaaaag cccaaaggag ttacattctt acgaatgtaa ctcctttggg         50

<210> SEQ ID NO 630
<211> LENGTH: 50
<212> TYPE: RNA
<213> ORGANISM: Artificial Sequence
<220> FEATURE:
<223> OTHER INFORMATION: Hairpin vector - hPTP1B H1.2-HP4

<400> SEQUENCE: 630
uuugcccaaa ggaguuacau ucguaagaau guaacuccuu gggcuuuuu          50

<210> SEQ ID NO 631
<211> LENGTH: 50
<212> TYPE: RNA
<213> ORGANISM: Artificial Sequence
<220> FEATURE:
<223> OTHER INFORMATION: Hairpin vector - hPTP1B H1.2-HP4

<400> SEQUENCE: 631
cuagaaaaag cccaaaggag uuacauucuu acgaauguaa cuccuuuggg         50

<210> SEQ ID NO 632
<211> LENGTH: 55
<212> TYPE: DNA
<213> ORGANISM: Artificial Sequence
<220> FEATURE:
<223> OTHER INFORMATION: Hairpin vector - hPTP1B H1.2-HP9

<400> SEQUENCE: 632
tttgcccaaa ggagttacat tccctgggta agaatgtaac tcctttgggc ttttt   55

<210> SEQ ID NO 633
<211> LENGTH: 55
<212> TYPE: DNA
<213> ORGANISM: Artificial Sequence
<220> FEATURE:
<223> OTHER INFORMATION: Hairpin vector - hPTP1B H1.2-HP9

<400> SEQUENCE: 633
ctagaaaaag cccaaaggag ttacattctt acccagggaa tgtaactcct ttggg   55

<210> SEQ ID NO 634
<211> LENGTH: 55
<212> TYPE: RNA
<213> ORGANISM: Artificial Sequence
<220> FEATURE:
<223> OTHER INFORMATION: Hairpin vector - hPTP1B H1.2-HP9

<210> SEQ ID NO 634
<211> LENGTH: 55
<212> TYPE: RNA
<213> ORGANISM: Artificial Sequence
<220> FEATURE:
<223> OTHER INFORMATION: Hairpin vector - hPTP1B H1.2-HP9

<400> SEQUENCE: 634
uuugcccaaa ggaguuacau ucccgggua agaauguaac uccuuugggc uuuuu    55

<210> SEQ ID NO 635
<211> LENGTH: 55
<212> TYPE: RNA
<213> ORGANISM: Artificial Sequence
<220> FEATURE:
<223> OTHER INFORMATION: Hairpin vector - hPTP1B H1.2-HP9

<400> SEQUENCE: 635
cuagaaaaag cccaaaggag uuacauucuu acccagggaa uguaacuccu uggg     55

<210> SEQ ID NO 636
<211> LENGTH: 50
<212> TYPE: DNA
<213> ORGANISM: Artificial Sequence
<220> FEATURE:
<223> OTHER INFORMATION: Hairpin vector - mPTP1B M1.1-HP4

<400> SEQUENCE: 636
tttgaagccc agaggagcta taagaatata gctcctctgg gcttcttttt          50

<210> SEQ ID NO 637
<211> LENGTH: 50
<212> TYPE: DNA
<213> ORGANISM: Artificial Sequence
<220> FEATURE:
<223> OTHER INFORMATION: Hairpin vector - mPTP1B M1.1-HP4

<400> SEQUENCE: 637
ctagaaaaag aagcccagag gagctatatt cttatagctc ctctgggctt          50

<210> SEQ ID NO 638
<211> LENGTH: 50
<212> TYPE: RNA
<213> ORGANISM: Artificial Sequence
<220> FEATURE:
<223> OTHER INFORMATION: Hairpin vector - mPTP1B M1.1-HP4

<400> SEQUENCE: 638
uuugaagccc agaggagcua uaagaauaua gcuccucugg gcuucuuuuu          50

<210> SEQ ID NO 639
<211> LENGTH: 50
<212> TYPE: RNA
<213> ORGANISM: Artificial Sequence
<220> FEATURE:
<223> OTHER INFORMATION: Hairpin vector - mPTP1B M1.1-HP4

<400> SEQUENCE: 639
cuagaaaaag aagcccagag gagcuauauu cuuauagcuc cucgggcuu           50

<210> SEQ ID NO 640
<211> LENGTH: 55
<212> TYPE: DNA
<213> ORGANISM: Artificial Sequence
<220> FEATURE:
<223> OTHER INFORMATION: Hairpin vector - mPTP1B M1.1-HP9

<400> SEQUENCE: 640
tttgaagccc agaggagcta tagggtgaga atatagctcc tctgggcttc ttttt    55

<210> SEQ ID NO 641
<211> LENGTH: 55

```
<212> TYPE: DNA
<213> ORGANISM: Artificial Sequence
<220> FEATURE:
<223> OTHER INFORMATION: Hairpin vector - mPTP1B M1.1-HP9

<400> SEQUENCE: 641
ctagaaaaag aagcccagag gagctatatt ctcaccctat agctcctctg ggctt          55

<210> SEQ ID NO 642
<211> LENGTH: 55
<212> TYPE: RNA
<213> ORGANISM: Artificial Sequence
<220> FEATURE:
<223> OTHER INFORMATION: Hairpin vector - mPTP1B M1.1-HP9

<400> SEQUENCE: 642
uuugaagccc agaggagcua uagggugaga auauagcucc ucgggcuuc uuuuu          55

<210> SEQ ID NO 643
<211> LENGTH: 55
<212> TYPE: RNA
<213> ORGANISM: Artificial Sequence
<220> FEATURE:
<223> OTHER INFORMATION: Hairpin vector - mPTP1B M1.1-HP9

<400> SEQUENCE: 643
cuagaaaaag aagcccagag gagcuauauu cucacccuau agcuccucug ggcuu          55

<210> SEQ ID NO 644
<211> LENGTH: 21
<212> TYPE: DNA
<213> ORGANISM: Artificial Sequence
<220> FEATURE:
<223> OTHER INFORMATION: Oligonucleotide selected from scanning open
      reading frame of TC45 mRNA

<400> SEQUENCE: 644
aacagauaca gagauguaag c                                              21

<210> SEQ ID NO 645
<211> LENGTH: 21
<212> TYPE: DNA
<213> ORGANISM: Artificial Sequence
<220> FEATURE:
<223> OTHER INFORMATION: Oligonucleotide selected from scanning open
      reading frame of TC45 mRNA

<400> SEQUENCE: 645
aagcccauau gaucacaguc g                                              21

<210> SEQ ID NO 646
<211> LENGTH: 21
<212> TYPE: DNA
<213> ORGANISM: Artificial Sequence
<220> FEATURE:
<223> OTHER INFORMATION: Small interefering RNA - DSP3.4

<400> SEQUENCE: 646
ggugacacau auucugucut t                                              21

<210> SEQ ID NO 647
<211> LENGTH: 19
<212> TYPE: RNA
<213> ORGANISM: Artificial Sequence
<220> FEATURE:
<223> OTHER INFORMATION: Small interefering RNA - DSP3.4
```

-continued

<400> SEQUENCE: 647
ggugacacau auucugucu                                              19

<210> SEQ ID NO 648
<211> LENGTH: 19
<212> TYPE: RNA
<213> ORGANISM: Artificial Sequence
<220> FEATURE:
<223> OTHER INFORMATION: Small interefering RNA - DSP3.4

<400> SEQUENCE: 648
agacagaaua ugugucacc                                              19

<210> SEQ ID NO 649
<211> LENGTH: 21
<212> TYPE: DNA
<213> ORGANISM: Artificial Sequence
<220> FEATURE:
<223> OTHER INFORMATION: Small interefering RNA - DSP3.4
<220> FEATURE:
<221> NAME/KEY: misc_feature
<222> LOCATION: 20, 21
<223> OTHER INFORMATION: n = A,T,C,G or U

<400> SEQUENCE: 649
ggugacacau auucugucun n                                           21

<210> SEQ ID NO 650
<211> LENGTH: 21
<212> TYPE: DNA
<213> ORGANISM: Artificial Sequence
<220> FEATURE:
<223> OTHER INFORMATION: Small interefering RNA - DSP3.4
<220> FEATURE:
<221> NAME/KEY: misc_feature
<222> LOCATION: 1, 2
<223> OTHER INFORMATION: n = A,T,C,G or U

<400> SEQUENCE: 650
nnagacagaa uaugugucac c                                           21

<210> SEQ ID NO 651
<211> LENGTH: 21
<212> TYPE: DNA
<213> ORGANISM: Artificial Sequence
<220> FEATURE:
<223> OTHER INFORMATION: Small interefering RNA - DHFR.1

<400> SEQUENCE: 651
gaccugguuc uccauuccut t                                           21

<210> SEQ ID NO 652
<211> LENGTH: 19
<212> TYPE: RNA
<213> ORGANISM: Artificial Sequence
<220> FEATURE:
<223> OTHER INFORMATION: Small interefering RNA - DHFR.1

<400> SEQUENCE: 652
gaccugguuc uccauuccu                                              19

<210> SEQ ID NO 653
<211> LENGTH: 19
<212> TYPE: RNA
<213> ORGANISM: Artificial Sequence
<220> FEATURE:
<223> OTHER INFORMATION: Small interefering RNA - DHFR.1

<400> SEQUENCE: 653
aggaauggag aaccagguc                                                19

<210> SEQ ID NO 654
<211> LENGTH: 21
<212> TYPE: DNA
<213> ORGANISM: Artificial Sequence
<220> FEATURE:
<223> OTHER INFORMATION: Small interefering RNA - DHFR.1
<220> FEATURE:
<221> NAME/KEY: misc_feature
<222> LOCATION: 20, 21
<223> OTHER INFORMATION: n = A,T,C,G or U

<400> SEQUENCE: 654
gaccugguuc uccauuccun n                                             21

<210> SEQ ID NO 655
<211> LENGTH: 21
<212> TYPE: DNA
<213> ORGANISM: Artificial Sequence
<220> FEATURE:
<223> OTHER INFORMATION: Small interefering RNA - DHFR.1
<220> FEATURE:
<221> NAME/KEY: misc_feature
<222> LOCATION: 1, 2
<223> OTHER INFORMATION: n = A,T,C,G or U

<400> SEQUENCE: 655
nnaggaaugg agaaccaggu c                                             21

<210> SEQ ID NO 656
<211> LENGTH: 21
<212> TYPE: DNA
<213> ORGANISM: Artificial Sequence
<220> FEATURE:
<223> OTHER INFORMATION: Small interefering RNA - DHFR.3

<400> SEQUENCE: 656
gcaguguauu ugcuagguct t                                             21

<210> SEQ ID NO 657
<211> LENGTH: 19
<212> TYPE: RNA
<213> ORGANISM: Artificial Sequence
<220> FEATURE:
<223> OTHER INFORMATION: Small interefering RNA - DHFR.3

<400> SEQUENCE: 657
gcaguguauu ugcuagguc                                                19

<210> SEQ ID NO 658
<211> LENGTH: 19
<212> TYPE: RNA
<213> ORGANISM: Artificial Sequence
<220> FEATURE:
<223> OTHER INFORMATION: Small interefering RNA - DHFR.3

<400> SEQUENCE: 658
gaccuagcaa auacacugc                                                19

<210> SEQ ID NO 659
<211> LENGTH: 21
<212> TYPE: DNA
<213> ORGANISM: Artificial Sequence
<220> FEATURE:

```
<223> OTHER INFORMATION: Small interefering RNA - DHFR.3
<220> FEATURE:
<221> NAME/KEY: misc_feature
<222> LOCATION: 20, 21
<223> OTHER INFORMATION: n = A,T,C,G or U

<400> SEQUENCE: 659
gcaguguauu ugcuaggucn n                                              21

<210> SEQ ID NO 660
<211> LENGTH: 21
<212> TYPE: DNA
<213> ORGANISM: Artificial Sequence
<220> FEATURE:
<223> OTHER INFORMATION: Small interefering RNA - DHFR.3
<220> FEATURE:
<221> NAME/KEY: misc_feature
<222> LOCATION: 1, 2
<223> OTHER INFORMATION: n = A,T,C,G or U

<400> SEQUENCE: 660
nngaccuagc aaauacacug c                                              21

<210> SEQ ID NO 661
<211> LENGTH: 21
<212> TYPE: DNA
<213> ORGANISM: Artificial Sequence
<220> FEATURE:
<223> OTHER INFORMATION: Small interefering RNA - DHFR.4

<400> SEQUENCE: 661
gucagcgagc agguucucat t                                              21

<210> SEQ ID NO 662
<211> LENGTH: 19
<212> TYPE: RNA
<213> ORGANISM: Artificial Sequence
<220> FEATURE:
<223> OTHER INFORMATION: Small interefering RNA - DHFR.4

<400> SEQUENCE: 662
gucagcgagc agguucuca                                                 19

<210> SEQ ID NO 663
<211> LENGTH: 19
<212> TYPE: RNA
<213> ORGANISM: Artificial Sequence
<220> FEATURE:
<223> OTHER INFORMATION: Small interefering RNA - DHFR.4

<400> SEQUENCE: 663
ugagaaccug cucgcugac                                                 19

<210> SEQ ID NO 664
<211> LENGTH: 21
<212> TYPE: DNA
<213> ORGANISM: Artificial Sequence
<220> FEATURE:
<223> OTHER INFORMATION: Small interefering RNA - DHFR.4
<220> FEATURE:
<221> NAME/KEY: misc_feature
<222> LOCATION: 20, 21
<223> OTHER INFORMATION: n = A,T,C,G or U

<400> SEQUENCE: 664
gucagcgagc agguucucan n                                              21
```

```
<210> SEQ ID NO 665
<211> LENGTH: 21
<212> TYPE: DNA
<213> ORGANISM: Artificial Sequence
<220> FEATURE:
<223> OTHER INFORMATION: Small interefering RNA - DHFR.4
<220> FEATURE:
<221> NAME/KEY: misc_feature
<222> LOCATION: 1, 2
<223> OTHER INFORMATION: n = A,T,C,G or U

<400> SEQUENCE: 665
nnugagaacc ugcucgcuga c                                              21

<210> SEQ ID NO 666
<211> LENGTH: 21
<212> TYPE: DNA
<213> ORGANISM: Artificial Sequence
<220> FEATURE:
<223> OTHER INFORMATION: Small interefering RNA - TYMS.1

<400> SEQUENCE: 666
ccaaacgugu guucuggaat t                                              21

<210> SEQ ID NO 667
<211> LENGTH: 19
<212> TYPE: RNA
<213> ORGANISM: Artificial Sequence
<220> FEATURE:
<223> OTHER INFORMATION: Small interefering RNA - TYMS.1

<400> SEQUENCE: 667
ccaaacgugu guucuggaa                                                 19

<210> SEQ ID NO 668
<211> LENGTH: 19
<212> TYPE: RNA
<213> ORGANISM: Artificial Sequence
<220> FEATURE:
<223> OTHER INFORMATION: Small interefering RNA - TYMS.1

<400> SEQUENCE: 668
uuccagaaca cacguuugg                                                 19

<210> SEQ ID NO 669
<211> LENGTH: 21
<212> TYPE: DNA
<213> ORGANISM: Artificial Sequence
<220> FEATURE:
<223> OTHER INFORMATION: Small interefering RNA - TYMS.1
<220> FEATURE:
<221> NAME/KEY: misc_feature
<222> LOCATION: 20, 21
<223> OTHER INFORMATION: n = A,T,C,G or U

<400> SEQUENCE: 669
ccaaacgugu guucuggaan n                                              21

<210> SEQ ID NO 670
<211> LENGTH: 21
<212> TYPE: DNA
<213> ORGANISM: Artificial Sequence
<220> FEATURE:
<223> OTHER INFORMATION: Small interefering RNA - TYMS.1
<220> FEATURE:
<221> NAME/KEY: misc_feature
<222> LOCATION: 1, 2
<223> OTHER INFORMATION: n = A,T,C,G or U
```

```
<400> SEQUENCE: 670
nnuuccagaa cacacguuug g                                               21

<210> SEQ ID NO 671
<211> LENGTH: 21
<212> TYPE: DNA
<213> ORGANISM: Artificial Sequence
<220> FEATURE:
<223> OTHER INFORMATION: Small interefering RNA - TYMS.2

<400> SEQUENCE: 671
ccaacccuga cgacagaagt t                                               21

<210> SEQ ID NO 672
<211> LENGTH: 19
<212> TYPE: RNA
<213> ORGANISM: Artificial Sequence
<220> FEATURE:
<223> OTHER INFORMATION: Small interefering RNA - TYMS.2

<400> SEQUENCE: 672
ccaacccuga cgacagaag                                                  19

<210> SEQ ID NO 673
<211> LENGTH: 19
<212> TYPE: RNA
<213> ORGANISM: Artificial Sequence
<220> FEATURE:
<223> OTHER INFORMATION: Small interefering RNA - TYMS.2

<400> SEQUENCE: 673
cuucugucgu caggguugg                                                  19

<210> SEQ ID NO 674
<211> LENGTH: 21
<212> TYPE: DNA
<213> ORGANISM: Artificial Sequence
<220> FEATURE:
<223> OTHER INFORMATION: Small interefering RNA - TYMS.2
<220> FEATURE:
<221> NAME/KEY: misc_feature
<222> LOCATION: 20, 21
<223> OTHER INFORMATION: n = A,T,C,G or U

<400> SEQUENCE: 674
ccaacccuga cgacagaagn n                                               21

<210> SEQ ID NO 675
<211> LENGTH: 21
<212> TYPE: DNA
<213> ORGANISM: Artificial Sequence
<220> FEATURE:
<223> OTHER INFORMATION: Small interefering RNA - TYMS.2
<220> FEATURE:
<221> NAME/KEY: misc_feature
<222> LOCATION: 1, 2
<223> OTHER INFORMATION: n = A,T,C,G or U

<400> SEQUENCE: 675
nncuucuguc gucaggguug g                                               21

<210> SEQ ID NO 676
<211> LENGTH: 21
<212> TYPE: DNA
<213> ORGANISM: Artificial Sequence
<220> FEATURE:
<223> OTHER INFORMATION: Small interefering RNA - TYMS.3
```

```
<400> SEQUENCE: 676
gccaggugac uuuauacact t                                               21

<210> SEQ ID NO 677
<211> LENGTH: 19
<212> TYPE: RNA
<213> ORGANISM: Artificial Sequence
<220> FEATURE:
<223> OTHER INFORMATION: Small interefering RNA - TYMS.3

<400> SEQUENCE: 677
gccaggugac uuuauacac                                                  19

<210> SEQ ID NO 678
<211> LENGTH: 19
<212> TYPE: RNA
<213> ORGANISM: Artificial Sequence
<220> FEATURE:
<223> OTHER INFORMATION: Small interefering RNA - TYMS.3

<400> SEQUENCE: 678
guguauaaag ucaccuggc                                                  19

<210> SEQ ID NO 679
<211> LENGTH: 21
<212> TYPE: DNA
<213> ORGANISM: Artificial Sequence
<220> FEATURE:
<223> OTHER INFORMATION: Small interefering RNA - TYMS.3
<220> FEATURE:
<221> NAME/KEY: misc_feature
<222> LOCATION: 20, 21
<223> OTHER INFORMATION: n = A,T,C,G or U

<400> SEQUENCE: 679
gccaggugac uuuauacacn n                                               21

<210> SEQ ID NO 680
<211> LENGTH: 21
<212> TYPE: DNA
<213> ORGANISM: Artificial Sequence
<220> FEATURE:
<223> OTHER INFORMATION: Small interefering RNA - TYMS.3
<220> FEATURE:
<221> NAME/KEY: misc_feature
<222> LOCATION: 1, 2
<223> OTHER INFORMATION: n = A,T,C,G or U

<400> SEQUENCE: 680
nnguguauaa agucaccugg c                                               21

<210> SEQ ID NO 681
<211> LENGTH: 21
<212> TYPE: DNA
<213> ORGANISM: Artificial Sequence
<220> FEATURE:
<223> OTHER INFORMATION: Small interefering RNA - TYMS.4

<400> SEQUENCE: 681
cccagaccuu ucccaaagct t                                               21

<210> SEQ ID NO 682
<211> LENGTH: 19
<212> TYPE: RNA
<213> ORGANISM: Artificial Sequence
<220> FEATURE:
```

<223> OTHER INFORMATION: Small interefering RNA - TYMS.4

<400> SEQUENCE: 682
cccagaccuu ucccaaagc                                                  19

<210> SEQ ID NO 683
<211> LENGTH: 19
<212> TYPE: RNA
<213> ORGANISM: Artificial Sequence
<220> FEATURE:
<223> OTHER INFORMATION: Small interefering RNA - TYMS.4

<400> SEQUENCE: 683 gcuugggaa aggucuggg                                                   19

<210> SEQ ID NO 684
<211> LENGTH: 21
<212> TYPE: DNA
<213> ORGANISM: Artificial Sequence
<220> FEATURE:
<223> OTHER INFORMATION: Small interefering RNA - TYMS.4
<220> FEATURE:
<221> NAME/KEY: misc_feature
<222> LOCATION: 20, 21
<223> OTHER INFORMATION: n = A,T,C,G or U

<400> SEQUENCE: 684
cccagaccuu ucccaaagcn n                                               21

<210> SEQ ID NO 685
<211> LENGTH: 21
<212> TYPE: DNA
<213> ORGANISM: Artificial Sequence
<220> FEATURE:
<223> OTHER INFORMATION: Small interefering RNA - TYMS.4
<220> FEATURE:
<221> NAME/KEY: misc_feature
<222> LOCATION: 1, 2
<223> OTHER INFORMATION: n = A,T,C,G or U

<400> SEQUENCE: 685
nngcuuuggg aaaggucugg g                                               21

<210> SEQ ID NO 686
<211> LENGTH: 21
<212> TYPE: DNA
<213> ORGANISM: Artificial Sequence
<220> FEATURE:
<223> OTHER INFORMATION: Small interefering RNA - TOP1.1

<400> SEQUENCE: 686
gauagagccu ccuggacuut t                                               21

<210> SEQ ID NO 687
<211> LENGTH: 19
<212> TYPE: RNA
<213> ORGANISM: Artificial Sequence
<220> FEATURE:
<223> OTHER INFORMATION: Small interefering RNA - TOP1.1

<400> SEQUENCE: 687
gauagagccu ccuggacuu                                                  19

<210> SEQ ID NO 688
<211> LENGTH: 19
<212> TYPE: RNA
<213> ORGANISM: Artificial Sequence

```
<220> FEATURE:
<223> OTHER INFORMATION: Small interefering RNA - TOP1.1

<400> SEQUENCE: 688
aaguccagga ggcucuauc                                                    19

<210> SEQ ID NO 689
<211> LENGTH: 21
<212> TYPE: DNA
<213> ORGANISM: Artificial Sequence
<220> FEATURE:
<223> OTHER INFORMATION: Small interefering RNA - TOP1.1
<220> FEATURE:
<221> NAME/KEY: misc_feature
<222> LOCATION: 20, 21
<223> OTHER INFORMATION: n = A,T,C,G or U

<400> SEQUENCE: 689
gauagagccu ccuggacuun n                                                 21

<210> SEQ ID NO 690
<211> LENGTH: 21
<212> TYPE: DNA
<213> ORGANISM: Artificial Sequence
<220> FEATURE:
<223> OTHER INFORMATION: Small interefering RNA - TOP1.1
<220> FEATURE:
<221> NAME/KEY: misc_feature
<222> LOCATION: 1, 2
<223> OTHER INFORMATION: n = A,T,C,G or U

<400> SEQUENCE: 690
nnaaguccag gaggcucuau c                                                 21

<210> SEQ ID NO 691
<211> LENGTH: 21
<212> TYPE: DNA
<213> ORGANISM: Artificial Sequence
<220> FEATURE:
<223> OTHER INFORMATION: Small interefering RNA - TOP1.2

<400> SEQUENCE: 691
guccggcaug auaacaaggt t                                                 21

<210> SEQ ID NO 692
<211> LENGTH: 19
<212> TYPE: RNA
<213> ORGANISM: Artificial Sequence
<220> FEATURE:
<223> OTHER INFORMATION: Small interefering RNA - TOP1.2

<400> SEQUENCE: 692
guccggcaug auaacaagg                                                    19

<210> SEQ ID NO 693
<211> LENGTH: 19
<212> TYPE: RNA
<213> ORGANISM: Artificial Sequence
<220> FEATURE:
<223> OTHER INFORMATION: Small interefering RNA - TOP1.2

<400> SEQUENCE: 693
ccuuguuauc augccggac                                                    19

<210> SEQ ID NO 694
<211> LENGTH: 21
<212> TYPE: DNA
```

```
<213> ORGANISM: Artificial Sequence
<220> FEATURE:
<223> OTHER INFORMATION: Small interefering RNA - TOP1.2
<220> FEATURE:
<221> NAME/KEY: misc_feature
<222> LOCATION: 20, 21
<223> OTHER INFORMATION: n = A,T,C,G or U

<400> SEQUENCE: 694
guccggcaug auaacaaggn n                                              21

<210> SEQ ID NO 695
<211> LENGTH: 21
<212> TYPE: DNA
<213> ORGANISM: Artificial Sequence
<220> FEATURE:
<223> OTHER INFORMATION: Small interefering RNA - TOP1.2
<220> FEATURE:
<221> NAME/KEY: misc_feature
<222> LOCATION: 1, 2
<223> OTHER INFORMATION: n = A,T,C,G or U

<400> SEQUENCE: 695
nnccuuguua ucaugccgga c                                              21

<210> SEQ ID NO 696
<211> LENGTH: 21
<212> TYPE: DNA
<213> ORGANISM: Artificial Sequence
<220> FEATURE:
<223> OTHER INFORMATION: Small interefering RNA - TOP1.3

<400> SEQUENCE: 696
ggagaaacag cggacacugt t                                              21

<210> SEQ ID NO 697
<211> LENGTH: 19
<212> TYPE: RNA
<213> ORGANISM: Artificial Sequence
<220> FEATURE:
<223> OTHER INFORMATION: Small interefering RNA - TOP1.3

<400> SEQUENCE: 697
ggagaaacag cggacacug                                                 19

<210> SEQ ID NO 698
<211> LENGTH: 19
<212> TYPE: RNA
<213> ORGANISM: Artificial Sequence
<220> FEATURE:
<223> OTHER INFORMATION: Small interefering RNA - TOP1.3

<400> SEQUENCE: 698
caguguccgc uguuucucc                                                 19

<210> SEQ ID NO 699
<211> LENGTH: 21
<212> TYPE: DNA
<213> ORGANISM: Artificial Sequence
<220> FEATURE:
<223> OTHER INFORMATION: Small interefering RNA - TOP1.3
<220> FEATURE:
<221> NAME/KEY: misc_feature
<222> LOCATION: 20, 21
<223> OTHER INFORMATION: n = A,T,C,G or U

<400> SEQUENCE: 699
ggagaaacag cggacacugn n                                              21
```

<210> SEQ ID NO 700
<211> LENGTH: 21
<212> TYPE: DNA
<213> ORGANISM: Artificial Sequence
<220> FEATURE:
<223> OTHER INFORMATION: Small interefering RNA - TOP1.3
<220> FEATURE:
<221> NAME/KEY: misc_feature
<222> LOCATION: 1, 2
<223> OTHER INFORMATION: n = A,T,C,G or U

<400> SEQUENCE: 700
nncagugucc gcuguuucuc c                                              21

<210> SEQ ID NO 701
<211> LENGTH: 21
<212> TYPE: DNA
<213> ORGANISM: Artificial Sequence
<220> FEATURE:
<223> OTHER INFORMATION: Small interefering RNA - TOP1.4

<400> SEQUENCE: 701
gcagcccgag gaugaucuut t                                              21

<210> SEQ ID NO 702
<211> LENGTH: 19
<212> TYPE: RNA
<213> ORGANISM: Artificial Sequence
<220> FEATURE:
<223> OTHER INFORMATION: Small interefering RNA - TOP1.4

<400> SEQUENCE: 702
gcagcccgag gaugaucuu                                                 19

<210> SEQ ID NO 703
<211> LENGTH: 19
<212> TYPE: RNA
<213> ORGANISM: Artificial Sequence
<220> FEATURE:
<223> OTHER INFORMATION: Small interefering RNA - TOP1.4

<400> SEQUENCE: 703
aagaucaucc ucgggcugc                                                 19

<210> SEQ ID NO 704
<211> LENGTH: 21
<212> TYPE: DNA
<213> ORGANISM: Artificial Sequence
<220> FEATURE:
<223> OTHER INFORMATION: Small interefering RNA - TOP1.4
<220> FEATURE:
<221> NAME/KEY: misc_feature
<222> LOCATION: 20, 21
<223> OTHER INFORMATION: n = A,T,C,G or U

<400> SEQUENCE: 704
gcagcccgag gaugaucuun n                                              21

<210> SEQ ID NO 705
<211> LENGTH: 21
<212> TYPE: DNA
<213> ORGANISM: Artificial Sequence
<220> FEATURE:
<223> OTHER INFORMATION: Small interefering RNA - TOP1.4
<220> FEATURE:
<221> NAME/KEY: misc_feature
<222> LOCATION: 1, 2

<223> OTHER INFORMATION: n = A,T,C,G or U

<400> SEQUENCE: 705
nnaagaucau ccucgggcug c              21

<210> SEQ ID NO 706
<211> LENGTH: 21
<212> TYPE: DNA
<213> ORGANISM: Artificial Sequence
<220> FEATURE:
<223> OTHER INFORMATION: Small interefering RNA - IKK.1

<400> SEQUENCE: 706
gagucuccuc ugggaagct t              21

<210> SEQ ID NO 707
<211> LENGTH: 19
<212> TYPE: RNA
<213> ORGANISM: Artificial Sequence
<220> FEATURE:
<223> OTHER INFORMATION: Small interefering RNA - IKK.1

<400> SEQUENCE: 707
gagucuccuc ugggaagc              19

<210> SEQ ID NO 708
<211> LENGTH: 19
<212> TYPE: RNA
<213> ORGANISM: Artificial Sequence
<220> FEATURE:
<223> OTHER INFORMATION: Small interefering RNA - IKK.1

<400> SEQUENCE: 708
gcuuccccag aggagacuc              19

<210> SEQ ID NO 709
<211> LENGTH: 21
<212> TYPE: DNA
<213> ORGANISM: Artificial Sequence
<220> FEATURE:
<223> OTHER INFORMATION: Small interefering RNA - IKK.1
<220> FEATURE:
<221> NAME/KEY: misc_feature
<222> LOCATION: 20, 21
<223> OTHER INFORMATION: n = A,T,C,G or U

<400> SEQUENCE: 709
gagucuccuc ugggaagcn n              21

<210> SEQ ID NO 710
<211> LENGTH: 21
<212> TYPE: DNA
<213> ORGANISM: Artificial Sequence
<220> FEATURE:
<223> OTHER INFORMATION: Small interefering RNA - IKK.1
<220> FEATURE:
<221> NAME/KEY: misc_feature
<222> LOCATION: 1, 2
<223> OTHER INFORMATION: n = A,T,C,G or U

<400> SEQUENCE: 710
nngcuucccc agaggagacu c              21

<210> SEQ ID NO 711
<211> LENGTH: 21
<212> TYPE: DNA
<213> ORGANISM: Artificial Sequence

```
<220> FEATURE:
<223> OTHER INFORMATION: Small interefering RNA - IKK.2

<400> SEQUENCE: 711
ggaguuccuc augugcaagt t                                              21

<210> SEQ ID NO 712
<211> LENGTH: 19
<212> TYPE: RNA
<213> ORGANISM: Artificial Sequence
<220> FEATURE:
<223> OTHER INFORMATION: Small interefering RNA - IKK.2

<400> SEQUENCE: 712
ggaguuccuc augugcaag                                                 19

<210> SEQ ID NO 713
<211> LENGTH: 19
<212> TYPE: RNA
<213> ORGANISM: Artificial Sequence
<220> FEATURE:
<223> OTHER INFORMATION: Small interefering RNA - IKK.2

<400> SEQUENCE: 713
cuugcacaug aggaacucc                                                 19

<210> SEQ ID NO 714
<211> LENGTH: 21
<212> TYPE: DNA
<213> ORGANISM: Artificial Sequence
<220> FEATURE:
<223> OTHER INFORMATION: Small interefering RNA - IKK.2
<220> FEATURE:
<221> NAME/KEY: misc_feature
<222> LOCATION: 20, 21
<223> OTHER INFORMATION: n = A,T,C,G or U

<400> SEQUENCE: 714
ggaguuccuc augugcaagn n                                              21

<210> SEQ ID NO 715
<211> LENGTH: 21
<212> TYPE: DNA
<213> ORGANISM: Artificial Sequence
<220> FEATURE:
<223> OTHER INFORMATION: Small interefering RNA - IKK.2
<220> FEATURE:
<221> NAME/KEY: misc_feature
<222> LOCATION: 1, 2
<223> OTHER INFORMATION: n = A,T,C,G or U

<400> SEQUENCE: 715
nncuugcaca ugaggaacuc c                                              21

<210> SEQ ID NO 716
<211> LENGTH: 21
<212> TYPE: DNA
<213> ORGANISM: Artificial Sequence
<220> FEATURE:
<223> OTHER INFORMATION: Small interefering RNA - IKK.3

<400> SEQUENCE: 716
ggccucugug aaagcccagt t                                              21

<210> SEQ ID NO 717
<211> LENGTH: 19
<212> TYPE: RNA
```

```
<213> ORGANISM: Artificial Sequence
<220> FEATURE:
<223> OTHER INFORMATION: Small interefering RNA - IKK.3

<400> SEQUENCE: 717
ggccucugug aaagcccag                                                   19

<210> SEQ ID NO 718
<211> LENGTH: 19
<212> TYPE: RNA
<213> ORGANISM: Artificial Sequence
<220> FEATURE:
<223> OTHER INFORMATION: Small interefering RNA - IKK.3

<400> SEQUENCE: 718
cugggcuuuc acagaggcc                                                   19

<210> SEQ ID NO 719
<211> LENGTH: 21
<212> TYPE: DNA
<213> ORGANISM: Artificial Sequence
<220> FEATURE:
<223> OTHER INFORMATION: Small interefering RNA - IKK.3
<220> FEATURE:
<221> NAME/KEY: misc_feature
<222> LOCATION: 20, 21
<223> OTHER INFORMATION: n = A,T,C,G or U

<400> SEQUENCE: 719
ggccucugug aaagcccagn n                                                21

<210> SEQ ID NO 720
<211> LENGTH: 21
<212> TYPE: DNA
<213> ORGANISM: Artificial Sequence
<220> FEATURE:
<223> OTHER INFORMATION: Small interefering RNA - IKK.3
<220> FEATURE:
<221> NAME/KEY: misc_feature
<222> LOCATION: 1, 2
<223> OTHER INFORMATION: n = A,T,C,G or U

<400> SEQUENCE: 720
nncugggcuu ucacagaggc c                                                21

<210> SEQ ID NO 721
<211> LENGTH: 21
<212> TYPE: DNA
<213> ORGANISM: Artificial Sequence
<220> FEATURE:
<223> OTHER INFORMATION: Small interefering RNA - IKK.4

<400> SEQUENCE: 721
cacgcugcuc uugauguggt t                                                21

<210> SEQ ID NO 722
<211> LENGTH: 19
<212> TYPE: RNA
<213> ORGANISM: Artificial Sequence
<220> FEATURE:
<223> OTHER INFORMATION: Small interefering RNA - IKK.4

<400> SEQUENCE: 722
cacgcugcuc uugaugugg                                                   19

<210> SEQ ID NO 723
<211> LENGTH: 19
```

```
<212> TYPE: RNA
<213> ORGANISM: Artificial Sequence
<220> FEATURE:
<223> OTHER INFORMATION: Small interefering RNA - IKK.4

<400> SEQUENCE: 723
ccacaucaag agcagcgug                                                    19

<210> SEQ ID NO 724
<211> LENGTH: 21
<212> TYPE: DNA
<213> ORGANISM: Artificial Sequence
<220> FEATURE:
<223> OTHER INFORMATION: Small interefering RNA - IKK.4
<220> FEATURE:
<221> NAME/KEY: misc_feature
<222> LOCATION: 20, 21
<223> OTHER INFORMATION: n = A,T,C,G or U

<400> SEQUENCE: 724
cacgcugcuc uugauguggn n                                                 21

<210> SEQ ID NO 725
<211> LENGTH: 21
<212> TYPE: DNA
<213> ORGANISM: Artificial Sequence
<220> FEATURE:
<223> OTHER INFORMATION: Small interefering RNA - IKK.4
<220> FEATURE:
<221> NAME/KEY: misc_feature
<222> LOCATION: 1, 2
<223> OTHER INFORMATION: n = A,T,C,G or U

<400> SEQUENCE: 725
nnccacauca agagcagcgu g                                                 21

<210> SEQ ID NO 726
<211> LENGTH: 21
<212> TYPE: DNA
<213> ORGANISM: Artificial Sequence
<220> FEATURE:
<223> OTHER INFORMATION: Small interefering RNA - MKK4.1

<400> SEQUENCE: 726
gugggcaaau aauggcagut t                                                 21

<210> SEQ ID NO 727
<211> LENGTH: 19
<212> TYPE: RNA
<213> ORGANISM: Artificial Sequence
<220> FEATURE:
<223> OTHER INFORMATION: Small interefering RNA - MKK4.1

<400> SEQUENCE: 727
gugggcaaau aauggcagu                                                    19

<210> SEQ ID NO 728
<211> LENGTH: 19
<212> TYPE: RNA
<213> ORGANISM: Artificial Sequence
<220> FEATURE:
<223> OTHER INFORMATION: Small interefering RNA - MKK4.1

<400> SEQUENCE: 728
acugccauua uuugcccac                                                    19

<210> SEQ ID NO 729
```

```
<211> LENGTH: 21
<212> TYPE: DNA
<213> ORGANISM: Artificial Sequence
<220> FEATURE:
<223> OTHER INFORMATION: Small interefering RNA - MKK4.1
<220> FEATURE:
<221> NAME/KEY: misc_feature
<222> LOCATION: 20, 21
<223> OTHER INFORMATION: n = A,T,C,G or U

<400> SEQUENCE: 729
gugggcaaau aauggcagun n                                           21

<210> SEQ ID NO 730
<211> LENGTH: 21
<212> TYPE: DNA
<213> ORGANISM: Artificial Sequence
<220> FEATURE:
<223> OTHER INFORMATION: Small interefering RNA - MKK4.1
<220> FEATURE:
<221> NAME/KEY: misc_feature
<222> LOCATION: 1, 2
<223> OTHER INFORMATION: n = A,T,C,G or U

<400> SEQUENCE: 730
nnacugccau uauuugccca c                                           21

<210> SEQ ID NO 731
<211> LENGTH: 21
<212> TYPE: DNA
<213> ORGANISM: Artificial Sequence
<220> FEATURE:
<223> OTHER INFORMATION: Small interefering RNA - MKK4.2

<400> SEQUENCE: 731
cugugaaagc acuaaaccat t                                           21

<210> SEQ ID NO 732
<211> LENGTH: 19
<212> TYPE: RNA
<213> ORGANISM: Artificial Sequence
<220> FEATURE:
<223> OTHER INFORMATION: Small interefering RNA - MKK4.2

<400> SEQUENCE: 732
cugugaaagc acuaaacca                                              19

<210> SEQ ID NO 733
<211> LENGTH: 19
<212> TYPE: RNA
<213> ORGANISM: Artificial Sequence
<220> FEATURE:
<223> OTHER INFORMATION: Small interefering RNA - MKK4.2

<400> SEQUENCE: 733
ugguuuagug cuuucacag                                              19

<210> SEQ ID NO 734
<211> LENGTH: 21
<212> TYPE: DNA
<213> ORGANISM: Artificial Sequence
<220> FEATURE:
<223> OTHER INFORMATION: Small interefering RNA - MKK4.2
<220> FEATURE:
<221> NAME/KEY: misc_feature
<222> LOCATION: 20, 21
<223> OTHER INFORMATION: n = A,T,C,G or U

<400> SEQUENCE: 734
```

-continued

```
cugugaaagc acuaaaccan n                                              21

<210> SEQ ID NO 735
<211> LENGTH: 21
<212> TYPE: DNA
<213> ORGANISM: Artificial Sequence
<220> FEATURE:
<223> OTHER INFORMATION: Small interefering RNA - MKK4.2
<220> FEATURE:
<221> NAME/KEY: misc_feature
<222> LOCATION: 1, 2
<223> OTHER INFORMATION: n = A,T,C,G or U

<400> SEQUENCE: 735
nnugguuuag ugcuuucaca g                                              21

<210> SEQ ID NO 736
<211> LENGTH: 21
<212> TYPE: DNA
<213> ORGANISM: Artificial Sequence
<220> FEATURE:
<223> OTHER INFORMATION: Small interefering RNA - MKK4.3

<400> SEQUENCE: 736
ggagauccuc cgcagcugat t                                              21

<210> SEQ ID NO 737
<211> LENGTH: 19
<212> TYPE: RNA
<213> ORGANISM: Artificial Sequence
<220> FEATURE:
<223> OTHER INFORMATION: Small interefering RNA - MKK4.3

<400> SEQUENCE: 737
ggagauccuc cgcagcuga                                                 19

<210> SEQ ID NO 738
<211> LENGTH: 19
<212> TYPE: RNA
<213> ORGANISM: Artificial Sequence
<220> FEATURE:
<223> OTHER INFORMATION: Small interefering RNA - MKK4.3

<400> SEQUENCE: 738
ucagcugcgg aggaucucc                                                 19

<210> SEQ ID NO 739
<211> LENGTH: 21
<212> TYPE: DNA
<213> ORGANISM: Artificial Sequence
<220> FEATURE:
<223> OTHER INFORMATION: Small interefering RNA - MKK4.3
<220> FEATURE:
<221> NAME/KEY: misc_feature
<222> LOCATION: 20, 21
<223> OTHER INFORMATION: n = A,T,C,G or U

<400> SEQUENCE: 739
ggagauccuc cgcagcugan n                                              21

<210> SEQ ID NO 740
<211> LENGTH: 21
<212> TYPE: DNA
<213> ORGANISM: Artificial Sequence
<220> FEATURE:
<223> OTHER INFORMATION: Small interefering RNA - MKK4.3
<220> FEATURE:
```

```
<221> NAME/KEY: misc_feature
<222> LOCATION: 1, 2
<223> OTHER INFORMATION: n = A,T,C,G or U

<400> SEQUENCE: 740
nnucagcugc ggaggaucuc c                                              21

<210> SEQ ID NO 741
<211> LENGTH: 21
<212> TYPE: DNA
<213> ORGANISM: Artificial Sequence
<220> FEATURE:
<223> OTHER INFORMATION: Small interefering RNA - MKK4.4

<400> SEQUENCE: 741
gcucuuuaua cuuuggccut t                                              21

<210> SEQ ID NO 742
<211> LENGTH: 19
<212> TYPE: RNA
<213> ORGANISM: Artificial Sequence
<220> FEATURE:
<223> OTHER INFORMATION: Small interefering RNA - MKK4.4

<400> SEQUENCE: 742
gcucuuuaua cuuuggccu                                                 19

<210> SEQ ID NO 743
<211> LENGTH: 19
<212> TYPE: RNA
<213> ORGANISM: Artificial Sequence
<220> FEATURE:
<223> OTHER INFORMATION: Small interefering RNA - MKK4.4

<400> SEQUENCE: 743
aggccaaagu auaaagagc                                                 19

<210> SEQ ID NO 744
<211> LENGTH: 21
<212> TYPE: DNA
<213> ORGANISM: Artificial Sequence
<220> FEATURE:
<223> OTHER INFORMATION: Small interefering RNA - MKK4.4
<220> FEATURE:
<221> NAME/KEY: misc_feature
<222> LOCATION: 20, 21
<223> OTHER INFORMATION: n = A,T,C,G or U

<400> SEQUENCE: 744
gcucuuuaua cuuuggccun n                                              21

<210> SEQ ID NO 745
<211> LENGTH: 21
<212> TYPE: DNA
<213> ORGANISM: Artificial Sequence
<220> FEATURE:
<223> OTHER INFORMATION: Small interefering RNA - MKK4.4
<220> FEATURE:
<221> NAME/KEY: misc_feature
<222> LOCATION: 1, 2
<223> OTHER INFORMATION: n = A,T,C,G or U

<400> SEQUENCE: 745
nnaggccaaa guauaaagag c                                              21

<210> SEQ ID NO 746
<211> LENGTH: 21
```

```
<212> TYPE: DNA
<213> ORGANISM: Artificial Sequence
<220> FEATURE:
<223> OTHER INFORMATION: Small interefering RNA - MKK7.1

<400> SEQUENCE: 746
gcagacgggc uaccugacct t                                              21

<210> SEQ ID NO 747
<211> LENGTH: 19
<212> TYPE: RNA
<213> ORGANISM: Artificial Sequence
<220> FEATURE:
<223> OTHER INFORMATION: Small interefering RNA - MKK7.1

<400> SEQUENCE: 747
gcagacgggc uaccugacc                                                 19

<210> SEQ ID NO 748
<211> LENGTH: 19
<212> TYPE: RNA
<213> ORGANISM: Artificial Sequence
<220> FEATURE:
<223> OTHER INFORMATION: Small interefering RNA - MKK7.1

<400> SEQUENCE: 748
ggucagguag cccgucugc                                                 19

<210> SEQ ID NO 749
<211> LENGTH: 21
<212> TYPE: DNA
<213> ORGANISM: Artificial Sequence
<220> FEATURE:
<223> OTHER INFORMATION: Small interefering RNA - MKK7.1
<220> FEATURE:
<221> NAME/KEY: misc_feature
<222> LOCATION: 20, 21
<223> OTHER INFORMATION: n = A,T,C,G or U

<400> SEQUENCE: 749
gcagacgggc uaccugaccn n                                              21

<210> SEQ ID NO 750
<211> LENGTH: 21
<212> TYPE: DNA
<213> ORGANISM: Artificial Sequence
<220> FEATURE:
<223> OTHER INFORMATION: Small interefering RNA - MKK7.1
<220> FEATURE:
<221> NAME/KEY: misc_feature
<222> LOCATION: 1, 2
<223> OTHER INFORMATION: n = A,T,C,G or U

<400> SEQUENCE: 750
nnggucaggu agcccgucug c                                              21

<210> SEQ ID NO 751
<211> LENGTH: 21
<212> TYPE: DNA
<213> ORGANISM: Artificial Sequence
<220> FEATURE:
<223> OTHER INFORMATION: Small interefering RNA - MKK7.2

<400> SEQUENCE: 751
cacggacguc uucaucgcct t                                              21

<210> SEQ ID NO 752
```

```
<211> LENGTH: 19
<212> TYPE: RNA
<213> ORGANISM: Artificial Sequence
<220> FEATURE:
<223> OTHER INFORMATION: Small interefering RNA - MKK7.2

<400> SEQUENCE: 752
cacggacguc uucaucgcc                                                    19

<210> SEQ ID NO 753
<211> LENGTH: 19
<212> TYPE: RNA
<213> ORGANISM: Artificial Sequence
<220> FEATURE:
<223> OTHER INFORMATION: Small interefering RNA - MKK7.2

<400> SEQUENCE: 753
ggcgaugaag acguccgug                                                    19

<210> SEQ ID NO 754
<211> LENGTH: 21
<212> TYPE: DNA
<213> ORGANISM: Artificial Sequence
<220> FEATURE:
<223> OTHER INFORMATION: Small interefering RNA - MKK7.2
<220> FEATURE:
<221> NAME/KEY: misc_feature
<222> LOCATION: 20, 21
<223> OTHER INFORMATION: n = A,T,C,G or U

<400> SEQUENCE: 754
cacggacguc uucaucgccn n                                                 21

<210> SEQ ID NO 755
<211> LENGTH: 21
<212> TYPE: DNA
<213> ORGANISM: Artificial Sequence
<220> FEATURE:
<223> OTHER INFORMATION: Small interefering RNA - MKK7.2
<220> FEATURE:
<221> NAME/KEY: misc_feature
<222> LOCATION: 1, 2
<223> OTHER INFORMATION: n = A,T,C,G or U

<400> SEQUENCE: 755
nnggcgauga agacguccgu g                                                 21

<210> SEQ ID NO 756
<211> LENGTH: 21
<212> TYPE: DNA
<213> ORGANISM: Artificial Sequence
<220> FEATURE:
<223> OTHER INFORMATION: Small interefering RNA - MKK7.3

<400> SEQUENCE: 756
gaagcggaug cagggcccct t                                                 21

<210> SEQ ID NO 757
<211> LENGTH: 19
<212> TYPE: RNA
<213> ORGANISM: Artificial Sequence
<220> FEATURE:
<223> OTHER INFORMATION: Small interefering RNA - MKK7.3

<400> SEQUENCE: 757
gaagcggaug cagggcccc                                                    19
```

```
<210> SEQ ID NO 758
<211> LENGTH: 19
<212> TYPE: RNA
<213> ORGANISM: Artificial Sequence
<220> FEATURE:
<223> OTHER INFORMATION: Small interefering RNA - MKK7.3

<400> SEQUENCE: 758
ggggcccugc auccgcuuc                                                    19

<210> SEQ ID NO 759
<211> LENGTH: 21
<212> TYPE: DNA
<213> ORGANISM: Artificial Sequence
<220> FEATURE:
<223> OTHER INFORMATION: Small interefering RNA - MKK7.3
<220> FEATURE:
<221> NAME/KEY: misc_feature
<222> LOCATION: 20, 21
<223> OTHER INFORMATION: n = A,T,C,G or U

<400> SEQUENCE: 759
gaagcggaug cagggccccn n                                                 21

<210> SEQ ID NO 760
<211> LENGTH: 21
<212> TYPE: DNA
<213> ORGANISM: Artificial Sequence
<220> FEATURE:
<223> OTHER INFORMATION: Small interefering RNA - MKK7.3
<220> FEATURE:
<221> NAME/KEY: misc_feature
<222> LOCATION: 1, 2
<223> OTHER INFORMATION: n = A,T,C,G or U

<400> SEQUENCE: 760 nngggggcccu gcauccgcuu c                                                21

<210> SEQ ID NO 761
<211> LENGTH: 21
<212> TYPE: DNA
<213> ORGANISM: Artificial Sequence
<220> FEATURE:
<223> OTHER INFORMATION: Small interefering RNA - MKK7.4

<400> SEQUENCE: 761
cugcaagacg gacuuugagt t                                                 21

<210> SEQ ID NO 762
<211> LENGTH: 19
<212> TYPE: RNA
<213> ORGANISM: Artificial Sequence
<220> FEATURE:
<223> OTHER INFORMATION: Small interefering RNA - MKK7.4

<400> SEQUENCE: 762
cugcaagacg gacuuugag                                                    19

<210> SEQ ID NO 763
<211> LENGTH: 19
<212> TYPE: RNA
<213> ORGANISM: Artificial Sequence
<220> FEATURE:
<223> OTHER INFORMATION: Small interefering RNA - MKK7.4

<400> SEQUENCE: 763
cucaaagucc gucuugcag                                                    19
```

<210> SEQ ID NO 764
<211> LENGTH: 21
<212> TYPE: DNA
<213> ORGANISM: Artificial Sequence
<220> FEATURE:
<223> OTHER INFORMATION: Small interefering RNA - MKK7.4
<220> FEATURE:
<221> NAME/KEY: misc_feature
<222> LOCATION: 20, 21
<223> OTHER INFORMATION: n = A,T,C,G or U

<400> SEQUENCE: 764
cugcaagacg gacuuugagn n                                              21

<210> SEQ ID NO 765
<211> LENGTH: 21
<212> TYPE: DNA
<213> ORGANISM: Artificial Sequence
<220> FEATURE:
<223> OTHER INFORMATION: Small interefering RNA - MKK7.4
<220> FEATURE:
<221> NAME/KEY: misc_feature
<222> LOCATION: 1, 2
<223> OTHER INFORMATION: n = A,T,C,G or U

<400> SEQUENCE: 765
nncucaaagu ccgucuugca g                                              21

<210> SEQ ID NO 766
<211> LENGTH: 55
<212> TYPE: DNA
<213> ORGANISM: Artificial Sequence
<220> FEATURE:
<223> OTHER INFORMATION: Hairpin Vector - HP53-HP9

<400> SEQUENCE: 766
tttgactcca gtggtaatct acttcaagag agtagattac cactggagtc ttttt         55

<210> SEQ ID NO 767
<211> LENGTH: 55
<212> TYPE: DNA
<213> ORGANISM: Artificial Sequence
<220> FEATURE:
<223> OTHER INFORMATION: Hairpin Vector - HP53-HP9

<400> SEQUENCE: 767
ctagaaaaag actccagtgg taatctactc tcttgaagta gattaccact ggagt         55

<210> SEQ ID NO 768
<211> LENGTH: 55
<212> TYPE: RNA
<213> ORGANISM: Artificial Sequence
<220> FEATURE:
<223> OTHER INFORMATION: Hairpin Vector - HP53-HP9

<400> SEQUENCE: 768
uuugacucca gugguaaucu acuucaagag aguagauuac cacuggaguc uuuuu         55

<210> SEQ ID NO 769
<211> LENGTH: 55
<212> TYPE: RNA
<213> ORGANISM: Artificial Sequence
<220> FEATURE:
<223> OTHER INFORMATION: Hairpin Vector - HP53-HP9

<400> SEQUENCE: 769
cuagaaaaag acuccagugg uaaucuacuc ucuugaagua gauuaccacu ggagu         55

```
<210> SEQ ID NO 770
<211> LENGTH: 19
<212> TYPE: RNA
<213> ORGANISM: Artificial Sequence
<220> FEATURE:
<223> OTHER INFORMATION: Small interefering RNA - TCPTP1

<400> SEQUENCE: 770
aacagauaca gagauguaa                                                    19

<210> SEQ ID NO 771
<211> LENGTH: 19
<212> TYPE: RNA
<213> ORGANISM: Artificial Sequence
<220> FEATURE:
<223> OTHER INFORMATION: Small interefering RNA - TCPTP1

<400> SEQUENCE: 771
uuacaucucu guaucuguu                                                    19

<210> SEQ ID NO 772
<211> LENGTH: 21
<212> TYPE: DNA
<213> ORGANISM: Artificial Sequence
<220> FEATURE:
<223> OTHER INFORMATION: Small interefering RNA - TCPTP1
<220> FEATURE:
<221> NAME/KEY: misc_feature
<222> LOCATION: 20, 21
<223> OTHER INFORMATION: n = A,T,C,G or U

<400> SEQUENCE: 772
aacagauaca gagauguaan n                                                 21

<210> SEQ ID NO 773
<211> LENGTH: 21
<212> TYPE: DNA
<213> ORGANISM: Artificial Sequence
<220> FEATURE:
<223> OTHER INFORMATION: Small interefering RNA - TCPTP1
<220> FEATURE:
<221> NAME/KEY: misc_feature
<222> LOCATION: 1, 2
<223> OTHER INFORMATION: n = A,T,C,G or U

<400> SEQUENCE: 773
nnuuacaucu cuguaucugu u                                                 21

<210> SEQ ID NO 774
<211> LENGTH: 19
<212> TYPE: RNA
<213> ORGANISM: Artificial Sequence
<220> FEATURE:
<223> OTHER INFORMATION: Small interefering RNA - TCPTP2

<400> SEQUENCE: 774
aagcccauau gaucacagu                                                    19

<210> SEQ ID NO 775
<211> LENGTH: 19
<212> TYPE: RNA
<213> ORGANISM: Artificial Sequence
<220> FEATURE:
<223> OTHER INFORMATION: Small interefering RNA - TCPTP2

<400> SEQUENCE: 775
```

-continued

```
<210> SEQ ID NO 776
<211> LENGTH: 21
<212> TYPE: DNA
<213> ORGANISM: Artificial Sequence
<220> FEATURE:
<223> OTHER INFORMATION: Small interefering RNA - TCPTP2
<220> FEATURE:
<221> NAME/KEY: misc_feature
<222> LOCATION: 20, 21
<223> OTHER INFORMATION: n = A,T,C,G or U

<400> SEQUENCE: 776
aagcccauau gaucacagun n                                             21

<210> SEQ ID NO 777
<211> LENGTH: 21
<212> TYPE: DNA
<213> ORGANISM: Artificial Sequence
<220> FEATURE:
<223> OTHER INFORMATION: Small interefering RNA - TCPTP2
<220> FEATURE:
<221> NAME/KEY: misc_feature
<222> LOCATION: 1, 2
<223> OTHER INFORMATION: n = A,T,C,G or U

<400> SEQUENCE: 777
nnacugugau cauaugggcu u                                             21

<210> SEQ ID NO 778
<211> LENGTH: 926
<212> TYPE: DNA
<213> ORGANISM: Homo sapiens

<400> SEQUENCE: 778
ccccgccgct cctcctccct gtaacatgcc atagtgcgcc tgcgaccaca cggccggggc    60
gctagcgttc gccttcagcc accatgggga atgggatgaa caagatcctg cccggcctgt   120
acatcggcaa cttcaaagat gccagagacg cggaacaatt gagcaagaac aaggtgacac   180
atattctgtc tgtccacgat agtgccaggc ctatgttgga gggagttaaa tacctgtgca   240
tcccagcagc ggattcacca tctcaaaacc tgacaagaca tttcaaagaa agtattaaat   300
tcattcacga gtgccggctc cgcggtgaga gctgccttgt acactgcctg gccggggtct   360
ccaggagcgt gacactggtg atcgcataca tcatgaccgt cactgacttt ggctgggagg   420
atgccctgca caccgtgcgt gctgggagat cctgtgccaa ccccaacgtg ggcttccaga   480
gacagctcca ggagtttgag aagcatgagg tccatcagta tcggcagtgg ctgaaggaag   540
aatatggaga gagccctttg caggatgcag aagaagccaa aaacattctg gccgctccag   600
gaattctgaa gttctgggcc tttctcagaa gactgtaatg tacctgaagt ttctgaaata   660
ttgcaaaccc gcagagttta ggctggtgct gccaaaaaga aaagcaacat agagtttaag   720
tatccagtag tgatttgtaa acttgttttt catttgaagc tgaatatata cgtagtcatg   780
tttatgttga gaactaagga tattctttag caagagaaaa tattttcccc ttatccccac   840
tgctgtggag gtttctgtac ctcgcttgga tgcctgtaag gatcccggga gccttgccgc   900
actgccttgt gggtggcttg gcgctc                                       926

<210> SEQ ID NO 779
<211> LENGTH: 184
<212> TYPE: PRT
<213> ORGANISM: Homo sapiens
```

<400> SEQUENCE: 779

Met Gly Asn Gly Met Asn Lys Ile Leu Pro Gly Leu Tyr Ile Gly Asn
1               5                   10                  15

Phe Lys Asp Ala Arg Asp Ala Glu Gln Leu Ser Lys Asn Lys Val Thr
            20                  25                  30

His Ile Leu Ser Val His Asp Ser Ala Arg Pro Met Leu Glu Gly Val
        35                  40                  45

Lys Tyr Leu Cys Ile Pro Ala Ala Asp Ser Pro Ser Gln Asn Leu Thr
    50                  55                  60

Arg His Phe Lys Glu Ser Ile Lys Phe Ile His Glu Cys Arg Leu Arg
65                  70                  75                  80

Gly Glu Ser Cys Leu Val His Cys Leu Ala Gly Val Ser Arg Ser Val
                85                  90                  95

Thr Leu Val Ile Ala Tyr Ile Met Thr Val Thr Asp Phe Gly Trp Glu
            100                 105                 110

Asp Ala Leu His Thr Val Arg Ala Gly Arg Ser Cys Ala Asn Pro Asn
        115                 120                 125

Val Gly Phe Gln Arg Gln Leu Gln Glu Phe Glu Lys His Glu Val His
    130                 135                 140

Gln Tyr Arg Gln Trp Leu Lys Glu Glu Tyr Gly Glu Ser Pro Leu Gln
145                 150                 155                 160

Asp Ala Glu Glu Ala Lys Asn Ile Leu Ala Ala Pro Gly Ile Leu Lys
                165                 170                 175

Phe Trp Ala Phe Leu Arg Arg Leu
            180

<210> SEQ ID NO 780
<211> LENGTH: 707
<212> TYPE: DNA
<213> ORGANISM: Homo sapiens

<400> SEQUENCE: 780
tgacccgctg tcctgtgccc tttcccagcg atgggcgtgc agcccccaa cttctcctgg      60
gtgcttccgg gccggctggc gggactggcg ctgccgcggc tccccgccca ctaccagttc     120
ctgttggacc tggcgtgcg gcacctggtg tccctgacgg agcgcgggcc ccctcacagc     180
gacagctgcc ccggcctcac cctgcaccgc ctgcgcatcc ccgacttctg cccgccggcc     240
cccgaccaga tcgaccgctt cgtgcagatc gtggacgagg ccaacgcacg gggagaggct     300
gtgggagtgc actgtgctct gggctttggc cgcactggca ccatgctggc ctgttacctg     360
gtgaaggagc ggggcttggc tgcaggagat gccattgctg aaatccgacg actacgaccc     420
ggctccatcg agacctatga gcaggagaaa gcagtcttcc agttctacca gcgaacgaaa     480
taagggcct tagtacccctt ctaccaggcc ctcactcccc ttcccatgt tgtcgatggg      540
gccagagatg aagggaagtg gactaaagta ttaaaccctc tagctcccat ggctgaaga      600
cactgaagta gcccacccct gcaggcaggt cctgattgaa ggggaggctt gtactgcttt     660
gttgaataaa tgagttttac gaaccaaaaa aaaaaaaaa aaaaaaa                    707

<210> SEQ ID NO 781
<211> LENGTH: 150
<212> TYPE: PRT
<213> ORGANISM: Homo sapiens

<400> SEQUENCE: 781

```
Met Gly Val Gln Pro Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
            20                  25                  30

Asp Leu Gly Val Arg His Leu Val Ser Leu Thr Glu Arg Gly Pro Pro
            35                  40                  45

His Ser Asp Ser Cys Pro Gly Leu Thr Leu His Arg Leu Arg Ile Pro
        50                  55                  60

Asp Phe Cys Pro Pro Ala Pro Asp Gln Ile Asp Arg Phe Val Gln Ile
65                  70                  75                  80

Val Asp Glu Ala Asn Ala Arg Gly Glu Ala Val Gly Val His Cys Ala
                85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
            115                 120                 125

Arg Pro Gly Ser Ile Glu Thr Tyr Glu Gln Glu Lys Ala Val Phe Gln
            130                 135                 140

Phe Tyr Gln Arg Thr Lys
145                 150

<210> SEQ ID NO 782
<211> LENGTH: 833
<212> TYPE: DNA
<213> ORGANISM: Homo sapiens

<400> SEQUENCE: 782
ggccccccgt tccccgccag gctgcaggcg tcgggcctgg gccgtcaggg cagctgtgac      60
cggatcgctt cccgggcggc gagctggggg tgcacccgga ccgccgcccc cgggatcatg     120
ggcaatggca tgaccaaggt acttcctgga ctctacctcg gaaacttcat tgatgccaaa     180
gacctggatc agctgggccg aaataagatc acacacatca tctctatcca tgagtcaccc     240
cagcctctgc tgcaggatat cacctacctt cgcatcccgg tcgctgatac ccctgaggta     300
cccatcaaaa agcacttcaa gaatgtatc aacttcatcc actgctgccg ccttaatggg     360
gggaactgcc ttgtgcactg ctttgcaggc atctctcgca gcaccacgat tgtgacagcg     420
tatgtgatga ctgtgacggg gctaggctgg cgggacgtgc ttgaagccat caaggccacc     480
aggcccatcg ccaaccccaa cccaggcttt aggcagcagc ttgaagagtt tggctgggcc     540
agttcccaga agcttcgccg gcagctggag gagcgcttcg gcgagagccc cttccgcgac     600
gaggaggagt tgcgcgcgct gctgccgctg tgcaagcgct gccggcaggg ctccgcgacc     660
tcggcctcct ccgccgggcc gcactcagca gcctccgagg gaaccgtgca gcgcctggtg     720
ccgcgcacgc cccgggaagc ccaccggccg ctgccgctgc tggcgcgcgt caagcagact     780
ttctcttgcc tccccggtg tctgtcccgc aagggcggca gtgaggatg cag             833

<210> SEQ ID NO 783
<211> LENGTH: 235
<212> TYPE: PRT
<213> ORGANISM: Homo sapiens

<400> SEQUENCE: 783

Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr
            20                  25                  30
```

His Ile Ile Ser Ile His Glu Ser Pro Gln Pro Leu Leu Gln Asp Ile
            35                  40                  45

Thr Tyr Leu Arg Ile Pro Val Ala Asp Thr Pro Glu Val Pro Ile Lys
 50                  55                  60

Lys His Phe Lys Glu Cys Ile Asn Phe Ile His Cys Cys Arg Leu Asn
 65                  70                  75                  80

Gly Gly Asn Cys Leu Val His Cys Phe Ala Gly Ile Ser Arg Ser Thr
                 85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
            115                 120                 125

Pro Gly Phe Arg Gln Gln Leu Glu Glu Phe Gly Trp Ala Ser Ser Gln
    130                 135                 140

Lys Leu Arg Arg Gln Leu Glu Glu Arg Phe Gly Glu Ser Pro Phe Arg
145                 150                 155                 160

Asp Glu Glu Glu Leu Arg Ala Leu Leu Pro Leu Cys Lys Arg Cys Arg
                165                 170                 175

Gln Gly Ser Ala Thr Ser Ala Ser Ser Ala Gly Pro His Ser Ala Ala
            180                 185                 190

Ser Glu Gly Thr Val Gln Arg Leu Val Pro Arg Thr Pro Arg Glu Ala
            195                 200                 205

His Arg Pro Leu Pro Leu Leu Ala Arg Val Lys Gln Thr Phe Ser Cys
    210                 215                 220

Leu Pro Arg Cys Leu Ser Arg Lys Gly Gly Lys
225                 230                 235

<210> SEQ ID NO 784
<211> LENGTH: 1711
<212> TYPE: DNA
<213> ORGANISM: Homo sapiens

<400> SEQUENCE: 784
cctgggaaga agttatctat ctctcgagtg acattcaaga tataccgtac ccctcggttc     60
tgtaagtcct ctaagttgga ggcattccat tctgagccgg ccccatgacc ctgagcacgt    120
tggcccgcaa gaggaaggcg cccctcgctt gcacctgcag cctcggtggc cccgacatga    180
ttccttactt ctccgccaac gcggtcatct cgcagaacgc catcaaccag ctcatcagcg    240
agagctttct aactgtcaaa ggtgctgccc ttttctacc acggggaaat ggctcatcca    300
caccaagaat cagccacaga cggaacaagc atgcaggcga tctccaacag catctccaag    360
caatgttcat tttactccgc ccagaagaca acatcaggct ggctgtaaga ctggaaagta    420
cttaccagaa tcgaacacgc tatatggtag tggtttcaac taatggtaga caagacactg    480
aagaaagcat cgtcctagga atggatttct cctctaatga cagtagcact tgtaccatgg    540
gcttagtttt gcctctctgg agcgacacgc taattcattt ggatggtgat ggtgggttca    600
gtgtatcgac ggataacaga gttcacatat tcaaacctgt atctgtgcag gcaatgtggt    660
ctgcactaca gagcttacac aaggcttgtg aagtcgccag agcgcataac tactacccag    720
gcagcctatt tctcacttgg gtgagttatt atgagagcca tatcaactca gatcaatcct    780
cagtcaatga atggaatgca atgcaagatg tacagtccca ccggcccgac tctccagctc    840
tcttcaccga catacctact gaacgtgaac aacagaaaag gctaattaaa accaaattaa    900
gggagatcat gatgcagaag gatttggaga atattacatc caaagagata agaacagagt    960

-continued

```
tggaaatgca aatggtgtgc aacttgcggg aattcaagga atttatagac aatgaaatga   1020
tagtgatcct tggtcaaatg gatagcccta cacagatatt tgagcatgtg ttcctgggct   1080
cagaatggaa tgcctccaac ttagaggact tacagaaccg aggggtacgg tatatcttga   1140
atgtcactcg agagatagat aacttcttcc caggagtctt tgagtatcat aacattcggg   1200
tatatgatga gagggcaacg gatctcctgg cgtactggaa tgacacttac aaattcatct   1260
ctaaagcaaa gaaacatgga tctaaatgcc ttgtgcactg caaaatgggg gtgagtcgct   1320
cagcctccac cgtgattgcc tatgcaatga aggaatatgg ctggaatctg gaccgagcct   1380
atgactatgt gaaagaaaga cgaacggtaa ccaagcccaa cccaagcttc atgagacaac   1440
tggaagagta tcaggggatc ttgctggcaa gcttcctagg cttgattcat ggagggaggg   1500
acaagccctg gggagagaaa agcacagaat tgagtcagt agatctggtt tccattcctg    1560
gttcaccctc ttgctgcaac cctgagaagt tacttcacat ttctcatcct tacctgaccc   1620
catctataaa atgaaaatca agagatccat ctcacagggt tattgtgaat aaaaatgtgt   1680
ttgaatgttt ataaaaaaaa aaaaaaaaa a                                   1711
```

<210> SEQ ID NO 785
<211> LENGTH: 509
<212> TYPE: PRT
<213> ORGANISM: Homo sapiens

<400> SEQUENCE: 785

```
Met Thr Leu Ser Thr Leu Ala Arg Lys Arg Lys Ala Pro Leu Ala Cys
1               5                   10                  15

Thr Cys Ser Leu Gly Gly Pro Asp Met Ile Pro Tyr Phe Ser Ala Asn
            20                  25                  30

Ala Val Ile Ser Gln Asn Ala Ile Asn Gln Leu Ile Ser Glu Ser Phe
        35                  40                  45

Leu Thr Val Lys Gly Ala Ala Leu Phe Leu Pro Arg Gly Asn Gly Ser
    50                  55                  60

Ser Thr Pro Arg Ile Ser His Arg Arg Asn Lys His Ala Gly Asp Leu
65                  70                  75                  80

Gln Gln His Leu Gln Ala Met Phe Ile Leu Leu Arg Pro Glu Asp Asn
                85                  90                  95

Ile Arg Leu Ala Val Arg Leu Glu Ser Thr Tyr Gln Asn Arg Thr Arg
            100                 105                 110

Tyr Met Val Val Val Ser Thr Asn Gly Arg Gln Asp Thr Glu Glu Ser
        115                 120                 125

Ile Val Leu Gly Met Asp Phe Ser Ser Asn Asp Ser Ser Thr Cys Thr
    130                 135                 140

Met Gly Leu Val Leu Pro Leu Trp Ser Asp Thr Leu Ile His Leu Asp
145                 150                 155                 160

Gly Asp Gly Gly Phe Ser Val Ser Thr Asp Asn Arg Val His Ile Phe
                165                 170                 175

Lys Pro Val Ser Val Gln Ala Met Trp Ser Ala Leu Gln Ser Leu His
            180                 185                 190

Lys Ala Cys Glu Val Ala Arg Ala His Asn Tyr Tyr Pro Gly Ser Leu
        195                 200                 205

Phe Leu Thr Trp Val Ser Tyr Tyr Glu Ser His Ile Asn Ser Asp Gln
    210                 215                 220

Ser Ser Val Asn Glu Trp Asn Ala Met Gln Asp Val Gln Ser His Arg
225                 230                 235                 240
```

```
Pro Asp Ser Pro Ala Leu Phe Thr Asp Ile Pro Thr Glu Arg Glu Arg
                245                 250                 255

Thr Glu Arg Leu Ile Lys Thr Lys Leu Arg Glu Ile Met Met Gln Lys
            260                 265                 270

Asp Leu Glu Asn Ile Thr Ser Lys Glu Ile Arg Thr Glu Leu Glu Met
        275                 280                 285

Gln Met Val Cys Asn Leu Arg Glu Phe Lys Glu Phe Ile Asp Asn Glu
    290                 295                 300

Met Ile Val Ile Leu Gly Gln Met Asp Ser Pro Thr Gln Ile Phe Glu
305                 310                 315                 320

His Val Phe Leu Gly Ser Glu Trp Asn Ala Ser Asn Leu Glu Asp Leu
                325                 330                 335

Gln Asn Arg Gly Val Arg Tyr Ile Leu Asn Val Thr Arg Glu Ile Asp
            340                 345                 350

Asn Phe Phe Pro Gly Val Phe Glu Tyr His Asn Ile Arg Val Tyr Asp
        355                 360                 365

Glu Glu Ala Thr Asp Leu Leu Ala Tyr Trp Asn Asp Thr Tyr Lys Phe
    370                 375                 380

Ile Ser Lys Ala Lys Lys His Gly Ser Lys Cys Leu Val His Cys Lys
385                 390                 395                 400

Met Gly Val Ser Arg Ser Ala Ser Thr Val Ile Ala Tyr Ala Met Lys
                405                 410                 415

Glu Tyr Gly Trp Asn Leu Asp Arg Ala Tyr Asp Tyr Val Lys Glu Arg
            420                 425                 430

Arg Thr Val Thr Lys Pro Asn Pro Ser Phe Met Arg Gln Leu Glu Glu
        435                 440                 445

Tyr Gln Gly Ile Leu Leu Ala Ser Phe Leu Gly Leu Ile His Gly Gly
    450                 455                 460

Arg Asp Lys Pro Trp Gly Glu Lys Ser Thr Glu Phe Glu Ser Val Asp
465                 470                 475                 480

Leu Val Ser Ile Pro Gly Ser Pro Ser Cys Cys Asn Pro Glu Lys Leu
                485                 490                 495

Leu His Ile Ser His Pro Tyr Leu Thr Pro Ser Ile Lys
            500                 505

<210> SEQ ID NO 786
<211> LENGTH: 1165
<212> TYPE: DNA
<213> ORGANISM: Homo sapiens

<400> SEQUENCE: 786
ggccagtggg ggtggctggg cgtgcggctg ctacatgccc cacggaccag aacctcccga      60
cgcggccagg ccccggcaca cccagctgca gaaaggagag aaaatccctt ggctctaaaa     120
tgacatctgg agaagtgaag acaagcctca agaatgccta ctcatctgcc aagaggctgt     180
cgccgaagat ggaggaggaa gggaggagg aggactactg caccctgga gcctttgagc      240 tggagcggct cttctggaag gcagtcccc agtacaccca cgtcaacgag gtctggccca     300
agctctacat ggcgatgag gcgacggcgc tggaccgcta taggctgcag aaggcggggt     360
tcacgcacgt gctgaacgcg gcccacgccc gctggaacgt ggacactggg cccgactact     420
accgcgacat ggacatccag taccacggcg tggaggccga cgacctgccc accttcgacc     480
tcagtgtctt cttctacccg gcggcagcct tcatcgacag agcgctaagc gacgaccaca     540
gtaagatcct ggttcactgc gtcatgggcc gcagccggtc agccaccctg gtcctggcct     600
```

```
acctgatgat ccacaaggac atgaccctgg tggacgccat ccagcaagtg gccaagaacc    660
gctgcgtcct cccgaaccgg ggcttttttga agcagctccg ggagctggac aagcagctgg   720
tgcagcagag cgacggtcc cagcgccagg acggtgagga ggaggatggc agggagctgt     780
aggcccgact cacagggcca gcagaggcac ttggggacag aggggagagg cagaacatag    840
ccctggccta ggactccaga gaagggatgg tgaaaccgaa gctcgactct tccaaaccat    900
cttgttcaac ttccccatgt gtgctgggga cagggaggac ccagagctgc ccccgggcag    960
agctgagcgc tcagcctctc agcaaaatgg gaggacggg ctccccggct ctgggtcaca     1020
gaggagcatg ccacgctgca ccaagtctcc tgctttggtt ttgtttttttt ggtgagaagg   1080 aagagggaaa aagatttta aaatgtgtag gcagtatgtt gtgattaaac gtttggcttt     1140
gtccaaaaaa aaaaaaaaaa aaaaa                                          1165
```

<210> SEQ ID NO 787
<211> LENGTH: 220
<212> TYPE: PRT
<213> ORGANISM: Homo sapiens

<400> SEQUENCE: 787

```
Met Thr Ser Gly Glu Val Lys Thr Ser Leu Lys Asn Ala Tyr Ser Ser
1               5                   10                  15

Ala Lys Arg Leu Ser Pro Lys Met Glu Glu Gly Glu Glu Glu Glu Asp
                20                  25                  30

Tyr Cys Thr Pro Gly Ala Phe Glu Leu Glu Arg Leu Phe Trp Lys Gly
            35                  40                  45

Ser Pro Gln Tyr Thr His Val Asn Glu Val Trp Pro Lys Leu Tyr Ile
        50                  55                  60

Gly Asp Glu Ala Thr Ala Leu Asp Arg Tyr Arg Leu Gln Lys Ala Gly
65                  70                  75                  80

Phe Thr His Val Leu Asn Ala Ala His Gly Arg Trp Asn Val Asp Thr
                85                  90                  95

Gly Pro Asp Tyr Tyr Arg Asp Met Asp Ile Gln Tyr His Gly Val Glu
            100                 105                 110

Ala Asp Asp Leu Pro Thr Phe Asp Leu Ser Val Phe Phe Tyr Pro Ala
        115                 120                 125

Ala Ala Phe Ile Asp Arg Ala Leu Ser Asp His Ser Lys Ile Leu
        130                 135                 140

Val His Cys Val Met Gly Arg Ser Arg Ser Ala Thr Leu Val Leu Ala
145                 150                 155                 160

Tyr Leu Met Ile His Lys Asp Met Thr Leu Val Asp Ala Ile Gln Gln
                165                 170                 175

Val Ala Lys Asn Arg Cys Val Leu Pro Asn Arg Gly Phe Leu Lys Gln
            180                 185                 190

Leu Arg Glu Leu Asp Lys Gln Leu Val Gln Gln Arg Arg Ser Gln
        195                 200                 205

Arg Gln Asp Gly Glu Glu Glu Asp Gly Arg Glu Leu
    210                 215                 220
```

<210> SEQ ID NO 788
<211> LENGTH: 2276
<212> TYPE: DNA
<213> ORGANISM: Homo sapiens

<400> SEQUENCE: 788

```
ctgccccgcg tccggtcccg agcgggcctc cctcgggcca gcccgatgtg accgagccca      60
gcggagcctg agcaaggagc gggtccgtcg cggagccgga gggcgggagg aacatgacat     120
cgcggagatg gtttcaccca aatatcactg gtgtggaggc agaaaaccta ctgttgacaa     180
gaggagttga tggcagtttt ttggcaaggc ctagtaaaag taaccctgga gacttcacac     240
tttccgttag aagaaatgga gctgtcaccc acatcaagat tcagaacact ggtgattact     300
atgacctgta tggaggggag aaatttgcca ctttggctga gttggtccag tattacatgg     360
aacatcacgg gcaattaaaa gagaagaatg gagatgtcat tgagcttaaa tatcctctga     420
actgtgcaga tcctacctct gaaaggtggt tcatgacaga tctctctggg aaagaagcag     480
agaaattatt aactgaaaaa ggaaaacatg gtagttttct tgtacgagag agccagagcc     540
accctggaga ttttgttctt tctgtgcgca ctggtgatga caaaggggag agcaatgacg     600
gcaagtctaa agtgacccat gttatgattc gctgtcagga actgaaatac gacgttggtg     660
gaggagaacg gtttgattct ttgacagatc ttgtggaaca ttataagaag aatcctatgg     720
tggaaacatt gggtacagta ctacaactca agcagcccct taacacgact cgtataaatg     780
ctgctgaaat agaaagcaga gttcgagaac taagcaaatt agctgagacc acagataaag     840
tcaaacaagg cttttgggaa gaatttgaga cactacaaca acaggagtgc aaacttctct     900
acagccgaaa agagggtcaa aggcaagaaa acaaaaacaa aatagatat aaaaacatcc     960
tgcccttga tcataccagg gttgtcctac acgatggtga tcccaatgag cctgtttcag    1020
attacatcaa tgcaaatatc atcatgcctg aatttgaaac caagtgcaac aattcaaagc    1080
ccaaaaagag ttacattgcc acacaaggct gcctgcaaaa cacggtgaat gacttttggc    1140
ggatggtgtt ccaagaaaac tcccgagtga ttgtcatgac aacgaaagaa gtggagagag    1200
gaaagagtaa atgtgtcaaa tactggcctg atgagtatgc tctaaaagaa tatggcgtca    1260
tgcgtgttag gaacgtcaaa gaaagcgccg ctcatgacta tacgctaaga gaacttaaac    1320
tttcaaaggt tggacaaggg aatacggaga gaacggtctg gcaataccac tttcggacct    1380
ggccggacca cggcgtgccc agcgaccctg ggggcgtgct ggacttcctg gaggaggtgc    1440
accataagca ggagagcatc atggatgcag ggccggtcgt ggtgcactgc agtgctggaa    1500
ttggccggac agggacgttc attgtgattg atattcttat tgacatcatc agagagaaag    1560
gtgttgactg cgatattgac gttcccaaaa ccatccagat ggtgcggtct cagaggtcag    1620
ggatggtcca gacagaagca cagtaccgat ttatctatat ggcggtccag cattatattg    1680
aaacactaca gcgcaggatt gaagaagagc agaaaagcaa gaggaaaggg cacgaatata    1740
caaatattaa gtattctcta gcggaccaga cgagtggaga tcagagccct ctcccgcctt    1800
gtactccaac gccaccctgt gcagaaatga gagaagacag tgctagagtc tatgaaaacg    1860
tgggcctgat gcaacagcag aaaagtttca gatgagaaaa cctgccaaaa cttcagcaca    1920
gaaatagatg tggactttca ccctctccct aaaaagatca agaacagacg caagaaagtt    1980
tatgtgaaga cagaatttgg atttggaagg cttgcaatgt ggttgactac cttttgataa    2040
gcaaaatttg aaaccattta agaccactgt attttaact caacaatacc tgcttcccaa    2100
ttactcattt cctcagataa gaagaaatca tctctacaat gtagacaaca ttatatttta    2160
tagaatttgt ttgaaattga ggaagcagtt aaattgtgcg ctgtatttg cagattatgg    2220
ggattcaaat tctagtaata ggcttttta tttttatttt tatacccta accagg         2276
```

<210> SEQ ID NO 789
<211> LENGTH: 593

```
<212> TYPE: PRT
<213> ORGANISM: Homo sapiens

<400> SEQUENCE: 789

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400
```

```
Leu Lys Leu Ser Lys Val Gly Gln Gly Asn Thr Glu Arg Thr Val Trp
            405                 410                 415
Gln Tyr His Phe Arg Thr Trp Pro Asp His Gly Val Pro Ser Asp Pro
        420                 425                 430
Gly Gly Val Leu Asp Phe Leu Glu Glu Val His His Lys Gln Glu Ser
    435                 440                 445
Ile Met Asp Ala Gly Pro Val Val His Cys Ser Ala Gly Ile Gly
450                 455                 460
Arg Thr Gly Thr Phe Ile Val Ile Asp Ile Leu Ile Asp Ile Arg
465                 470                 475                 480
Glu Lys Gly Val Asp Cys Asp Ile Asp Val Pro Lys Thr Ile Gln Met
                485                 490                 495
Val Arg Ser Gln Arg Ser Gly Met Val Gln Thr Glu Ala Gln Tyr Arg
            500                 505                 510
Phe Ile Tyr Met Ala Val Gln His Tyr Ile Glu Thr Leu Gln Arg Arg
        515                 520                 525
Ile Glu Glu Glu Gln Lys Ser Lys Arg Lys Gly His Glu Tyr Thr Asn
    530                 535                 540
Ile Lys Tyr Ser Leu Ala Asp Gln Thr Ser Gly Asp Gln Ser Pro Leu
545                 550                 555                 560
Pro Pro Cys Thr Pro Thr Pro Pro Cys Ala Glu Met Arg Glu Asp Ser
                565                 570                 575
Ala Arg Val Tyr Glu Asn Val Gly Leu Met Gln Gln Gln Lys Ser Phe
            580                 585                 590
Arg

<210> SEQ ID NO 790
<211> LENGTH: 2121
<212> TYPE: DNA
<213> ORGANISM: Homo sapiens

<400> SEQUENCE: 790
cgccaggcct ggagggggt  ctgtgcgcgg ccggctggct ctgccccgcg tccggtcccg    60
agcgggcctc cctcgggcca gcccgatgtg accgagccca gcggagcctg agcaaggagc   120
gggtccgtcg cggagccgga gggcgggagg aacatgacat cgcggagatg gtttcaccca   180
aatatcactg gtgtggaggc agaaaaccta ctgttgacaa gaggagttga tggcagtttt   240
ttggcaaggc ctagtaaaag taaccctgga gacttcacac tttccgttag aagaaatgga   300
gctgtcaccc acatcaagat tcagaacact ggtgattact atgacctgta tggaggggag   360
aaatttgcca ctttggctga gttggtccag tattacatgg aacatcacgg caattaaaa    420
gagaagaatg gagatgtcat tgagcttaaa tatcctctga actgtgcaga tcctacctct   480
gaaaggtggt tcatggaca  tctctctggg aagaagcag  agaaattatt aactgaaaaa   540
ggaaaacatg gtagttttct tgtacgagag agccagagcc accctggaga ttttgttctt   600
tctgtgcgca ctggtgatga caaggggag  agcaatgacg gcaagtctaa agtgacccat   660
gttatgattc gctgtcagga actgaaatac gacgttggtg gaggagaacg gtttgattct   720
ttgacagatc ttgtggaaca ttataagaag aatcctatgg tggaaacatt gggtacagta   780
ctacaactca agcagcccct taacacgact cgtataaatg ctgctgaaat agaaagcaga   840
gttcgagaac taagcaaatt agctgagacc agataaag   tcaaacaagg cttttgggaa   900
gaatttgaga cactacaaca acaggagtgc aaacttctct acagccgaaa agagggtcaa   960
```

-continued

```
aggcaagaaa acaaaaacaa aaatagatat aaaaacatcc tgcccttgga tcataccagg    1020
gttgtcctac acgatggtga tcccaatgag cctgtttcag attacatcaa tgcaaatatc    1080
atcatgcctg aatttgaaac caagtgcaac aattcaaagc ccaaaaagag ttacattgcc    1140
acacaaggct gcctgcaaaa cacggtgaat gacttttggc ggatggtgtt ccaagaaaac    1200
tcccgagtga ttgtcatgac aacgaaagaa gtggagagag gaaagagtaa atgtgtcaaa    1260
tactggcctg atgagtatgc tctaaaagaa tatggcgtca tgcgtgttag gaacgtcaaa    1320
gaaagcgccg ctcatgacta tacgctaaga gaacttaaac tttcaaaggt tggacaaggg    1380
aatacggaga gaacggtctg gcaataccac tttcggacct ggccggacca cggcgtgccc    1440
agcgaccctg ggggcgtgct ggacttcctg gaggaggtgc accataagca ggagagcatc    1500
atggatgcag gccggtcgt ggtgcactgc agtgctggaa ttggccggac agggacgttc    1560
attgtgattg atattcttat tgacatcatc agagagaaag gtgttgactg cgatattgac    1620
gttcccaaaa ccatccagat ggtgcggtct caggagtcag ggatggtcca gacagaagca    1680
cagtaccgat ttatctatat ggcggtccag cattatattg aaacactaca gcgcaggatt    1740
gaagaagagc agaaaagcaa gaggaaaggg cacgaatata caaatattaa gtattctcta    1800
gcggaccaga cgagtggaga tcagagccct ctcccgcctt gtactccaac gccaccctgt    1860
gcagaaatga gaagacag tgctagagtc tatgaaaacg tgggcctgat gcaacagcag    1920
aaaagtttca gatgagaaaa cctgccaaaa cttcagcaca gaaatagatg tggactttca    1980
ccctctccct aaaaagatca gaacagacg caagaaagtt tatgtgaaga cagaatttgg    2040
atttggaagg cttgcaatgt ggttgactac cttttgataa gcaaaatttg aaaccattta    2100
aagaccactg tattttaact c                                              2121
```

<210> SEQ ID NO 791
<211> LENGTH: 593
<212> TYPE: PRT
<213> ORGANISM: Homo sapiens

<400> SEQUENCE: 791

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
```

-continued

```
                165                 170                 175
Leu Lys Tyr Asp Val Gly Gly Glu Arg Phe Asp Ser Leu Thr Asp
            180                 185                 190
Leu Val Glu His Tyr Lys Lys Asn Pro Met Val Glu Thr Leu Gly Thr
        195                 200                 205
Val Leu Gln Leu Lys Gln Pro Leu Asn Thr Thr Arg Ile Asn Ala Ala
    210                 215                 220
Glu Ile Glu Ser Arg Val Arg Glu Leu Ser Lys Leu Ala Glu Thr Thr
225                 230                 235                 240
Asp Lys Val Lys Gln Gly Phe Trp Glu Glu Phe Glu Thr Leu Gln Gln
                245                 250                 255
Gln Glu Cys Lys Leu Leu Tyr Ser Arg Lys Glu Gly Gln Arg Gln Glu
            260                 265                 270
Asn Lys Asn Lys Asn Arg Tyr Lys Asn Ile Leu Pro Phe Asp His Thr
        275                 280                 285
Arg Val Val Leu His Asp Gly Asp Pro Asn Glu Pro Val Ser Asp Tyr
    290                 295                 300
Ile Asn Ala Asn Ile Ile Met Pro Glu Phe Glu Thr Lys Cys Asn Asn
305                 310                 315                 320
Ser Lys Pro Lys Lys Ser Tyr Ile Ala Thr Gln Gly Cys Leu Gln Asn
                325                 330                 335
Thr Val Asn Asp Phe Trp Arg Met Val Phe Gln Glu Asn Ser Arg Val
            340                 345                 350
Ile Val Met Thr Thr Lys Glu Val Glu Arg Gly Lys Ser Lys Cys Val
        355                 360                 365
Lys Tyr Trp Pro Asp Glu Tyr Ala Leu Lys Glu Tyr Gly Val Met Arg
    370                 375                 380
Val Arg Asn Val Lys Glu Ser Ala Ala His Asp Tyr Thr Leu Arg Glu
385                 390                 395                 400
Leu Lys Leu Ser Lys Val Gly Gln Gly Asn Thr Glu Arg Thr Val Trp
                405                 410                 415
Gln Tyr His Phe Arg Thr Trp Pro Asp His Gly Val Pro Ser Asp Pro
            420                 425                 430
Gly Gly Val Leu Asp Phe Leu Glu Glu Val His His Lys Gln Glu Ser
        435                 440                 445
Ile Met Asp Ala Gly Pro Val Val His Cys Ser Ala Gly Ile Gly
    450                 455                 460
Arg Thr Gly Thr Phe Ile Val Ile Asp Ile Leu Ile Asp Ile Ile Arg
465                 470                 475                 480
Glu Lys Gly Val Asp Cys Asp Ile Asp Val Pro Lys Thr Ile Gln Met
                485                 490                 495
Val Arg Ser Gln Arg Ser Gly Met Val Gln Thr Glu Ala Gln Tyr Arg
            500                 505                 510
Phe Ile Tyr Met Ala Val Gln His Tyr Ile Glu Thr Leu Gln Arg Arg
        515                 520                 525
Ile Glu Glu Glu Gln Lys Ser Lys Arg Lys Gly His Glu Tyr Thr Asn
    530                 535                 540
Ile Lys Tyr Ser Leu Ala Asp Gln Thr Ser Gly Asp Gln Ser Pro Leu
545                 550                 555                 560
Pro Pro Cys Thr Pro Thr Pro Cys Ala Glu Met Arg Glu Asp Ser
                565                 570                 575
Ala Arg Val Tyr Glu Asn Val Gly Leu Met Gln Gln Lys Ser Phe
            580                 585                 590
```

Arg

<210> SEQ ID NO 792
<211> LENGTH: 2654
<212> TYPE: DNA
<213> ORGANISM: Homo sapiens

<400> SEQUENCE: 792

| | | | | | |
|---|---|---|---|---|---|
| agccggagct | ggagccgagg | cggcggcggg | acgcggccgg | ccggacaaat | ttcctgctag | 60 |
| gctgcggacg | agcgggcggc | aggagccggc | gcgagcggct | tcaggaaccc | acggcctctg | 120 |
| cgcgtccccg | cgaccettct | tcgcgcccgg | cgaagacagc | cgggcgcccc | ggagggcggc | 180 |
| gggcaggcgc | ccgggagatg | cggagcctcc | gctgcagcgc | gatctgcgcg | accagaccgg | 240 |
| ccccccgag | actatagcct | tcactttccc | tcggtccacc | atggagccct | tgtgtccact | 300 |
| cctgctggtg | ggttttagct | tgccgctcgc | cagggctctc | aggggcaacg | agaccactgc | 360 |
| cgacagcaac | gagacaacca | cgacctcagg | ccctccggac | ccgggcgcct | cccagccgct | 420 |
| gctggcctgg | ctgctactgc | cgctgctgct | cctcctcctc | gtgctccttc | tcgccgccta | 480 |
| cttcttcagg | ttcaggaagc | agaggaaagc | tgtggtcagc | accagcgaca | agaagatgcc | 540 |
| caacggaatc | ttggaggagc | aagagcagca | aagggtgatg | ctgctcagca | ggtcaccctc | 600 |
| agggcccaag | aagtattttc | ccatccccgt | ggagcacctg | aggaggaga | tccgtatcag | 660 |
| atccgccgac | gactgcaagc | agtttcggga | ggagttcaac | tcattgccat | ctggacacat | 720 |
| acaaggaact | tttgaactgg | caaataaaga | agaaaacaga | gaaaaaaca | gatatcccaa | 780 |
| catccttccc | aatgaccatt | ctagggtgat | tctgagccaa | ctggatggaa | ttccctgttc | 840 |
| agactacatc | aatgcttcct | acatagatgg | ttacaaagaa | aagaataaat | tcatagcagc | 900 |
| tcaaggtccc | aaacaggaaa | cggttaacga | cttctggaga | atggtctggg | agcaaaagtc | 960 |
| tgcgaccatc | gtcatgttaa | caaacttgaa | agaaaggaaa | gaggaaaagt | gccatcagta | 1020 |
| ctggcccgac | caaggctgct | ggacctatgg | aaacatccgg | gtgtgcgtgg | aggactgcgt | 1080 |
| ggttttggtc | gactacacca | tccggaagtt | ctgcatacag | ccacagctcc | ccgacggctg | 1140 |
| caaagccccc | aggctggtct | cacagctgca | cttcaccagc | tggcccgact | tcggagtgcc | 1200 |
| ttttaccccc | attgggatgc | tgaagttcct | caagaaagta | aagacgctca | accccgtgca | 1260 |
| cgctgggccc | atcgtggtcc | actgtagcgc | gggcgtgggc | cggacgggca | ccttcattgt | 1320 |
| gatcgatgcc | atgatggcca | tgatgcacgc | ggagcagaag | gtggatgtgt | ttgaatttgt | 1380 |
| gtctcgaatc | cgtaatcagc | gccctcagat | ggttcaaacg | gatatgcagt | acacgttcat | 1440 |
| ctaccaagcc | ttactcgagt | actacctcta | cggggacaca | gagctggacg | tgtcctccct | 1500 |
| ggagaagcac | ctgcagacca | tgcacggcac | caccacccac | ttcgacaaga | tcgggctgga | 1560 |
| ggaggagttc | aggaaattga | caaatgtccg | gatcatgaag | agaacatga | ggacgggcaa | 1620 |
| cttgccggca | aacatgaaga | aggccagggt | catccagatc | atcccgtatg | acttcaaccg | 1680 |
| agtgatcctt | tccatgaaaa | ggggtcaaga | atacacagac | tacatcaacg | catccttcat | 1740 |
| agacggctac | cgacagaagg | actatttcat | cgccacccag | gggcccactgg | cacacacggt | 1800 |
| tgaggacttc | tggaggatga | tctgggaatg | gaaatcccac | actatcgtga | tgctgacgga | 1860 |
| ggtgcaggag | agagagcagg | ataaatgcta | ccagtattgg | ccaaccgagg | gctcagttac | 1920 |
| tcatggagaa | ataacgattg | agataaagaa | tgatacccctt | tcagaagcca | tcagtatacg | 1980 |
| agactttctg | gtcactctca | atcagccca | ggcccgccag | gaggagcagg | tccgagtagt | 2040 |

-continued

```
gcgccagttt cacttccacg gctggcctga gatcgggatt cccgccgagg gcaaaggcat    2100
gattgacctc atcgcagccg tgcagaagca gcagcagcag acaggcaacc accccatcac    2160
cgtgcactgc agtgccggag ctgggcgaac aggtacattc atagccctca gcaacatttt    2220
ggagcgagta aaagccgagg gacttttaga tgtatttcaa gctgtgaaga gtttacgact    2280
tcagagacca catatggtgc aaaccctgga acagtatgaa ttctgctaca agtggtaca    2340 agattttatt gatatatttt ctgattatgc taatttcaaa tgaagattcc tgccttaaaa    2400 tatttttttaa tttaatggtc agtatatttt gtaaaaatca tgttaattta tttcatagtt    2460
gacattaata tcttccctaa tttctttgta tatattttgt tatgccttaa aggccacctg    2520
ctatacagtt gttaaatctt aaatatgctt tttaaaaatt ggaataatgt attaaggtca    2580
aataatatcc cataaaatat atatttctgc taatattagt aaatatctta attttttaaaa    2640 aaaaaaaaaa aaaa                                                        2654
```

<210> SEQ ID NO 793
<211> LENGTH: 700
<212> TYPE: PRT
<213> ORGANISM: Homo sapiens

<400> SEQUENCE: 793

```
Met Glu Pro Leu Cys Pro Leu Leu Leu Val Gly Phe Ser Leu Pro Leu
1               5                   10                  15

Ala Arg Ala Leu Arg Gly Asn Glu Thr Thr Ala Asp Ser Asn Glu Thr
            20                  25                  30

Thr Thr Thr Ser Gly Pro Pro Asp Pro Gly Ala Ser Gln Pro Leu Leu
        35                  40                  45

Ala Trp Leu Leu Pro Leu Leu Leu Leu Leu Val Leu Leu Leu
    50                  55                  60

Ala Ala Tyr Phe Phe Arg Phe Arg Lys Gln Arg Lys Ala Val Val Ser
65                  70                  75                  80

Thr Ser Asp Lys Lys Met Pro Asn Gly Ile Leu Glu Glu Gln Glu Gln
                85                  90                  95

Gln Arg Val Met Leu Leu Ser Arg Ser Pro Ser Gly Pro Lys Lys Tyr
            100                 105                 110

Phe Pro Ile Pro Val Glu His Leu Glu Glu Ile Arg Ile Arg Ser
        115                 120                 125

Ala Asp Asp Cys Lys Gln Phe Arg Glu Glu Phe Asn Ser Leu Pro Ser
    130                 135                 140

Gly His Ile Gln Gly Thr Phe Glu Leu Ala Asn Lys Glu Glu Asn Arg
145                 150                 155                 160

Glu Lys Asn Arg Tyr Pro Asn Ile Leu Pro Asn Asp His Ser Arg Val
                165                 170                 175

Ile Leu Ser Gln Leu Asp Gly Ile Pro Cys Ser Asp Tyr Ile Asn Ala
            180                 185                 190

Ser Tyr Ile Asp Gly Tyr Lys Glu Lys Asn Lys Phe Ile Ala Ala Gln
        195                 200                 205

Gly Pro Lys Gln Glu Thr Val Asn Asp Phe Trp Arg Met Val Trp Glu
    210                 215                 220

Gln Lys Ser Ala Thr Ile Val Met Leu Thr Asn Leu Lys Glu Arg Lys
225                 230                 235                 240

Glu Glu Lys Cys His Gln Tyr Trp Pro Asp Gln Gly Cys Trp Thr Tyr
                245                 250                 255

Gly Asn Ile Arg Val Cys Val Glu Asp Cys Val Val Leu Val Asp Tyr
```

-continued

```
                260                 265                 270
Thr Ile Arg Lys Phe Cys Ile Gln Pro Gln Leu Pro Asp Gly Cys Lys
            275                 280                 285
Ala Pro Arg Leu Val Ser Gln Leu His Phe Thr Ser Trp Pro Asp Phe
        290                 295                 300
Gly Val Pro Phe Thr Pro Ile Gly Met Leu Lys Phe Leu Lys Lys Val
305                 310                 315                 320
Lys Thr Leu Asn Pro Val His Ala Gly Pro Ile Val His Cys Ser
            325                 330                 335
Ala Gly Val Gly Arg Thr Gly Thr Phe Ile Val Ile Asp Ala Met Met
        340                 345                 350
Ala Met Met His Ala Glu Gln Lys Val Asp Val Phe Glu Phe Val Ser
            355                 360                 365
Arg Ile Arg Asn Gln Arg Pro Gln Met Val Gln Thr Asp Met Gln Tyr
        370                 375                 380
Thr Phe Ile Tyr Gln Ala Leu Leu Glu Tyr Tyr Leu Tyr Gly Asp Thr
385                 390                 395                 400
Glu Leu Asp Val Ser Ser Leu Glu Lys His Leu Gln Thr Met His Gly
            405                 410                 415
Thr Thr Thr His Phe Asp Lys Ile Gly Leu Glu Glu Glu Phe Arg Lys
        420                 425                 430
Leu Thr Asn Val Arg Ile Met Lys Glu Asn Met Arg Thr Gly Asn Leu
            435                 440                 445
Pro Ala Asn Met Lys Lys Ala Arg Val Ile Gln Ile Ile Pro Tyr Asp
        450                 455                 460
Phe Asn Arg Val Ile Leu Ser Met Lys Arg Gly Gln Glu Tyr Thr Asp
465                 470                 475                 480
Tyr Ile Asn Ala Ser Phe Ile Asp Gly Tyr Arg Gln Lys Asp Tyr Phe
            485                 490                 495
Ile Ala Thr Gln Gly Pro Leu Ala His Thr Val Glu Asp Phe Trp Arg
        500                 505                 510
Met Ile Trp Glu Trp Lys Ser His Thr Ile Val Met Leu Thr Glu Val
            515                 520                 525
Gln Glu Arg Glu Gln Asp Lys Cys Tyr Gln Tyr Trp Pro Thr Glu Gly
        530                 535                 540
Ser Val Thr His Gly Glu Ile Thr Ile Glu Ile Lys Asn Asp Thr Leu
545                 550                 555                 560
Ser Glu Ala Ile Ser Ile Arg Asp Phe Leu Val Thr Leu Asn Gln Pro
            565                 570                 575
Gln Ala Arg Gln Glu Glu Gln Val Arg Val Val Arg Gln Phe His Phe
        580                 585                 590
His Gly Trp Pro Glu Ile Gly Ile Pro Ala Glu Gly Lys Gly Met Ile
        595                 600                 605
Asp Leu Ile Ala Ala Val Gln Lys Gln Gln Gln Thr Gly Asn His
            610                 615                 620
Pro Ile Thr Val His Cys Ser Ala Gly Ala Gly Arg Thr Gly Thr Phe
625                 630                 635                 640
Ile Ala Leu Ser Asn Ile Leu Glu Arg Val Lys Ala Glu Gly Leu Leu
            645                 650                 655
Asp Val Phe Gln Ala Val Lys Ser Leu Arg Leu Gln Arg Pro His Met
        660                 665                 670
Val Gln Thr Leu Glu Gln Tyr Glu Phe Cys Tyr Lys Val Val Gln Asp
            675                 680                 685
```

Phe Ile Asp Ile Phe Ser Asp Tyr Ala Asn Phe Lys
   690             695             700

<210> SEQ ID NO 794
<211> LENGTH: 2263
<212> TYPE: DNA
<213> ORGANISM: Homo sapiens

<400> SEQUENCE: 794

| | | | | | |
|---|---|---|---|---|---|
| ctgagaggct | gggtggctgg | gcctgggaga | cacacagagg | ccaggcctta | gcgcggctca | 60 |
| gccatgagca | acaggagtag | cttttcccgg | ctcacctggt | tcaggaagca | gaggaaagct | 120 |
| gtggtcagca | ccagcgacaa | gaagatgccc | aacggaatct | ggaggagca | agagcagcaa | 180 |
| agggtgatgc | tgctcagcag | gtcacccctca | gggcccaaga | agtattttcc | catcccgtg | 240 |
| gagcacctgg | aggaggagat | ccgtatcaga | tccgccgacg | actgcaagca | gtttcgggag | 300 |
| gagttcaact | cattgccatc | tggacacata | caaggaactt | ttgaactggc | aaataaagaa | 360 |
| gaaaacagag | aaaaaaacag | atatcccaac | atccttccca | atgaccattc | tagggtgatt | 420 |
| ctgagccaac | tggatggaat | tccctgttca | gactacatca | atgcttccta | catagatggt | 480 |
| tacaaagaga | agaataaatt | catagcagct | caaggtccca | acaggaaac | ggttaacgac | 540 |
| ttctggagaa | tggtctggga | gcaaaagtct | gcgaccatcg | tcatgttaac | aaacttgaaa | 600 |
| gaaaggaaag | aggaaaagtg | ccatcagtac | tggcccgacc | aaggctgctg | gacctatgga | 660 |
| aacatccggg | tgtgcgtgga | ggactgcgtg | gttttggtcg | actacaccat | ccggaagttc | 720 |
| tgcatacagc | cacagctccc | cgacggctgc | aaagccccca | ggctggtctc | acagctgcac | 780 |
| ttcaccagct | ggcccgactt | cggagtgcct | tttaccccca | ttgggatgct | gaagttcctc | 840 |
| aagaaagtaa | agacgctcaa | ccccgtgcac | gctgggccca | tcgtggtcca | ctgtagcgcg | 900 |
| ggcgtgggcc | ggacgggcac | cttcattgtg | atcgatgcca | tgatggccat | gatgcacgcg | 960 |
| gagcagaagg | tggatgtgtt | tgaatttgtg | tctcgaatcc | gtaatcagcg | ccctcagatg | 1020 |
| gttcaaacgg | atatgcagta | cacgttcatc | taccaagcct | tactcgagta | ctacctctac | 1080 |
| ggggacacag | agctggacgt | gtcctccctg | gagaagcacc | tgcagaccat | gcacggcacc | 1140 |
| accacccact | tcgacaagat | cgggctggag | gaggagttca | ggaaattgac | aaatgtccgg | 1200 |
| atcatgaagg | agaacatgag | gacgggcaac | ttgccggcaa | acatgaagaa | ggccagggtc | 1260 |
| atccagatca | tcccgtatga | cttcaaccga | gtgatccttt | ccatgaaaag | gggtcaagaa | 1320 |
| tacacagact | acatcaacgc | atccttcata | gacggctacc | gacagaagga | ctatttcatc | 1380 |
| gccacccagg | ggccactggc | acacacggtt | gaggacttct | ggaggatgat | ctgggaatgg | 1440 |
| aaatcccaca | ctatcgtgat | gctgacggag | gtgcaggaga | gagcagga | taatgctac | 1500 |
| cagtattggc | caaccgaggg | ctcagttact | catggagaaa | taacgattga | gataaagaat | 1560 |
| gatacccttt | cagaagccat | cagtatacga | gactttctgg | tcactctcaa | tcagccccag | 1620 |
| gcccgccagg | aggagcaggt | ccgagtagtg | cgccagtttc | acttccacgg | ctggcctgag | 1680 |
| atcgggattc | ccgccgaggg | caaaggcatg | attgacctca | tcgcagccgt | gcagaagcag | 1740 |
| cagcagcaga | caggcaacca | ccccatcacc | gtgcactgca | gtgccggagc | tgggcgaaca | 1800 |
| ggtacattca | tagccctcag | caacatttg | gagcgagtaa | aagccgaggg | acttttagat | 1860 |
| gtatttcaag | ctgtgaagag | tttacgactt | cagagaccac | atatggtgca | aaccctggaa | 1920 |
| cagtatgaat | tctgctacaa | agtggtacaa | gatttttattg | atatattttc | tgattatgct | 1980 |
| aatttcaaat | gaagattcct | gccttaaaat | atttttttaat | ttaatggtca | gtatattttg | 2040 |

```
taaaaatcat gttaatttat ttcatagttg acattaatat cttccctaat ttctttgtat    2100 atatttgtt  atgccttaaa ggccacctgc tatacagttg ttaaatctta aatatgcttt    2160
ttaaaaattg gaataatgta ttaaggtcaa ataatatccc ataaaatata tatttctgct    2220
aatattagta aatatcttaa tttttaaaaa aaaaaaaaaa aaa                      2263
```

<210> SEQ ID NO 795
<211> LENGTH: 642
<212> TYPE: PRT
<213> ORGANISM: Homo sapiens

<400> SEQUENCE: 795

```
Met Ser Asn Arg Ser Ser Phe Ser Arg Leu Thr Trp Phe Arg Lys Gln
1               5                   10                  15

Arg Lys Ala Val Val Ser Thr Ser Asp Lys Lys Met Pro Asn Gly Ile
            20                  25                  30

Leu Glu Gln Glu Gln Gln Arg Val Met Leu Leu Ser Arg Ser Pro
        35                  40                  45

Ser Gly Pro Lys Lys Tyr Phe Pro Ile Pro Val Glu His Leu Glu Glu
    50                  55                  60

Glu Ile Arg Ile Arg Ser Ala Asp Asp Cys Lys Gln Phe Arg Glu Glu
65                  70                  75                  80

Phe Asn Ser Leu Pro Ser Gly His Ile Gln Gly Thr Phe Glu Leu Ala
                85                  90                  95

Asn Lys Glu Glu Asn Arg Glu Lys Asn Arg Tyr Pro Asn Ile Leu Pro
            100                 105                 110

Asn Asp His Ser Arg Val Ile Leu Ser Gln Leu Asp Gly Ile Pro Cys
        115                 120                 125

Ser Asp Tyr Ile Asn Ala Ser Tyr Ile Asp Gly Tyr Lys Glu Lys Asn
    130                 135                 140

Lys Phe Ile Ala Ala Gln Gly Pro Lys Gln Glu Thr Val Asn Asp Phe
145                 150                 155                 160

Trp Arg Met Val Trp Glu Gln Lys Ser Ala Thr Ile Val Met Leu Thr
                165                 170                 175

Asn Leu Lys Glu Arg Lys Glu Lys Cys His Gln Tyr Trp Pro Asp
            180                 185                 190

Gln Gly Cys Trp Thr Tyr Gly Asn Ile Arg Val Cys Val Glu Asp Cys
        195                 200                 205

Val Val Leu Val Asp Tyr Thr Ile Arg Lys Phe Cys Ile Gln Pro Gln
    210                 215                 220

Leu Pro Asp Gly Cys Lys Ala Pro Arg Leu Val Ser Gln Leu His Phe
225                 230                 235                 240

Thr Ser Trp Pro Asp Phe Gly Val Pro Phe Thr Pro Ile Gly Met Leu
                245                 250                 255

Lys Phe Leu Lys Lys Val Lys Thr Leu Asn Pro Val His Ala Gly Pro
            260                 265                 270

Ile Val Val His Cys Ser Ala Gly Val Gly Arg Thr Gly Thr Phe Ile
        275                 280                 285

Val Ile Asp Ala Met Met Ala Met Met His Ala Glu Gln Lys Val Asp
    290                 295                 300

Val Phe Glu Phe Val Ser Arg Ile Arg Asn Gln Arg Pro Gln Met Val
305                 310                 315                 320

Gln Thr Asp Met Gln Tyr Thr Phe Ile Tyr Gln Ala Leu Leu Glu Tyr
                325                 330                 335
```

```
Tyr Leu Tyr Gly Asp Thr Glu Leu Asp Val Ser Ser Leu Glu Lys His
            340                 345                 350
Leu Gln Thr Met His Gly Thr Thr Thr His Phe Asp Lys Ile Gly Leu
        355                 360                 365
Glu Glu Glu Phe Arg Lys Leu Thr Asn Val Arg Ile Met Lys Glu Asn
    370                 375                 380
Met Arg Thr Gly Asn Leu Pro Ala Asn Met Lys Lys Ala Arg Val Ile
385                 390                 395                 400
Gln Ile Ile Pro Tyr Asp Phe Asn Arg Val Ile Leu Ser Met Lys Arg
                405                 410                 415
Gly Gln Glu Tyr Thr Asp Tyr Ile Asn Ala Ser Phe Ile Asp Gly Tyr
            420                 425                 430
Arg Gln Lys Asp Tyr Phe Ile Ala Thr Gln Gly Pro Leu Ala His Thr
        435                 440                 445
Val Glu Asp Phe Trp Arg Met Ile Trp Glu Trp Lys Ser His Thr Ile
    450                 455                 460
Val Met Leu Thr Glu Val Gln Glu Arg Glu Gln Asp Lys Cys Tyr Gln
465                 470                 475                 480
Tyr Trp Pro Thr Glu Gly Ser Val Thr His Gly Glu Ile Thr Ile Glu
                485                 490                 495
Ile Lys Asn Asp Thr Leu Ser Glu Ala Ile Ser Ile Arg Asp Phe Leu
            500                 505                 510
Val Thr Leu Asn Gln Pro Gln Ala Arg Gln Glu Glu Gln Val Arg Val
        515                 520                 525
Val Arg Gln Phe His Phe His Gly Trp Pro Glu Ile Gly Ile Pro Ala
    530                 535                 540
Glu Gly Lys Gly Met Ile Asp Leu Ile Ala Ala Val Gln Lys Gln Gln
545                 550                 555                 560
Gln Gln Thr Gly Asn His Pro Ile Thr Val His Cys Ser Ala Gly Ala
                565                 570                 575
Gly Arg Thr Gly Thr Phe Ile Ala Leu Ser Asn Ile Leu Glu Arg Val
            580                 585                 590
Lys Ala Glu Gly Leu Leu Asp Val Phe Gln Ala Val Lys Ser Leu Arg
        595                 600                 605
Leu Gln Arg Pro His Met Val Gln Thr Leu Glu Gln Tyr Glu Phe Cys
    610                 615                 620
Tyr Lys Val Val Gln Asp Phe Ile Asp Ile Phe Ser Asp Tyr Ala Asn
625                 630                 635                 640
Phe Lys
```

<210> SEQ ID NO 796
<211> LENGTH: 844
<212> TYPE: DNA
<213> ORGANISM: Homo sapiens

<400> SEQUENCE: 796

```
gcacgagctg cagagggagg cggcactggt ctcgacgtgg ggcggccagc gatgaagccg      60
cccagttcaa tacaaacaag tgagtttgac tcatcagatg aagagcctat tgaagatgaa     120
cagactccaa ttcatatatc atggctatct ttgtcacgag tgaattgttc tcagtttctc     180
ggtttatgtg ctcttccagg ttgtaaattt aaagatgtta gaagaaatgt ccaaaaagat     240
acagaagaac taaagagctg tggtatacaa gacatatttg ttttctgcac cagagggaa     300
ctgtcaaaat atagagtccc aaaccttctg gatctctacc agcaatgtgg aattatcacc     360
```

```
catcatcatc aatcgcaga tggagggact cctgacatag ccagctgctg tgaaataatg      420
gaagagctta aacctgcct taaaaattac cgaaaaacct taatacactg ctatggagga      480
cttgggagat cttgtcttgt agctgcttgt ctcctactat acctgtctga cacaatatca    540
ccagagcaag ccatagacag cctgcgagac ctaagaggat ccggggcaat acagaccatc    600
aagcaataca attatcttca tgagtttcgg gacaaattag ctgcacatct atcatcaaga    660
gattcacaat caagatctgt atcaagataa aggaattcaa atagcatata tatgaccatg    720
tctgaaatgt cagttctcta gcataatttg tattgaaatg aaaccaccag tgttatcaac    780
ttgaatgtaa atgtacatgt gcagatattc ctaaagtttt attgacaaaa aaaaaaaaaa    840
aaaa                                                                 844
```

<210> SEQ ID NO 797
<211> LENGTH: 212
<212> TYPE: PRT
<213> ORGANISM: Homo sapiens

<400> SEQUENCE: 797

```
Met Lys Pro Pro Ser Ser Ile Gln Thr Ser Glu Phe Asp Ser Ser Asp
 1               5                  10                  15

Glu Glu Pro Ile Glu Asp Glu Gln Thr Pro Ile His Ile Ser Trp Leu
            20                  25                  30

Ser Leu Ser Arg Val Asn Cys Ser Gln Phe Leu Gly Leu Cys Ala Leu
        35                  40                  45

Pro Gly Cys Lys Phe Lys Asp Val Arg Arg Asn Val Gln Lys Asp Thr
    50                  55                  60

Glu Glu Leu Lys Ser Cys Gly Ile Gln Asp Ile Phe Val Phe Cys Thr
65                  70                  75                  80

Arg Gly Glu Leu Ser Lys Tyr Arg Val Pro Asn Leu Leu Asp Leu Tyr
                85                  90                  95

Gln Gln Cys Gly Ile Ile Thr His His His Pro Ile Ala Asp Gly Gly
            100                 105                 110

Thr Pro Asp Ile Ala Ser Cys Cys Glu Ile Met Glu Glu Leu Thr Thr
        115                 120                 125

Cys Leu Lys Asn Tyr Arg Lys Thr Leu Ile His Cys Tyr Gly Gly Leu
    130                 135                 140

Gly Arg Ser Cys Leu Val Ala Ala Cys Leu Leu Leu Tyr Leu Ser Asp
145                 150                 155                 160

Thr Ile Ser Pro Glu Gln Ala Ile Asp Ser Leu Arg Asp Leu Arg Gly
                165                 170                 175

Ser Gly Ala Ile Gln Thr Ile Lys Gln Tyr Asn Tyr Leu His Glu Phe
            180                 185                 190

Arg Asp Lys Leu Ala Ala His Leu Ser Ser Arg Asp Ser Gln Ser Arg
        195                 200                 205

Ser Val Ser Arg
    210
```

<210> SEQ ID NO 798
<211> LENGTH: 1396
<212> TYPE: DNA
<213> ORGANISM: Homo sapiens

<400> SEQUENCE: 798

```
tgactatcca gctctgagag acgggagttt ggagttgccc gctttacttt ggttgggttg      60
```

```
ggggggggcgg cgggctgttt tgttcctttt cttttttaag agttgggttt tcttttttaa    120
ttatccaaac agtgggcagc ttcctccccc acacccaagt atttgcacaa tatttgtgcg    180
gggtatgggg gtgggttttt aaatctcgtt tctcttggac aagcacaggg atctcgttct    240
cctcattttt tgggggtgtg tgggacttc tcaggtcgtg tccccagcct tctctgcagt    300
cccttctgcc ctgccgggcc cgtcgggagg cgccatggct cggatgaacc gcccggcccc    360
ggtggaggtg agctacaaac acatgcgctt cctcatcacc acaacccca ccaacgccac    420
gctcagcacc ttcattgagg acctgaagaa gtacggggct accactgtgg tgcgtgtgtg    480
tgaagtgacc tatgacaaaa cgccgctgga aaggatggc atcaccgttg tggactggcc    540
gtttgacgat ggggcgcccc cgcccggcaa ggtagtggaa gactggctga gcctggtgaa    600
ggccaagttc tgtgaggccc ccggcagctg cgtggctgtg cactgcgtgg cgggcctggg    660
ccgggctcca gtccttgtgg cgctggcgct tattgagagc gggatgaagt acgaggacgc    720
catccagttc atccgccaga gcgccgcgg agccatcaac agcaagcagc tcacctacct    780
ggagaaatac cggcccaaac agaggctgcg gttcaaagac ccacacacgc acaagacccg    840
gtgctgcgtt atgtagctca ggaccttggc tgggcctggt cgtcatgtag gtcaggacct    900
tggctggacc tggaggccct gcccagccct gctctgccca gcccagcagg ggctccaggc    960
cttggctggc ccacatcgc cttttcctcc ccgacacctc cgtgcacttg tgtccgagga   1020
gcgaggagcc cctcgggccc tgggtggcct ctgggccctt tctcctgtct ccgccactcc   1080
ctctggcggc gctggccgtg gctctgtctc tctgaggtgg gtcgggcgcc ctctgcccgc   1140
cccctcccac accagccagg ctggtctcct ctagcctgtt tgttgtgggg tgggggtata   1200
ttttgtaacc actgggcccc cagccccctct tttgcgaccc cttgtcctga cctgttctcg   1260
gcaccttaaa ttattagacc ccggggcagt caggtgctcc ggacacccga aggcaataaa   1320
acaggagccg tgaaaaaaaa aaaaaaaaa aaaaaaaaa aaaaaaaaa aaaaaaaaa     1380
aaaaaaaaaa aaaaaa                                                   1396
```

<210> SEQ ID NO 799
<211> LENGTH: 173
<212> TYPE: PRT
<213> ORGANISM: Homo sapiens

<400> SEQUENCE: 799

```
Met Ala Arg Met Asn Arg Pro Ala Pro Val Glu Val Ser Tyr Lys His
1               5                   10                  15

Met Arg Phe Leu Ile Thr His Asn Pro Thr Asn Ala Thr Leu Ser Thr
            20                  25                  30

Phe Ile Glu Asp Leu Lys Lys Tyr Gly Ala Thr Thr Val Val Arg Val
        35                  40                  45

Cys Glu Val Thr Tyr Asp Lys Thr Pro Leu Glu Lys Asp Gly Ile Thr
    50                  55                  60

Val Val Asp Trp Pro Phe Asp Asp Gly Ala Pro Pro Gly Lys Val
65                  70                  75                  80

Val Glu Asp Trp Leu Ser Leu Val Lys Ala Lys Phe Cys Glu Ala Pro
                85                  90                  95

Gly Ser Cys Val Ala Val His Cys Val Ala Gly Leu Gly Arg Ala Pro
            100                 105                 110

Val Leu Val Ala Leu Ala Leu Ile Glu Ser Gly Met Lys Tyr Glu Asp
        115                 120                 125

Ala Ile Gln Phe Ile Arg Gln Lys Arg Arg Gly Ala Ile Asn Ser Lys
```

```
          130                 135                 140
Gln Leu Thr Tyr Leu Glu Lys Tyr Arg Pro Lys Gln Arg Leu Arg Phe
145                 150                 155                 160

Lys Asp Pro His Thr His Lys Thr Arg Cys Cys Val Met
                165                 170

<210> SEQ ID NO 800
<211> LENGTH: 3925
<212> TYPE: DNA
<213> ORGANISM: Homo sapiens

<400> SEQUENCE: 800
agcggggctg cgcgaagtca tcgctgttcc agacagcgat gactcgagag cggtgggggt       60
ggcggcgcga tcggccgggc tgtaaccgtc gtctgtccgg gagcggctgg agcggcagcg      120
gcggccgggc acggcgcgag gtgacgccac agggcagcgg cggcagcgga ggcagcggcg      180
gcagcaggag acgcagcggc ggccgcagca gcagcagcaa gacggactcg tggagacgcg      240
ccgccgccgc cgccgccggg ccgggccggg tgtcgcgcgc cgaggctggg ggggagtcgt      300
cgccgccgcc gccaccgcta ccgccgccgc gccgccgcc gaggtgactg aggagagagg       360
cgcctcctcg ctcccgccac cgccggactt caatgcccag tccccagctc gccagcgttt      420
ttcgttggaa tatacgttgc acatttatgg cgattctgag tgtgagggca gacttctgcc      480
aggctcagca cagcattttc gctgacaagt gagcttggag gttctatgtg ccataattaa      540
cattgccttg aagactcctg acaccgaga ctggcctcag aaatagttgg cttttttttt       600
tttttaattg caagcatatt tcttttaatg actccagtaa aattaagcat caagtaaaca      660
agtggaaagt gacctacact tttaacttgt ctcactagtg cctaaatgta gtaaaggctg      720
cttaagtttt gtatgtagtt ggattttttg gagtccgaat atttccatct gcagaaattg      780
aggcccaaat tgaatttgga ttcaagtgga ttctaaatac tttgcttatc ttgaagagag      840
aagcttcata aggaataaac aagttgaata gagaaaacac tgattgataa taggcatttt      900 agtggtctt ttaatgtttt ctgctgtgaa acatttcaag atttattgat ttttttttt        960 cactttcccc atcacactca cacgcacgct cacacttttt atttgccata atgaaccgtc     1020
cagcccctgt ggagatctcc tatgagaaca tgcgttttct gataactcac aaccctacca     1080
atgctactct caacaagttc acagaggaac ttaagaagta tggagtgacg actttggttc     1140
gagtttgtga tgctacatat gataaagctc cagttgaaaa agaaggaatc cacgttctag     1200
attggccatt tgatgatgga gctccacccc ctaatcagat agtagatgat tggttaaacc     1260
tgttaaaaac caaatttcgt gaagagccag gttgctgtgt tgcagtgcat tgtgttgcag     1320
gattgggaag ggcacctgtg ctggttgcac ttgctttgat tgaatgtgga atgaagtacg     1380
aagatgcagt tcagtttata agacaaaaaa gaaggggagc gttcaattcc aaacagctgc     1440
tttatttgga gaaataccga cctaagatgc gattacgctt cagagatacc aatgggcatt     1500
gctgtgttca gtagaaggaa atgtaaacga aggctgactt gattgtgcca tttagaggga     1560
actcttggta cctggaaatg tgaatctgga atattacctg tgtcatcaaa gtagtgatgg     1620
attcagtact cctcaaccac tctcctaatg attggaacaa agcaaacaa aaagaaatc       1680 tctctataaa atgaataaaa tgtttaagaa agagaaaga gaaaggaat taattcagtg       1740 aaggatgatt tgctcctag ttttggagtt tgaatttctg ccaggattga attattttga      1800
aatctcctgt cttttaaac ttttcaaaa taggtctcta aggaaaacca gcagaacatt       1860
aggcctgtgc aaaaccatct gtttggggag cacactcttc cattatgctt ggcacataga     1920
```

| | | |
|---|---|---|
| tctccctgtg gtgggatttt ttttttccct tttttttgtgg gggagggttg gtggtatatt | 1980 |
| tttcccctct tttttccttc ctctcctaca tctccctttt cccccgatcc aagttgtaga | 2040 |
| tggaatagaa gcccttgttg ctgtagatgt gcgtgcagtc tggcagcctt aagcccacct | 2100 |
| gggcactttt agataaaaaa aaaaaaaaac aaaaaacaac accaaaaaaa cagcagtgat | 2160 |
| atatatattc caggtggttt ttagtctttta ctgatgaaag ggtgttcatg ttagtttctt | 2220 |
| caaaaccccta tctaatacta ggcaaagtag ccaagagcct tttgttttgt ttttattttg | 2280 |
| ataaattagt ggagaaatgg cattttaaga ggagtctctt ctcaacttac ctgagagtcg | 2340 |
| aattcttctc ttccctaacc aatgaagcta agtggttatc ccagaaactt gtcttctaaa | 2400 |
| agggaggact ccaggccatc aataaagatg tccaggcagt gagcgtactt tttacaccct | 2460 |
| gtagaattgt gggctgtagc gttactctga ttttctgtct agtatcagag aatgctggta | 2520 |
| gcttaaaatt tttatttttag gacttgtact ctgaattttc aggaaccgtc aaaggagcag | 2580 |
| cagcaaattc acatattttc gacttgagaa atgcttgtgg tatgtgtttt ccaaactgcc | 2640 |
| ccctatatgt aaagttcagt ttaaccactg attgccttgt tattactagg ttttttgaga | 2700 |
| ttaaaaaaaa aaaatccctg gtttaaaacc aacaatgatg cctagtgagt atgtgtccac | 2760 |
| aggccataac agggtagaag agagacatcg tgcaacccaa tgagtagtga agggactgtg | 2820 |
| ttgcttgtga agcggtgtag tagcattttt gcagattctt ggctgggttt agtgtactga | 2880 |
| tctagaaaag ctgttttttct gctcctttgt ggaaggcagt tatgatcagg ctgcatggac | 2940 |
| aaaagcaggta gaggggcacc atcagggggct cttgcactat tttcacctct aaatattacg | 3000 |
| tactcagtag tgccctgctt ctagggctct gaatacgggc ttaaagtcat cttgtcctgc | 3060 |
| tggaatttgc tgtgcagagc cataagcctc ccattttgtt agcgtcagct aggccaatag | 3120 |
| gaacagaccg ggaccttgtc tcacactgat gatacctcac atgttgaccg gctatgtgaa | 3180 |
| ctgcctattt cctatgctgg agttttgatt tttaactaaa cgcaaatctg tagattctct | 3240 |
| cctctcccat cccagaaaac aaaacaaaat aatgcttttc gaaattgttt ctaggacttt | 3300 |
| aaaacataat ggtatatcca aaattctttta tttcagaatg caacaataga ttccattaat | 3360 |
| atagactcaa gatcaaaaca gcatacctgc taagctaaga tagatggtgt tgattccact | 3420 |
| gggttttgat caatacaata acaaaccttt ttcctttgac atactctgaa ttttgttgtt | 3480 |
| tgggggagg gggtgtgtgt gtgtgtgtgt gtgtgtgtgt gtattgtgtg tgtgtgtgtg | 3540 |
| tgcacgcgca gtgtccatca gtatcagtgc ctgcctgagt taggaaaatt acattcctgg | 3600 |
| ttctgtattg aggagaagga tgtataaagc aacatgaaac attagccctc cttttatttt | 3660 |
| aaagactaat gttaattgtt cttaaaactg gatttttttt ccttaaagca attttttttct | 3720 |
| tttcgattta atgaagtatt gctagctgaa gccagtttga catagagaga tgtcagattg | 3780 |
| atttgaaagg tgtgcagcct gatttaaaac caaacccctga acccttttaa agaacaataa | 3840 |
| aacatatttt acacgctcaa aaaaaaaaaa aaaaaaaaa aaaaaaaaa aaaaaaaaa | 3900 |
| aaaaaaaaaa aaaaaaaaaa aaaaa | 3925 |

<210> SEQ ID NO 801
<211> LENGTH: 167
<212> TYPE: PRT
<213> ORGANISM: Homo sapiens

<400> SEQUENCE: 801

Met Asn Arg Pro Ala Pro Val Glu Ile Ser Tyr Glu Asn Met Arg Phe
1               5                   10                  15

```
Leu Ile Thr His Asn Pro Thr Asn Ala Thr Leu Asn Lys Phe Thr Glu
         20                  25                  30

Glu Leu Lys Lys Tyr Gly Val Thr Thr Leu Val Arg Val Cys Asp Ala
             35                  40                  45

Thr Tyr Asp Lys Ala Pro Val Glu Lys Glu Gly Ile His Val Leu Asp
 50                  55                  60

Trp Pro Phe Asp Asp Gly Ala Pro Pro Asn Gln Ile Val Asp Asp
 65                  70                  75                  80

Trp Leu Asn Leu Leu Lys Thr Lys Phe Arg Glu Glu Pro Gly Cys Cys
                 85                  90                  95

Val Ala Val His Cys Val Ala Gly Leu Gly Arg Ala Pro Val Leu Val
                100                 105                 110

Ala Leu Ala Leu Ile Glu Cys Gly Met Lys Tyr Glu Asp Ala Val Gln
                115                 120                 125

Phe Ile Arg Gln Lys Arg Arg Gly Ala Phe Asn Ser Lys Gln Leu Leu
         130                 135                 140

Tyr Leu Glu Lys Tyr Arg Pro Lys Met Arg Leu Arg Phe Arg Asp Thr
145                 150                 155                 160

Asn Gly His Cys Cys Val Gln
                165
```

<210> SEQ ID NO 802
<211> LENGTH: 1785
<212> TYPE: DNA
<213> ORGANISM: Homo sapiens

<400> SEQUENCE: 802

```
atggcagcgg agtcagggga actaatcggg gcttgtgagt tcatgaaaga tcggttatat        60
tttgctactt taaggaatag accaaaaagc acagtaaata cccactattt ctccatcgat       120
gaggagctgg tctatgaaaa tttctatgca gattttggac cgctgaactt ggcaatggtg       180
tacagatatt gctgcaaact aaacaagaaa ctaaaatcat acagtttgtc aagaaagaaa       240
atagtgcact acacctgttt tgaccaacgg aaaagagcaa atgcagcatt tttgataggt       300
gcctatgcag taatctattt aaagaagaca ccagaagaag cctacagagc actcctgtct       360
ggctcaaacc cccctatct tccattcagg gatgcttcct ttggaaattg cacttacaat       420
ctcaccattc tcgactgttt gcagggaatc agaaagggat acaacatgg attttttgac       480
tttgagacat tgatgtgga tgaatatgaa cattatgagc gagttgaaaa tggtgacttc       540
aactggattg ttccaggaaa attttagca tttagtggac acatcctaa agcaaaatt        600
gagaatggtt atcctcttca cgcccctgaa gcctactttc cttatttcaa aaagcataat       660
gtgactgcag ttgtgaggct aaacaaaaag atttatgagg caaagcgctt cacagacgct       720
ggcttcgagc actatgacct cttcttcata gatggcagca cacccagtga acatcgtg        780
cgaaggttcc tgaacatctg tgagaacacc gaaggggcca tcgccgttca ctgcaaagct       840
ggtcttggaa gaacagggac attgatagcc tgttatgtaa tgaaacacta caggtttaca       900
catgctgaaa taattgcttg gattagaata tgccggccag gctctattat aggaccccag       960
cagcacttcc tggaagaaaa acaagcatcg ttgtgggtcc aaggagacat tttccgatcc      1020
aaactgaaaa atcgaccatc cagtgaagga agtattaata aaattcttc tggcctagat       1080
gatatgtcta ttggtggaaa tcttttcaaaa acacaaaaca tggaacgatt tggagaggat      1140
aacttagaag atgatgatgt ggaaatgaaa aatggtataa cccagggaga caaactacgt      1200
```

-continued

```
gccttaaaaa gtcagagaca gccacgtacc tcaccatcct gtgcatttag gtcagatgat  1260
acaaaaggac atccaagagc agtgtcccag cctttcagat taagttcatc cctgcaagga  1320
tctgcagtta ctttgaagac atcaaaaatg gcactgtccc cttcagcaac ggccaagagg  1380
atcaacagaa cttctttgtc ttcgggtgcc actgtaagaa gcttttccat aaactcccgg  1440
ctagccagtt tctagggaa cttgaatgct gcaacagatg atccagagaa caaaagacc   1500 tcctcatcct ctaaggcagg cttcacagcc agcccgttta ccaacctctt gaatggcagc  1560
tcccagccaa ctaccagaaa ttaccctgag ctcaacaata atcagtacaa cagaagcagc  1620
aacagcaacg ggggcaacct gaacagcccc ccaggccccc acagcgccaa dacagaggag  1680
cacaccacca tcctccgacc ctcctacacc gggctttctt cttcttcagc gagattcctg  1740
agccgttcta tcccttccct tcagtctgaa tatgttcatt actaa                  1785
```

<210> SEQ ID NO 803
<211> LENGTH: 594
<212> TYPE: PRT
<213> ORGANISM: Homo sapiens

<400> SEQUENCE: 803

```
Met Ala Ala Glu Ser Gly Glu Leu Ile Gly Ala Cys Glu Phe Met Lys
1               5                   10                  15

Asp Arg Leu Tyr Phe Ala Thr Leu Arg Asn Arg Pro Lys Ser Thr Val
            20                  25                  30

Asn Thr His Tyr Phe Ser Ile Asp Glu Glu Leu Val Tyr Glu Asn Phe
        35                  40                  45

Tyr Ala Asp Phe Gly Pro Leu Asn Leu Ala Met Val Tyr Arg Tyr Cys
    50                  55                  60

Cys Lys Leu Asn Lys Lys Leu Lys Ser Tyr Ser Leu Ser Arg Lys Lys
65                  70                  75                  80

Ile Val His Tyr Thr Cys Phe Asp Gln Arg Lys Arg Ala Asn Ala Ala
                85                  90                  95

Phe Leu Ile Gly Ala Tyr Ala Val Ile Tyr Leu Lys Lys Thr Pro Glu
            100                 105                 110

Glu Ala Tyr Arg Ala Leu Leu Ser Gly Ser Asn Pro Pro Tyr Leu Pro
        115                 120                 125

Phe Arg Asp Ala Ser Phe Gly Asn Cys Thr Tyr Asn Leu Thr Ile Leu
    130                 135                 140

Asp Cys Leu Gln Gly Ile Arg Lys Gly Leu Gln His Gly Phe Phe Asp
145                 150                 155                 160

Phe Glu Thr Phe Asp Val Asp Glu Tyr Glu His Tyr Glu Arg Val Glu
                165                 170                 175

Asn Gly Asp Phe Asn Trp Ile Val Pro Gly Lys Phe Leu Ala Phe Ser
            180                 185                 190

Gly Pro His Pro Lys Ser Lys Ile Glu Asn Gly Tyr Pro Leu His Ala
        195                 200                 205

Pro Glu Ala Tyr Phe Pro Tyr Phe Lys Lys His Asn Val Thr Ala Val
    210                 215                 220

Val Arg Leu Asn Lys Lys Ile Tyr Glu Ala Lys Arg Phe Thr Asp Ala
225                 230                 235                 240

Gly Phe Glu His Tyr Asp Leu Phe Phe Ile Asp Gly Ser Thr Pro Ser
                245                 250                 255

Asp Asn Ile Val Arg Arg Phe Leu Asn Ile Cys Glu Asn Thr Glu Gly
            260                 265                 270
```

```
Ala Ile Ala Val His Cys Lys Ala Gly Leu Gly Arg Thr Gly Thr Leu
        275                 280                 285
Ile Ala Cys Tyr Val Met Lys His Tyr Arg Phe Thr His Ala Glu Ile
        290                 295                 300
Ile Ala Trp Ile Arg Ile Cys Arg Pro Gly Ser Ile Gly Pro Gln
305                 310                 315                 320
Gln His Phe Leu Glu Glu Lys Gln Ala Ser Leu Trp Val Gln Gly Asp
                325                 330                 335
Ile Phe Arg Ser Lys Leu Lys Asn Arg Pro Ser Ser Glu Gly Ser Ile
            340                 345                 350
Asn Lys Ile Leu Ser Gly Leu Asp Asp Met Ser Ile Gly Gly Asn Leu
        355                 360                 365
Ser Lys Thr Gln Asn Met Glu Arg Phe Gly Glu Asp Asn Leu Glu Asp
        370                 375                 380
Asp Asp Val Glu Met Lys Asn Gly Ile Thr Gln Gly Asp Lys Leu Arg
385                 390                 395                 400
Ala Leu Lys Ser Gln Arg Gln Pro Arg Thr Ser Pro Ser Cys Ala Phe
                405                 410                 415
Arg Ser Asp Asp Thr Lys Gly His Pro Arg Ala Val Ser Gln Pro Phe
            420                 425                 430
Arg Leu Ser Ser Ser Leu Gln Gly Ser Ala Val Thr Leu Lys Thr Ser
        435                 440                 445
Lys Met Ala Leu Ser Pro Ser Ala Thr Ala Lys Arg Ile Asn Arg Thr
        450                 455                 460
Ser Leu Ser Ser Gly Ala Thr Val Arg Ser Phe Ser Ile Asn Ser Arg
465                 470                 475                 480
Leu Ala Ser Ser Leu Gly Asn Leu Asn Ala Ala Thr Asp Asp Pro Glu
                485                 490                 495
Asn Lys Lys Thr Ser Ser Ser Lys Ala Gly Phe Thr Ala Ser Pro
            500                 505                 510
Phe Thr Asn Leu Leu Asn Gly Ser Ser Gln Pro Thr Thr Arg Asn Tyr
        515                 520                 525
Pro Glu Leu Asn Asn Gln Tyr Asn Arg Ser Ser Asn Ser Asn Gly
        530                 535                 540
Gly Asn Leu Asn Ser Pro Pro Gly Pro His Ser Ala Lys Thr Glu Glu
545                 550                 555                 560
His Thr Thr Ile Leu Arg Pro Ser Tyr Thr Gly Leu Ser Ser Ser Ser
                565                 570                 575
Ala Arg Phe Leu Ser Arg Ser Ile Pro Ser Leu Gln Ser Glu Tyr Val
            580                 585                 590
His Tyr
```

<210> SEQ ID NO 804
<211> LENGTH: 2646
<212> TYPE: DNA
<213> ORGANISM: Homo sapiens
<220> FEATURE:
<221> NAME/KEY: misc_feature
<222> LOCATION: 2300
<223> OTHER INFORMATION: n = A,T,C or G

<400> SEQUENCE: 804

```
atgaagcgga aaagcgagcg gcggtcgagc tgggccgccg cgccccctg ctcgcggcgc        60 tgctcgtcga cctcgccggg tgtgaagaag atccgcagct ccacgcagca agacccgcgc       120
cgccgggacc cccaggacga cgtgtacctg gacatcaccg atcgcctttg ttttgccatt      180
```

-continued

| | |
|---|---|
| ctctacagca gaccaaagag tgcatcaaat gtacattatt tcagcataga taatgaactt | 240 |
| gaatatgaga acttctacgc agattttgga ccactcaatc tggcaatggt ttacagatat | 300 |
| tgttgcaaga tcaataagaa attaaagtcc attacaatgt taaggaagaa aattgttcat | 360 |
| tttactggct ctgatcagag aaaacaagca aatgctgcct tccttgttgg atgctacatg | 420 |
| gttatatatt tggggagaac cccagaagaa gcatatagaa tattaatctt tggagagaca | 480 |
| tcctatattc ctttcagaga tgctgcctat ggaagttgca atttctacat tacacttctt | 540 |
| gactgttttc atgcagtaaa gaaggcaatg cagtatggct tccttaattt caactcattt | 600 |
| aaccttgatg aatatgaaca ctatgaaaaa gcagaaaatg gagatttaaa ttggataata | 660 |
| ccagaccgat ttattgcctt ctgtggacct cattcaagag ccagacttga aagtggttac | 720 |
| caccaacatt ctcctgagac ttatattcaa tattttaaga atcacaatgt tactaccatt | 780 |
| attcgtctga ataaaaggat gtatgatgcc aaacgcttta cggatgctgg cttcgatcac | 840 |
| catgatcttt tctttgcgga tggcagcacc cctactgatg ccattgtcaa agaattccta | 900 |
| gatatctgtg aaaatgctga gggtgccatt gcagtacatt gcaaagctgg ccttggtcgc | 960 |
| acgggcactc tgatagcctg ctacatcatg aagcattaca ggatgacagc agccgagacc | 1020 |
| attgcgtggg tcaggatctg cagacctggc tcggtgattg ggcctcagca gcagttttttg | 1080 |
| gtgatgaagc aaaccaacct ctggctggaa ggggactatt ttcgtcagaa gttaaagggg | 1140 |
| caggagaatg gacaacacag agcagccttc tccaaacttc tctctggcgt tgatgacatt | 1200 |
| tccataaatg gggtcgagaa tcaagatcag caagaacccg aaccgtacag tgatgatgac | 1260 |
| gaaatcaatg gagtgacaca aggtgataga cttcgggcct tgaaaagcag aagacaatcc | 1320 |
| aaaacaaacg ctattcctct cactctctcc atttcaagga ctaaaacagt cttgcgttaa | 1380 |
| gtaaaaacct gtgaccagag ctgaaggaag actctaggac tgaaaactgc aacagaaatt | 1440 |
| agcacaattt gaaaacaaaa caaaattgca aaagccttag ttgcttttc cacctaagaa | 1500 |
| gttgatcaat ggagaaaatg tccactggag tttgaataat gaactttgag tttgggtgca | 1560 |
| agcaaatgac tcagaagg gtccagctct caagctgaat gacaaacatg ctgttgtaaa | 1620 |
| tttagtctca ggtgtaaata cccaagccct ctggtaccca gggagctggc tggtctgtgg | 1680 |
| tgcatgtgtg tccctgtgat ggcaatcatt gtagttgctg gccttcagaa gaattgagga | 1740 |
| tctgatggag gttttttatg tatttatttt ctgttcacct tgtgaccctg tgtcaaaatt | 1800 |
| tataaagata caaaggcat tactgaaatg gtactttctg taatttgata ctatttggct | 1860 |
| taatcatctt cacttgacta tttgtaatac tgttgtaatg ttaactctgt taagtaccca | 1920 |
| agctgcttgt cttccaccaa agagtgcttt attaacaaga atctgtgaaa atcacattta | 1980 |
| aacactgttg catgttgtaa gaccaggtgg taccttagta acctaaaact tgcaagagaa | 2040 |
| tattaatggt agctttagaa gactcaggag gagaaactga cttcagagtt ggaagatgtt | 2100 |
| gcaagtcgtt cctttttctg tccttcaggg actgaagaac tgggaggctg cccattgttt | 2160 |
| ggttgccagt catacaaatt aaaatcatat ttccttccat gaatggaaga aacacactat | 2220 |
| tggttttttcc ccttggaaac agcaatccca ataatgtcg gcttacaaaa aaaaaagtta | 2280 |
| ccacttttt agagtccttn ccctgtaaca ttgattttt ttttcccta tgagatccac | 2340 |
| ctaaggccat tgacgtggcc tgcgatctca gtgacaatga tctgctttct ggatctcact | 2400 |
| gttgcctttg gttagggaac acagagtgct ctcccgcag ccctactgga acacagcaga | 2460 |
| gtctgtgcca tgaagcagtt acagaaacag aattgatgtg ctgctaaaaa aaaaaaaaaa | 2520 |

```
aatgggccc gggggggcgt ccgccggccc tgcgggccgc cggtgaaata ccactactct    2580
gatcgttttt tcactgaccc ggtgaggcgg ggggggcgagc cccgagggggc tctcgcttct   2640 ggcgcg                                                              2646
```

<210> SEQ ID NO 805
<211> LENGTH: 459
<212> TYPE: PRT
<213> ORGANISM: Homo sapiens

<400> SEQUENCE: 805

```
Met Lys Arg Lys Ser Glu Arg Ser Ser Trp Ala Ala Pro Pro
1               5                   10                  15

Cys Ser Arg Arg Cys Ser Ser Thr Ser Pro Gly Val Lys Lys Ile Arg
                20                  25                  30

Ser Ser Thr Gln Gln Asp Pro Arg Arg Asp Pro Gln Asp Asp Val
                35                  40                  45

Tyr Leu Asp Ile Thr Asp Arg Leu Cys Phe Ala Ile Leu Tyr Ser Arg
        50                  55                  60

Pro Lys Ser Ala Ser Asn Val His Tyr Phe Ser Ile Asp Asn Glu Leu
65                  70                  75                  80

Glu Tyr Glu Asn Phe Tyr Ala Asp Phe Gly Pro Leu Asn Leu Ala Met
                85                  90                  95

Val Tyr Arg Tyr Cys Cys Lys Ile Asn Lys Lys Leu Lys Ser Ile Thr
                100                 105                 110

Met Leu Arg Lys Lys Ile Val His Phe Thr Gly Ser Asp Gln Arg Lys
            115                 120                 125

Gln Ala Asn Ala Ala Phe Leu Val Gly Cys Tyr Met Val Ile Tyr Leu
        130                 135                 140

Gly Arg Thr Pro Glu Glu Ala Tyr Arg Ile Leu Ile Phe Gly Glu Thr
145                 150                 155                 160

Ser Tyr Ile Pro Phe Arg Asp Ala Ala Tyr Gly Ser Cys Asn Phe Tyr
                165                 170                 175

Ile Thr Leu Leu Asp Cys Phe His Ala Val Lys Lys Ala Met Gln Tyr
            180                 185                 190

Gly Phe Leu Asn Phe Asn Ser Phe Asn Leu Asp Glu Tyr Glu His Tyr
        195                 200                 205

Glu Lys Ala Glu Asn Gly Asp Leu Asn Trp Ile Ile Pro Asp Arg Phe
    210                 215                 220

Ile Ala Phe Cys Gly Pro His Ser Arg Ala Arg Leu Glu Ser Gly Tyr
225                 230                 235                 240

His Gln His Ser Pro Glu Thr Tyr Ile Gln Tyr Phe Lys Asn His Asn
                245                 250                 255

Val Thr Thr Ile Ile Arg Leu Asn Lys Arg Met Tyr Asp Ala Lys Arg
            260                 265                 270

Phe Thr Asp Ala Gly Phe Asp His His Asp Leu Phe Phe Ala Asp Gly
        275                 280                 285

Ser Thr Pro Thr Asp Ala Ile Val Lys Glu Phe Leu Asp Ile Cys Glu
    290                 295                 300

Asn Ala Glu Gly Ala Ile Ala Val His Cys Lys Ala Gly Leu Gly Arg
305                 310                 315                 320

Thr Gly Thr Leu Ile Ala Cys Tyr Ile Met Lys His Tyr Arg Met Thr
                325                 330                 335

Ala Ala Glu Thr Ile Ala Trp Val Arg Ile Cys Arg Pro Gly Ser Val
            340                 345                 350
```

```
Ile Gly Pro Gln Gln Gln Phe Leu Val Met Lys Gln Thr Asn Leu Trp
        355                 360                 365

Leu Glu Gly Asp Tyr Phe Arg Gln Lys Leu Lys Gly Gln Glu Asn Gly
    370                 375                 380

Gln His Arg Ala Ala Phe Ser Lys Leu Leu Ser Gly Val Asp Asp Ile
385                 390                 395                 400

Ser Ile Asn Gly Val Glu Asn Gln Asp Gln Gln Glu Pro Glu Pro Tyr
                405                 410                 415

Ser Asp Asp Glu Ile Asn Gly Val Thr Gln Gly Asp Arg Leu Arg
            420                 425                 430

Ala Leu Lys Ser Arg Arg Gln Ser Lys Thr Asn Ala Ile Pro Leu Thr
        435                 440                 445

Leu Ser Ile Ser Arg Thr Lys Thr Val Leu Arg
        450                 455

<210> SEQ ID NO 806
<211> LENGTH: 3415
<212> TYPE: DNA
<213> ORGANISM: Rattus norvegicus

<400> SEQUENCE: 806
ctcgcgggac acagagagag aagcaccggt gcttgtgcct ggcgcctgcc gagtccccga      60
cgctcgcccg tccgcgccgc tgcccgtggc ggccgcgtct ctgaaccgcg ggtcgtgtt     120 tgtgtttgac ccgcgggcgc tggcgcgtgg cacgggctga agcgtgcagc ggggcggggg     180
ccggcgcacg gaggcggagg aagacgagcg ggagtccggg caggcccggc ggcgccatgg     240
aactgggccc ggagcccccc caccgccgcc gcctgctctt cacttgcagc cccactcctg     300
cgccgcagcc cacggggaag gtgcagtttg cgcgcgtcac gtgctggcgga ctgtcccctg     360 tcaccaacct gacggtcacc atggaccagc tggaagggct gggcagtgac tatgagaaac     420
caatggacgt gagaaatagc agcagtctac agagaatggg ctcctctgaa tcgactgatt     480
caggtttctg tctagattct cctgggccct tggacagtaa agaaaacctt gaaatttccc     540
tgaggagaat aaattgccta cctcagaagc tcttggggtg tagcccagcg ctaaagagga     600
gccattctga ttctctagac acgacatct ttcaactcat tgaccaggat gaaaataaag     660
aaaatgaagc atttgaattt aaaaagccaa taagacctgc atctcgtggc tgcctgaatg     720
ctcacgttca cgaggaaagt aaggacccct ttacacacag gcagaattca gccccagctc     780
ggatgctgtc ttcaaatgaa agtgacatta gtgaatcagg aaatttcagt cctctttta     840 caccccagtc acctgtgaaa gcagtttgt ctgatgagga tgatggcttc atagaccttc     900
tggatggaga gaatctgaag aatgatgagg agaccccgtc gtgcatgtca gcctctggaa     960 ccgctccct tgtcatgaga agacctacaa accttgccga tcgatgtgga ctgtttgact    1020
cccctccccc gtgcagctcc accagcagct gcagcactcg ggcagtgaag agagcagacc    1080
gatctcatga ggagtctcct cgaggtacaa agcggaggaa gagcagtgag gccagtccag    1140
tgaaggcaga tgttccggag ccaacgcagc ttccacacca gtctctctcc ctgacatctt    1200
tccccaaagg aaccattgag aacattttcc acagtgaccc aagagaacctt ataggggatt    1260 tctccaaggg ttacctcttt catacggtct ctgggaagca tcaggattgt gaaatatattt    1320 ctccagaaat tatggcatct gttttgaatg gcaagtttgc caatctcatt aaagagtttg    1380
ttatcattga ctgccgatac ccatatgaat atgaaggagg gcacatcaag ggtgccgtga    1440
acttgcacat ggaagaagag gttgaggagt tcttactcaa gaaacctatc gtgcccgctg    1500
```

```
acggcaagcg tgtcattgtc gtgttccact gtgagttctc ctctgagaga ggccctcgga    1560
tgtgccgata tgtacgggaa cgagataggc ttggcaatga ataccccaaa ctccactacc    1620
ctgagctgta tgtcctgaag gggggataca aggagttctt tttgaaatgc cagtctcact    1680
gtgaaccccc cagctaccga ccgatgcacc atgaagactt taaagaagac ctaaagaagt    1740
tccgcaccaa gagccggacc tgggcagggg agaagagcaa aagggagatg tacagtcgcc    1800
tgaagaagct ttgaggccaa atggcagtga cctgagcttc cctccgccct gtccctttgt    1860
ccctttgctg tagagcagta agcaaagggg ccagctatac ggcacctgga ccctggagaa    1920
aaacctgggc cttccatgcc ttgaacctcc tacactccca ggttggagcc caggcatcct    1980
gccgtcacac tcttctgtga gagtccttcc ctgtcaggac tgtctgccaa gctggacaa     2040
gctcggcaca ggctggcaca ggctcgagtc tagtctggaa cgccacgtca ggctgctccg    2100
actaagcatc ccctgaagaa gtgcccaggc ctctcatgag gggagagaag ccactgaagt    2160
gctgctggcc aaataccaaa gataggctgg aaggggagag gtcctcatgg atgactcttt    2220
aatttattca gcctcatcaa ttattttatt attgttttaa ttcctcaaga cttttacttt    2280
actgcttcaa agtcaaaata ctgccattct aggtagagtt ttatcatcct aggaactacc    2340
tctactttta atttaaaaaa aaaacatggg gcagggataa gaaaaaaggc aaacctgtta    2400
agtgtgggca gcgcaaggaa ctcagtcacc cctaggaggc gctgtagact ggtattgctg    2460
ctattcaaag tcaaggactg agatgctggt cagagcctgc accaaccaga tccaggcttg    2520
gctacaggac ataagctaac cttcccagac ctacttctgc cctttgtgag ttcctttggg    2580
gagagtcttg tctgtactcc tggtcccagg tccccgtgac agtgactggt gtgggagttg    2640
caggaaggca catcaagcca cccccaggcc agtactggaa tgttgaagtg taccccaagg    2700
tgggagtggg gaggcatgga aaagtggagt ccacagagta agggaggagc atgcccactg    2760
aatgtccttt agaaaaaaaa aaaagtcatt ttatgagtca gagtatccaa tcagtgttgg    2820
gtgggcacct aagcttgagc aggggcggg aagcccgggc tgttacagac gactgtagaa    2880
tttctcagga gggcgtagta aattttgaag tcaaaagttc tgggtttcat catgttttaa    2940
ttgagggaca gagtggtgaa acacatcagt tacccctaa tctaaccccg tggaagtgag    3000
gctctgggga atgcctccca tctaaggagc tggcccgttt tgattctgtc agtgtcctcg    3060
ggcaccagcc tccctgccat ctgtgctcca ttggggtcat gccaggtttt cttaggaag    3120
agtctcccct cttaacctct gctttctatt ctggggtgg ggagggaatc aatgatattg    3180
aagatggcta gttgctttgt taagggtttg agtttgcatt tggctataaa acaaatcttg    3240
ttaaaaatat gtggagagca agggaatgag cagcctcttc ttcggtgtgt tgaagtatgt    3300
cctagttttc ccctggtctg gtttgtagag attctgttag ttgaatgcct tcaaggagaa    3360
tgaatggctt tcagattgta ccagcttagc tagcattgtt aaccagctgc tgcag         3415
```

<210> SEQ ID NO 807
<211> LENGTH: 525
<212> TYPE: PRT
<213> ORGANISM: Rattus norvegicus

<400> SEQUENCE: 807

Met Glu Leu Gly Pro Glu Pro Pro His Arg Arg Leu Leu Phe Thr
1               5                  10                  15

Cys Ser Pro Thr Pro Ala Pro Gln Pro Thr Gly Lys Val Gln Phe Gly
            20                  25                  30

-continued

```
Ala Ser Arg Ala Gly Gly Leu Ser Pro Val Thr Asn Leu Thr Val Thr
    35                  40                  45

Met Asp Gln Leu Glu Gly Leu Gly Ser Asp Tyr Glu Lys Pro Met Asp
    50                  55                  60

Val Arg Asn Ser Ser Leu Gln Arg Met Gly Ser Ser Glu Ser Thr
65                  70                  75                  80

Asp Ser Gly Phe Cys Leu Asp Ser Pro Gly Pro Leu Asp Ser Lys Glu
                85                  90                  95

Asn Leu Glu Ile Ser Leu Arg Arg Ile Asn Cys Leu Pro Gln Lys Leu
                100                 105                 110

Leu Gly Cys Ser Pro Ala Leu Lys Arg Ser His Ser Asp Ser Leu Asp
        115                 120                 125

His Asp Ile Phe Gln Leu Ile Asp Gln Asp Glu Asn Lys Glu Asn Glu
    130                 135                 140

Ala Phe Glu Phe Lys Lys Pro Ile Arg Pro Ala Ser Arg Gly Cys Leu
145                 150                 155                 160

Asn Ala His Val His Glu Glu Ser Lys Asp Pro Phe Thr His Arg Gln
                165                 170                 175

Asn Ser Ala Pro Ala Arg Met Leu Ser Ser Asn Glu Ser Asp Ile Ser
                180                 185                 190

Glu Ser Gly Asn Phe Ser Pro Leu Phe Thr Pro Gln Ser Pro Val Lys
        195                 200                 205

Ala Ser Leu Ser Asp Glu Asp Asp Gly Phe Ile Asp Leu Leu Asp Gly
    210                 215                 220

Glu Asn Leu Lys Asn Asp Glu Glu Thr Pro Ser Cys Met Ser Ser Leu
225                 230                 235                 240

Trp Thr Ala Pro Leu Val Met Arg Arg Pro Thr Asn Leu Ala Asp Arg
                245                 250                 255

Cys Gly Leu Phe Asp Ser Pro Ser Pro Cys Ser Ser Thr Ser Ser Cys
                260                 265                 270

Ser Thr Arg Ala Val Lys Arg Ala Asp Arg Ser His Glu Glu Ser Pro
        275                 280                 285

Arg Gly Thr Lys Arg Lys Ser Ser Glu Ala Ser Pro Val Lys Ala
    290                 295                 300

Asp Val Pro Glu Pro Thr Gln Leu Pro His Gln Ser Leu Ser Leu Thr
305                 310                 315                 320

Ser Phe Pro Lys Gly Thr Ile Glu Asn Ile Phe His Ser Asp Pro Arg
                325                 330                 335

Asp Leu Ile Gly Asp Phe Ser Lys Gly Tyr Leu Phe His Thr Val Ser
                340                 345                 350

Gly Lys His Gln Asp Leu Lys Tyr Ile Ser Pro Glu Ile Met Ala Ser
        355                 360                 365

Val Leu Asn Gly Lys Phe Ala Asn Leu Ile Lys Glu Phe Val Ile Ile
    370                 375                 380

Asp Cys Arg Tyr Pro Tyr Glu Tyr Glu Gly Gly His Ile Lys Gly Ala
385                 390                 395                 400

Val Asn Leu His Met Glu Glu Val Glu Phe Leu Leu Lys Lys
                405                 410                 415

Pro Ile Val Pro Ala Asp Gly Lys Arg Val Ile Val Phe His Cys
                420                 425                 430

Glu Phe Ser Ser Glu Arg Gly Pro Arg Met Cys Arg Tyr Val Arg Glu
        435                 440                 445

Arg Asp Arg Leu Gly Asn Glu Tyr Pro Lys Leu His Tyr Pro Glu Leu
```

```
                  450              455              460
Tyr Val Leu Lys Gly Gly Tyr Lys Glu Phe Phe Leu Lys Cys Gln Ser
465              470              475              480

His Cys Glu Pro Pro Ser Tyr Arg Pro Met His His Glu Asp Phe Lys
                485              490              495

Glu Asp Leu Lys Lys Phe Arg Thr Lys Ser Arg Thr Trp Ala Gly Glu
            500              505              510

Lys Ser Lys Arg Glu Met Tyr Ser Arg Leu Lys Lys Leu
            515              520              525

<210> SEQ ID NO 808
<211> LENGTH: 31868
<212> TYPE: DNA
<213> ORGANISM: Homo sapiens

<400> SEQUENCE: 808
```

| | | | | | |
|---|---|---|---|---|---|
| ccagggtctg | tgagccctcc | agagttgggc | cctggtggtc | gagtccagtc | ctgggggtca | 60 |
| ttgcattccc | tccctcatta | taaaatgggg | cctggaggcc | cggggcggaa | gaaagggtc | 120 |
| cacaatactg | cacggttaga | ggccgagcca | aggctggatc | cggccagacc | tccacaggtc | 180 |
| ttccttagcc | tccacattgc | ctcagagtgt | ggggcgcccg | gctgggggcg | aggtagcgga | 240 |
| ggcccaaagg | gggccgaagc | taactggacg | gcagctcgcg | atgggaacta | cgcttcccag | 300 |
| catgcgacgg | ggcaaagggg | cctttcagcc | gcgagcagcg | cctcgcaggt | tctgctggga | 360 |
| gttttcattg | acctctgctc | cccctctcat | tttgatcccc | gctcttctgc | tctgggctcc | 420 |
| gccccttct | gagagccgat | gacctggcag | agtcccgcga | gccgctttct | tcttcccctc | 480 |
| tcattggccc | agcctagctg | ccattcggtt | gagaggagga | gaagttgctt | actgattggt | 540 |
| ggattccgtt | tggcgccaac | taggaaaggg | gggcggggca | gcagctggcc | ccactgagcc | 600 |
| gctattaccg | cgaaaggccg | gcctggctgc | gacagcctgg | gtaagaggtg | taggtcggct | 660 |
| tggttttctg | ctacccggag | ctgggcaagc | gggtgggaga | acagcgaaga | cagcgtgagc | 720 |
| ctgggccgtt | gcctcgaggc | tctcgcccgg | cttctcttgc | cgacccgcca | cgtttgtttg | 780 |
| gatttaatct | tcaggttgcc | ggcgcccgcc | cgcccgctgg | cctcgcggtg | tgagagggaa | 840 |
| gcacccgtgc | ctgtggctgg | tggctggcgc | ctggagggtc | cgcacacccg | cccgccgcg | 900 |
| ccgcttgccc | gcggcagccg | cgtccctgaa | ccgcggagtc | gtgtttgtgt | ttgacccgcg | 960 |
| ggcgccggtg | gcgcgcggcc | gaggccggtg | tcgcgcgggc | ggggcggtcg | cggcggaggc | 1020 |
| agaggaagag | ggagcgggag | ctctgcgagg | ccggcgccg | ccatggaact | gggcccggag | 1080 |
| cccccgcacc | gccgccgcct | gctcttcgcc | tgcagccccc | ctcccgcgtc | gcagcccgtc | 1140 |
| gtgaaggcgc | tatttggcgc | ttcagccgcc | ggggactgt | cgcctgtcac | caacctgacc | 1200 |
| gtcactatgg | accagctgca | gggtctgggc | aggtaaggag | agaccggcgg | gcggtgctcc | 1260 |
| gggcccctgg | cctcggtgtc | ggcctcggag | agatcaggcc | aggaaacgga | ccgggagaag | 1320 |
| ggcgagaccc | gtccgtccgg | gttcgccgct | cggggacagc | cgggctaggg | cctgccatgt | 1380 |
| gcacccccgc | ccgggcggaa | tgttgggcgg | gagaggccgt | cgggaccttc | caggggaaga | 1440 |
| ggtggagatc | cttgggccta | agcccgagcc | aggcccacct | tcaccccttt | cggattgctc | 1500 |
| cgtactctcc | ttctatctct | atccctggaa | gctctttgga | atctacccc | gcggggaaaa | 1560 |
| tcaggctctt | ctaggcactc | actttcaccc | tttgctaaac | catcctcagg | atcttcgttt | 1620 |
| gctgtgatct | ttgttcctcc | tcaacaaagg | accatggcat | tttctttcct | ggcgtttatg | 1680 |
| taaaatcatc | tcagtccctc | gccctgtgca | cattcctgat | gtccactctg | ctgctttcct | 1740 |

```
aaggccaggt cttttttaccc aactttcaga aagcttcctg ggcttttcct gatagcaaaa    1800
aatgcatccc acgtgttttc ccgcggaaga gctactttcc cttcaatctc tggcatcccg    1860
tttgctaagc acatgtcttg tgcgtttccc aacttctgaa aagcagaaag tgtcctgttc    1920
aactttcatc ccgactctgt ctcagtactt agaacacatg ctttttatttt aggaaatacc   1980
ccaacatttg ccatagccat cataacctgc aatgtggtcc aaggccatgc ccacccactc    2040
ctttttttctc ctttgcccaa gtgctaattg ggtgttcaga gtggcaaagt gggatctttg   2100
ccacttgtgg tgtggcctag aaatggtttc tggcagcctg gctgcttctt aatctcatgg    2160
cctatctcct gcatgtgacc ttttaattat atcctataaa tcattcatgg tttatttctg    2220
ttggtttcag tgattatgag caaccactgg aggtgaagaa caacagtaat ctgcagagaa    2280
tgggctcctc cgagtcaaca gattcaggta tttaagtctg ctgtgtgggg agcaatactc    2340
tgaatttcct gaaacatgcc ttttcaccca ggaggttagt tttggtgaga acttgaggaa    2400
gtcatggcat tgggtgataa acttttttttt tttttttttt gagacagagt ttcgctcttg    2460
tcgcccaggc tggagtgcaa tggcatgatc tcagctcact gtaacctcca cctcccgggt    2520
tcaagtgatt ctcctgcctc agcctcccga gtagctggga ttacaggcat gcaccaccac    2580
acccggctaa ttttgtattt tttagtagag cagggttttc ttcatgttgg tcagcctggt    2640
ctcgaattca aacctcagg tgatccgcct tcctcggcct cccaaagtgc tgggattaca     2700
gcgtgagcca ccgcgcccgg tgataaacat tattgagaac aatacaaagg agcccttgtg    2760
gctgtttatg aagaaaggaa ataggtttca aatgtctata aggaggtggt gtgtgcttgc    2820
ccttgaagga tgggtagtaa agtataattc accataccac tgtaagtggc attcaggcaa    2880
tcttactggt taaaatacag gatcaaatga ttggaagtac agtgtcatga aatcatttca    2940
gtgatgctgc tatggaggaa attgccagtg catttcattc ttcatgaatt catattactg    3000
cagagtttat ctgtatttgt acagataaga ccattggtgc aaagatcctt taggttaaag    3060
gaactgcaag agcaagtctt aaaatgtaat gtaggcttct gtatgtagaa tgtaatttaa    3120
tatagaactg gggataggat tatcacttgt agcagtgtgg tgagcaaggg ctgtaacacc    3180
tcactttcca taaggctgta tagacacatg agctatgggt gggtgggtct gcgtcatctg    3240
agctggcata ttagtaatgc tgaacagtgt ctccttcacc ctgctgcctt ttgtgagatg    3300
gacaccttgg tgtcattttg ttaaaggcag caagtgcttg ccttgcatgt catgaccagt    3360
agttgtattt ttcttttttca ttttgagaca aggtctcaac tctgtcaccc aggcaacctc   3420
tgcctcccag atttagagaa ttcttctgcc tcagcttccc tagtagctgg aattacaggt    3480
gtgggtctca aacttctgat ctcaggtgat ccacccactt cgacctccca aagtgctgag    3540
attacagggg tgagctactg cacctggcct tttttttttt tttttttga cagggtct      3600
tgctctgttt tccaggtctc aggctggtgt acagtgcac aatcagggtt cactgtagct     3660
tcaactttcc gagctcaagc gaacctccca ctccagcctc cccaagtagc tgggactaca    3720
gacacgtgcc accacaccca actaatttt tttttaactt tggtagagtc aagtctcact     3780
atgttgcccc aggcttgttt tgaacttgtg gcctcaagcc atcagcctgc ctcagcctcc    3840
caaagtattg gaatcacagg tgtgagccac tgtgcctggt cagtagttgt attttttcaag   3900
cctcatatga tttgacaagg taaaacgttt aaaaactatg ccaagaaaat ctggtaccta    3960
ttgtttctat ggttggaact cacagaaagt tatctgggtc acctctatct gaataaccaa    4020
acaatcatga tatgaatcag ttttattcac cctcttctca aatcctatttt cccttgatgt   4080
```

```
tatttgcaaa taggagaaaa aacagtaaat acgctatgaa aatattaaga cttgtacaaa    4140
catgacattt ttgacaatct aatagacgta acatcaattc tggcaaaagt acaagccatg    4200
aatatttgtt gcctgactta aataaagacc caggtacttt gtttagtgtt ttaattttaa    4260
tgacaaaatg gtgttttttg tattatttct tgagaggttt ttttttttccc cataggtttc    4320
tgtctagatt ctcctgggcc attggacagt aagaaaagt atgtattcac tgctttcaaa    4380
tgtttatatg tagaaaaaac gtgtctaaac ttaaatacct tatttaaatg aagttcttca    4440
tacactggac tggagccctg gatttacctg tgcctagaaa cactctggaa tctcaagaat    4500
gaatagtttg tgtcagcaat tttcagaact ttttctcctt tattttagct ataattttgg    4560
tgttctgttt gggtcttacc caaacccttta ctctgtgctc tgacatcata gccttacaag    4620
aacatgtggg gtttttttgt tgtttgttt gtttgtttct gaggcagagt ctcactctgc    4680
cgcccaggct agagtgcagt ggctcactgc aacctccacc tcccaggttc aactgattct    4740
cctgcctcag cctcccgagt agctgggact acaggagtgc accaccacac ccggttaatt    4800
tttgtatttt tagtagacac gaggtttcat cgtgttggcc aggccaggag ttcgagactc    4860
ctgagactcc tgacctcgtg atataccctc ctcggcctcc catagtgccc atagtgctgg    4920
gattacatgt gtgagccacc gcgcccagcc gaatgtgtgt attttaagaa aagacatggg    4980
tttgtttttt ttcacctaga agtctagtgt tgggggtgct cctgagaaca ggacagcttc    5040
agaaatttat tctcccatct cttgcctaaa atgggagtct gtgactgtac ccccaagcta    5100
caggctaaac actatctctc tgctaatatg aataacctctt tacttgttttt attctcatta    5160
tttaccttct gatctcatta cagccttgaa aatcctatga gaagaataca ttccctacct    5220
gtaagttagt tccttgttta ttttgagcta ataacctgtta tctgttcctt agctaccagc    5280
atgaccttga taggagactt aatttagaga gtaaaaactg cttttcttta gtctcttttg    5340
agacaaggtc ttgctctgtc acccaggctg gagtgcagtg gcaaaatctt ggctcactgc    5400
aacctctgct tccctggctc aagtgatcct cccacctcaa cttccagagg agctgggact    5460
atatataggt gcacaccatc acacccggct gattttttgta ttttttgtag acatgggggt    5520
ctcactctgt tgcccaggct ggtttcaaac tcctgcctcg gcctcccaaa gtgctaggat    5580
tataggcaag agccactatt cccagccttt ccttagtctc ataagtactc aagatgttcg    5640
gtctggagga atttgtcctc catctctaac agagctttat taaaccagga agggttcttt    5700
tgatgcaaat gttatttggg gattgatttg gcactgtaat ccctgttgag ggggcactg    5760
tagaccttgt gaggttagct gtaaacccat ggaatggaaa cttctatgct gtgtcctggc    5820
tgtgtcctgg caaggtggat tcctggccac atttactggt tacctactgc agtgtgtgag    5880
gagctagtct acccccctatt caaccccccct tttttttctt ttgagaactg aattttccac    5940
tgaaatttta tttgtgtgcc ttaattattt tccttttttta ctttgatagc agaagctgtt    6000
gggatgtagt ccagctctga agaggagcca ttctgattct cttgaccatg acatctttca    6060
gctcatcgac ccagatgaga acaaggaaaa tgtgagtgtg acttcaatgt actaacctga    6120
ggcagaggtg aaacccacag gctgtcagtg gcttagaagt ggctgggctg ctttctggga    6180
gactaaactt ggccattatg tgcggtcttt ggagtcagag aattctgggt ttggatcctg    6240
cttactagct gtgtgatgtt ggcaaattct tctctttttta atctttgctc ttttgtaaaa    6300
taggagtagt aataccttttt agggatgttg tggcaataag taagattatg tatgaagtat    6360
tgaaaatggt gcctgacagg cgggagttgc tcagattgta gctcacagga gtaattacat    6420
gtacaaatag tgtttgtctg gaaggctctg cccaggctgt ccttgcctct ttgctctgac    6480
```

```
cctgaaatga attgtaagct taggaaaagg ctctttggca gtatttgtaa gaacgggtc    6540 aacaagttct agggaatctc agagtaactg aaatggtggc ttggaaggtg aatttctggt   6600
tatctaccct gaatgagcct ggcttttttg ttcttttaga cattgcacag agtaggcatc   6660
caaaacagtt gtaatttttt cagccttctc tctactgtat ttctatatat ttactttctc   6720
cccttttcca ttcctgctga aatgccacag ttcataatcc ttgtccttac aatcttcagg   6780
tttagtgtga aacccactgc ctccatgaac tctcctgatg atttctttat caacctggga   6840
agtgtcatga gaaagaatat ggaaatgagt tccagccttg agtgcttgga acagtgtatc   6900
agcctctagt gcttttacc agggcaaagc tgtactgatg cctggttttc ccccgaaata    6960
gcttctcagg gttgcttgcc tggagctttg ttttaaaggg aaaacagcat agatggtggt   7020
taaagagctc tcactctgga gttgtcctgt tttacttcaa tattttgggc acattcctta   7080
acctgcaagg tctagttttc tcacctgtaa aatcgggaca atcaggttgt atttgatggt   7140
taaaaagtta atgcacagaa agtacttagt actgtgttgg catagaaatc actgtaatat   7200
tagccattac tgcttttttt ttttttttga ttcttcatgg ttttatttct ctcagaactt   7260
taaaatgtga acattctata attcagccag tctttacttc caggtaactt ctttattggg   7320
tcgcaatacc cttttaaata acatgctctt gttccggaag gtagttagcc gttcatcact   7380 cttttctgtct aaataacatc cagtgacaaa tcccataggg acaagaacat gaacccagtg   7440
gtcccgcaca atctgaagta agttccaccat gatagctgca gcctcagtgc cgaccgcgac   7500
cccgagacca agggcaacgg ggaactcagc cacccacgcc agtgctagcc attactgctt   7560
ttaatactta attatgagtt cttaagtgaa tattttaggg caagggacct gtgagtgttt   7620
tcattccata aagtggaatc atacgatatg tattctatca tatctggctt taaaaaacat   7680
tatgcttgta agaatcgtcc acgttgagta aaccagtagg gcttttttt tttcattgc    7740 ttttagtata gaatagaata attataagta gaaaaaatta tctccagttg gtaggaagag   7800
gtggaaaata tgaagccctg aaacagatgg acctagatgg aaaatttga caactattca    7860 caggcaatta tattagattt tatttatttt tgctttagat tcagaaagt ttgtgattta    7920 gcttattcat cgtgttttgt atatttggca gatacttgtg ttaggaaata cagtatgaca   7980
agaaaaagat gttactttag aagttagctg ttgacagagc cttggaaatt cttagttacg   8040
cagatctatt gttggaatta ggtgaaactt taatttggag gcagaaaggt gatcagtgcc   8100
cactttcttg cctctttcac ccaagctgag gcctgagttg gttttcatgg acagtagatg   8160
tctcaactat gtcttgcagg aagcctttga gtttaagaag ccagtaagac ctgtatctcg   8220
tggctgcctg cactctcatg gactccagga gggtaaagat ctcttcacac agaggcagaa   8280
ctctgcccca gctcggatgg tatgtgctct ggctttcata ggggaattcc tgacaggaag   8340
aaaggattaa aacaccttct ttcatccaga attgaaggca ctacagtagc actagctgtt   8400
tttaccttga ctttgtcttt tgaaattaga ctgtcaagca ttcttggtgg ttttgctgtg   8460
tctggagaac agacaggcgg tagtaagagt gggagatggt gtttgaaata ttggagttgt   8520
gcaaggaata atcgaccttg ttaatctggg aaatcctggg tcatcctaaa tgtatgtatg   8580
gtgggattat atctcttcct atttttttct ttttttcttt tttttttttt aagggctttc   8640
tggcaaaaac cggaaagcct gcgagacaaa ttttaaaaga gccgtaacac tagatctctt   8700
acttaaaact tggtctttac tatgcattct aagtgcttct caaggaactg agagagagc    8760 acttgacttc ttccaaaggt ggtttgttaa gaacagttat gggccaggtg ccatggctca   8820
```

```
tgcctataat ctcagcactt tggaaaactg agacaggagg atcgcttgag tcctgggcag    8880
catagtgaga ccacatctct attttttta tttttaattt ttttaaagaa ctattatgga    8940
ttacagtgaa tgctcaggct gctgggcagt tttggggtca ctcgtttcag ggctatgtat    9000
ttgccagaca gggactgtca ttacttccaa agtttcctgc tgttggtctg aattggatta    9060
actgatagca tctatagatt ggagaggccc aacttgagca agatgaccac atttggcttc    9120
caggtttacc taggatctta aatctgaaaa tatacctttc caatctgctt tgtgttctga    9180
ggttcagcca gtattgttac tctgtctatc atttgcacaa agcacttta tatgttcttg    9240 tcttgtgaag tggagttaat ccacttgaac agattaggaa agtaccacta gagaggtttg    9300
gatgatttac caaggatat acataagtag gaaaccagga tttaatgatc tctggctggg    9360
tgtggtggct catggctgta atcccagcac tttgggaggc cgaggtggga ggatcacatg    9420
aggtcaggag ttcaagacag cctgggtaac atagtgagac cctatctgta caaagttaaa    9480
aaataagctg agtgtggtgg cttgttccta tagtcccaat tagtcgggag ctgaagtgg     9540 gaggattgct tgagcccaag aattcgaggc tgcagtgagc tatgatcaga ccactgtact    9600
ccagcctgga caatgaatcc ctgtctcaat aaacaatctc taaattccca agtacacagt    9660
aatgctttaa gagttgggta tcagaaacaa tatatttggt gtgtgcttag cgactagagc    9720
ctgtatcaca tctgcaccta ggaatcccag aacatacctc acaaatgttg gtgtgatata    9780
gtgtgagctt tcgtgataaa ggtactgccc cataataaag ttatctaccc ctaggctaaa    9840
aaaatttgcc atttcccaga gtgtgcactt ggggaggact agagactgct cagaacttgt    9900
tttatattgt gaagcaaagc taatgccaga accagaatag gccagctgca gagaggattc    9960
cttggtgcat gatccactca gaaaatcaga gggccactta actaacaaca gattcatacc    10020
ccaaagagat ttggattta aggattactt gtaggtcata acattgggac taccctgcta    10080
ctgtgaaaaa aataactcta aacttttttt tctggatttg aaagtgccta gaaaataaat    10140
aattcagtat tagcagtgtt tgtattggta ggatttatct tcaggtgtgg atttatgagc    10200
agttttctca aatttctat attccatgtt tagaggtttc ccaaaaaag tatgactata     10260 ggttggctaa tgaggtaccg ccattttaat tccaggaatg gttttctcct agggagatag    10320
tgtggtgaga agagtttgga ttttggagtc aaacagatga ggtgtataat cttggtaacc    10380
tcttaagcac cagtttcctg atttgctaaa gaaaaaggaa aggattagct acctttagtg    10440
tattgtgagg cttctattgg attatatgta taaagattat atcgtagtat ctggcacaca    10500
gtaattcctc gtttaaaaac tgagcattta aatcccaagt ctaaagaacg aggatagatt    10560
ttatagaagg aagttaccct ttattccccc ctgtcagaac tggagttata tataagtgca    10620
ttctctaggc cattttatgg tctttataga gatttgcatc tgcttgccct aactcatttc    10680
agcagattct catactgtca cagtcctcaa tgctgatcgg tgttcactga tgcaaccttc    10740
taataaaaga aaccttgttc ttcacaagag gctatctcta gtacccatta taaggtgaat    10800
tgcttctggc aagagttctc tgtaaaggct actgactact cagggctgtg tgtggtcatc    10860
aaatcattta taatcttggg atacattttc atataatcag taatggctaa aattttgctt    10920
tgtataacaa gtataacata gtatgttttc atcataaaaa ctagtgaccc attcaaggaa    10980
atgaaagtgg atcagagctc tcattattaa tccatgaatt ttgtcttaca gctttcctca    11040
aatgaaagag atagcagtga accagggaat tcattcctc tttttacacc ccagtcacct     11100
gtgacagcca ctttgtctga tgaggatgat ggcttcgtgg accttctcga tggagagaat    11160
ctgaaggtac cgtgtgtgtg tgtgtgtgtt cctatttgtt ctactaatta attacctctg    11220
```

```
gagaaggcat gtgatgtgaa aaagaacagc aacagcagtt ccccgggggct tgcttagctg   11280 atatttttgt tcatttggtg ataattcatt taataatagg gctaccagcc ttattaaatc   11340
ctttggattg ggggatgggg gcatcaaaag aagacacatg atccttctta ccctgaagga   11400
gctaactaac aatctatatg caagaaacat gaaatcagaa cggtatagga tggtacatta   11460
aggatacttc ctatccaggc ctatctggta ttgttcaggg agaaacacac ctaaagcact   11520
taaacaaatg ttagtctcta caggctcttt ttaaaatcag ttttttctgtt tctttagaat   11580 gaggaggaga ccccctcgtg catggcaagc ctctggacag ctcctctcgt catgagaact   11640
acaaaccttg tgagttgttc tagtgtgtct ggaggaagcc ctgcgtgatt ggggcactgg   11700
acagagtagt ccttagttga gtatagccaa agattgaaat gcatgatagg atttggggat   11760 ctgggttttta ggcctcactt tggctaccta caaattatga cctttagtca tgatatctct   11820
ctgcatgtct cctgatgtat aaggagtgtg ggttaggagg gaccatggtc attcctagct   11880
tttaccatct agtcagtttg aaaaaagcct atctgaagcc tttagcctga atactttact   11940
ttttttaggt tattctcatt tatattccac agaacctagc ataaaattag acaagcaaca   12000
gtaactcaca ggattttttt tgtttctgtg ttttttgttt tttttttga dacggagtct   12060 cgctcttgtt gcccattcta gagtgcagtg gcacaatctt ggctcactgc aacctctgcc   12120
tcccaggttc aagtgattct cctgcctcag cctcccgagt agctgggatt acaggtgcct   12180
gccaccacac ccagctaatc tttgtatttt cagtagagac ggggttacat tatgttggcc   12240
aggctagtct cgatctcctg acctcaggtg atctgcccac ctcgacctcc caaagtgctg   12300
ggattacagg catgagccac tgtgcctggc tggatgtttt tgttgctgt tttgtttgtt   12360 tgttttgttt tgttttgttt ttcattgaaa atacctacct gaggctgggt attttcaggt   12420
agatattttc gattttaaaa attatatata atatatattt tatatatata tatatatata   12480
tatactcaca cacacacata cacagtatag atttgtgttt ccatcaggga tactttcaaa   12540
cagaaagcat agtatatgta gatacagaat ctatagtgta tgtgtgtata tatattcaaa   12600
atcacatata tatacacaca catacacatg ctatagattc gtgttttcat catagggata   12660
ctttcaaagt tagaagcaag aatgtgccta tacagatata tacacctgta tgttcagaga   12720
tatacaccct taggtacaca tctaaattga taagttcata ttttttaatt ctcaataacc   12780
tgaactataa ttacagaaca aatgagctac agttttttttg tttgtttgtt ttgttttgtt   12840
tttgagacag agtctccctc tgttgcccag gctggggtgc agtgcagtgg tgtagtcttg   12900
acttgctgca acctctgcct cctgggttca agtgcttctt ctggctcagc cttctgagta   12960
gctgggacta caggcttacg ccaccactcc cggctaattt ttttggtatt tttagtagag   13020
acgaggtttc actatgttgg ccaggctggt ctcgaactct tgacctcagg tgatccatcc   13080
acctgcctcc caaagtgctg ggattacagg catgagccac cgtgcccagc caagctacag   13140
ttttgagatc acttatggat tatagtacat tcatgtgcat agcttttgag aaaatatgtt   13200
aacgcagtac aaatgttatg agtaaattta ccaggtcatt ttgataggca taaaattaca   13260
taaaatgtga gaacactttg gaagtggctg ttagtttttat agatttgatt ttagagtcat   13320
aagcatgggc ttgtaagctc ttaatagtgg ggaaatgtct tccacaaatg gttattacaa   13380
actaaccatt gctgggagct gtaatggaaa ataaacttca cacaaaagag gaagaaaatc   13440
cccggtctct atgggagcag atgtgggagt gatccattct actggggact atcaggaaga   13500
tttcaaagaa gtgacattga aatgttagca tcaacttgaa aatgaatggt ttactgagat   13560
```

```
gtgaaaggac attctgtgca gaaggaaaag ccaggccaag acacatggag tcgagaatag    13620
gctgagatgc gtttagagag ctgactcttg ctaccactgg tcagattggc ttcccttggg    13680
ctctggaaaa tttgtcttta tttatttatt tatttattga gacagagtct tgctctgtca    13740
cccaggctgg agtgcagtgg tgcaaatctt agctcactgc aaccaccacc tcctggtttc    13800
aagtgattct cgtgcctcag cctcctgggt agctgggatt aaaggcacgc accaccacac    13860
ctggctaatt ttttgtatt tttaatagag atggggtttc ttcatgttgg ccaggctgtt    13920
attgaacttg tgacctcaag tgatcccaca gtgttgggat tacaggcgtg agccaccgcg    13980
cccagcctgg gaaattagtc tttaaaagac caagtagaaa aaaagacttt gaacacaatt    14040
ttgaaaggca tttgctactc tgcccatccc cactccctcc aaatttacca tcttaactat    14100
accttaacca aagatgcccc catttttatt ataacctggc tactgtgcat cttttctgga    14160
tttaagtggg gtatttaaac ccgttgacct gcttaattaa gcaaggtgca agtaataaaa    14220
tggaggggaa gataggcaag ccaaaaatgt gttcctgact ggaaggtcac acttctcttg    14280
acgcaggatt atgtagacag ttttgtgag ggcaaaggac gttttgctca tctctatata    14340
atgtcagctg agtatatatt cattgagcac taagtgctca gtgcctacta tgtgccaggc    14400
cctgtgagag ttgctaggac tagatgaatc ggcagtgtct gttggctaat ttagaattga    14460
tcttagatca tcccaggaaa ccttcggttt atttgtctta ccattcaagt gaacaggttt    14520
taatgaaaga tgggtctgtc tgttttttt cctgtaagga caaccgatgc aagctgtttg    14580
actccccttc cctgtgtagc tccagcactc ggtcagtgtt gaagagacca gaacgatctc    14640
aagaggagtc tccacctgga agtacaaaga ggaggaagag catgtctggg gccagcccca    14700
aagagtcaac taatccagag aaggcccatg aggttagttt cctaggttcc tttttgctct    14760
agcacagata ctgtattttt cagttctaaa aatttctact tagtggttca tttatttct    14820
ttgctaagat ttgctggggt tttgtggggt tgtgtgtgtg tgtgggtgtg tgtgtgttc    14880
ttttaataga gatgggatct agcgatgttg cccacgctgg tcctgaactc ctagcctcaa    14940
gtgatcctcc tgccttggcc tcccaaagca ctgggattac aagtgtgagc caccacacct    15000
ggctgatact tggctgtttt catgttggtt tttcatttgc tttgagtatg ttcataattg    15060
cctgttgaag catttttaag atggctgctt taaaatcttt gtaagacaaa tccaacatcc    15120
atccatagtg ttgttggcat ctgttgattg tcttttcctg ttcaagttgg gattttctg    15180
gttcttggta tgaccggtga ttcttccatt gtctcctgta tatttgtgag tctccggtct    15240
atgtaaattt tacgttttag caggcttcct ctgatactgc aagaaaggca tgggtggaag    15300
tccgggttcc ccagcacaaa ctccattgac accttgggtg gggacttgtc tcattattgc    15360
tgggaggag tggaagttca ttccatcccc gtggggtggt gactggggca ctgtatgaca    15420
gctgggcaaa ggtggaggcc cccgcttgct gttggccata attgtttctg tgttgactag    15480
tagaatgatt attgtctaaa agtcttctgc ctcaatagge catcctttgc ctaggagag    15540
caggcttttc ttggggcttg ttgtgttgct gtctccagct tcatgagttg aatggttaac    15600
tcattcgttt ttaattttct tatttctgga taaatctatt tgaatctatg aatttcccac    15660
tgctttagat ttgtctcata acttttgacc tgaaatgttt ttattatcat tgttgtaga    15720
tattttattt cctttaatc cagacctatc atggcctatt aaatacttga ttttataaa    15780
ggtctgtctt tttttttttt tttttgaga cgctctgtcg cccaggctgg agtgcagtgg    15840
cgcgatctca gctcactgca agctctgcct cccgggttca tgccattctc ctgcttcagc    15900
ctcccagtag ctgggactac aggaccccgc caccacgcct ggctaatttt ttgtattttt    15960
```

```
agtagagacg gggtttcaca gtgttagcta ggatggtctc catctcctga ccttgtgatc    16020
cgcccgcctc agcctcctaa agtgctggaa ttacaggcgt gagccactgc gcccagccct    16080
gtctgtctaa ttcttcaagt taattcattg cattgctcat agttgtatag ctgttttgt     16140 tgtttcctgt ttctgagaca gggtctctct gtcacccagg ctggagtgca gtggcatgat    16200
ctccgctcac tgcactctcc acctcccagg ctcaagcagt cctcccacct caggctctca    16260
agcagctggg actataggtg tgtgccacca aacccagcta attttttgtat tttttgtaga    16320 gacaggcttt cgccatgttg cgcaggctgg tctcaaactc ctgggctcag gcaatcctc     16380 ccgccttggc ctcccaaagt gccaggatca taggtgttag acacagcacc tggcatgggt    16440
gagctagtgt catggttgtc tgggcctaag tcctatggtc ctttgtgtta ttttttctat    16500
ttattctgtg gctagacaca caaaacactg gtttatttgt atgttttttcc ttcattatac   16560 tgtccttata ttgaggtttg gtattaagca ttataaaatg gtgaactacc tgtgttttct    16620
gtggcatgaa aaggtttaag taaatctcat cacagtctta aaaggttaga gagatgacag    16680
ctaggaaaac atttagcatt taggcctact gccttatcgt atctgctttt gtttttaatg   16740
ctttatgaat gtttttaaag tattgttcta aaagaatatt ttaataattg catagtattt    16800
ttgtttgggg agagttgttt ggttttggtt tttgttctttt ttgtttgtgg ggggcacagg   16860
gtctagcgct gtcactcagg ctggagtgca ctagcacgat cacagctcag tacagcctcc    16920
atgggctcaa gcactcctcc cgcctcagcc ccctagcag ctgggactac aggcatgcac     16980
caccatgccc agttaattta aaaaaaattt ttttttattt tttgtagaaa agaggtctta   17040
ctgtgttgcc caggctggcc ttgaattcct gggctcaagc agtcctccca cctcagcctc    17100
caaagtatct gggactacag gcacaggcca gtgcacctgg ccgatagtgt tttgacttac    17160
aagtatacta gaaataattg aataaatcac cttctggaca tttagaattt cccttcccct    17220 gatttttcctt ttatttctaa ttaaaaatga aattctgggt tataagggca agaacatttg   17280
tgaaacttta cattgtatac atgtcagaaa atatctatca atatttaata atattctggc    17340
tgagtgctgt ggttcactcc tgtaatccca gcactttggg aggacaaggc gggtggatca    17400
cgaggtcagg agttccatac cagcctggcc aatatggtga acctgtct ctactgaaaa       17460 tacaaaaat agctgggtgt ggtggtatga gcctgtaatc ccagctgctc aggaggctga     17520
ggcaggagaa tcgcttgaac ccgggaaatg gaggttgcag tgagcagaga tcacgccact    17580
gcactccagc ctgggtgata gagtgagatt tcatctcaaa aaaaaaaaa aaagaatatt    17640 cattttctttt ttctttctttt ttgagacacg ctggagtgca gtggcaggat cttggctcac    17700
ggcaacctcc gcctccccag ttcaagcaag tctctgcctc agcctcctga gtagctggga    17760
ttacaggtgc ccactgccac gcctggctaa tttttttttgt atttttagta gaggcggagt    17820
ttcaccaagt tggccaggct ggtcttgaac tcctgacctc aggtgatata tccgccttgg    17880
cctcccaaag tgctggggtt acaggtgtga gccactgtgc ccggccagaa tattcatttt    17940
cttttaccgt aatagagatt gacctttta tttccatatt tgtaaaactt tttttggata      18000
aaataatact gttaataatt attttgtata tatattggcc ctcatgtttt ggtttatttt    18060
catatatttt aattttttagt attttaaatt ccattgtgga gaaaatgtca agcattgcta   18120
gagtacagtt atcatacctg tgatattgtg aaatatatat ttagtcttct tccccttctg     18180
tcatataact cctaaaatct ttggaatatc caaggtcata tcttttttgta tactaatgat    18240 tgatagcttc agggtgggac tggtcactgg aaagacagag acatgattag aggttggaac    18300
```

```
tttcagcccc accctccaat gtctacggaa aggagagggg ctaaaggtca agttgatcac   18360
tcatggccaa tggtttaatc aatcatttct atgtaatgaa gcctccctaa aaccttgaaa   18420
ggacagggtt cagagagctt ctggatagct gaacacatgg aggttcctgg aggttggggc   18480
acccaaggag agcatggcag ctccatgtcc cttctcccat acctcaccct atgcatgtct   18540
tcttctatat cctttgaata tccttcataa taaactggta aatgtgtttt cttgagttct   18600
gtgagccact tctagcaaat taaacccaaa gaagggtca tgggaacccc tacttaaagc   18660
tggtggtcgt agatcagaag atccagaggc ccaactggtg tctgaagggt ggtgtggttt   18720
tgaggactgg gccctcaact tcctgatctg acgctctgca ggtagatagt gtcagaattg   18780
aattggacgg cacccagcta ttttccactg cagaactgct tgcttgcttg cttgcttgct   18840
ggtagggaga aatcccctca tatctggggg taacagcact tctgtcttct gttgctgttg   18900
agtgagggaa taagaaaaat cactttgagt ttgtggggtg ttttcctcac acaaacatat   18960
catacagggc taaatttctg ggtgttttt tgtttgtttt tttttttgag accaagtctc   19020
gctctgtcgc ccagactgga gtgccatggg tcgatctctg ctcactgcaa cctccgcctc   19080
tcaggttcca gcaattctcc cgcctcagcc tcccaagtag ctgggactac aggcgcccac   19140
caccacgcct ggctaatttt ttatatttt agtagagacg gggtttcacc atgttggcaa   19200
ggctggtctc gaacccctga catcaagtga tccactcacc tcggcctccc aaagtgctgg   19260
gattacaggc atgagccacc acgcccggca gagctaaatt tcttactatc aaatgtcaaa   19320
tatccagtct gggttcagtt ttccccagtt gtctcctaag tacttttaca gtttatttgt   19380
taaaatctgg atccaaataa agtctataca ctgtagttgg tcaataggtc tcttactctt   19440
cagatttcag tgctccatct gtttccctct tgcatatttt tatttgttga agagctcaag   19500
tcatttgtcc tgcaaaggtt cccacagtcc tgtggggtct tcagacattg tcttctatcc   19560
cctatattgc cttaacctaa ctctggaaag gatggattga attccagttc tatttgtttg   19620
gcaagaatat cacataggtg attttgtcta ctttgatcag gaagtataat gtgccaggca   19680
gccattggtg attgctgccc agatttttta cttcatttca ccagggtttc agaaagatga   19740
tactgcagtt tttacattct ttcctcatta attagctaga atatatctat aaagagaaac   19800
ttacactcat caaacactgt ggttacccct gggaaaggca ggatgaatat tggatctctt   19860
tatttgccag tttccaaata atgccctacc aagcatcttc caaagttgaa agcaagactt   19920
atagttgttt ttcaataata atcaggaatt catgggttaa acatttaat gtgtttctgt   19980 gtattacaag tattatcctt ttactcaaat tatccccttt ttaacagctg gcttcctctt   20040
ctcattgaat aaagctaaga cgtaggccgg gcgcggtggc tcacacctgt aatcccagca   20100
ctttgggagg ccaaggcagg cagatcacct gaggccagga gttcaagacc atctggccaa   20160
catggtgaaa ccccgtctct actaaaaata caaaaattag ctgggcgtgg tggcgcacac   20220
ctatagtctc agctgctctg gaggctgcgg cagaatcgct tgaacctggg aggcagaggt   20280
tacagtgagc caagatcact gtactccagc ctgcactcca ctcctgtact ccactgcact   20340
ccagcctgag cgacagagcg agactctgtc tttttaaaaa aaaaaaaaa aaaaagttaa   20400 gacatacttt ttctaaactt aatcctagtt ttaaccccc ttgtttcttt ctcttttct   20460 ggagatagtt tcagtctgtc acccaggctg gagtgcagtg gcaccatcac cacttgctgt   20520
agcctcgacc tccccaggct caggtgatcc tcccacttca gcctcccaag tagctgggac   20580
tacaggcaca caccaccatg cccagcttgt gtgtgtgtgt gtgtgtgt gtgtgtgtgt   20640 gtgtgtgtgt gtgtgtggac agggtcttgc tctttgatct ggtctggaac tcctgggctc   20700
```

```
aagcgattca cctgccttgc ccaggctggt ctggaactcc tgggctcaag tgagtaaccc   20760
accttggcct cccaaagtgc tgggattaca ggcatgagcc aaaccacctg cacccccttt   20820 ttttttttt tttttaagg aaggaaggaa aacttagttt cagagcaatt cggttagaca   20880 ctgaataat aggagaccta gtcaataacc cacatctgtt tttgttcact ccagattcaa   20940
taaaataaaa taaaaacttc ttactaaatg taggcattaa cattttagtc tcctcgagac   21000
atgctccaag tgaatgtttt cagaagttcc attcagaacc cttgtctcat tctctacctt   21060
tgatttgtta cagactcttc atcagtcttt atccctggca tcttccccca aaggaaccat   21120
tgagaacatt ttggacaatg acccaaggga ccttatagga gacttctcca aggtaattgc   21180
aagcagagct gctctggcaa gtgtaggagg gagtgtgggt atttagaatc ccactcagcc   21240
tgtctccctc cccagggtgg ttcctggcat acctccaaaa ggacacagtt aaaagaatgt   21300
taaaggtagg gaagcaaact tagtttctca tgatcaggta tatgttggtt tctgagactg   21360
tagatatcac tatagctgat gggcagtttt aggtagggag ctgtccacca accaccttga   21420
ttgtaaccca aagactaggc tctctgggaa ctgtgttatt ataaaaatag taattagcag   21480
gatagtgtac agcagaaata aatctgtagc cacactacaa gtctgcatgt tgaaaggtta   21540
tcttagaagg tctgggattg agactgaatt tctccgttca gagaagcttg gccattgagg   21600
gaaaagaccc tccaggaagt ctagaggaag atcttctaat agcctgatat actacatgaa   21660
ggcttggctg cagtaaaata caaggctagg acagggaatg tgtcaatagc agcttcttta   21720
atcacatttt gacttgaagg ttaccagatc aatgttttat tcattaattt agttaacatt   21780
tattgaagca cttatgtgtt aggcagagat tccaaaatga gatacagttc cttccctcaa   21840
agaatttagc atgtggttgg agaggtgaga cgtgaactac atgtaccaca tggtagactg   21900
aaataaattt tagtgaggtg taaacataaa cagcatgccg tgagaagtaa aagggtttat   21960
cttggctagg gggttgggga acgtctgggg ttgggccgtt gatatttcag cccaaatggg   22020
ttttgaagga acggagaatg aagagaacaa gcaaagatcc agctgtatcc tcagttttgg   22080
aaccttctct tgtttggcag ggagagatgt ggtcttacta tgttgctcag gctgtagtgc   22140
agtggctatt cgcacatgct atcatagtac actgtagcct caaacttatg gcctcaagtg   22200 ctcccctgc ctcagcctcc caagtagctg ggactacagg catgcaccac cacactcagt   22260
ggaattttca acttgaattg aggcctggtt atatttgtct taatgggcct atgcatgggg   22320
atagatgaac tcttggctca gccagtcacc ctaatgagta attgctaatg tgtgcatctt   22380
cctcctcaag gctgggctag gtctcttttt ttcctatccc cagtgcctgg caccatgctg   22440
gacatagcag gtgctcagta aatgagtgaa atctgtatgt ttaagtgcta ttcgcagtct   22500
aactactgac gtgtggattc ttgacaaaag caggaggaaa atgagattac ctgaggtttc   22560
tttatttaaa tctgccttac tagctaggta accttggata aggtgctcaa aatgggaata   22620 atataccctca ttggtttgtg tgaaaattaa atgtcaggat gttaatgaag taactagaag   22680
agtaactagt gtgtactaac taatgttttgt ttgcttgttt gtttgtttgt tttttgagag   22740
ggagtcttgc tctgtcaccc aggctggagt gcagtggtgc aatctcagct cactgcaacc   22800
tccgcctcct gtgattcaag cgattttccc actccagcct tccgagtagc tgggactata   22860
ggtgcatgct aacgcccggc taattttttgt attttttaaaa gagttggggt ttcaccatgt   22920
tggccaggct tgtctcgaac tcctgacctc aggtgatcca ctagcctcgg cctcccaaag   22980
tgctgggatt acaggtgtga gccaccgtgc ctggccatta atgtttgttt tttaaagat    23040
```

```
gcctcctacc agccagacaa aacagtataa gtgtgaataa tatataggct ttcagattct    23100
ctaagtatct tttttctttt ttaagggtta tctctttcat acagttgctg ggaaacatca    23160
ggatttaaaa tacatctctc cagaaattgt aagtccatcc ttttgaaacc caccacacat    23220
cgggtacttg aatctagttt tccctgacgg tcaaagttga ttctccctaa ttttctctca    23280
acagatggca tctgttttga atggcaagtt tgccaacctc attaaagagt ttgttatcat    23340
cgactgtcga tacccatatg aatacgaggg aggccacatc aaggtatgga ttcctgagac    23400
ttgctgtaga aggagcccta aacaggatct gtggttttaa agtggggagg acagtgacac    23460
ctggccactt agctcatatg ctagttgtta gaattttgaa acaatacagt gagtgtggaa    23520
ggcatttgat tccgggtgct cttaacgaat gttcccttgt ctgcaatact ctctaccacc    23580
ttgtgctaca gttattcttc atgtttgtcc ctcacaccat cattatcaag gacacttgta    23640
ggaggtaccc actgatgttt aagtcattcg ggggacaaga atgggtttca tagcatttaa    23700
gaggcttggg taccaatgtc tgagcacccc agggctcctg atgaggagaa gaccatctct    23760
ggcaacatgt cctggtgtct gtgccaggct tagtgatgcc tccaaagttg attgttcagc    23820
aagctgcctg gtggaggggc gtgttgggac acacgttccc aagaagaaag gaactgattt    23880
tgccatttta atctttttt tttttttttt tttgagacag agtccgctct gtcgccaggc    23940
tggagtgcag tggcatgatc tcggatcacc acaacctctg cctcctgggt tcaagcaatt    24000
ctcctgcctc agccttccaa gtagctggga ctacaggtgc acgctgccac gcccggctaa    24060
tttttttttt tttttagtag agacggggtt tcaccatgtt gcccgggctg gtctcaaact    24120
cctgagctca ggcaaaccgc ccgcctcagc ctcccaaagt gctaggatta caggcatgag    24180
ccacggcgcc tggcctgcca ttttaatgtt ttacccgatt aatagtgttt aaatatagta    24240
aggaggtact ttaaatacga tgttactgtt tgccattgtc ttgtggcttt tgaaaatccc    24300
caaatttata aaactaccta taagtgtac cattgtcata tttgaattgc ccatttccag    24360
tccccatgtg cattactgta tgatgaacgt gtacggaccc acaaagctcc attgagatac    24420
aggtgccaaa tggtctactg ggctattcag ctagaagaac tgcaaaaatc acaaactggt    24480
cttgtggact taaagatcac tcttgatgaa tcattacatc ttgctgaatc attacttcat    24540
gtgtgaaacg tgcaggttcc aagggtctct gttgtcttca cagggtgcag tgaacttgca    24600
catggaagaa gaggttgaag acttcttatt gaagaagccc attgtaccta ctgatggcaa    24660
gcgtgtcatt gttgtgtttc actgcgagtt ttcttctgag agaggtcccc gcatgtgagt    24720
gctgcacgga actgggttct ggggcacagg ctccatgatg cttttgtggg acatggtggt    24780
ttgtggcttg cacttggagc atattttagc atatcaagca acctctggca cataacaagc    24840
cattttcata tgtaattta tcctgaggtg aactttggct cttccagtct ccccgactgt    24900
ccttagtctg atctgtgggg ctactgttct catgtgacct ccttcaagta caaagtgacc    24960
gttccttatg caaatgccag aaaagtgtga agttctcatt ctgtaaaacc tcatatgata    25020
tgatgctttg aaacacttga tattattacc aatttcaggg tgaaaagaaa aagggggcc    25080
aaagagctgc ccatcagtca tctgtgtcca ttctaaaagg attgcaagcc tgctgtttgt    25140
caggcactga caataaaaat gtaactacag taaaacacag tacagtaaaa ataccacagc    25200
gagcaggacc aacaaggacc ctactgcagc agagatccaa gtgggatcc gtataaatgc    25260
taggaggaca ggcagagagg taggacagag agtgcagctt aactaggatg gtccaaggga    25320
gacttctgca ggaccacgtt cttatgccac ctttttattt tgaaccaatt tattttaaaa    25380
aacatttttta aattaaaaaa tttcaatttt ttttttttga cggagttttg ctcttgttgc    25440
```

```
ccaggctgga gtgcagtggc acaatctctt ctcactgcaa cctctgcctc ccaggttcaa    25500
gcagttctcc tgcctcagcc tcccaagtag ctgggattac aggcatgcgc catcacgccc    25560
ggctaatttt gtattttag tagaggcagg gtttctacat gttggtcagg ctggtcttga     25620
actcccgacc ttaggtgatc cgcctgcctc agcctcccaa agtagtggga ttacaggcgt    25680
gagccactgc acctggcttt ttctttcttt ctttctttct ttttttttt ttttttgag      25740 gcagaggcac actgttttca cccagactgg aatgcagtgg catgatctcg gctcactgca    25800
acctccacct cctgggttca gcgattctc ctgcctcagc ctcctgagta gctgggataa      25860
caggcgtgca ccaccacacc cggctaattt ttgtatttgt agtagagatg ggggtttcac    25920
catgttggcc gggctggtct tgaactcctg acctcaggtg atccacccgc cttgacctcc    25980
caaagtgctg ggattacagg tgtgagccac cacgcccagc agaaatttca aattttgaga    26040
tggggtctta atatattggc caggttggtc tcaaactcct ggcctcaagc aatcctctct    26100
ccttggcctc caaagtgcta ggattgcagg catgagccac tgtgcccacc cctttgaacc    26160 ttttttttt tttgagacgg agtctcgctc tgtcacccag gctggagtgc agtggcacaa     26220
tctcgactta ctgcaagctc cgcctcctgg gttcatgcca ttctcctgcc tcagcctccc    26280
gagtagctgg gactacaggt gcccaccatc acgcctggct aattttttg tatttttagt     26340 agagacaggg tttcaccatt ttagccagga tggtctccat ctcctgacct tgcgatctgc    26400
ccgtctcggc ctcccaaagt gcttggatta caggcgtgag ccactgcgcc tgacctgaac    26460
cattttaaag ctcaagaaga ggtgaggtta tggctgggca cagtggcacc tgtaatccca    26520
acactttggg aggccgaggc aggaggatca cttgctcggg agtttcagac cagaccaacc    26580
tgggtaacac agtgggacca cacctctaca aaaaatagga ggtgggagga tcgtttgagc    26640
ccagcaggtc gaggctgtgg tgagccatga tcatgccact gtactccagc ctaggtgaca    26700
gagtgagatt ctgtctctct ctcacacaca cacacacaca cacacacaca cacacaaagg    26760
ttatacttgc acacacttca cctgattta ttaattttta acattttgtc acatttgtat      26820
gtacatgctc tacacacagg caactacagt acaacttgac acttttgact gtcatctcat    26880
aagtccttca aacatctgtc tccaaaggat gctcattcat gaatggaatt attcactcag    26940 cagtttttt gtttgtttgt ttgagatgta gtcttgctct gccacccaga ctggagtgca     27000
gtggtgcgat ctcggatcac tgcaacctcc acctcccggg ttcaagcaat tctcctgcct    27060
caggctccca gtagctggg actacggggtg catgccacca tgccaagcta atgtttgtat    27120
ttttagtaga cacgggggttt tgctacattg gccaggctgg tctcgaactc ctgacctcaa    27180
gtgatctacc cgcctcagcc tcccaaagtg ctgggattat aggcctgaaa caaactaatc    27240
tggacacaca tacacacaca tgtaaattgt ttttaaaccc acaaaagatg ctgctctctt    27300
ttttttttat ttttgagtca gggtcagtct ctgttgtcca ggctggagta cagtggcagg    27360
agcacagctc actgtagcct ctgcctccca ggctcaagtg attctcccac ctcagcctcc    27420
caggaagcta ggaccacaaa catgcatcac catgcctggc taattttgt attttttata     27480 gagacagggt ctcactgtgt tgcccaggct ggtctcaaac tcctgggctc aggcaatcct    27540
ggcctcccaa agtgcttgga ttacaggtgt gagccgccat gcccagccca aaagatgcta    27600
ttctcttaat ctctcatttc cccatcttcc tctttaacac ctctaatata aaggacatta    27660
ttataccata ttgaaacttc acctagatat acagaaaacg ccccatctct gtattctgta    27720
tttgcaagct gcatgtttat atcaccatct acagatacc cttacacttc gttccccact    27780
```

```
tgagtttcgc catcactggc tttctgttgt tccactgggg aaagatttgg gattcacagg    27840
tgaactcttt tttttttttt tttttttttt tgagttggaa tctcgccctt tcgcccaggc    27900
tggaatgcag tggcacaatc tcggctcact gcagcctcct cctcccgggt tcaagcattt    27960
ctctgcctca gcctcccaag tagctgggat tacaggcacc tgccaccacg cccagctaat    28020
ttttttgtagt tttagtagac acagggtttc actatcttgg ccaggctggt ctcgaactcc    28080
tgacctcgtg atccaccgcc tcagcctccc aaagtgctgg aattacaggt gtgagccacc    28140
gcgcccagcc aaactccttt taaccacagg caaatggttt aagctacgtg ctgcagagga    28200
agctgctgcc catccctcat gagcagctaa caaaggcccc aaaccactga gcttcaagag    28260
aaaatcagca gatactcttg gctcttgtgt accagatacc tttctagata ctgagggaga    28320
agagcagtga acaaaacaga ccaaaaaatc tctgccttca tggaacttac atttcggagt    28380
ggacaggaga tcgagaccag cctggccaac atggtgaaat cccgtctcta ctaaaaatac    28440
aaaaattagc caggcgtggt ggcggacacc tgtaatccca gctactttgg aggctgaggc    28500
aggagcatcc cttgaaccca ggaggcagag gttgcagtga ccgagatcg cgccagtgca    28560
ctccagcctg ggcgacagag tgagactcca tctcaaaaaa aaaaaaaaaa aggtgactgg    28620
gtgcggtggc taactcctgt aatcccaaca ctttgggagg ccaaggcagg tggatcacaa    28680
ggtcaagagg tcgagaccat cctggccaac atggtgaagc cccatctcta ctaaacatac    28740
aaaaatcagc tgggcggtgg cacgcgcctg tagtcccagc tatttgggag gctgaggcag    28800
gagaattgct tgaacccggg agacggagat tgcagtgagc ctgaggtcac gcccttgcac    28860
tccagcctgg tgacagagtg agattctgtc tcagaaaaaa gaaggtgctt cagaggaaaa    28920
taaggccagt ggtggagctc ccaggcaggc tggaggaaca gtagtggggc tgcaggggct    28980
ggcgtggggt gaacaagggg cagagcagca gtagggcct gtagagctgt aggcctctga    29040
aggacttggg gcctcgggct ttttcaccaa gggcgaggca gtaagcagcc attggctgga    29100
tattgaagac cattcagtcc aagtagagga tagaaacagg gccccgaggc aggagcaagt    29160
tcagcctctt taaagccac agaaagaaac aagcccactt atgtagaagg aggtgagtga    29220
gggagcctgg ctgaagagaa ggctggggtg gagaaagcaa ggggaagctg gctcatatag    29280
tgaaaacttg ccacaaactg tggtggtgaa ggtgctgggc aggactcaga tgctaggatt    29340
gttggagaaa ggaaaattgg ggaagagacc atctactggc actggctgtg agtgctgctc    29400
atgtggccag gaacttgcaa ctcagcactg attgtttcta agaataaatg tcaagttggg    29460
aagatgtgta taaggggac ttagaccaca actgctgctt tgactgcgtt gccttgttgc    29520
tgtgctggaa aagctaaccc tgctttggcc ttccttcccc tgactaggtg ccggtatgtg    29580
agagagagag atcgcctggg taatgaatac cccaaactcc actaccctga gctgtatgtc    29640
ctgaaggggg gatacaagga gttctttatg aaatgccagg taagactggg gttgtggaga    29700
gcatctctcc tcccctgccc ccagtggtag actaatggat ctgtctggtg gtcatgactt    29760
tctttccagg ggtcggggga caaggtgggt atctgctgaa cccaaagaaa gcccctgtag    29820
aactggctcc ctaggtctgc ctggccgctt tcagccttgt agccctaggc agagaggaaa    29880
ccaggttgtg ggtgtgaggc aggtgtaccc taaccttatt ctctcctgtc ccctcagtct    29940
tactgtgagc cccctagcta ccggcccatg caccacgagg actttaaaga agacctgaag    30000
aagttccgca ccaagagccg gacctgggca ggggagaaga gcaagaggga gatgtacagt    30060
cgtctgaaga agctctgagg gcggcaggac cagccagcag cagcccaagc ttccctccat    30120
cccccttttac cctctttgct gcagagaaac ttaagcaaag gggacagctg tgtgacattt    30180
```

```
ggagaggggg cctgggactt ccatgcctta aacctacctc ccacactccc aaggttggag    30240
cccagggcat cttgctggct acgcctcttc tgtccctgtt agacgtcctc cgtccatatc    30300
agaactgtgc cacaatgcag ttctgagcac cgtgtcaagc tgctctgagc acagtggga    30360 tgaaccagcc ggggccttat cgggctccag ccatctcatg aggggagagg agacggaggg    30420
gagtagagaa gttacacaga aatgctgctg gccaaatagc aaagacaacc tgggaaggaa    30480
aggtctttgt gggataatcc atatgtttaa tttattcaac ttcatcaatc actttatttt    30540
attttttttt ctaactcctg gagacttatt ttactgcttc attaggttga aatactgcca    30600
ttctaggtag ggttttatta tcccagggac tacctcggct tttaatttaa aaaaaaaaaa    30660
gaagtgggta agaaaatgca aacctgttat aagttatcgg acagaaagct aggtgctctg    30720 tcaccccag gaggcgctgt ggtactgggg ctgctgctat ttaagccaag aactgaggtc    30780
ctggtgagag cgttggaccc aggcttggct gcctgacata agctaaatct cccagaccca    30840
ccactggcta ccgatatcta tttggtggga ggtgtggccc tgttcttcct caccccagtt    30900
ccatgacatt ggctggtata ggagccacag tcaggaaagc acttgaggca gcatctgttg    30960
ggccaccccc ggctcagtgc tggaatgttg cagtgtaggt ttcccaggga agggggtgg    31020 gggtaggtgg gctccacagg atggggaagg agcatgtcca ctgagtatct tccttatgtt    31080
gctgtgatat tgatagcttt tatttttctaa tttttaaaaa atggtcatat tatgagtcaa    31140
agagtatcaa atcagtgttg gatgaccac ccaagggtga ggagaggggc tggaagccct    31200
gggcattagg agaagggagt gggtgctggc atggacatga ctggatagaa ttttctcagg    31260
agggagcttg gtggattttg aaggtaaaac tttctgggtt tatcatgttt taattttaga    31320
gacagggagt gatgaatcat caccggttgt ccccttatct aactccataa aagtgggaat    31380
ttcaaaagaa cacctcatcc aaggagctgg ggcagacttc attgattcta gagagacctg    31440
tttcagtgcc tactcatccc tgccctctgg tgccagcctc cttaccatca cggcttcact    31500
gaggtgtagg tgggttttc ttaaacagga gacagtctct cccctcttac ctcaacttct    31560
tggggtggga atcagtgata ctggagatgg ctagttgctg tgttacgggt ttgagttaca    31620
tttggctata aaacaatctt gttgggaaaa atgtggggga gaggacttct tcctacacgc    31680
gcattgagac agattccaac tggttaatga tattgtttgt aagaaagaga ttctgttggt    31740
tgactgccta aagagaaagg tgggatggcc ttcagattat accagcttag ctagcattac    31800
taaccaactg ttggaagctc tgaaaataaa agatcttgaa cccatgctct ctgcctagtt    31860
cttgatgg                                                             31868
```

<210> SEQ ID NO 809
<211> LENGTH: 524
<212> TYPE: PRT
<213> ORGANISM: Homo sapiens

<400> SEQUENCE: 809

Met Glu Leu Gly Pro Glu Pro Pro His Arg Arg Leu Leu Phe Ala
1               5                   10                  15

Cys Ser Pro Pro Ala Ser Gln Pro Val Val Lys Ala Leu Phe Gly
                20                  25                  30

Ala Ser Ala Ala Gly Gly Leu Ser Pro Val Thr Asn Leu Thr Val Thr
                35                  40                  45

Met Asp Gln Leu Gln Gly Leu Gly Ser Asp Tyr Glu Gln Pro Leu Glu
    50                  55                  60

-continued

```
Val Lys Asn Asn Ser Asn Leu Gln Arg Met Gly Ser Glu Ser Thr
 65                  70                  75                  80

Asp Ser Gly Phe Cys Leu Asp Ser Pro Gly Pro Leu Asp Ser Lys Glu
                 85                  90                  95

Asn Leu Glu Asn Pro Met Arg Arg Ile His Ser Leu Pro Gln Lys Leu
            100                 105                 110

Leu Gly Cys Ser Pro Ala Leu Lys Arg Ser His Ser Asp Ser Leu Asp
        115                 120                 125

His Asp Ile Phe Gln Leu Ile Asp Pro Asp Glu Asn Lys Glu Asn Glu
    130                 135                 140

Ala Phe Glu Phe Lys Lys Pro Val Arg Pro Val Ser Arg Gly Cys Leu
145                 150                 155                 160

His Ser His Gly Leu Gln Glu Gly Lys Asp Leu Phe Thr Gln Arg Gln
                165                 170                 175

Asn Ser Ala Pro Ala Arg Met Leu Ser Ser Asn Glu Arg Asp Ser Ser
            180                 185                 190

Glu Pro Gly Asn Phe Ile Pro Leu Phe Thr Pro Gln Ser Pro Val Thr
        195                 200                 205

Ala Thr Leu Ser Asp Glu Asp Asp Gly Phe Val Asp Leu Leu Asp Gly
    210                 215                 220

Glu Asn Leu Lys Asn Glu Glu Thr Pro Ser Cys Met Ala Ser Leu
225                 230                 235                 240

Trp Thr Ala Pro Leu Val Met Arg Thr Thr Asn Leu Asp Asn Arg Cys
                245                 250                 255

Lys Leu Phe Asp Ser Pro Ser Leu Cys Ser Ser Ser Thr Arg Ser Val
            260                 265                 270

Leu Lys Arg Pro Glu Arg Ser Gln Glu Glu Ser Pro Pro Gly Ser Thr
        275                 280                 285

Lys Arg Arg Lys Ser Met Ser Gly Ala Ser Pro Lys Glu Ser Thr Asn
    290                 295                 300

Pro Glu Lys Ala His Glu Thr Leu His Gln Ser Leu Ser Leu Ala Ser
305                 310                 315                 320

Ser Pro Lys Gly Thr Ile Glu Asn Ile Leu Asp Asn Asp Pro Arg Asp
                325                 330                 335

Leu Ile Gly Asp Phe Ser Lys Gly Tyr Leu Phe His Thr Val Ala Gly
            340                 345                 350

Lys His Gln Asp Leu Lys Tyr Ile Ser Pro Glu Ile Met Ala Ser Val
        355                 360                 365

Leu Asn Gly Lys Phe Ala Asn Leu Ile Lys Glu Phe Val Ile Ile Asp
    370                 375                 380

Cys Arg Tyr Pro Tyr Glu Tyr Glu Gly Gly His Ile Lys Gly Ala Val
385                 390                 395                 400

Asn Leu His Met Glu Glu Glu Val Glu Asp Phe Leu Leu Lys Lys Pro
                405                 410                 415

Ile Val Pro Thr Asp Gly Lys Arg Val Ile Val Val Phe His Cys Glu
            420                 425                 430

Phe Ser Ser Glu Arg Gly Pro Arg Met Cys Arg Tyr Val Arg Glu Arg
        435                 440                 445

Asp Arg Leu Gly Asn Glu Tyr Pro Lys Leu His Tyr Pro Glu Leu Tyr
    450                 455                 460

Val Leu Lys Gly Gly Tyr Lys Glu Phe Phe Met Lys Cys Gln Ser Tyr
465                 470                 475                 480

Cys Glu Pro Pro Ser Tyr Arg Pro Met His His Glu Asp Phe Lys Glu
```

```
                   485                 490                 495
Asp Leu Lys Lys Phe Arg Thr Lys Ser Arg Thr Trp Ala Gly Glu Lys
            500                 505                 510

Ser Lys Arg Glu Met Tyr Ser Arg Leu Lys Lys Leu
        515                 520

<210> SEQ ID NO 810
<211> LENGTH: 2940
<212> TYPE: DNA
<213> ORGANISM: Homo sapiens

<400> SEQUENCE: 810
```

| | | | | | |
|---|---|---|---|---|---|
| gccagctgtg | ccggcgtttg | ttggctgccc | tgcgcccggc | cctccagcca | gccttctgcc | 60 |
| ggccccgccg | cgatggaggt | gccccagccg | agcccgcgc | caggctcggc | tctcagtcca | 120 |
| gcaggcgtgt | gcggtggcgc | ccagcgtccg | ggccacctcc | cgggcctcct | gctgggatct | 180 |
| catggcctcc | tggggtcccc | ggtgcgggcg | gccgcttcct | cgccggtcac | caccctcacc | 240 |
| cagaccatgc | acgacctcgc | cgggctcggc | agccgcagcc | gcctgacgca | cctatccctg | 300 |
| tctcgacggg | catccgaatc | ctccctgtcg | tctgaatcct | ccgaatcttc | tgatgcaggt | 360 |
| ctctgcatgg | attcccccag | ccctatggac | cccacatgg | cggagcagac | gtttgaacag | 420 |
| gccatccagg | cagccagccg | gatcattcga | aacgagcagt | ttgccatcag | acgcttccag | 480 |
| tctatgccgg | tgaggctgct | gggccacagc | cccgtgcttc | ggaacatcac | caactcccag | 540 |
| gcgcccgacg | gccggaggaa | gagcgaggcg | ggcagtggag | ctgccagcag | ctctggggaa | 600 |
| gacaaggaga | atgatggatt | tgtcttcaag | atgccatgga | agcccacaca | tcccagctcc | 660 |
| acccatgctc | tggcagagtg | ggccagccgc | agggaagcct | ttgcccagag | acccagctcg | 720 |
| gccccgacc | tgatgtgtct | cagtcctgac | cggaagatgg | aagtggagga | gctcagcccc | 780 |
| ctggccctag | gtcgcttctc | tctgaccccct | gcagagggg | atactgagga | agatgatgga | 840 |
| tttgtggaca | tcctagagag | tgacttaaag | gatgatgatg | cagttccccc | aggcatggag | 900 |
| agtctcatta | gtgccccact | ggtcaagacc | ttggaaaagg | aagaggaaaa | ggacctcgtc | 960 |
| atgtacagca | agtgccagcg | gctcttccgc | tctccgtcca | tgcctgcag | cgtgatccgg | 1020 |
| cccatcctca | agaggctgga | gcggcccag | gacaggaca | cgcccgtgca | gaataagcgg | 1080 |
| aggcggagcg | tgacccctcc | tgaggagcag | caggaggctg | aggaacctaa | agcccgcgtc | 1140 |
| ctccgctcaa | aatcactgtg | tcacgatgag | atcgagaacc | tcctggacag | tgaccaccga | 1200 |
| gagctgattg | gagattactc | taaggccttc | ctcctacaga | cagtagacgg | aaagcaccaa | 1260 |
| gacctcaagt | acatctcacc | agaaacgatg | gtggccctat | tgacgggcaa | gttcagcaac | 1320 |
| atcgtggata | agtttgtgat | tgtagactgc | agataccct | atgaatatga | aggcgggcac | 1380 |
| atcaagactg | cggtgaactt | gccctggaa | cgcgacgccg | agagcttcct | actgaagagc | 1440 |
| cccatcgcgc | cctgtagcct | ggacaagaga | gtcatcctca | ttttccactg | tgaattctca | 1500 |
| tctgagcgtg | ggccccgcat | gtgccgtttc | atcagggaac | gagaccgtgc | tgtcaacgac | 1560 |
| taccccagcc | tctactaccc | tgagatgtat | atcctgaaag | gcggctacaa | ggagttcttc | 1620 |
| cctcagcacc | cgaacttctg | tgaaccccag | gactaccggc | ccatgaacca | cgaggccttc | 1680 |
| aaggatgagc | taaagacctt | ccgcctcaag | actcgcagct | gggctgggga | gcggagccgg | 1740 |
| cgggagctct | gtagccggct | gcaggaccag | tgaggggcct | gcgccagtcc | tgctacctcc | 1800 |
| cttgcctttc | gaggcctgaa | gccagctgcc | ctatgggcct | gccgggctga | gggcctgctg | 1860 |
| gaggcctcag | gtgctgtcca | tgggaaagat | ggtgtggtgt | cctgcctgtc | tgccccagcc | 1920 |

```
cagattcccc tgtgtcatcc catcattttc catatcctgg tgccccccac ccctggaaga   1980
gcccagtctg ttgagttagt taagttgggt taataccagc ttaaaggcag tattttgtgt   2040
cctccaggag cttcttgttt ccttgttagg gttaacccct catcttcctg tgtcctgaaa   2100
cgctcctttg tgtgtgtgtc agctgaggct ggggagagcc gtggtccctg aggatgggtc   2160
agagctaaac tccttcctgg cctgagagtc agctctctgc cctgtgtact tcccgggcca   2220
gggctgcccc taatctctgt aggaaccgtg gtatgtctgc catgttgccc ctttctcttt   2280 tccccttttcc tgtcccacca tacgagcacc tccagcctga acagaagctc ttactctttc   2340
ctatttcagt gttacctgtg tgcttggtct gtttgacttt acgcccatct caggacactt   2400
ccgtagactg tttaggttcc cctgtcaaat atcagttacc cactcggtcc cagttttgtt   2460
gccccagaaa gggatgttat tatccttggg ggctcccagg gcaagggtta aggcctgaat   2520
catgagcctg ctggaagccc agccccctact gctgtgaacc ctggggcctg actgctcaga   2580
acttgctgct gtcttgttgc ggatggatgg aaggttggat ggatgggtgg atggccgtgg   2640
atggccgtgg atgcgcagtg ccttgcatac ccaaaccagg tgggagcgtt ttgttgagca   2700
tgacacctgc agcaggaata tatgtgtgcc tatttgtgtg gacaaaaata tttacactta   2760
gggtttggag ctattcaaga ggaaatgtca cagaagcagc taaaccaagg actgagcacc   2820
ctctggattc tgaatctcaa gatggggggca gggctgtgct tgaaggccct gctgagtcat   2880
ctgttagggc cttggttcaa taaagcactg agcaagttga gaaaaaaaaa aaaaaaaaa    2940
```

```
<210> SEQ ID NO 811
<211> LENGTH: 566
<212> TYPE: PRT
<213> ORGANISM: Homo sapiens

<400> SEQUENCE: 811

Met Glu Val Pro Gln Pro Glu Pro Ala Pro Gly Ser Ala Leu Ser Pro
1               5                   10                  15

Ala Gly Val Cys Gly Gly Ala Gln Arg Pro Gly His Leu Pro Gly Leu
            20                  25                  30

Leu Leu Gly Ser His Gly Leu Leu Gly Ser Pro Val Arg Ala Ala Ala
        35                  40                  45

Ser Ser Pro Val Thr Thr Leu Thr Gln Thr Met His Asp Leu Ala Gly
    50                  55                  60

Leu Gly Ser Arg Ser Arg Leu Thr His Leu Ser Leu Ser Arg Arg Ala
65                  70                  75                  80

Ser Glu Ser Ser Leu Ser Ser Glu Ser Ser Glu Ser Ser Asp Ala Gly
                85                  90                  95

Leu Cys Met Asp Ser Pro Ser Pro Met Asp Pro His Met Ala Glu Gln
            100                 105                 110

Thr Phe Glu Gln Ala Ile Gln Ala Ala Ser Arg Ile Ile Arg Asn Glu
        115                 120                 125

Gln Phe Ala Ile Arg Arg Phe Gln Ser Met Pro Val Arg Leu Leu Gly
    130                 135                 140

His Ser Pro Val Leu Arg Asn Ile Thr Asn Ser Gln Ala Pro Asp Gly
145                 150                 155                 160

Arg Arg Lys Ser Glu Ala Gly Ser Gly Ala Ala Ser Ser Ser Gly Glu
                165                 170                 175

Asp Lys Glu Asn Asp Gly Phe Val Phe Lys Met Pro Trp Lys Pro Thr
            180                 185                 190
```

```
His Pro Ser Ser Thr His Ala Leu Ala Glu Trp Ala Ser Arg Arg Glu
        195                 200                 205
Ala Phe Ala Gln Arg Pro Ser Ser Ala Pro Asp Leu Met Cys Leu Ser
    210                 215                 220
Pro Asp Arg Lys Met Glu Val Glu Glu Leu Ser Pro Leu Ala Leu Gly
225                 230                 235                 240
Arg Phe Ser Leu Thr Pro Ala Glu Gly Asp Thr Glu Glu Asp Asp Gly
            245                 250                 255
Phe Val Asp Ile Leu Glu Ser Asp Leu Lys Asp Asp Asp Ala Val Pro
                260                 265                 270
Pro Gly Met Glu Ser Leu Ile Ser Ala Pro Leu Val Lys Thr Leu Glu
        275                 280                 285
Lys Glu Glu Lys Asp Leu Val Met Tyr Ser Lys Cys Gln Arg Leu
    290                 295                 300
Phe Arg Ser Pro Ser Met Pro Cys Ser Val Ile Arg Pro Ile Leu Lys
305                 310                 315                 320
Arg Leu Glu Arg Pro Gln Asp Arg Asp Thr Pro Val Gln Asn Lys Arg
            325                 330                 335
Arg Arg Ser Val Thr Pro Pro Glu Glu Gln Gln Glu Ala Glu Glu Pro
                340                 345                 350
Lys Ala Arg Val Leu Arg Ser Lys Ser Leu Cys His Asp Glu Ile Glu
        355                 360                 365
Asn Leu Leu Asp Ser Asp His Arg Glu Leu Ile Gly Asp Tyr Ser Lys
    370                 375                 380
Ala Phe Leu Leu Gln Thr Val Asp Gly Lys His Gln Asp Leu Lys Tyr
385                 390                 395                 400
Ile Ser Pro Glu Thr Met Val Ala Leu Leu Thr Gly Lys Phe Ser Asn
            405                 410                 415
Ile Val Asp Lys Phe Val Ile Val Asp Cys Arg Tyr Pro Tyr Glu Tyr
                420                 425                 430
Glu Gly Gly His Ile Lys Thr Ala Val Asn Leu Pro Leu Glu Arg Asp
        435                 440                 445
Ala Glu Ser Phe Leu Leu Lys Ser Pro Ile Ala Pro Cys Ser Leu Asp
    450                 455                 460
Lys Arg Val Ile Leu Ile Phe His Cys Glu Phe Ser Ser Glu Arg Gly
465                 470                 475                 480
Pro Arg Met Cys Arg Phe Ile Arg Glu Arg Asp Arg Ala Val Asn Asp
            485                 490                 495
Tyr Pro Ser Leu Tyr Tyr Pro Glu Met Tyr Ile Leu Lys Gly Gly Tyr
                500                 505                 510
Lys Glu Phe Phe Pro Gln His Pro Asn Phe Cys Glu Pro Gln Asp Tyr
        515                 520                 525
Arg Pro Met Asn His Glu Ala Phe Lys Asp Glu Leu Lys Thr Phe Arg
    530                 535                 540
Leu Lys Thr Arg Ser Trp Ala Gly Glu Arg Ser Arg Arg Glu Leu Cys
545                 550                 555                 560
Ser Arg Leu Gln Asp Gln
            565
```

<210> SEQ ID NO 812
<211> LENGTH: 2115
<212> TYPE: DNA
<213> ORGANISM: Homo sapiens

<400> SEQUENCE: 812

-continued

```
ggtcaacgcc tgcggctgtt gatattcttg ctcagaggcc gtaactttgg ccttctgctc      60
agggaagact ctgagtccga cgttggccta cccagtcgga aggcagagct gcaatctagt     120
taactacctc ctttccccta gatttccttt cattctgctc aagtcttcgc ctgtgtccga     180
tccctatcta ctttctctcc tcttgtagca agcctcagac tccaggcttg agctaggttt     240
tgttttctc ctggtgagaa ttcgaagacc atgtctacgg aactcttctc atccacaaga      300
gaggaaggaa gctctggctc aggacccagt tttaggtcta atcaaaggaa aatgttaaac     360
ctgctcctgg agagagacac ttcctttacc gtctgtccag atgtccctag aactccagtg     420
ggcaaatttc ttggtgattc tgcaaaccta agcatttgt ctggaggaac cccaaaatgt      480
tgcctcgatc tttcgaatct tagcagtggg gagataactg ccactcagct taccacttct     540
gcagaccttg atgaaactgg tcacctggat tcttcaggac ttcaggaagt gcatttagct     600
gggatgaatc atgaccagca cctaatgaaa tgtagcccag cacagcttct ttgtagcact     660
ccgaatggtt tggaccgtgg ccatagaaag agagatgcaa tgtgtagttc atctgcaaat     720
aaagaaaatg acaatggaaa cttggtggac agtgaaatga atatttggg cagtcccatt      780
actactgttc caaaattgga taaaaatcca aacctaggag aagaccaggc agaagagatt     840
tcagatgaat taatggagtt ttccctgaaa gatcaagaag caaaggtgag cagaagtggc     900
ctatatcgct ccccgtcgat gccagagaac ttgaacaggc caagactgaa gcaggtggaa     960
aaattcaagg acaacacaat accagataaa gttaaaaaa agtattttc tggccaagga     1020
aagctcagga agggcttatg tttaaagaag acagtctctc tgtgtgacat tactatcact    1080
cagatgctgg aggaagattc taaccagggg cacctgattg gtgatttttc caaggtatgt    1140
gcgctgccaa ccgtgtcagg gaaacaccaa gatctgaagt atgtcaaccc agaaacagtg    1200
gctgccttac tgtcggggaa gttccagggt ctgattgaga gttttatgt cattgattgt    1260
cgctatccat atgagtatct gggaggacac atccagggag ccttaaactt atatagtcag   1320
gaagaactgt ttaacttctt tctgaagaag cccatcgtcc ctttggacac ccagaagaga   1380
ataatcatcg tgttccactg tgaattctcc tcagagaggg gccccgaat gtgccgctgt    1440
ctgcgtgaag aggacaggtc tctgaaccag tatcctgcat tgtactaccc agagctatat   1500
atccttaaag gcggctacag agacttcttt ccagaatata tggaactgtg tgaaccacag   1560
agctactgcc ctatgcatca tcaggaccac aagactgagt tgctgaggtg tcgaagccag   1620
agcaaagtgc aggaaggga gcggcagctg cgggagcaga ttgccccttct ggtgaaggac   1680
atgagcccat gataacattc cagccactgg ctgctaacaa gtcaccaaaa agacactgca   1740
gaaaccctga gcagaaagag gccttctgga tggccaaacc caagattatt aaaagatgtc   1800
tctgcaaacc aacaggctac caacttgtat ccaggcctgg gaatggatta ggtttcagca   1860
gagctgaaag ctggtggcag agtcctggag ctggctctat aaggcagcct tgagttgcat   1920
agagatttgt attggttcag ggaactctgg cattcctttt cccaactcct catgtcttct   1980
cacaagccag ccaactcttt ctctctgggc ttcgggctat gcaagagcgt tgtctacctt   2040
ctttctttgt attttccttc tttgtttccc cctctttctt ttttaaaaat ggaaaaataa   2100
acactacaga atgag                                                    2115
```

<210> SEQ ID NO 813
<211> LENGTH: 473
<212> TYPE: PRT
<213> ORGANISM: Homo sapiens -continued

```
<400> SEQUENCE: 813

Met Ser Thr Glu Leu Phe Ser Ser Thr Arg Glu Gly Ser Ser Gly
1               5                   10                  15

Ser Gly Pro Ser Phe Arg Ser Asn Gln Arg Lys Met Leu Asn Leu Leu
            20                  25                  30

Leu Glu Arg Asp Thr Ser Phe Thr Val Cys Pro Asp Val Pro Arg Thr
        35                  40                  45

Pro Val Gly Lys Phe Leu Gly Asp Ser Ala Asn Leu Ser Ile Leu Ser
50                  55                  60

Gly Gly Thr Pro Lys Cys Cys Leu Asp Leu Ser Asn Leu Ser Ser Gly
65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Ser Pro Ala Gln Leu Leu Cys
        115                 120                 125

Ser Thr Pro Asn Gly Leu Asp Arg Gly His Arg Lys Arg Asp Ala Met
130                 135                 140

Cys Ser Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Glu Ile Ser Asp
            180                 185                 190

Glu Leu Met Glu Phe Ser Leu Lys Asp Gln Glu Ala Lys Val Ser Arg
        195                 200                 205

Ser Gly Leu Tyr Arg Ser Pro Ser Met Pro Glu Asn Leu Asn Arg Pro
210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
            260                 265                 270

Leu Glu Glu Asp Ser Asn Gln Gly His Leu Ile Gly Asp Phe Ser Lys
        275                 280                 285

Val Cys Ala Leu Pro Thr Val Ser Gly Lys His Gln Asp Leu Lys Tyr
290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                325                 330                 335

Leu Gly Gly His Ile Gln Gly Ala Leu Asn Leu Tyr Ser Gln Glu Glu
            340                 345                 350

Leu Phe Asn Phe Phe Leu Lys Lys Pro Ile Val Pro Leu Asp Thr Gln
        355                 360                 365

Lys Arg Ile Ile Ile Val Phe His Cys Glu Phe Ser Ser Glu Arg Gly
370                 375                 380

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
                405                 410                 415
```

Arg Asp Phe Phe Pro Glu Tyr Met Glu Leu Cys Glu Pro Gln Ser Tyr
            420                 425                 430

Cys Pro Met His His Gln Asp His Lys Thr Glu Leu Leu Arg Cys Arg
        435                 440                 445

Ser Gln Ser Lys Val Gln Glu Gly Glu Arg Gln Leu Arg Glu Gln Ile
    450                 455                 460

Ala Leu Leu Val Lys Asp Met Ser Pro
465                 470

<210> SEQ ID NO 814
<211> LENGTH: 1896
<212> TYPE: DNA
<213> ORGANISM: Homo sapiens

<400> SEQUENCE: 814

| | | | | | |
|---|---|---|---|---|---|
| ggtcaacgcc | tgcggctgtt | gatattcttg | ctcagaggcc | gtaactttgg | ccttctgctc | 60 |
| agggaagact | ctgagtccga | cgttggccta | cccagtcgga | aggcagagct | gcaatctagt | 120 |
| taactacctc | cttccccta | gatttccttt | cattctgctc | aagtcttcgc | ctgtgtccga | 180 |
| tccctatcta | ctttctctcc | tcttgtagca | agcctcagac | tccaggcttg | agctaggttt | 240 |
| tgttttctc | ctggtgagaa | ttcgaagacc | atgtctacgg | aactcttctc | atccacaaga | 300 |
| gaggaaggaa | gctctggctc | aggacccagt | tttaggtcta | atcaaaggaa | aatgttaaac | 360 |
| ctgctcctgg | agagagacac | ttcctttacc | gtctgtccag | atgtccctag | aactccagtg | 420 |
| ggcaaatttc | ttggtgattc | tgcaaaccta | agcattttgt | ctgggtcacc | tggattcttc | 480 |
| aggacttcag | gaagtgcatt | tagctgggat | gacaatggaa | acttggtgga | cagtgaaatg | 540 |
| aaatatttgg | gcagtcccat | tactactgtt | ccaaaattgg | ataaaaatcc | aaacctagga | 600 |
| gaagaccagg | cagaagagat | ttcagatgaa | ttaatggagt | tttccctgaa | agatcaagaa | 660 |
| gcaaaggtga | gcagaagtgg | cctatatcgc | tccccgtcga | tgccagagaa | cttgaacagg | 720 |
| ccaagactga | agcaggtgga | aaaattcaag | acaacacaa | taccagataa | agttaaaaaa | 780 |
| aagtattttt | ctggccaagg | aaagctcagg | aagggcttat | gtttaaagaa | gacagtctct | 840 |
| ctgtgtgaca | ttactatcac | tcagatgctg | gaggaagatt | ctaaccaggg | gcacctgatt | 900 |
| ggtgattttt | ccaaggtatg | tgcgctgcca | accgtgtcag | ggaaacacca | agatctgaag | 960 |
| tatgtcaacc | agaaacagt | ggctgcctta | ctgtcgggga | agttccaggg | tctgattgag | 1020 |
| aagttttatg | tcattgattg | tcgctatcca | tgagtgatc | tgggaggaca | catccaggga | 1080 |
| gccttaaact | tatatagtca | ggaagaactg | tttaacttct | ttctgaagaa | gcccatcgtc | 1140 |
| cctttggaca | cccagaagag | aataatcatc | gtgttccact | gtgaattctc | ctcagagagg | 1200 |
| ggccccgaa | tgtgccgctg | tctgcgtgaa | gaggacaggt | ctctgaacca | gtatcctgca | 1260 |
| ttgtactacc | cagagctata | tatccttaaa | ggcggctaca | gagacttctt | tccagaatat | 1320 |
| atggaactgt | gtgaaccaca | gagctactgc | cctatgcatc | atcaggacca | caagactgag | 1380 |
| ttgctgaggt | gtcgaagcca | gagcaaagtg | caggaagggg | agcggcagct | gcgggagcag | 1440 |
| attgcccttc | tggtgaagga | catgagccca | tgataacatt | ccagccactg | gctgctaaca | 1500 |
| agtcaccaaa | aagacactgc | agaaaccctg | agcagaaaga | ggccttctgg | atggccaaac | 1560 |
| ccaagattat | taaagatgt | ctctgcaaac | caacaggcta | ccaacttgta | tccaggcctg | 1620 |
| ggaatggatt | aggtttcagc | agagctgaaa | gctggtggca | gagtcctgga | gctggctcta | 1680 |
| taaggcagcc | ttgagttgca | tagagatttg | tattggttca | gggaactctg | gcattccttt | 1740 |

-continued

```
tcccaactcc tcatgtcttc tcacaagcca gccaactctt tctctctggg cttcgggcta    1800
tgcaagagcg ttgtctacct tctttctttg tattttcctt ctttgtttcc ccctctttct    1860
tttttaaaaa tggaaaaata aacactacag aatgag                              1896
```

<210> SEQ ID NO 815
<211> LENGTH: 400
<212> TYPE: PRT
<213> ORGANISM: Homo sapiens

<400> SEQUENCE: 815

```
Met Ser Thr Glu Leu Phe Ser Ser Thr Arg Glu Glu Gly Ser Ser Gly
 1               5                  10                  15

Ser Gly Pro Ser Phe Arg Ser Asn Gln Arg Lys Met Leu Asn Leu Leu
            20                  25                  30

Leu Glu Arg Asp Thr Ser Phe Thr Val Cys Pro Asp Val Pro Arg Thr
        35                  40                  45

Pro Val Gly Lys Phe Leu Gly Asp Ser Ala Asn Leu Ser Ile Leu Ser
    50                  55                  60

Gly Ser Pro Gly Phe Phe Arg Thr Ser Gly Ser Ala Phe Ser Trp Asp
65                  70                  75                  80

Asp Asn Gly Asn Leu Val Asp Ser Glu Met Lys Tyr Leu Gly Ser Pro
                85                  90                  95

Ile Thr Thr Val Pro Lys Leu Asp Lys Asn Pro Asn Leu Gly Glu Asp
            100                 105                 110

Gln Ala Glu Glu Ile Ser Asp Glu Leu Met Glu Phe Ser Leu Lys Asp
        115                 120                 125

Gln Glu Ala Lys Val Ser Arg Ser Gly Leu Tyr Arg Ser Pro Ser Met
    130                 135                 140

Pro Glu Asn Leu Asn Arg Pro Arg Leu Lys Gln Val Glu Lys Phe Lys
145                 150                 155                 160

Asp Asn Thr Ile Pro Asp Lys Val Lys Lys Tyr Phe Ser Gly Gln
                165                 170                 175

Gly Lys Leu Arg Lys Gly Leu Cys Leu Lys Lys Thr Val Ser Leu Cys
            180                 185                 190

Asp Ile Thr Ile Thr Gln Met Leu Glu Glu Asp Ser Asn Gln Gly His
        195                 200                 205

Leu Ile Gly Asp Phe Ser Lys Val Cys Ala Leu Pro Thr Val Ser Gly
    210                 215                 220

Lys His Gln Asp Leu Lys Tyr Val Asn Pro Glu Thr Val Ala Ala Leu
225                 230                 235                 240

Leu Ser Gly Lys Phe Gln Gly Leu Ile Glu Lys Phe Tyr Val Ile Asp
                245                 250                 255

Cys Arg Tyr Pro Tyr Glu Tyr Leu Gly Gly His Ile Gln Gly Ala Leu
            260                 265                 270

Asn Leu Tyr Ser Gln Glu Glu Leu Phe Asn Phe Leu Lys Lys Pro
        275                 280                 285

Ile Val Pro Leu Asp Thr Gln Lys Arg Ile Ile Val Phe His Cys
    290                 295                 300

Glu Phe Ser Ser Glu Arg Gly Pro Arg Met Cys Arg Cys Leu Arg Glu
305                 310                 315                 320

Glu Asp Arg Ser Leu Asn Gln Tyr Pro Ala Leu Tyr Tyr Pro Glu Leu
                325                 330                 335

Tyr Ile Leu Lys Gly Gly Tyr Arg Asp Phe Phe Pro Glu Tyr Met Glu
            340                 345                 350
```

Leu Cys Glu Pro Gln Ser Tyr Cys Pro Met His His Gln Asp His Lys
          355                 360                 365

Thr Glu Leu Leu Arg Cys Arg Ser Gln Ser Lys Val Gln Glu Gly Glu
        370                 375                 380

Arg Gln Leu Arg Glu Gln Ile Ala Leu Leu Val Lys Asp Met Ser Pro
385                 390                 395                 400

<210> SEQ ID NO 816
<211> LENGTH: 3318
<212> TYPE: DNA
<213> ORGANISM: Homo sapiens

<400> SEQUENCE: 816

| | |
|---|---|
| gtgatgcgta gttccggctg ccggttgaca tgaagaagca gcagcggcta gggcggcggt | 60 |
| agctgcaggg gtcggggatt gcagcgggcc tcggggctaa gagcgcgacg cggcctagag | 120 |
| cggcagacgc cgcagtgggc cgagaaggag gcgcagcagc cgccctggcc cgtcatggag | 180 |
| atggaaaagg agttcgagca gatcgacaag tccgggagct gggcggccat ttaccaggat | 240 |
| atccgacatg aagccagtga cttcccatgt agagtggcca agcttcctaa gaacaaaaac | 300 |
| cgaaataggt acagagacgt cagtcccttt gaccatagtc ggattaaact acatcaagaa | 360 |
| gataatgact atatcaacgc tagttttgata aaaatggaag aagcccaaag gagttacatt | 420 |
| cttacccagg gccctttgcc taacacatgc ggtcactttt gggagatggt gtgggagcag | 480 |
| aaaagcaggg gtgtcgtcat gctcaacaga gtgatggaga aaggttcgtt aaaatgcgca | 540 |
| caatactggc cacaaaaaga agaaaaagag atgatctttg aagacacaaa tttgaaatta | 600 |
| acattgatct ctgaagatat caagtcatat tatacagtgc gacagctaga attggaaaac | 660 |
| cttacaaccc aagaaactcg agagatctta catttccact ataccacatg gcctgacttt | 720 |
| ggagtccctg aatcaccagc ctcattcttg aactttcttt tcaaagtccg agagtcaggg | 780 |
| tcactcagcc ggagcacgg gcccgttgtg gtgcactgca gtgcaggcat cggcaggtct | 840 |
| ggaaccttct gtctggctga tacctgcctc ttgctgatgg acaagaggaa agacccttct | 900 |
| tccgttgata tcaagaaagt gctgttagaa atgaggaagt ttcggatggg gctgatccag | 960 |
| acagccgacc agctgcgctt ctcctacctg gctgtgatcg aaggtgccaa attcatcatg | 1020 |
| ggggactctt ccgtgcagga tcagtggaag gagctttccc acgaggacct ggagccccca | 1080 |
| cccgagcata tccccccacc tccccggcca cccaaacgaa tcctggagcc acacaatggg | 1140 |
| aaaatgcaggg agttcttccc aaatcaccag tgggtgaagg aagagaccca ggaggataaa | 1200 |
| gactgcccca tcaaggaaga aaaaggaagc cccttaaatg ccgcacccta cggcatcgaa | 1260 |
| agcatgagtc aagacactga agttagaagt cgggtcgtgg ggggaagtct tcgaggtgcc | 1320 |
| caggctgcct ccccagccaa aggggagccg tcactgcccg agaaggacga ggaccatgca | 1380 |
| ctgagttact ggaagccctt cctggtcaac atgtgcgtgg ctacggtcct cacggccggc | 1440 |
| gcttacctct gctacaggtt cctgttcaac agcaacacat agcctgaccc tcctccactc | 1500 |
| cacctccacc cactgtccgc ctctgcccgc agagcccacg cccgactagc aggcatgccg | 1560 |
| cggtaggtaa gggccgccgg accgcgtaga gagccgggcc ccggacggac gttggttctg | 1620 |
| cactaaaacc catcttcccc ggatgtgtgt ctcaccectc atcctttac tttttgcccc | 1680 |
| ttccactttg agtaccaaat ccacaagcca tttttttgagg agagtgaaag agagtaccat | 1740 |
| gctggcggcg cagagggaag gggcctacac ccgtctgggg gctcgcccca cccagggctc | 1800 |
| cctcctggag catcccaggc gggcggcacg ccaacagccc cccccttgaa tctgcaggga | 1860 |

```
gcaactctcc actccatatt tatttaaaca attttttccc caaaggcatc catagtgcac    1920
tagcattttc ttgaaccaat aatgtattaa aattttttga tgtcagcctt gcatcaaggg    1980
ctttatcaaa aagtacaata ataaatcctc aggtagtact gggaatggaa ggctttgcca    2040
tgggcctgct gcgtcagacc agtactggga aggaggacgg ttgtaagcag ttgttattta    2100
gtgatattgt gggtaacgtg agaagataga acaatgctat aatatataat gaacacgtgg    2160
gtatttaata agaaacatga tgtgagatta ctttgtcccg cttattctcc tccctgttat    2220
ctgctagatc tagttctcaa tcactgctcc cccgtgtgta ttagaatgca tgtaaggtct    2280
tcttgtgtcc tgatgaaaaa tatgtgcttg aaatgagaaa ctttgatctc tgcttactaa    2340
tgtgccccat gtccaagtcc aacctgcctg tgcatgacct gatcattaca tggctgtggt    2400
tcctaagcct gttgctgaag tcattgtcgc tcagcaatag ggtgcagttt ccaggaata     2460 ggcatttgcc taattcctgg catgacactc tagtgacttc ctggtgaggc ccagcctgtc    2520
ctggtacagc agggtcttgc tgtaactcag acattccaag ggtatgggaa gccatattca    2580
cacctcacgc tctggacatg atttagggaa gcaggacac ccccgcccc ccacctttgg      2640 gatcagcctc cgccattcca agtcaacact cttcttgagc agaccgtgat ttggaagaga    2700
ggcacctgct ggaaaccaca cttcttgaaa cagcctgggt gacggtcctt taggcagcct    2760
gccgccgtct ctgtcccggt tcaccttgcc gagagaggcg cgtctgcccc accctcaaac    2820 cctgtgggc ctgatggtgc tcacgactct cctgcaaag ggaactgaag acctccacat      2880
taagtggctt tttaacatga aaacacggc agctgtagct cccgagctac tctcttgcca     2940
gcattttcac attttgcctt tctcgtggta gaagccagta cagagaaatt ctgtggtggg    3000
aacattcgag gtgtcaccct gcagagctat ggtgaggtgt ggataaggct taggtgccag    3060
gctgtaagca ttctgagctg ggcttgttgt ttttaagtcc tgtatatgta tgtagtagtt    3120
tgggtgtgta tatatagtag catttcaaaa tggacgtact ggtttaacct cctatccttg    3180
gagagcagct ggctctccac cttgttacac attatgttag agaggtagcg agctgctctg    3240
ctatatgcct taagccaata tttactcatc aggtcattat ttttttacaat ggccatggaa    3300 taaaccattt ttacaaaa                                                   3318
```

<210> SEQ ID NO 817
<211> LENGTH: 435
<212> TYPE: PRT
<213> ORGANISM: Homo sapiens

<400> SEQUENCE: 817

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
          115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
            165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
            195                 200                 205

Gly Pro Val Val Val His Cys Ser Ala Gly Ile Gly Arg Ser Gly Thr
        210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
                260                 265                 270

Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Pro Glu
        290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Lys Gly Ser
            340                 345                 350

Pro Leu Asn Ala Ala Pro Tyr Gly Ile Glu Ser Met Ser Gln Asp Thr
            355                 360                 365

Glu Val Arg Ser Arg Val Val Gly Gly Ser Leu Arg Gly Ala Gln Ala
        370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 818
<211> LENGTH: 2346
<212> TYPE: DNA
<213> ORGANISM: Mus musculus

<400> SEQUENCE: 818
gaattcggga tccttttgca cattcctagt tagcagtgca tactcatcag actggagatg    60
tttaatgaca tcagggaacc aaacggacaa cccatagtac ccgaagacag ggtgaaccag   120
acaatcgtaa gcttgatggt gttttccctg actgggtagt tgaagcatct catgaatgtc   180
agccaaattc cgtacagttc ggtgcggatc cgaacgaaac acctcctgta ccaggttccc   240

```
gtgtcgctct caatttcaat cagctcatct atttgtttgg gagtcttgat tttatttacc      300
gtgaagacct tctctggctg cccccgggct ctcatgttgg tgtcatgaat taacttcaga      360
atcatccagg cttcatcatg tttccccacc tccagcaaga accgagggct ttctggcatg      420
aaggtgagag ccaccacaga ggagacgcat gggagcgcac agacgatgac gaagacgcgc      480
cacgtgtgga actggtaggc tgaacccatg ctgaagctcc acccgtagtg gggaatgatg      540
gcccaggcat ggcggaggct agatgccgcc aatcatccag aacatgcaga agccgctgct      600
ggggagcttg ggctgcggt ggtggcgggt gacgggcttc gggacgcgga gcgacgcggc       660
ctagcgcggc ggacggccgt gggaactcgg gcagccgacc cgtcccgcca tggagatgga      720
gaaggagttc gaggagatcg acaaggctgg gaactgggcg gctatttacc aggacattcg      780
acatgaagcc agcgacttcc catgcaaagt cgcgaagctt cctaagaaca aaaaccggaa      840
caggtaccga gatgtcagcc ttttgacca cagtcggatt aaattgcacc aggaagataa       900
tgactatatc aatgccagct tgataaaaat ggaagaagcc cagaggagct atattctcac      960
ccagggccct ttaccaaaca catgtgggca cttctgggag atggtgtggg agcagaagag     1020
caggggcgtg gtcatgctca accgcatcat ggagaaaggc tcgttaaaat gtgcccagta     1080
ttggccacag caagaagaaa aggagatggt ctttgatgac acaggtttga agttgacact     1140
aatctctgaa gatgtcaagt catattacac agtacgacag ttggagttgg aaaacctgac     1200
taccaaggag actcgagaga tcctgcattt ccactacacc acatggcctg actttggagt     1260
ccccgagtca ccggcttctt tcctcaattt cctttttcaaa gtccgagagt caggctcact     1320
cagcctggag catggcccca ttgtggtcca ctgcagcgcc ggcatcggga ggtcagggac     1380
cttctgtctg gctgacacct gcctcttact gatggacaag aggaaagacc catcttccgt     1440
ggacatcaag aaagtactgc tggagatgcg caggttccgc atgggctca tccagactgc      1500 cgaccagctg cgcttctcct acctggctgt catcgagggc gccaagttca tcatgggcga     1560
ctcgtcagtg caggatcagt ggaaggagct ctcccgggag gatctagacc ttccacccga     1620
gcacgtgccc ccacctcccc ggccaccaa acgcacactg gagcctcaca cggaagtg       1680 caaggagctc ttctccagcc accagtgggt gagcgaggag acctgtgggg atgaagacag     1740
cctggccaga gaggaaggca gagcccagtc aagtgccatg cacagcgtga gcagcatgag     1800
tccagacact gaagttagga gacggatggt gggtggaggt cttcaaagtg ctcaggcgtc     1860
tgtccccacc gaggaagagc tgtcctccac tgaggaggaa cacaaggcac attggccaag     1920
tcactggaag cccttcctgg tcaatgtgtg catggccacg ctcctggcca ccggcgcgta     1980
cttgtgctac cgggtgtgtt ttcactgaca gactgggagg cactgccact gcccagctta     2040
ggatgcggtc tgcggcgtct gacctggtgt agagggaaca acaactcgca agcctgctct     2100
ggaactggaa gggcctgccc caggagggta ttagtgcact gggctttgaa ggagcccctg     2160
gtcccacgaa cagagtctaa tctcagggcc ttaacctgtt caggagaagt agaggaaatg     2220
ccaaatactc ttcttgctct cacctcactc ctccccttc tctgattcat ttgtttttgg      2280
aaaaaaaaaa aaaagaatt acaacacatt gttgttttta acatttataa aggcaggccc      2340
gaattc                                                                2346
```

<210> SEQ ID NO 819
<211> LENGTH: 432
<212> TYPE: PRT
<213> ORGANISM: Mus musculus

<400> SEQUENCE: 819

```
Met Glu Met Glu Lys Glu Phe Glu Glu Ile Asp Lys Ala Gly Asn Trp
1               5                   10                  15

Ala Ala Ile Tyr Gln Asp Ile Arg His Glu Ala Ser Asp Phe Pro Cys
            20                  25                  30

Lys Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Ile Met Glu Lys Gly Ser Leu Lys Cys Ala Gln Tyr Trp Pro Gln Gln
        115                 120                 125

Glu Glu Lys Glu Met Val Phe Asp Asp Thr Gly Leu Lys Leu Thr Leu
    130                 135                 140

Ile Ser Glu Asp Val Lys Ser Tyr Tyr Thr Val Arg Gln Leu Glu Leu
145                 150                 155                 160

Glu Asn Leu Thr Thr Lys Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Leu Glu His
        195                 200                 205

Gly Pro Ile Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Arg Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser Arg Glu Asp Leu Asp Leu Pro Pro Glu
    290                 295                 300

His Val Pro Pro Pro Arg Pro Pro Lys Arg Thr Leu Glu Pro His Asn
305                 310                 315                 320

Asn Gly Lys Cys Lys Glu Leu Phe Ser Ser His Gln Trp Val Ser Glu
                325                 330                 335

Glu Thr Cys Gly Asp Glu Asp Ser Leu Ala Arg Glu Gly Arg Ala
            340                 345                 350

Gln Ser Ser Ala Met His Ser Val Ser Met Ser Pro Asp Thr Glu
        355                 360                 365

Val Arg Arg Arg Met Val Gly Gly Leu Gln Ser Ala Gln Ala Ser
    370                 375                 380

Val Pro Thr Glu Glu Leu Ser Ser Thr Glu Glu His Lys Ala
385                 390                 395                 400

His Trp Pro Ser His Trp Lys Pro Phe Leu Val Asn Val Cys Met Ala
                405                 410                 415
```

Thr Leu Leu Ala Thr Gly Ala Tyr Leu Cys Tyr Arg Val Cys Phe His
            420                 425                 430

<210> SEQ ID NO 820
<211> LENGTH: 4127
<212> TYPE: DNA
<213> ORGANISM: Rattus novegicus

<400> SEQUENCE: 820

| | | | | | |
|---|---|---|---|---|---|
| agccgctgct | ggggaggttg | gggctgaggt | ggtggcgggc | gacgggcctc | gagacgcgga | 60 |
| gcgacgcggc | ctagcgcggc | ggacggccga | gggaactcgg | gcagtcgtcc | cgtcccgcca | 120 |
| tggaaatgga | gaaggaattc | gagcagatcg | ataaggctgg | gaactgggcg | gctatttacc | 180 |
| aggatattcg | acatgaagcc | agtgacttcc | catgcagaat | agcgaaactt | cctaagaaca | 240 |
| aaaaccggaa | caggtaccga | gatgtcagcc | cttttgacca | cagtcggatt | aaattgcatc | 300 |
| aggaagataa | tgactatatc | aatgccagct | tgataaaaat | ggaggaagcc | cagaggagct | 360 |
| atatcctcac | ccagggccct | ttaccaaaca | cgtgcgggca | cttctgggag | atggtgtggg | 420 |
| agcagaagag | caggggcgtg | gtcatgctca | accgcatcat | ggagaaaggc | tcgttaaaat | 480 |
| gtgcccagta | ttggccacag | aaagaagaaa | aagagatggt | cttcgatgac | accaatttga | 540 |
| agctgacact | gatctctgaa | gatgtcaagt | catattacac | agtacggcag | ttggagttgg | 600 |
| agaacctggc | tacccaggag | gctcgagaga | tcctgcattt | ccactacacc | acctggcctg | 660 |
| actttggagt | ccctgagtca | cctgcctctt | tcctcaattt | cctattcaaa | gtccgagagt | 720 |
| caggctcact | cagcccagag | cacggcccca | ttgtggtcca | ctgcagtgct | ggcattggca | 780 |
| ggtcagggac | cttctgcctg | gctgacacct | gcctcttact | gatggacaag | aggaaagacc | 840 |
| cgtcctctgt | ggacatcaag | aaagtgctgt | tggagatgcg | caggttccgc | atggggctca | 900 |
| tccagacggc | cgaccaactg | cgcttctcct | acctggctgt | gatcgagggt | gcaaagttca | 960 |
| tcatgggcga | ctcgtcagtg | caggatcagt | ggaaggagct | ttcccatgaa | gacctggagc | 1020 |
| ctccccctga | gcacgtgccc | ccacctcccc | ggccacccaa | acgcacattg | agcctcaca | 1080 |
| atggcaagtg | caaggagctc | ttctccaacc | accagtgggg | gagcgaggag | agctgtgagg | 1140 |
| atgaggacat | cctggccaga | gaggaaagca | gagccccctc | aattgctgtg | cacagcatga | 1200 |
| gcagtatgag | tcaagacact | gaagttagga | acggatggg | gggtggaggt | cttcaaagtg | 1260 |
| ctcaggcatc | tgtccccact | gaggaagagc | tgtccccaac | cgaggaggaa | caaaaggcac | 1320 |
| acaggccagt | tcactggaag | cccttcctgg | tcaacgtgtg | catggccacg | gccctggcga | 1380 |
| ctggcgcgta | cctctgttac | cgggtatgtt | tcactgaca | gactgctgtg | aggcatgagc | 1440 |
| gtggtgggcg | ctgccactgc | caggttagg | atttggtctg | cggcgtctaa | cctggtgtag | 1500 |
| aagaaacaac | agcttacaag | cctgtggtgg | aactggaagg | gccagcccca | ggaggggcat | 1560 |
| ctgtgcactg | ggctttgaag | gagcccctgg | tcccaagaac | agagtctaat | ctcagggcct | 1620 |
| taacctgttc | aggagaagta | gaggaaatgc | caaatactct | tcttgctctc | acctcactcc | 1680 |
| tcccctttct | ctggttcgtt | tgttttttgga | aaaaaaaaa | aaagaattac | aacacattgt | 1740 |
| tgttttaac | atttataaag | gcaggttttt | gttatttta | gagaaaacaa | agatgctag | 1800 |
| gcactggtga | gattctcttg | tgcccttgg | catgtgatca | gattcacgat | ttacgtttat | 1860 |
| ttccggggga | gggtcccacc | tgtcaggact | gtaaagttcc | tgctggcttg | gtcagccccc | 1920 |
| ccacccccc | accccgagct | tgcaggtgcc | ctgctgtgag | gagagcagca | gcagaggctg | 1980 |
| cccctggaca | gaagcccagc | tctgcttccc | tcaggtgtcc | ctgcgtttcc | atcctccttc | 2040 |

| | | |
|---|---|---|
| tttgtgaccg ccatcttgca gatgacccag tcctcagcac cccaccctg cagatgggtt | 2100 |
| tctccgaggg cctgcctcag ggtcatcaga ggttggctgc cagcttagag ctggggcttc | 2160 |
| catttgattg gaaagtcatt actattctat gtagaagcca ctccactgag gtgtaaagca | 2220 |
| agactcataa aggaggagcc ttggtgtcat ggaagtcact ccgcgcgcag gacctgtaac | 2280 |
| aacctctgaa acactcagtc ctgctgcagt gacgtccttg aaggcatcag acagatgatt | 2340 |
| tgcagactgc caagacttgt cctgagccgt gatttttaga gtctggactc atgaaacacc | 2400 |
| gccgagcgct tactgtgcag cctctgatgc tggttggctg aggctgcggg gaggtggaca | 2460 |
| ctgtgggtgc atccagtgca gttgcttttg tgcagttggg tccagcagca cagcccgcac | 2520 |
| tccagcctca gctgcaggcc acagtggcca tggaggccgc cagagcgagc tggggtggat | 2580 |
| gcttgttcac ttggagcagc cttcccagga cgtgcagctc ccttcctgct tgtccttct | 2640 |
| gcttccttcc ctggagtagc aagcccacga gcaatcgtga ggggtgtgag ggagctgcag | 2700 |
| aggcatcaga gtggcctgca gcggcgtgag gccccttccc ctccgacacc cccctccaga | 2760 |
| ggagccgctc cactgttatt tattcacttt gcccacagac accctgagt gagcacaccc | 2820 |
| tgaaactgac cgtgtaaggt gtcagcctgc acccaggacc gtcaggtgca gcaccgggtc | 2880 |
| agtcctaggg ttgaggtagg actgacacag ccactgtgtg gctggtgctg ggcaggggc | 2940 |
| aggagctgag ggtcttagaa gcaatcttca ggaacagaca acagtggtga catgtaaagt | 3000 |
| ccctgtggct actgatgaca tgtgtaggat gaaggctggc ctttctccca tgactttcta | 3060 |
| gatcccgttc cccgtctgct ttccctgtga gttagaaaac acacaggctc ctgtcctggt | 3120 |
| ggtgccgtgt gcttgacatg ggaaacttag atgcctgctc actggcgggc acctcggcat | 3180 |
| cgccaccact cagagtgaga gcagtgctgt ccagtgccga ggccgcctga ctcccggcag | 3240 |
| gactcttcag gctctggcct gccccagcac accccgctgg atctcagaca ttccacaccc | 3300 |
| acacctcatt ccctggacac ttgggcaagc aggcccgccc ttccacctct ggggtcagcc | 3360 |
| cctccattcc gagttcacac tgctctggag caggccagga ccggaagcaa ggcagctggt | 3420 |
| gaggagcacc ctcctgggaa cagtgtaggt gacagtcctg agagtcagct tgctagcgct | 3480 |
| gctggcacca gtcaccttgc tcagaagtgt gtggctcttg aggctgaaga gactgatgat | 3540 |
| ggtgctcatg actcttctgt gaggggaact tgaccttcac attgggtggc ttttttaaa | 3600 |
| ataagcgaag gcagctggaa ctccagtctg cctcttgcca gcacttcaca ttttgccttt | 3660 |
| cacccagaga agccagcaca gagccactgg ggaaggcgat ggccttgcct gcacaggctg | 3720 |
| aggagatggc tcagccggcg tccaggctgt gtctggagca gggggtgcac agcagcctca | 3780 |
| caggtggggg cctcagagca ggcgctgccc tgtcccctgc cccgctggag gcagcaaagc | 3840 |
| tgctgcatgc cttaagtcaa tacttactca gcagggcgct ctcgttctct ctctctctct | 3900 |
| ctctctctct ctctctctct ctctctctct ctctaaatgg ccatagaata aaccatttta | 3960 |
| caaaataaa agccaacaac aaagtgctct ggaatagcac ctttgcagga gcgggggtg | 4020 |
| tctcagggtc ttctgtgacc tcaccgaact gtccgactgc accgtttcca acttgtgtct | 4080 |
| cactaatggg tctgcattag ttgcaacaat aaatgttttt aaagaac | 4127 |

<210> SEQ ID NO 821
<211> LENGTH: 432
<212> TYPE: PRT
<213> ORGANISM: Rattus norvegicus

<400> SEQUENCE: 821

-continued

```
Met Glu Met Glu Lys Glu Phe Glu Gln Ile Asp Lys Ala Gly Asn Trp
1               5                   10                  15

Ala Ala Ile Tyr Gln Asp Ile Arg His Glu Ala Ser Asp Phe Pro Cys
            20                  25                  30

Arg Ile Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
                100                 105                 110

Ile Met Glu Lys Gly Ser Leu Lys Cys Ala Gln Tyr Trp Pro Gln Lys
            115                 120                 125

Glu Glu Lys Glu Met Val Phe Asp Asp Thr Asn Leu Lys Leu Thr Leu
        130                 135                 140

Ile Ser Glu Asp Val Lys Ser Tyr Tyr Thr Val Arg Gln Leu Glu Leu
145                 150                 155                 160

Glu Asn Leu Ala Thr Gln Glu Ala Arg Glu Ile Leu His Phe His Tyr
                165                 170                 175

Thr Thr Trp Pro Asp Phe Gly Val Pro Glu Ser Pro Ala Ser Phe Leu
                180                 185                 190

Asn Phe Leu Phe Lys Val Arg Glu Ser Gly Ser Leu Ser Pro Glu His
            195                 200                 205

Gly Pro Ile Val Val His Cys Ser Ala Gly Ile Gly Arg Ser Gly Thr
210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Arg Phe
            245                 250                 255

Arg Met Gly Leu Ile Gln Thr Ala Asp Gln Leu Arg Phe Ser Tyr Leu
                260                 265                 270

Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Pro Glu
    290                 295                 300

His Val Pro Pro Pro Arg Pro Pro Lys Arg Thr Leu Glu Pro His
305                 310                 315                 320

Asn Gly Lys Cys Lys Glu Leu Phe Ser Asn His Gln Trp Val Ser Glu
            325                 330                 335

Glu Ser Cys Glu Asp Glu Asp Ile Leu Ala Arg Glu Glu Ser Arg Ala
                340                 345                 350

Pro Ser Ile Ala Val His Ser Met Ser Ser Met Ser Gln Asp Thr Glu
            355                 360                 365

Val Arg Lys Arg Met Val Gly Gly Leu Gln Ser Ala Gln Ala Ser
                370                 375                 380

Val Pro Thr Glu Glu Leu Ser Pro Thr Glu Glu Gln Lys Ala
385                 390                 395                 400

His Arg Pro Val His Trp Lys Pro Phe Leu Val Asn Val Cys Met Ala
                405                 410                 415

Thr Ala Leu Ala Thr Gly Ala Tyr Leu Cys Tyr Arg Val Cys Phe His
```

<210> SEQ ID NO 822
<211> LENGTH: 2287
<212> TYPE: DNA
<213> ORGANISM: Homo sapiens

<400> SEQUENCE: 822

| | | | | | |
|---|---|---|---|---|---|
| gggggggcctg | agcctctccg | ccggcgcagg | ctctgctcgc | gccagctcgc | tcccgcagcc | 60 |
| atgcccacca | ccatcgagcg | ggagttcgaa | gagttggata | tcagcgtcg | ctggcagccg | 120 |
| ctgtacttgg | aaattcgaaa | tgagtccat | gactatcctc | atagagtggc | caagtttcca | 180 |
| gaaaacagaa | atcgaaacag | atacagagat | gtaagcccat | atgatcacag | tcgtgttaaa | 240 |
| ctgcaaaatg | ctgagaatga | ttatattaat | gccagtttag | ttgacataga | agaggcacaa | 300 |
| aggagttaca | tcttaacaca | gggtccactt | cctaacacat | gctgccattt | ctggcttatg | 360 |
| gtttggcagc | agaagaccaa | agcagttgtc | atgctgaacc | gcattgtgga | gaaagaatcg | 420 |
| gttaaatgtg | cacagtactg | gccaacagat | gaccaagaga | tgctgtttaa | agaaacagga | 480 |
| ttcagtgtga | agctcttgtc | agaagatgtg | aagtcgtatt | atacagtaca | tctactacaa | 540 |
| ttagaaaata | tcaatagtgg | tgaaaccaga | acaatatctc | actttcatta | tactacctgg | 600 |
| ccagattttg | gagtccctga | atcaccagct | tcatttctca | atttcttgtt | taaagtgaga | 660 |
| gaatctggct | ccttgaaccc | tgaccatggg | cctgcggtga | tccactgtag | tgcaggcatt | 720 |
| gggcgctctg | gcaccttctc | tctggtagac | acttgtcttg | ttttgatgga | aaaaggagat | 780 |
| gatattaaca | taaacaagt | gttactgaac | atgagaaaat | accgaatggg | tcttattcag | 840 |
| accccagatc | aactgagatt | ctcatacatg | gctataatag | aaggagcaaa | atgtataaag | 900 |
| ggagattcta | gtatacagaa | acgatggaaa | gaactttcta | aggaagactt | atctcctgcc | 960 |
| tttgatcatt | caccaaacaa | aataatgact | gaaaaataca | atgggaacag | ataggtcta | 1020 |
| gaagaagaaa | aactgacagg | tgaccgatgt | acaggacttt | cctctaaaat | gcaagataca | 1080 |
| atggaggaga | acagtgagag | tgctctacgg | aaacgtattc | gagaggacag | aaaggccacc | 1140 |
| acagctcaga | aggtgcagca | gatgaaacag | aggctaaatg | agaatgaacg | aaaaagaaaa | 1200 |
| aggtggttat | attggcaacc | tattctcact | aagatggggt | ttatgtcagt | cattttggtt | 1260 |
| ggcgcttttg | ttggctggag | actgttttt | cagcaaaatg | ccctataaac | aattaatttt | 1320 |
| gcccagcaag | cttctgcact | agtaactgac | agtgctacat | taatcatagg | ggtttgtctg | 1380 |
| cagcaaacgc | ctcatatccc | aaaaacggtg | cagtagaata | gacatcaacc | agataagtga | 1440 |
| tatttacagt | cacaagccca | acatctcagg | actcttgact | gcaggttcct | ctgaaccccca | 1500 |
| aactgtaaat | ggctgtctaa | aataaagaca | ttcatgtttg | ttaaaaactg | gtaaattttg | 1560 |
| caactgtatt | catacatgtc | aaacacagta | tttcacctga | ccaacattga | gatatccttt | 1620 |
| atcacaggat | ttgtttttgg | aggctatctg | gatttaacc | tgcacttgat | ataagcaata | 1680 |
| aatattgtgg | tttatctac | gttattggaa | agaaaatgac | atttaaataa | tgtgtgtaat | 1740 |
| gtataatgta | ctattgacat | gggcatcaac | acttttattc | ttaagcattt | cagggtaaat | 1800 |
| atatttttata | agtatctatt | taatcttttg | tagttaactg | tacttttttaa | gagctcaatt | 1860 |
| tgaaaaatct | gttactaaaa | aaaaaaattg | tatgtcgatt | gaattgtact | ggatacattt | 1920 |
| tccatttttc | taaaaagaag | tttgatatga | gcagttagaa | gttggaataa | gcaatttcta | 1980 |
| ctatatattg | catttctttt | atgttttaca | gttttcccca | ttttaaaaag | aaaagcaaac | 2040 |
| aaagaaacaa | aagttttttcc | taaaaatatc | tttgaaggaa | aattctcctt | actgggatag | 2100 |

```
tcaggtaaac agttggtcaa gactttgtaa agaaattggt ttctgtaaat cccattattg    2160
atatgtttat ttttcatgaa aatttcaatg tagttggggt agattatgat ttaggaagca    2220
aaagtaagaa gcagcatttt atgattcata atttcagttt actagactga agttttgaag    2280
taaaccc                                                              2287
```

<210> SEQ ID NO 823
<211> LENGTH: 415
<212> TYPE: PRT
<213> ORGANISM: Homo sapiens

<400> SEQUENCE: 823

```
Met Pro Thr Thr Ile Glu Arg Glu Phe Glu Glu Leu Asp Thr Gln Arg
1               5                   10                  15

Arg Trp Gln Pro Leu Tyr Leu Glu Ile Arg Asn Glu Ser His Asp Tyr
            20                  25                  30

Pro His Arg Val Ala Lys Phe Pro Glu Asn Arg Asn Asn Arg Tyr
        35                  40                  45

Arg Asp Val Ser Pro Tyr Asp His Ser Arg Val Lys Leu Gln Asn Ala
    50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Gln Lys Thr Lys Ala Val Val Met Leu
            100                 105                 110

Asn Arg Ile Val Glu Lys Glu Ser Val Lys Cys Ala Gln Tyr Trp Pro
        115                 120                 125

Thr Asp Asp Gln Glu Met Leu Phe Lys Glu Thr Gly Phe Ser Val Lys
    130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
        195                 200                 205

His Gly Pro Ala Val Ile His Cys Ser Ala Gly Ile Gly Arg Ser Gly
    210                 215                 220

Thr Phe Ser Leu Val Asp Thr Cys Leu Val Leu Met Glu Lys Gly Asp
225                 230                 235                 240

Asp Ile Asn Ile Lys Gln Val Leu Leu Asn Met Arg Lys Tyr Arg Met
                245                 250                 255

Gly Leu Ile Gln Thr Pro Asp Gln Leu Arg Phe Ser Tyr Met Ala Ile
            260                 265                 270

Ile Glu Gly Ala Lys Cys Ile Lys Gly Asp Ser Ser Ile Gln Lys Arg
        275                 280                 285

Trp Lys Glu Leu Ser Lys Glu Asp Leu Ser Pro Ala Phe Asp His Ser
    290                 295                 300

Pro Asn Lys Ile Met Thr Glu Lys Tyr Asn Gly Asn Arg Ile Gly Leu
305                 310                 315                 320

Glu Glu Glu Lys Leu Thr Gly Asp Arg Cys Thr Gly Leu Ser Ser Lys
                325                 330                 335
```

```
Met Gln Asp Thr Met Glu Glu Asn Ser Glu Ser Ala Leu Arg Lys Arg
                340                 345                 350

Ile Arg Glu Asp Arg Lys Ala Thr Thr Ala Gln Lys Val Gln Gln Met
            355                 360                 365

Lys Gln Arg Leu Asn Glu Asn Glu Arg Lys Arg Lys Arg Trp Leu Tyr
    370                 375                 380

Trp Gln Pro Ile Leu Thr Lys Met Gly Phe Met Ser Val Ile Leu Val
385                 390                 395                 400

Gly Ala Phe Val Gly Trp Arg Leu Phe Phe Gln Gln Asn Ala Leu
                405                 410                 415

<210> SEQ ID NO 824
<211> LENGTH: 2477
<212> TYPE: DNA
<213> ORGANISM: Homo sapiens

<400> SEQUENCE: 824
```

| | | | | | |
|---|---|---|---|---|---|
| gctcgggcgc | cgagtctgcg | cgctgacgtc | cgacgctcca | ggtactttcc | ccacggccga | 60 |
| cagggcttgg | cgtgggggcg | gggcgcggcg | cgcagcgcgc | atgcgccgca | gcgccagcgc | 120 |
| tctccccgga | tcgtgcgggg | cctgagcctc | tccgccggcg | caggctctgc | tcgcgccagc | 180 |
| tcgctcccgc | agccatgccc | accaccatcg | agcgggagtt | cgaagagttg | gatactcagc | 240 |
| gtcgctggca | gccgctgtac | ttggaaattc | gaaatgagtc | ccatgactat | cctcatagag | 300 |
| tggccaagtt | tccagaaaac | agaaatcgaa | acagatacag | agatgtaagc | ccatatgatc | 360 |
| acagtcgtgt | taaactgcaa | atgctgagaa | tgattatatt | aatgccagtt | tagttgaca | 420 |
| tagaagaggc | acaaaggagt | tacatcttaa | cacagggtcc | acttcctaac | acatgctgcc | 480 |
| atttctggct | tatggtttgg | cagcagaaga | ccaaagcagt | tgtcatgctg | aaccgcattg | 540 |
| tggagaaaga | atcggttaaa | tgtgcacagt | actggccaac | agatgaccaa | gagatgctgt | 600 |
| ttaaagaaac | aggattcagt | gtgaagctct | tgtcagaaga | tgtgaagtcg | tattatacag | 660 |
| tacatctact | acaattagaa | aatatcaata | gtggtgaaac | cagaacaata | tctcactttc | 720 |
| attatactac | ctggccagat | tttggagtcc | ctgaatcacc | agcttcattt | ctcaatttct | 780 |
| tgtttaaagt | gagagaatct | ggctccttga | accctgacca | tgggcctgcg | gtgatccact | 840 |
| gtagtgcagg | cattgggcgc | tctggcacct | tctctctggt | agacacttgt | cttgttttga | 900 |
| tggaaaaagg | agatgatatt | aacataaaac | aagtgttact | gaacatgaga | aaataccgaa | 960 |
| tgggtcttat | tcagacccca | gatcaactga | gattctcata | catggctata | atagaaggag | 1020 |
| caaaatgtat | aaagggagat | tctagtatac | agaaacgatg | gaaagaactt | tctaaggaag | 1080 |
| acttatctcc | tgcctttgat | cattcaccaa | acaaataat | gactgaaaaa | tacaatggga | 1140 |
| acagaatagg | tctagaagaa | gaaaaactga | caggtgaccg | atgtacagga | cttcctcta | 1200 |
| aaatgcaaga | tacaatggag | gagaacagtg | agagtgctct | acggaaacgt | attcgagagg | 1260 |
| acagaaaggc | caccacagct | cagaaggtgc | agcagatgaa | acagaggcta | aatgagaatg | 1320 |
| aacgaaaaag | aaaaaggtgg | ttatattggc | aacctattct | cactaagatg | gggtttatgt | 1380 |
| cagtcatttt | ggttggcgct | tttgttggct | ggagactgtt | ttttcagcaa | aatgccctat | 1440 |
| aaacaattaa | ttttgcccag | caagcttctg | cactagtaac | tgacagtgct | acattaatca | 1500 |
| taggggtttg | tctgcagcaa | acgcctcata | tcccaaaaac | ggtgcagtag | aatagacatc | 1560 |
| aaccagataa | gtgatattta | cagtcacaag | cccaacatct | caggactctt | gactgcaggt | 1620 |
| tcctctgaac | cccaaactgt | aaatggctgt | ctaaaataaa | gacattcatg | tttgttaaaa | 1680 |

```
actggtaaat tttgcaactg tattcataca tgtcaaacac agtatttcac ctgaccaaca    1740
ttgagatatc ctttatcaca ggatttgttt ttggaggcta tctggatttt aacctgcact    1800
tgatataagc aataaatatt gtggttttat ctacgttatt ggaaagaaaa tgacatttaa    1860
ataatgtgtg taatgtataa tgtactattg acatgggcat caacactttt attcttaagc    1920
atttcagggt aaatatattt tataagtatc tatttaatct tttgtagtta actgtacttt    1980
ttaagagctc aatttgaaaa atctgttact aaaaaaaaaa attgtatgtc gattgaattg    2040
tactggatac attttccatt tttctaaaaa gaagtttgat atgagcagtt agaagttgga    2100
ataagcaatt tctactatat attgcatttc ttttatgttt tacagttttc cccatttaa    2160 aaagaaaagc aaacaaagaa acaaaagttt ttcctaaaaa tatctttgaa ggaaaattct    2220
ccttactggg atagtcaggt aaacagttgg tcaagacttt gtaaagaaat tggtttctgt    2280
aaatcccatt attgatatgt ttattttca tgaaaatttc aatgtagttg gggtagatta    2340
tgatttagga agcaaaagta agaagcagca ttttatgatt cataatttca gtttactaga    2400
ctgaagtttt gaagtaaaca cttttcagtt tctttctact tcaataaata gtatgattat    2460
atgcaaacct taaaaaa                                                     2477

<210> SEQ ID NO 825
<211> LENGTH: 415
<212> TYPE: PRT
<213> ORGANISM: Homo sapiens

<400> SEQUENCE: 825

Met Pro Thr Thr Ile Glu Arg Glu Phe Glu Glu Leu Asp Thr Gln Arg
1               5                   10                  15

Arg Trp Gln Pro Leu Tyr Leu Glu Ile Arg Asn Glu Ser His Asp Tyr
            20                  25                  30

Pro His Arg Val Ala Lys Phe Pro Glu Asn Arg Asn Arg Asn Arg Tyr
        35                  40                  45

Arg Asp Val Ser Pro Tyr Asp His Ser Arg Val Lys Leu Gln Asn Ala
    50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Gln Lys Thr Lys Ala Val Val Met Leu
            100                 105                 110

Asn Arg Ile Val Glu Lys Glu Ser Val Lys Cys Ala Gln Tyr Trp Pro
        115                 120                 125

Thr Asp Asp Gln Glu Met Leu Phe Lys Glu Thr Gly Phe Ser Val Lys
    130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
        195                 200                 205

His Gly Pro Ala Val Ile His Cys Ser Ala Gly Ile Gly Arg Ser Gly
    210                 215                 220
```

```
Thr Phe Ser Leu Val Asp Thr Cys Leu Val Leu Met Glu Lys Gly Asp
225                 230                 235                 240

Asp Ile Asn Ile Lys Gln Val Leu Leu Asn Met Arg Lys Tyr Arg Met
            245                 250                 255

Gly Leu Ile Gln Thr Pro Asp Gln Leu Arg Phe Ser Tyr Met Ala Ile
        260                 265                 270

Ile Glu Gly Ala Lys Cys Ile Lys Gly Asp Ser Ser Ile Gln Lys Arg
    275                 280                 285

Trp Lys Glu Leu Ser Lys Glu Asp Leu Ser Pro Ala Phe Asp His Ser
290                 295                 300

Pro Asn Lys Ile Met Thr Glu Lys Tyr Asn Gly Asn Arg Ile Gly Leu
305                 310                 315                 320

Glu Glu Glu Lys Leu Thr Gly Asp Arg Cys Thr Gly Leu Ser Ser Lys
                325                 330                 335

Met Gln Asp Thr Met Glu Glu Asn Ser Glu Ser Ala Leu Arg Lys Arg
            340                 345                 350

Ile Arg Glu Asp Arg Lys Ala Thr Thr Ala Gln Lys Val Gln Gln Met
        355                 360                 365

Lys Gln Arg Leu Asn Glu Asn Glu Arg Lys Arg Lys Trp Leu Tyr
370                 375                 380

Trp Gln Pro Ile Leu Thr Lys Met Gly Phe Met Ser Val Ile Leu Val
385                 390                 395                 400

Gly Ala Phe Val Gly Trp Arg Leu Phe Phe Gln Gln Asn Ala Leu
                405                 410                 415

<210> SEQ ID NO 826
<211> LENGTH: 1714
<212> TYPE: DNA
<213> ORGANISM: Homo sapiens

<400> SEQUENCE: 826
gctcgggcgc cgagtctgcg cgctgacgtc cgacgctcca ggtactttcc ccacggccga      60
cagggcttgg cgtgggggcg gggcgcggcg cgcagcgcgc atgcgccgca gcgccagcgc     120
tctcccggga tcgtgcgggg cctgagcctc tccgccggcg caggctctgc tcgcgccagc     180
tcgctcccgc agccatgccc accaccatcg agcgggagtt cgaagagttg atactcagc      240 gtcgctggca gccgctgtac ttggaaattc gaaatgagtc ccatgactat cctcatagag     300
tggccaagtt tccagaaaac agaaatcgaa acagatacag agatgtaagc ccatatgatc     360
acagtcgtgt taaactgcaa aatgctgaga atgattatat taatgccagt ttagttgaca     420
tagaagaggc acaaaggagt tacatcttaa cacagggtcc acttcctaac acatgctgcc     480
atttctggct tatggtttgg cagcagaaga ccaaagcagt tgtcatgctg aaccgcattg     540
tggagaaaga atcggttaaa tgtgcacagt actggccaac agatgaccaa gagatgctgt     600
ttaaagaaac aggattcagt gtgaagctct tgtcagaaga tgtgaagtcg tattatacag     660
tacatctact acaattagaa aatatcaata gtggtgaaac cagaacaata tctcactttc     720
attatactac ctggccagat tttggagtcc tgaatcacc agcttcattt ctcaatttct     780
tgtttaaagt gagagaatct ggctccttga accctgacca tgggcctgcg gtgatccact     840
gtagtgcagg cattgggcgc tctggcacct tctctctggt agacacttgt cttgttttga     900
tggaaaaagg agatgatatt aacataaaac aagtgttact gaacatgaga aaataccgaa     960
tgggtcttat tcagacccca gatcaactga gattctcata catggctata atagaaggag    1020
caaaatgtat aaagggagat tctagtatac agaaaacgatg gaaagaactt tctaaggaag    1080
```

-continued

```
acttatctcc tgcctttgat cattcaccaa acaaaataat gactgaaaaa tacaatggga    1140
acagaatagg tctagaagaa gaaaaactga caggtgaccg atgtacagga ctttcctcta    1200
aaatgcaaga tacaatggag gagaacagtg agagtgctct acggaaacgt attcgagagg    1260
acagaaaggc caccacagct cagaaggtgc agcagatgaa acagaggcta atgagaatg     1320 aacgaaaaag aaaaaggcca agattgacag cacctaata ttcatgactt gagaatattc     1380
tgcagctata aattttgaac cattgatgtg caaagcaaga cctgaagccc actccggaaa    1440
ctaaagtgag gctcgctaac cctctagatt gcctcacagt tgtttgttta caaagtaaac    1500
tttacatcca ggggatgaag agcacccacc agcagaagac tttgcagaac ctttaattgg    1560
atgtgttaag tgtttttaat gagtgtatga aatgtagaaa gatgtacaag aaataaatta    1620
ggagagatta ctttgtattg tactgccatt cctactgtat ttttatactt tttggcagca    1680
ttaaatattt ttgttaaata aaaaaaaaaa aaaa                                1714
```

<210> SEQ ID NO 827
<211> LENGTH: 387
<212> TYPE: PRT
<213> ORGANISM: Homo sapiens

<400> SEQUENCE: 827

```
Met Pro Thr Thr Ile Glu Arg Glu Phe Glu Glu Leu Asp Thr Gln Arg
1               5                   10                  15

Arg Trp Gln Pro Leu Tyr Leu Glu Ile Arg Asn Glu Ser His Asp Tyr
                20                  25                  30

Pro His Arg Val Ala Lys Phe Pro Glu Asn Arg Asn Arg Asn Arg Tyr
            35                  40                  45

Arg Asp Val Ser Pro Tyr Asp His Ser Arg Val Lys Leu Gln Asn Ala
        50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Gln Lys Thr Lys Ala Val Val Met Leu
            100                 105                 110

Asn Arg Ile Val Glu Lys Glu Ser Val Lys Cys Ala Gln Tyr Trp Pro
        115                 120                 125

Thr Asp Asp Gln Glu Met Leu Phe Lys Glu Thr Gly Phe Ser Val Lys
    130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
        195                 200                 205

His Gly Pro Ala Val Ile His Cys Ser Ala Gly Ile Gly Arg Ser Gly
    210                 215                 220

Thr Phe Ser Leu Val Asp Thr Cys Leu Val Leu Met Glu Lys Gly Asp
225                 230                 235                 240

Asp Ile Asn Ile Lys Gln Val Leu Leu Asn Met Arg Lys Tyr Arg Met
                245                 250                 255
```

```
Gly Leu Ile Gln Thr Pro Asp Gln Leu Arg Phe Ser Tyr Met Ala Ile
            260                 265                 270
Ile Glu Gly Ala Lys Cys Ile Lys Gly Asp Ser Ser Ile Gln Lys Arg
        275                 280                 285
Trp Lys Glu Leu Ser Lys Glu Asp Leu Ser Pro Ala Phe Asp His Ser
    290                 295                 300
Pro Asn Lys Ile Met Thr Glu Lys Tyr Asn Gly Asn Arg Ile Gly Leu
305                 310                 315                 320
Glu Glu Glu Lys Leu Thr Gly Asp Arg Cys Thr Gly Leu Ser Ser Lys
                325                 330                 335
Met Gln Asp Thr Met Glu Glu Asn Ser Glu Ser Ala Leu Arg Lys Arg
            340                 345                 350
Ile Arg Glu Asp Arg Lys Ala Thr Thr Ala Gly Lys Val Gln Gln Met
        355                 360                 365
Lys Gln Arg Leu Asn Glu Asn Glu Arg Lys Arg Lys Arg Pro Arg Leu
    370                 375                 380
Thr Asp Thr
385

<210> SEQ ID NO 828
<211> LENGTH: 1555
<212> TYPE: DNA
<213> ORGANISM: Mus musculus

<400> SEQUENCE: 828
tctccccgga tagagcgggg cccgagcctg tccgctgtgg tagttccgct cggctgcccc      60
gccgccatgt cggcaaccat cgagcgggag ttcgaggaac tggatgctca gtgtcgctgg     120
cagccgttat acttggaaat tcgaaatgaa tcccatgact atcctcatag agtggccaag     180
tttccagaaa acagaaaccg aaacagatac agagatgtaa gcccatatga tcacagtcgt     240
gttaaactgc aaagtactga aaatgattat attaatgcca gcttagttga catagaagag     300
gcacaaagaa gttacatctt aacacagggc ccacttccga cacatgctgc catttctgg      360
ctcatggtgt ggcagcaaaa gaccaaagca gttgtcatgc taaaccgaac tgtagaaaaa     420
gaatcggtta atgtgcaca gtactggcca acggatgaca gagaaatggt gtttaaggaa      480
acgggattca gtgtgaagct cttatctgaa gatgtaaaat catattatac agtacatcta     540
ctacagttag aaaatatcaa tactggtgaa acgagaacca tatctcactt ccattatacc     600
acctggccag atttggggt tccagagtca ccagcttcat ttctaaactt cttgtttaaa      660
gttagagaat ctggttgttt gaccctgac catggacctg cagtgatcca ttgcagtgcg      720
ggcatcgggc gctctggcac cttctctctt gtagatacct gtcttgttct gatggaaaaa     780
ggagaggatg ttaatgtgaa acaattatta ctgaatatga aaagtatcg aatgggactt      840
attcagacac cggaccaact cagattctcc tacatggcca aatagaagg agcaaagtac      900
acaaaggag attcaaatat acagaaacgg tggaagaac tttctaaaga agatttatct       960
cctatttgtg atcattcaca gaacagagtg atggttgaga agtacaatgg aagagaata     1020
ggttcagaag atgaaaagtt aacagggctt ccttctaagg tgcaggatac tgtggaggag    1080
agcagtgaga gcattctacg gaaacgtatt cgagaggata aaaggctac gacggctcag     1140
aaggtgcagc agatgaaaca gaggctaaat gaaactgaac gaaaagaaaa aggccaaga    1200
ttgacagaca cctaaatgtt catgacttga gactattctg cagctataaa atttgaacct    1260
ttgatgtgca aagcaagacc tgaagcccac tccggaaact aaagtgaggc ttgctaaccc    1320
```

-continued

```
tgtagattgc ctcacaagtt gtctgtttac aaagtaagct ttccatccag gggatgaaga    1380
acgccaccag cagaagactt gcaaacccct taatttgatg tattgttttt taacatgtgt    1440
atgaaatgta aaagatgta aaggaaataa attaggagcg actactttgt attgtactgc     1500
cattcctaat gtattttat acttttggc agcattaaat attttatta aatag             1555
```

<210> SEQ ID NO 829
<211> LENGTH: 382
<212> TYPE: PRT
<213> ORGANISM: Mus musculus

<400> SEQUENCE: 829

```
Met Ser Ala Thr Ile Glu Arg Glu Phe Glu Glu Leu Asp Ala Gln Cys
1               5                   10                  15

Arg Trp Gln Pro Leu Tyr Leu Glu Ile Arg Asn Glu Ser His Asp Tyr
            20                  25                  30

Pro His Arg Val Ala Lys Phe Pro Glu Asn Arg Asn Arg Asn Arg Tyr
        35                  40                  45

Arg Asp Val Ser Pro Tyr Asp His Ser Arg Val Lys Leu Gln Ser Thr
    50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Gln Lys Thr Lys Ala Val Val Met Leu
            100                 105                 110

Asn Arg Thr Val Glu Lys Glu Ser Val Lys Cys Ala Gln Tyr Trp Pro
        115                 120                 125

Thr Asp Asp Arg Glu Met Val Phe Lys Glu Thr Gly Phe Ser Val Lys
    130                 135                 140

Leu Leu Ser Glu Asp Val Lys Ser Tyr Tyr Thr Val His Leu Leu Gln
145                 150                 155                 160

Leu Glu Asn Ile Asn Thr Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Cys Leu Thr Pro Asp
        195                 200                 205

His Gly Pro Ala Val Ile His Cys Ser Ala Gly Ile Gly Arg Ser Gly
    210                 215                 220

Thr Phe Ser Leu Val Asp Thr Cys Leu Val Leu Met Glu Lys Gly Glu
225                 230                 235                 240

Asp Val Asn Val Lys Gln Leu Leu Leu Asn Met Arg Lys Tyr Arg Met
                245                 250                 255

Gly Leu Ile Gln Thr Pro Asp Gln Leu Arg Phe Ser Tyr Met Ala Ile
            260                 265                 270

Ile Glu Gly Ala Lys Tyr Thr Lys Gly Asp Ser Asn Ile Gln Lys Arg
        275                 280                 285

Trp Lys Glu Leu Ser Lys Glu Asp Leu Ser Pro Ile Cys Asp His Ser
    290                 295                 300

Gln Asn Arg Val Met Val Glu Lys Tyr Asn Gly Lys Arg Ile Gly Ser
305                 310                 315                 320

Glu Asp Glu Lys Leu Thr Gly Leu Pro Ser Lys Val Gln Asp Thr Val
                325                 330                 335
```

Glu Ser Ser Glu Ser Ile Leu Arg Lys Arg Ile Arg Glu Asp Arg
                340                 345                 350

Lys Ala Thr Thr Ala Gln Lys Val Gln Gln Met Lys Gln Arg Leu Asn
                355                 360                 365

Glu Thr Glu Arg Lys Arg Lys Arg Pro Arg Leu Thr Asp Thr
            370                 375                 380

<210> SEQ ID NO 830
<211> LENGTH: 1666
<212> TYPE: DNA
<213> ORGANISM: Homo sapiens

<400> SEQUENCE: 830

| | | | | | |
|---|---|---|---|---|---|
| ggccccccgt | tccccgccag | gctgcaggcg | tcgggcctgg | gccgtcaggg | cagctgtgac | 60 |
| cggatcgctt | cccgggcggc | gagctggggg | tgcacccgga | ccgccgcccc | cgggatcatg | 120 |
| ggcaatggca | tgaccaaggt | acttcctgga | ctctacctcg | gaaacttcat | tgatgccaaa | 180 |
| gacctggatc | agctgggccg | aaataagatc | acacacatca | tctctatcca | tgagtcaccc | 240 |
| cagcctctgc | tgcaggatat | cacctacctt | cgcatcccgg | tcgctgatac | ccctgaggta | 300 |
| cccatcaaaa | agcacttcaa | agaatgtatc | aacttcatcc | actgctgccg | ccttaatggg | 360 |
| gggaactgcc | ttgtgcactg | ctttgcaggc | atctctcgca | gcaccacgat | tgtgacagcg | 420 |
| tatgtgatga | ctgtgacggg | gctaggctgg | cgggacgtgc | ttgaagccat | caaggccacc | 480 |
| aggcccatcg | ccaaccccaa | cccaggcttt | aggcagcagc | ttgaagagtt | tggctgggcc | 540 |
| agttcccaga | agggtgccag | acataggacc | tcaaaaacct | ctggtgccca | atgccctccg | 600 |
| atgacttcag | caacctggat | ggtcaccgga | cccaaagtac | cagatctgtc | tgtgcttcgg | 660 |
| tgaggaggac | ccgggcccca | cacagcaccc | caaggagcag | ctcatcatgg | cggacgtgca | 720 |
| ggtgcagctt | cggcctggga | gctcgtcctg | cactctaagt | gcctcaaccg | agcgcccaga | 780 |
| tgggtcctca | cccctggca | accccgatgg | catcactcac | cttcaatgca | gctgcctcca | 840 |
| tcctaagcga | gccgcttcct | cttcttgtac | ccgctgaagg | cagcccccaa | caggggggct | 900 |
| ccctactccc | acccaaccct | gcccacacta | agcccataga | cttggggcct | ccccggcac | 960 |
| atcacccagg | tctgccggac | ggcagaggtg | gatcgcggcc | ttccactcct | ctgtcacggg | 1020 |
| gccccggaac | tcgagagtag | gccacaccgc | ccccagctg | ggcatggggc | ttcggcagga | 1080 |
| aactgaactt | gatcttgagg | ccccagaaag | gcagcaactg | gagcagaagc | aagacttcat | 1140 |
| ctcttgctga | cagcccaatt | tgtcaatagc | gctttcctca | gagccagcct | taacctgctg | 1200 |
| ttgagtccat | taaacgtttt | gcttaaagtt | tttaccaata | attagatcat | cagggttgtt | 1260 |
| tagtgtggga | tcaagccata | acaaaactgc | ctagcctctc | aggggcctag | aatttacaga | 1320 |
| accttcctcc | tccctgcagc | aagtctctct | tctttattct | ggggctggg | aaggatccca | 1380 |
| aaacagggaa | cttggccgaa | ccctgggctt | tggatgctaa | ccactgaagt | accagcacct | 1440 |
| gtaggatgct | gtctttgaag | aaactgaggc | ggacctccaa | atgcagccct | aaggcagagg | 1500 |
| tcaacgtgga | agaccagccc | ttctccaagc | cccactggtc | tttgcaagct | gtacgttgta | 1560 |
| ggcaatctga | gaactggaaa | gggggactac | aaccagaaag | ttggttaccc | tgccatggga | 1620 |
| ataaagtagc | tgttttccac | cccaaaaaaa | aaaaaaaaa | aaaaaa | | 1666 |

<210> SEQ ID NO 831
<211> LENGTH: 181
<212> TYPE: PRT
<213> ORGANISM: Homo sapiens

<400> SEQUENCE: 831

```
Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr
            20                  25                  30

His Ile Ile Ser Ile His Glu Ser Pro Gln Pro Leu Leu Gln Asp Ile
        35                  40                  45

Thr Tyr Leu Arg Ile Pro Val Ala Asp Thr Pro Glu Val Pro Ile Lys
    50                  55                  60

Lys His Phe Lys Glu Cys Ile Asn Phe Ile His Cys Cys Arg Leu Asn
65                  70                  75                  80

Gly Gly Asn Cys Leu Val His Cys Phe Ala Gly Ile Ser Arg Ser Thr
                85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
        115                 120                 125

Pro Gly Phe Arg Gln Gln Leu Glu Glu Phe Gly Trp Ala Ser Ser Gln
    130                 135                 140

Lys Gly Ala Arg His Arg Thr Ser Lys Thr Ser Gly Ala Gln Cys Pro
145                 150                 155                 160

Pro Met Thr Ser Ala Thr Trp Met Val Thr Gly Pro Lys Val Pro Asp
                165                 170                 175

Leu Ser Val Leu Arg
            180
```

<210> SEQ ID NO 832
<211> LENGTH: 1807
<212> TYPE: DNA
<213> ORGANISM: Homo sapiens

<400> SEQUENCE: 832

```
ggccccccgt tccccgccag gctgcaggcg tcgggcctgg gccgtcaggg cagctgtgac      60
cggatcgctt cccgggcggc gagctggggg tgcacccgga ccgccgcccc cgggatcatg     120
ggcaatggca tgaccaaggt acttcctgga ctctacctcg gaaacttcat tgatgccaaa     180
gacctggatc agctgggccg aaataagatc acacacatca tctctatcca tgagtcaccc     240
cagcctctgc tgcaggatat cacctacctt cgcatcccgg tcgctgatac ccctgaggta     300
cccatcaaaa agcacttcaa agaatgtatc aacttcatcc actgctgccg ccttaatggg     360
gggaactgcc ttgtgcactg ctttgcaggc atctctcgca gcaccacgat tgtgacagcg     420
tatgtgatga ctgtgacggg gctaggctgg cgggacgtgc ttgaagccat caaggccacc     480
aggcccatcg ccaaccccaa cccaggcttt aggcagcagc ttgaagagtt tggctgggcc     540
agttcccaga agggtgccag acataggacc tcaaaaacct tggtgcccaa tgccctccg      600
atgacttcag caacctgcct gctggctgca cgtgtggctc ttctctccgc agcgctggtg     660
cgcgaagcca ccgggcgcac agcccagcgc tgtcgtctga gtccgcgggc ggccgccgag     720
cgcctgctgg ggccgccacc tcacgttgca gcaggatggt caccggaccc aaagtaccag     780
atctgtctgt gcttcggtga ggaggacccg ggccccacac agcaccccaa ggagcagctc     840
atcatggcgg acgtgcaggt gcagcttcgg cctgggagct cgtcctgcac tctaagtgcc     900
tcaaccgagc gccagatgg gtcctcaacc cctggcaacc ccgatggcat cactcacctt      960
caatgcagct gcctccatcc taagcgagcc gcttcctctt cttgtacccg ctgaaggcag    1020
```

-continued

```
cccccaacag gggggctccc tactcccacc caaccctgcc cacactaagc ccatagactt    1080
ggggcctccc cggcggcaca tcacccaggt ctgccggacg gcagaggtgg atcgcggcct    1140
tccactcctc tgtcacgggg ccccggaact cgagagtagg ccacaccgcc ccccagctgg    1200
gcatggggct tcggcaggaa actgaacttg atcttgaggc cccagaaagg cagcaactgg    1260
agcagaagca agacttcatc tcttgctgac agcccaattt gtcaatagcg ctttcctcag    1320
agccagcctt aacctgctgt tgagtccatt aaaacgtttg cttaaagttt ttaccaataa    1380
ttagatcatc agggttgttt agtgtgggat caagccataa caaaactgcc tagcctctca    1440
ggggcctaga atttacagaa ccttcctcct ccctgcagct agtctctctt ctttattctg    1500
ggggctggga aggatcccaa aacagggaac ttggccgaac cctgggcttt ggatgctaac    1560
cactgaagta ccagcacctg taggatgctg tctttgaaga aactgaggcg gacctccaaa    1620
tgcagcccta aggcagaggt caacgtggaa gaccagccct tctccaagcc ccactggtct    1680
ttgcaagctg tacgttgtag gcaatctgag aactggaaag ggggactaca accagaaagt    1740
tggttaccct gccatgggaa taaagtagct gttttccacc caaaaaaaa aaaaaaaaa     1800 aaaaaaa                                                             1807
```

<210> SEQ ID NO 833
<211> LENGTH: 298
<212> TYPE: PRT
<213> ORGANISM: Homo sapiens

<400> SEQUENCE: 833

```
Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr
            20                  25                  30

His Ile Ile Ser Ile His Glu Ser Pro Gln Pro Leu Leu Gln Asp Ile
        35                  40                  45

Thr Tyr Leu Arg Ile Pro Val Ala Asp Thr Pro Glu Val Pro Ile Lys
    50                  55                  60

Lys His Phe Lys Glu Cys Ile Asn Phe Ile His Cys Cys Arg Leu Asn
65                  70                  75                  80

Gly Gly Asn Cys Leu Val His Cys Phe Ala Gly Ile Ser Arg Ser Thr
                85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
        115                 120                 125

Pro Gly Phe Arg Gln Gln Leu Glu Glu Phe Gly Trp Ala Ser Ser Gln
    130                 135                 140

Lys Gly Ala Arg His Arg Thr Ser Lys Thr Ser Gly Ala Gln Cys Pro
145                 150                 155                 160

Pro Met Thr Ser Ala Thr Cys Leu Leu Ala Ala Arg Val Ala Leu Leu
                165                 170                 175

Ser Ala Ala Leu Val Arg Glu Ala Thr Gly Arg Thr Ala Gln Arg Cys
            180                 185                 190

Arg Leu Ser Pro Arg Ala Ala Ala Glu Arg Leu Leu Gly Pro Pro
        195                 200                 205

His Val Ala Ala Gly Trp Ser Pro Asp Pro Lys Tyr Gln Ile Cys Leu
    210                 215                 220
```

Cys Phe Gly Glu Glu Asp Pro Gly Pro Thr Gln His Pro Lys Glu Gln
225                 230                 235                 240

Leu Ile Met Ala Asp Val Gln Val Gln Leu Arg Pro Gly Ser Ser Ser
                245                 250                 255

Cys Thr Leu Ser Ala Ser Thr Glu Arg Pro Asp Gly Ser Thr Pro
                260                 265                 270

Gly Asn Pro Asp Gly Ile Thr His Leu Gln Cys Ser Cys Leu His Pro
            275                 280                 285

Lys Arg Ala Ala Ser Ser Ser Cys Thr Arg
        290                 295

<210> SEQ ID NO 834
<211> LENGTH: 1268
<212> TYPE: DNA
<213> ORGANISM: Homo sapiens

<400> SEQUENCE: 834

```
ggccccccgt tccccgccag gctgcaggcg tcgggcctgg gccgtcaggg cagctgtgac        60
cggatcgctt cccgggcggc gagctggggg tgcacccgga ccgccgcccc gggatcatg        120
ggcaatggca tgaccaaggt acttcctgga ctctacctcg gaaacttcat tgatgccaaa       180
gacctggatc agctgggccg aaataagatc acacacatca tctctatcca tgagtcaccc       240
cagcctctgc tgcaggatat cacctacctt cgcatcccgg tcgctgatac ccctgaggta       300
cccatcaaaa agcacttcaa gaatgtatc aacttcatcc actgctgccg ccttaatggg       360
gggaactgcc ttgtgcactg ctttgcaggc atctctcgca gcaccacgat tgtgacagcg       420
tatgtgatga ctgtgacggg gctaggctgg cgggacgtgc ttgaagccat caaggccacc      480
aggcccatcg ccaaccccaa cccaggcttt aggcagcagc ttgaagagtt tggctgggcc       540
agttcccaga agggtgccag acataggacc tcaaaaacct ctggtgccca atgccctccg       600
atgacttcag caacctggat ggtcaccgga cccaaagtac cagatctgtc tgtgcttcgg       660
tgaggaggac ccgggcccca cacagcaccc aaggagcag ctcatcatgg cggacgtgca        720
ggtgcagctt cggcctggga gctcgtcctg cactctaagt gcctcaaccg agcgcccaga       780
tgggtcctca ccccctggca acccgatgg catcactcac cttcaatgca gcttgcctcc       840
atcctaagcg agccgcttcc tcttcttgta cccgctgaag gcaagccccc aacaggggg       900
ctccctactc ccacccaacc ctgcccacac taagcccata gacttggggc ctccccggc        960
acatcaccca ggtctgccgg acggcagagg tggatcgcgg ccttccactc ctctgtcacg     1020
gggcccgga actcgagagt aggcctcacc gccccccagc tgggcatggg gcttcggcag      1080
gaaactgaac ttgatcttga ggccagcaga aaggcagcaa ctggagcaga agcaagactt     1140
catctcttgc tgacagccca atttgtcaat agcgctttcc tcagagccag ccttaacctg     1200
ctgttgagtc cattaaaacg tttgcttaaa gtttttacca ataaaaaaaa aaaaaaaaa     1260
aaaaaaaa                                                               1268
```

<210> SEQ ID NO 835
<211> LENGTH: 181
<212> TYPE: PRT
<213> ORGANISM: Homo sapiens

<400> SEQUENCE: 835

Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr

```
                    20                  25                  30
His Ile Ile Ser Ile His Glu Ser Pro Gln Pro Leu Leu Gln Asp Ile
         35                  40                  45

Thr Tyr Leu Arg Ile Pro Val Ala Asp Thr Pro Glu Val Pro Ile Lys
 50                  55                  60

Lys His Phe Lys Glu Cys Ile Asn Phe Ile His Cys Cys Arg Leu Asn
65                  70                  75                  80

Gly Gly Asn Cys Leu Val His Cys Phe Ala Gly Ile Ser Arg Ser Thr
             85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
            115                 120                 125

Pro Gly Phe Arg Gln Gln Leu Glu Glu Phe Gly Trp Ala Ser Ser Gln
            130                 135                 140

Lys Gly Ala Arg His Arg Thr Ser Lys Thr Ser Gly Ala Gln Cys Pro
145                 150                 155                 160

Pro Met Thr Ser Ala Thr Trp Met Val Thr Gly Pro Lys Val Pro Asp
                165                 170                 175

Leu Ser Val Leu Arg
            180
```

```
<210> SEQ ID NO 836
<211> LENGTH: 1045
<212> TYPE: DNA
<213> ORGANISM: Homo sapiens

<400> SEQUENCE: 836
ggccccccgt tccccgccag gctgcaggcg tcgggcctgg gccgtcaggg cagctgtgac      60
cggatcgctt cccgggcggc gagctggggg tgcacccgga ccgccgcccc cgggatcatg     120
ggcaatggca tgaccaaggt acttcctgga ctctacctcg gaaacttcat tgatgccaaa     180
gacctggatc agctgggccg aaataagatc acacacatca tctctatcca tgagtcaccc     240
cagcctctgc tgcaggatat cacctacctt cgcatcccgg tcgctgatac ccctgaggta     300
cccatcaaaa agcacttcaa gaatgtatc aacttcatcc actgctgccg ccttaatggg     360
gggaactgcc ttgtgcactg cttttgcagg catctctcgca gcaccacgat tgtgacagcg     420
tatgtgatga ctgtgacggg gctaggctgg cgggacgtgc ttgaagccat caaggccacc     480
aggcccatcg ccaaccccaa cccaggcttt aggcagcagc ttgaagagtt tggctgggcc     540
agttcccaga gggtgccag acataggacc tcaaaaacct ctggtgccca atgccctccg     600
atgacttcag caacctggat ggtcaccgga cccaaagtac cagatctgtc tgtgcttcgg     660
tgaggaggac ccgggcccca cacagcaccc aaggagcag ctcatcatgg cggacctagt     720
ctctcttctt tattctgggg gctgggaagg atcccaaaac agggaacttg ccgaaccct     780
gggctttgga tgctaaccac tgaagtacca gcacctgtag gatgctgtct ttgaagaaac     840
tgaggcggac ctccaaatgc agccctaagg cagaggtcaa cgtggaagac cagccctct     900
ccaagcccca ctggtctttg caagctgtac gttgtaggca atctgagaac tggaaagggg     960
gactacaacc agaaagttgg ttaccctgcc atgggaataa agtagctgtt ttccacccca    1020
taaaaaaaaa aaaaaaaaaa aaaaa                                           1045

<210> SEQ ID NO 837
<211> LENGTH: 181
```

<212> TYPE: PRT
<213> ORGANISM: Homo sapiens

<400> SEQUENCE: 837

```
Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr
            20                  25                  30

His Ile Ile Ser Ile His Glu Ser Pro Gln Pro Leu Leu Gln Asp Ile
        35                  40                  45

Thr Tyr Leu Arg Ile Pro Val Ala Asp Thr Pro Glu Val Pro Ile Lys
    50                  55                  60

Lys His Phe Lys Glu Cys Ile Asn Phe Ile His Cys Cys Arg Leu Asn
65                  70                  75                  80

Gly Gly Asn Cys Leu Val His Cys Phe Ala Gly Ile Ser Arg Ser Thr
                85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
        115                 120                 125

Pro Gly Phe Arg Gln Gln Leu Glu Glu Phe Gly Trp Ala Ser Ser Gln
    130                 135                 140

Lys Gly Ala Arg His Arg Thr Ser Lys Thr Ser Gly Ala Gln Cys Pro
145                 150                 155                 160

Pro Met Thr Ser Ala Thr Trp Met Val Thr Gly Pro Lys Val Pro Asp
                165                 170                 175

Leu Ser Val Leu Arg
            180
```

<210> SEQ ID NO 838
<211> LENGTH: 982
<212> TYPE: DNA
<213> ORGANISM: Homo sapiens

<400> SEQUENCE: 838

```
ggcccccgt tccccgccag gctgcaggcg tcgggcctgg gccgtcaggg cagctgtgac      60
cggatcgctt cccgggcggc gagctggggg tgcacccgga ccgccgcccc cgggatcatg     120
ggcaatggca tgaccaaggt acttcctgga ctctacctcg gaaacttcat tgatgccaaa     180
gacctggatc agctgggccg aaataagatc acacacatca tctctatcca tgagtcaccc     240
cagcctctgc tgcaggatat cacctacctt cgcatcccgg tcgctgatac ccctgaggta     300
cccatcaaaa agcacttcaa agaatgtatc aacttcatcc actgctgccg ccttaatggg     360
gggaactgcc ttgtgcactg ctttgcaggc atctctcgca gcaccacgat tgtgacagcg     420
tatgtgatga ctgtgacggg gctaggctgg cgggacgtgc ttgaagccat caaggccacc     480
aggcccatcg ccaaccccaa cccaggcttt aggcagcagc ttaagagttt ggctgggcca     540
gttcccagaa ggatggtcac cggacccaaa gtaccagatc tgtctgtgct tcggtgagga     600
ggacccgggc cccacacagc accccaagga gcagctcatc atggcggacc tagtctctct     660
tctttattct gggggctggg aaggatccca aacagggaa cttggccgaa ccctgggctt      720
tggatgctaa ccactgaagt accagcacct gtaggatgct gtctttgaag aaactgaggc     780
ggacctccaa atgcagccct aaggcagagg tcaacgtgga agaccagccc ttctccaagc     840
cccactggtc tttgcaagct gtacgttgta ggcaatctga gaactggaaa ggggactac      900
```

-continued

```
aaccagaaag ttggttaccc tgccatggga ataaagtagc tgttttccac cccccaaaaa    960
aaaaaaaaaa aaaaaaaaaa aa                                              982

<210> SEQ ID NO 839
<211> LENGTH: 159
<212> TYPE: PRT
<213> ORGANISM: Homo sapiens

<400> SEQUENCE: 839

Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr
            20                  25                  30

His Ile Ile Ser Ile His Glu Ser Pro Gln Pro Leu Leu Gln Asp Ile
        35                  40                  45

Thr Tyr Leu Arg Ile Pro Val Ala Asp Thr Pro Glu Val Pro Ile Lys
    50                  55                  60

Lys His Phe Lys Glu Cys Ile Asn Phe Ile His Cys Cys Arg Leu Asn
65                  70                  75                  80

Gly Gly Asn Cys Leu Val His Cys Phe Ala Gly Ile Ser Arg Ser Thr
                85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
        115                 120                 125

Pro Gly Phe Arg Gln Gln Leu Lys Ser Leu Ala Gly Pro Val Pro Arg
    130                 135                 140

Arg Met Val Thr Gly Pro Lys Val Pro Asp Leu Ser Val Leu Arg
145                 150                 155

<210> SEQ ID NO 840
<211> LENGTH: 1064
<212> TYPE: DNA
<213> ORGANISM: Homo sapiens

<400> SEQUENCE: 840
ggccccccgt tccccgccag gctgcaggcg tcgggcctgg gccgtcaggg cagctgtgac     60
cggatcgctt cccgggcggc gagctggggg tgcacccgga ccgccgcccc cgggatcatg    120
ggcaatggca tgaccaaggt acttcctgga ctctacctcg gaaacttcat tgatgccaaa    180
gacctggatc agctgggccg aaataagatc acacacatca tctctatcca tgagtcaccc    240
cagcctctgc tgcaggatat cacctacctt cgcatcccgg tcgctgatac ccctgaggta    300
cccatcaaaa agcacttcaa agaatgtatc aacttcatcc actgctgccg ccttaatggg    360
gggaactgcc ttgtgcactg ctttgcaggc atctctcgca gcaccacgat tgtgacagcg    420
tatgtgatga ctgtgacggg gctaggctgg cgggacgtgc ttgaagccat caaggccacc    480
aggcccatcg ccaaccccaa cccaggcttt aggcagcagc ttgaagagtt ggctgggcc     540 agttcccaga agggcttttta ccaacctcat aagctgttgt gagaaccaat tgagacactg    600
caggaaagtg tttagccagg cccagcactg atgagcagtc ggatggtcac cggacccaaa    660
gtaccagatc tgtctgtgct tcggtgagga ggacccgggc ccacacagc acccccaagga   720 gcagctcatc atggcggacc tagtctctct tctttattct gggggctggg aaggatccca    780
aaacagggaa cttggccgaa ccctgggctt tggatgctaa ccactgaagt accagcacct    840
gtaggatgct gtctttgaag aaactgaggc ggacctccaa atgcagccct aaggcagagg    900
```

-continued

```
tcaacgtgga agaccagccc ttctccaagc cccactggtc tttgcaagct gtacgttgta    960
ggcaatctga gaactggaaa gggggactac aaccagaaag ttggttaccc tgccatggga   1020
ataaagtagc tgttttccaa aaaaaaaaaa aaaaaaaaaa aaaa                    1064
```

<210> SEQ ID NO 841
<211> LENGTH: 154
<212> TYPE: PRT
<213> ORGANISM: Homo sapiens

<400> SEQUENCE: 841

```
Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr
            20                  25                  30

His Ile Ile Ser Ile His Glu Ser Pro Gln Pro Leu Leu Gln Asp Ile
        35                  40                  45

Thr Tyr Leu Arg Ile Pro Val Ala Asp Thr Pro Glu Val Pro Ile Lys
    50                  55                  60

Lys His Phe Lys Glu Cys Ile Asn Phe Ile His Cys Cys Arg Leu Asn
65                  70                  75                  80

Gly Gly Asn Cys Leu Val His Cys Phe Ala Gly Ile Ser Arg Ser Thr
                85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
        115                 120                 125

Pro Gly Phe Arg Gln Gln Leu Glu Glu Phe Gly Trp Ala Ser Ser Gln
    130                 135                 140

Lys Gly Phe Tyr Gln Pro His Lys Leu Leu
145                 150
```

<210> SEQ ID NO 842
<211> LENGTH: 19
<212> TYPE: RNA
<213> ORGANISM: Artificial Sequence
<220> FEATURE:
<223> OTHER INFORMATION: Small interfering RNA - PRL-3

<400> SEQUENCE: 842

```
agacccggug cugcguuau                                                  19
```